(12) United States Patent
Paszty et al.

(10) Patent No.: US 7,872,106 B2
(45) Date of Patent: Jan. 18, 2011

(54) SCLEROSTIN-BINDING ANTIBODIES

(75) Inventors: Christopher J. Paszty, Ventura, CA (US); Martyn K. Robinson, Woodburn Green (GB); Kevin Graham, Thousand Oaks, CA (US); Alistair J. Henry, Middlesex (GB); Kelly S. Warmington, Newbury Park, CA (US); John Latham, Seattle, WA (US); Hsieng S. Lu, Westlake Village, CA (US); Alastair Lawson, Hampshire (GB); Andy Popplewell, Berkshire (GB); Wenyan Shen, Wayne, PA (US); David G. Winkler, Arlington, MA (US); Aaron G. Winters, Ventura, CA (US)

(73) Assignees: Amgen Inc., Thousand Oaks, CA (US); UCB Pharma S.A., Brussels (BE)

( * ) Notice: Subject to any disclaimer, the term of this patent is extended or adjusted under 35 U.S.C. 154(b) by 0 days.

(21) Appl. No.: 12/276,889

(22) Filed: Nov. 24, 2008

(65) Prior Publication Data

US 2009/0304713 A1 Dec. 10, 2009

Related U.S. Application Data

(62) Division of application No. 11/411,003, filed on Apr. 25, 2006, now Pat. No. 7,592,429.

(60) Provisional application No. 60/792,645, filed on Apr. 17, 2006, provisional application No. 60/782,244, filed on Mar. 13, 2006, provisional application No. 60/776,847, filed on Feb. 24, 2006, provisional application No. 60/677,583, filed on May 3, 2005.

(51) Int. Cl.
*C07K 16/00* (2006.01)
*C07K 16/18* (2006.01)
*C07K 16/28* (2006.01)

(52) U.S. Cl. .................. 530/388.24; 530/387.1; 530/387.3; 530/388.1; 530/388.15

(58) Field of Classification Search ........................ None
See application file for complete search history.

(56) References Cited

U.S. PATENT DOCUMENTS

| | | | |
|---|---|---|---|
| 4,331,647 A | 5/1982 | Goldenberg | |
| 4,376,110 A | 3/1983 | David et al. | |
| 4,411,993 A | 10/1983 | Gillis | |
| 4,427,115 A | 1/1984 | Laipply | |
| 4,543,439 A | 9/1985 | Frackelton, Jr. et al. | |
| RE32,011 E | 10/1985 | Zimmerman et al. | |
| 4,837,440 A | 6/1989 | Burtscher et al. | |
| 4,902,614 A | 2/1990 | Wakabayashi et al. | |
| 5,070,108 A | 12/1991 | Margolis | |
| 5,145,684 A | 9/1992 | Liversidge et al. | |
| 5,223,409 A | 6/1993 | Ladner et al. | |
| 5,399,363 A | 3/1995 | Liversidge et al. | |
| 5,453,492 A | 9/1995 | Butzow et al. | |
| 5,466,468 A | 11/1995 | Schneider et al. | |
| 5,543,158 A | 8/1996 | Gref et al. | |
| 5,552,157 A | 9/1996 | Yagi et al. | |
| 5,565,213 A | 10/1996 | Nakamori et al. | |
| 5,567,434 A | 10/1996 | Szoka, Jr. | |
| 5,627,052 A | 5/1997 | Schrader et al. | |
| 5,641,515 A | 6/1997 | Ramtoola et al. | |
| 5,698,426 A | 12/1997 | Huse | |
| 5,738,868 A | 4/1998 | Shinkarenko et al. | |
| 5,780,263 A | 7/1998 | Hastings et al. | |
| 5,795,587 A | 8/1998 | Gao et al. | |
| 5,811,238 A | 9/1998 | Stemmer et al. | |
| 5,830,721 A | 11/1998 | Stemmer et al. | |
| 5,837,458 A | 11/1998 | Minshull et al. | |
| 5,877,397 A | 3/1999 | Lonberg et al. | |
| 6,054,561 A | 4/2000 | Ring | |
| 6,057,421 A | 5/2000 | Muller et al. | |
| 6,117,911 A | 9/2000 | Grainger et al. | |
| 6,133,426 A | 10/2000 | Gonzalez et al. | |
| 6,180,370 B1 | 1/2001 | Queen et al. | |
| 6,207,153 B1 | 3/2001 | Dan et al. | |
| 6,395,511 B1 | 5/2002 | Brunkow et al. | |
| 6,489,445 B1 | 12/2002 | Brunkow et al. | |
| 6,495,736 B1 | 12/2002 | Brunkow et al. | |

(Continued)

FOREIGN PATENT DOCUMENTS

JP 4-141095 5/1992

(Continued)

OTHER PUBLICATIONS

The Merck Manuals Online Medical Library, [online]. Whitehouse Station, NJ: Merck Research Laboratories, 2006-2007. [retrieved on May 6, 2010]. Retrieved from the Internet: <URL: http://www.merck.com/mmpe/print/sec15/ch199/ch199b.html>. Anorexia Nervosa, pp. 1-4.*

Anonymous, Amgen presents denosumab and sclerostin antibody data at American Society for Bone and Mineral Research Annual Meeting. Amgen Media Press Release. www.amgen.com/media/media_pr_detail.jsp?releaseID=907028 (2006).

Eli Lilly Statement of Grounds of Appeal, Opposition to European Patent Application No. 1133558 B1, dated Sep. 28, 2009.

Declaration filed in connection with the European Patent EP 1133558 Opposition, Expert opinion of Prof. Dr. Thomas Muller, dated Sep. 23, 2009.

Winkler et al., Osteocyte control of bone formation via sclerostin, a novel BMP antagonist, *EMBO J.* 22(23): 6267-76 (2003).

(Continued)

*Primary Examiner*—Sharon Wen
(74) *Attorney, Agent, or Firm*—Marshall, Gerstein & Borun LLP

(57) ABSTRACT

Compositions and methods relating to epitopes of sclerostin protein, and sclerostin binding agents, such as antibodies capable of binding to sclerostin, are provided.

25 Claims, 25 Drawing Sheets

U.S. PATENT DOCUMENTS

| | | |
|---|---|---|
| 6,703,199 B1 | 3/2004 | Koide |
| 6,803,453 B1 | 10/2004 | Brunkow et al. |
| 6,806,055 B2 | 10/2004 | Berman et al. |
| 6,815,201 B2 | 11/2004 | Pinter |
| 6,818,748 B2 | 11/2004 | Fulton et al. |
| 7,192,583 B2 | 3/2007 | Brunkow et al. |
| 7,226,902 B2 | 6/2007 | Winkler et al. |
| 2003/0165410 A1 | 9/2003 | Taylor |
| 2003/0186915 A1 | 10/2003 | Pan et al. |
| 2003/0022904 A1 | 12/2003 | Sutherland et al. |
| 2004/0009535 A1 | 1/2004 | Brunkow et al. |
| 2004/0023356 A1 | 2/2004 | Krumlauf et al. |
| 2004/0058321 A1 | 3/2004 | Brunkow et al. |
| 2004/0141875 A1 | 7/2004 | Doshi |
| 2004/0146888 A1 | 7/2004 | Paszty et al. |
| 2004/0158045 A1 | 8/2004 | Brunkow et al. |
| 2005/0014650 A1 | 1/2005 | Seitz et al. |
| 2005/0106683 A1 | 5/2005 | Winkler et al. |
| 2005/0238646 A1 | 10/2005 | Ledbetter et al. |
| 2006/0233801 A1 | 10/2006 | Brunkow et al. |
| 2007/0072797 A1 | 3/2007 | Robinson et al. |
| 2007/0110747 A1 | 5/2007 | Paszty et al. |
| 2007/0292444 A1 | 12/2007 | Krumlauf et al. |
| 2008/0182788 A1 | 7/2008 | Brunkow et al. |
| 2008/0234219 A1 | 9/2008 | Brunkow et al. |
| 2009/0074763 A1 | 3/2009 | Padhi et al. |

FOREIGN PATENT DOCUMENTS

| | | |
|---|---|---|
| WO | WO-91/13152 | 9/1991 |
| WO | WO-92/02551 | 2/1992 |
| WO | WO-92/06693 | 4/1992 |
| WO | WO-95/30003 | 11/1995 |
| WO | WO-98/21335 | 5/1998 |
| WO | WO-99/03996 | 1/1999 |
| WO | WO-99/06554 | 2/1999 |
| WO | WO-99/15556 | 4/1999 |
| WO | WO-00/32773 | 6/2000 |
| WO | WO-00/75317 | 12/2000 |
| WO | WO-01/64885 | 9/2001 |
| WO | WO-01/92308 | 12/2001 |
| WO | WO-01/98491 | 12/2001 |
| WO | WO-2004/098491 | 12/2001 |
| WO | WO-02/24888 | 3/2002 |
| WO | WO-03/050513 | 6/2003 |
| WO | WO-03/087763 | 10/2003 |
| WO | WO-03/106657 | 12/2003 |
| WO | WO-2004/082608 | 9/2004 |
| WO | WO-2005/003158 | 1/2005 |
| WO | WO-2005/014650 | 2/2005 |
| WO | WO-2006/102070 | 9/2006 |
| WO | WO-2006/119062 | 11/2006 |
| WO | WO-2006/119107 | 11/2006 |
| WO | WO-2008/061013 | 5/2008 |
| WO | WO-2008/115732 | 9/2008 |
| WO | WO-2008/133722 | 11/2008 |
| WO | WO-2009/039175 | 3/2009 |

OTHER PUBLICATIONS van Bezooijen et al., Sost/sclerostin, an osteocyte-derived negative regulator of bone formation, *Cytokine Growth Factor Rev.*, 16: 319-27 (2005).

Li et al., Sclerostin binds to LRP5/6 and antagonizes canonical Wnt signaling, *J. Biol. Chem.* 280(20): 19883-7 (2005).

Declaration filed in connection with the European Patent EP 1133558 Opposition, Expert opinion of Dr. Walter Sebald, dated Sep. 24, 2009.

Kirsch et al., BMP-2 antagonists emerge from alterations in the low-affinity binding epitope for receptor BMPR-II, *EMBO J.* 19(13): 3314-24 (2000).

Heinecke et al., Receptor oligomerization and beyond: A case study in bone morphogenetic proteins, *BMC Biol.* 7: 59 (2009).

Declaration filed in connection with the European Patent EP 1133558 Opposition, Expert opinion of Prof. Dr. Edgar Wingender, dated Sep. 24, 2009.

Mayer et al., Differentiation of osteogenetic cells: Systems and regulators, *Z. Orthop.*, 130: 276-84 (1992)—Abstract Only.

Blum et al., Study plan for German students in the summer of 1998, University Bioinformatik lecture announcement (1998).

Baxevanis (Ed.) et al., Bioinformatics: A practical guide to the analysis of genes and proteins, John Wiley & Sons, Inc. p. 234 (1998).

Bishop (Ed.), Guide to Human Genome Computing, Second Edition, Academic Press, Chapter 1: Introduction to human genome computer via the world wide web, pp. 1-14 (2003).

Declaration filed in connection with the European Patent EP 1133558 Opposition, Expert opinion of Dr. Auristela Freire de Paes Alves, Ph.D., dated Sep. 9, 2009.

Eli Lilly, Biacore experiment comparison results, Setup assay to measure BMP binding to captured SOST, referenced on p. 41 of reference C193 dated Sep. 28, 2009.

Mayer et al., Differentiation of osteogenetic cells: Systems and regulators, *Z. Orthop.*, 130: 276-84 (1992)—Abstract Only.

Albertsen et al., A physical map and candidate genes in the BRCA1 region on chromosome 17q12-21, *Nat. Genet.* 7: 472-479 (1994).

Alting-Mees et al., Monoclonal antibody expression libraries: a rapid alternative to hybridomas. *Strategies in Molecular Biology*, 3:1-9 (1990).

Alves et al., Sclerosteosis: A marker of Dutch ancestry? *Rev. Bras. Genet.* 4: 825-34 (1982).

Angel et al., A single amino acid substitution abolishes the heterogeneity of chimeric mouse/human (IgG4) antibody. *Mol. Immunol.* 30(1):105-108 (1993).

Avsian-Kretchmer et al., Comparative genomic analysis of the eight-membered ring cysteine knot-containing bone morphogenetic protein antagonists. *Mol. Endocrinol.* 18: 1-12 (2004).

Babcook et al., A novel strategy for generating monoclonal antibodies from single, isolated lymphocytes producing antibodies of defined specificities. *Proc. Natl. Acad. Sci.* (USA), 93:7843-7848 (1996).

Baines et al., Purification of Immunoglobulin G (IgG), Methods in Molecular Biology. The Humana Press, Inc. vol. 10, Chapter 8, pp. 79-104 (1992).

Balemans et al., Extracellular Regulation of BMP Signaling in Vertebrates: A cocktail of Modulators. *Dev. Biol.* 250:231-250 (2002).

Balemans et al., Increased bone density in sclerosteosis is due to the deficiency of a novel secreted protein (SOST). *Hum. Mol. Genet.* 10: 537-43 (2001).

Balemans et al. Localization of the Gene for Sclerosteosis to the van Buchem Disease-Gene Region on Chromosome 17q12-q21. *Am. J. Hum. Genet.*, 64:1661-9 (1999).

Balint et al., Antibody engineering by parsimonious mutagenesis. *Gene.* 137: 109-18 (1993).

Beighton et al., The clinical features of sclerosteosis. A review of the manifestations in twenty-five affected individuals. *Ann. Intern. Med.* 84:393-397 (1976).

Beighton et al., The syndromic status of sclerosteosis and van Buchem disease. *Clin. Genet.* 25: 175-81 (1984).

Bendayan, Possibilities of false immunocytochemical results generated by the use of monoclonal antibodies: The example of the anti-proinsulin antibody. *J. Histochem. Cytochem.* 43: 881-6 (1995).

Bendig, Methods: A Companion to Methods in Ezymology. 8: 83-93 (1995).

Berman et al., The protein data bank. *Acta Crystallogr. D. Biol. Crystallogr.* 58: 899-907 (2002).

Bird et al., Single-chain antigen-binding proteins. *Science*, 242:423-426 (1988).

Black et al., A somatic cell hybrid map of the long arc of human chromosome 17, containing the familial breast cancer locus (BRCAI) *Am. J. Hum. Genet.* 52: 702-10 (1993).

Boden et al., Glucocorticoid-induced differentiation of fetal rat calvarial osteoblasts is mediated by bone morphogenetic protein-6. *Endocrinology*, 138(7):2820-2828 (1997).

Boerner et al., Production of antigen-specific human monoclonal antibodies from in vitro-primed human splenocytes. *J. Immunol.*, 147:86-95 (1991).

Bonaldo et al., Normalization and subtraction: two approaches to facilitate gen discovery, *Genome Res.* 6(9): 791-806 (1996).
Bondestam, Ligands & Signaling Components of the Transforming Growth Factor, Helsinki University Biomedical Dissertations (2002).
Bork et al., Go hunting in sequence databases by watch out for the traps. *Trends Genet.* 12: 4225-7 (1996).
Bost et al., Antibodies against a peptide sequence within the HIV envelope protein crossreacts with human interleukin-2. *Immunol. Invest.*, 17(6&7):577-586 (1988).
Bostrom et al., Immunolocalization and expression of bone morphogenetic proteins 2 and 4 in fracture healing. *J. Orthop. Res.*, 13:357-367 (1995).
Bouffard et al., A physical map of human chromosome 7: An integrated YAC contig map with average STS spacing of 79 kb. *Genome Res.* 7: 673-92 (1997).
Bowie et al., Deciphering the message in protein sequences: tolerance to amino acid substitutions. *Science*, 247(4948):1306-1310 (1990).
Bowie et al., A method to identify protein sequences that fold into a known three-dimensional structure. *Science*, 253:164-170 (1991).
Bradley et al., Modifying the mouse: design and desire. *Bio/Technology*, 10:534-539 (1992).
Brenner et al., Population statistics of protein structures: lessons from structural classifications. *Curr. Opin. Struct. Biol.*, 7(3):369-376 (1997).
Bruggemann et al., Production of human antibody repertoires in transgenic mice. *Curr. Opin. Biotechnol.*, 8:455-458 (1997).
Brunkow et al., Bone Dysplasia sclerosteosis results from loss of the sost gene product: A novel cysteine knon-containing protein. *Am. J. Hum. Genet.* 68: 577-89 (2001).
Burton et al., Human antibodies from combinatorial libraries. *Adv. Immunol.*, 57:191-280 (1994).
Byrne et al., CD4+CD45RBHi T cell transfer induced colitis in mice is accompanied by osteopenia which is treatable with recombinant human osteoprotegerin. *Gut*, 54:78-86 (2005).
Campbell et al., Totipotency or multipotentiality of cultured cells: Applications and progress. *Theriogenology*, 47:63-72 (1997).
Chan et al., A new paradigm in the treatment of osteoporosis: Wnt pathway proteins and their antagonists. *Curr. Opin. Invest. Drugs.* 8:293-8 (2007).
Chandran et al., Recent trends in drug delivery systems: liposomal drug delivery system—preparation and characterisation. *Indian J. Exp. Biol.*, 35(8):801-809 (1997).
Charlier et al., A pore mutation in a novel KQT-like potassium channel gene in an idiopathic epilepsy family. *Nat. Genet.* 18: 53-55 (1998).
Chou et al., Prediction of the secondary structure of proteins from their amino acid sequences.*Adv. Enzymol. Relat. Areas Mol. Biol.* 47:45-148 (1978).
Chou et al., Empirical predictions of protein conformation. *Ann. Rev. Biochem.*, 47:251-276 (1978).
Clark, Antibody humanization: a case of the 'Emperor's new clothes'? *Immunology Today*, 21(8):397-402 (2000).
Colman, Effects of amino acid sequence changes on antibody-antigen interactions. *Res. Immunol.* 145: 33-6 (1994).
Collins, Identifying human disease genes by positional cloning.*The Harvey Lectures*. Series 86: 149-64 (1992).
Collins, Positional cloning moves from perditional to traditional. *Nat. Genet.* 9: 347-50 (1995).
Cook et al., Structural basis for a functional antagonist in the transforming growth factor beta superfamily. *J. Biol. Chem.*, 280(48):40177-40186 (2005).
Cormier, Markers of bone metabolism. *Curr. Opin. Rheumatol.* 7:243-8 (1995).
Couvreur et al., Polyalkylcyanoacrylates as colloidal drug carriers. *Crit. Rev. Ther. Drug Carrier Syst.*, 5(1):1-20 (1988).
Crameri et al., DNA shuffling of a family of genes from diverse species accelerates directed evolution. *Nature*, 391:288-291 (1998).
Dall'Acqua et al., Antibody humanization by framework shuffling. *Methods*, 36(1):43-60 (2005).
Davies et al., Affinity improvement of single antibody VH domains: Residues in all three hypervariable regions affect antigen binding. *Immunotechnology*. 2: 169-79 (1996).

Delmas et al., The use of biochemical markers of bone turnover in osteoporosis. *Osteoporosis International*. Suppl. 6: S2-17 (2000).
Durham et al., Alterations in insulin-like growth factor (IGF)-dependent IGF-binding protein-4 proteolysis in transformed osteoblastic cells. *Endocrinology*. 136: 1374-80 (1995).
Ebara et al., Mechanism for the action of bone morphogenetic proteins and regulation of their activity. *Spine*, 27(165):S10-S15 (2002).
Epstein et al., Endocrine function in sclerosteosis. *S. Afr. Med. J.*, 55:1105-1110 (1979).
Frost et al., On the rat model of human osteopenias and osteoporoses. *Bone Miner*. 18:227-236 (1992).
Gazzerro et al., Potential drug targets within bone morphogenetic protein signaling pathways. *Curr. Opin. Pharmacol*. 7: 325-3 (2007).
Genbank Accession No. AA393768, 1997.
Genbank Accession No. AAB33865, 1995.
Genbank Accession No. BAA19765, 1999.
Genbank Accession No. CAA88759, 1997.
Genbank Accession No. D38082, 1999.
Genbank Accession No. D79813, 1996.
Genbank Accession No. D89675, 1999.
Genbank Accession No. NM_001203, 2003.
Genbank Accession No. NM_001204, 2003.
Genbank Accession No. NM_004329, 2004.
Genbank Accession No. NM_030849, 2003.
Genbank Accession No. NM_033346, 2003.
Genbank Accession No. NP_001194, 2003.
Genbank Accession No. S75359, 2000.
Genbank Accession No. U25110, 1996.
Genbank Accession No. Z48923, 1997.
Gencic et al., Conservative amino acid substitution in the myelin proteolipid protein of jimpymsd mice. *J. Neurosci.* 10(1): 117-24 (1990).
Geysen et al., Cognitive features of continuous antigenic determinants. *J. Mol. Recognit.* 1(1):32-41 (1988).
Gitelman et al., Vgr-1/BMP-6 induces osteoblastic differentiation of pluripotential mesenchymal cells. *Cell Growth Differ.* 6:827-836 (1995).
Glasky et al., Stability of specific immunoglobulin secretion by EBV-transformed lymphoblastoid cells and human-murine heterohybridomas. *Hybridoma*, 8:377-389 (1989).
Green et al., Antigen-specific human monoclonal antibodies from mice engineered with human Ig heavy and light chain YACs. *Nature Genet.*, 7:13-21 (1994).
Greene et al., Screening Recombinant DNA Libraries. Current Protocols in Molecular Biology. vol. 1, Chapter 6 (1990).
Gribskov et al., Profile analysis. *Methods Enzymol.*, 183:146-159 (1990).
Gribskov et al., Profile analysis: detection of distantly related proteins. *Proc. Nat. Acad. Sci.* (USA), 84(13):4355-4358 (1987).
Groeneveld et al., Bone morphogenetic proteins in human bone regeneration. *Eur. J. Endocrinol.*, 142:9-21 (2000).
Groppe et al., Structural basis of BMP signaling inhibition by the cysteine knot protein noggin. *Nature*. 420: 636-42 (2002).
Guinness-Hey et al., Increased trabecular bone mass in rats treated with human synthetic parathyroid hormone. *Metab. Bone Dis. Relat. Res.*, 5:177-181 (1984).
Harlow et al., Antibodies: A Laboratory Manual. Cold Spring Harbor Laboratory, Cold Spring Harbor, NY. 141-57 (1988).
Harris, Processing of C-terminal lysine and arginine residues of proteins isolated from mammalian cell culture. *J. Chromatogr.A*. 705:129-134 (1995).
Hart et al., Crystal structure of the human TbetaR2 ectodomain--Tgf-beta3 complex. *Nat. Struc. Biol.*, 9(3):203-208 (2002).
Hay et al., ATCC cell lines and hybridomas. American Type Culture Collection 8$^{th}$ Ed. 149, 258,428 (1994).
Hill et al., Multiple extracellular signals promote osteoblast survival and apoptosis. *Endocrinology*, 138(9):3849-3858 (1997).
Hillier et al., Generation and analysis of 280,000 human expressed sequence tags. *Genome Res.* 6: 807-28 (1996).
Hock et al., Osteoblast apoptosis and bone turnover. *J. Bone Miner. Res.*, 16(6):975-984 (2001).

Hoffman et al., BMP signaling pathways in cartilage and bone formation. *Critical Review in Eukaryotic Gene Expression.* 11: 23-45 (2001).

Holliger et al., Engineered antibody fragments and the rise of single domains. *Nat. Biotechnol.* 23(9):1126-1136 (2005).

Holm et al., Protein folds and families: sequence and structure alignments. *Nucleic Acid Res.,* 27(1):244-247 (1999).

Holt et al., Domain antibodies: proteins for therapy. *Trends Biotechnol.* 21: 484-90 (2003).

Hoogenboom et al., By-passing immunisation. Human antibodies from synthetic repertoires of germline VH gene segments rearranged in vitro. *J. Mol. Biol.* 227:381-388 (1992).

Hsu et al., The xenopus dorsalizing factor gremlin identifies a novel family of secreted protein that antagonize BMP activities. *Molec. Cell.* 1: 673-83 (1998).

Huse et al., Generation of a large combinatorial library of the immunoglobulin repertoire in phage lambda. *Science,* 246:1275-1281 (1989).

Hwang et al., Use of human germline genes in a CDR homology-based approach to antibody humanization. *Methods,* 36(1):35-42 (2005).

Iemura et al., Direct binding of follistatin to a complex of bone-morphogenetic protein and its receptor inhibits ventral and epidermal cell fates in early xenopus embryo. *Proc. Natl. Acad. Sci.* USA. 95: 9337-42 (1998).

Innis et al., Evolutionary trace analysis of TGF-β and related growth factors: Implications for site-directed mutagenesis. *Protein Engineering.* 13: 829-47 (2000).

Jakobovits et al., Production of antigen-specific human antibodies from mice engineered with human heavy and light chain YACs. *Ann. N. Y. Acad. Sci.,* 764:525-535 (1995).

Jee et al., Overview: animal models of osteopenia and osteoporosis. *J. Musculoskelet. Neuronal. Interact.,* 1:193-207 (2001).

Jilka et al., Increased bone formation by prevention of osteoblast apoptosis with parathyroid hormone. *J. Clin. Invest.,* 104:439-446 (1999).

Jones, Progress in protein structure prediction. *Curr. Opin. Struct. Biol.,* 7(3):377-387 (1997).

Kabat et al., *Sequences of Proteins of Immunological Interest,* U.S. Department of Health and Human Services, NIH, USA (1987) (Table of Contents).

Kalu, The ovariectomized rat model of postmenopausal bone loss. *Bone Miner.* 15:175-192 (1991).

Kang et al., Linkage of recognition and replication functions by assembling combinatorial antibody Fab libraries along phage surfaces. *Proc. Natl. Acad. Sci.* (USA), 88:4363-4366 (1991).

Katagiri et al., The non-osteogenic mouse pluripotent cell line, C3H10T1/2, is induced to differentiate into osteoblastic cells by recombinant human bone morphogenetic protein-2. *Biochem. Biophys. Res. Comm.,* 172(1):295-299 (1990).

Kawabata et al., Signal transduction by bone morphogenetic protein. *Cytokine Growth Factor Reviews.* 9: 49-61 (1998).

Keller et al., Molecular recognition of BMP-2 and BMP receptor IA. *Nat. Struct. Mol. Biol.,* 11(5):481-488 (2004).

Khalil, TGF-beta: from latent to active. *Microbes Infect.* 1(15):1255-1263 (1999).

Khosla et al., Concise review of primary-care physicians. Treatment options for osteoporosis. *Mayo Clin. Proc.* 70: 978-82 (1995).

Kohler et al., Continuous cultures of fused cells secreting antibody of predefined specificity. *Nature.* 256: 495-7 (1975).

Koli et al., Latency, activation, and binding proteins of TGF-beta. *Microscopy Res. Tech.,* 52:354-362 (2001).

Koreth et al., Microsatellites and PCR genomic analysis. *J. Pathology.* 178: 239-348 (1996).

Kramer et al., The gapped duplex DNA approach to oligonucleotide-directed mutation construction. *Nucleic Acids Res.,* 12:9441-56 (1984).

Kunkel et al., Rapid and efficient site-specific mutagenesis without phenotypic selection. *Methods Enzymol.,* 154:367-382 (1987).

Kunkel, Rapid and efficient site-specific mutagenesis without phenotypic selection. *Proc. Natl. Acad. Sci.* (USA), 82:488-492 (1985).

Kurahasi et al., Regions of genomic instability on 22q11 and 11q23 as the etiology for the recurrent constitutional t(11;22). *Hum. Molec. Genet.* 9: 1665-70 (2000).

Kusu et al., Sclerostin in a novel secreted osteoclast-derived bone morphogenetic protein antagonist with unique ligand specificity. *J. Biol. Chem.* 278: 24113-7 (2003).

Lasic, Novel applications of liposomes. *Trends Biotechnol.,* 16(7):307-321 (1998).

Latham et al., The biochemical and cellular characterization of sclerostin, the causative gene for sclerosteosis. *Calc. Tissue Int.* 70: Abstract 1-10: 244 (2002).

Leppert et al., Benign familial neonatal epilepsy with mutations in two potassium channel genes. *Curr. Opin. Neurol.* 12: 143-7 (1999).

Li et al., Sclerostin binds to LRP5/6 and antagonizes canonical Wnt signaling. *J. Biol. Chem.* 280: 19883-7 (2005).

Lian et al., Bone formation: Osteoblast lineage cells, growth factors, matrix proteins, and the minerialization process. Primer on the Metabolic Bone Disease and Disorders of Mineral Metabolism. 4th Edition, 14-29 (1999).

Linear human genomic DNA from chromosome 17, EMBL Accession No. AC003098.

Linear mRNA, human EST, EMBL Accession No. AA393939.

Linear mRNA, rat Est, EMBL Accession numner AI113131.

Lonberg et al., Antigen-specific human antibodies from mice comprising four distinct genetic modifications. *Nature.* 368:856-9 (1994).

Low et al., Mimicking somatic hypermutation: affinity maturation of antibodies displayed on bacteriophage using a bacterial mutator strain. *J. Mol. Biol.,* 260:359-368 (1996).

Margalit, Liposome-mediated drug targeting in topical and regional therapies. *Crit. Rev. Ther. Drug Carrier Syst.,* 12(2-3):233-261 (1995).

Marks et al., By-passing immunization: building high affinity human antibodies by chain shuffling. *Bio/Technology,* 10:779-783 (1992).

Miyazono et al., TGF-β signal by smad proteins. *Adv. Immunol.* 75: 115-57 (2000).

Miyazono et al., Divergence and convergence of TGF-β/BMP signaling. *J. Cell. Physiol.* 187: 265-76 (2001).

Mori et al., A novel amino acid substitution at the receptor-binding site on the hemagglutinin of H3N2 influenza A viruses isolated from 6 cases with acute encephalopathy during the 1997-1998 season in Tokyo. *Arch. Virol*. 144: 147-155 (1999).
Moult, The current state of the art in protein structure prediction. *Curr. Opin. Biotech*., 7(4):422-427 (1996).
Mullins et al., Transgenesis in the rat and larger mammals. *J. Clin. Invest*., 97(7):1557-1560 (1996).
Nagaraja et al., X chromosome map at 75-kb STS resolution, revealing extremes of recombination and GC content. *Genome Res*. 7: 210-22 (1997).
Nakase et al., Transient and localized expression of bone morphogenetic protein 4 messenger RNA during fracture healing. *J. Bone Miner. Res*., 9(5):651-659 (1994).
Nelson et al., Positional cloning reaches maturity. *Curr. Opin. Genet. Dev*. 5: 298-303 (1995).
Nickel et al., The crystal structure of the BMP-2: BMPR-IA comples and the generation of BMP-2 antagonists. *J. Bone Joint Surg*. 83-A: Suppl. 1: S7-14 (2001).
Nicolas et al., An age-related decrease in the concentration of insulin-like growth factor binding protein-5 in human cortical bone, *Calcif. Tissue Int*. 57: 206-12 (1995).
Nifuji et al., Coordinated expression of noggin and bone morphogenetic proteins (BMPs) during early skeletogenesis and induction of noggin expression by BMP-7. *J. Bone Miner. Res*. 14(12):2057-2066 (1999).
Nisonoff et al., Separation of univalent fragments from the bivalent rabbit antibody molecule by reduction of disulfide bonds. Arch. Biochem. Biophys., 89:230-244 (1960).
Nygren et al., Scaffolds for engineering novel binding sites in proteins. *Curr. Opin. Struct. Biol*., 7:463-469 (1997).
Oelgeschlager et al., The evolutionarily conserved Bmp-binding protein Twisted gastrulation promotes BMP signalling. *Nature*, 405:757-763 (2000).
OMM #607625, Niemann-pick disease, type C2 (2007).

Ominsky et al., Sclerostin monoclonal antibody treatment increases bone strength in aged osteopenic ovariectomized rats. *J. Bone. Min. Res.* 21(1): S44PRES1161 (2006). Abstract Only.

Oreffo et al., Human bone marrow osteoprogenitors express estrogen receptor-alpha and bone morphogenetic proteins 2 and 4 mRNA during osteoblastic differentiation. *J. Cell. Biochem.*, 75:382-392 (1999).

Oshima et al., TGF-beta receptor type II deficiency results in defects of yolk sac hematopoiesis and vasculogenesis. *Dev. Biol.*, 179:297-302 (1996).

Padhi et al., Anti-sclerostin antibody increases markers of bone formation in healthy postmenopausal women. *J. Bone Min. Res.* 22: S37 (2007).

Padlan et al., Structure of an antibody-antigen complex: crystal structure of the HyHEL-10 Fab-lysozyme complex. *Proc. Natl. Acad. Sci. USA.* 86: 5938-42 (1989).

Pandey et al., Nucleotide sequence database: A gold mine for biologists. *TIBS.* 24: 276-80 (1999).

Patel et al., Current and potential future drug treatments for osteoporosis. *Ann. Rheumatic Dis.* 55: 700-14 (1996).

Patten et al., Applications of DNA shuffling to pharmaceuticals and vaccines. *Curr. Opin. Biotechnol.*, 8:724-733 (1997).

Piccolo et al., The head inducer Cerberus is a multifunctional antagonist of nodal, BMP and Wnt signals. *Nature.* 397: 707-10 (1999).

Piek et al., Specificity, diversity, and regulation in TGF-beta superfamily signaling. *FASEB J.* 13:2105-2124 (1999).

Pietromonaco et al., Protein kinase C-θ phosphorylation of moesin in the actin-binding sequence. *J. Biol. Chem.* 273: 7594-603 (1998).

Pittenger et al., Multilineage potential of adult human mesenchymal stem cells. *Science.* 284: 143-7 (1999).

Pluckthun et al., Expression of functional antibody Fv and Fab fragments in *Escherichia coli. Methods Enzymol.*, 178:497-515 (1989).

Pockwinse et al., Expression of cell growth and bone specific genes at single cell resolution during development of bone tissue-like organization in primary osteoblast cultures. *J. Cell. Biochem.* 49: 310-23 (1992).

Poole et al., Sclerostin is a delayed secreted product of osteocytes that inhibit bone formation. *FASEB J.* 19: 1842-4 (2005).

Porter, The hydrolysis of rabbit y-globulin and antibodies with crystalline papain. *Biochem. J.*, 73:119-126 (1959).

Quintanar-Guerrero et al., Preparation techniques and mechanisms of formation of biodegradable nanoparticles from preformed polymers. *Drug Dev. Ind. Pharm.*, 24(12):1113-1128 (1998).

Rawaldi et al., BMP-2 controls alkaline phosphatase expression and osteoblast mineralization by a Wnt autocrine loop. *J. Bone Min. Res.* 18: 1845-53 (2003).

Reddi et al., Interplay between bone morphogenetic proteins and cognate binding proteins in bone and cartilage development: noggin, chordin and DAN. *Arthritis Res.* 3(1):1-5 (2000).

Riggs et al., Overview of osteoporosis. *West J. Med.* 154: 63-77 (1991).

Robinson et al., The sclerostin antibody project. *Hum. Antibodies.* 16: 36 (2007).

Rudikoff et al., Single amino acid substitution altering antigen-binding specificity. *Proc. Natl. Acad. Sci. USA.* 79(6): 1979-83 (1982).

Sali et al., Comparative protein modeling by satisfaction of spatial restraints. *J. Mol. Biol.* 234: 779-815 (1993).

Sambrook et al., "Synthetic Oligonucleotide Probes," *Molecular Cloning—A Laboratory Manual*, Ch.11:11.1-11.19 and 11.58-11.61 (1989).

Sanger et al., DNA sequencing with chain-terminating inhibitors. *Proc. Natl. Acad. Sci.* USA, 74:5463-7 (1997).

Sastry et al., Cloning of the immunological repertoire in *Escherichia coli* for generation of monoclonal catalytic antibodies: construction of a heavy chain variable region-specific cDNA library. *Proc. Natl. Acad. Sci.* (USA), 86:5728-5732 (1989).

Scatchard et al., The attractions of proteins for small molecules and ions. *Ann. N.Y. Acad. Sci.*, 51:660-672 (1949).

Scheufler et al., Crystal structure of human bone morphogenetic protein-2 at 2.7 A resolution. *J. Mol. Biol.* 287: 103-15 (1999).

Schlebusch et al., Production of a single-chain fragment of the murine anti-idiotypic antibody ACA125 as phage-displayed and soluble antibody by recombinant phage antibody technique. *Hybridoma*, 16:47-52 (1997).

Schlunegger et al., Refined crystal structure of human transforming growth factor β2 at 1.95 A resolution. *J. Mol. Biol.* 231: 445-58 (1993).

Schmitt et al., Bone morphogenetic proteins: An update on basic biology and clinical relevance. *J. Orthop. Res.* 17: 269-78 (1999).

Serra et al., Expression of a truncated, kinase-defective TGF-β type II receptor in mouse skeleton tissue promotes terminal chondrocyte differentiation and osteoarthritis. *J. Cell. Biol.* 139: 541-52 (1997).

Sigmund, Viewpoint: are studies in genetically altered mice out of control? *Arterioscler. Thromb. Vasc. Biol.* 20: 1425-9 (2000).

Sippl et al., Threading thrills and threats. *Structure.* 4(1): 15-9 (1996).

Sivakumar et al., New insights into extracellular matrix assembly and reorganization from dynamic imaging of extracellular matrix proteins in living osteoblasts. *J. Cell. Sci.*, 119(7):1350-1360 (2006).

Smith et al., Glucocorticoids inhibit developmental stage-specific osteoblast cell cycle. Dissociation of cyclin A-cyclin-dependent kinase 2 from E2F4-p130 complexes. *J. Biol. Chem.* 275: 19992-20001 (2000).

Smith et al., TGF β inhibitors: New and unexpected requirements in vertebrate development. *TIG.* 15: 3-5 (1999).

Staehling-Hampton et al., A. 52-kb deletion in the SOST-MEOX1 intergenic region on 17g12-q21 is associated with van Buchem disease in the Dutch population. *Am. J. Med. Gen.* 110: 144-52 (2002).

Sudo et al., In vitro differentiation and calcification in a new clonal osteogenic cell line derived from newborn mouse calvaria.. *Cell Biol.* 96:191-198 (1983).

Sutherland et al., Sclerostin promotes the apoptosis of human osteoblastic cells: a novel regulation of bone formation. *Bone*, 35:828-835 (2004).

Suzawa et al., Extracellular matrix-associated bone morphogenetic proteins are essential for differentiation of murine osteoblastic cells in vitro. *Endocrinology*, 140:2125-2133 (1999).

Takakura, Drug delivery systems in gene therapy. *Nippon Rinsho*, 56(3):691-695 (1998) (Abstract Only).

Tam et al., TGF-β receptor expression on human keratinocytes: A 150 kDa GPI-anchored TGF- β binding protein forms a heteromeric complex with type I and type II receptors. *J. Cell. Biochem.* 70: 573-86 (1998).

Taylor et al., Human immunoglobulin transgenes undergo rearrangement, somatic mutation and class switching in mice that lack endogenous IgM. *Int. Immun.*, 6:579-91 (1994).

The Merck Manual-Second Home Edition, Ch. 61:1-3 (2005).

Thompson et al., Affinity maturation of a high-affinity human monoclonal antibody against the third hypervariable loop of human immunodeficiency virus: use of phage display to improve affinity and broaden strain reactivity. *J. Mol. Biol.*, 256:77-88 (1996).

Thornton et al., Protein structure. Prediction of progress at last. *Nature*, 354:105-106 (1991).

van Bezooijen et al., Sclerostin is an osteocyte-expressed negative regulator of hone formation, but not a classical BMP antagonist. *J. Exp. Med.* 199: 805-14 (2004).

van Bezooijen et al., Wnt but Not BMP Signaling Is Involved in the Inhibitory Action of Sclerostin on BMP-Stimulated Bone Formation. *J. Bone. Miner. Res.* 22:19-28 (2007).

Van Hul et al., Van Buchem disease (Hyperostosis cortica is Genera isata) maps to chromosome 17q12-q21. *Am. J. Hum. Genet.* 2: 391-9 (1998).

Vanier et al., Recent advances in elucidating Niemann-Pick C disease. *Brain Pathology.* 8: 163-74 (1998).

Von Bubnoff et al., Intracellular BMP signaling regulation in vertebrates: Pathway or network. *Dev. Biol.* 239: 1-14 (2001).

Wall, Transgenic livestock: Progress and prospects for the future. *Theriogenology.* 45(1): 57-68 (1996).

Wang, Bone morphogenetic proteins (BMPs): therapeutic potential in healing bony defects. *Trends Biotechnol.* 11:379-383 (1993).

Warmington et al., Sclerostin monoclonal antibody treatment of osteoporotic rats completely reverses one year of ovariectomy-induced systemic bone loss. *J Bone Min. Res.*20: S22 (2005).

Warmington et al., Sclerostin antagonism in adult rodent, via monoclonal antibody mediated blockade, increases bone mineral density and implicated sclerostin as a key regulator of bone mass during adulthood. *J. Bone Min. Res*. 19: S56-7 (2004).
Winkler et al., Osteocyte control of bone formation via sclerostin, a novel BMP antagonist. *EMBO* J. 22: 6267-76 (2003).
Winkler et al., Sclerostin inhibition of Wnt-3a-induced C3H10T1/2 cell differentiation is indirect and mediated by bone morphogenetic proteins. *J. Biol. Chem*. 280: 2498-502 (2005).
Winter et al., Making antibodies by phage display technology. *Annu. Rev. Immunol*., 12:433-455 (1994).
Wolff et al., Monoclonal antibody homodimers: enhanced antitumor activity in nude mice. *Cancer Res.*, 53:2560-2565 (1993).
Yanagita et al., USAG-1: a bone morphogenetic protein antagonist abundantly expressed in the kidney. *Biochem. Biophys. Res. Comm*. 316: 490-550 (2004).
Yang et al., CDR walking mutagenesis for the affinity maturation of a potent human anti-HIV-1 antibody into the picomolar range. *J. Mol. Biol.*, 254:392-403 (1995).
Zambaux et al., Influence of experimental parameters on the characteristics of poly(lactic acid) nanoparticles prepared by a double emulsion method. *J. Controlled Release*, 50(1-3):31-40 (1998).
Zhang et al., Humanization of an anti-human TNF-alpha antibody by variable region resurfacing with the aid of molecular modeling. *Mol. Immunol*. 42(12):1445-1451 (2005).
Zimmerman et al., The Spemann organizer noggin binds and inactivates bone morphogenetic protein 4. *Cell*. 86: 599-606 (1996).
zur Muhlen et al., Solid lipid nanoparticles (SLN) for controlled drug delivery—drug release and release mechanism. *Eur. J. Pharm. Biopharm.*, 45(2):149-155 (1998).
Declaration of Dr. Martyn Robinson.
Declaration of Dr. Mary E. Brunkow.
Expert Opinion from Dr. Catalina Lopez-Correa, dated Mar. 6, 2009.
Written submission of Eli Lilly and Company Limiter to European Patent Office, dated May 29, 2007, Opposition to European Patent No. 1133558.
Written submission of UCB S.A., Proprietor's Response to Opposition, dated Mar. 14, 2008, Opposition to European Patent No. 1133558.
European Patent Office Communication, dated Nov. 4, 2008, Opposition to European Patent No. 1133558.
Written submission— Observation by a Third Party According to EPC.
Written Submission of Eli Lilly & Company, dated Mar. 9, 2009, Opposition to European Patent No. 1133558.
Written submission of UCB S.A., Proprietor's Preliminary Response to the Opponent's submission of Mar. 9, 2009, dated Mar. 20, 2009, Opposition to European Patent No. 1133558.
European Search Report, European Patent Office, EP 04 77 6553, dated Jan. 29, 2009.
International Search Report, European Patent Office, PCT/US2008/086864, dated Mar. 20, 2009.
Written Opinion of International Searching Authority, European Patent Office, PCT/US2008/086864, dated Mar. 20, 2009.
International Preliminary Report on Patentability, European Patent Office, PCT/US2008/086864, dated Nov. 6, 2007.
International Search Report, European Patent Office, PCT/US2004/018910, dated Mar. 30, 2005.
Written Opinion of International Searching Authority, European Patent Office, PCT/US2004/018910, dated Mar. 30, 2005.
International Preliminary Report on Patentability, PCT/US2004/018910, dated Dec. 19, 2005.
International Search Report, European Patent Office, PCT/US2006/016345, dated Feb. 8, 2007.
Written Opinion of the International Searching Authority, European Patent Office, PCT/US2006/016345, dated Feb. 8, 2007.
International Preliminary Report on Patentability, PCT/US2006/016345, dated Nov. 6, 2007.
International Search Report, European Patent Office, PCT/US2006/016441, dated Nov. 8, 2006.
Written Opinion of the International Searching Authority, European Patent Office, PCT/US2006/016441, dated Nov. 8, 2007.
International Preliminary Report on Patentability, PCT/US2006/016441, dated Nov. 8, 2007.
International Search Report, European Patent Office, PCT/US2004/018912, dated Mar. 29, 2005.
Written Opinion of the International Searching Authority, European Patent Office, PCT/US2004/018912, dated Mar. 29, 2005.
International Preliminary Report of Patentability, PCT/US2004/018912, dated Dec. 19, 2005.
International Search Report, European Patent Office, PCT/US1999/027990, dated Apr. 7, 2000.
Written Opinion of the International Searching Authority, European Patent Office, PCT/US1999/027990, dated Apr. 7, 2000.
International Preliminary Report on Patentability, PCT/US1999/027990, dated Mar. 16, 2001.
International Search Report, European Patent Office, PCT/US2004/07565, dated Nov. 5, 2004.
Written Opinion of the International Searching Authority, PCT/US2004/07565, dated Nov. 5, 2004.
International Preliminary Report on Patentability, PCT/US2004/07565, dated Sep. 16, 2005.
International Search Report, European Patent Office, PCT/US2007/084276, dated Sep. 26, 2008.
Written Opinion of the International Searching Authority, European Patent Office, PCT/US2007/084276, dated Sep. 26, 2008.
International Search Report, European Patent Office, PCT/US2007/084280, dated Jan. 27, 2009.
Written Opinion of the International Searching Authority, PCT/US2007/084280, dated Jan. 27, 2009.
Anonymous, Amgen presents denosumab and sclerostin antibody data at American Society for Bone and Mineral Research Annual Meeting. Amgen Media Press Release (2006).
Anonymous, UCB on track. UCB News (2007).
Lowik et al., Wnt signaling is involved in the inhibitory action of sclerostin on BMP-stimulated bone formation. *J. Musculoskeleton Neuronal Interact*. 6: 357 (2006).
Lui, et al., Human type II receptor for bone morphogenic proteins (BMPs): extension of the two-kinase receptor model to the BMPs. *Mol. Cell. Biol*. 15(7):3479-3486 (1995).
Malone et al., Bone anabolism achieved by reducing sclerostin bioavailability with an anti-sclerostin antibody. 37th International Sun Valley Workshop on Skeletal Tissue Biology. Aug. 5-8, 2007.
Padhi et al., OC35—Effects of anti-sclerostin monoclonal antibody in healthy postmenopausal women. *Osteoporosis Int*. 19: Suppl. 1: S19 (2008).
Pignatti et al., Tracking disease genes by reverse genetics. *J. Psychiat. Res*. 26: 287-98 (1992).
Reddi et al., Interplay between bone morphogenetic protein and cognate binding proteins in bone and cartilage development: Noggin, chordin and DAN, Center for Tissue Regeneration and Repair, Dept. of Ortho. Surgery, U.S. Davis School of Medicine, Sacramento, CA (2000).
Rosenzweig et al., Cloning and characterization of a human type II receptor for bone morphogenetic proteins. *Proc. Natl. Acad. Sci, USA*, 92:7632-7636 (1995).
Takeda, Expression of serine/threonine kinase receptors during ectopic bone formation induced by bone morphogenetic protein (BMP). *Kokubyo Gakkai Zasshi*, 61(4):512-26 (1994) (Abstract Only).
U.S. Appl. No. 11/411,003, Office Action dated Nov. 30, 2007.
U.S. Appl. No. 11/411,003, Office Action dated May 9, 2008.
U.S. Appl. No. 11/411,003, Office Action dated Jan. 27, 2009.
U.S. Appl. No. 11/399,210, Office Action dated Jan. 16, 2008.
U.S. Appl. No. 11/399,210, Office Action dated Jun. 20, 2008.
U.S. Appl. No. 11/399,210, Office Action dated Nov. 17, 2008.
U.S. Appl. No. 10/868,497, Office Action dated May 15, 2007.
U.S. Appl. No. 12/109,029, Office Action dated Oct. 19, 2009.
U.S. Appl. No. 12/109,029, Office Action dated Apr. 8, 2010.
U.S. Appl. No. 11/410,540, Office Action dated Mar. 31, 2008.
U.S. Appl. No. 11/410,540, Office Action dated Sep. 25, 2008.
U.S. Appl. No. 11/410,540, Office Action dated Mar. 19, 2009.

U.S. Appl. No. 11/410,540, Office Action dated Oct. 28, 2009.
U.S. Appl. No. 11/410,540, Office Action dated Apr. 27, 2010.
International Preliminary Report on Patentability, PCT/US2007/084280, dated May 12, 2009.

International Preliminary Report on Patentability, PCT/US2007/084276, dated May 12, 2009.

\* cited by examiner

A.

```
  1 AQVLTQTPAS VSAAVGGTVT INCQSSQSVY DNNWLAWFQQ KPGQPPKLLI
 51 YDASDLASGV PSRFSGSGSG TQFTLTISGV QCADAATYYC QGAYNDVIYA
101 FGGGTEVVVK RTDAAPTVSI FPPSSEQLTS GGASVVCFLN NFYPKDINVK
151 WKIDGSERQN GVLNSWTDQD SKDSTYSMSS TLTLTKDEYE RHNSYTCEAT
201 HKTSTSPIVK SFNRNEC
```

B.

```
  1 QSLEESGGRL VTPGTPLTLT CTASGFSLSS YWMNWVRQAP GEGLEWIGTI
 51 DSGGRTDYAS WAKGRFTISR TSTTMDLKMT SLTTGDTARY FCARNWNLWG
101 QGTLVTVSSA STKGPSVYPL APGSAAQTNS MVTLGCLVKG YFPEPVTVTW
151 NSGSLSSGVH TFPAVLQSDL YTLSSSVTVP SSTWPSETVT CNVAHPASST
201 KVDKKIVPRD CGCKPCICTV PEVSSVFIFP PKPKDVLTIT LTPKVTCVVV
251 DISKDDPEVQ FSWFVDDVEV HTAQTQPREE QFNSTFRSVS ELPIMHQDWL
301 NGKEFKCRVN SAAFPAPIEK TISKTKGRPK APQVYTIPPP KEQMAKDKVS
351 LTCMITDFFP EDITVEWQWN GQPAENYKNT QPIMNTNGSY FVYSKLNVQK
401 SNWEAGNTFT CSVLHEGLHN HHTEKSLSHS PGK
```

```
  1 QIVLTQSPTI VSASPGEKVT LICSASSSVS FVDWFQQKPG TSPKRWIYRT
 51 SNLGFGVPAR FSGGGSGTSH SLTISRMEAE DAATYYCQQR STYPPTFGAG
101 TKLELKRADA APTVSIFPPS SEQLTSGGAS VVCFLNNFYP KDINVKWKID
151 GSERQNGVLN SWTDQDSKDS TYSMSSTLTL TKDEYERHNS YTCEATHKTS
201 TSPIVKSFNR NEC
```

B.

```
  1 QVTLKESGPG ILQPSQTLSL TCSFSGFSLS TSGMGVGWIR HPSGKNLEWL
 51 AHIWWDDVKR YNPVLKSRLT ISKDTSNSQV FLKIANVDTA DTATYYCARI
101 EDFDYDEEYY AMDYWGQGTS VIVSSAKTTP PSVYPLAPGS AAQTNSMVTL
151 GCLVKGYFPE PVTVTWNSGS LSSGVHTFPA VLQSDLYTLS SSVTVPSSTW
201 PSETVTCNVA HPASSTKVDK KIVPRDCGCK PCICTVPEVS SVFIFPPKPK
251 DVLTITLTPK VTCVVVDISK DDPEVQFSWF VDDVEVHTAQ TQPREEQFNS
301 TFRSVSELPI MHQDWLNGKE FKCRVNSAAF PAPIEKTISK TKGRPKAPQV
351 YTIPPPKEQM AKDKVSLTCM ITDFFPEDIT VEWQWNGQPA ENYKNTQPIM
401 DTDGSYFVYS KLNVQKSNWE AGNTFTCSVL HEGLHNHHTE KSLSHSPGK
```

```
  1 DIVLTQSPAS LTVSLGLRAT ISCKASQSVD YDGDSYMNWY QQKPGQPPKL
 51 LIYAASNLES GIPARFSGNG SGTDFTLNIH PVEEEDAVTY YCQQSNEDPW
101 TFGGGTKLEI KRADAAPTVS IFPPSSEQLT SGGASVVCFL NNFYPKDINV
151 KWKIDGSERQ NGVLNSWTDQ DSKDSTYSMS STLTLTKDEY ERHNSYTCEA
201 THKTSTSPIV KSFNRNEC
```

B.

```
  1 EVQLQQSGPE LVKPGTSVKM SCKASGYTFT DCYMNWVKQS HGKSLEWIGD
 51 INPFNGGTTY NQKFKGKATL TVDKSSSTAY MQLNSLTSDD SAVYYCARSH
101 YYFDGRVPWD AMDYWGQGTS VTVSSAKTTP PSVYPLAPGS AAQTNSMVTL
151 GCLVKGYFPE PVTVTWNSGS LSSGVHTFPA VLQSDLYTLS SSVTVPSSTW
201 PSETVTCNVA HPASSTKVDK KIVPRDCGCK PCICTVPEVS SVFIFPPKPK
251 DVLTITLTPK VTCVVVDISK DDPEVQFSWF VDDVEVHTAQ TQPREEQFNS
301 TFRSVSELPI MHQDWLNGKE FKCRVNSAAF PAPIEKTISK TKGRPKAPQV
351 YTIPPPKEQM AKDKVSLTCM ITDFFPEDIT VEWQWNGQPA ENYKNTQPIM
401 DTDGSYFIYS KLNVQKSNWE AGNTFTCSVL HEGLHNHHTE KSLSHSPGK
```

```
  1 DVQMIQSPSS LSASLGDIVT MTCQASQGTS INLNWFQQKP GKAPKLLIYG
 51 SSNLEDGVPS RFSGSRYGTD FTLTISSLED EDLATYFCLQ HSYLPYTFGG
101 GTKLEIKRAD AAPTVSIFPP SSEQLTSGGA SVVCFLNNFY PKDINVKWKI
151 DGSERQNGVL NSWTDQDSKD STYSMSSTLT LTKDEYERHN SYTCEATHKT
201 STSPIVKSFN RNEC
```

B.

```
  1 EVQLQQSGPE LVTPGASVKI SCKASGYTFT DHYMSWVKQS HGKSLEWIGD
 51 INPYSGETTY NQKFKGTATL TVDKSSSIAY MEIRGLTSED SAVYYCARDD
101 YDASPFAYWG QGTLVTVSAA KTTPPSVYPL APGSAAQTNS MVTLGCLVKG
151 YFPEPVTVTW NSGSLSSGVH TFPAVLQSDL YTLSSSVTVP SSTWPSETVT
201 CNVAHPASST KVDKKIVPRD CGCKPCICTV PEVSSVFIFP PKPKDVLTIT
251 LTPKVTCVVV DISKDDPEVQ FSWFVDDVEV HTAQTQPREE QFNSTFRSVS
301 ELPIMHQDWL NGKEFKCRVN SPAFFAPIEK TISKTKGRPK APQVYTIPPP
351 KEQMAKDKVS LTCMITDFFP EDITVEWQWN GQPAENYKNT QPIMDTDGSY
401 FIYSKLNVQK SNWEAGNTFT CSVLHEGLHN HHTEKSLSHS PGK
```

Figure 4

1  QGWQAFKNDA TEIIPELGEY PEPPPELENN KTMNRAENGG RPPHHPFETK

51  DVSEYS<u>C</u>REL HFTRYVTDGP <u>C</u>RSAKPVTEL V<u>C</u>SGQ<u>C</u>GPAR LLPNAIGRGK
             C1             C2            C3   C4

101  WWRPSGPDFR <u>C</u>IPDRYRAQR VQLL<u>C</u>PGGEA PRARKVRLVA S<u>CKC</u>KRLTRF
                C5              C6                    C7 C8

151  HNQSELKDFG TEAARPQKGR KPRPRARSAK ANQAELENAY

1  CAGGGGTGGC AGGCGTTCAA GAATGATGCC ACGGAAATCA TCCCCGAGCT
 51  CGGAGAGTAC CCCGAGCCTC CCCCAGAGCT CGAGAACAAC AAGACCATGA
101  ACCGGGCGGA GAACGGAGGG CGGCCTCCCC ACCACCCTT TGAGACCAAA
151  GACGTGTCCG AGTACAGCTG CCGCGAGCTG CACTTCACCC GCTACGTGAC
201  CGATGGGCCG TGCCGCAGCG CCAAGCCGGT CACCGAGCTG GTGTGCTCCG
251  GCCAGTGCGG CCCGGCGCGC CTGCTGCCCA ACGCCATCGG CCGGGGCAAG
301  TGGTGGCGAC CTAGTGGGCC CGACTTCCGC TGCATCCCCG ACCGCTACCG
351  CGCGCAGCGC GTGCAGCTGC TGTGTCCCGG TGGTGAGGCG CCGCGCCGC
401  GCAAGGTGCG CCTGGTGGCC TCGTGCAAGT TGCAAGGCCT CACCCGCTTC
451  CACAACCAGT CGGAGCTCAA GGACTTCGGG ACCGAGGCCG CTCGGCCGCA
501  GAAGGGCCGG AAGCCGCGG CCCGCGCCCG GAGCGCCAAA GCCAACCAGG
551  CCGAGCTGGA GAACGCCTAC

Figure 8

| Peptides | Seq.pos. | Obs. Mass | Sequence | |
|---|---|---|---|---|
| T19.2 | 65-72 | 2146.34 | 1. YVTDGP CR (910) | C2 |
| | 121-132 | (2145.8) | 2. VQLLCPGGEA PR (1239) | C6 |
| T20 | | 9620.8 (MALDI); 9638.41 (ESI-MS) | | |
| | 51-90 | (4419.1) | 1. DVSEYSCREL HFTRYVTDGP CRSAKPVTEL VCSGQCGPAR | |
| | 104-149 | (5226.2) | 2. PSGPDFR CIPDRYRAQR VQLLCPGGEA PRARKVRLVA SCKCKRLT R | |
| T20.6 | | 7105.7 (MALDI); 7122.0 (ESI-MS) | | |
| | 51-64 | 3944.5 | 1. DVSEYSCREL HFTR (1740.9) | C1 |
| | 101-117 | | 2. WWRPSGPPFR CIPDRYR (2206.6) | C5 |
| | 73-90 | 3177.0 | 3. SAKPVTELVC SGQCGPAR (1802.2) | C3, C4 |
| | 138-149 | | 4. LVASCKCKRL TR (1378.5) | C7, C8 |
| T21-22 | | 10,147 (MALDI); 10170.3 (ESI-MS) | | |
| | 51-90 | (4419.1) | 1. DVSEYSCREL HFTRYVTDGP CRSAKPVTEL VCSGQCGPAR | |
| | 101-149 | (5754.8) | 2. WWRPSGPDFR CIPDRYRAQR VQLLCPGGEA PRARKVRLVA SCKCKRLTR | |

Figure 11

| Peptides | Seq.pos. | Obs.Mass | Sequence |
|---|---|---|---|
| AspN14.6 | 34-47 | 1245.5 | ENGGRPPHHPF |
| | 12-25 | 1585.4 | EIIPELGFYP EPPP |
| | 158-184 | 2964.5 | DFGTEAARPQ KGRKPRPRAR SAKANQA |
| AspN18.6 | 9-50 | | DATEIIPELG EYPEPPPELE NNKTMNRAEN GGRPPHHPFE TK (Glycopeptide) |
| AspN22.7-23.5 | 51-154 | 11,740 | DVSEYSCREL HFTRYVTDGP CRSAKPVTEL VCSGQCGPAR LLPNAIGRGK WWRPSGPDFR CIPDRYRAQR VQLLCPGGEA PRARKVRLVA SCKCKRLTRF HNQS |

Figure 12

*A. Loop 2 epitope for Mab-A and Mab-B*
C4GPARLLPNAIGRGKWWRPSGPDFRC5
*B. T20.6 epitope for Mab-C and Mab-D*
DVSEYSC1RELHFTR SAKPVTELVC3SGQC4GPAR
WWRPSGPDFRC5IPDRYR LVASC7KC8KRLTR
T20.6

"T20.6 derivative 1 (cystine-knot + 4 arms)" epitope for Mab-D

C1RELHFTR    SAKPVTELVC3SGQC4

C5IPDRYR    LVASC7KC8

"T20.6 derivative 1 (cystine-knot + 4 arms)"

Figure 21

SEQUENCE LISTING

```
<160> NUMBER OF SEQ ID NOS: 396

<210> SEQ ID NO 1
<211> LENGTH: 190
<212> TYPE: PRT
<213> ORGANISM: Homo sapiens

<400> SEQUENCE: 1

Gln Gly Trp Gln Ala Phe Lys Asn Asp Ala Thr Glu Ile Ile Pro Glu
 1               5                  10                  15

Leu Gly Glu Tyr Pro Glu Pro Pro Glu Leu Glu Asn Asn Lys Thr
                20                  25                  30

Met Asn Arg Ala Glu Asn Gly Gly Arg Pro Pro His His Pro Phe Glu
            35                  40                  45

Thr Lys Asp Val Ser Glu Tyr Ser Cys Arg Glu Leu His Phe Thr Arg
        50                  55                  60

Tyr Val Thr Asp Gly Pro Cys Arg Ser Ala Lys Pro Val Thr Glu Leu
65                  70                  75                  80

Val Cys Ser Gly Gln Cys Gly Pro Ala Arg Leu Leu Pro Asn Ala Ile
                85                  90                  95

Gly Arg Gly Lys Trp Trp Arg Pro Ser Gly Pro Asp Phe Arg Cys Ile
            100                 105                 110

Pro Asp Arg Tyr Arg Ala Gln Arg Val Gln Leu Leu Cys Pro Gly Gly
        115                 120                 125

Glu Ala Pro Arg Ala Arg Lys Val Arg Leu Val Ala Ser Cys Lys Cys
    130                 135                 140

Lys Arg Leu Thr Arg Phe His Asn Gln Ser Glu Leu Lys Asp Phe Gly
145                 150                 155                 160

Thr Glu Ala Ala Arg Pro Gln Lys Gly Arg Lys Pro Arg Pro Arg Ala
                165                 170                 175

Arg Ser Ala Lys Ala Asn Gln Ala Glu Leu Glu Asn Ala Tyr
            180                 185                 190

<210> SEQ ID NO 2
<211> LENGTH: 14
<212> TYPE: PRT
<213> ORGANISM: Homo sapiens
```

```
<400> SEQUENCE: 2

Asp Val Ser Glu Tyr Ser Cys Arg Glu Leu His Phe Thr Arg
1               5                   10

<210> SEQ ID NO 3
<211> LENGTH: 18
<212> TYPE: PRT
<213> ORGANISM: Homo sapiens

<400> SEQUENCE: 3

Ser Ala Lys Pro Val Thr Glu Leu Val Cys Ser Gly Gln Cys Gly Pro
1               5                   10                  15

Ala Arg

<210> SEQ ID NO 4
<211> LENGTH: 16
<212> TYPE: PRT
<213> ORGANISM: Homo sapiens

<400> SEQUENCE: 4

Trp Trp Arg Pro Ser Gly Pro Asp Phe Arg Cys Ile Pro Asp Arg Tyr
1               5                   10                  15

<210> SEQ ID NO 5
<211> LENGTH: 12
<212> TYPE: PRT
<213> ORGANISM: Homo sapiens

<400> SEQUENCE: 5

Leu Val Ala Ser Cys Lys Cys Lys Arg Leu Thr Arg
1               5                   10

<210> SEQ ID NO 6
<211> LENGTH: 26
<212> TYPE: PRT
<213> ORGANISM: Homo sapiens

<400> SEQUENCE: 6

Cys Gly Pro Ala Arg Leu Leu Pro Asn Ala Ile Gly Arg Gly Lys Trp
1               5                   10                  15

Trp Arg Pro Ser Gly Pro Asp Phe Arg Cys
            20                  25

<210> SEQ ID NO 7
<211> LENGTH: 214
<212> TYPE: PRT
<213> ORGANISM: Mus musculus

<400> SEQUENCE: 7

Asp Val Gln Met Ile Gln Ser Pro Ser Ser Leu Ser Ala Ser Leu Gly
1               5                   10                  15

Asp Ile Val Thr Met Thr Cys Gln Ala Ser Gln Gly Thr Ser Ile Asn
            20                  25                  30

Leu Asn Trp Phe Gln Lys Pro Gly Lys Ala Pro Lys Leu Leu Ile
        35                  40                  45

Tyr Gly Ser Ser Asn Leu Glu Asp Gly Val Pro Ser Arg Phe Ser Gly
    50                  55                  60

Ser Arg Tyr Gly Thr Asp Phe Thr Leu Thr Ile Ser Ser Leu Glu Asp
65                  70                  75                  80

Glu Asp Leu Ala Thr Tyr Phe Cys Leu Gln His Ser Tyr Leu Pro Tyr
                85                  90                  95
```

```
Thr Phe Gly Gly Gly Thr Lys Leu Glu Ile Lys Arg Ala Asp Ala Ala
                100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
        210

<210> SEQ ID NO 8
<211> LENGTH: 645
<212> TYPE: DNA
<213> ORGANISM: Mus musculus

<400> SEQUENCE: 8
gatgtccaga tgattcagtc tccatcctcc ctgtctgcat ctttgggaga catagtcacc     60
atgacttgcc aggcaagtca gggcactagc attaattaa actggtttca gcaaaaacca    120
gggaaggctc ctaagctcct gatctatggt tcaagcaact tggaagatgg ggtcccatca    180
aggttcagtg gcagtagata tgggacagat ttcactctca ccatcagcag cctggaggat    240
gaagatctgg caacttattt ctgtctacaa catagttatc cccgtacac gttcggaggg    300
gggaccaagc tggaaataaa acgggctgat gctgcaccaa ctgtatccat cttcccacca    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gttag                    645

<210> SEQ ID NO 9
<211> LENGTH: 236
<212> TYPE: PRT
<213> ORGANISM: Mus musculus

<400> SEQUENCE: 9

Met Asn Thr Arg Ala Pro Ala Glu Phe Leu Gly Phe Leu Leu Leu Trp
1               5                   10                  15

Phe Leu Gly Ala Arg Cys Asp Val Gln Met Ile Gln Ser Pro Ser Ser
            20                  25                  30

Leu Ser Ala Ser Leu Gly Asp Ile Val Thr Met Thr Cys Gln Ala Ser
        35                  40                  45

Gln Gly Thr Ser Ile Asn Leu Asn Trp Phe Gln Gln Lys Pro Gly Lys
    50                  55                  60

Ala Pro Lys Leu Leu Ile Tyr Gly Ser Ser Asn Leu Glu Asp Gly Val
65                  70                  75                  80

Pro Ser Arg Phe Ser Gly Ser Arg Tyr Gly Thr Asp Phe Thr Leu Thr
```

```
                     85                  90                  95
Ile Ser Ser Leu Glu Asp Glu Asp Leu Ala Thr Tyr Phe Cys Leu Gln
                100                 105                 110

His Ser Tyr Leu Pro Tyr Thr Phe Gly Gly Gly Thr Lys Leu Glu Ile
                115                 120                 125

Lys Arg Ala Asp Ala Ala Pro Thr Val Ser Ile Phe Pro Pro Ser Ser
                130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
                180                 185                 190

Ser Thr Tyr Ser Met Ser Ser Thr Leu Thr Leu Thr Lys Asp Glu Tyr
                195                 200                 205

Glu Arg His Asn Ser Tyr Thr Cys Glu Ala Thr His Lys Thr Ser Thr
                210                 215                 220

Ser Pro Ile Val Lys Ser Phe Asn Arg Asn Glu Cys
225                 230                 235
```

<210> SEQ ID NO 10
<211> LENGTH: 711
<212> TYPE: DNA
<213> ORGANISM: Mus musculus

<400> SEQUENCE: 10

```
atgaacacga gggcccctgc tgagttcctt gggttcctgt tgctctggtt tttaggtgcc     60
agatgtgatg tccagatgat tcagtctcca tcctccctgt ctgcatcttt gggagacata    120
gtcaccatga cttgccaggc aagtcagggc actagcatta atttaaactg gtttcagcaa    180
aaaccaggga aggctcctaa gctcctgatc tatggttcaa gcaacttgga agatggggtc    240
ccatcaaggt tcagtggcag tagatatggg acagatttca ctctcaccat cagcagcctg    300
gaggatgaag atctggcaac ttatttctgt ctacaacata gttatctccc gtacacgttc    360
ggagggggga ccaagctgga aataaaacgg gctgatgctg caccaactgt atccatcttc    420
ccaccatcca gtgagcagtt aacatctgga ggtgcctcag tcgtgtgctt cttgaacaac    480
ttctacccca agacatcaa tgtcaagtgg aagattgatg gcagtgaacg acaaaatggc     540
gtcctgaaca gttggactga tcaggacagc aaagacagca cctacagcat gagcagcacc    600
ctcacgttga ccaaggacga gtatgaacga cataacagct atacctgtga ggccactcac    660
aagacatcaa cttcacccat tgtcaagagc ttcaacagga atgagtgtta g              711
```

<210> SEQ ID NO 11
<211> LENGTH: 443
<212> TYPE: PRT
<213> ORGANISM: Mus musculus

<400> SEQUENCE: 11

```
Glu Val Gln Leu Gln Gln Ser Gly Pro Glu Leu Val Thr Pro Gly Ala
  1               5                  10                  15

Ser Val Lys Ile Ser Cys Lys Ala Ser Gly Tyr Thr Phe Thr Asp His
                 20                  25                  30

Tyr Met Ser Trp Val Lys Gln Ser His Gly Lys Ser Leu Glu Trp Ile
             35                  40                  45

Gly Asp Ile Asn Pro Tyr Ser Gly Glu Thr Thr Tyr Asn Gln Lys Phe
```

```
                50                  55                  60
Lys Gly Thr Ala Thr Leu Thr Val Asp Lys Ser Ser Ile Ala Tyr
 65                  70                  75                  80

Met Glu Ile Arg Gly Leu Thr Ser Glu Asp Ser Ala Val Tyr Tyr Cys
                 85                  90                  95

Ala Arg Asp Asp Tyr Asp Ala Ser Pro Phe Ala Tyr Trp Gly Gln Gly
                100                 105                 110

Thr Leu Val Thr Val Ser Ala Ala Lys Thr Thr Pro Pro Ser Val Tyr
                115                 120                 125

Pro Leu Ala Pro Gly Ser Ala Ala Gln Thr Asn Ser Met Val Thr Leu
130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
                180                 185                 190

Thr Trp Pro Ser Glu Thr Val Thr Cys Asn Val Ala His Pro Ala Ser
                195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
                260                 265                 270

Trp Phe Val Asp Asp Val Glu Val His Thr Ala Gln Thr Gln Pro Arg
    275                 280                 285

Glu Glu Gln Phe Asn Ser Thr Phe Arg Ser Val Ser Glu Leu Pro Ile
                290                 295                 300

Met His Gln Asp Trp Leu Asn Gly Lys Glu Phe Lys Cys Arg Val Asn
305                 310                 315                 320

Ser Pro Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
                340                 345                 350

Gln Met Ala Lys Asp Lys Val Ser Leu Thr Cys Met Ile Thr Asp Phe
    355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Ile Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
                420                 425                 430

Thr Glu Lys Ser Leu Ser His Ser Pro Gly Lys
                435                 440

<210> SEQ ID NO 12
<211> LENGTH: 1332
<212> TYPE: DNA
<213> ORGANISM: Mus musculus
```

<400> SEQUENCE: 12

```
gaggtccagc tgcaacagtc tggacctgaa ctggtgacgc ctggggcttc agtgaagata      60
tcttgtaagg cttctggata cacattcact gaccactaca tgagctgggt gaagcagagt     120
catggaaaaa gccttgagtg gattggagat attaatccct attctggtga aactacctac     180
aaccagaagt tcaagggcac ggccacattg actgtagaca agtcttccag tatagcctac     240
atggagatcc gcggcctgac atctgaggac tctgcagtct attactgtgc aagagatgat     300
tacgacgcct ctccgtttgc ttactggggc caagggactc tggtcactgt ctctgcagcc     360
aaaacgacac ccccatctgt ctatccactg gcccctggat ctgctgccca aactaactcc     420
atggtgaccc tgggatgcct ggtcaagggc tatttccctg agccagtgac agtgacctgg     480
aactctggat ccctgtccag cggtgtgcac accttcccag ctgtcctgca gtctgacctc     540
tacactctga gcagctcagt gactgtcccc tccagcacct ggcccagcga gaccgtcacc     600
tgcaacgttg cccacccggc cagcagcacc aaggtggaca agaaaattgt gcccagggat     660
tgtggttgta agccttgcat atgtacagtc ccagaagtat catctgtctt catcttcccc     720
ccaaagccca aggatgtgct caccattact ctgactccta aggtcacgtg tgttgtggta     780
gacatcagca aggatgatcc cgaggtccag ttcagctggt ttgtagatga tgtggaggtg     840
cacacagctc agacgcaacc ccgggaggag cagttcaaca gcactttccg ctcagtcagt     900
gaacttccca tcatgcacca ggactggctc aatggcaagg agttcaaatg cagggtcaac     960
agtccagctt tccctgcccc catcgagaaa accatctcca aaaccaaagg cagaccgaag    1020
gctccacagg tgtacaccat tccacctccc aaggagcaga tggccaagga taaagtcagt    1080
ctgacctgca tgataacaga cttcttccct gaagacatta ctgtggagtg cagtggaat     1140
gggcagccag cggagaacta caagaacact cagcccatca tggacacaga tggctcttac    1200
ttcatctaca gcaagctcaa tgtgcagaag agcaactggg aggcaggaaa tactttcacc    1260
tgctctgtgt tacatgaggg cctgcacaac caccatactg agaagagcct ctcccactct    1320
cctggtaaat ga                                                        1332
```

<210> SEQ ID NO 13
<211> LENGTH: 462
<212> TYPE: PRT
<213> ORGANISM: Mus musculus

<400> SEQUENCE: 13

```
Met Arg Cys Arg Trp Ile Phe Leu Phe Leu Leu Ser Gly Thr Ala Gly
  1               5                  10                  15

Val Leu Ser Glu Val Gln Leu Gln Gln Ser Gly Pro Glu Leu Val Thr
             20                  25                  30

Pro Gly Ala Ser Val Lys Ile Ser Cys Lys Ala Ser Gly Tyr Thr Phe
         35                  40                  45

Thr Asp His Tyr Met Ser Trp Val Lys Gln Ser His Gly Lys Ser Leu
     50                  55                  60

Glu Trp Ile Gly Asp Ile Asn Pro Tyr Ser Gly Glu Thr Thr Tyr Asn
 65                  70                  75                  80

Gln Lys Phe Lys Gly Thr Ala Thr Leu Thr Val Asp Lys Ser Ser Ser
                 85                  90                  95

Ile Ala Tyr Met Glu Ile Arg Gly Leu Thr Ser Glu Asp Ser Ala Val
            100                 105                 110

Tyr Tyr Cys Ala Arg Asp Asp Tyr Asp Ala Ser Pro Phe Ala Tyr Trp
```

```
                        115                 120                 125
Gly Gln Gly Thr Leu Val Thr Val Ser Ala Ala Lys Thr Thr Pro Pro
    130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Pro Ser Ser Thr Trp Pro Ser Glu Thr Val Thr Cys Asn Val Ala His
    210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
            260                 265                 270

Lys Val Thr Cys Val Val Val Asp Ile Ser Lys Asp Asp Pro Glu Val
        275                 280                 285

Gln Phe Ser Trp Phe Val Asp Asp Val Glu Val His Thr Ala Gln Thr
    290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Pro Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
        355                 360                 365

Pro Lys Glu Gln Met Ala Lys Asp Lys Val Ser Leu Thr Cys Met Ile
    370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
                405                 410                 415

Gly Ser Tyr Phe Ile Tyr Ser Lys Leu Asn Val Gln Lys Ser Asn Trp
            420                 425                 430

Glu Ala Gly Asn Thr Phe Thr Cys Ser Val Leu His Glu Gly Leu His
        435                 440                 445

Asn His His Thr Glu Lys Ser Leu Ser His Ser Pro Gly Lys
    450                 455                 460

<210> SEQ ID NO 14
<211> LENGTH: 1389
<212> TYPE: DNA
<213> ORGANISM: Mus musculus

<400> SEQUENCE: 14
atgagatgca ggtggatctt tctctttctc ctgtcaggaa ctgcaggtgt cctctctgag      60
gtccagctgc aacagtctgg acctgaactg gtgacgcctg ggcttcagt gaagatatct     120 tgtaaggctt ctggatacac attcactgac cactacatga gctgggtgaa gcagagtcat     180
```

```
ggaaaaagcc ttgagtggat tggagatatt aatccctatt ctggtgaaac tacctacaac      240
cagaagttca agggcacggc cacattgact gtagacaagt cttccagtat agcctacatg      300
gagatccgcg gcctgacatc tgaggactct gcagtctatt actgtgcaag agatgattac      360
gacgcctctc cgtttgctta ctggggccaa gggactctgg tcactgtctc tgcagccaaa      420
acgacacccc catctgtcta tccactggcc cctggatctg ctgcccaaac taactccatg      480
gtgaccctgg gatgcctggt caagggctat ttccctgagc cagtgacagt gacctggaac      540
tctggatccc tgtccagcgg tgtgcacacc ttcccagctg tcctgcagtc tgacctctac      600
actctgagca gctcagtgac tgtcccctcc agcacctggc ccagcgagac cgtcacctgc      660
aacgttgccc acccggccag cagcaccaag gtggacaaga aaattgtgcc cagggattgt      720
ggttgtaagc cttgcatatg tacagtccca gaagtatcat ctgtcttcat cttcccccca      780
aagcccaagg atgtgctcac cattactctg actcctaagg tcacgtgtgt tgtggtagac      840
atcagcaagg atgatcccga ggtccagttc agctggtttg tagatgatgt ggaggtgcac      900
acagctcaga cgcaaccccg ggaggagcag ttcaacagca ctttccgctc agtcagtgaa      960
cttcccatca tgcaccagga ctggctcaat ggcaaggagt tcaaatgcag ggtcaacagt     1020
ccagctttcc ctgcccccat cgagaaaacc atctccaaaa ccaaaggcag accgaaggct     1080
ccacaggtgt acaccattcc acctcccaag gagcagatgg ccaaggataa agtcagtctg     1140
acctgcatga taacagactt cttccctgaa gacattactg tggagtggca gtggaatggg     1200
cagccagcgg agaactacaa gaacactcag cccatcatgg acacagatgg ctcttacttc     1260
atctacagca agctcaatgt gcagaagagc aactgggagg caggaaatac tttcacctgc     1320
tctgtgttac atgagggcct gcacaaccac catactgaga agagcctctc ccactctcct     1380
ggtaaatga                                                             1389
```

<210> SEQ ID NO 15
<211> LENGTH: 218
<212> TYPE: PRT
<213> ORGANISM: Mus musculus

<400> SEQUENCE: 15

```
Asp Ile Val Leu Thr Gln Ser Pro Ala Ser Leu Thr Val Ser Leu Gly
1               5                  10                  15

Leu Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Asn Gly Ser Gly Thr Asp Phe Thr Leu Asn Ile His
65                  70                  75                  80

Pro Val Glu Glu Glu Asp Ala Val Thr Tyr Tyr Cys Gln Gln Ser Asn
                85                  90                  95

Glu Asp Pro Trp Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160
```

Asn Gly Val Leu Asn Ser Trp Thr Asp Gln Asp Ser Lys Asp Ser Thr
            165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
            195                 200                 205

Ile Val Lys Ser Phe Asn Arg Asn Glu Cys
            210                 215

<210> SEQ ID NO 16
<211> LENGTH: 657
<212> TYPE: DNA
<213> ORGANISM: Mus musculus

<400> SEQUENCE: 16
gacattgtgc tgacccaatc tccagcttct ttgactgtgt ctctaggcct gagggccacc     60
atctcctgca aggccagcca agtgttgat tatgatggtg atagttatat gaactggtac    120
cagcagaaac caggacagcc acccaaactc ctcatctatg ctgcatccaa tctagaatct    180
gggatcccag ccaggtttag tggcaatggg tctgggacag acttcaccct caacatccat    240
cctgtggagg aggaggatgc tgtaacctat tactgtcaac aaagtaatga ggatccgtgg    300
acgttcggtg gaggcaccaa gctggaaatc aaacggctg atgctgcacc aactgtatcc     360
atcttcccac catccagtga gcagttaaca tctggaggtg cctcagtcgt gtgcttcttg    420
aacaacttct accccaaaga catcaatgtc aagtggaaga ttgatggcag tgaacgacaa    480
aatggcgtcc tgaacagttg gactgatcag gacagcaaag acagcaccta cagcatgagc    540
agcaccctca cgttgaccaa ggacgagtat gaacgacata cagctatac ctgtgaggcc     600 actcacaaga catcaacttc acccattgtc aagagcttca caggaatga gtgttag      657

<210> SEQ ID NO 17
<211> LENGTH: 238
<212> TYPE: PRT
<213> ORGANISM: Mus musculus

<400> SEQUENCE: 17

Met Glu Thr Asp Thr Ile Leu Leu Trp Val Leu Leu Leu Trp Val Pro
  1               5                  10                  15

Gly Ser Thr Gly Asp Ile Val Leu Thr Gln Ser Pro Ala Ser Leu Thr
             20                  25                  30

Val Ser Leu Gly Leu Arg Ala Thr Ile Ser Cys Lys Ala Ser Gln Ser
         35                  40                  45

Val Asp Tyr Asp Gly Asp Ser Tyr Met Asn Trp Tyr Gln Gln Lys Pro
     50                  55                  60

Gly Gln Pro Pro Lys Leu Leu Ile Tyr Ala Ala Ser Asn Leu Glu Ser
 65                  70                  75                  80

Gly Ile Pro Ala Arg Phe Ser Gly Asn Gly Ser Gly Thr Asp Phe Thr
                 85                  90                  95

Leu Asn Ile His Pro Val Glu Glu Asp Ala Val Thr Tyr Tyr Cys
            100                 105                 110

Gln Gln Ser Asn Glu Asp Pro Trp Thr Phe Gly Gly Gly Thr Lys Leu
            115                 120                 125

Glu Ile Lys Arg Ala Asp Ala Ala Pro Thr Val Ser Ile Phe Pro Pro
            130                 135                 140

Ser Ser Glu Gln Leu Thr Ser Gly Gly Ala Ser Val Val Cys Phe Leu

```
           145                 150                 155                 160
Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 18
<211> LENGTH: 717
<212> TYPE: DNA
<213> ORGANISM: Mus musculus

<400> SEQUENCE: 18
atggagacag acacaatcct gctatgggtg ctgctgctct gggttccagg ctccactggt      60
gacattgtgc tgacccaatc tccagcttct ttgactgtgt ctctaggcct gagggccacc     120
atctcctgca aggccagcca agtgttgat tatgatggtg atagtttat gaactggtac       180 cagcagaaac aggacagcc acccaaactc ctcatctatg ctgcatccaa tctagaatct      240
gggatcccag ccaggtttag tggcaatggg tctgggacag acttcaccct caacatccat      300
cctgtggagg aggaggatgc tgtaacctat tactgtcaac aaagtaatga ggatccgtgg     360
acgttcggtg gaggcaccaa gctggaaatc aaacgggctg atgctgcacc aactgtatcc     420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600
agcaccctca cgttgaccaa ggacgagtat gaacgacata cagctatac ctgtgaggcc      660 actcacaaga catcaacttc acccattgtc aagagcttca caggaatga gtgttag        717

<210> SEQ ID NO 19
<211> LENGTH: 449
<212> TYPE: PRT
<213> ORGANISM: Mus musculus

<400> SEQUENCE: 19

Glu Val Gln Leu Gln Gln Ser Gly Pro Glu Leu Val Lys Pro Gly Thr
1               5                   10                  15

Ser Val Lys Met Ser Cys Lys Ala Ser Gly Tyr Thr Phe Thr Asp Cys
            20                  25                  30

Tyr Met Asn Trp Val Lys Gln Ser His Gly Lys Ser Leu Glu Trp Ile
        35                  40                  45

Gly Asp Ile Asn Pro Phe Asn Gly Gly Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Asn Ser Leu Thr Ser Asp Asp Ser Ala Val Tyr Tyr Cys
                85                  90                  95

Ala Arg Ser His Tyr Tyr Phe Asp Gly Arg Val Pro Trp Asp Ala Met
            100                 105                 110

Asp Tyr Trp Gly Gln Gly Thr Ser Val Thr Val Ser Ser Ala Lys Thr
```

-continued

```
                115                 120                 125
Thr Pro Pro Ser Val Tyr Pro Leu Ala Pro Gly Ser Ala Ala Gln Thr
    130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205

Val Ala His Pro Ala Ser Ser Thr Lys Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
            340                 345                 350

Ile Pro Pro Pro Lys Glu Gln Met Ala Lys Asp Lys Val Ser Leu Thr
        355                 360                 365

Cys Met Ile Thr Asp Phe Phe Pro Glu Asp Ile Thr Val Glu Trp Gln
    370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Ile Tyr Ser Lys Leu Asn Val Gln Lys
                405                 410                 415

Ser Asn Trp Glu Ala Gly Asn Thr Phe Thr Cys Ser Val Leu His Glu
            420                 425                 430

Gly Leu His Asn His His Thr Glu Lys Ser Leu Ser His Ser Pro Gly
        435                 440                 445

Lys
```

<210> SEQ ID NO 20
<211> LENGTH: 1350
<212> TYPE: DNA
<213> ORGANISM: Mus musculus

<400> SEQUENCE: 20

```
gaggtccagc tgcaacaatc tggacctgag ctggtgaagc ctgggacttc agtgaagatg    60
tcctgtaagg cttctggata cacattcact gactgctaca tgaactgggt gaagcagagc   120
catgggaaga gccttgaatg gattggagat attaatcctt caacggtgg tactacctac   180 aaccagaagt tcaagggcaa ggccacattg actgtagaca atcctccag cacagcctac   240
```

```
atgcagctca acagcctgac atctgacgac tctgcagtct attactgtgc aagatcccat      300
tattacttcg atggtagagt cccttgggat gctatggact actggggtca aggaacctca      360
gtcaccgtct cctcagccaa aacgacaccc ccatctgtct atccactggc ccctggatct      420
gctgcccaaa ctaactccat ggtgaccctg ggatgcctgg tcaagggcta tttccctgag      480
ccagtgacag tgacctggaa ctctggatcc ctgtccagcg gtgtgcacac cttcccagct      540
gtcctgcagt ctgacctcta cactctgagc agctcagtga ctgtcccctc cagcacctgg      600
cccagcgaga ccgtcacctg caacgttgcc cacccggcca gcagcaccaa ggtggacaag      660
aaaattgtgc cagggattg tggttgtaag ccttgcatat gtacagtccc agaagtatca       720
tctgtcttca tcttcccccc aaagcccaag gatgtgctca ccattactct gactcctaag      780
gtcacgtgtg ttgtggtaga catcagcaag gatgatcccg aggtccagtt cagctggttt      840
gtagatgatg tggaggtgca cacagctcag acgcaacccc gggaggagca gttcaacagc      900
actttccgct cagtcagtga acttcccatc atgcaccagg actggctcaa tggcaaggag      960
ttcaaatgca gggtcaacag tgcagctttc cctgccccca tcgagaaaac catctccaaa     1020
accaaaggca gaccgaaggc tccacaggtg tacaccattc cacctcccaa ggagcagatg     1080
gccaaggata aagtcagtct gacctgcatg ataacagact tcttccctga agacattact     1140
gtggagtggc agtggaatgg gcagccagcg gagaactaca agaacactca gcccatcatg     1200
gacacagatg gctcttactt catctacagc aagctcaatg tgcagaagag caactgggag     1260
gcaggaaata ctttcacctg ctctgtgtta catgagggcc tgcacaacca ccatactgag     1320
aagagcctct cccactctcc tggtaaatga                                     1350
```

```
<210> SEQ ID NO 21
<211> LENGTH: 468
<212> TYPE: PRT
<213> ORGANISM: Mus musculus

<400> SEQUENCE: 21

Met Gly Trp Asn Trp Ile Phe Leu Phe Leu Leu Ser Gly Thr Ala Gly
  1               5                  10                  15

Val Tyr Ser Glu Val Gln Leu Gln Gln Ser Gly Pro Glu Leu Val Lys
                 20                  25                  30

Pro Gly Thr Ser Val Lys Met Ser Cys Lys Ala Ser Gly Tyr Thr Phe
             35                  40                  45

Thr Asp Cys Tyr Met Asn Trp Val Lys Gln Ser His Gly Lys Ser Leu
         50                  55                  60

Glu Trp Ile Gly Asp Ile Asn Pro Phe Asn Gly Gly Thr Thr Tyr Asn
 65                  70                  75                  80

Gln Lys Phe Lys Gly Lys Ala Thr Leu Thr Val Asp Lys Ser Ser Ser
                 85                  90                  95

Thr Ala Tyr Met Gln Leu Asn Ser Leu Thr Ser Asp Asp Ser Ala Val
                100                 105                 110

Tyr Tyr Cys Ala Arg Ser His Tyr Tyr Phe Asp Gly Arg Val Pro Trp
            115                 120                 125

Asp Ala Met Asp Tyr Trp Gly Gln Gly Thr Ser Val Thr Val Ser Ser
        130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175
```

```
Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
            260                 265                 270

Thr Ile Thr Leu Thr Pro Lys Val Thr Cys Val Val Val Asp Ile Ser
        275                 280                 285

Lys Asp Asp Pro Glu Val Gln Phe Ser Trp Phe Val Asp Asp Val Glu
290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
                325                 330                 335

Gly Lys Glu Phe Lys Cys Arg Val Asn Ser Ala Ala Phe Pro Ala Pro
            340                 345                 350

Ile Glu Lys Thr Ile Ser Lys Thr Lys Gly Arg Pro Lys Ala Pro Gln
        355                 360                 365

Val Tyr Thr Ile Pro Pro Pro Lys Glu Gln Met Ala Lys Asp Lys Val
370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
                405                 410                 415

Pro Ile Met Asp Thr Asp Gly Ser Tyr Phe Ile Tyr Ser Lys Leu Asn
            420                 425                 430

Val Gln Lys Ser Asn Trp Glu Ala Gly Asn Thr Phe Thr Cys Ser Val
        435                 440                 445

Leu His Glu Gly Leu His Asn His His Thr Glu Lys Ser Leu Ser His
450                 455                 460

Ser Pro Gly Lys
465

<210> SEQ ID NO 22
<211> LENGTH: 1407
<212> TYPE: DNA
<213> ORGANISM: Mus musculus

<400> SEQUENCE: 22
atgggatgga actggatctt tctcttcctc ttgtcaggaa ctgcaggtgt ctactctgag     60
gtccagctgc aacaatctgg acctgagctg gtgaagcctg gacttcagt gaagatgtcc    120 tgtaaggctt ctggatacac attcactgac tgctacatga actgggtgaa gcagagccat    180
gggaagagcc ttgaatggat tggagatatt aatccttca acgtggtac tacctacaac    240 cagaagttca aggcaaggc cacattgact gtagacaaat cctccagcac agcctacatg    300
cagctcaaca gcctgacatc tgacgactct gcagtctatt actgtgcaag atcccattat    360
tacttcgatg gtagagtccc ttgggatgct atggactact ggggtcaagg aacctcagtc    420
```

```
accgtctcct cagccaaaac gacaccccca tctgtctatc cactggcccc tggatctgct    480
gcccaaacta actccatggt gaccctggga tgcctggtca agggctattt ccctgagcca    540
gtgacagtga cctggaactc tggatccctg tccagcggtg tgcacacctt cccagctgtc    600
ctgcagtctg acctctacac tctgagcagc tcagtgactg tcccctccag cacctggccc    660
agcgagaccg tcacctgcaa cgttgcccac ccggccagca gcaccaaggt ggacaagaaa    720
attgtgccca gggattgtgg ttgtaagcct tgcatatgta cagtcccaga agtatcatct    780
gtcttcatct ccccccaaa gcccaaggat gtgctcacca ttactctgac tcctaaggtc    840
acgtgtgttg tggtagacat cagcaaggat gatcccgagg tccagttcag ctggtttgta    900
gatgatgtgg aggtgcacac agctcagacg caaccccggg aggagcagtt caacagcact    960
ttccgctcag tcagtgaact tcccatcatg caccaggact ggctcaatgg caaggagttc   1020
aaatgcaggg tcaacagtgc agcttttccct gccccccatcg agaaaaccat ctccaaaacc   1080
aaaggcagac cgaaggctcc acaggtgtac accattccac ctcccaagga gcagatggcc   1140
aaggataaag tcagtctgac ctgcatgata acagacttct tccctgaaga cattactgtg   1200
gagtggcagt ggaatgggca gccagcggag aactacaaga cactcagcc catcatggac   1260 acagatggct cttacttcat ctacagcaag ctcaatgtgc agaagagcaa ctgggaggca   1320
ggaaatactt tcacctgctc tgtgttacat gagggcctgc acaaccacca tactgagaag   1380
agcctctccc actctcctgg taaatga                                        1407

<210> SEQ ID NO 23
<211> LENGTH: 217
<212> TYPE: PRT
<213> ORGANISM: Rabbit-Mouse Chimera

<400> SEQUENCE: 23

Ala Gln Val Leu Thr Gln Thr Pro Ala Ser Val Ser Ala Ala Val Gly
  1               5                  10                  15

Gly Thr Val Thr Ile Asn Cys Gln Ser Ser Gln Ser Val Tyr Asp Asn
             20                  25                  30

Asn Trp Leu Ala Trp Phe Gln Gln Lys Pro Gly Gln Pro Pro Lys Leu
         35                  40                  45

Leu Ile Tyr Asp Ala Ser Asp Leu Ala Ser Gly Val Pro Ser Arg Phe
     50                  55                  60

Ser Gly Ser Gly Ser Gly Thr Gln Phe Thr Leu Thr Ile Ser Gly Val
 65                  70                  75                  80

Gln Cys Ala Asp Ala Ala Thr Tyr Tyr Cys Gln Gly Ala Tyr Asn Asp
                 85                  90                  95

Val Ile Tyr Ala Phe Gly Gly Gly Thr Glu Val Val Lys Arg Thr
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190
```

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215

<210> SEQ ID NO 24
<211> LENGTH: 654
<212> TYPE: DNA
<213> ORGANISM: Rabbit-Mouse Chimera

<400> SEQUENCE: 24
gcgcaagtgc tgacccagac tccagcctcc gtgtctgcag ctgtgggagg cacagtcacc    60
atcaattgcc agtccagtca gagtgtttat gataacaact ggttagcctg gtttcagcag   120
aaaccagggc agcctcccaa gctcctgatt tatgatgcat ccgatctggc atctggggtc   180
ccatcgcggt tcagtggcag tggatctggg acacagttca ctctcaccat cagcggcgtg   240
cagtgtgccg atgctgccac ttactactgt caaggcgctt ataatgatgt tatttatgct   300
ttcggcggag ggaccgaggt ggtggtcaaa cgtacggatg ctgcaccaac tgtatccatc   360
ttcccaccat ccagtgagca gttaacatct ggaggtgcct cagtcgtgtg cttcttgaac   420
aacttctacc ccaaagacat caatgtcaag tggaagattg atggcagtga acgacaaaat   480
ggcgtcctga cagttggac tgatcaggac agcaaagaca gcacctacag catgagcagc   540
accctcacgt tgaccaagga cgagtatgaa cgacataaca gctatacctg tgaggccact   600
cacaagacat caacttcacc cattgtcaag agcttcaaca ggaatgagtg ttag         654

<210> SEQ ID NO 25
<211> LENGTH: 239
<212> TYPE: PRT
<213> ORGANISM: Rabbit-Mouse Chimera

<400> SEQUENCE: 25

Met Asp Thr Arg Ala Pro Thr Gln Leu Leu Gly Leu Leu Leu Leu Trp
  1               5                  10                  15

Leu Pro Gly Ala Thr Phe Ala Gln Val Leu Thr Gln Thr Pro Ala Ser
             20                  25                  30

Val Ser Ala Ala Val Gly Gly Thr Val Thr Ile Asn Cys Gln Ser Ser
         35                  40                  45

Gln Ser Val Tyr Asp Asn Asn Trp Leu Ala Trp Phe Gln Gln Lys Pro
     50                  55                  60

Gly Gln Pro Pro Lys Leu Leu Ile Tyr Asp Ala Ser Asp Leu Ala Ser
 65                  70                  75                  80

Gly Val Pro Ser Arg Phe Ser Gly Ser Gly Ser Gly Thr Gln Phe Thr
                 85                  90                  95

Leu Thr Ile Ser Gly Val Gln Cys Ala Asp Ala Ala Thr Tyr Tyr Cys
            100                 105                 110

Gln Gly Ala Tyr Asn Asp Val Ile Tyr Ala Phe Gly Gly Gly Thr Glu
        115                 120                 125

Val Val Val Lys Arg Thr Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

```
Ser Lys Asp Ser Thr Tyr Ser Met Ser Ser Thr Leu Thr Leu Thr Lys
        195                 200                 205
Asp Glu Tyr Glu Arg His Asn Ser Tyr Thr Cys Glu Ala Thr His Lys
        210                 215                 220
Thr Ser Thr Ser Pro Ile Val Lys Ser Phe Asn Arg Asn Glu Cys
225                 230                 235
```

```
<210> SEQ ID NO 26
<211> LENGTH: 720
<212> TYPE: DNA
<213> ORGANISM: Rabbit-Mouse Chimera

<400> SEQUENCE: 26
atggacacga gggcccccac tcagctgctg gggctcctgc tgctctggct cccaggtgcc    60
acatttgcgc aagtgctgac ccagactcca gcctccgtgt ctgcagctgt gggaggcaca   120
gtcaccatca attgccagtc cagtcagagt gtttatgata caactggtt  agcctggttt   180
cagcagaaac cagggcagcc tcccaagctc ctgatttatg atgcatccga tctggcatct   240
ggggtcccat cgcggttcag tggcagtgga tctgggacac agttcactct caccatcagc   300
ggcgtgcagt gtgccgatgc tgccacttac tactgtcaag gcgcttataa tgatgttatt   360
tatgctttcg gcggagggac cgaggtggtg gtcaaacgta cggatgctgc accaactgta   420
tccatcttcc caccatccag tgagcagtta acatctggag gtgcctcagt cgtgtgcttc   480
ttgaacaact ctaccccaa  agacatcaat gtcaagtgga gattgatgg  cagtgaacga   540
caaaatggcg tcctgaacag ttggactgat caggacagca agacagcac  ctacagcatg   600
agcagcaccc tcacgttgac caaggacgag tatgaacgac ataacagcta cctgtgtgag   660
gccactcaca agacatcaac ttcacccatt gtcaagagct caacaggaa  tgagtgttag   720
```

```
<210> SEQ ID NO 27
<211> LENGTH: 433
<212> TYPE: PRT
<213> ORGANISM: Artificial Sequence
<220> FEATURE:
<223> OTHER INFORMATION: Humanized antibody

<400> SEQUENCE: 27

Gln Ser Leu Glu Glu Ser Gly Gly Arg Leu Val Thr Pro Gly Thr Pro
1               5                  10                  15
Leu Thr Leu Thr Cys Thr Ala Ser Gly Phe Ser Leu Ser Ser Tyr Trp
            20                  25                  30
Met Asn Trp Val Arg Gln Ala Pro Gly Glu Gly Leu Glu Trp Ile Gly
        35                  40                  45
Thr Ile Asp Ser Gly Gly Arg Thr Asp Tyr Ala Ser Trp Ala Lys Gly
    50                  55                  60
Arg Phe Thr Ile Ser Arg Thr Ser Thr Thr Met Asp Leu Lys Met Thr
65                  70                  75                  80
Ser Leu Thr Thr Gly Asp Thr Ala Arg Tyr Phe Cys Ala Arg Asn Trp
                85                  90                  95
Asn Leu Trp Gly Gln Gly Thr Leu Val Thr Val Ser Ser Ala Ser Thr
            100                 105                 110
Lys Gly Pro Ser Val Tyr Pro Leu Ala Pro Gly Ser Ala Ala Gln Thr
        115                 120                 125
Asn Ser Met Val Thr Leu Gly Cys Leu Val Lys Gly Tyr Phe Pro Glu
    130                 135                 140
```

```
Pro Val Thr Val Thr Trp Asn Ser Gly Ser Leu Ser Ser Gly Val His
145                 150                 155                 160

Thr Phe Pro Ala Val Leu Gln Ser Asp Leu Tyr Thr Leu Ser Ser Ser
            165                 170                 175

Val Thr Val Pro Ser Ser Thr Trp Pro Ser Glu Thr Val Thr Cys Asn
        180                 185                 190

Val Ala His Pro Ala Ser Ser Thr Lys Val Asp Lys Lys Ile Val Pro
    195                 200                 205

Arg Asp Cys Gly Cys Lys Pro Cys Ile Cys Thr Val Pro Glu Val Ser
210                 215                 220

Ser Val Phe Ile Phe Pro Pro Lys Pro Lys Asp Val Leu Thr Ile Thr
225                 230                 235                 240

Leu Thr Pro Lys Val Thr Cys Val Val Val Asp Ile Ser Lys Asp Asp
            245                 250                 255

Pro Glu Val Gln Phe Ser Trp Phe Val Asp Asp Val Glu Val His Thr
        260                 265                 270

Ala Gln Thr Gln Pro Arg Glu Glu Gln Phe Asn Ser Thr Phe Arg Ser
    275                 280                 285

Val Ser Glu Leu Pro Ile Met His Gln Asp Trp Leu Asn Gly Lys Glu
290                 295                 300

Phe Lys Cys Arg Val Asn Ser Ala Ala Phe Pro Ala Pro Ile Glu Lys
305                 310                 315                 320

Thr Ile Ser Lys Thr Lys Gly Arg Pro Lys Ala Pro Gln Val Tyr Thr
            325                 330                 335

Ile Pro Pro Pro Lys Glu Gln Met Ala Lys Asp Lys Val Ser Leu Thr
        340                 345                 350

Cys Met Ile Thr Asp Phe Phe Pro Glu Asp Ile Thr Val Glu Trp Gln
    355                 360                 365

Trp Asn Gly Gln Pro Ala Glu Asn Tyr Lys Asn Thr Gln Pro Ile Met
370                 375                 380

Asn Thr Asn Gly Ser Tyr Phe Val Tyr Ser Lys Leu Asn Val Gln Lys
385                 390                 395                 400

Ser Asn Trp Glu Ala Gly Asn Thr Phe Thr Cys Ser Val Leu His Glu
            405                 410                 415

Gly Leu His Asn His His Thr Glu Lys Ser Leu Ser His Ser Pro Gly
        420                 425                 430

Lys
```

<210> SEQ ID NO 28
<211> LENGTH: 1302
<212> TYPE: DNA
<213> ORGANISM: Artificial Sequence
<220> FEATURE:
<223> OTHER INFORMATION: Humanized antibody

<400> SEQUENCE: 28

```
cagtcgctgg aggagtccgg gggtcgcctg gtcacgcctg ggacacccct gacactcacc      60
tgcacagcct ctggattctc cctcagtagt tattggatga ctgggtccg ccaggctcca     120 ggggaggggc tggaatggat cggaaccatt gattctggtg gtaggacgga ctacgcgagc    180
tgggcaaaag gccgattcac catctccaga acctcgacta cgatggatct gaaaatgacc    240
agtctgacga ccggggacac ggcccgttat ttctgtgcca gaaattggaa cttgtggggc    300
caaggcaccc tcgtcaccgt ctcgagcgct tctacaaagg gcccatctgt ctatccactg    360
gcccctggat ctgctgccca aactaactcc atggtgaccc tgggatgcct ggtcaagggc    420
```

-continued

```
tatttccctg agccagtgac agtgacctgg aactctggat ccctgtccag cggtgtgcac    480
accttcccag ctgtcctgca gtctgacctc tacactctga gcagctcagt gactgtcccc    540
tccagcacct ggcccagcga gaccgtcacc tgcaacgttg cccacccggc cagcagcacc    600
aaggtggaca agaaaattgt gcccagggat tgtggttgta agccttgcat atgtacagtc    660
ccagaagtat catctgtctt catcttcccc ccaaagccca aggatgtgct caccattact    720
ctgactccta aggtcacgtg tgttgtggta gacatcagca aggatgatcc cgaggtccag    780
ttcagctggt ttgtagatga tgtggaggtg cacacagctc agacgcaacc ccgggaggag    840
cagttcaaca gcactttccg ctcagtcagt gaacttccca tcatgcacca ggactggctc    900
aatggcaagg agttcaaatg cagggtcaac agtgcagctt ccctgccccc atcgagaaaa    960
accatctcca aaccaaagg cagaccgaag gctccacagg tgtacaccat tccacctccc   1020
aaggagcaga tggccaagga taaagtcagt ctgacctgca tgataacaga cttcttccct   1080
gaagacatta ctgtggagtg gcagtggaat gggcagccag cggagaacta caagaacact   1140
cagcccatca tggacacaga tggctcttac ttcgtctaca gcaagctcaa tgtgcagaag   1200
agcaactggg aggcaggaaa tactttcacc tgctctgtgt tacatgaggg cctgcacaac   1260
caccatactg agaagagcct ctcccactct cctggtaaat ga                      1302
```

<210> SEQ ID NO 29
<211> LENGTH: 452
<212> TYPE: PRT
<213> ORGANISM: Artificial Sequence
<220> FEATURE:
<223> OTHER INFORMATION: Humanized antibody

<400> SEQUENCE: 29

```
Met Glu Thr Gly Leu Arg Trp Leu Leu Leu Val Ala Val Leu Lys Gly
  1               5                  10                  15

Val His Cys Gln Ser Leu Glu Glu Ser Gly Gly Arg Leu Val Thr Pro
             20                  25                  30

Gly Thr Pro Leu Thr Leu Thr Cys Thr Ala Ser Gly Phe Ser Leu Ser
         35                  40                  45

Ser Tyr Trp Met Asn Trp Val Arg Gln Ala Pro Gly Glu Gly Leu Glu
     50                  55                  60

Trp Ile Gly Thr Ile Asp Ser Gly Gly Arg Thr Asp Tyr Ala Ser Trp
 65                  70                  75                  80

Ala Lys Gly Arg Phe Thr Ile Ser Arg Thr Ser Thr Thr Met Asp Leu
                 85                  90                  95

Lys Met Thr Ser Leu Thr Thr Gly Asp Thr Ala Arg Tyr Phe Cys Ala
            100                 105                 110

Arg Asn Trp Asn Leu Trp Gly Gln Gly Thr Leu Val Thr Val Ser Ser
        115                 120                 125

Ala Ser Thr Lys Gly Pro Ser Val Tyr Pro Leu Ala Pro Gly Ser Ala
    130                 135                 140

Ala Gln Thr Asn Ser Met Val Thr Leu Gly Cys Leu Val Lys Gly Tyr
145                 150                 155                 160

Phe Pro Glu Pro Val Thr Val Thr Trp Asn Ser Gly Ser Leu Ser Ser
                165                 170                 175

Gly Val His Thr Phe Pro Ala Val Leu Gln Ser Asp Leu Tyr Thr Leu
            180                 185                 190

Ser Ser Ser Val Thr Val Pro Ser Ser Thr Trp Pro Ser Glu Thr Val
        195                 200                 205
```

```
Thr Cys Asn Val Ala His Pro Ala Ser Ser Thr Lys Val Asp Lys Lys
        210                 215                 220

Ile Val Pro Arg Asp Cys Gly Cys Lys Pro Cys Ile Cys Thr Val Pro
225                 230                 235                 240

Glu Val Ser Ser Val Phe Ile Phe Pro Pro Lys Pro Lys Asp Val Leu
                245                 250                 255

Thr Ile Thr Leu Thr Pro Lys Val Thr Cys Val Val Asp Ile Ser
            260                 265                 270

Lys Asp Asp Pro Glu Val Gln Phe Ser Trp Phe Val Asp Asp Val Glu
        275                 280                 285

Val His Thr Ala Gln Thr Gln Pro Arg Glu Glu Gln Phe Asn Ser Thr
    290                 295                 300

Phe Arg Ser Val Ser Glu Leu Pro Ile Met His Gln Asp Trp Leu Asn
305                 310                 315                 320

Gly Lys Glu Phe Lys Cys Arg Val Asn Ser Ala Ala Phe Pro Ala Pro
                325                 330                 335

Ile Glu Lys Thr Ile Ser Lys Thr Lys Gly Arg Pro Lys Ala Pro Gln
            340                 345                 350

Val Tyr Thr Ile Pro Pro Pro Lys Glu Gln Met Ala Lys Asp Lys Val
        355                 360                 365

Ser Leu Thr Cys Met Ile Thr Asp Phe Phe Pro Glu Asp Ile Thr Val
    370                 375                 380

Glu Trp Gln Trp Asn Gly Gln Pro Ala Glu Asn Tyr Lys Asn Thr Gln
385                 390                 395                 400

Pro Ile Met Asn Thr Asn Gly Ser Tyr Phe Val Tyr Ser Lys Leu Asn
                405                 410                 415

Val Gln Lys Ser Asn Trp Glu Ala Gly Asn Thr Phe Thr Cys Ser Val
            420                 425                 430

Leu His Glu Gly Leu His Asn His Thr Glu Lys Ser Leu Ser His
        435                 440                 445

Ser Pro Gly Lys
    450

<210> SEQ ID NO 30
<211> LENGTH: 1359
<212> TYPE: DNA
<213> ORGANISM: Artificial Sequence
<220> FEATURE:
<223> OTHER INFORMATION: Humanized antibody

<400> SEQUENCE: 30
atggagactg ggctgcgctg gcttctcctg gtcgctgtgc tcaaaggtgt ccactgtcag    60
tcgctggagg agtccggggg tcgcctggtc acgcctggga cacccctgac actcacctgc   120
acagcctctg gattctccct cagtagttat tggatgaact gggtccgcca ggctccaggg   180
gaggggctgg aatggatcgg aaccattgat tctggtggta ggacggacta cgcgagctgg   240
gcaaaaggcc gattcaccat ctccagaacc tcgactacga tggatctgaa aatgaccagt   300
ctgacgaccg gggacacggc ccgttatttc tgtgccagaa attggaactt gtggggccaa   360
ggcaccctcg tcaccgtctc gagcgcttct acaaagggcc catctgtcta tccactggcc   420
cctggatctg ctgcccaaac taactccatg gtgaccctgg atgcctggt caagggctat   480 ttccctgagc cagtgacagt gacctggaac tctggatccc tgtccagcgg tgtgcacacc   540
ttcccagctg tcctgcagtc tgacctctac actctgagca gctcagtgac tgtcccctcc   600
```

```
agcacctggc ccagcgagac cgtcacctgc aacgttgccc acccggccag cagcaccaag    660
gtggacaaga aaattgtgcc cagggattgt ggttgtaagc cttgcatatg tacagtccca    720
gaagtatcat ctgtcttcat cttccccca aagcccaagg atgtgctcac cattactctg     780
actcctaagg tcacgtgtgt tgtggtagac atcagcaagg atgatcccga ggtccagttc    840
agctggtttg tagatgatgt ggaggtgcac acagctcaga cgcaaccccg ggaggagcag    900
ttcaacagca ctttccgctc agtcagtgaa cttcccatca tgcaccagga ctggctcaat    960
ggcaaggagt tcaaatgcag ggtcaacagt gcagctttcc ctgcccccat cgagaaaacc   1020
atctccaaaa ccaaggcag accgaaggct ccacaggtgt acaccattcc acctcccaag    1080
gagcagatgg ccaaggataa agtcagtctg acctgcatga taacagactt cttccctgaa   1140
gacattactg tggagtggca gtggaatggg cagccagcgg agaactacaa gaacactcag   1200
cccatcatgg acacagatgg ctcttacttc gtctacagca agctcaatgt gcagaagagc   1260
aactgggagc aggaaaatac tttcacctgc tctgtgttac atgagggcct gcacaaccac   1320
catactgaga agagcctctc ccactctcct ggtaaatga                          1359
```

```
<210> SEQ ID NO 31
<211> LENGTH: 213
<212> TYPE: PRT
<213> ORGANISM: Mus musculus

<400> SEQUENCE: 31

Gln Ile Val Leu Thr Gln Ser Pro Thr Ile Val Ser Ala Ser Pro Gly
  1               5                  10                  15

Glu Lys Val Thr Leu Ile Cys Ser Ala Ser Ser Ser Val Ser Phe Val
             20                  25                  30

Asp Trp Phe Gln Gln Lys Pro Gly Thr Ser Pro Lys Arg Trp Ile Tyr
         35                  40                  45

Arg Thr Ser Asn Leu Gly Phe Gly Val Pro Ala Arg Phe Ser Gly Gly
     50                  55                  60

Gly Ser Gly Thr Ser His Ser Leu Thr Ile Ser Arg Met Glu Ala Glu
 65                  70                  75                  80

Asp Ala Ala Thr Tyr Tyr Cys Gln Gln Arg Ser Thr Tyr Pro Pro Thr
                 85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 32
<211> LENGTH: 642
```

<212> TYPE: DNA
<213> ORGANISM: Mus musculus

<400> SEQUENCE: 32

```
caaattgttc tcacccagtc tccaacaatc gtgtctgcat ctccagggga gaaggtcacc    60
ctaatctgca gtgccagttc aagtgtaagt ttcgtggact ggttccagca gaagccaggc   120
acttctccca aacgctggat ttacagaaca tccaacctgg ttttggagt ccctgctcgc    180
ttcagtggcg gtggatctgg gacctctcac tctctcacaa tcagccgaat ggaggctgaa   240
gatgctgcca cttattactg ccagcaaagg agtacttacc cacccacgtt cggtgctggg   300
accaagctgg aactgaaacg ggctgatgct gcaccaactg tatccatctt cccaccatcc   360
agtgagcagt taacatctgg aggtgcctca gtcgtgtgct tcttgaacaa cttctacccc   420
aaagacatca atgtcaagtg gaagattgat ggcagtgaac gacaaaatgg cgtcctgaac   480
agttggactg atcaggacag caaagacagc acctacagca tgagcagcac cctcacgttg   540
accaaggacg agtatgaacg acataacagc tatacctgtg aggccactca caagacatca   600
acttcaccca ttgtcaagag cttcaacagg aatgagtgtt ag                     642
```

<210> SEQ ID NO 33
<211> LENGTH: 235
<212> TYPE: PRT
<213> ORGANISM: Mus musculus

<400> SEQUENCE: 33

```
Met His Phe Gln Val Gln Ile Phe Ser Phe Leu Leu Ile Ser Ala Ser
 1               5                  10                  15

Val Ile Val Ser Arg Gly Gln Ile Val Leu Thr Gln Ser Pro Thr Ile
            20                  25                  30

Val Ser Ala Ser Pro Gly Glu Lys Val Thr Leu Ile Cys Ser Ala Ser
        35                  40                  45

Ser Ser Val Ser Phe Val Asp Trp Phe Gln Gln Lys Pro Gly Thr Ser
    50                  55                  60

Pro Lys Arg Trp Ile Tyr Arg Thr Ser Asn Leu Gly Phe Gly Val Pro
65                  70                  75                  80

Ala Arg Phe Ser Gly Gly Gly Ser Gly Thr Ser His Ser Leu Thr Ile
                85                  90                  95

Ser Arg Met Glu Ala Glu Asp Ala Ala Thr Tyr Tyr Cys Gln Gln Arg
            100                 105                 110

Ser Thr Tyr Pro Pro Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235
```

<210> SEQ ID NO 34
<211> LENGTH: 708
<212> TYPE: DNA
<213> ORGANISM: Mus musculus

<400> SEQUENCE: 34

```
atgcattttc aagtgcagat tttcagcttc ctgctaatca gtgcctcagt catagtgtcc      60
agagggcaaa ttgttctcac ccagtctcca acaatcgtgt ctgcatctcc aggggagaag     120
gtcaccctaa tctgcagtgc cagttcaagt gtaagtttcg tggactggtt ccagcagaag     180
ccaggcactt ctcccaaacg ctggatttac agaacatcca acctgggttt tggagtccct     240
gctcgcttca gtggcggtgg atctgggacc tctcactctc tcacaatcag ccgaatggag     300
gctgaagatg ctgccactta ttactgccag caaggagta cttacccacc acgttcggt      360
gctgggacca gctggaact gaaacgggct gatgctgcac caactgtatc catcttccca     420
ccatccagtg agcagttaac atctggaggt gcctcagtcg tgtgcttctt gaacaacttc     480
tacccaaag acatcaatgt caagtggaag attgatggca gtgaacgaca aaatggcgtc     540
ctgaacagtt ggactgatca ggacagcaaa gacagcacct acagcatgag cagcacccc    600
acgttgacca aggacgagta tgaacgacat aacagctata cctgtgaggc cactcacaag     660
acatcaactt cacccattgt caagagcttc aacaggaatg agtgttag                 708
```

<210> SEQ ID NO 35
<211> LENGTH: 449
<212> TYPE: PRT
<213> ORGANISM: Mus musculus

<400> SEQUENCE: 35

```
Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Ser Thr Ser
            20                  25                  30

Gly Met Gly Val Gly Trp Ile Arg His Pro Ser Gly Lys Asn Leu Glu
        35                  40                  45

Trp Leu Ala His Ile Trp Trp Asp Asp Val Lys Arg Tyr Asn Pro Val
    50                  55                  60

Leu Lys Ser Arg Leu Thr Ile Ser Lys Asp Thr Ser Asn Ser Gln Val
65                  70                  75                  80

Phe Leu Lys Ile Ala Asn Val Asp Thr Ala Asp Thr Ala Thr Tyr Tyr
                85                  90                  95

Cys Ala Arg Ile Glu Asp Phe Asp Tyr Asp Glu Glu Tyr Tyr Ala Met
            100                 105                 110

Asp Tyr Trp Gly Gln Gly Thr Ser Val Ile Val Ser Ser Ala Lys Thr
        115                 120                 125

Thr Pro Pro Ser Val Tyr Pro Leu Ala Pro Gly Ser Ala Ala Gln Thr
    130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205
```

Val Ala His Pro Ala Ser Ser Thr Lys Val Asp Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
            340                 345                 350

Ile Pro Pro Pro Lys Glu Gln Met Ala Lys Asp Lys Val Ser Leu Thr
        355                 360                 365

Cys Met Ile Thr Asp Phe Phe Pro Glu Asp Ile Thr Val Glu Trp Gln
    370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Val Tyr Ser Lys Leu Asn Val Gln Lys
                405                 410                 415

Ser Asn Trp Glu Ala Gly Asn Thr Phe Thr Cys Ser Val Leu His Glu
            420                 425                 430

Gly Leu His Asn His His Thr Glu Lys Ser Leu Ser His Ser Pro Gly
        435                 440                 445

Lys

<210> SEQ ID NO 36
<211> LENGTH: 1350
<212> TYPE: DNA
<213> ORGANISM: Mus musculus

<400> SEQUENCE: 36
caggttactc tgaaagagtc tggccctggg atattgcagc cctcccagac cctcagtctg      60
acttgttctt tctctgggtt ttcactgagc acttctggta tgggtgtagg ctggattcgt     120
cacccatcag ggaagaatct ggagtggctg gcacacattt ggtgggatga tgtcaagcgc     180
tataacccag tcctgaagag ccgactgact atctccaagg atacctccaa cagccaggta     240
ttcctcaaga tcgccaatgt ggacactgca gatactgcca catactactg tgctcgaata     300
gaggactttg attacgacga ggagtattat gctatggact actggggtca aggaacctca     360
gtcatcgtct cctcagccaa aacgacaccc ccatctgtct atccactggc ccctggatct     420
gctgcccaaa ctaactccat ggtgaccctg gatgcctgg tcaagggcta tttccctgag     480
ccagtgacag tgacctggaa ctctggatcc ctgtccagcg gtgtgcacac cttcccagct     540
gtcctgcagt ctgacctcta cactctgagc agctcagtga ctgtcccctc agcacctgg     600 cccagcgaga ccgtcacctg caacgttgcc cacccggcca gcagcaccaa ggtggacaag     660
aaaattgtgc ccagggattg tggttgtaag ccttgcatat gtacagtccc agaagtatca     720

-continued

```
tctgtcttca tcttcccccc aaagcccaag gatgtgctca ccattactct gactcctaag      780
gtcacgtgtg ttgtggtaga catcagcaag gatgatcccg aggtccagtt cagctggttt      840
gtagatgatg tggaggtgca cacagctcag acgcaacccc gggaggagca gttcaacagc      900
actttccgct cagtcagtga acttcccatc atgcaccagg actggctcaa tggcaaggag      960
ttcaaatgca gggtcaacag tgcagctttc cctgccccca tcgagaaaac catctccaaa     1020
accaaaggca gaccgaaggc tccacaggtg tacaccattc cacctcccaa ggagcagatg     1080
gccaaggata aagtcagtct gacctgcatg ataacagact tcttccctga agacattact     1140
gtggagtggc agtggaatgg gcagccagcg agaactaca agaacactca gcccatcatg     1200
gacacagatg gctcttactt cgtctacagc aagctcaatg tgcagaagag caactgggag     1260
gcaggaaata ctttcacctg ctctgtgtta catgagggcc tgcacaacca ccatactgag     1320
aagagcctct cccactctcc tggtaaatga                                      1350
```

<210> SEQ ID NO 37
<211> LENGTH: 468
<212> TYPE: PRT
<213> ORGANISM: Mus musculus

<400> SEQUENCE: 37

```
Met Gly Arg Leu Thr Ser Ser Phe Leu Leu Ile Val Pro Ala Tyr
  1               5                  10                  15

Val Leu Ser Gln Val Thr Leu Lys Glu Ser Gly Pro Gly Ile Leu Gln
                 20                  25                  30

Pro Ser Gln Thr Leu Ser Leu Thr Cys Ser Phe Ser Gly Phe Ser Leu
             35                  40                  45

Ser Thr Ser Gly Met Gly Val Gly Trp Ile Arg His Pro Ser Gly Lys
         50                  55                  60

Asn Leu Glu Trp Leu Ala His Ile Trp Trp Asp Asp Val Lys Arg Tyr
 65                  70                  75                  80

Asn Pro Val Leu Lys Ser Arg Leu Thr Ile Ser Lys Asp Thr Ser Asn
                 85                  90                  95

Ser Gln Val Phe Leu Lys Ile Ala Asn Val Asp Thr Ala Asp Thr Ala
                100                 105                 110

Thr Tyr Tyr Cys Ala Arg Ile Glu Asp Phe Asp Tyr Asp Glu Glu Tyr
            115                 120                 125

Tyr Ala Met Asp Tyr Trp Gly Gln Gly Thr Ser Val Ile Val Ser Ser
        130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
    210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255
```

```
Glu Val Ser Ser Val Phe Ile Phe Pro Pro Lys Pro Lys Asp Val Leu
            260                 265                 270

Thr Ile Thr Leu Thr Pro Lys Val Thr Cys Val Val Asp Ile Ser
    275                 280                 285

Lys Asp Asp Pro Glu Val Gln Phe Ser Trp Phe Val Asp Val Glu
290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
                325                 330                 335

Gly Lys Glu Phe Lys Cys Arg Val Asn Ser Ala Ala Phe Pro Ala Pro
                340                 345                 350

Ile Glu Lys Thr Ile Ser Lys Thr Lys Gly Arg Pro Lys Ala Pro Gln
            355                 360                 365

Val Tyr Thr Ile Pro Pro Pro Lys Glu Gln Met Ala Lys Asp Lys Val
    370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
                405                 410                 415

Pro Ile Met Asp Thr Asp Gly Ser Tyr Phe Val Tyr Ser Lys Leu Asn
                420                 425                 430

Val Gln Lys Ser Asn Trp Glu Ala Gly Asn Thr Phe Thr Cys Ser Val
            435                 440                 445

Leu His Glu Gly Leu His Asn His Thr Glu Lys Ser Leu Ser His
    450                 455                 460

Ser Pro Gly Lys
465

<210> SEQ ID NO 38
<211> LENGTH: 1407
<212> TYPE: DNA
<213> ORGANISM: Mus musculus

<400> SEQUENCE: 38
atgggcaggc ttacttcttc attcctgcta ctgattgtcc ctgcatatgt cctgtcccag      60
gttactctga aagagtctgg ccctgggata ttgcagccct cccagaccct cagtctgact     120
tgttctttct ctgggttttc actgagcact tctggtatgg gtgtaggctg gattcgtcac    180
ccatcaggga agaatctgga gtggctggca cacatttggt gggatgatgt caagcgctat    240
aacccagtcc tgaagagccg actgactatc tccaaggata cctccaacag ccaggtattc    300
ctcaagatcg ccaatgtgga cactgcagat actgccacat actactgtgc tcgaatagag    360
gactttgatt acgacgagga gtattatgct atggactact ggggtcaagg aacctcagtc    420
atcgtctcct cagccaaaac gacaccccca tctgtctatc cactggcccc tggatctgct    480
gcccaaacta actccatggt gaccctggga tgcctggtca agggctattt ccctgagcca    540
gtgacagtga cctggaactc tggatccctg tccagcggtg tgcacacctt ccagctgtc     600 ctgcagtctg acctctacac tctgagcagc tcagtgactg tcccctccag cacctggccc    660
agcgagaccg tcacctgcaa cgttgcccac ccgccagca gcaccaaggt ggacaagaaa    720
attgtgccca gggattgtgg ttgtaagcct tgcatatgta cagtcccaga agtatcatct    780
gtcttcatct tccccccaaa gcccaaggat gtgctcacca ttactctgac tcctaaggtc    840
acgtgtgttg tggtagacat cagcaaggat gatcccgagg tccagttcag ctggtttgta    900
```

-continued

```
gatgatgtgg aggtgcacac agctcagacg caaccccggg aggagcagtt caacagcact    960
ttccgctcag tcagtgaact tcccatcatg caccaggact ggctcaatgg caaggagttc   1020
aaatgcaggg tcaacagtgc agctttccct gcccccatcg agaaaaccat ctccaaaacc   1080
aaaggcagac cgaaggctcc acaggtgtac accattccac ctcccaagga gcagatggcc   1140
aaggataaag tcagtctgac ctgcatgata acagacttct tccctgaaga cattactgtg   1200
gagtggcagt ggaatgggca gccagcggag aactacaaga acactcagcc catcatggac   1260
acagatggct cttacttcgt ctacagcaag ctcaatgtgc agaagagcaa ctgggaggca   1320
ggaaatactt tcacctgctc tgtgttacat gagggcctgc acaaccacca tactgagaag   1380
agcctctccc actctcctgg taaatga                                        1407

<210> SEQ ID NO 39
<211> LENGTH: 5
<212> TYPE: PRT
<213> ORGANISM: Mus musculus

<400> SEQUENCE: 39

Asp His Tyr Met Ser
 1               5

<210> SEQ ID NO 40
<211> LENGTH: 17
<212> TYPE: PRT
<213> ORGANISM: Mus musculus

<400> SEQUENCE: 40

Asp Ile Asn Pro Tyr Ser Gly Glu Thr Thr Tyr Asn Gln Lys Phe Lys
 1               5                   10                  15

Gly

<210> SEQ ID NO 41
<211> LENGTH: 10
<212> TYPE: PRT
<213> ORGANISM: Mus musculus

<400> SEQUENCE: 41

Asp Asp Tyr Asp Ala Ser Pro Phe Ala Tyr
 1               5                   10

<210> SEQ ID NO 42
<211> LENGTH: 11
<212> TYPE: PRT
<213> ORGANISM: Mus musculus

<400> SEQUENCE: 42

Gln Ala Ser Gln Gly Thr Ser Ile Asn Leu Asn
 1               5                   10

<210> SEQ ID NO 43
<211> LENGTH: 7
<212> TYPE: PRT
<213> ORGANISM: Mus musculus

<400> SEQUENCE: 43

Gly Ser Ser Asn Leu Glu Asp
 1               5

<210> SEQ ID NO 44
<211> LENGTH: 9

```

```
<212> TYPE: PRT
<213> ORGANISM: Mus musculus

<400> SEQUENCE: 44

Leu Gln His Ser Tyr Leu Pro Tyr Thr
1               5

<210> SEQ ID NO 45
<211> LENGTH: 5
<212> TYPE: PRT
<213> ORGANISM: Mus musculus

<400> SEQUENCE: 45

Asp Cys Tyr Met Asn
1               5

<210> SEQ ID NO 46
<211> LENGTH: 17
<212> TYPE: PRT
<213> ORGANISM: Mus musculus

<400> SEQUENCE: 46

Asp Ile Asn Pro Phe Asn Gly Gly Thr Thr Tyr Asn Gln Lys Phe Lys
1               5                   10                  15

Gly

<210> SEQ ID NO 47
<211> LENGTH: 16
<212> TYPE: PRT
<213> ORGANISM: Mus musculus

<400> SEQUENCE: 47

Ser His Tyr Tyr Phe Asp Gly Arg Val Pro Trp Asp Ala Met Asp Tyr
1               5                   10                  15

<210> SEQ ID NO 48
<211> LENGTH: 15
<212> TYPE: PRT
<213> ORGANISM: Mus musculus

<400> SEQUENCE: 48

Lys Ala Ser Gln Ser Val Asp Tyr Asp Gly Asp Ser Tyr Met Asn
1               5                   10                  15

<210> SEQ ID NO 49
<211> LENGTH: 7
<212> TYPE: PRT
<213> ORGANISM: Mus musculus

<400> SEQUENCE: 49

Ala Ala Ser Asn Leu Glu Ser
1               5

<210> SEQ ID NO 50
<211> LENGTH: 9
<212> TYPE: PRT
<213> ORGANISM: Mus musculus

<400> SEQUENCE: 50

Gln Gln Ser Asn Glu Asp Pro Trp Thr
1               5

<210> SEQ ID NO 51
<211> LENGTH: 5
```

```
<212> TYPE: PRT
<213> ORGANISM: Rabbit-Mouse Chimera

<400> SEQUENCE: 51

Ser Tyr Trp Met Asn
1               5

<210> SEQ ID NO 52
<211> LENGTH: 16
<212> TYPE: PRT
<213> ORGANISM: Rabbit-Mouse Chimera

<400> SEQUENCE: 52

Thr Ile Asp Ser Gly Gly Arg Thr Asp Tyr Ala Ser Trp Ala Lys Gly
1               5                   10                  15

<210> SEQ ID NO 53
<211> LENGTH: 4
<212> TYPE: PRT
<213> ORGANISM: Rabbit-Mouse Chimera

<400> SEQUENCE: 53

Asn Trp Asn Leu
1

<210> SEQ ID NO 54
<211> LENGTH: 13
<212> TYPE: PRT
<213> ORGANISM: Rabbit-Mouse Chimera

<400> SEQUENCE: 54

Gln Ser Ser Gln Ser Val Tyr Asp Asn Asn Trp Leu Ala
1               5                   10

<210> SEQ ID NO 55
<211> LENGTH: 7
<212> TYPE: PRT
<213> ORGANISM: Rabbit-Mouse Chimera

<400> SEQUENCE: 55

Asp Ala Ser Asp Leu Ala Ser
1               5

<210> SEQ ID NO 56
<211> LENGTH: 10
<212> TYPE: PRT
<213> ORGANISM: Rabbit-Mouse Chimera

<400> SEQUENCE: 56

Gln Gly Ala Tyr Asn Asp Val Ile Tyr Ala
1               5                   10

<210> SEQ ID NO 57
<211> LENGTH: 7
<212> TYPE: PRT
<213> ORGANISM: Mus musculus

<400> SEQUENCE: 57

Thr Ser Gly Met Gly Val Gly
1               5

<210> SEQ ID NO 58
<211> LENGTH: 16
<212> TYPE: PRT
<213> ORGANISM: Mus musculus
```

```
<400> SEQUENCE: 58

His Ile Trp Trp Asp Asp Val Lys Arg Tyr Asn Pro Val Leu Lys Ser
1               5                   10                  15

<210> SEQ ID NO 59
<211> LENGTH: 14
<212> TYPE: PRT
<213> ORGANISM: Mus musculus

<400> SEQUENCE: 59

Glu Asp Phe Asp Tyr Asp Glu Glu Tyr Tyr Ala Met Asp Tyr
1               5                   10

<210> SEQ ID NO 60
<211> LENGTH: 10
<212> TYPE: PRT
<213> ORGANISM: Mus musculus

<400> SEQUENCE: 60

Ser Ala Ser Ser Ser Val Ser Phe Val Asp
1               5                   10

<210> SEQ ID NO 61
<211> LENGTH: 7
<212> TYPE: PRT
<213> ORGANISM: Mus musculus

<400> SEQUENCE: 61

Arg Thr Ser Asn Leu Gly Phe
1               5

<210> SEQ ID NO 62
<211> LENGTH: 9
<212> TYPE: PRT
<213> ORGANISM: Mus musculus

<400> SEQUENCE: 62

Gln Gln Arg Ser Thr Tyr Pro Pro Thr
1               5

<210> SEQ ID NO 63
<211> LENGTH: 20
<212> TYPE: PRT
<213> ORGANISM: Homo sapiens

<400> SEQUENCE: 63

Cys Gly Pro Ala Arg Leu Leu Pro Asn Ala Ile Gly Arg Gly Lys Trp
1               5                   10                  15

Trp Arg Pro Ser
            20

<210> SEQ ID NO 64
<211> LENGTH: 20
<212> TYPE: PRT
<213> ORGANISM: Homo sapiens

<400> SEQUENCE: 64

Gly Pro Ala Arg Leu Leu Pro Asn Ala Ile Gly Arg Gly Lys Trp Trp
1               5                   10                  15

Arg Pro Ser Gly
            20
```

```
<210> SEQ ID NO 65
<211> LENGTH: 20
<212> TYPE: PRT
<213> ORGANISM: Homo sapiens

<400> SEQUENCE: 65

Pro Ala Arg Leu Leu Pro Asn Ala Ile Gly Arg Gly Lys Trp Trp Arg
1               5                   10                  15

Pro Ser Gly Pro
            20

<210> SEQ ID NO 66
<211> LENGTH: 20
<212> TYPE: PRT
<213> ORGANISM: Homo sapiens

<400> SEQUENCE: 66

Ala Arg Leu Leu Pro Asn Ala Ile Gly Arg Gly Lys Trp Trp Arg Pro
1               5                   10                  15

Ser Gly Pro Asp
            20

<210> SEQ ID NO 67
<211> LENGTH: 20
<212> TYPE: PRT
<213> ORGANISM: Homo sapiens

<400> SEQUENCE: 67

Arg Leu Leu Pro Asn Ala Ile Gly Arg Gly Lys Trp Trp Arg Pro Ser
1               5                   10                  15

Gly Pro Asp Phe
            20

<210> SEQ ID NO 68
<211> LENGTH: 20
<212> TYPE: PRT
<213> ORGANISM: Homo sapiens

<400> SEQUENCE: 68

Leu Leu Pro Asn Ala Ile Gly Arg Gly Lys Trp Trp Arg Pro Ser Gly
1               5                   10                  15

Pro Asp Phe Arg
            20

<210> SEQ ID NO 69
<211> LENGTH: 20
<212> TYPE: PRT
<213> ORGANISM: Homo sapiens

<400> SEQUENCE: 69

Leu Pro Asn Ala Ile Gly Arg Gly Lys Trp Trp Arg Pro Ser Gly Pro
1               5                   10                  15

Asp Phe Arg Cys
            20

<210> SEQ ID NO 70
<211> LENGTH: 14
<212> TYPE: PRT
<213> ORGANISM: Homo sapiens

<400> SEQUENCE: 70

Ser Ala Lys Pro Val Thr Glu Leu Val Cys Ser Gly Gln Cys
1               5                   10
```

<210> SEQ ID NO 71
<211> LENGTH: 7
<212> TYPE: PRT
<213> ORGANISM: Homo sapiens

<400> SEQUENCE: 71

Leu Val Ala Ser Cys Lys Cys
1               5

<210> SEQ ID NO 72
<211> LENGTH: 8
<212> TYPE: PRT
<213> ORGANISM: Homo sapiens

<400> SEQUENCE: 72

Cys Arg Glu Leu His Phe Thr Arg
1               5

<210> SEQ ID NO 73
<211> LENGTH: 7
<212> TYPE: PRT
<213> ORGANISM: Homo sapiens

<400> SEQUENCE: 73

Cys Ile Pro Asp Arg Tyr Arg
1               5

<210> SEQ ID NO 74
<211> LENGTH: 399
<212> TYPE: DNA
<213> ORGANISM: Artificial Sequence
<220> FEATURE:
<223> OTHER INFORMATION: Humanized antibody sequence

<400> SEQUENCE: 74

```
atggacacga gggcccccac tcagctgctg gggctcctgc tgctctggct cccaggtgcc    60
acatttgctc aagttctgac ccagagtcca agcagtctct ccgccagcgt aggcgatcgt   120
gtgactatta cctgtcaatc tagtcagagc gtgtatgata caattggct  ggcgtggtac   180
cagcaaaaac cgggcaaagc cccgaagctg ctcatctatg acgcgtccga tctggctagc   240
ggtgtgccaa gccgtttcag tggcagtggc agcggtactg actttaccct cacaatttcg   300
tctctccagc cggaagattt cgccacttac tattgtcaag gtgcttacaa cgatgtgatt   360
tatgccttcg gtcagggcac taaagtagaa atcaaacgt                          399
```

<210> SEQ ID NO 75
<211> LENGTH: 133
<212> TYPE: PRT
<213> ORGANISM: Artificial Sequence
<220> FEATURE:
<223> OTHER INFORMATION: Humanized antibody sequence

<400> SEQUENCE: 75

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Ser Pro Ser Ser
            20                  25                  30

Leu Ser Ala Ser Val Gly Asp Arg Val Thr Ile Thr Cys Gln Ser Ser
        35                  40                  45

Gln Ser Val Tyr Asp Asn Asn Trp Leu Ala Trp Tyr Gln Gln Lys Pro
    50                  55                  60

Gly Lys Ala Pro Lys Leu Leu Ile Tyr Asp Ala Ser Asp Leu Ala Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gly Ala Tyr Asn Asp Val Ile Tyr Ala Phe Gly Gln Gly Thr Lys
        115                 120                 125

Val Glu Ile Lys Arg
    130

<210> SEQ ID NO 76
<211> LENGTH: 393
<212> TYPE: DNA
<213> ORGANISM: Artificial Sequence
<220> FEATURE:
<223> OTHER INFORMATION: Humanized antibody sequence

<400> SEQUENCE: 76
atggagactg ggctgcgctg gcttctcctg gtcgctgtgc tcaaaggtgt ccactgtgag    60
gtgcagctgt tggagtctgg aggcgggctt gtccagcctg agggagcct gcgtctctct    120 tgtgcagcaa gcggcttcag cttatcctct tactggatga attgggtgcg gcaggcacct    180
gggaagggcc tggagtgggt gggcaccatt gattccggag ccgtacaga ctacgcgtct    240 tgggcaaagg ccgtttcac catttcccgc gacaactcca aaataccat gtacctccag    300 atgaactctc tccgcgcaga ggacacagca cgttattact gtgcacgcaa ctggaatctg    360
tggggtcaag gtactcttgt aacagtctcg agc                                 393

<210> SEQ ID NO 77
<211> LENGTH: 131
<212> TYPE: PRT
<213> ORGANISM: Artificial Sequence
<220> FEATURE:
<223> OTHER INFORMATION: Humanized antibody sequence

<400> SEQUENCE: 77

Met Glu Thr Gly Leu Arg Trp Leu Leu Leu Val Ala Val Leu Lys Gly
1               5                   10                  15

Val His Cys Glu Val Gln Leu Leu Glu Ser Gly Gly Gly Leu Val Gln
                20                  25                  30

Pro Gly Gly Ser Leu Arg Leu Ser Cys Ala Ala Ser Gly Phe Ser Leu
        35                  40                  45

Ser Ser Tyr Trp Met Asn Trp Val Arg Gln Ala Pro Gly Lys Gly Leu
    50                  55                  60

Glu Trp Val Gly Thr Ile Asp Ser Gly Gly Arg Thr Asp Tyr Ala Ser
65                  70                  75                  80

Trp Ala Lys Gly Arg Phe Thr Ile Ser Arg Asp Asn Ser Lys Asn Thr
                85                  90                  95

Met Tyr Leu Gln Met Asn Ser Leu Arg Ala Glu Asp Thr Ala Arg Tyr
            100                 105                 110

Tyr Cys Ala Arg Asn Trp Asn Leu Trp Gly Gln Gly Thr Leu Val Thr
        115                 120                 125

Val Ser Ser
    130

<210> SEQ ID NO 78

```
<211> LENGTH: 11
<212> TYPE: PRT
<213> ORGANISM: Mus musculus

<400> SEQUENCE: 78

Arg Ala Ser Gln Asp Ile Ser Asn Tyr Leu Asn
1               5                   10

<210> SEQ ID NO 79
<211> LENGTH: 7
<212> TYPE: PRT
<213> ORGANISM: Mus musculus

<400> SEQUENCE: 79

Tyr Thr Ser Arg Leu Leu Ser
1               5

<210> SEQ ID NO 80
<211> LENGTH: 9
<212> TYPE: PRT
<213> ORGANISM: Mus musculus

<400> SEQUENCE: 80

Gln Gln Gly Asp Thr Leu Pro Tyr Thr
1               5

<210> SEQ ID NO 81
<211> LENGTH: 11
<212> TYPE: PRT
<213> ORGANISM: Mus musculus

<400> SEQUENCE: 81

Arg Ala Ser Gln Asp Ile Ser Asn Tyr Leu Asn
1               5                   10

<210> SEQ ID NO 82
<211> LENGTH: 24
<212> TYPE: PRT
<213> ORGANISM: Rattus norvegicus

<400> SEQUENCE: 82

Gln Gly Trp Gln Ala Phe Lys Asn Asp Ala Thr Glu Ile Ile Pro Gly
1               5                   10                  15

Leu Arg Glu Tyr Pro Glu Pro Pro
            20

<210> SEQ ID NO 83
<211> LENGTH: 20
<212> TYPE: PRT
<213> ORGANISM: Rattus norvegicus

<400> SEQUENCE: 83

Thr Glu Ile Ile Pro Gly Leu Arg Glu Tyr Pro Glu Pro Pro Gln Glu
1               5                   10                  15

Leu Glu Asn Asn
            20

<210> SEQ ID NO 84
<211> LENGTH: 20
<212> TYPE: PRT
<213> ORGANISM: Rattus norvegicus

<400> SEQUENCE: 84

Pro Glu Pro Pro Gln Glu Leu Glu Asn Asn Gln Thr Met Asn Arg Ala
```

-continued

```
                1               5                  10                  15

Glu Asn Gly Gly
            20

<210> SEQ ID NO 85
<211> LENGTH: 20
<212> TYPE: PRT
<213> ORGANISM: Rattus norvegicus

<400> SEQUENCE: 85

Glu Asn Gly Gly Arg Pro Pro His His Pro Tyr Asp Thr Lys Asp Val
 1               5                  10                  15

Ser Glu Tyr Ser
            20

<210> SEQ ID NO 86
<211> LENGTH: 14
<212> TYPE: PRT
<213> ORGANISM: Rattus norvegicus

<400> SEQUENCE: 86

Cys Arg Glu Leu His Tyr Thr Arg Phe Val Thr Asp Gly Pro
 1               5                  10

<210> SEQ ID NO 87
<211> LENGTH: 25
<212> TYPE: PRT
<213> ORGANISM: Rattus norvegicus

<400> SEQUENCE: 87

Cys Arg Glu Leu His Tyr Thr Arg Phe Val Thr Asp Gly Pro Ser Arg
 1               5                  10                  15

Ser Ala Lys Pro Val Thr Glu Leu Val
            20                  25

<210> SEQ ID NO 88
<211> LENGTH: 23
<212> TYPE: PRT
<213> ORGANISM: Rattus norvegicus

<400> SEQUENCE: 88

Cys Arg Ser Ala Lys Pro Val Thr Glu Leu Val Ser Ser Gly Gln Ser
 1               5                  10                  15

Gly Pro Arg Ala Arg Leu Leu
            20

<210> SEQ ID NO 89
<211> LENGTH: 25
<212> TYPE: PRT
<213> ORGANISM: Rattus norvegicus

<400> SEQUENCE: 89

Cys Gly Pro Ala Arg Leu Leu Pro Asn Ala Ile Gly Arg Val Lys Trp
 1               5                  10                  15

Trp Arg Pro Asn Gly Pro Asp Phe Arg
            20                  25

<210> SEQ ID NO 90
<211> LENGTH: 20
<212> TYPE: PRT
<213> ORGANISM: Rattus norvegicus

<400> SEQUENCE: 90
```

```
Arg Ala Gln Arg Val Gln Leu Leu Cys Pro Gly Gly Ala Ala Pro Arg
 1               5                  10                  15

Ser Arg Lys Val
            20

<210> SEQ ID NO 91
<211> LENGTH: 16
<212> TYPE: PRT
<213> ORGANISM: Rattus norvegicus

<400> SEQUENCE: 91

Pro Gly Gly Ala Ala Pro Arg Ser Arg Lys Val Arg Leu Val Ala Ser
 1               5                  10                  15

<210> SEQ ID NO 92
<211> LENGTH: 23
<212> TYPE: PRT
<213> ORGANISM: Rattus norvegicus

<400> SEQUENCE: 92

Lys Arg Leu Thr Arg Phe His Asn Gln Ser Glu Leu Lys Asp Phe Gly
 1               5                  10                  15

Pro Glu Thr Ala Arg Pro Gln
            20

<210> SEQ ID NO 93
<211> LENGTH: 16
<212> TYPE: PRT
<213> ORGANISM: Rattus norvegicus

<400> SEQUENCE: 93

Ile Pro Asp Arg Tyr Ala Gln Arg Val Gln Leu Leu Ser Pro Gly Gly
 1               5                  10                  15

<210> SEQ ID NO 94
<211> LENGTH: 24
<212> TYPE: PRT
<213> ORGANISM: Rattus norvegicus

<400> SEQUENCE: 94

Ser Glu Leu Lys Asp Phe Gly Pro Glu Thr Ala Arg Pro Gln Lys Gly
 1               5                  10                  15

Arg Lys Pro Arg Pro Arg Ala Arg
            20

<210> SEQ ID NO 95
<211> LENGTH: 23
<212> TYPE: PRT
<213> ORGANISM: Rattus norvegicus

<400> SEQUENCE: 95

Lys Gly Arg Lys Pro Arg Pro Arg Ala Arg Gly Ala Lys Ala Asn Gln
 1               5                  10                  15

Ala Glu Leu Glu Asn Ala Tyr
            20

<210> SEQ ID NO 96
<211> LENGTH: 18
<212> TYPE: PRT
<213> ORGANISM: Rattus norvegicus

<400> SEQUENCE: 96
```

```
Pro Asn Ala Ile Gly Arg Val Lys Trp Trp Arg Pro Asn Gly Pro Asp
1               5                   10                  15

Phe Arg

<210> SEQ ID NO 97
<211> LENGTH: 22
<212> TYPE: PRT
<213> ORGANISM: Rattus norvegicus

<400> SEQUENCE: 97

Lys Trp Trp Arg Pro Asn Gly Pro Asp Phe Arg Cys Ile Pro Asp Arg
1               5                   10                  15

Tyr Arg Ala Gln Arg Val
            20

<210> SEQ ID NO 98
<211> LENGTH: 213
<212> TYPE: PRT
<213> ORGANISM: Rattus norvegicus

<400> SEQUENCE: 98

Met Gln Leu Ser Leu Ala Pro Cys Leu Ala Cys Leu Leu Val His Ala
1               5                   10                  15

Ala Phe Val Ala Val Glu Ser Gln Gly Trp Gln Ala Phe Lys Asn Asp
            20                  25                  30

Ala Thr Glu Ile Ile Pro Gly Leu Arg Glu Tyr Pro Glu Pro Pro Gln
        35                  40                  45

Glu Leu Glu Asn Asn Gln Thr Met Asn Arg Ala Glu Asn Gly Gly Arg
    50                  55                  60

Pro Pro His His Pro Tyr Asp Thr Lys Asp Val Ser Glu Tyr Ser Cys
65                  70                  75                  80

Arg Glu Leu His Tyr Thr Arg Phe Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Val Lys Trp Trp Arg Pro Asn
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Ala Ala Pro Arg Ser Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Pro Glu Thr Ala Arg Pro Gln Lys Gly
            180                 185                 190

Arg Lys Pro Arg Pro Arg Ala Arg Gly Ala Lys Ala Asn Gln Ala Glu
        195                 200                 205

Leu Glu Asn Ala Tyr
    210

<210> SEQ ID NO 99
<211> LENGTH: 7
<212> TYPE: PRT
<213> ORGANISM: Mus musculus

<400> SEQUENCE: 99

Tyr Thr Ser Arg Leu His Ser
1               5
```

```
<210> SEQ ID NO 100
<211> LENGTH: 9
<212> TYPE: PRT
<213> ORGANISM: Mus musculus

<400> SEQUENCE: 100

Gln Gln Gly Asp Thr Leu Pro Tyr Thr
1               5

<210> SEQ ID NO 101
<211> LENGTH: 11
<212> TYPE: PRT
<213> ORGANISM: Mus musculus

<400> SEQUENCE: 101

Arg Ala Ser Gln Val Ile Thr Asn Tyr Leu Tyr
1               5                   10

<210> SEQ ID NO 102
<211> LENGTH: 7
<212> TYPE: PRT
<213> ORGANISM: Mus musculus

<400> SEQUENCE: 102

Tyr Thr Ser Arg Leu His Ser
1               5

<210> SEQ ID NO 103
<211> LENGTH: 9
<212> TYPE: PRT
<213> ORGANISM: Mus musculus

<400> SEQUENCE: 103

Gln Gln Gly Asp Thr Leu Pro Tyr Thr
1               5

<210> SEQ ID NO 104
<211> LENGTH: 11
<212> TYPE: PRT
<213> ORGANISM: Mus musculus

<400> SEQUENCE: 104

Arg Ala Ser Gln Asp Ile Ser Asn Tyr Leu Asn
1               5                   10

<210> SEQ ID NO 105
<211> LENGTH: 7
<212> TYPE: PRT
<213> ORGANISM: Mus musculus

<400> SEQUENCE: 105

Tyr Thr Ser Arg Leu Leu Ser
1               5

<210> SEQ ID NO 106
<211> LENGTH: 9
<212> TYPE: PRT
<213> ORGANISM: Mus musculus

<400> SEQUENCE: 106

Gln Gln Gly Asp Thr Leu Pro Tyr Thr
1               5
```

```
<210> SEQ ID NO 107
<211> LENGTH: 11
<212> TYPE: PRT
<213> ORGANISM: Mus musculus

<400> SEQUENCE: 107

Arg Ala Ser Gln Asp Ile Ser Asn Tyr Leu Asn
1               5                   10

<210> SEQ ID NO 108
<211> LENGTH: 7
<212> TYPE: PRT
<213> ORGANISM: Mus musculus

<400> SEQUENCE: 108

Tyr Thr Ser Arg Leu Phe Ser
1               5

<210> SEQ ID NO 109
<211> LENGTH: 9
<212> TYPE: PRT
<213> ORGANISM: Mus musculus

<400> SEQUENCE: 109

Gln Gln Gly Asp Thr Leu Pro Tyr Thr
1               5

<210> SEQ ID NO 110
<211> LENGTH: 11
<212> TYPE: PRT
<213> ORGANISM: Mus musculus

<400> SEQUENCE: 110

Arg Ala Ser Gln Asp Ile Ser Asn Tyr Leu Asn
1               5                   10

<210> SEQ ID NO 111
<211> LENGTH: 7
<212> TYPE: PRT
<213> ORGANISM: Mus musculus

<400> SEQUENCE: 111

Tyr Thr Ser Arg Leu Leu Ser
1               5

<210> SEQ ID NO 112
<211> LENGTH: 9
<212> TYPE: PRT
<213> ORGANISM: Mus musculus

<400> SEQUENCE: 112

Gln Gln Gly Asp Thr Leu Pro Tyr Thr
1               5

<210> SEQ ID NO 113
<211> LENGTH: 11
<212> TYPE: PRT
<213> ORGANISM: Mus musculus

<400> SEQUENCE: 113

Arg Ala Ser Gln Asp Ile Ser Asn Tyr Leu Asn
1               5                   10

<210> SEQ ID NO 114
<211> LENGTH: 7
```

```
<212> TYPE: PRT
<213> ORGANISM: Mus musculus

<400> SEQUENCE: 114

Tyr Thr Ser Thr Leu Gln Ser
 1               5

<210> SEQ ID NO 115
<211> LENGTH: 9
<212> TYPE: PRT
<213> ORGANISM: Mus musculus

<400> SEQUENCE: 115

Gln Gln Gly Asp Thr Leu Pro Tyr Thr
 1               5

<210> SEQ ID NO 116
<211> LENGTH: 12
<212> TYPE: PRT
<213> ORGANISM: Mus musculus

<400> SEQUENCE: 116

Ser Val Ser Ser Ser Ile Ser Ser Ser Asn Leu His
 1               5                  10

<210> SEQ ID NO 117
<211> LENGTH: 213
<212> TYPE: PRT
<213> ORGANISM: Mus musculus

<400> SEQUENCE: 117

Gln Ile Val Leu Ser Gln Ser Pro Ala Ile Leu Ser Thr Ser Pro Gly
 1               5                  10                  15

Glu Lys Val Thr Met Thr Cys Arg Ala Ser Ser Ser Val Tyr Tyr Met
                20                  25                  30

His Trp Tyr Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Thr Arg Val Glu Ala Glu
 65                  70                  75                  80

Asp Ala Ala Thr Tyr Tyr Cys Gln Gln Trp Ser Ser Asp Pro Leu Thr
                 85                 90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

<210> SEQ ID NO 118
<211> LENGTH: 642
<212> TYPE: DNA
<213> ORGANISM: Mus musculus

<400> SEQUENCE: 118

```
caaattgttc tctcccagtc tccagcaatc ctgtctacat ctccagggga gaaggtcaca    60
atgacttgca gggccagctc aagtgtatat tacatgcact ggtaccagca gaagccagga   120
tcctccccca aaccctggat ttatgccaca tccaacctgg cttctggagt ccctgttcgc   180
ttcagtggca gtgggtctgg gacctcttac tctctcacaa tcaccagagt ggaggctgaa   240
gatgctgcca cttattactg ccagcagtgg agtagtgacc cactcacgtt cggtgctggg   300
accaagctgg agctgaaacg ggctgatgct gcaccaactg tatccatctt cccaccatcc   360
agtgagcagt taacatctgg aggtgcctca gtcgtgtgct tcttgaacaa cttctacccc   420
aaagacatca atgtcaagtg gaagattgat ggcagtgaac gacaaaatgg cgtcctgaac   480
agttggactg atcaggacag caaagacagc acctacagca tgagcagcac cctcacgttg   540
accaaggacg agtatgaacg cataacagc tatacctgtg aggccactca caagacatca   600
acttcacccca ttgtcaagag cttcaacagg aatgagtgtt ag                    642
```

<210> SEQ ID NO 119
<211> LENGTH: 235
<212> TYPE: PRT
<213> ORGANISM: Mus musculus

<400> SEQUENCE: 119

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Thr Ser Pro Gly Glu Lys Val Thr Met Thr Cys Arg Ala Ser
        35                  40                  45

Ser Ser Val Tyr Tyr Met His Trp Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Thr Arg Val Glu Ala Glu Asp Ala Ala Thr Tyr Tyr Cys Gln Gln Trp
            100                 105                 110

Ser Ser Asp Pro Leu Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser

```
                210                 215                 220
Pro Ile Val Lys Ser Phe Asn Arg Asn Glu Cys
225                 230                 235

<210> SEQ ID NO 120
<211> LENGTH: 708
<212> TYPE: DNA
<213> ORGANISM: Mus musculus

<400> SEQUENCE: 120 atggatttc  aagtgcagat  tttcagcttc  ctgctaatca  gtgcttcagt  cattatgtcc      60
aggggacaaa  ttgttctctc  ccagtctcca  gcaatcctgt  ctacatctcc  aggggagaag     120
gtcacaatga  cttgcagggc  cagctcaagt  gtatattaca  tgcactggta  ccagcagaag     180
ccaggatcct  cccccaaacc  ctggatttat  gccacatcca  acctggcttc  tggagtccct     240
gttcgcttca  gtggcagtgg  gtctgggacc  tcttactctc  tcacaatcac  cagagtggag     300
gctgaagatg  ctgccactta  ttactgccag  cagtggagta  gtgacccact  cacgttcggt     360
gctgggacca  agctggagct  gaaacgggct  gatgctgcac  caactgtatc  catcttccca     420
ccatccagtg  agcagttaac  atctggaggt  gcctcagtcg  tgtgcttctt  gaacaacttc     480
taccccaaag  acatcaatgt  caagtggaag  attgatggca  gtgaacgaca  aaatggcgtc     540
ctgaacagtt  ggactgatca  ggacagcaaa  gacagcacct  acagcatgag  cagcacctc     600 acgttgacca  aggacgagta  tgaacgacat  aacagctata  cctgtgaggc  cactcacaag     660
acatcaactt  cacccattgt  caagagcttc  aacaggaatg  agtgttag                  708

<210> SEQ ID NO 121
<211> LENGTH: 445
<212> TYPE: PRT
<213> ORGANISM: Mus musculus

<400> SEQUENCE: 121

Glu Val Gln Val Gln Gln Ser Gly Pro Glu Leu Val Lys Pro Gly Ala
 1               5                  10                  15

Ser Val Lys Leu Ser Cys Thr Ala Ser Gly Phe Asn Ile Lys Asp Tyr
            20                  25                  30

Phe Ile His Trp Val Lys Gln Arg Pro Glu Gln Gly Leu Glu Trp Ile
        35                  40                  45

Gly Arg Leu Asp Pro Glu Asp Gly Glu Ser Asp Tyr Ala Pro Lys Phe
    50                  55                  60

Gln Asp Lys Ala Ile Met Thr Ala Asp Thr Ser Asn Thr Ala Tyr
65                  70                  75                  80

Leu Gln Leu Arg Ser Leu Thr Ser Glu Asp Thr Ala Ile Tyr Tyr Cys
                85                  90                  95

Glu Arg Glu Asp Tyr Asp Gly Thr Tyr Thr Phe Phe Pro Tyr Trp Gly
            100                 105                 110

Gln Gly Thr Leu Val Thr Val Ser Ala Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
```

```
                180                 185                 190
Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
        210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
                260                 265                 270

Phe Ser Trp Phe Val Asp Asp Val Glu Val His Thr Ala Gln Thr Gln
            275                 280                 285

Pro Arg Glu Glu Gln Phe Asn Ser Thr Phe Arg Ser Val Ser Glu Leu
        290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Ile Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445

<210> SEQ ID NO 122
<211> LENGTH: 1338
<212> TYPE: DNA
<213> ORGANISM: Mus musculus

<400> SEQUENCE: 122
gaggttcagg tgcagcagtc tgggccagaa cttgtgaagc caggggcctc agtcaagttg      60
tcctgcacag cttctggctt caacattaaa gactacttta cactgggt gaagcagagg       120 cctgaacagg gcctggagtg gattggaagg cttgatcctg aggatggtga aagtgattat      180
gccccgaagt tccaggacaa ggccattatg acagcagaca catcatccaa cacagcctat     240
cttcagctca gaagcctgac atctgaggac actgccatct attattgtga gagaggac       300 tacgatggta cctacacctt ttttccttac tggggccaag ggactctggt cactgtctct     360
gcagccaaaa cgaccccccc atctgtctat ccactggccc ctggatctgc tgcccaaact     420
aactccatgg tgaccctggg atgcctggtc aagggctatt tccctgagcc agtgacagtg     480
acctggaact ctggatccct gtccagcggt gtgcacacct tcccagctgt cctgcagtct     540
gacctctaca ctctgagcag ctcagtgact gtccccctcca gcacctggcc cagcgagacc    600
gtcacctgca acgttgccca cccggccagc agcaccaagg tggacaagaa aattgtgccc    660
```

-continued

```
agggattgtg gttgtaagcc ttgcatatgt acagtcccag aagtatcatc tgtcttcatc    720
ttccccccaa agcccaagga tgtgctcacc attactctga ctcctaaggt cacgtgtgtt    780
gtggtagaca tcagcaagga tgatcccgag gtccagttca gctggtttgt agatgatgtg    840
gaggtgcaca cagctcagac gcaaccccgg gaggagcagt tcaacagcac tttccgctca    900
gtcagtgaac ttcccatcat gcaccaggac tggctcaatg gcaaggagtt caaatgcagg    960
gtcaacagtg cagctttccc tgcccccatc gagaaaacca tctccaaaac caaaggcaga    1020
ccgaaggctc cacaggtgta caccattcca cctcccaagg agcagatggc caaggataaa    1080
gtcagtctga cctgcatgat aacagacttc ttccctgaag acattactgt ggagtggcag    1140
tggaatgggc agccagcgga gaactacaag aacactcagc ccatcatgga cacagatggc    1200
tcttacttca tctacagcaa gctcaatgtg cagaagagca actgggaggc aggaaatact    1260
ttcacctgct ctgtgttaca tgagggcctg cacaaccacc atactgagaa gagcctctcc    1320
cactctcctg gtaaatga                                                   1338
```

<210> SEQ ID NO 123
<211> LENGTH: 464
<212> TYPE: PRT
<213> ORGANISM: Mus musculus

<400> SEQUENCE: 123

```
Met Lys Cys Ser Trp Val Ile Phe Phe Leu Met Ala Val Val Thr Gly
  1               5                  10                  15

Val Asn Ser Glu Val Gln Val Gln Gln Ser Gly Pro Glu Leu Val Lys
             20                  25                  30

Pro Gly Ala Ser Val Lys Leu Ser Cys Thr Ala Ser Gly Phe Asn Ile
         35                  40                  45

Lys Asp Tyr Phe Ile His Trp Val Lys Gln Arg Pro Glu Gln Gly Leu
     50                  55                  60

Glu Trp Ile Gly Arg Leu Asp Pro Glu Asp Gly Glu Ser Asp Tyr Ala
 65                  70                  75                  80

Pro Lys Phe Gln Asp Lys Ala Ile Met Thr Ala Asp Thr Ser Ser Asn
                 85                  90                  95

Thr Ala Tyr Leu Gln Leu Arg Ser Leu Thr Ser Glu Asp Thr Ala Ile
            100                 105                 110

Tyr Tyr Cys Glu Arg Glu Asp Tyr Asp Gly Thr Tyr Thr Phe Phe Pro
        115                 120                 125

Tyr Trp Gly Gln Gly Thr Leu Val Thr Val Ser Ala Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
```

```
                245                 250                 255
Val Phe Ile Phe Pro Pro Lys Pro Lys Asp Val Leu Thr Ile Thr Leu
            260                 265                 270

Thr Pro Lys Val Thr Cys Val Val Asp Ile Ser Lys Asp Asp Pro
            275                 280                 285

Glu Val Gln Phe Ser Trp Phe Val Asp Asp Val Glu Val His Thr Ala
            290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
            355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
            405                 410                 415

Thr Asp Gly Ser Tyr Phe Ile Tyr Ser Lys Leu Asn Val Gln Lys Ser
            420                 425                 430

Asn Trp Glu Ala Gly Asn Thr Phe Thr Cys Ser Val Leu His Glu Gly
            435                 440                 445

Leu His Asn His His Thr Glu Lys Ser Leu Ser His Ser Pro Gly Lys
    450                 455                 460

<210> SEQ ID NO 124
<211> LENGTH: 1395
<212> TYPE: DNA
<213> ORGANISM: Mus musculus

<400> SEQUENCE: 124
atgaaatgca gctgggtcat cttcttcctg atggcagtgg ttacaggggt caattcagag    60
gttcaggtgc agcagtctgg ccagaacttg tgaagccag ggcctcagt caagttgtcc    120 tgcacagctt ctggcttcaa cattaaagac tactttatac actgggtgaa gcagaggcct    180
gaacagggcc tggagtggat tggaaggctt gatcctgagg atggtgaaag tgattatgcc    240
ccgaagttcc aggacaaggc cattatgaca gcagacacat catccaacac agcctatctt    300
cagctcagaa gcctgacatc tgaggacact gccatctatt attgtgagag agaggactac    360 gatggtaccta caccttttt tccttactgg ggccaaggga ctctggtcac tgtctctgca    420
gccaaaacga cacccccatc tgtctatcca ctggcccctg gatctgctgc ccaaactaac    480
tccatggtga ccctgggatg cctggtcaag ggctatttcc ctgagccagt gacagtgacc    540
tggaactctg gatccctgtc agcggtgtg cacaccttcc cagctgtcct gcagtctgac    600
ctctacactc tgagcagctc agtgactgtc ccctccagca cctggcccag cgagaccgtc    660
acctgcaacg ttgcccaccc ggccagcagc accaaggtgg acaagaaaat tgtgcccagg    720
gattgtggtt gtaagccttg catatgtaca gtcccagaag tatcatctgt cttcatcttc    780
cccccaaagc caaggatgt gctcaccatt actctgactc taaggtcac gtgtgttgtg    840 gtagacatca gcaaggatga tcccgaggtc cagttcagct ggtttgtaga tgatgtggag    900
```

```
gtgcacacag ctcagacgca accccgggag gagcagttca acagcacttt ccgctcagtc    960
agtgaacttc ccatcatgca ccaggactgg ctcaatggca aggagttcaa atgcagggtc   1020
aacagtgcag cttttccctgc ccccatcgag aaaaccatct ccaaaaccaa aggcagaccg   1080
aaggctccac aggtgtacac cattccacct cccaaggagc agatggccaa ggataaagtc   1140
agtctgacct gcatgataac agacttcttc cctgaagaca ttactgtgga gtggcagtgg   1200
aatgggcagc cagcggagaa ctacaagaac actcagccca tcatggacac agatggctct   1260
tacttcatct acagcaagct caatgtgcag aagagcaact gggaggcagg aaatactttc   1320
acctgctctg tgttacatga gggcctgcac aaccaccata ctgagaagag cctctcccac   1380
tctcctggta aatga                                                    1395

<210> SEQ ID NO 125
<211> LENGTH: 215
<212> TYPE: PRT
<213> ORGANISM: Mus musculus

<400> SEQUENCE: 125

Glu Ile Val Leu Thr Gln Ser Pro Ala Leu Met Ala Ala Ser Pro Gly
 1               5                  10                  15

Glu Lys Val Thr Ile Thr Cys Ser Val Ser Ser Thr Ile Ser Ser Asn
            20                  25                  30

His Leu His Trp Phe Gln Gln Lys Ser Asp Thr Ser Pro Lys Pro Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Leu Thr Phe Gly Ala Gly Thr Lys Leu Glu Leu Arg Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215

<210> SEQ ID NO 126
<211> LENGTH: 648
<212> TYPE: DNA
<213> ORGANISM: Mus musculus

<400> SEQUENCE: 126
gaaattgtgc tcacccagtc tccagcactc atggctgcat ctcgggggga gaaggtcacc     60
atcacctgca gtgtcagttc aactataagt tccaaccact gcactggttt ccagcagaag    120
```

-continued

```
tcagacacct cccccaaacc ctggatttat ggcacatcca acctggcttc tggagtccct    180
gttcgcttca gtggcagtgg atctgggacc tcttattctc tcacaatcag cagcatggag    240
gctgaggatg ctgccactta ttactgtcaa cagtggagta gttacccact cacgttcggc    300
gctgggacca agctggagct gagacgggct gatgctgcac caactgtatc catcttccca    360
ccatccagtg agcagttaac atctggaggt gcctcagtcg tgtgcttctt gaacaacttc    420
taccccaaag acatcaatgt caagtggaag attgatggca gtgaacgaca aaatggcgtc    480
ctgaacagtt ggactgatca ggacagcaaa gacagcacct acagcatgag cagcaccctc    540
acgttgacca aggacgagta tgaacgacat aacagctata cctgtgaggc cactcacaag    600
acatcaactt cacccattgt caagagcttc aacaggaatg agtgttag                 648
```

<210> SEQ ID NO 127
<211> LENGTH: 237
<212> TYPE: PRT
<213> ORGANISM: Mus musculus

<400> SEQUENCE: 127

```
Met Asp Phe His Val Gln Ile Phe Ser Phe Met Leu Ile Ser Val Thr
  1               5                  10                  15

Val Ile Leu Ser Ser Gly Glu Ile Val Leu Thr Gln Ser Pro Ala Leu
             20                  25                  30

Met Ala Ala Ser Pro Gly Glu Lys Val Thr Ile Thr Cys Ser Val Ser
         35                  40                  45

Ser Thr Ile Ser Ser Asn His Leu His Trp Phe Gln Gln Lys Ser Asp
     50                  55                  60

Thr Ser Pro Lys Pro Trp Ile Tyr Gly Thr Ser Asn Leu Ala Ser Gly
 65                  70                  75                  80

Val Pro Val Arg Phe Ser Gly Ser Gly Ser Gly Thr Ser Tyr Ser Leu
                 85                  90                  95

Thr Ile Ser Ser Met Glu Ala Glu Asp Ala Ala Thr Tyr Tyr Cys Gln
            100                 105                 110

Gln Trp Ser Ser Tyr Pro Leu Thr Phe Gly Ala Gly Thr Lys Leu Glu
        115                 120                 125

Leu Arg Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235
```

<210> SEQ ID NO 128
<211> LENGTH: 714
<212> TYPE: DNA
<213> ORGANISM: Mus musculus

<400> SEQUENCE: 128

-continued

```
atggattttc atgtgcagat tttcagcttc atgctaatca gtgtcacagt cattttgtcc    60
agtggagaaa ttgtgctcac ccagtctcca gcactcatgg ctgcatctcc ggggagaag    120
gtcaccatca cctgcagtgt cagttcaact ataagttcca accacttgca ctggttccag   180
cagaagtcag acacctcccc caaaccctgg atttatggca catccaacct ggcttctgga   240
gtccctgttc gcttcagtgg cagtggatct gggacctctt attctctcac aatcagcagc   300
atggaggctg aggatgctgc cacttattac tgtcaacagt ggagtagtta cccactcacg   360
ttcggcgctg ggaccaagct ggagctgaga cgggctgatg ctgcaccaac tgtatccatc   420
ttcccaccat ccagtgagca gttaacatct ggaggtgcct cagtcgtgtg cttcttgaac   480
aacttctacc ccaaagacat caatgtcaag tggaagattg atggcagtga acgacaaaat   540
ggcgtcctga acagttggac tgatcaggac agcaaagaca gcacctacag catgagcagc   600
acccacgt tgaccaagga cgagtatgaa cgacataaca gctatacctg tgaggccact   660
cacaagacat caacttcacc cattgtcaag agcttcaaca ggaatgagtg ttag        714
```

<210> SEQ ID NO 129
<211> LENGTH: 449
<212> TYPE: PRT
<213> ORGANISM: Mus musculus

<400> SEQUENCE: 129

```
Glu Val Gln Leu Gln Gln Ser Gly Ala Glu Leu Val Arg Pro Gly Ala
 1               5                  10                  15

Leu Val Lys Leu Ser Cys Thr Ala Ser Asp Phe Asn Ile Lys Asp Phe
            20                  25                  30

Tyr Leu His Trp Met Arg Gln Arg Pro Glu Gln Gly Leu Asp Trp Ile
        35                  40                  45

Gly Arg Ile Asp Pro Glu Asn Gly Asp Thr Leu Tyr Asp Pro Lys Phe
    50                  55                  60

Gln Asp Lys Ala Thr Leu Thr Thr Asp Thr Ser Ser Asn Thr Ala Tyr
65                  70                  75                  80

Leu Gln Leu Ser Gly Leu Thr Ser Glu Thr Thr Ala Val Tyr Tyr Cys
                85                  90                  95

Ser Arg Glu Ala Asp Tyr Phe His Asp Gly Thr Ser Tyr Trp Tyr Phe
            100                 105                 110

Asp Val Trp Gly Ala Gly Thr Thr Ile Thr Val Ser Ser Ala Lys Thr
        115                 120                 125

Thr Pro Pro Ser Val Tyr Pro Leu Ala Pro Gly Ser Ala Ala Gln Thr
    130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205

Val Ala His Pro Ala Ser Ser Thr Lys Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
```

```
            245                 250                 255
Leu Thr Pro Lys Val Thr Cys Val Val Asp Ile Ser Lys Asp Asp
            260                 265                 270

Pro Glu Val Gln Phe Ser Trp Phe Val Asp Asp Val Glu Val His Thr
            275                 280                 285

Ala Gln Thr Gln Pro Arg Glu Glu Gln Phe Asn Ser Thr Phe Arg Ser
        290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
            340                 345                 350

Ile Pro Pro Pro Lys Glu Gln Met Ala Lys Asp Lys Val Ser Leu Thr
            355                 360                 365

Cys Met Ile Thr Asp Phe Phe Pro Glu Asp Ile Thr Val Glu Trp Gln
        370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Ile Tyr Ser Lys Leu Asn Val Gln Lys
                405                 410                 415

Ser Asn Trp Glu Ala Gly Asn Thr Phe Thr Cys Ser Val Leu His Glu
            420                 425                 430

Gly Leu His Asn His His Thr Glu Lys Ser Leu Ser His Ser Pro Gly
            435                 440                 445

Lys

<210> SEQ ID NO 130
<211> LENGTH: 1350
<212> TYPE: DNA
<213> ORGANISM: Mus musculus

<400> SEQUENCE: 130
gaggttcagc tgcagcagtc tggggctgaa cttgtgaggc caggggcctt agtcaagttg      60
tcctgcacag cttctgactt caacattaaa gacttctatc tacactggat gaggcagcgg     120
cctgaacagg gcctggactg gattggaagg attgatcctg agaatggtga tactttatat     180
gacccgaagt tccaggacaa ggccactctt acaacagaca catcctccaa cacagcctac     240
ctgcagctca gcggcctgac atctgagacc actgccgtct attactgttc tagagaggcg     300
gattatttcc acgatggtac ctcctactgg tacttcgatg tctggggcgc agggaccaca     360
atcaccgtct cctcagccaa acgacacccc catctgtctc tccactggcc cctggatct     420 gctgcccaaa ctaactccat ggtgaccctg ggatgcctgg tcaagggcta tttccctgag     480
ccagtgacag tgacctggaa ctctggatcc ctgtccagcg tgtgcacac cttcccagct     540 gtcctgcagt ctgacctcta cactctgagc agctcagtga ctgtcccctc agcacctgg     600 cccagcgaga ccgtcacctg caacgttgcc cacccggcca gcagcaccaa ggtggacaag     660
aaaattgtgc ccagggattg tggttgtaag ccttgcatat gtacagtccc agaagtatca     720
tctgtcttca tcttcccccc aaagcccaag gatgtgctca ccattactct gactcctaag     780
gtcacgtgtg ttgtggtaga catcagcaag gatgatcccg aggtccagtt cagctggttt     840
gtagatgatg tggaggtgca cacagctcag acgcaacccc gggaggagca gttcaacagc     900
actttccgct cagtcagtga acttcccatc atgcaccagg actggctcaa tggcaaggag     960
```

```
ttcaaatgca gggtcaacag tgcagctttc cctgccccca tcgagaaaac catctccaaa    1020
accaaaggca gaccgaaggc tccacaggtg tacaccattc cacctcccaa ggagcagatg    1080
gccaaggata aagtcagtct gacctgcatg ataacagact tcttccctga agacattact    1140
gtggagtggc agtggaatgg gcagccagcg agaactaca agaacactca gcccatcatg    1200
gacacagatg gctcttactt catctacagc aagctcaatg tgcagaagag caactgggag    1260
gcaggaaata ctttcacctg ctctgtgtta catgagggcc tgcacaacca ccatactgag    1320
aagagcctct cccactctcc tggtaaatga                                    1350
```

<210> SEQ ID NO 131
<211> LENGTH: 468
<212> TYPE: PRT
<213> ORGANISM: Mus musculus

<400> SEQUENCE: 131

```
Met Lys Cys Ser Trp Val Ile Phe Phe Leu Met Ala Val Val Thr Gly
 1               5                   10                  15

Val Asn Ser Glu Val Gln Leu Gln Gln Ser Gly Ala Glu Leu Val Arg
            20                  25                  30

Pro Gly Ala Leu Val Lys Leu Ser Cys Thr Ala Ser Asp Phe Asn Ile
        35                  40                  45

Lys Asp Phe Tyr Leu His Trp Met Arg Gln Arg Pro Glu Gln Gly Leu
    50                  55                  60

Asp Trp Ile Gly Arg Ile Asp Pro Glu Asn Gly Asp Thr Leu Tyr Asp
65                  70                  75                  80

Pro Lys Phe Gln Asp Lys Ala Thr Leu Thr Thr Asp Thr Ser Ser Asn
                85                  90                  95

Thr Ala Tyr Leu Gln Leu Ser Gly Leu Thr Ser Glu Thr Thr Ala Val
            100                 105                 110

Tyr Tyr Cys Ser Arg Glu Ala Asp Tyr Phe His Asp Gly Thr Ser Tyr
        115                 120                 125

Trp Tyr Phe Asp Val Trp Gly Ala Gly Thr Thr Ile Thr Val Ser Ser
    130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
    210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
            260                 265                 270

Thr Ile Thr Leu Thr Pro Lys Val Thr Cys Val Val Val Asp Ile Ser
        275                 280                 285

Lys Asp Asp Pro Glu Val Gln Phe Ser Trp Phe Val Asp Asp Val Glu
    290                 295                 300
```

```
Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
                325                 330                 335

Gly Lys Glu Phe Lys Cys Arg Val Asn Ser Ala Ala Phe Pro Ala Pro
            340                 345                 350

Ile Glu Lys Thr Ile Ser Lys Thr Lys Gly Arg Pro Lys Ala Pro Gln
        355                 360                 365

Val Tyr Thr Ile Pro Pro Lys Glu Gln Met Ala Lys Asp Lys Val
    370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
                405                 410                 415

Pro Ile Met Asp Thr Asp Gly Ser Tyr Phe Ile Tyr Ser Lys Leu Asn
            420                 425                 430

Val Gln Lys Ser Asn Trp Glu Ala Gly Asn Thr Phe Thr Cys Ser Val
        435                 440                 445

Leu His Glu Gly Leu His Asn His His Thr Glu Lys Ser Leu Ser His
    450                 455                 460

Ser Pro Gly Lys
465

<210> SEQ ID NO 132
<211> LENGTH: 1407
<212> TYPE: DNA
<213> ORGANISM: Mus musculus

<400> SEQUENCE: 132
atgaaatgca gctgggtcat cttcttcctg atggcagtgg ttacaggggt caattcagag      60
gttcagctgc agcagtctgg ggctgaactt gtgaggccag ggccttagt caagttgtcc     120 tgcacagctt ctgacttcaa cattaaagac ttctatctac actggatgag gcagcggcct     180
gaacagggcc tggactggat tggaaggatt gatcctgaga atggtgatac tttatatgac     240
ccgaagttcc aggacaaggc cactcttaca acagacacat cctccaacac agcctacctg     300
cagctcagcg gcctgacatc tgagaccact gccgtctatt actgttctag agaggcggat     360
tatttccacg atggtacctc ctactggtac ttcgatgtct ggggcgcagg gaccacaatc     420
accgtctcct cagccaaaac gacaccccca tctgtctatc cactggcccc tggatctgct     480
gcccaaacta actccatggt gaccctggga tgcctggtca agggctattt ccctgagcca     540
gtgacagtga cctggaactc tggatccctg tccagcggtg tgcacacctt cccagctgtc     600
ctgcagtctg acctctacac tctgagcagc tcagtgactg tcccctccag cacctggccc     660
agcgagaccg tcacctgcaa cgttgcccac ccggccagca gcaccaaggt ggacaagaaa     720
attgtgccca gggattgtgg ttgtaagcct tgcatatgta cagtcccaga agtatcatct     780
gtcttcatct tcccccaaa gcccaaggat gtgctcacca ttactctgac tcctaaggtc     840
acgtgtgttg tggtagacat cagcaaggat gatcccgagg tccagttcag ctggtttgta     900
gatgatgtgg aggtgcacac agctcagacg caaccccggg aggagcagtt caacagcact     960
ttccgctcag tcagtgaact tcccatcatg caccaggact ggctcaatgg caaggagttc    1020
aaatgcaggg tcaacagtgc agcttttcct gcccccatcg agaaaaccat ctccaaaacc    1080
aaaggcagac cgaaggctcc acaggtgtac accattccac ctccaaggga gcagatggcc    1140
```

```
aaggataaag tcagtctgac ctgcatgata acagacttct tccctgaaga cattactgtg    1200
gagtggcagt ggaatgggca gccagcgag  aactacaaga acactcagcc catcatggac    1260
acagatggct cttacttcat ctacagcaag ctcaatgtgc agaagagcaa ctgggaggca    1320
ggaaatactt tcacctgctc tgtgttacat gagggcctgc acaaccacca tactgagaag    1380
agcctctccc actctcctgg taaatga                                        1407
```

<210> SEQ ID NO 133
<211> LENGTH: 214
<212> TYPE: PRT
<213> ORGANISM: Mus musculus

<400> SEQUENCE: 133

```
Asp Ile Gln Met Thr Gln Ile Thr Ser Ser Leu Ser Ala Ser Leu Gly
  1               5                  10                  15

Asp Arg Val Ser Ile Ser Cys Arg Ala Ser Gln Asp Ile Ser Asn Tyr
             20                  25                  30

Leu Asn Trp Tyr Gln Gln Lys Pro Asp Gly Thr Phe Lys Leu Leu Ile
         35                  40                  45

Phe Tyr Thr Ser Arg Leu Leu Ser Gly Val Pro Ser Arg Phe Ser Gly
     50                  55                  60

Ser Gly Ser Gly Thr Asp Tyr Ser Leu Thr Ile Tyr Asn Leu Glu Gln
 65                  70                  75                  80

Glu Asp Phe Ala Thr Tyr Phe Cys Gln Gln Gly Asp Thr Leu Pro Tyr
                 85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 134
<211> LENGTH: 645
<212> TYPE: DNA
<213> ORGANISM: Mus musculus

<400> SEQUENCE: 134

```
gatatccaga tgacacagat tacatcctcc ctgtctgcct ctctgggaga cagggtctcc     60
atcagttgca gggcaagtca agacattagc aattatttaa actggtatca gcagaaacca    120
gatggaactt ttaaactcct tatcttctac acatcaagat tactctcagg agtcccatca    180
aggttcagtg gcagtgggtc tggaacagat tattctctca ccatttacaa cctggagcaa    240
gaagattttg ccacttactt ttgccaacag ggagatacgc ttccgtacac tttcggaggg    300
```

```
gggaccaagc tggaaataaa acgggctgat gctgcaccaa ctgtatccat cttcccacca    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gttag                    645
```

<210> SEQ ID NO 135
<211> LENGTH: 234
<212> TYPE: PRT
<213> ORGANISM: Mus musculus

<400> SEQUENCE: 135

```
Met Met Ser Ser Ala Gln Phe Leu Gly Leu Leu Leu Cys Phe Gln
 1               5                  10                  15

Gly Thr Arg Cys Asp Ile Gln Met Thr Gln Ile Thr Ser Ser Leu Ser
                20                  25                  30

Ala Ser Leu Gly Asp Arg Val Ser Ile Ser Cys Arg Ala Ser Gln Asp
            35                  40                  45

Ile Ser Asn Tyr Leu Asn Trp Tyr Gln Gln Lys Pro Asp Gly Thr Phe
        50                  55                  60

Lys Leu Leu Ile Phe Tyr Thr Ser Arg Leu Leu Ser Gly Val Pro Ser
 65                  70                  75                  80

Arg Phe Ser Gly Ser Gly Ser Gly Thr Asp Tyr Ser Leu Thr Ile Tyr
                    85                  90                  95

Asn Leu Glu Gln Glu Asp Phe Ala Thr Tyr Phe Cys Gln Gln Gly Asp
                100                 105                 110

Thr Leu Pro Tyr Thr Phe Gly Gly Gly Thr Lys Leu Glu Ile Lys Arg
            115                 120                 125

Ala Asp Ala Ala Pro Thr Val Ser Ile Phe Pro Pro Ser Ser Glu Gln
        130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 136
<211> LENGTH: 705
<212> TYPE: DNA
<213> ORGANISM: Mus musculus

<400> SEQUENCE: 136

```
atgatgtcct ctgctcagtt ccttggtctc ctgttgctct gttttcaagg taccagatgt     60
gatatccaga tgacacagat tacatcctcc ctgtctgcct ctctgggaga cagggtctcc    120
atcagttgca gggcaagtca agacattagc aattatttaa actggtatca gcagaaacca    180
```

```
gatggaactt ttaaactcct tatcttctac acatcaagat tactctcagg agtcccatca    240
aggttcagtg gcagtgggtc tggaacagat tattctctca ccatttacaa cctggagcaa    300
gaagattttg ccacttactt ttgccaacag ggagatacgc ttccgtacac tttcggaggg    360
gggaccaagc tggaaataaa acgggctgat gctgcaccaa ctgtatccat cttcccacca    420
tccagtgagc agttaacatc tggaggtgcc tcagtcgtgt gcttcttgaa caacttctac    480
cccaaagaca tcaatgtcaa gtggaagatt gatggcagtg aacgacaaaa tggcgtcctg    540
aacagttgga ctgatcagga cagcaaagac agcacctaca gcatgagcag caccctcacg    600
ttgaccaagg acgagtatga acgacataac agctatacct gtgaggccac tcacaagaca    660
tcaacttcac ccattgtcaa gagcttcaac aggaatgagt gttag                    705
```

```
<210> SEQ ID NO 137
<211> LENGTH: 447
<212> TYPE: PRT
<213> ORGANISM: Mus musculus

<400> SEQUENCE: 137
```

```
Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gln Gly Lys Thr Leu Glu Trp Ile
        35                  40                  45

Gly Glu Ile Asn Pro Asn Ser Gly Gly Ala Gly Tyr Asn Gln Lys Phe
    50                  55                  60

Lys Gly Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Ala Gly Thr Thr Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285
```

```
Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445

<210> SEQ ID NO 138
<211> LENGTH: 1344
<212> TYPE: DNA
<213> ORGANISM: Mus musculus

<400> SEQUENCE: 138
gaggtccaac tgcaacagtc tggacctgaa ctaatgaagc ctggggcttc agtgaagatg      60
tcctgcaagg cttctggata cattcact gactacaaca tgcactgggt gaagcagaac     120
caaggaaaga ccctagagtg gataggagaa attaatccta acagtggtgg tgctggctac     180
aaccagaagt tcaagggcaa ggccacattg actgtagaca gtcctccac cacagcctac     240 atggagctcc gcagcctgac atctgaggac tctgcagtct attactgtgc aagattgggc     300
tacgatgata tctacgacga ctggtacttc gatgtctggg gcgcaggga cacggtcacc     360 gtctcctcag ccaaaacgac acccccatct gtctatccac tggcccctgg atctgctgcc     420
caaactaact ccatggtgac cctgggatgc ctggtcaagg gctatttccc tgagccagtg     480
acagtgacct ggaactctgg atccctgtcc agcggtgtgc acaccttccc agctgtcctg     540
cagtctgacc tctacactct gagcagctca gtgactgtcc cctccagcac ctggcccagc     600
gagaccgtca cctgcaacgt tgcccacccg gccagcagca ccaaggtgga caagaaaatt     660
gtgcccaggg attgtggttg taagccttgc atatgtacag tcccagaagt atcatctgtc     720
ttcatcttcc ccccaaagcc caaggatgtg ctcaccatta ctctgactcc taaggtcacg     780
tgtgttgtgg tagacatcag caaggatgat cccgaggtcc agttcagctg gtttgtagat     840
gatgtggagg tgcacacagc tcagacgcaa ccccgggagg agcagttcaa cagcactttc     900
cgctcagtca gtgaacttcc catcatgcac caggactggc tcaatggcaa ggagttcaaa     960
tgcagggtca acagtgcagc tttccctgcc ccatcgaga aaaccatctc caaaaccaaa    1020
ggcagaccga aggctccaca ggtgtacacc attccacctc ccaaggagca gatggccaag    1080
gataaagtca gtctgacctg catgataaca gacttcttcc ctgaagacat tactgtggag    1140
tggcagtgga atgggcagcc agcggagaac tacaagaaca ctcagcccat catggacaca    1200
```

```
gatggctctt acttcatcta cagcaagctc aatgtgcaga agagcaactg ggaggcagga    1260
aatactttca cctgctctgt gttacatgag ggcctgcaca accaccatac tgagaagagc    1320
ctctcccact ctcctggtaa atga                                            1344
```

<210> SEQ ID NO 139
<211> LENGTH: 466
<212> TYPE: PRT
<213> ORGANISM: Mus musculus

<400> SEQUENCE: 139

```
Met Gly Trp Ser Trp Thr Phe Leu Phe Leu Leu Ser Gly Thr Ala Gly
 1               5                  10                  15

Val Leu Ser Glu Val Gln Leu Gln Gln Ser Gly Pro Glu Leu Met Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Val Lys Gln Asn Gln Lys Thr Leu
    50                  55                  60

Glu Trp Ile Gly Glu Ile Asn Pro Asn Ser Gly Ala Gly Tyr Asn
65                  70                  75                  80

Gln Lys Phe Lys Gly Lys Ala Thr Leu Thr Val Asp Lys Ser Thr
                85                  90                  95

Thr Ala Tyr Met Glu Leu Arg Ser Leu Thr Ser Glu Asp Ser Ala Val
            100                 105                 110

Tyr Tyr Cys Ala Arg Leu Gly Tyr Asp Asp Ile Tyr Asp Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350
```

```
Lys Thr Ile Ser Lys Thr Lys Gly Arg Pro Lys Ala Pro Gln Val Tyr
            355                 360                 365

Thr Ile Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465
```

<210> SEQ ID NO 140
<211> LENGTH: 1401
<212> TYPE: DNA
<213> ORGANISM: Mus musculus

<400> SEQUENCE: 140

```
atgggatgga gctggacctt tctcttcctc ctgtcaggaa ctgcaggtgt cctctctgag      60
gtccaactgc aacagtctgg acctgaacta atgaagcctg ggcttcagt gaagatgtcc     120
tgcaaggctt ctggatatac attcactgac tacaacatgc actgggtgaa gcagaaccaa     180
ggaaagaccc tagagtggat aggagaaatt aatcctaaca gtggtggtgc tggctacaac     240
cagaagttca gggcaaggc cacattgact gtagacaagt cctccaccac agcctacatg     300
gagctccgca gcctgacatc tgaggactct gcagtctatt actgtgcaag attgggctac     360
gatgatatct acgacgactg gtacttcgat gtctggggcg cagggaccac ggtcaccgtc     420
tcctcagcca aaacgacacc cccatctgtc tatccactgg ccctgtgatc tgctgcccaa     480
actaactcca tggtgaccct gggatgcctg gtcaagggct atttccctga ccagtgaca     540
gtgacctgga actctggatc cctgtccagc ggtgtgcaca ccttcccagc tgtcctgcag     600
tctgacctct acactctgag cagctcagtg actgtcccct ccagcacctg gcccagcgag     660
accgtcacct gcaacgttgc cacccggcc agcagcacca aggtggacaa gaaaattgtg     720
cccagggatt gtggttgtaa gccttgcata tgtacagtcc cagaagtatc atctgtcttc     780
atcttccccc caaagcccaa ggatgtgctc accattactc tgactcctaa ggtcacgtgt     840
gttgtggtag acatcagcaa ggatgatccc gaggtccagt tcagctggtt tgtagatgat     900
gtggaggtgc acacagctca gacgcaaccc cggaggagc agttcaacag cactttccgc     960
tcagtcagtg aacttcccat catgcaccag gactggctca atggcaagga gttcaaatgc    1020
agggtcaaca gtgcagcttt ccctgccccc atcgagaaaa ccatctccaa aaccaaaggc    1080
agaccgaagg ctccacaggt gtacaccatt ccacctccca aggagcagat ggccaaggat    1140
aaagtcagtc tgacctgcat gataacagac ttcttccctg aagacattac tgtggagtgg    1200
cagtggaatg ggcagccagc ggagaactac aagaacactc agcccatcat ggacacagat    1260
ggctcttact tcatctacag caagctcaat gtgcagaaga gcaactggga ggcaggaaat    1320
actttcacct gctctgtgtt acatgagggc ctgcacaacc accatactga gaagagcctc    1380
```
tcccactctc ctggtaaatg a 1401

```
<210> SEQ ID NO 141
<211> LENGTH: 214
<212> TYPE: PRT
<213> ORGANISM: Artificial Sequence
<220> FEATURE:
<223> OTHER INFORMATION: Humanized antibody sequence

<400> SEQUENCE: 141
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 142
<211> LENGTH: 642
<212> TYPE: DNA
<213> ORGANISM: Artificial Sequence
<220> FEATURE:
<223> OTHER INFORMATION: Humanized antibody sequence

<400> SEQUENCE: 142
```
gacatccaga tgacccagtc tccatcctcc ctctccgcat ccgtaggcga ccgcgtaacc    60
ataacatgta gagcatctca agatatttcc aactatttga attggtacca acaaaaaccc   120
ggcaaagcac ctaaactcct catttactat acatcaagac ctctctccgg cgttccatca   180
cgattctcag gctccggctc cggcacagat ttcacactca ctatttcctc cctccaacca   240
gaagattttg caacctatta ctgtcaacaa ggcgatacac tcccatacac attcggcggc   300
ggcacaaaag ttgaaattaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480

-continued

```
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                         642
```

<210> SEQ ID NO 143
<211> LENGTH: 236
<212> TYPE: PRT
<213> ORGANISM: Artificial Sequence
<220> FEATURE:
<223> OTHER INFORMATION: Humanized antibody sequence

<400> SEQUENCE: 143

```
Met Asp Met Arg Val Pro Ala Gln Leu Leu Gly Leu Leu Leu Leu Trp
 1               5                  10                  15

Leu Arg Gly Ala Arg Cys Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Asp Ile Ser Asn Tyr Leu Asn Trp Tyr Gln Gln Lys Pro Gly Lys
        50                  55                  60

Ala Pro Lys Leu Leu Ile Tyr Tyr Thr Ser Arg Leu Leu Ser Gly Val
 65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Gly Asp Thr Leu Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 144
<211> LENGTH: 708
<212> TYPE: DNA
<213> ORGANISM: Artificial Sequence
<220> FEATURE:
<223> OTHER INFORMATION: Humanized antibody sequence

<400> SEQUENCE: 144

```
atggacatga gggtcccgc tcagctcctg gggctcctgc tactctggct ccgaggtgcc      60
agatgtgaca tccagatgac ccagtctcca tcctccctct ccgcatccgt aggcgaccgc     120
gtaaccataa catgtagagc atctcaagat atttccaact atttgaattg gtaccaacaa     180
aaacccggca agcacctaa actcctcatt tactatacat caagactcct ctccggcgtt     240
```

```
ccatcacgat tctcaggctc cggctccggc acagatttca cactcactat ttcctccctc    300
caaccagaag attttgcaac ctattactgt caacaaggcg atacactccc atacacattc    360
ggcggcggca caaagttga aattaaacgt acggtggctg caccatctgt cttcatcttc     420
ccgccatctg atgagcagtt gaaatctgga actgcctctg ttgtgtgcct gctgaataac    480
ttctatccca gagaggccaa agtacagtgg aaggtggata cgccctcca atcgggtaac     540 tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgt                  708
```

<210> SEQ ID NO 145
<211> LENGTH: 449
<212> TYPE: PRT
<213> ORGANISM: Artificial Sequence
<220> FEATURE:
<223> OTHER INFORMATION: Humanized antibody sequence

<400> SEQUENCE: 145

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ser Gly Gly Ala Gly Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
```

```
                275                 280                 285
Ala Lys Thr Lys Pro Arg Glu Glu Gln Phe Asn Ser Thr Phe Arg Val
        290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 146
<211> LENGTH: 1347
<212> TYPE: DNA
<213> ORGANISM: Artificial Sequence
<220> FEATURE:
<223> OTHER INFORMATION: Humanized antibody sequence

<400> SEQUENCE: 146
gaggtgcagc tggtgcagag cggcgccgag gtaaaaaaac aggagcaag cgttaaagtt      60 tcttgtaaag caagcggata cattttaca gattacaaca tgcattgggt aagacaagcg     120
ccaggacaag gattggaatg gatgggcgaa attaaccta atagtggagg agcaggctac     180
aatcaaaaat tcaaagggag agttacaatg acaacagaca caagcacttc aacagcatat     240
atggaactgc gatcacttag aagcgacgat acagctgtat actattgcgc acgacttggg     300
tatgatgata tatatgatga ctggtatttc gatgtttggg ccagggaac aacagttacc     360 gtctctagtg cctccaccaa gggcccatcg gtcttccccc tggcgccctg ctccaggagc     420
acctccgaga gcacagcggc cctgggctgc ctggtcaagg actacttccc cgaaccggtg     480
acggtgtcgt ggaactcagg cgctctgacc agcggcgtgc acaccttccc agctgtccta     540
cagtcctcag gactctactc cctcagcagc gtggtgaccg tgccctccag caacttcggc     600
acccagacct acacctgcaa cgtagatcac aagcccagca caccaaggt ggacaagaca     660 gttgagcgca aatgttgtgt cgagtgccca ccgtgcccag caccacctgt ggcaggaccg     720
tcagtcttcc tcttcccccc aaaacccaag gacaccctca tgatctcccg gacccctgag     780
gtcacgtgcg tggtggtgga cgtgagccac gaagacccg aggtccagtt caactggtac     840
gtggacggcg tggaggtgca taatgccaag acaaagccac gggaggagca gttcaacagc     900
acgttccgtg tggtcagcgt cctcaccgtt gtgcaccagg actggctgaa cggcaaggag     960
tacaagtgca aggtctccaa caaaggcctc ccagccccca tcgagaaaac catctccaaa    1020
accaaagggc agccccgaga accacaggtg tacaccctgc ccccatcccg ggaggagatg    1080
```

-continued

```
accaagaacc aggtcagcct gacctgcctg gtcaaaggct tctacccag cgacatcgcc    1140 gtggagtggg agagcaatgg gcagccggag aacaactaca agaccacacc tcccatgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347
```

<210> SEQ ID NO 147
<211> LENGTH: 468
<212> TYPE: PRT
<213> ORGANISM: Artificial Sequence
<220> FEATURE:
<223> OTHER INFORMATION: Humanized antibody sequence

<400> SEQUENCE: 147

```
Met Asp Trp Thr Trp Arg Ile Leu Phe Leu Val Ala Ala Thr Gly
 1               5                  10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Asn Met His Trp Val Arg Gln Ala Pro Gly Gln Gly Leu
    50                  55                  60

Glu Trp Met Gly Glu Ile Asn Pro Asn Ser Gly Gly Ala Gly Tyr Asn
65                  70                  75                  80

Gln Lys Phe Lys Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Leu Gly Tyr Asp Asp Ile Tyr Asp Asp Trp Tyr
        115                 120                 125

Phe Asp Val Trp Gly Gln Gly Thr Thr Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
```

```
            305                 310                 315                 320
Phe Arg Val Val Ser Val Leu Thr Val Val His Gln Asp Trp Leu Asn
                325                 330                 335
Gly Lys Glu Tyr Lys Cys Lys Val Ser Asn Lys Gly Leu Pro Ala Pro
            340                 345                 350
Ile Glu Lys Thr Ile Ser Lys Thr Lys Gly Gln Pro Arg Glu Pro Gln
        355                 360                 365
Val Tyr Thr Leu Pro Pro Ser Arg Glu Glu Met Thr Lys Asn Gln Val
    370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Met Leu Asp Ser Asp Gly Ser Phe Phe Leu Tyr Ser Lys Leu Thr
            420                 425                 430
Val Asp Lys Ser Arg Trp Gln Gln Gly Asn Val Phe Ser Cys Ser Val
        435                 440                 445
Met His Glu Ala Leu His Asn His Tyr Thr Gln Lys Ser Leu Ser Leu
    450                 455                 460
Ser Pro Gly Lys
465

<210> SEQ ID NO 148
<211> LENGTH: 1404
<212> TYPE: DNA
<213> ORGANISM: Mus musculus

<400> SEQUENCE: 148
atggactgga cctggaggat cctcttcttg gtggcagcag ccacaggagc ccactccgag      60
gtgcagctgg tgcagagcgg cgccgaggta aaaaaaccag agcaagcgt taaagttct      120 tgtaaagcaa gcggatatac atttacagat acaacatgc attgggtaag acaagcgcca     180
ggacaaggat tggaatggat gggcgaaatt aaccctaata gtggaggagc aggctacaat     240
caaaaattca agggagagt acaatgaca acagacaca gcacttcaac agcatatatg       300
gaactgcgat cacttagaag cgacgataca gctgtatact attgcgcacg acttgggtat     360
gatgatatat atgatgactg gtatttcgat gtttggggcc agggaacaac agttaccgtc     420
tctagtgcct ccaccaaggg cccatcggtc ttcccctgg cgccctgctc caggagcacc     480
tccgagagca gcggccct gggctgcctg gtcaaggact acttccccga accggtgacg     540
gtgtcgtgga actcaggcgc tctgaccagc ggcgtgcaca ccttcccagc tgtcctacag     600
tcctcaggac tctactccct cagcagcgtg gtgaccgtgc cctccagcaa cttcggcacc     660
cagacctaca cctgcaacgt agatcacaag cccagcaaca ccaaggtgga caagacagtt     720
gagcgcaaat gttgtgtcga gtgcccaccg tgcccagcac cacctgtggc aggaccgtca     780
gtcttcctct tccccccaaa acccaaggac accctcatga tctcccggac ccctgaggtc     840
acgtgcgtgg tggtggacgt gagccacgaa gaccccgagg tccagttcaa ctggtacgtg     900
gacggcgtgg aggtgcataa tgccaagaca aagccacggg aggagcagtt caacagcacg     960
ttccgtgtgg tcagcgtcct caccgttgtg caccaggact ggctgaacgg caaggagtac    1020
aagtgcaagg tctccaacaa aggcctccca gcccccatcg agaaaaccat ctccaaaacc    1080
aaagggcagc ccgagaacc acaggtgtac accctgcccc catcccggga ggagatgacc    1140
aagaaccagg tcagcctgac ctgcctggtc aaaggcttct accccagcga catcgccgtg    1200
```

```
gagtgggaga gcaatgggca gccggagaac aactacaaga ccacacctcc catgctggac    1260
tccgacggct ccttcttcct ctacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaa                                           1404
```

<210> SEQ ID NO 149
<211> LENGTH: 214
<212> TYPE: PRT
<213> ORGANISM: Mus musculus

<400> SEQUENCE: 149

```
Asp Ile Gln Met Thr Gln Thr Thr Ser Ser Leu Ser Ala Ser Leu Gly
 1               5                   10                  15

Asp Arg Val Thr Ile Ser Cys Arg Ala Ser Gln Asp Ile Ser Asn Tyr
            20                  25                  30

Leu Asn Trp Phe Gln Gln Lys Pro Asp Gly Thr Leu Lys Leu Leu Ile
        35                  40                  45

Phe Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asp Thr Leu Pro Tyr
                85                  90                  95

Thr Phe Gly Gly Gly Thr Lys Leu Glu Ile Arg Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 150
<211> LENGTH: 645
<212> TYPE: DNA
<213> ORGANISM: Mus musculus

<400> SEQUENCE: 150

```
gatatccaga tgacacagac tacatcctcc ctgtctgcct ctctgggaga cagagtcacc     60
atcagttgca gggcaagtca ggacattagc aattatttaa actggtttca gcagaaacca    120
gatggaactc ttaaactcct gatcttctac acatcaagat acactcagg agttccatca     180 aggttcagtg gcagtgggtc tggaacagat tattctctca ccattagcaa cctggagcaa    240
gaagatattg ccacttactt ttgccaacag ggtgatacgc ttccgtacac gttcggggg     300 gggaccaagc tggaaataag acgggctgat gctgcaccaa ctgtatccat cttcccacca    360
```

```
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gttag                    645
```

<210> SEQ ID NO 151
<211> LENGTH: 234
<212> TYPE: PRT
<213> ORGANISM: Mus musculus

<400> SEQUENCE: 151

Met Met Ser Ser Ala Gln Phe Leu Gly Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Phe Gln Gln Lys Pro Asp Gly Thr Leu
    50                  55                  60

Lys Leu Leu Ile Phe Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asp
            100                 105                 110

Thr Leu Pro Tyr Thr Phe Gly Gly Gly Thr Lys Leu Glu Ile Arg Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 152
<211> LENGTH: 705
<212> TYPE: DNA
<213> ORGANISM: Mus musculus

<400> SEQUENCE: 152

```
atgatgtcct ctgctcagtt ccttggtctc ctgttgctct gttttcaagg taccagatgt     60
gatatccaga tgacacagac tacatcctcc ctgtctgcct ctctgggaga cagagtcacc    120
atcagttgca gggcaagtca ggacattagc aattatttaa actggtttca gcagaaacca    180
gatggaactc ttaaactcct gatcttctac acatcaagat acactcagg agttccatca    240
```

```
aggttcagtg gcagtgggtc tggaacagat tattctctca ccattagcaa cctggagcaa    300
gaagatattg ccacttactt ttgccaacag ggtgatacgc ttccgtacac gttcggggggg   360 gggaccaagc tggaaataag acgggctgat gctgcaccaa ctgtatccat cttcccacca    420
tccagtgagc agttaacatc tggaggtgcc tcagtcgtgt gcttcttgaa caacttctac    480
cccaaagaca tcaatgtcaa gtggaagatt gatggcagtg aacgacaaaa tggcgtcctg    540
aacagttgga ctgatcagga cagcaaagac agcacctaca gcatgagcag caccctcacg    600
ttgaccaagg acgagtatga acgacataac agctatacct gtgaggccac tcacaagaca    660
tcaacttcac ccattgtcaa gagcttcaac aggaatgagt gttag                    705
```

```
<210> SEQ ID NO 153
<211> LENGTH: 447
<212> TYPE: PRT
<213> ORGANISM: Mus musculus

<400> SEQUENCE: 153
```

| | | | | | | | | | | | | | | |
|---|---|---|---|---|---|---|---|---|---|---|---|---|---|---|
| Glu | Val | Gln | Leu | Gln | Gln | Ser | Gly | Pro | Glu | Leu | Met | Lys | Pro | Gly | Ala |
| 1 | | | | 5 | | | | | 10 | | | | | 15 | |

| Ser | Val | Lys | Met | Ser | Cys | Lys | Ala | Ser | Gly | Tyr | Thr | Phe | Thr | Asp | Tyr |
|---|---|---|---|---|---|---|---|---|---|---|---|---|---|---|---|
| | | | 20 | | | | | 25 | | | | | 30 | | |

Asn Met His Trp Val Lys Gln Asn Gly Lys Ser Leu Glu Trp Ile
             35                  40                  45

Gly Glu Ile Asn Pro Asn Ser Gly Ser Gly Tyr Asn Gln Lys Phe
 50                  55                  60

Lys Gly Lys Ala Thr Leu Thr Val Asp Lys Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Leu Val Tyr Asp Gly Ser Tyr Glu Asp Trp Tyr Phe Asp Val
             100                 105                 110

Trp Gly Ala Gly Thr Thr Val Thr Val Ser Ser Ala Lys Thr Thr Pro
         115                 120                 125

Pro Ser Val Tyr Pro Leu Ala Pro Gly Ser Ala Ala Gln Thr Asn Ser
     130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                 165                 170                 175

Pro Ala Val Leu Gln Ser Asp Leu Tyr Thr Leu Ser Ser Ser Val Thr
             180                 185                 190

Val Pro Ser Ser Thr Trp Pro Ser Glu Thr Val Thr Cys Asn Val Ala
         195                 200                 205

His Pro Ala Ser Ser Thr Lys Val Asp Lys Lys Ile Val Pro Arg Asp
     210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                 245                 250                 255

Pro Lys Val Thr Cys Val Val Val Asp Ile Ser Lys Asp Asp Pro Glu
             260                 265                 270

Val Gln Phe Ser Trp Phe Val Asp Asp Val Glu Val His Thr Ala Gln
         275                 280                 285

Thr Gln Pro Arg Glu Glu Gln Phe Asn Ser Thr Phe Arg Ser Val Ser

```
            290                 295                 300
Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445

<210> SEQ ID NO 154
<211> LENGTH: 1344
<212> TYPE: DNA
<213> ORGANISM: Mus musculus

<400> SEQUENCE: 154
gaggtccagc tgcaacagtc tggacctgaa ctaatgaagc ctggggcttc agtgaagatg      60
tcctgcaagg cttctggata cacattcact gactacaaca tgcactgggt gaaacagaac     120
caaggaaaga gcctagagtg gataggagaa attaatccta acagtggtgg tagtggctac     180
aaccaaaagt tcaagggcaa ggccacattg actgtagaca gtcttccag cacagcctac     240
atggagctcc gcagcctgac atctgaggac tctgcagtct attactgtgc aagattggtc     300
tacgatggca gctacgagga ctggtacttc gatgtctggg gcgcagggac cacggtcacc     360
gtctcctcag ccaaaacgac acccccatct gtctatccac tggcccctgg atctgctgcc     420
caaactaact ccatggtgac cctgggatgc ctggtcaagg gctatttccc tgagccagtg     480
acagtgacct ggaactctgg atccctgtcc agcggtgtgc acaccttccc agctgtcctg     540
cagtctgacc tctacactct gagcagctca gtgactgtcc cctccagcac ctggcccagc     600
gagaccgtca cctgcaacgt tgcccacccg gccagcagca ccaaggtgga caagaaaatt     660
gtgcccaggg attgtggttg taagccttgc atatgtacag tcccagaagt atcatctgtc     720
ttcatcttcc ccccaaagcc caaggatgtg ctcaccatta ctctgactcc taaggtcacg     780
tgtgttgtgg tagacatcag caaggatgat cccgaggtcc agttcagctg gtttgtagat     840
gatgtggagg tgcacacagc tcagacgcaa ccccgggagg agcagttcaa cagcactttc     900
cgctcagtca gtgaacttcc catcatgcac caggactggc tcaatggcaa ggagttcaaa     960
tgcagggtca acagtgcagc tttccctgcc cccatcgaga aaaccatctc caaaaccaaa    1020
ggcagaccga aggctccaca ggtgtacacc attccacctc caaggagca gatggccaag    1080
gataaagtca gtctgacctg catgataaca gacttcttcc ctgaagacat tactgtggag    1140
tggcagtgga atgggcagcc agcgagaac tacaagaaca ctcagcccat catggacaca    1200
gatggctctt acttcatcta cagcaagctc aatgtgcaga gagcaactg ggaggcagga    1260
```

```
aatactttca cctgctctgt gttacatgag ggcctgcaca accaccatac tgagaagagc      1320
ctctcccact ctcctggtaa atga                                              1344
```

<210> SEQ ID NO 155
<211> LENGTH: 466
<212> TYPE: PRT
<213> ORGANISM: Mus musculus

<400> SEQUENCE: 155

```
Met Gly Trp Ser Trp Thr Phe Leu Phe Leu Leu Ser Gly Thr Ala Gly
1               5                   10                  15

Val Leu Ser Glu Val Gln Leu Gln Gln Ser Gly Pro Glu Leu Met Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Val Lys Gln Asn Gln Gly Lys Ser Leu
    50                  55                  60

Glu Trp Ile Gly Glu Ile Asn Pro Asn Ser Gly Ser Gly Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Arg Leu Val Tyr Asp Gly Ser Tyr Glu Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
```

355                 360                 365
Thr Ile Pro Pro Pro Lys Glu Gln Met Ala Lys Asp Lys Val Ser Leu
        370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
            435                 440                 445

Glu Gly Leu His Asn His His Thr Glu Lys Ser Leu Ser His Ser Pro
    450                 455                 460

Gly Lys
465

<210> SEQ ID NO 156
<211> LENGTH: 1401
<212> TYPE: DNA
<213> ORGANISM: Mus musculus

<400> SEQUENCE: 156

| | |
|---|---:|
| atgggatgga gctggacctt tctcttcctc ctgtcaggaa ctgcaggtgt cctctctgag | 60 |
| gtccagctgc aacagtctgg acctgaacta atgaagcctg gggcttcagt gaagatgtcc | 120 |
| tgcaaggctt ctggatacac attcactgac tacaacatgc actgggtgaa acagaaccaa | 180 |
| ggaaagagcc tagagtggat tggagaaatt aatcctaaca gtggtggtag tggctacaac | 240 |
| caaaagttca aggcaaggc cacattgact gtagacaagt cttccagcac agcctacatg | 300 |
| gagctccgca gcctgacatc tgaggactct gcagtctatt actgtgcaag attggtctac | 360 |
| gatggcagct acgaggactg gtacttcgat gtctggggcg cagggaccac ggtcaccgtc | 420 |
| tcctcagcca aaacgacacc cccatctgtc tatccactgg cccctggatc tgctgcccaa | 480 |
| actaactcca tggtgaccct gggatgcctg gtcaagggct atttccctga gccagtgaca | 540 |
| gtgacctgga actctggatc cctgtccagc ggtgtgcaca ccttcccagc tgtcctgcag | 600 |
| tctgacctct acactctgag cagctcagtg actgtcccct ccagcacctg gcccagcgag | 660 |
| accgtcacct gcaacgttgc cacccggcc agcagcacca aggtggacaa gaaaattgtg | 720 |
| cccaggggat tgtggttgtaa gccttgcata tgtacagtcc agaagtatc atctgtcttc | 780 |
| atcttccccc caaagcccaa ggatgtgctc accattactc tgactcctaa ggtcacgtgt | 840 |
| gttgtggtag acatcagcaa ggatgatccc gaggtccagt tcagctggtt tgtagatgat | 900 |
| gtggaggtgc acacagctca gacgcaaccc cgggaggagc agttcaacag cactttccgc | 960 |
| tcagtcagtg aacttcccat catgcaccag gactggctca atggcaagga gttcaaatgc | 1020 |
| agggtcaaca gtgcagcttt ccctgccccc atcgagaaaa ccatctccaa aaccaaaggc | 1080 |
| agaccgaagg ctccacaggt gtacaccatt ccacctccca aggagcagat ggccaaggat | 1140 |
| aaagtcagtc tgacctgcat gataacagac ttcttccctg aagacattac tgtggagtgg | 1200 |
| cagtggaatg ggcagccagc ggagaactac aagaacactc agcccatcat ggacacagat | 1260 |
| ggctcttact tcatctacag caagctcaat gtgcagaaga gcaactggga ggcaggaaat | 1320 |
| actttcacct gctctgtgtt acatgagggc ctgcacaacc accatactga gaagagcctc | 1380 |
| tcccactctc ctggtaaatg a | 1401 |

<210> SEQ ID NO 157
<211> LENGTH: 214
<212> TYPE: PRT
<213> ORGANISM: Mus musculus

<400> SEQUENCE: 157

```
Asp Ile Gln Met Thr Gln Thr Thr Ser Ser Leu Ser Ala Ser Leu Gly
 1               5                  10                  15

Asp Arg Val Thr Ile Cys Cys Arg Ala Ser Gln Val Ile Thr Asn Tyr
            20                  25                  30

Leu Tyr Trp Tyr Gln Gln Lys Pro Asp Gly Thr Phe Lys Leu Leu Ile
        35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
           100                 105                 110

Pro Thr Val Ser Ile Phe Pro Pro Ser Ser Glu Gln Leu Thr Ser Gly
       115                 120                 125

Gly Ala Ser Val Val Cys Phe Leu Asn Asn Phe Tyr Pro Lys Asp Ile
   130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 158
<211> LENGTH: 642
<212> TYPE: DNA
<213> ORGANISM: Mus musculus

<400> SEQUENCE: 158

```
gatatccaga tgacacagac tacatcctcc ctgtctgcct ctctgggaga cagagtcacc      60
atctgttgca gggcaagtca ggtcattacc aattatttat actggtatca gcagaaacca     120
gatggaactt ttaaactcct gatctactac acatcaagat tacactcagg agtcccatca     180
aggttcagtg gcagtgggtc tggaacagat tattctctca ccattagcaa cctggaacag     240
gaagatattg ccacttactt ttgccaacag ggtgatacgc ttccgtacac gttcggaggg     300
gggaccaagc tggaaataaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag cacctcacg      540
ttgaccaagg acgagtatga acgacataac agctatacct gtgaggccac tcacaagaca     600
tcaacttcac ccattgtcaa gagcttcaac aggaatgagt gt                        642
```

<210> SEQ ID NO 159
<211> LENGTH: 234
<212> TYPE: PRT
<213> ORGANISM: Mus musculus

<400> SEQUENCE: 159

```
Met Met Ser Ser Ala Gln Phe Leu Gly Leu Leu Leu Cys Phe Gln
 1               5                  10                  15

Gly Thr Arg Cys Asp Ile Gln Met Thr Gln Thr Ser Ser Leu Ser
                20                  25                  30

Ala Ser Leu Gly Asp Arg Val Thr Ile Cys Cys Arg Ala Ser Gln Val
                35                  40                  45

Ile Thr Asn Tyr Leu Tyr Trp Tyr Gln Gln Lys Pro Asp Gly Thr Phe
 50                  55                  60

Lys Leu Leu Ile Tyr Tyr Thr Ser Arg Leu His Ser Gly Val Pro Ser
 65                  70                  75                  80

Arg Phe Ser Gly Ser Gly Ser Gly Thr Asp Tyr Ser Leu Thr Ile Ser
                    85                  90                  95

Asn Leu Glu Gln Glu Asp Ile Ala Thr Tyr Phe Cys Gln Gln Gly Asp
                100                 105                 110

Thr Leu Pro Tyr Thr Phe Gly Gly Gly Thr Lys Leu Glu Ile Lys Arg
                115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
                180                 185                 190

Tyr Ser Met Ser Ser Thr Leu Thr Leu Thr Lys Asp Glu Tyr Glu Arg
                195                 200                 205

His Asn Ser Tyr Thr Cys Glu Ala Thr His Lys Thr Ser Thr Ser Pro
                210                 215                 220

Ile Val Lys Ser Phe Asn Arg Asn Glu Cys
225                 230
```

<210> SEQ ID NO 160
<211> LENGTH: 702
<212> TYPE: DNA
<213> ORGANISM: Mus musculus

<400> SEQUENCE: 160

| atgatgtcct ctgctcagtt cctttggtctc ctgttgctct gttttcaagg taccagatgt | 60 |
| gatatccaga tgacacagac tacatcctcc ctgtctgcct ctctgggaga cagagtcacc | 120 |
| atctgttgca gggcaagtca ggtcattacc aattatttat actggtatca gcagaaacca | 180 |
| gatggaactt ttaaactcct gatctactac acatcaagat acactcagg agtcccatca | 240 |
| aggttcagtg gcagtgggtc tggaacagat tattctctca ccattagcaa cctggaacag | 300 |
| gaagatattg ccacttactt ttgccaacag ggtgatacgc ttccgtacac gttcggaggg | 360 |
| gggaccaagc tggaaataaa acgggctgat gctgcaccaa ctgtatccat cttcccacca | 420 |
| tccagtgagc agttaacatc tggaggtgcc tcagtcgtgt gcttcttgaa caacttctac | 480 |
| cccaaagaca tcaatgtcaa gtggaagatt gatggcagtg aacgacaaaa tggcgtcctg | 540 |

-continued

```
aacagttgga ctgatcagga cagcaaagac agcacctaca gcatgagcag caccctcacg    600
ttgaccaagg acgagtatga acgacataac agctatacct gtgaggccac tcacaagaca    660
tcaacttcac ccattgtcaa gagcttcaac aggaatgagt gt                       702
```

<210> SEQ ID NO 161
<211> LENGTH: 447
<212> TYPE: PRT
<213> ORGANISM: Mus musculus

<400> SEQUENCE: 161

```
Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Met Lys Gln Asn Gly Lys Ser Leu Glu Trp Ile
        35                  40                  45

Gly Glu Ile Asn Pro Asn Ser Gly Gly Ala Gly Tyr Asn Gln Gln Phe
    50                  55                  60

Lys Gly Lys Ala Thr Leu Thr Val Asp Lys Ser Ser Arg Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Val Gly Asn Tyr Glu Asp Trp Tyr Phe Asp Val
            100                 105                 110

Trp Gly Ala Gly Thr Thr Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
```

```
              340             345             350
Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445

<210> SEQ ID NO 162
<211> LENGTH: 1341
<212> TYPE: DNA
<213> ORGANISM: Mus musculus

<400> SEQUENCE: 162
gaggtccagc tgcaacagtc tggacctgaa ctaatgaagc ctggggcttc agtgaagatg      60
tcctgcaagg cttctggata cacattcact gactacaaca tgcactggat gaagcagaac     120
caaggaaaga gcctagaatg gataggagaa attaatccta acagtggtgg tgctggctac     180
aaccagcagt tcaaaggcaa ggccacattg actgtagaca gtcctccag acagcctac      240
atggagctcc gcagcctgac atctgaggac tctgcagtct attactgtgc aagattgggc     300
tacgttggta attacgagga ctggtacttc gatgtctggg gcgcagggac cacggtcacc     360
gtctcctcag ccaaaacgac accccatct gtctatccac tggcccctgg atctgctgcc     420
caaactaact ccatggtgac cctgggatgc ctggtcaagg ctatttccc tgagccagtg      480
acagtgacct ggaactctgg atccctgtcc agcggtgtgc acaccttccc agctgtcctg     540
cagtctgacc tctacactct gagcagctca gtgactgtcc cctccagcac ctggcccagc     600
gagaccgtca cctgcaacgt tgcccacccg gccagcagca ccaaggtgga caagaaaatt     660
gtgcccaggg attgtggttg taagccttgc atatgtacag tcccagaagt atcatctgtc     720
ttcatcttcc ccccaaagcc caaggatgtg ctcaccatta ctctgactcc taaggtcacg     780
tgtgttgtgg tagacatcag caaggatgat cccgaggtcc agttcagctg gtttgtagat     840
gatgtggagg tgcacacagc tcagacgcaa ccccgggagg agcagttcaa cagcactttc     900
cgctcagtca gtgaacttcc catcatgcac caggactggc tcaatggcaa ggagttcaaa     960
tgcagggtca acagtgcagc tttccctgcc cccatcgaga aaaccatctc caaaaccaaa    1020
ggcagaccga aggctccaca ggtgtacacc attccacctc caaggagca gatggccaag    1080
gataaagtca gtctgacctg catgataaca gacttcttcc ctgaagacat tactgtggag    1140
tggcagtgga atgggcagcc agcggagaac tacaagaaca ctcagcccat catggacaca    1200
gatggctctt acttcatcta cagcaagctc aatgtgcaga gagcaactg ggaggcagga    1260
aatactttca cctgctctgt gttacatgag ggcctgcaca accaccatac tgagaagagc    1320
ctctcccact ctcctggtaa a                                             1341

<210> SEQ ID NO 163
<211> LENGTH: 466
<212> TYPE: PRT
<213> ORGANISM: Mus musculus
```

<400> SEQUENCE: 163

```
Met Gly Trp Ser Trp Thr Phe Leu Phe Leu Leu Ser Gly Thr Ala Gly
 1               5                  10                  15

Val Leu Ser Glu Val Gln Leu Gln Gln Ser Gly Pro Glu Leu Met Lys
             20                  25                  30

Pro Gly Ala Ser Val Lys Met Ser Cys Lys Ala Ser Gly Tyr Thr Phe
         35                  40                  45

Thr Asp Tyr Asn Met His Trp Met Lys Gln Asn Gln Gly Lys Ser Leu
     50                  55                  60

Glu Trp Ile Gly Glu Ile Asn Pro Asn Ser Gly Ala Gly Tyr Asn
 65                  70                  75                  80

Gln Gln Phe Lys Gly Lys Ala Thr Leu Thr Val Asp Lys Ser Ser Arg
                 85                  90                  95

Thr Ala Tyr Met Glu Leu Arg Ser Leu Thr Ser Glu Asp Ser Ala Val
            100                 105                 110

Tyr Tyr Cys Ala Arg Leu Gly Tyr Val Gly Asn Tyr Glu Asp Trp Tyr
        115                 120                 125

Phe Asp Val Trp Gly Ala Gly Thr Thr Val Thr Val Ser Ser Ala Lys
130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
```

```
                   405                 410                 415
Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465

<210> SEQ ID NO 164
<211> LENGTH: 1398
<212> TYPE: DNA
<213> ORGANISM: Mus musculus

<400> SEQUENCE: 164
atgggatgga gctggacctt tctcttcctc ctgtcaggaa ctgcaggtgt cctctctgag      60
gtccagctgc aacagtctgg acctgaacta atgaagcctg ggcttcagt gaagatgtcc     120 tgcaaggctt ctggatacac attcactgac tacaacatgc actggatgaa gcagaaccaa     180
ggaaagagcc tagaatggat aggagaaatt aatcctaaca gtggtggtgc tggctacaac     240
cagcagttca aggcaaggc cacattgact gtagacaagt cctccaggac agcctacatg     300
gagctccgca gcctgacatc tgaggactct gcagtctatt actgtgcaag attgggctac     360
gttggtaatt acgaggactg gtacttcgat gtctggggcg cagggaccac ggtcaccgtc     420
tcctcagcca aaacgacacc cccatctgtc tatccactgg ccctggatc tgctgcccaa     480 actaactcca tggtgaccct gggatgcctg gtcaagggct atttccctga gccagtgaca     540
gtgacctgga actctggatc cctgtccagc ggtgtgcaca ccttcccagc tgtcctgcag     600
tctgacctct acactctgag cagctcagtg actgtcccct ccagcacctg gcccagcgag     660
accgtcacct gcaacgttgc ccacccggcc agcagcacca aggtggacaa gaaaattgtg     720
cccagggatt gtggttgtaa gccttgcata tgtacagtcc cagaagtatc atctgtcttc     780
atcttccccc caaagcccaa ggatgtgctc accattactc tgactcctaa ggtcacgtgt     840
gttgtggtag acatcagcaa ggatgatccc gaggtccagt tcagctggtt tgtagatgat     900
gtggaggtgc acacagctca gacgcaaccc cgggaggagc agttcaacag cactttccgc     960
tcagtcagtg aacttcccat catgcaccag actggctca atggcaagga gttcaaatgc    1020
agggtcaaca gtgcagcttt ccctgccccc atcgagaaaa ccatctccaa aaccaaaggc    1080
agaccgaagg ctccacaggt gtacaccatt ccacctccca aggagcagat ggccaaggat    1140
aaagtcagtc tgacctgcat gataacagac ttcttccctg aagacattac tgtggagtgg    1200
cagtggaatg ggcagccagc ggagaactac aagaacactc agcccatcat ggacacagat    1260
ggctcttact tcatctacag caagctcaat gtgcagaaga caactgggga ggcaggaaat    1320
actttcacct gctctgtgtt acatgagggc ctgcacaacc accatactga aagagcctc    1380 tcccactctc ctggtaaa                                                    1398

<210> SEQ ID NO 165
<211> LENGTH: 214
<212> TYPE: PRT
<213> ORGANISM: Mus musculus

<400> SEQUENCE: 165

Asp Ile Gln Met Thr Gln Thr Thr Ser Ser Leu Ser Ala Ser Leu Gly
```

```
  1               5                  10                 15
Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
            35                  40                  45

Phe Tyr Thr Ser Arg Leu Leu Ser Gly Val Pro Ser Arg Phe Ser Gly
            50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
            130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
    210

<210> SEQ ID NO 166
<211> LENGTH: 645
<212> TYPE: DNA
<213> ORGANISM: Mus musculus

<400> SEQUENCE: 166
gatatccaga tgacacagac tacatcctcc ctgtctgcct ctctgggaga cagggtctcc      60
atcagttgca gggcaagtca agacattagc aattatttaa actggtatca gcagaaacca     120
gatggaactt ttaaactcct tatcttctac acatcaagat tactctcagg agtcccatca     180
aggttcagtg gcagtgggtc tggaacagat tattctctca ccatttacaa cctggagcaa     240
gaagattttg ccacttactt ttgccaacag ggagatacgc ttccgtacac tttcggaggg     300
gggaccaaac tggaaataaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag caccctcacg     540
ttgaccaagg acgagtatga acgacataac agctatacct gtgaggccac tcacaagaca     600
tcaacttcac ccattgtcaa gagcttcaac aggaatgagt gttag                     645

<210> SEQ ID NO 167
<211> LENGTH: 234
<212> TYPE: PRT
<213> ORGANISM: Mus musculus

<400> SEQUENCE: 167
```

| Met | Met | Ser | Ser | Ala | Gln | Phe | Leu | Gly | Leu | Leu | Leu | Cys | Phe | Gln |
| 1 | | | | 5 | | | | | 10 | | | | | 15 |

Gly Thr Arg Cys Asp Ile Gln Met Thr Gln Thr Ser Ser Leu Ser
            20                  25                  30

Ala Ser Leu Gly Asp Arg Val Ser Ile Ser Cys Arg Ala Ser Gln Asp
         35                  40                  45

Ile Ser Asn Tyr Leu Asn Trp Tyr Gln Gln Lys Pro Asp Gly Thr Phe
50                      55                  60

Lys Leu Leu Ile Phe Tyr Thr Ser Arg Leu Leu Ser Gly Val Pro Ser
65                  70                  75                  80

Arg Phe Ser Gly Ser Gly Ser Gly Thr Asp Tyr Ser Leu Thr Ile Tyr
                85                  90                  95

Asn Leu Glu Gln Glu Asp Phe Ala Thr Tyr Phe Cys Gln Gln Gly Asp
                100                 105                 110

Thr Leu Pro Tyr Thr Phe Gly Gly Gly Thr Lys Leu Glu Ile Lys Arg
            115                 120                 125

Ala Asp Ala Ala Pro Thr Val Ser Ile Phe Pro Pro Ser Ser Glu Gln
        130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 168
<211> LENGTH: 705
<212> TYPE: DNA
<213> ORGANISM: Mus musculus

<400> SEQUENCE: 168
atgatgtcct ctgctcagtt ccttggtctc ctgttgctct gttttcaagg taccagatgt    60
gatatccaga tgacacagac tacatcctcc ctgtctgcct ctctgggaga cagggtctcc   120
atcagttgca gggcaagtca agacattagc aattatttaa actggtatca gcagaaacca   180
gatggaactt ttaaactcct tatcttctac acatcaagat tactctcagg agtcccatca   240
aggttcagtg gcagtgggtc tggaacagat tattctctca ccatttacaa cctggagcaa   300
gaagattttg ccacttactt ttgccaacag ggagatacgc ttccgtacac tttcggaggg   360
gggaccaaac tggaaataaa acgggctgat gctgcaccaa ctgtatccat cttcccacca   420
tccagtgagc agttaacatc tggaggtgcc tcagtcgtgt gcttcttgaa caacttctac   480
cccaaagaca tcaatgtcaa gtggaagatt gatggcagtg aacgacaaaa tggcgtcctg   540
aacagttgga ctgatcagga cagcaaagac agcacctaca gcatgagcag cacccttacg   600
ttgaccaagg acgagtatga acgacataac agctatacct gtgaggccac tcacaagaca   660
tcaacttcac ccattgtcaa gagcttcaac aggaatgagt gttag              705

<210> SEQ ID NO 169

```
<211> LENGTH: 447
<212> TYPE: PRT
<213> ORGANISM: Mus musculus

<400> SEQUENCE: 169
```

| | | | | | | | | | | | | | | | |
|---|---|---|---|---|---|---|---|---|---|---|---|---|---|---|---|
| Glu | Val | Gln | Leu | Gln | Gln | Ser | Gly | Pro | Glu | Leu | Met | Lys | Pro | Gly | Ala |
| 1 | | | | 5 | | | | | 10 | | | | | 15 | |
| Ser | Val | Lys | Met | Ser | Cys | Lys | Ala | Ser | Gly | Tyr | Thr | Phe | Thr | Asp | Tyr |
| | | | 20 | | | | | 25 | | | | | 30 | | |
| Asn | Met | His | Trp | Val | Lys | Gln | Asn | Gly | Lys | Thr | Leu | Asp | Trp | Ile | |
| | | 35 | | | | | 40 | | | | | 45 | | | |
| Gly | Glu | Ile | Asn | Pro | Asn | Ser | Gly | Gly | Ala | Gly | Tyr | Asn | Gln | Lys | Phe |
| | 50 | | | | | 55 | | | | | 60 | | | | |
| Lys | Gly | Lys | Ala | Thr | Leu | Thr | Val | Asp | Lys | Ser | Ser | Thr | Thr | Ala | Tyr |
| 65 | | | | | 70 | | | | | 75 | | | | | 80 |
| Met | Glu | Leu | Arg | Ser | Leu | Thr | Ser | Glu | Asp | Ser | Ala | Val | Tyr | Tyr | Cys |
| | | | | 85 | | | | | 90 | | | | | 95 | |
| Ala | Arg | Leu | Gly | Tyr | Asp | Asp | Ile | Tyr | Asp | Asp | Trp | Tyr | Phe | Asp | Val |
| | | | 100 | | | | | 105 | | | | | 110 | | |
| Trp | Gly | Ala | Gly | Thr | Thr | Val | Thr | Val | Ser | Ser | Ala | Lys | Thr | Thr | Pro |
| | | | 115 | | | | | 120 | | | | | 125 | | |
| Pro | Ser | Val | Tyr | Pro | Leu | Ala | Pro | Gly | Ser | Ala | Ala | Gln | Thr | Asn | Ser |
| | 130 | | | | | 135 | | | | | 140 | | | | |
| Met | Val | Thr | Leu | Gly | Cys | Leu | Val | Lys | Gly | Tyr | Phe | Pro | Glu | Pro | Val |
| 145 | | | | | 150 | | | | | 155 | | | | | 160 |
| Thr | Val | Thr | Trp | Asn | Ser | Gly | Ser | Leu | Ser | Ser | Gly | Val | His | Thr | Phe |
| | | | | 165 | | | | | 170 | | | | | 175 | |
| Pro | Ala | Val | Leu | Gln | Ser | Asp | Leu | Tyr | Thr | Leu | Ser | Ser | Ser | Val | Thr |
| | | | 180 | | | | | 185 | | | | | 190 | | |
| Val | Pro | Ser | Ser | Thr | Trp | Pro | Ser | Glu | Thr | Val | Thr | Cys | Asn | Val | Ala |
| | | | 195 | | | | | 200 | | | | | 205 | | |
| His | Pro | Ala | Ser | Ser | Thr | Lys | Val | Asp | Lys | Lys | Ile | Val | Pro | Arg | Asp |
| | 210 | | | | | 215 | | | | | 220 | | | | |
| Cys | Gly | Cys | Lys | Pro | Cys | Ile | Cys | Thr | Val | Pro | Glu | Val | Ser | Ser | Val |
| 225 | | | | | 230 | | | | | 235 | | | | | 240 |
| Phe | Ile | Phe | Pro | Pro | Lys | Pro | Lys | Asp | Val | Leu | Thr | Ile | Thr | Leu | Thr |
| | | | | 245 | | | | | 250 | | | | | 255 | |
| Pro | Lys | Val | Thr | Cys | Val | Val | Val | Asp | Ile | Ser | Lys | Asp | Asp | Pro | Glu |
| | | | 260 | | | | | 265 | | | | | 270 | | |
| Val | Gln | Phe | Ser | Trp | Phe | Val | Asp | Asp | Val | Glu | Val | His | Thr | Ala | Gln |
| | | | 275 | | | | | 280 | | | | | 285 | | |
| Thr | Gln | Pro | Arg | Glu | Glu | Gln | Phe | Asn | Ser | Thr | Phe | Arg | Ser | Val | Ser |
| | 290 | | | | | 295 | | | | | 300 | | | | |
| Glu | Leu | Pro | Ile | Met | His | Gln | Asp | Trp | Leu | Asn | Gly | Lys | Glu | Phe | Lys |
| 305 | | | | | 310 | | | | | 315 | | | | | 320 |
| Cys | Arg | Val | Asn | Ser | Ala | Ala | Phe | Pro | Ala | Pro | Ile | Glu | Lys | Thr | Ile |
| | | | | 325 | | | | | 330 | | | | | 335 | |
| Ser | Lys | Thr | Lys | Gly | Arg | Pro | Lys | Ala | Pro | Gln | Val | Tyr | Thr | Ile | Pro |
| | | | 340 | | | | | 345 | | | | | 350 | | |
| Pro | Pro | Lys | Glu | Gln | Met | Ala | Lys | Asp | Lys | Val | Ser | Leu | Thr | Cys | Met |
| | | | 355 | | | | | 360 | | | | | 365 | | |
| Ile | Thr | Asp | Phe | Phe | Pro | Glu | Asp | Ile | Thr | Val | Glu | Trp | Gln | Trp | Asn |
| | 370 | | | | | 375 | | | | | 380 | | | | |
| Gly | Gln | Pro | Ala | Glu | Asn | Tyr | Lys | Asn | Thr | Gln | Pro | Ile | Met | Asp | Thr |

```
                385                 390                 395                 400
Asp Gly Ser Tyr Phe Ile Tyr Ser Lys Leu Asn Val Gln Lys Ser Asn
                    405                 410                 415

Trp Glu Ala Gly Asn Thr Phe Thr Cys Ser Val Leu His Glu Gly Leu
                420                 425                 430

His Asn His His Thr Glu Lys Ser Leu Ser His Ser Pro Gly Lys
            435                 440                 445
```

```
<210> SEQ ID NO 170
<211> LENGTH: 1344
<212> TYPE: DNA
<213> ORGANISM: Mus musculus

<400> SEQUENCE: 170
```

| | | | | | |
|---|---|---|---|---|---|
| gaggtccaac | tgcaacagtc | tggacctgaa | ctaatgaagc | tggggcttca | gtgaagatg | 60 |
| tcctgcaagg | cttctggata | cattcact | gactacaaca | tgcactgggt | gaagcagaac | 120 |
| caaggaaaga | ccctagactg | gataggagaa | attaatccta | acagtggtgg | tgctggctac | 180 |
| aaccagaagt | tcaagggcaa | ggccacattg | actgtagaca | agtcctccac | cacagcctac | 240 |
| atggagctcc | gcagcctgac | atctgaggac | tctgcagtct | attactgtgc | aagattgggc | 300 |
| tacgatgata | tctacgacga | ctggtacttc | gatgtctggg | gcgcagggac | cacggtcacc | 360 |
| gtctcctcag | ccaaaacgac | cccccatct | gtctatccac | tggcccctgg | atctgctgcc | 420 |
| caaactaact | ccatggtgac | cctgggatgc | ctggtcaagg | gctatttccc | tgagccagtg | 480 |
| acagtgacct | ggaactctgg | atccctgtcc | agcggtgtgc | acaccttccc | agctgtcctg | 540 |
| cagtctgacc | tctacactct | gagcagctca | gtgactgtcc | cctccagcac | ctggcccagc | 600 |
| gagaccgtca | cctgcaacgt | tgcccacccg | gccagcagca | caaggtgga | caagaaaatt | 660 |
| gtgcccaggg | attgtggttg | taagccttgc | atatgtacag | tcccagaagt | atcatctgtc | 720 |
| ttcatcttcc | ccccaaagcc | caaggatgtg | ctcaccatta | ctctgactcc | taaggtcacg | 780 |
| tgtgttgtgg | tagacatcag | caaggatgat | cccgaggtcc | agttcagctg | gtttgtagat | 840 |
| gatgtggagg | tgcacacagc | tcagacgcaa | ccccgggagg | agcagttcaa | cagcactttc | 900 |
| cgctcagtca | gtgaacttcc | catcatgcac | caggactggc | tcaatggcaa | ggagttcaaa | 960 |
| tgcagggtca | acagtgcagc | tttccctgcc | cccatcgaga | aaaccatctc | caaaaccaaa | 1020 |
| ggcagaccga | aggctccaca | ggtgtacacc | attccacctc | caaggagca | gatggccaag | 1080 |
| gataaagtca | gtctgacctg | catgataaca | gacttcttcc | ctgaagacat | tactgtggag | 1140 |
| tggcagtgga | atgggcagcc | agcggagaac | tacaagaaca | ctcagcccat | catggacaca | 1200 |
| gatggctctt | acttcatcta | cagcaagctc | aatgtgcaga | gagcaactg | ggaggcagga | 1260 |
| aatactttca | cctgctctgt | gttacatgag | ggcctgcaca | accaccatac | tgagaagagc | 1320 |
| ctctccccact | ctcctggtaa | atga | | | | 1344 |

```
<210> SEQ ID NO 171
<211> LENGTH: 466
<212> TYPE: PRT
<213> ORGANISM: Mus musculus

<400> SEQUENCE: 171
```

```
Met Gly Trp Ser Trp Thr Phe Leu Phe Leu Leu Ser Gly Thr Ala Gly
 1               5                   10                  15

Val Leu Ser Glu Val Gln Leu Gln Gln Ser Gly Pro Glu Leu Met Lys
                20                  25                  30
```

```
Pro Gly Ala Ser Val Lys Met Ser Cys Lys Ala Ser Gly Tyr Thr Phe
            35                  40                  45

Thr Asp Tyr Asn Met His Trp Val Lys Gln Asn Gln Gly Lys Thr Leu
     50                  55                  60

Asp Trp Ile Gly Glu Ile Asn Pro Asn Ser Gly Gly Ala Gly Tyr Asn
 65                  70                  75                  80

Gln Lys Phe Lys Gly Lys Ala Thr Leu Thr Val Asp Lys Ser Ser Thr
                 85                  90                  95

Thr Ala Tyr Met Glu Leu Arg Ser Leu Thr Ser Glu Asp Ser Ala Val
                100                 105                 110

Tyr Tyr Cys Ala Arg Leu Gly Tyr Asp Asp Ile Tyr Asp Asp Trp Tyr
            115                 120                 125

Phe Asp Val Trp Gly Ala Gly Thr Thr Val Thr Val Ser Ser Ala Lys
     130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
     195                 200                 205

Ser Val Thr Val Pro Ser Ser Thr Trp Pro Ser Glu Thr Val Thr Cys
210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
     275                 280                 285

Asp Pro Glu Val Gln Phe Ser Trp Phe Val Asp Val Glu Val His
290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
     355                 360                 365

Thr Ile Pro Pro Pro Lys Glu Gln Met Ala Lys Asp Lys Val Ser Leu
370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
     435                 440                 445

Glu Gly Leu His Asn His His Thr Glu Lys Ser Leu Ser His Ser Pro
```

-continued

```
       450                 455                 460
Gly Lys
465

<210> SEQ ID NO 172
<211> LENGTH: 1401
<212> TYPE: DNA
<213> ORGANISM: Mus musculus

<400> SEQUENCE: 172
atgggatgga gctggacctt tctcttcctc ctgtcaggaa ctgcaggtgt cctctctgag      60
gtccaactgc aacagtctgg acctgaacta atgaagcctg ggcttcagt gaagatgtcc     120 tgcaaggctt ctggatatac attcactgac tacaacatgc actgggtgaa gcagaaccaa    180
ggaaagaccc tagactggat aggagaaatt aatcctaaca gtggtggtgc tggctacaac    240
cagaagttca gggcaaggc cacattgact gtagacaagt cctccaccac agcctacatg     300
gagctccgca gcctgacatc tgaggactct gcagtctatt actgtgcaag attgggctac    360
gatgatatct acgacgactg gtacttcgat gtctggggcg cagggaccac ggtcaccgtc    420
tcctcagcca aaacgacacc cccatctgtc tatccactgg ccctggatc tgctgcccaa    480 actaactcca tggtgaccct gggatgcctg gtcaagggct atttccctga gccagtgaca    540
gtgacctgga actctggatc cctgtccagc ggtgtgcaca ccttcccagc tgtcctgcag    600
tctgacctct acactctgag cagctcagtg actgtcccct ccagcacctg gcccagcgag    660
accgtcacct gcaacgttgc ccacccggcc agcagcacca aggtggacaa gaaaattgtg    720
cccagggatt gtggttgtaa gccttgcata tgtacagtcc cagaagtatc atctgtcttc    780
atcttccccc caaagcccaa ggatgtgctc accattactc tgactcctaa ggtcacgtgt    840
gttgtggtag acatcagcaa ggatgatccc gaggtccagt tcagctggtt tgtagatgat    900
gtggaggtgc acacagctca gacgcaaccc cgggaggagc agttcaacag cactttccgc    960
tcagtcagtg aacttcccat catgcaccag gactggctca atggcaagga gttcaaatgc   1020
agggtcaaca gtgcagcttt ccctgccccc atcgagaaaa ccatctccaa aaccaaaggc   1080
agaccgaagg ctccacaggt gtacaccatt ccacctccca aggagcagat ggccaaggat   1140
aaagtcagtc tgacctgcat gataacagac ttcttccctg aagacattac tgtggagtgg   1200
cagtggaatg ggcagccagc ggagaactac aagaacactc agcccatcat ggacacagat   1260
ggctcttact tcatctacag caagctcaat gtgcagaaga caactgggaa ggcaggaaat   1320
actttcacct gctctgtgtt acatgagggc ctgcacaacc accatactga aagagcctc    1380 tcccactctc ctggtaaatg a                                              1401

<210> SEQ ID NO 173
<211> LENGTH: 214
<212> TYPE: PRT
<213> ORGANISM: Mus musculus

<400> SEQUENCE: 173

Asp Ile Gln Met Thr Gln Ile Thr Ser Ser Leu Ser Ala Ser Leu Gly
  1               5                  10                  15

Asp Arg Val Ser Ile Ser Cys Arg Ala Ser Gln Asp Ile Ser Asn Tyr
             20                  25                  30

Leu Asn Trp Tyr Gln Gln Lys Pro Asp Gly Thr Phe Lys Leu Leu Ile
         35                  40                  45

Phe Tyr Thr Ser Arg Leu Phe Ser Gly Val Pro Ser Arg Phe Ser Gly
```

```
                50                  55                  60
Ser Gly Ser Gly Thr Asp Tyr Ser Leu Thr Ile Tyr Asn Leu Glu Gln
 65                  70                  75                  80

Glu Asp Phe Ala Thr Tyr Phe Cys Gln Gln Gly Asp Thr Leu Pro Tyr
                 85                  90                  95

Thr Phe Gly Gly Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 174
<211> LENGTH: 642
<212> TYPE: DNA
<213> ORGANISM: Mus musculus

<400> SEQUENCE: 174

```
gatatccaga tgacacagat tacatcctcc ctgtctgcct ctctgggaga cagggtctcc      60
atcagttgca gggcaagtca agacattagc aattatttaa attggtatca gcagaaacca     120
gatggaactt ttaaactcct tatcttctac acatcaagat tattttcagg agtcccatca     180
aggttcagtg gcagtgggtc tggaacagat tattctctca ccatttacaa cctggagcaa     240
gaagattttg ccacttactt ttgccaacag ggagatacgc ttccgtacac tttcggaggg     300
gggaccaagg tggaaataaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag cacctcacg     540
ttgaccaagg acgagtatga acgacataac agctatacct gtgaggccac tcacaagaca     600
tcaacttcac ccattgtcaa gagcttcaac aggaatgagt gt                        642
```

<210> SEQ ID NO 175
<211> LENGTH: 234
<212> TYPE: PRT
<213> ORGANISM: Mus musculus

<400> SEQUENCE: 175

```
Met Met Ser Ser Ala Gln Phe Leu Gly Leu Leu Leu Leu Cys Phe Gln
 1               5                  10                  15

Gly Thr Arg Cys Asp Ile Gln Met Thr Gln Ile Thr Ser Ser Leu Ser
                20                  25                  30

Ala Ser Leu Gly Asp Arg Val Ser Ile Ser Cys Arg Ala Ser Gln Asp
            35                  40                  45
```

```
Ile Ser Asn Tyr Leu Asn Trp Tyr Gln Gln Lys Pro Asp Gly Thr Phe
 50                  55                  60
Lys Leu Leu Ile Phe Tyr Thr Ser Arg Leu Phe Ser Gly Val Pro Ser
 65                  70                  75                  80
Arg Phe Ser Gly Ser Gly Ser Gly Thr Asp Tyr Ser Leu Thr Ile Tyr
                 85                  90                  95
Asn Leu Glu Gln Glu Asp Phe Ala Thr Tyr Phe Cys Gln Gln Gly Asp
            100                 105                 110
Thr Leu Pro Tyr Thr Phe Gly Gly Gly Thr Lys Val Glu Ile Lys Arg
        115                 120                 125
Ala Asp Ala Ala Pro Thr Val Ser Ile Phe Pro Pro Ser Ser Glu Gln
    130                 135                 140
Leu Thr Ser Gly Gly Ala Ser Val Val Cys Phe Leu Asn Asn Phe Tyr
145                 150                 155                 160
Pro Lys Asp Ile Asn Val Lys Trp Lys Ile Asp Gly Ser Glu Arg Gln
                165                 170                 175
Asn Gly Val Leu Asn Ser Trp Thr Asp Gln Asp Ser Lys Asp Ser Thr
            180                 185                 190
Tyr Ser Met Ser Ser Thr Leu Thr Leu Thr Lys Asp Glu Tyr Glu Arg
        195                 200                 205
His Asn Ser Tyr Thr Cys Glu Ala Thr His Lys Thr Ser Thr Ser Pro
    210                 215                 220
Ile Val Lys Ser Phe Asn Arg Asn Glu Cys
225                 230

<210> SEQ ID NO 176
<211> LENGTH: 702
<212> TYPE: DNA
<213> ORGANISM: Mus musculus

<400> SEQUENCE: 176
atgatgtcct ctgctcagtt ccttggtctc ctgttgctct gttttcaagg taccagatgt    60
gatatccaga tgacacagat tacatcctcc ctgtctgcct ctctgggaga cagggtctcc   120
atcagttgca gggcaagtca agacattagc aattatttaa attggtatca gcagaaacca   180
gatggaactt ttaaactcct tatcttctac acatcaagat tatttcagg agtcccatca    240 aggttcagtg gcagtgggtc tggaacagat tattctctca ccatttacaa cctggagcaa   300
gaagattttg ccacttactt ttgccaacag ggagatacgc ttccgtacac tttcggaggg   360
gggaccaagg tggaaataaa acgggctgat gctgcaccaa ctgtatccat cttcccacca   420
tccagtgagc agttaacatc tggaggtgcc tcagtcgtgt gcttcttgaa caacttctac   480
cccaaagaca tcaatgtcaa gtggaagatt gatggcagtg aacgacaaaa tggcgtcctg   540
aacagttgga ctgatcagga cagcaaagac agcacctaca gcatgagcag cacactcacg   600
ttgaccaagg acgagtatga acgacataac agctatacct gtgaggccac tcacaagaca   660
tcaacttcac ccattgtcaa gagcttcaac aggaatgagt gt                      702

<210> SEQ ID NO 177
<211> LENGTH: 450
<212> TYPE: PRT
<213> ORGANISM: Mus musculus

<400> SEQUENCE: 177

Glu Val Gln Leu Gln Gln Ser Gly Pro Glu Leu Met Lys Pro Gly Thr
 1               5                  10                  15
```

-continued

```
Ser Val Lys Met Ser Cys Lys Ala Ser Gly Tyr Thr Phe Thr Asp Tyr
         20                  25                  30

Asn Met His Trp Val Lys Gln Thr Gln Gly Lys Thr Leu Glu Trp Ile
         35                  40                  45

Gly Glu Ile Asn Pro Asn Ser Gly Gly Ala Gly Tyr Asn Gln Lys Phe
 50                  55                  60

Lys Gly Lys Ala Thr Leu Thr Val Asp Lys Ser Ser Thr Thr Ala Tyr
 65                  70                  75                  80

Met Glu Leu Arg Ser Leu Thr Ser Glu Asp Ser Ala Val Tyr Tyr Cys
             85                  90                  95

Ala Lys Leu Gly Tyr Asp Asp Ile Tyr Asp Asp Trp Tyr Phe Asp Val
                100                 105                 110

Trp Gly Ala Gly Thr Thr Val Thr Val Ser Ser Ala Lys Thr Thr Ala
                115                 120                 125

Pro Ser Val Tyr Pro Leu Ala Pro Val Cys Gly Asp Thr Thr Gly Ser
130                 135                 140

Ser Val Thr Leu Gly Cys Leu Val Lys Gly Tyr Phe Pro Glu Pro Val
145                 150                 155                 160

Thr Leu Thr Trp Asn Ser Gly Ser Leu Ser Ser Asp Val His Thr Phe
                165                 170                 175

Pro Ala Leu Leu Gln Ser Gly Leu Tyr Thr Leu Ser Ser Ser Val Thr
                180                 185                 190

Val Thr Thr Trp Pro Ser Gln Thr Ile Thr Cys Asn Val Ala His Pro
                195                 200                 205

Ala Ser Ser Thr Lys Val Asp Lys Lys Ile Glu Pro Arg Gly Ser Pro
210                 215                 220

Thr His Lys Pro Cys Pro Pro Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Met Val Thr Cys Val Val Asp Val Ser Glu Asp
                260                 265                 270

Asp Pro Asp Val His Val Ser Trp Phe Val Asn Asn Val Glu Val His
                275                 280                 285

Thr Ala Gln Thr Gln Thr His Arg Glu Asp Tyr Asn Ser Thr Ile Arg
290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Ala Leu Pro Ala Pro Ile Glu
                325                 330                 335

Arg Thr Ile Ser Lys Pro Lys Gly Pro Val Arg Ala Pro Gln Val Tyr
                340                 345                 350

Val Leu Pro Pro Pro Glu Glu Glu Met Thr Lys Lys Gln Val Thr Leu
                355                 360                 365

Thr Cys Met Ile Thr Asp Phe Met Pro Glu Asp Ile Tyr Val Glu Trp
        370                 375                 380

Thr Asn Asn Gly Gln Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
                420                 425                 430

Glu Gly Leu His Asn His His Thr Thr Lys Ser Phe Ser Arg Thr Pro
```

Gly Lys
    450

<210> SEQ ID NO 178
<211> LENGTH: 1350
<212> TYPE: DNA
<213> ORGANISM: Mus musculus

<400> SEQUENCE: 178

```
gaggtccaac tgcaacagtc tggacctgaa ctaatgaagc tgggacttc  agtgaagatg      60
tcctgcaagg cttctggata cattcact gactacaaca tgcactgggt gaagcagacc      120
caaggaaaga ccctagagtg gataggagaa attaatccta cagtggtgg tgctggctac     180
aaccagaagt tcaagggcaa ggccacattg actgtagaca agtcctccac cacagcctac    240
atggagctcc gcagcctgac atctgaggac tctgcagtct attactgtgc aaaattgggc    300
tacgatgata tctacgacga ctggtatttc gatgtctggg gcgcaggga  cacggtcacc    360
gtctcctcag ccaaaacaac agccccatcg gtctatccac tggcccctgt gtgtggagat    420
acaactggct cctcggtgac tctaggatgc ctggtcaagg gttatttccc tgagccagtg    480
accttgacct ggaactctgg atccctgtcc agtgatgtgc acaccttccc agctctcctg    540
cagtctggcc tctacaccct cagcagctca gtgactgtaa ccacctggcc cagccagacc    600
atcacctgca atgtggccca cccggcaagc agcaccaaag tggacaagaa aattgagccc    660
agagggtccc caacacataa accctgtcct ccatgcccag ctcctaacct cttgggtgga    720
ccatccgtct tcatcttccc tccaaagatc aaggatgtac tcatgatctc cctgagcccc    780
atggtcacgt gtgtggtggt ggatgtgagc gaggatgacc cagatgtcca tgtcagctgg    840
ttcgtgaaca acgtggaagt acacacagct cagacacaaa cccatagaga ggattacaac    900
agtactatcc gggtggtcag tgccctcccc atccagcacc aggactggat gagtggcaag    960
gagttcaaat gcaaggtcaa caacaaagcc ctcccagcgc ccatcgagag aaccatctca    1020
aaacccaaag ggccagtaag agctccacag gtatatgtct tgcctccacc agaagaagag    1080
atgactaaga acaggtcac tctgacctgc atgatcacag acttcatgcc tgaagacatt     1140
tacgtggagt ggaccaacaa cgggcaaaca gagctaaact acaagaacac tgaaccagtc    1200
ctggactctg atggttctta cttcatgtac agcaagctga gagtggaaaa gaagaactgg    1260
gtggaaagaa atagcactc ctgttcagtg gtccacgagg gtctgcacaa tcaccacacg     1320
actaagagct tctcccggac tccgggtaaa                                      1350
```

<210> SEQ ID NO 179
<211> LENGTH: 469
<212> TYPE: PRT
<213> ORGANISM: Mus musculus

<400> SEQUENCE: 179

Met Gly Trp Ser Trp Thr Phe Leu Phe Leu Leu Ser Gly Thr Ala Gly
 1               5                   10                  15

Val Leu Ser Glu Val Gln Leu Gln Gln Ser Gly Pro Glu Leu Met Lys
            20                  25                  30

Pro Gly Thr Ser Val Lys Met Ser Cys Lys Ala Ser Gly Tyr Thr Phe
        35                  40                  45

Thr Asp Tyr Asn Met His Trp Val Lys Gln Thr Gln Gly Lys Thr Leu
    50                  55                  60

```
Glu Trp Ile Gly Glu Ile Asn Pro Asn Ser Gly Gly Ala Gly Tyr Asn
 65                  70                  75                  80

Gln Lys Phe Lys Gly Lys Ala Thr Leu Thr Val Asp Lys Ser Ser Thr
                 85                  90                  95

Thr Ala Tyr Met Glu Leu Arg Ser Leu Thr Ser Glu Asp Ser Ala Val
            100                 105                 110

Tyr Tyr Cys Ala Lys Leu Gly Tyr Asp Asp Ile Tyr Asp Asp Trp Tyr
        115                 120                 125

Phe Asp Val Trp Gly Ala Gly Thr Thr Val Thr Val Ser Ser Ala Lys
    130                 135                 140

Thr Thr Ala Pro Ser Val Tyr Pro Leu Ala Pro Val Cys Gly Asp Thr
145                 150                 155                 160

Thr Gly Ser Ser Val Thr Leu Gly Cys Leu Val Lys Gly Tyr Phe Pro
                165                 170                 175

Glu Pro Val Thr Leu Thr Trp Asn Ser Gly Ser Leu Ser Ser Asp Val
            180                 185                 190

His Thr Phe Pro Ala Leu Leu Gln Ser Gly Leu Tyr Thr Leu Ser Ser
        195                 200                 205

Ser Val Thr Val Thr Thr Trp Pro Ser Gln Thr Ile Thr Cys Asn Val
210                 215                 220

Ala His Pro Ala Ser Ser Thr Lys Val Asp Lys Lys Ile Glu Pro Arg
225                 230                 235                 240

Gly Ser Pro Thr His Lys Pro Cys Pro Pro Cys Pro Ala Pro Asn Leu
                245                 250                 255

Leu Gly Gly Pro Ser Val Phe Ile Phe Pro Pro Lys Ile Lys Asp Val
            260                 265                 270

Leu Met Ile Ser Leu Ser Pro Met Val Thr Cys Val Val Val Asp Val
        275                 280                 285

Ser Glu Asp Asp Pro Asp Val His Val Ser Trp Phe Val Asn Asn Val
290                 295                 300

Glu Val His Thr Ala Gln Thr Gln Thr His Arg Glu Asp Tyr Asn Ser
305                 310                 315                 320

Thr Ile Arg Val Val Ser Ala Leu Pro Ile Gln His Gln Asp Trp Met
                325                 330                 335

Ser Gly Lys Glu Phe Lys Cys Lys Val Asn Asn Lys Ala Leu Pro Ala
            340                 345                 350

Pro Ile Glu Arg Thr Ile Ser Lys Pro Lys Gly Pro Val Arg Ala Pro
        355                 360                 365

Gln Val Tyr Val Leu Pro Pro Glu Glu Glu Met Thr Lys Lys Gln
    370                 375                 380

Val Thr Leu Thr Cys Met Ile Thr Asp Phe Met Pro Glu Asp Ile Tyr
385                 390                 395                 400

Val Glu Trp Thr Asn Asn Gly Gln Thr Glu Leu Asn Tyr Lys Asn Thr
                405                 410                 415

Glu Pro Val Leu Asp Ser Asp Gly Ser Tyr Phe Met Tyr Ser Lys Leu
            420                 425                 430

Arg Val Glu Lys Lys Asn Trp Val Glu Arg Asn Ser Tyr Ser Cys Ser
        435                 440                 445

Val Val His Glu Gly Leu His Asn His His Thr Thr Lys Ser Phe Ser
    450                 455                 460

Arg Thr Pro Gly Lys
465
```

```
<210> SEQ ID NO 180
<211> LENGTH: 1407
<212> TYPE: DNA
<213> ORGANISM: Mus musculus

<400> SEQUENCE: 180
atgggatgga gctggacctt tctcttcctc ctgtcaggaa ctgcaggtgt cctctctgag      60
gtccaactgc aacagtctgg acctgaacta atgaagcctg gacttcagt gaagatgtcc     120
tgcaaggctt ctggatatac attcactgac tacaacatgc actgggtgaa gcagacccaa     180
ggaaagaccc tagagtggat aggagaaatt aatcctaaca gtggtggtgc tggctacaac     240
cagaagttca agggcaaggc cacattgact gtagacaagt cctccaccac agcctacatg     300
gagctccgca gcctgacatc tgaggactct gcagtctatt actgtgcaaa attgggctac     360
gatgatatct acgacgactg gtatttcgat gtctggggcg cagggaccac ggtcaccgtc     420
tcctcagcca aaacaacagc cccatcggtc tatccactgg ccctgtgtg tggagataca     480
actggctcct cggtgactct aggatgcctg gtcaagggtt atttccctga gccagtgacc     540
ttgacctgga actctggatc cctgtccagt gatgtgcaca ccttcccagc tctcctgcag     600
tctggcctct acaccctcag cagctcagtg actgtaacca cctggcccag ccagaccatc     660
acctgcaatg tggcccaccc ggcaagcagc accaaagtgg acaagaaaat tgagcccaga     720
gggtccccaa cacataaacc ctgtcctcca tgcccagctc ctaacctctt gggtggacca     780
tccgtcttca tcttccctcc aaagatcaag gatgtactca tgatctccct gagccccatg     840
gtcacgtgtg tggtggtgga tgtgagcgag gatgacccag atgtccatgt cagctggttc     900
gtgaacaacg tggaagtaca cacagctcag acacaaaccc atagagagga ttacaacagt     960
actatccggg tggtcagtgc cctccccatc cagcaccagg actggatgag tggcaaggag    1020
ttcaaatgca aggtcaacaa caaagccctc ccagcgccca tcgagagaac catctcaaaa    1080
cccaaagggc agtaagagc tccacaggta tatgtcttgc ctccaccaga agaagagatg    1140
actaagaaac aggtcactct gacctgcatg atcacagact tcatgcctga agacatttac    1200
gtggagtgga ccaacaacgg gcaaacagag ctaaactaca gaacactga accagtcctg    1260
gactctgatg gttcttactt catgtacagc aagctgagag tggaaaagaa gaactgggtg    1320
gaaagaaata gctactcctg ttcagtggtc cacgagggtc tgcacaatca ccacgact    1380
aagagcttct cccggactcc gggtaaa                                         1407

<210> SEQ ID NO 181
<211> LENGTH: 214
<212> TYPE: PRT
<213> ORGANISM: Mus musculus

<400> SEQUENCE: 181
```

Asp Ile Gln Met Thr Gln Thr Thr Ser Ser Leu Ser Ala Ser Leu Gly
 1               5                  10                  15

Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Phe Tyr Thr Ser Arg Leu Leu Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr

```
                        85                  90                  95
Thr Phe Gly Gly Gly Thr Lys Leu Glu Ile Lys Arg Ala Asp Ala Ala
                    100                 105                 110
Pro Thr Val Ser Ile Phe Pro Leu Ser Ser Glu Gln Leu Thr Ser Gly
                115                 120                 125
Gly Ala Ser Val Val Cys Phe Leu Asn Asn Phe Tyr Pro Lys Asp Ile
            130                 135                 140
Asn Val Lys Trp Lys Ile Asp Gly Ser Glu Arg Gln Asn Gly Val Leu
145                 150                 155                 160
Asn Ser Trp Thr Asp Gln Asp Ser Lys Asp Ser Thr Tyr Ser Met Ser
                165                 170                 175
Ser Thr Leu Thr Leu Thr Lys Asp Glu Tyr Glu Arg His Asn Ser Tyr
            180                 185                 190
Thr Cys Glu Ala Thr His Lys Thr Ser Thr Ser Pro Ile Val Lys Ser
        195                 200                 205
Phe Asn Arg Asn Glu Cys
    210

<210> SEQ ID NO 182
<211> LENGTH: 645
<212> TYPE: DNA
<213> ORGANISM: Mus musculus

<400> SEQUENCE: 182
gatatccaga tgacacagac tacatcctcc ctgtctgcct ctctgggaga cagggtctcc     60
atcagttgca gggcaagtca agacattagc aattatttaa actggtatca gcagaaacca    120
gatggaactt ttaaactcct tatcttctac acatcaagat tactctcagg agtcccatca    180
aggttcagtg gcagtgggtc tggaacagat tattctctca ccatttacaa cctggagcaa    240
gaagattttg ccacttactt ttgccaacag ggagatacgc ttccgtacac tttcggaggg    300
gggaccaaac tggaaataaa acgggctgat gctgcaccaa ctgtatccat cttcccacta    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag cacccctcacg   540 ttgaccaagg acgagtatga acgacataac agctatacct gtgaggccac tcacaagaca    600
tcaacttcac ccattgtcaa gagcttcaac aggaatgagt gttag                    645

<210> SEQ ID NO 183
<211> LENGTH: 234
<212> TYPE: PRT
<213> ORGANISM: Mus musculus

<400> SEQUENCE: 183

Met Met Ser Ser Ala Gln Phe Leu Gly Leu Leu Leu Leu Cys Phe Gln
  1               5                  10                  15
Gly Thr Arg Cys Asp Ile Gln Met Thr Gln Thr Thr Ser Ser Leu Ser
                 20                  25                  30
Ala Ser Leu Gly Asp Arg Val Ser Ile Ser Cys Arg Ala Ser Gln Asp
             35                  40                  45
Ile Ser Asn Tyr Leu Asn Trp Tyr Gln Gln Lys Pro Asp Gly Thr Phe
         50                  55                  60
Lys Leu Leu Ile Phe Tyr Thr Ser Arg Leu Leu Ser Gly Val Pro Ser
 65                  70                  75                  80
```

-continued

```
Arg Phe Ser Gly Ser Gly Ser Gly Thr Asp Tyr Ser Leu Thr Ile Tyr
                 85                  90                  95

Asn Leu Glu Gln Glu Asp Phe Ala Thr Tyr Phe Cys Gln Gln Gly Asp
            100                 105                 110

Thr Leu Pro Tyr Thr Phe Gly Gly Gly Thr Lys Leu Glu Ile Lys Arg
        115                 120                 125

Ala Asp Ala Ala Pro Thr Val Ser Ile Phe Pro Leu Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

```
<210> SEQ ID NO 184
<211> LENGTH: 705
<212> TYPE: DNA
<213> ORGANISM: Mus musculus

<400> SEQUENCE: 184
atgatgtcct ctgctcagtt ccttggtctc ctgttgctct gttttcaagg taccagatgt      60
gatatccaga tgacacagac tacatcctcc ctgtctgcct ctctgggaga cagggtctcc     120
atcagttgca gggcaagtca agacattagc aattatttaa actggtatca gcagaaacca     180
gatggaactt ttaaactcct tatcttctac acatcaagat tactctcagg agtcccatca     240
aggttcagtg gcagtgggtc tggaacagat tattctctca ccatttacaa cctggagcaa     300
gaagattttg ccacttactt ttgccaacag ggagatacgc ttccgtacac tttcggaggg     360
gggaccaaac tggaaataaa acgggctgat gctgcaccaa ctgtatccat cttcccacta     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag caccctcacg     600
ttgaccaagg acgagtatga acgacataac agctatacct gtgaggccac tcacaagaca     660
tcaacttcac ccattgtcaa gagcttcaac aggaatgagt gttag                     705
```

```
<210> SEQ ID NO 185
<211> LENGTH: 447
<212> TYPE: PRT
<213> ORGANISM: Mus musculus

<400> SEQUENCE: 185

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gly Lys Thr Leu Glu Trp Ile
        35                  40                  45
```

-continued

```
Gly Glu Ile Asn Pro Asn Ser Gly Gly Ala Gly Tyr Asn Gln Lys Phe
 50                  55                  60
Lys Gly Lys Ala Thr Leu Thr Val Asp Lys Ser Ser Thr Thr Ala Tyr
 65                  70                  75                  80
Met Glu Leu Arg Ser Leu Thr Ser Glu Asp Ser Ala Val Tyr Tyr Cys
                 85                  90                  95
Ala Arg Leu Gly Tyr Asp Asp Ile Tyr Asp Asp Trp Tyr Phe Asp Val
            100                 105                 110
Trp Gly Ala Gly Thr Thr Val Thr Val Ser Ser Ala Lys Thr Thr Pro
        115                 120                 125
Pro Ser Val Tyr Pro Leu Ala Pro Gly Ser Ala Ala Gln Thr Asn Ser
    130                 135                 140
Met Val Thr Leu Gly Cys Leu Val Lys Gly Tyr Phe Pro Glu Pro Val
145                 150                 155                 160
Thr Val Thr Trp Asn Ser Gly Ser Leu Ser Ser Gly Val His Thr Phe
                165                 170                 175
Pro Ala Val Leu Gln Ser Asp Leu Tyr Thr Leu Ser Ser Ser Val Thr
            180                 185                 190
Val Pro Ser Ser Thr Trp Pro Ser Glu Thr Val Thr Cys Asn Val Ala
        195                 200                 205
His Pro Ala Ser Ser Thr Lys Val Asp Lys Lys Ile Val Pro Arg Asp
    210                 215                 220
Cys Gly Cys Lys Pro Cys Ile Cys Thr Val Pro Glu Val Ser Ser Val
225                 230                 235                 240
Phe Ile Phe Pro Pro Lys Pro Lys Asp Val Leu Thr Ile Thr Leu Thr
                245                 250                 255
Pro Lys Val Thr Cys Val Val Asp Ile Ser Lys Asp Asp Pro Glu
            260                 265                 270
Val Gln Phe Ser Trp Phe Val Asp Asp Val Glu Val His Thr Ala Gln
        275                 280                 285
Thr Gln Pro Arg Glu Glu Gln Phe Asn Ser Thr Phe Arg Ser Val Ser
    290                 295                 300
Glu Leu Pro Ile Met His Gln Asp Trp Leu Asn Gly Lys Glu Phe Lys
305                 310                 315                 320
Cys Arg Val Asn Ser Ala Ala Phe Pro Ala Pro Ile Glu Lys Thr Ile
                325                 330                 335
Ser Lys Thr Lys Gly Arg Pro Lys Ala Pro Gln Val Tyr Thr Ile Pro
            340                 345                 350
Pro Pro Lys Glu Gln Met Ala Lys Asp Lys Val Ser Leu Thr Cys Met
        355                 360                 365
Ile Thr Asp Phe Phe Pro Glu Asp Ile Thr Val Glu Trp Gln Trp Asn
    370                 375                 380
Gly Gln Pro Ala Glu Asn Tyr Lys Asn Thr Gln Pro Ile Met Asp Thr
385                 390                 395                 400
Asp Gly Ser Tyr Phe Ile Tyr Ser Lys Leu Asn Val Gln Lys Ser Asn
                405                 410                 415
Trp Glu Ala Gly Asn Thr Phe Thr Cys Ser Val Leu His Glu Gly Leu
            420                 425                 430
His Asn His His Thr Glu Lys Ser Leu Ser His Ser Pro Gly Lys
        435                 440                 445

<210> SEQ ID NO 186
<211> LENGTH: 1344
<212> TYPE: DNA
```

<213> ORGANISM: Mus musculus

<400> SEQUENCE: 186

```
gaggtccaac tgcaacagtc tggacctgaa ctaatgaagc ctggggcttc agtgaagatg      60
tcctgcaagg cttctggata tacattcact gactacaaca tgcactgggt gaagcagaac     120
caaggaaaga ccctagaatg gataggagaa attaatccta acagtggtgg tgctggctac     180
aaccagaagt tcaagggcaa ggccacattg actgtagaca agtcctccac cacagcctac     240
atggagctcc gcagcctgac atctgaggac tctgcagtct attactgtgc aagattgggc     300
tacgatgata tctacgacga ctggtacttc gatgtctggg gcgcagggac cacggtcacc     360
gtctcctcag ccaaaacgac accccatct gtctatccac tggcccctgg atctgctgcc      420
caaactaact ccatggtgac cctgggatgc ctggtcaagg gctatttccc tgagccagtg     480
acagtgacct ggaactctgg atccctgtcc agcggtgtgc acccttccc agctgtcctg      540
cagtctgacc tctacactct gagcagctca gtgactgtcc cctccagcac ctggcccagc     600
gagaccgtca cctgcaacgt tgcccacccg gccagcagca ccaaggtgga caagaaaatt     660
gtgcccaggg attgtggttg taagccttgc atatgtacag tcccagaagt atcatctgtc     720
ttcatcttcc ccccaaagcc caaggatgtg ctcaccatta ctctgactcc taaggtcacg     780
tgtgttgtgg tagacatcag caaggatgat cccgaggtcc agttcagctg gtttgtagat     840
gatgtggagg tgcacacagc tcagacgcaa ccccggggag agcagttcaa cagcactttc     900
cgctcagtca gtgaacttcc catcatgcac caggactggc tcaatggcaa ggagttcaaa     960
tgcagggtca acagtgcagc ttttcctgcc cccatcgaga aaaccatctc caaaaccaaa    1020
ggcagaccga aggctccaca ggtgtacacc attccacctc caaggagca gatggccaag    1080
gataaagtca gtctgacctg catgataaca gacttcttcc ctgaagacat tactgtggag    1140
tggcagtgga atgggcagcc agcggagaac tacaagaaca ctcagcccat catggacaca    1200
gatggctctt acttcatcta cagcaagctc aatgtgcaga gagcaactg ggaggcagga    1260
aatactttca cctgctctgt gttacatgag ggcctgcaca accaccatac tgagaagagc    1320
ctctcccact ctcctggtaa atga                                          1344
```

<210> SEQ ID NO 187
<211> LENGTH: 466
<212> TYPE: PRT
<213> ORGANISM: Mus musculus

<400> SEQUENCE: 187

```
Met Gly Trp Ser Trp Thr Phe Leu Phe Leu Leu Ser Gly Thr Ala Gly
  1               5                  10                  15

Val Leu Ser Glu Val Gln Leu Gln Gln Ser Gly Pro Glu Leu Met Lys
             20                  25                  30

Pro Gly Ala Ser Val Lys Met Ser Cys Lys Ala Ser Gly Tyr Thr Phe
         35                  40                  45

Thr Asp Tyr Asn Met His Trp Val Lys Gln Asn Gln Gly Lys Thr Leu
     50                  55                  60

Glu Trp Ile Gly Glu Ile Asn Pro Asn Ser Gly Gly Ala Gly Tyr Asn
 65                  70                  75                  80

Gln Lys Phe Lys Gly Lys Ala Thr Leu Thr Val Asp Lys Ser Ser Thr
                 85                  90                  95

Thr Ala Tyr Met Glu Leu Arg Ser Leu Thr Ser Glu Asp Ser Ala Val
            100                 105                 110
```

```
Tyr Tyr Cys Ala Arg Leu Gly Tyr Asp Asp Ile Tyr Asp Asp Trp Tyr
        115                 120                 125

Phe Asp Val Trp Gly Ala Gly Thr Thr Val Thr Val Ser Ser Ala Lys
130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
            165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Val Glu Val His
290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465

<210> SEQ ID NO 188
<211> LENGTH: 1401
<212> TYPE: DNA
<213> ORGANISM: Mus musculus

<400> SEQUENCE: 188
atgggatgga gctggaccct tctcttcctc ctgtcaggaa ctgcaggtgt cctctctgag      60
```

```
gtccaactgc aacagtctgg acctgaacta atgaagcctg gggcttcagt gaagatgtcc      120
tgcaaggctt ctggatatac attcactgac tacaacatgc actgggtgaa gcagaaccaa      180
ggaaagaccc tagaatggat aggagaaatt aatcctaaca gtggtggtgc tggctacaac      240
cagaagttca gggcaaggc cacattgact gtagacaagt cctccaccac agcctacatg       300
gagctccgca gcctgacatc tgaggactct gcagtctatt actgtgcaag attgggctac      360
gatgatatct acgacgactg gtacttcgat gtctggggcg cagggaccac ggtcaccgtc      420
tcctcagcca aaacgacacc cccatctgtc tatccactgg cccctggatc tgctgcccaa      480
actaactcca tggtgaccct gggatgcctg gtcaagggct atttccctga ccagtgaca       540
gtgacctgga actctggatc cctgtccagc ggtgtgcaca ccttcccagc tgtcctgcag      600
tctgacctct acactctgag cagctcagtg actgtcccct ccagcacctg gcccagcgag      660
accgtcacct gcaacgttgc ccacccggcc agcagcacca aggtggacaa gaaaattgtg      720
cccaggggatt gtggttgtaa gccttgcata tgtacagtcc cagaagtatc atctgtcttc     780
atcttccccc caaagcccaa ggatgtgctc accattactc tgactcctaa ggtcacgtgt      840
gttgtggtag acatcagcaa ggatgatccc gaggtccagt tcagctggtt tgtagatgat      900
gtggaggtgc acacagctca gacgcaaccc cgggaggagc agttcaacag cactttccgc      960
tcagtcagtg aacttcccat catgcaccag gactggctca atggcaagga gttcaaatgc     1020
agggtcaaca gtgcagcttt ccctgccccc atcgagaaaa ccatctccaa aaccaaaggc     1080
agaccgaagg ctccacaggt gtacaccatt ccacctccca aggagcagat ggccaaggat     1140
aaagtcagtc tgacctgcat gataacagac ttcttccctg aagacattac tgtggagtgg     1200
cagtggaatg ggcagccagc ggagaactac aagaacactc agcccatcat ggacacagat     1260
ggctcttact tcatctacag caagctcaat gtgcagaaga gcaactggga ggcaggaaat     1320
actttcacct gctctgtgtt acatgagggc ctgcacaacc accatactga aagagcctc      1380
tcccactctc ctggtaaatg a                                               1401

<210> SEQ ID NO 189
<211> LENGTH: 213
<212> TYPE: PRT
<213> ORGANISM: Mus musculus

<400> SEQUENCE: 189

Gln Ile Val Leu Ser Gln Ser Pro Ala Phe Leu Ser Val Ser Pro Gly
  1               5                  10                  15

Asp Lys Val Thr Met Thr Cys Arg Ala Ser Ser Ser Ile Ser Tyr Ile
             20                  25                  30

His Trp Phe Gln Gln Lys Pro Gly Ser Ser Pro Arg Ser Trp Ile Tyr
         35                  40                  45

Ala Thr Ser Asn Leu Ala Ser Gly Val Pro Gly Arg Phe Ser Gly Ser
     50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Asp Pro Leu Thr
                 85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
```

```
                130                 135                 140
Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
                180                 185                 190

Cys Glu Ala Thr His Lys Thr Ser Thr Ser Pro Ile Val Lys Ser Phe
                195                 200                 205

Asn Arg Asn Glu Cys
    210

<210> SEQ ID NO 190
<211> LENGTH: 642
<212> TYPE: DNA
<213> ORGANISM: Mus musculus

<400> SEQUENCE: 190
caaattgttc tctcccagtc tccagcattc ctgtctgtat ctccagggga taaggtcaca    60
atgacttgca gggccagctc aagtataagt tacatacact ggtttcagca gaagccagga   120
tcctccccca gatcctggat ttatgccaca tccaacctgg cttctggagt ccctggtcgc   180
ttcagtggca gtgggtctgg gacctcttac tctctcacaa tcagcagagt ggaggctgag   240
gatgctgcca cttattactg ccagcagtgg agtagtgacc cactcacgtt cggtgctggg   300
accaagctgg agctgaaacg ggctgatgct gcaccaactg tatccatctt cccaccatcc   360
agtgagcagt taacatctgg aggtgcctca gtcgtgtgct tcttgaacaa cttctacccc   420
aaagacatca atgtcaagtg gaagattgat ggcagtgaac gacaaaatgg cgtcctgaac   480
agttggactg atcaggacag caaagacagc acctacagca tgagcagcac cctcacgttg   540
accaaggacg agtatgaacg acataacagc tatacctgtg aggccactca caagacatca   600
acttcaccca ttgtcaagag cttcaacagg aatgagtgtt ag                     642

<210> SEQ ID NO 191
<211> LENGTH: 235
<212> TYPE: PRT
<213> ORGANISM: Mus musculus

<400> SEQUENCE: 191

Met Asp Phe Gln Val Gln Ile Phe Ser Phe Leu Leu Ile Ser Ala Ser
 1                5                  10                  15

Val Ile Met Ser Arg Gly Gln Ile Val Leu Ser Gln Ser Pro Ala Phe
                20                  25                  30

Leu Ser Val Ser Pro Gly Asp Lys Val Thr Met Thr Cys Arg Ala Ser
            35                  40                  45

Ser Ser Ile Ser Tyr Ile His Trp Phe Gln Gln Lys Pro Gly Ser Ser
        50                  55                  60

Pro Arg Ser Trp Ile Tyr Ala Thr Ser Asn Leu Ala Ser Gly Val Pro
65                  70                  75                  80

Gly Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
                100                 105                 110

Ser Ser Asp Pro Leu Thr Phe Gly Ala Gly Thr Lys Leu Glu Leu Lys
            115                 120                 125
```

```
Arg Ala Asp Ala Ala Pro Thr Val Ser Ile Phe Pro Pro Ser Ser Glu
    130                 135                 140
```

```
Gln Leu Thr Ser Gly Gly Ala Ser Val Val Cys Phe Leu Asn Asn Phe
145                 150                 155                 160
```

```
Tyr Pro Lys Asp Ile Asn Val Lys Trp Lys Ile Asp Gly Ser Glu Arg
                165                 170                 175
```

```
Gln Asn Gly Val Leu Asn Ser Trp Thr Asp Gln Asp Ser Lys Asp Ser
            180                 185                 190
```

```
Thr Tyr Ser Met Ser Ser Thr Leu Thr Leu Thr Lys Asp Glu Tyr Glu
        195                 200                 205
```

```
Arg His Asn Ser Tyr Thr Cys Glu Ala Thr His Lys Thr Ser Thr Ser
    210                 215                 220
```

```
Pro Ile Val Lys Ser Phe Asn Arg Asn Glu Cys
225                 230                 235
```

<210> SEQ ID NO 192
<211> LENGTH: 708
<212> TYPE: DNA
<213> ORGANISM: Mus musculus

<400> SEQUENCE: 192

```
atggattttc aagtgcagat tttcagcttc ctgctaatca gtgcttcagt cataatgtcc    60
agaggacaaa ttgttctctc ccagtctcca gcattcctgt ctgtatctcc aggggataag   120
gtcacaatga cttgcagggc cagctcaagt ataagttaca tacactggtt tcagcagaag   180
ccaggatcct cccccagatc ctggatttat gccacatcaa acctggcttc tggagtccct   240
ggtcgcttca gtggcagtgg gtctgggacc tcttactctc tcacaatcag cagagtggag   300
gctgaggatg ctgccactta ttactgccag cagtggagta gtgacccact cacgttcggt   360
gctgggacca agctggagct gaaacgggct gatgctgcac caactgtatc catcttccca   420
ccatccagtg agcagttaac atctggaggt gcctcagtcg tgtgcttctt gaacaacttc   480
taccccaaag acatcaatgt caagtggaag attgatggca gtgaacgaca aaatggcgtc   540
ctgaacagtt ggactgatca ggacagcaaa gacagcacct acagcatgag cagcaccctc   600
acgttgacca aggacgagta tgaacgacat aacagctata cctgtgaggc cactcacaag   660
acatcaactt cacccattgt caagagcttc aacaggaatg agtgttag             708
```

<210> SEQ ID NO 193
<211> LENGTH: 445
<212> TYPE: PRT
<213> ORGANISM: Mus musculus

<400> SEQUENCE: 193

```
Glu Val Gln Leu Gln Gln Ser Gly Ala Asp Leu Val Gln Pro Gly Ala
  1               5                  10                  15
```

```
Ser Val Lys Val Ser Cys Thr Ala Ser Gly Phe Asp Ile Lys Asp Tyr
             20                  25                  30
```

```
Tyr Ile His Trp Met Lys Gln Arg Pro Asp Gln Gly Leu Glu Trp Ile
         35                  40                  45
```

```
Gly Arg Val Asp Pro Asp Asn Gly Glu Thr Glu Phe Ala Pro Lys Phe
     50                  55                  60
```

```
Pro Gly Lys Ala Thr Phe Thr Thr Asp Thr Ser Ser Asn Thr Ala Tyr
 65                  70                  75                  80
```

```
Leu Gln Leu Arg Gly Leu Thr Ser Glu Asp Thr Ala Ile Tyr Tyr Cys
                 85                  90                  95
```

Gly Arg Glu Asp Tyr Asp Gly Thr Tyr Thr Trp Phe Pro Tyr Trp Gly
            100                 105                 110

Gln Gly Thr Leu Val Thr Val Ser Ala Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Ile Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445

<210> SEQ ID NO 194
<211> LENGTH: 1338
<212> TYPE: DNA
<213> ORGANISM: Mus musculus

<400> SEQUENCE: 194
gaagttcagc tgcaacagtc tggggcagac cttgtgcagc caggggcctc agtcaaggtg      60
tcctgcacag cttctggctt cgacattaag gactactata tacactggat gaaacagagg     120
cctgaccagg gcctggagtg gattggaagg gttgatcctg acaatggtga gactgaattt     180

```
gccccgaagt tcccgggcaa ggccactttt acaacagaca catcctccaa cacagcctac    240
ctacaactca gaggcctgac atctgaggac actgccatct attactgtgg gagagaagac    300
tacgatggta cctacacctg gtttccttat tggggccaag ggactctggt cactgtctct    360
gcagccaaaa cgacaccccc atctgtctat ccactggccc ctggatctgc tgcccaaact    420
aactccatgg tgaccctggg atgcctggtc aagggctatt tccctgagcc agtgacagtg    480
acctggaact ctggatccct gtccagcggt gtgcacacct cccagctgt cctgcagtct    540 gacctctaca ctctgagcag ctcagtgact gtccccctcca gcacctggcc cagcgagacc    600
gtcacctgca acgttgccca cccggccagc agcaccaagg tggacaagaa aattgtgccc    660
agggattgtg gttgtaagcc ttgcatatgt acagtcccag aagtatcatc tgtcttcatc    720
ttccccccaa agcccaagga tgtgctcacc attactctga ctcctaaggt cacgtgtgtt    780
gtggtagaca tcagcaagga tgatcccgag gtccagttca gctggtttgt agatgatgtg    840
gaggtgcaca cagctcagac gcaaccccgg gaggagcagt tcaacagcac tttccgctca    900
gtcagtgaac ttcccatcat gcaccaggac tggctcaatg gcaaggagtt caaatgcagg    960
gtcaacagtg cagctttccc tgcccccatc gagaaaacca tctccaaaac caaaggcaga    1020
ccgaaggctc acaggtgta caccattcca cctcccaagg agcagatggc caaggataaa    1080
gtcagtctga cctgcatgat aacagacttc ttccctgaag acattactgt ggagtggcag    1140
tggaatgggc agccagcgga gaactacaag aacactcagc ccatcatgga cacagatggc    1200
tcttacttca tctacagcaa gctcaatgtg cagaagagca ctgggaggc aggaaatact    1260 ttcacctgct ctgtgttaca tgagggcctg cacaaccacc atactgagaa gagcctctcc    1320
cactctcctg gtaaatga                                                 1338
```

<210> SEQ ID NO 195
<211> LENGTH: 464
<212> TYPE: PRT
<213> ORGANISM: Mus musculus

<400> SEQUENCE: 195

```
Met Lys Cys Ser Trp Val Ile Phe Phe Leu Met Ala Val Val Thr Gly
 1               5                  10                  15

Val Asn Ser Glu Val Gln Leu Gln Gln Ser Gly Ala Asp Leu Val Gln
            20                  25                  30

Pro Gly Ala Ser Val Lys Val Ser Cys Thr Ala Ser Gly Phe Asp Ile
        35                  40                  45

Lys Asp Tyr Tyr Ile His Trp Met Lys Gln Arg Pro Asp Gln Gly Leu
    50                  55                  60

Glu Trp Ile Gly Arg Val Asp Pro Asp Asn Gly Glu Thr Glu Phe Ala
65                  70                  75                  80

Pro Lys Phe Pro Gly Lys Ala Thr Phe Thr Thr Asp Thr Ser Ser Asn
                85                  90                  95

Thr Ala Tyr Leu Gln Leu Arg Gly Leu Thr Ser Glu Asp Thr Ala Ile
            100                 105                 110

Tyr Tyr Cys Gly Arg Glu Asp Tyr Asp Gly Thr Tyr Thr Trp Phe Pro
        115                 120                 125

Tyr Trp Gly Gln Gly Thr Leu Val Thr Val Ser Ala Ala Lys Thr Thr
    130                 135                 140

Pro Pro Ser Val Tyr Pro Leu Ala Pro Gly Ser Ala Ala Gln Thr Asn
145                 150                 155                 160
```

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Ile Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460

<210> SEQ ID NO 196
<211> LENGTH: 1395
<212> TYPE: DNA
<213> ORGANISM: Mus musculus

<400> SEQUENCE: 196
atgaaatgca gctgggtcat cttcttcctg atggcagtgg ttacaggggt caattcagaa      60
gttcagctgc aacagtctgg ggcagacctt gtgcagccag ggcctcagt caaggtgtcc      120 tgcacagctt ctggcttcga cattaaggac tactatatac actggatgaa acagaggcct      180
gaccagggcc tggagtggat tggaagggtt gatcctgaca atggtgagac tgaatttgcc      240
ccgaagttcc gggcaaggc cacttttaca acagacacat cctccaacac agcctaccta      300
caactcagag gcctgacatc tgaggacact gccatctatt actgtgggag agaagactac      360
gatggtacct acacctggtt tccttattgg ggccaaggga ctctggtcac tgtctctgca      420

```
gccaaaacga caccccatc tgtctatcca ctggcccctg gatctgctgc ccaaactaac      480
tccatggtga ccctgggatg cctggtcaag ggctatttcc ctgagccagt gacagtgacc      540
tggaactctg gatccctgtc cagcggtgtg cacaccttcc cagctgtcct gcagtctgac      600
ctctacactc tgagcagctc agtgactgtc ccctccagca cctggcccag cgagaccgtc      660
acctgcaacg ttgcccaccc ggccagcagc accaaggtgg acaagaaaat tgtgcccagg      720
gattgtggtt gtaagccttg catatgtaca gtcccagaag tatcatctgt cttcatcttc      780
cccccaaagc ccaaggatgt gctcaccatt actctgactc ctaaggtcac gtgtgttgtg      840
gtagacatca gcaaggatga tcccgaggtc cagttcagct ggtttgtaga tgatgtggag      900
gtgcacacag ctcagacgca accccgggag gagcagttca acagcacttt ccgctcagtc      960
agtgaacttc ccatcatgca ccaggactgg ctcaatggca aggagttcaa atgcagggtc     1020
aacagtgcag ctttccctgc ccccatcgag aaaaccatct ccaaaaccaa aggcagaccg     1080
aaggctccac aggtgtacac cattccacct cccaaggagc agatggccaa ggataaagtc     1140
agtctgacct gcatgataac agacttcttc cctgaagaca ttactgtgga gtggcagtgg     1200
aatgggcagc cagcggagaa ctacaagaac actcagccca tcatggacac agatggctct     1260
tacttcatct acagcaagct caatgtgcag aagagcaact gggaggcagg aaatactttc     1320
acctgctctg tgttacatga gggcctgcac aaccaccata ctgagaagag cctctcccac     1380
tctcctggta aatga                                                      1395

<210> SEQ ID NO 197
<211> LENGTH: 214
<212> TYPE: PRT
<213> ORGANISM: Mus musculus

<400> SEQUENCE: 197

Asp Leu Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Phe Tyr Thr Ser Thr Leu Gln Ser Gly Val Pro Ser Arg Phe Ser Gly
    50                  55                  60

Ser Gly Ser Gly Thr Asn Tyr Ser Leu Thr Ile Thr Asn Leu Glu Gln
65                  70                  75                  80

Asp Asp Ala Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
```

```
                195                 200                 205
Phe Asn Arg Asn Glu Cys
    210

<210> SEQ ID NO 198
<211> LENGTH: 645
<212> TYPE: DNA
<213> ORGANISM: Mus musculus

<400> SEQUENCE: 198
gatctccaga tgacacagac tacttcctcc ctgtctgcct ctctgggaga cagagtcacc      60
atcagttgca gggcaagtca ggacattagc aattatttaa actggtatca gcagaaacca     120
gatggaactg ttaagctcct gatcttctac acatcaacat acagtcagg agtcccatcg      180 aggttcagtg gcagtgggtc tggaacaaat tattctctca ccattaccaa cctggagcaa     240
gatgatgctg ccacttactt tgccaacag ggtgatacgc ttccgtacac gttcggaggg      300
gggaccaagc tggaaataaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag caccctcacg     540
ttgaccaagg acgagtatga cgacataac agctatacct gtgaggccac tcacaagaca      600
tcaacttcac ccattgtcaa gagcttcaac aggaatgagt gttag                     645

<210> SEQ ID NO 199
<211> LENGTH: 234
<212> TYPE: PRT
<213> ORGANISM: Mus musculus

<400> SEQUENCE: 199

Met Met Ser Ser Ala Gln Phe Leu Gly Leu Leu Leu Cys Phe Gln
1               5                   10                  15

Gly Ser Arg Cys Asp Leu Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Phe Tyr Thr Ser Thr Leu Gln Ser Gly Val Pro Ser
65                  70                  75                  80

Arg Phe Ser Gly Ser Gly Ser Gly Thr Asn Tyr Ser Leu Thr Ile Thr
                85                  90                  95

Asn Leu Glu Gln Asp Asp Ala Ala Thr Tyr Phe Cys Gln Gln Gly Asp
            100                 105                 110

Thr Leu Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190
```

```
Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
        210                 215                 220

Ile Val Lys Ser Phe Asn Arg Asn Glu Cys
225                 230
```

<210> SEQ ID NO 200
<211> LENGTH: 705
<212> TYPE: DNA
<213> ORGANISM: Mus musculus

<400> SEQUENCE: 200

```
atgatgtcct ctgctcagtt ccttggtctc ctgttgctct gttttcaagg ttccagatgt    60
gatctccaga tgacacagac tacttcctcc ctgtctgcct ctctgggaga cagagtcacc   120
atcagttgca gggcaagtca ggacattagc aattatttaa actggtatca gcagaaacca   180
gatggaactg ttaagctcct gatcttctac acatcaacat tacagtcagg agtcccatcg   240
aggttcagtg gcagtgggtc tggaacaaat tattctctca ccattaccaa cctggagcaa   300
gatgatgctg ccacttactt tgccaacagg gtgatacgc ttccgtacac gttcggaggg   360
gggaccaagc tggaaataaa acgggctgat gctgcaccaa ctgtatccat cttcccacca   420
tccagtgagc agttaacatc tggaggtgcc tcagtcgtgt gcttcttgaa caacttctac   480
cccaaagaca tcaatgtcaa gtggaagatt gatggcagtg aacgacaaaa tggcgtcctg   540
aacagttgga ctgatcagga cagcaaagac agcacctaca gcatgagcag caccctcacg   600
ttgaccaagg acgagtatga acgacataac agctatacct gtgaggccac tcacaagaca   660
tcaacttcac ccattgtcaa gagcttcaac aggaatgagt gttag              705
```

<210> SEQ ID NO 201
<211> LENGTH: 447
<212> TYPE: PRT
<213> ORGANISM: Mus musculus

<400> SEQUENCE: 201

```
Glu Val Gln Leu Gln Gln Ser Gly Pro Glu Leu Met Lys Pro Gly Ala
  1               5                  10                  15

Ser Val Lys Met Ser Cys Lys Ala Ser Gly Tyr Thr Phe Thr Asp Tyr
            20                  25                  30

Asn Met His Trp Met Lys Gln Asn Gly Lys Ser Leu Glu Trp Ile
        35                  40                  45

Gly Glu Ile Asn Pro Asn Ser Gly Ser Gly Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Tyr Gly Asn Tyr Glu Asp Trp Tyr Phe Asp Val
            100                 105                 110

Trp Gly Ala Gly Thr Thr Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160
```

Thr Val Thr Trp Asn Ser Gly Ser Leu Ser Ser Gly Val His Thr Phe
            165                 170                 175
Pro Ala Val Leu Gln Ser Asp Leu Tyr Thr Leu Ser Ser Val Thr
            180                 185                 190
Val Pro Ser Ser Thr Trp Pro Ser Glu Thr Val Thr Cys Asn Val Ala
        195                 200                 205
His Pro Ala Ser Ser Thr Lys Val Asp Lys Lys Ile Val Pro Arg Asp
210                 215                 220
Cys Gly Cys Lys Pro Cys Ile Cys Thr Val Pro Glu Val Ser Ser Val
225                 230                 235                 240
Phe Ile Phe Pro Pro Lys Pro Lys Asp Val Leu Thr Ile Thr Leu Thr
                245                 250                 255
Pro Lys Val Thr Cys Val Val Val Asp Ile Ser Lys Asp Asp Pro Glu
            260                 265                 270
Val Gln Phe Ser Trp Phe Val Asp Asp Val Glu Val His Thr Ala Gln
        275                 280                 285
Thr Gln Pro Arg Glu Glu Gln Phe Asn Ser Thr Phe Arg Ser Val Ser
    290                 295                 300
Glu Leu Pro Ile Met His Gln Asp Trp Leu Asn Gly Lys Glu Phe Lys
305                 310                 315                 320
Cys Arg Val Asn Ser Ala Ala Phe Pro Ala Pro Ile Glu Lys Thr Ile
                325                 330                 335
Ser Lys Thr Lys Gly Arg Pro Lys Ala Pro Gln Val Tyr Thr Ile Pro
            340                 345                 350
Pro Pro Lys Glu Gln Met Ala Lys Asp Lys Val Ser Leu Thr Cys Met
        355                 360                 365
Ile Thr Asp Phe Phe Pro Glu Asp Ile Thr Val Glu Trp Gln Trp Asn
    370                 375                 380
Gly Gln Pro Ala Glu Asn Tyr Lys Asn Thr Gln Pro Ile Met Asp Thr
385                 390                 395                 400
Asp Gly Ser Tyr Phe Ile Tyr Ser Lys Leu Asn Val Gln Lys Ser Asn
                405                 410                 415
Trp Glu Ala Gly Asn Thr Phe Thr Cys Ser Val Leu His Glu Gly Leu
            420                 425                 430
His Asn His His Thr Glu Lys Ser Leu Ser His Ser Pro Gly Lys
        435                 440                 445

<210> SEQ ID NO 202
<211> LENGTH: 1344
<212> TYPE: DNA
<213> ORGANISM: Mus musculus

<400> SEQUENCE: 202
gaggtccagt tgcaacagtc tggacctgaa ctaatgaagc ctggggcttc agtgaagatg      60
tcctgcaagg cttctggata cacattcact gactacaaca tgcactggat gaagcagaac     120
caaggaaaga gcctagagtg gataggagag attaatccta acagtggtgg ttctggttac     180
aaccagaagt tcaaaggcaa ggccacattg actgtagaca gtcctccag cacagcctac     240
atggagctcc gcagcctgac atctgaggac tctgcagtct attactgtgc aagattgggc     300
tactatggta actacgagga ctggtatttc gatgtctggg gcgcagggac cacggtcacc     360
gtctcctctg ccaaaacgac accccatct gtctatccac tggcccctgg atctgctgcc     420
caaactaact ccatggtgac cctgggatgc ctggtcaagg ctatttccc tgagccagtg     480
acagtgacct ggaactctgg atccctgtcc agcggtgtgc acaccttccc agctgtcctg     540

```
cagtctgacc tctacactct gagcagctca gtgactgtcc cctccagcac ctggcccagc    600
gagaccgtca cctgcaacgt tgcccacccg gccagcagca ccaaggtgga caagaaaatt    660
gtgcccaggg attgtggttg taagccttgc atatgtacag tcccagaagt atcatctgtc    720
ttcatcttcc ccccaaagcc caaggatgtg ctcaccatta ctctgactcc taaggtcacg    780
tgtgttgtgg tagacatcag caaggatgat cccgaggtcc agttcagctg gtttgtagat    840
gatgtggagg tgcacacagc tcagacgcaa ccccgggagg agcagttcaa cagcactttc    900
cgctcagtca gtgaacttcc catcatgcac caggactggc tcaatggcaa ggagttcaaa    960
tgcagggtca acagtgcagc tttccctgcc cccatcgaga aaaccatctc caaaaccaaa   1020
ggcagaccga aggctccaca ggtgtacacc attccacctc caaggagcaa tggccaag    1080
gataaagtca gtctgacctg catgataaca gacttcttcc ctgaagacat tactgtggag   1140
tggcagtgga atgggcagcc agcggagaac tacaagaaca ctcagcccat catggacaca   1200
gatggctctt acttcatcta cagcaagctc aatgtgcaga gagcaactg ggaggcagga   1260
aatactttca cctgctctgt gttacatgag ggcctgcaca accaccatac tgagaagagc   1320
ctctcccact ctcctggtaa atga                                          1344

<210> SEQ ID NO 203
<211> LENGTH: 466
<212> TYPE: PRT
<213> ORGANISM: Mus musculus

<400> SEQUENCE: 203

Met Gly Trp Ser Trp Thr Phe Leu Phe Leu Leu Ser Gly Thr Ser Gly
 1               5                  10                  15

Val Leu Ser Glu Val Gln Leu Gln Gln Ser Gly Pro Glu Leu Met Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Met Lys Gln Asn Gln Gly Lys Ser Leu
    50                  55                  60

Glu Trp Ile Gly Glu Ile Asn Pro Asn Ser Gly Ser Gly Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Arg Leu Gly Tyr Tyr Gly Asn Tyr Glu Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220
```

```
Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
            245                 250                 255

Ser Ser Val Phe Ile Phe Pro Pro Lys Pro Lys Asp Val Leu Thr Ile
                260                 265                 270

Thr Leu Thr Pro Lys Val Thr Cys Val Val Val Asp Ile Ser Lys Asp
            275                 280                 285

Asp Pro Glu Val Gln Phe Ser Trp Phe Val Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
                355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
                435                 440                 445

Glu Gly Leu His Asn His His Thr Glu Lys Ser Leu Ser His Ser Pro
    450                 455                 460

Gly Lys
465

<210> SEQ ID NO 204
<211> LENGTH: 1401
<212> TYPE: DNA
<213> ORGANISM: Mus musculus

<400> SEQUENCE: 204
atgggatgga gctggacctt tctcttcctc ctgtcaggaa cttcgggtgt cctctctgag      60
gtccagttgc aacagtctgg acctgaacta atgaagcctg gggcttcagt gaagatgtcc     120
tgcaaggctt ctggatacac attcactgac tacaacatgc actggatgaa gcagaaccaa     180
ggaaagagcc tagagtggat aggagagatt aatcctaaca gtggtggttc tggttacaac     240
cagaagttca aggcaaggc cacattgact gtagacaagt cctccagcac agcctacatg     300
gagctccgca gcctgacatc tgaggactct gcagtctatt actgtgcaag attgggctac     360
tatggtaact acgaggactg gtatttcgat gtctggggcg cagggaccac ggtcaccgtc     420
tcctctgcca aaacgacacc cccatctgtc tatccactgg cccctggatc tgctgcccaa     480
actaactcca tggtgaccct gggatgcctg gtcaagggct atttccctga gccagtgaca     540
gtgacctgga actctggatc cctgtccagc ggtgtgcaca ccttcccagc tgtcctgcag     600
tctgacctct acactctgag cagctcagtg actgtcccct ccagcacctg cccagcgag      660 accgtcacct gcaacgttgc cacccggcc agcagcacca aggtggacaa gaaaattgtg     720
```

-continued

```
cccagggatt gtggttgtaa gccttgcata tgtacagtcc cagaagtatc atctgtcttc    780
atcttccccc caaagcccaa ggatgtgctc accattactc tgactcctaa ggtcacgtgt    840
gttgtggtag acatcagcaa ggatgatccc gaggtccagt tcagctggtt tgtagatgat    900
gtggaggtgc acacagctca gacgcaaccc cgggaggagc agttcaacag cactttccgc    960
tcagtcagtg aacttcccat catgcaccag gactggctca atggcaagga gttcaaatgc   1020
agggtcaaca gtgcagcttt ccctgccccc atcgagaaaa ccatctccaa aaccaaaggc   1080
agaccgaagg ctccacaggt gtacaccatt ccacctccca aggagcagat ggccaaggat   1140
aaagtcagtc tgacctgcat gataacagac ttcttccctg aagacattac tgtggagtgg   1200
cagtggaatg ggcagccagc ggagaactac aagaacactc agcccatcat ggacacagat   1260
ggctcttact tcatctacag caagctcaat gtgcagaaga gcaactggga ggcaggaaat   1320
actttcacct gctctgtgtt acatgagggc ctgcacaacc accatactga aagagcctc    1380
tcccactctc ctggtaaatg a                                              1401
```

<210> SEQ ID NO 205
<211> LENGTH: 215
<212> TYPE: PRT
<213> ORGANISM: Mus musculus

<400> SEQUENCE: 205

```
Gln Ile Val Leu Thr Gln Ser Pro Ala Ile Met Ser Ala Ser Pro Gly
  1               5                  10                  15
Glu Lys Val Thr Met Thr Cys Arg Ala Ser Ser Ser Val Thr Ser Ser
             20                  25                  30
Tyr Leu Asn Trp Tyr Gln Gln Lys Pro Gly Ser Ser Pro Lys Leu Trp
         35                  40                  45
Ile Tyr Ser Thr Ser Asn Leu Ala Ser Gly Val Pro Ala Arg Phe Ser
     50                  55                  60
Gly Ser Gly Ser Gly Thr Ser Tyr Ser Leu Thr Ile Ser Ser Val Glu
 65                  70                  75                  80
Ala Glu Asp Ala Ala Thr Tyr Tyr Cys Gln Gln Tyr Asp Phe Phe Pro
                 85                  90                  95
Ser Thr Phe Gly Gly Gly Thr Lys Leu Glu Ile Lys Arg Ala Asp Ala
            100                 105                 110
Ala Pro Thr Val Ser Ile Phe Pro Pro Ser Ser Glu Gln Leu Thr Ser
        115                 120                 125
Gly Gly Ala Ser Val Val Cys Phe Leu Asn Asn Phe Tyr Pro Lys Asp
    130                 135                 140
Ile Asn Val Lys Trp Lys Ile Asp Gly Ser Glu Arg Gln Asn Gly Val
145                 150                 155                 160
Leu Asn Ser Trp Thr Asp Gln Asp Ser Lys Asp Ser Thr Tyr Ser Met
                165                 170                 175
Ser Ser Thr Leu Thr Leu Thr Lys Asp Glu Tyr Glu Arg His Asn Ser
            180                 185                 190
Tyr Thr Cys Glu Ala Thr His Lys Thr Ser Thr Ser Pro Ile Val Lys
        195                 200                 205
Ser Phe Asn Arg Asn Glu Cys
    210                 215
```

<210> SEQ ID NO 206
<211> LENGTH: 645
<212> TYPE: DNA

<213> ORGANISM: Mus musculus

<400> SEQUENCE: 206

```
cagattgttc tcacccagtc tccagcaatc atgtctgcat ctccagggga gaaggtcacc    60
atgacctgca gggccagctc aagtgtaact tccagttact tgaactggta ccagcagaag   120
ccaggatctt cccccaaact ctggatttat agcacatcca acctggcttc aggagtccca   180
gctcgcttca gtggcagtgg gtctgggacc tcttactctc tcacaatcag cagtgtggag   240
gctgaggatg ctgccactta ttactgccag cagtatgatt ttttcccatc gacgttcggt   300
ggaggcacca agctggaaat caagcgggct gatgctgcac caactgtatc catcttccca   360
ccatccagtg agcagttaac atctggaggt gcctcagtcg tgtgcttctt gaacaacttc   420
taccccaaag acatcaatgt caagtggaag attgatggca gtgaacgaca aaatggcgtc   480
ctgaacagtt ggactgatca ggacagcaaa gacagcacct acagcatgag cagcaccctc   540
acgttgacca aggacgagta tgaacgacat aacagctata cctgtgaggc cactcacaag   600
acatcaactt cacccatcgt caagagcttc aacaggaatg agtgt                   645
```

<210> SEQ ID NO 207
<211> LENGTH: 237
<212> TYPE: PRT
<213> ORGANISM: Mus musculus

<400> SEQUENCE: 207

```
Met Asp Ser Gln Val Gln Ile Phe Ser Phe Leu Leu Ile Ser Ala Leu
  1               5                  10                  15
Val Lys Met Ser Arg Gly Gln Ile Val Leu Thr Gln Ser Pro Ala Ile
             20                  25                  30
Met Ser Ala Ser Pro Gly Glu Lys Val Thr Met Thr Cys Arg Ala Ser
         35                  40                  45
Ser Ser Val Thr Ser Ser Tyr Leu Asn Trp Tyr Gln Gln Lys Pro Gly
     50                  55                  60
Ser Ser Pro Lys Leu Trp Ile Tyr Ser Thr Ser Asn Leu Ala Ser Gly
 65                  70                  75                  80
Val Pro Ala Arg Phe Ser Gly Ser Gly Ser Gly Thr Ser Tyr Ser Leu
                 85                  90                  95
Thr Ile Ser Ser Val Glu Ala Glu Asp Ala Ala Thr Tyr Tyr Cys Gln
            100                 105                 110
Gln Tyr Asp Phe Phe Pro Ser Thr Phe Gly Gly Gly Thr Lys Leu Glu
        115                 120                 125
Ile Lys Arg Ala Asp Ala Ala Pro Thr Val Ser Ile Phe Pro Pro Ser
    130                 135                 140
Ser Glu Gln Leu Thr Ser Gly Gly Ala Ser Val Val Cys Phe Leu Asn
145                 150                 155                 160
Asn Phe Tyr Pro Lys Asp Ile Asn Val Lys Trp Lys Ile Asp Gly Ser
                165                 170                 175
Glu Arg Gln Asn Gly Val Leu Asn Ser Trp Thr Asp Gln Asp Ser Lys
            180                 185                 190
Asp Ser Thr Tyr Ser Met Ser Ser Thr Leu Thr Leu Thr Lys Asp Glu
        195                 200                 205
Tyr Glu Arg His Asn Ser Tyr Thr Cys Glu Ala Thr His Lys Thr Ser
    210                 215                 220
Thr Ser Pro Ile Val Lys Ser Phe Asn Arg Asn Glu Cys
225                 230                 235
```

<210> SEQ ID NO 208
<211> LENGTH: 711
<212> TYPE: DNA
<213> ORGANISM: Mus musculus

<400> SEQUENCE: 208

```
atggattctc aagtgcagat tttcagcttc cttctaatca gtgccttagt caaaatgtcc      60
agaggacaga ttgttctcac ccagtctcca gcaatcatgt ctgcatctcc aggggagaag     120
gtcaccatga cctgcagggc cagctcaagt gtaacttcca gttacttgaa ctggtaccag     180
cagaagccag atcttccccc aaactctgg atttatagca catccaacct ggcttcagga     240
gtcccagctc gcttcagtgg cagtgggtct gggacctctt actctctcac aatcagcagt     300
gtggaggctg aggatgctgc cacttattac tgccagcagt atgatttttt cccatcgacg     360
ttcggtggag gcaccaagct ggaaatcaag cgggctgatg ctgcaccaac tgtatccatc     420
ttcccaccat ccagtgagca gttaacatct ggaggtgcct cagtcgtgtg cttcttgaac     480
aacttctacc ccaaagacat caatgtcaag tggaagattg atggcagtga acgacaaaat     540
ggcgtcctga cagttggac tgatcaggac agcaaagaca gcacctacag catgagcagc     600
accctcacgt tgaccaagga cgagtatgaa cgacataaca gctatacctg tgaggccact     660
cacaagacat caacttcacc catcgtcaag agcttcaaca ggaatgagtg t             711
```

<210> SEQ ID NO 209
<211> LENGTH: 445
<212> TYPE: PRT
<213> ORGANISM: Mus musculus

<400> SEQUENCE: 209

```
Glu Val Gln Leu Gln Gln Ser Gly Pro Glu Leu Val Lys Pro Gly Ala
  1               5                  10                  15

Ser Val Lys Met Ser Cys Lys Ala Ser Gly Tyr Thr Phe Thr Asp Tyr
             20                  25                  30

Tyr Met Asn Trp Val Lys Gln Ser His Gly Glu Ser Leu Glu Trp Ile
         35                  40                  45

Gly Asp Ile Asn Pro Tyr Asn Asp Asp Thr Thr Tyr Asn His Lys Phe
     50                  55                  60

Lys Gly Lys Ala Thr Leu Thr Val Asp Lys Ser Asn Thr Ala Tyr
 65                  70                  75                  80

Met Gln Leu Asn Ser Leu Thr Ser Glu Asp Ser Ala Val Tyr Tyr Cys
             85                  90                  95

Ala Arg Glu Thr Ala Val Ile Thr Thr Asn Ala Met Asp Tyr Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
            165                 170                 175

Val Leu Gln Ser Asp Leu Tyr Thr Leu Ser Ser Val Thr Val Pro
        180                 185                 190

Ser Ser Thr Trp Pro Ser Glu Thr Val Thr Cys Asn Val Ala His Pro
    195                 200                 205
```

```
Ala Ser Ser Thr Lys Val Asp Lys Lys Ile Val Pro Arg Asp Cys Gly
    210                 215                 220
Cys Lys Pro Cys Ile Cys Thr Val Pro Glu Val Ser Ser Val Phe Ile
225                 230                 235                 240
Phe Pro Pro Lys Pro Lys Asp Val Leu Thr Ile Thr Leu Thr Pro Lys
                245                 250                 255
Val Thr Cys Val Val Val Asp Ile Ser Lys Asp Asp Pro Glu Val Gln
            260                 265                 270
Phe Ser Trp Phe Val Asp Asp Val Glu Val His Thr Ala Gln Thr Gln
        275                 280                 285
Pro Arg Glu Glu Gln Phe Asn Ser Thr Phe Arg Ser Val Ser Glu Leu
    290                 295                 300
Pro Ile Met His Gln Asp Trp Leu Asn Gly Lys Glu Phe Lys Cys Arg
305                 310                 315                 320
Val Asn Ser Ala Ala Phe Pro Ala Pro Ile Glu Lys Thr Ile Ser Lys
                325                 330                 335
Thr Lys Gly Arg Pro Lys Ala Pro Gln Val Tyr Thr Ile Pro Pro Pro
            340                 345                 350
Lys Glu Gln Met Ala Lys Asp Lys Val Ser Leu Thr Cys Met Ile Thr
        355                 360                 365
Asp Phe Phe Pro Glu Asp Ile Thr Val Glu Trp Gln Trp Asn Gly Gln
    370                 375                 380
Pro Ala Glu Asn Tyr Lys Asn Thr Gln Pro Ile Met Asp Thr Asp Gly
385                 390                 395                 400
Ser Tyr Phe Ile Tyr Ser Lys Leu Asn Val Gln Lys Ser Asn Trp Glu
                405                 410                 415
Ala Gly Asn Thr Phe Thr Cys Ser Val Leu His Glu Gly Leu His Asn
            420                 425                 430
His His Thr Glu Lys Ser Leu Ser His Ser Pro Gly Lys
        435                 440                 445

<210> SEQ ID NO 210
<211> LENGTH: 1335
<212> TYPE: DNA
<213> ORGANISM: Mus musculus

<400> SEQUENCE: 210
gaggtccagc tgcaacaatc tggacctgag ctggtgaagc ctggggcttc agtgaagatg      60
tcctgtaagg cttctggata cacattcact gactactaca tgaactgggt gaagcagagc     120
catggagaga gccttgagtg gattggagat attaatcctt acaacgatga tactacctac     180
aaccacaagt tcaagggcaa ggccacattg actgtagaca atcctccaa cacagcctac      240 atgcagctca cagcctgac atctgaggac tctgcagtct attactgtgc aagagagacg      300
gccgttatta ctacgaatgc tatggactac tggggtcaag aacctcagt caccgtctcc      360 tcagccaaaa cgacaccccc atctgtctat ccactggccc ctggatctgc tgcccaaact     420
aactccatgg tgaccctggg atgcctggtc aagggctatt ccctgagcc agtgacagtg      480 acctggaact ctgatccct gtccagcggt gtgcacacct tcccagctgt cctgcagtct     540
gacctctaca ctctgagcag ctcagtgact gtcccctcca gcacctggcc cagcgagacc    600
gtcacctgca acgttgccca cccggccagc agcaccaagg tggacaagaa aattgtgccc    660
agggattgtg gttgtaagcc ttgcatatgt acagtcccag aagtatcatc tgtcttcatc    720 ttcccccaa agcccaagga tgtgctcacc attactctga ctcctaaggt cacgtgtgtt     780
```

-continued

```
gtggtagaca tcagcaagga tgatcccgag gtccagttca gctggtttgt agatgatgtg      840
gaggtgcaca cagctcagac gcaacccggg gaggagcagt tcaacagcac tttccgctca      900
gtcagtgaac ttcccatcat gcaccaggac tggctcaatg gcaaggagtt caaatgcagg      960
gtcaacagtg cagctttccc tgcccccatc gagaaaacca tctccaaaac caaaggcaga     1020
ccgaaggctc acaggtgta caccattcca cctcccaagg agcagatggc aaggataaa      1080 gtcagtctga cctgcatgat aacagacttc ttccctgaag acattactgt ggagtggcag     1140
tggaatgggc agccagcgga gaactacaag aacactcagc ccatcatgga cacagatggc     1200
tcttacttca tctacagcaa gctcaatgtg cagaagagca ctgggaggc aggaaatact      1260 ttcacctgct ctgtgttaca tgagggcctg cacaaccacc atactgagaa gagcctctcc     1320
cactctcctg gtaaa                                                       1335
```

<210> SEQ ID NO 211
<211> LENGTH: 464
<212> TYPE: PRT
<213> ORGANISM: Mus musculus

<400> SEQUENCE: 211

```
Met Gly Trp Asn Trp Ile Phe Leu Phe Leu Leu Ser Gly Thr Ala Gly
  1               5                  10                  15

Val Tyr Ser Glu Val Gln Leu Gln Gln Ser Gly Pro Glu Leu Val Lys
             20                  25                  30

Pro Gly Ala Ser Val Lys Met Ser Cys Lys Ala Ser Gly Tyr Thr Phe
         35                  40                  45

Thr Asp Tyr Tyr Met Asn Trp Val Lys Gln Ser His Gly Glu Ser Leu
     50                  55                  60

Glu Trp Ile Gly Asp Ile Asn Pro Tyr Asn Asp Thr Thr Tyr Asn
 65                  70                  75                  80

His Lys Phe Lys Gly Lys Ala Thr Leu Thr Val Asp Lys Ser Ser Asn
                 85                  90                  95

Thr Ala Tyr Met Gln Leu Asn Ser Leu Thr Ser Glu Asp Ser Ala Val
            100                 105                 110

Tyr Tyr Cys Ala Arg Glu Thr Ala Val Ile Thr Thr Asn Ala Met Asp
        115                 120                 125

Tyr Trp Gly Gln Gly Thr Ser Val Thr Val Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270
```

Thr Pro Lys Val Thr Cys Val Val Asp Ile Ser Lys Asp Asp Pro
            275                 280                 285

Glu Val Gln Phe Ser Trp Phe Val Asp Asp Val Glu Val His Thr Ala
290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
            355                 360                 365

Pro Pro Pro Lys Glu Gln Met Ala Lys Asp Lys Val Ser Leu Thr Cys
370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Ile Tyr Ser Lys Leu Asn Val Gln Lys Ser
            420                 425                 430

Asn Trp Glu Ala Gly Asn Thr Phe Thr Cys Ser Val Leu His Glu Gly
            435                 440                 445

Leu His Asn His His Thr Glu Lys Ser Leu Ser His Ser Pro Gly Lys
    450                 455                 460

<210> SEQ ID NO 212
<211> LENGTH: 1392
<212> TYPE: DNA
<213> ORGANISM: Mus musculus

<400> SEQUENCE: 212

| | |
|---|---:|
| atgggatgga actggatctt tctcttcctc ttgtcaggaa ctgcaggtgt ctactctgag | 60 |
| gtccagctgc aacaatctgg acctgagctg gtgaagcctg gggcttcagt gaagatgtcc | 120 |
| tgtaaggctt ctggatacac attcactgac tactacatga actgggtgaa gcagagccat | 180 |
| ggagagagcc ttagtggat tggagatatt aatccttaca cgatgatac tacctacaac | 240 |
| cacaagttca gggcaaggc cacattgact gtagacaaat cctccaacac agcctacatg | 300 |
| cagctcaaca gcctgacatc tgaggactct gcagtctatt actgtgcaag agagacggcc | 360 |
| gttattacta cgaatgctat ggactactgg ggtcaaggaa cctcagtcac cgtctcctca | 420 |
| gccaaaacga cacccccatc tgtctatcca ctggcccctg gatctgctgc ccaaactaac | 480 |
| tccatggtga ccctgggatg cctggtcaag ggctatttcc ctgagccagt gacagtgacc | 540 |
| tggaactctg gatccctgtc cagcggtgtg cacaccttcc cagctgtcct gcagtctgac | 600 |
| ctctacactc tgagcagctc agtgactgtc ccctccagca cctggcccag cgagaccgtc | 660 |
| acctgcaacg ttgcccaccc ggccagcagc accaaggtgg acaagaaaat tgtgcccagg | 720 |
| gattgtggtt gtaagccttg catatgtaca gtcccagaag tatcatctgt cttcatcttc | 780 |
| cccccaaagc ccaaggatgt gctcaccatt actctgactc taaggtcac gtgtgttgtg | 840 |
| gtagacatca gcaaggatga tcccgaggtc cagttcagct ggtttgtaga tgatgtggag | 900 |
| gtgcacacag ctcagacgca accccgggag gagcagttca acagcacttt ccgctcagtc | 960 |
| agtgaacttc ccatcatgca ccaggactgg ctcaatggca aggagttcaa atgcagggtc | 1020 |
| aacagtgcag cttttcctg cccatcgag aaaaccatct ccaaaaccaa aggcagaccg | 1080 |

```
aaggctccac aggtgtacac cattccacct cccaaggagc agatggccaa ggataaagtc    1140
agtctgacct gcatgataac agacttcttc cctgaagaca ttactgtgga gtggcagtgg    1200
aatgggcagc cagcggagaa ctacaagaac actcagccca tcatggacac agatggctct    1260
tacttcatct acagcaagct caatgtgcag aagagcaact gggaggcagg aaatactttc    1320
acctgctctg tgttacatga gggcctgcac aaccaccata ctgagaagag cctctcccac    1380
tctcctggta aa                                                        1392
```

<210> SEQ ID NO 213
<211> LENGTH: 215
<212> TYPE: PRT
<213> ORGANISM: Artificial Sequence
<220> FEATURE:
<223> OTHER INFORMATION: Humanized antibody sequence

<400> SEQUENCE: 213

```
Asp Ile Gln Leu Thr Gln Ser Pro Ser Phe Leu Ser Ala Ser Val Gly
 1               5                  10                  15

Asp Arg Val Thr Ile Thr Cys Arg Ala Ser Ser Ser Val Thr Ser Ser
            20                  25                  30

Tyr Leu Asn Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Tyr Asp Phe Phe Pro
                85                  90                  95

Ser Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 214
<211> LENGTH: 645
<212> TYPE: DNA
<213> ORGANISM: Artificial Sequence
<220> FEATURE:
<223> OTHER INFORMATION: Humanized antibody sequence

<400> SEQUENCE: 214

```
gacatccagc tgacccagag ccccagcttc ctttccgcat ccgttggtga ccgagtaaca    60
atcacatgcc gcgcctcatc ttcagttaca tcttcttatc ttaattggta tcaacaaaaa    120
```

```
ccaggaaaag cacctaaact tcttatatac tctacatcta atctcgcatc aggagttccc    180
tctcgatttt caggatctgg atcaggcaca gaatttacac ttactatatc atcactccaa    240
ccagaagact tcgccactta ttactgccaa caatacgatt tttttccaag cacattcgga    300
ggaggtacaa aagtagaaat caagcgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac cgagaaacac aaagtctacg cctgcgaagt cacccatcag    600
ggcctgagct cgcccgtcac aaagagcttc aacaggggag agtgt    645
```

```
<210> SEQ ID NO 215
<211> LENGTH: 237
<212> TYPE: PRT
<213> ORGANISM: Artificial Sequence
<220> FEATURE:
<223> OTHER INFORMATION: Humanized antibody sequence

<400> SEQUENCE: 215
```

```
Met Asp Met Arg Val Pro Ala Gln Leu Leu Gly Leu Leu Leu Leu Trp
 1               5                  10                  15

Leu Pro Gly Ala Arg Cys Asp Ile Gln Leu Thr Gln Ser Pro Ser Phe
                20                  25                  30

Leu Ser Ala Ser Val Gly Asp Arg Val Thr Ile Thr Cys Arg Ala Ser
            35                  40                  45

Ser Ser Val Thr Ser Ser Tyr Leu Asn Trp Tyr Gln Gln Lys Pro Gly
        50                  55                  60

Lys Ala Pro Lys Leu Leu Ile Tyr Ser Thr Ser Asn Leu Ala Ser Gly
 65                  70                  75                  80

Val Pro Ser Arg Phe Ser Gly Ser Gly Ser Gly Thr Glu Phe Thr Leu
                85                  90                  95

Thr Ile Ser Ser Leu Gln Pro Glu Asp Phe Ala Thr Tyr Tyr Cys Gln
            100                 105                 110

Gln Tyr Asp Phe Phe Pro Ser Thr Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

```
<210> SEQ ID NO 216
<211> LENGTH: 711
<212> TYPE: DNA
<213> ORGANISM: Artificial Sequence
<220> FEATURE:
```

<223> OTHER INFORMATION: Humanized antibody sequence

<400> SEQUENCE: 216

```
atggacatga gggtccccgc tcagctcctg gggctcctgc tactctggct cccaggtgcc    60
agatgtgaca tccagctgac ccagagcccc agcttccttt ccgcatccgt tggtgaccga   120
gtaacaatca catgccgcgc ctcatcttca gttacatctt cttatcttaa ttggtatcaa   180
caaaaaccag aaaagcacc taaacttctt atatactcta catctaatct cgcatcagga   240
gttccctctc gattttcagg atctggatca ggcacagaat ttacacttac tatatcatca   300
ctccaaccag aagacttcgc cacttattac tgccaacaat acgatttttt tccaagcaca   360
ttcggaggag gtacaaaagt agaaatcaag cgtacggtgg ctgcaccatc tgtcttcatc   420
ttcccgccat ctgatgagca gttgaaatct ggaactgcct ctgttgtgtg cctgctgaat   480
aacttctatc ccagagaggc caaagtacag tggaaggtgg ataacgccct caatcgggt    540
aactcccagg agagtgtcac agagcaggac agcaaggaca gcacctacag cctcagcagc   600
accctgacgc tgagcaaagc agactacgag aaacacaaag tctacgcctg cgaagtcacc   660
catcagggcc tgagctcgcc cgtcacaaag agcttcaaca ggggagagtg t             711
```

<210> SEQ ID NO 217
<211> LENGTH: 447
<212> TYPE: PRT
<213> ORGANISM: Artificial Sequence
<220> FEATURE:
<223> OTHER INFORMATION: Humanized antibody sequence

<400> SEQUENCE: 217

| | | | | | | | | | | | | | | |
|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Asp | Tyr |
| | | 20 | | | | | 25 | | | | | 30 | | | |
| Tyr | Met | Asn | Trp | Val | Arg | Gln | Ala | Pro | Gly | Gln | Arg | Leu | Glu | Trp | Met |
| | | | 35 | | | | | 40 | | | | | 45 | | |
| Gly | Asp | Ile | Asn | Pro | Tyr | Asn | Asp | Asp | Thr | Thr | Tyr | Asn | His | Lys | Phe |
| | | | | 50 | | | | | 55 | | | | | 60 | |
| Lys | Gly | Arg | Val | Thr | Ile | Thr | Arg | Asp | Thr | Ser | Ala | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Glu | Thr | Ala | Val | Ile | Thr | Thr | Asn | Ala | Met | Asp | Tyr | Trp | Gly |
| | | | 100 | | | | | 105 | | | | | 110 | | |
| Gln | Gly | Thr | Thr | Val | Thr | Val | Ser | Ser | Ala | Ser | Thr | Lys | Gly | Pro | Ser |
| | | | 115 | | | | | 120 | | | | | 125 | | |
| Val | Phe | Pro | Leu | Ala | Pro | Cys | Ser | Arg | Ser | Thr | Ser | Glu | Ser | Thr | Ala |
| | 130 | | | | | 135 | | | | | 140 | | | | |
| Ala | Leu | Gly | Cys | Leu | Val | Lys | Asp | Tyr | Phe | Pro | Glu | Pro | Val | Thr | Val |
| 145 | | | | | 150 | | | | | 155 | | | | | 160 |
| Ser | Trp | Asn | Ser | Gly | Ala | Leu | Thr | Ser | Gly | Val | His | Thr | Phe | Pro | Ala |
| | | | | 165 | | | | | 170 | | | | | 175 | |
| Val | Leu | Gln | Ser | Ser | Gly | Leu | Tyr | Ser | Leu | Ser | Ser | Val | Val | Thr | Val |
| | | | 180 | | | | | 185 | | | | | 190 | | |
| Pro | Ser | Ser | Asn | Phe | Gly | Thr | Gln | Thr | Tyr | Thr | Cys | Asn | Val | Asp | His |
| | | 195 | | | | | 200 | | | | | 205 | | | |
| Lys | Pro | Ser | Asn | Thr | Lys | Val | Asp | Lys | Thr | Val | Glu | Arg | Lys | Cys | Cys |
| | 210 | | | | | 215 | | | | | 220 | | | | |

```
Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 218
<211> LENGTH: 1341
<212> TYPE: DNA
<213> ORGANISM: Artificial Sequence
<220> FEATURE:
<223> OTHER INFORMATION: Humanized antibody sequence

<400> SEQUENCE: 218
gaggtgcagc tggtgcagag cggcgccgag gtcaagaaac ctggagcaag cgtaaaggtt      60
agttgcaaag catctggata cacatttacc gactactaca tgaattgggt acgacaagcc    120
cctggacaaa gacttgaatg gatgggagac attaacccctt ataacgacga cactacatac   180
aatcataaat ttaaaggaag agttacaatt acaagagata catccgcatc aaccgcctat    240
atggaacttt cctcattgag atctgaagac actgctgttt attactgtgc aagagaaact    300
gccgttatta ctactaacgc tatggattac tggggtcaag aaccactgt taccgtctct    360 agtgcctcca ccaagggccc atcggtcttc ccctggcgc cctgctccag gagcacctcc    420
gagagcacag cggccctggg ctgcctggtc aaggactact ccccgaacc ggtgacggtg    480 tcgtggaact caggcgctct gaccagcggc gtgcacacct tcccagctgt cctacagtcc    540
tcaggactct actccctcag cagcgtggtg accgtgccct ccagcaactt cggcacccag    600
acctacacct gcaacgtaga tcacaagccc agcaacacca aggtggacaa gacagttgag    660
cgcaaatgtt gtgtcgagtg cccaccgtgc ccagcaccac ctgtggcagg accgtcagtc    720
ttcctcttcc ccccaaaacc caaggacacc ctcatgatct cccggacccc tgaggtcacg    780
```

-continued

```
tgcgtggtgg tggacgtgag ccacgaagac cccgaggtcc agttcaactg gtacgtggac      840
ggcgtggagg tgcataatgc caagacaaag ccacgggagg agcagttcaa cagcacgttc      900
cgtgtggtca gcgtcctcac cgttgtgcac caggactggc tgaacggcaa ggagtacaag      960
tgcaaggtct ccaacaaagg cctcccagcc cccatcgaga aaaccatctc caaaaccaaa     1020
gggcagcccc gagaaccaca ggtgtacacc ctgcccccat cccgggagga tgaccaag      1080 aaccaggtca gcctgacctg cctggtcaaa ggcttctacc ccagcgacat cgccgtggag     1140
tgggagagca atgggcagcc ggagaacaac tacaagacca cacctcccat gctggactcc     1200
gacggctcct tcttcctcta cagcaagctc accgtggaca gagcaggtg gcagcagggg     1260 aacgtcttct catgctccgt gatgcatgag gctctgcaca accactacac gcagaagagc     1320
ctctccctgt ctccgggtaa a                                               1341
```

<210> SEQ ID NO 219
<211> LENGTH: 466
<212> TYPE: PRT
<213> ORGANISM: Artificial Sequence
<220> FEATURE:
<223> OTHER INFORMATION: Humanized antibody sequence

<400> SEQUENCE: 219

```
Met Asp Trp Thr Trp Arg Ile Leu Phe Leu Val Ala Ala Ala Thr Gly
  1               5                  10                  15

Ala His Ser Glu Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Asp Tyr Tyr Met Asn Trp Val Arg Gln Ala Pro Gly Gln Arg Leu
     50                  55                  60

Glu Trp Met Gly Asp Ile Asn Pro Tyr Asn Asp Thr Thr Tyr Asn
 65                  70                  75                  80

His Lys Phe Lys Gly Arg Val Thr Ile Thr Arg Asp Thr Ser Ala Ser
                 85                  90                  95

Thr Ala Tyr Met Glu Leu Ser Ser Leu Arg Ser Glu Asp Thr Ala Val
            100                 105                 110

Tyr Tyr Cys Ala Arg Glu Thr Ala Val Ile Thr Thr Asn Ala Met Asp
        115                 120                 125

Tyr Trp Gly Gln Gly Thr Thr Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
```

```
                    260                 265                 270
Ser Arg Thr Pro Glu Val Thr Cys Val Val Asp Val Ser His Glu
            275                 280                 285

Asp Pro Glu Val Gln Phe Asn Trp Tyr Val Asp Gly Val Glu Val His
        290                 295                 300

Asn Ala Lys Thr Lys Pro Arg Glu Glu Gln Phe Asn Ser Thr Phe Arg
305                 310                 315                 320

Val Val Ser Val Leu Thr Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 220
<211> LENGTH: 1398
<212> TYPE: DNA
<213> ORGANISM: Artificial Sequence
<220> FEATURE:
<223> OTHER INFORMATION: Humanized antibody sequence

<400> SEQUENCE: 220
atggactgga cctggaggat cctcttcttg gtggcagcag ccacaggagc ccactccgag      60
gtgcagctgg tgcagagcgg cgccgaggtc aagaaacctg agcaagcgt aaaggttagt     120 tgcaaagcat ctggatacac atttaccgac tactacatga attgggtacg acaagccct     180 ggacaaagac ttgaatggat gggagacatt aaccttata acgacgacac tacatacaat     240
cataaattta aggaagagt tacaattaca agagatacat ccgcatcaac cgcctatatg     300
gaactttcct cattgagatc tgaagacact gctgtttatt actgtgcaag agaaactgcc     360
gttattacta ctaacgctat ggattactgg ggtcaaggaa ccactgttac cgtctctagt     420
gcctccacca agggcccatc ggtcttcccc ctggcgccct gctccaggag cacctccgag     480
agcacagcgg ccctgggctg cctggtcaag gactacttcc ccgaaccggt gacggtgtcg     540
tggaactcag gcgctctgac cagcggcgtg cacaccttcc cagctgtcct acagtcctca     600
ggactctact ccctcagcag cgtggtgacc gtgccctcca gcaacttcgg cacccagacc     660
tacacctgca acgtagatca caagcccagc aacaccaagg tggacaagac agttgagcgc     720
aaatgttgtg tcgagtgccc accgtgccca gcaccacctg tggcaggacc gtcagtcttc     780
ctcttccccc caaaacccaa ggacaccctc atgatctccc ggaccctga ggtcacgtgc     840
```

-continued

```
gtggtggtgg acgtgagcca cgaagacccc gaggtccagt tcaactggta cgtggacggc    900
gtggaggtgc ataatgccaa gacaaagcca cgggaggagc agttcaacag cacgttccgt    960
gtggtcagcg tcctcaccgt tgtgcaccag gactggctga acggcaagga gtacaagtgc   1020
aaggtctcca acaaaggcct cccagccccc atcgagaaaa ccatctccaa aaccaaaggg   1080
cagccccgag aaccacaggt gtacaccctg cccccatccc gggaggagat gaccaagaac   1140
caggtcagcc tgacctgcct ggtcaaaggc ttctacccca gcgacatcgc cgtggagtgg   1200
gagagcaatg ggcagccgga gaacaactac aagaccacac ctcccatgct ggactccgac   1260
ggctccttct tcctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaa                                                  1398
```

<210> SEQ ID NO 221
<211> LENGTH: 215
<212> TYPE: PRT
<213> ORGANISM: Artificial Sequence
<220> FEATURE:
<223> OTHER INFORMATION: Humanized antibody sequence

<400> SEQUENCE: 221

```
Asp Ile Gln Met Thr Gln Ser Pro Ser Ser Leu Ser Ala Ser Val Gly
 1               5                  10                  15

Asp Arg Val Thr Ile Thr Cys Ser Val Ser Ser Thr Ile Ser Ser Asn
            20                  25                  30

His Leu His Trp Phe Gln Gln Lys Pro Gly Lys Ala Pro Lys Ser Leu
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Ser Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 222
<211> LENGTH: 645
<212> TYPE: DNA
<213> ORGANISM: Artificial Sequence
<220> FEATURE:
<223> OTHER INFORMATION: Humanized antibody sequence

<400> SEQUENCE: 222

```
gacatccaga tgacccagtc tccatcctcc ctctcagcat ccgtaggcga tagagttaca      60
ataacatgca gcgtatcatc aactatatca tcaaatcatc ttcattggtt ccaacagaaa     120
cccggcaaag cacctaaatc acttatatac ggcacatcaa atctcgcatc aggcgttcct     180
tcaagatttt caggctctgg ctcaggcacc gactttactc ttacaatatc ctccctccaa     240
cccgaagact tcgcaaccta ttactgtcaa caatggtcct catatccact cacatttggc     300
ggcggcacaa aagtagaaat taaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac cgagaaacac aaagtctacg cctgcgaagt cacccatcag     600
ggcctgagct cgcccgtcac aaagagcttc aacaggggag agtgt                      645
```

<210> SEQ ID NO 223
<211> LENGTH: 237
<212> TYPE: PRT
<213> ORGANISM: Artificial Sequence
<220> FEATURE:
<223> OTHER INFORMATION: Humanized antibody sequence

<400> SEQUENCE: 223

```
Met Asp Met Arg Val Pro Ala Gln Leu Leu Gly Leu Leu Leu Leu Trp
  1               5                  10                  15
Leu Arg Gly Ala Arg Cys Asp Ile Gln Met Thr Gln Ser Pro Ser Ser
                 20                  25                  30
Leu Ser Ala Ser Val Gly Asp Arg Val Thr Ile Thr Cys Ser Val Ser
             35                  40                  45
Ser Thr Ile Ser Ser Asn His Leu His Trp Phe Gln Gln Lys Pro Gly
         50                  55                  60
Lys Ala Pro Lys Ser Leu Ile Tyr Gly Thr Ser Asn Leu Ala Ser Gly
 65                  70                  75                  80
Val Pro Ser Arg Phe Ser Gly Ser Gly Ser Gly Thr Asp Phe Thr Leu
                 85                  90                  95
Thr Ile Ser Ser Leu Gln Pro Glu Asp Phe Ala Thr Tyr Tyr Cys Gln
                100                 105                 110
Gln Trp Ser Ser Tyr Pro Leu Thr Phe Gly Gly Gly Thr Lys Val Glu
            115                 120                 125
Ile Lys Arg Thr Val Ala Ala Pro Ser Val Phe Ile Phe Pro Pro Ser
        130                 135                 140
Asp Glu Gln Leu Lys Ser Gly Thr Ala Ser Val Val Cys Leu Leu Asn
145                 150                 155                 160
Asn Phe Tyr Pro Arg Glu Ala Lys Val Gln Trp Lys Val Asp Asn Ala
                165                 170                 175
Leu Gln Ser Gly Asn Ser Gln Glu Ser Val Thr Glu Gln Asp Ser Lys
            180                 185                 190
Asp Ser Thr Tyr Ser Leu Ser Ser Thr Leu Thr Leu Ser Lys Ala Asp
        195                 200                 205
Tyr Glu Lys His Lys Val Tyr Ala Cys Glu Val Thr His Gln Gly Leu
    210                 215                 220
Ser Ser Pro Val Thr Lys Ser Phe Asn Arg Gly Glu Cys
225                 230                 235
```

<210> SEQ ID NO 224
<211> LENGTH: 711
<212> TYPE: DNA
<213> ORGANISM: Artificial Sequence
<220> FEATURE:
<223> OTHER INFORMATION: Humanized antibody sequence

<400> SEQUENCE: 224

```
atggacatga gggtccccgc tcagctcctg ggctcctgc tactctggct ccgaggtgcc     60
agatgtgaca tccagatgac ccagtctcca tcctccctct cagcatccgt aggcgataga   120
gttacaataa catgcagcgt atcatcaact atatcatcaa atcatcttca ttggttccaa   180
cagaaacccg gcaaagcacc taaatcactt atatacggca catcaaatct cgcatcaggc   240
gttccttcaa gattttcagg ctctggctca ggcaccgact ttactcttac aatatcctcc   300
ctccaacccg aagacttcgc aacctattac tgtcaacaat ggtcctcata tccactcaca   360
tttggcggcg gcacaaaagt agaaattaaa cgtacggtgg ctgcaccatc tgtcttcatc   420
ttcccgccat ctgatgagca gttgaaatct ggaactgcct ctgttgtgtg cctgctgaat   480
aacttctatc ccagagaggc caaagtacag tggaaggtgg ataacgccct ccaatcgggt   540
aactcccagg agagtgtcac agagcaggac agcaaggaca gcacctacag cctcagcagc   600
accctgacgc tgagcaaagc agactacgag aaacacaaag tctacgcctg cgaagtcacc   660
catcagggcc tgagctcgcc cgtcacaaag agcttcaaca ggggagagtg t             711
```

<210> SEQ ID NO 225
<211> LENGTH: 451
<212> TYPE: PRT
<213> ORGANISM: Artificial Sequence
<220> FEATURE:
<223> OTHER INFORMATION: Humanized antibody sequence

<400> SEQUENCE: 225

```
Glu Val Gln Leu Val Gln Ser Gly Ala Glu Val Lys Lys Pro Gly Ala
 1               5                  10                  15

Ser Val Lys Val Ser Cys Lys Ala Ser Asp Phe Asn Ile Lys Asp Phe
            20                  25                  30

Tyr Leu His Trp Val Arg Gln Ala Pro Gly Gln Gly Leu Glu Trp Ile
        35                  40                  45

Gly Arg Ile Asp Pro Glu Asn Gly Asp Thr Leu Tyr Asp Pro Lys Phe
    50                  55                  60

Gln Asp Lys Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Asp Tyr Phe His Asp Gly Thr Ser Tyr Trp Tyr Phe
            100                 105                 110

Asp Val Trp Gly Arg Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
```

```
                180             185             190
Val Val Thr Val Pro Ser Ser Asn Phe Gly Thr Gln Thr Tyr Thr Cys
        195                 200                 205
Asn Val Asp His Lys Pro Ser Asn Thr Lys Val Asp Lys Thr Val Glu
    210                 215                 220
Arg Lys Cys Cys Val Glu Cys Pro Pro Cys Pro Ala Pro Pro Val Ala
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Gln Phe Asn Trp Tyr Val Asp Gly Val Glu Val
        275                 280                 285
His Asn Ala Lys Thr Lys Pro Arg Glu Glu Gln Phe Asn Ser Thr Phe
    290                 295                 300
Arg Val Val Ser Val Leu Thr Val Val His Gln Asp Trp Leu Asn Gly
305                 310                 315                 320
Lys Glu Tyr Lys Cys Lys Val Ser Asn Lys Gly Leu Pro Ala Pro Ile
                325                 330                 335
Glu Lys Thr Ile Ser Lys Thr Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Met Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 226
<211> LENGTH: 1353
<212> TYPE: DNA
<213> ORGANISM: Artificial Sequence
<220> FEATURE:
<223> OTHER INFORMATION: Humanized antibody sequence

<400> SEQUENCE: 226
gaggtgcagc tggtgcagtc tggggctgag gtgaagaagc ctggggcctc agtgaaggtc      60
tcctgcaagg cttctgactt caacattaaa gacttctatc tacactgggt gcgacaggcc     120
cctggacaag gcttgagtg gattggaagg attgatcctg agaatggtga tactttatat     180
gacccgaagt tccaggacaa ggtcaccatg accacagaca cgtccaccag cacagcctac     240
atggagctga ggagcctgag atctgacgac acggccgtgt attactgtgc gagagaggcg     300
gattatttcc acgatggtac ctcctactgg tacttcgatg tctggggccg tggcaccctg     360
gtcaccgtct ctagtgcctc caccaagggc ccatcggtct tccccctggc gccctgctcc     420
aggagcacct ccgagagcac agcggccctg ggctgcctgg tcaaggacta cttccccgaa     480
```

```
ccggtgacgg tgtcgtggaa ctcaggcgct ctgaccagcg gcgtgcacac cttcccagct    540
gtcctacagt cctcaggact ctactccctc agcagcgtgg tgaccgtgcc ctccagcaac    600
ttcggcaccc agacctacac ctgcaacgta gatcacaagc ccagcaacac caaggtggac    660
aagacagttg agcgcaaatg ttgtgtcgag tgccacccgt gcccagcacc acctgtggca    720
ggaccgtcag tcttcctctt ccccccaaaa cccaaggaca ccctcatgat ctcccggacc    780
cctgaggtca cgtgcgtggt ggtggacgtg agccacgaag acccagaggt ccagttcaac    840
tggtacgtgg acggcgtgga ggtgcataat gccaagacaa agccacggga ggagcagttc    900
aacagcacgt tccgtgtggt cagcgtcctc accgttgtgc accaggactg gctgaacggc    960
aaggagtaca agtgcaaggt ctccaacaaa ggcctcccag cccccatcga gaaaaccatc   1020
tccaaaacca agggcagcc cgagaaccac aggtgtaca ccctgcccc atcccgggag   1080 gagatgacca gaaccaggt cagcctgacc tgcctggtca aaggcttcta ccccagcgac   1140
atcgccgtgg agtgggagag caatgggcag ccggagaaca actacaagac cacacctccc   1200
atgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctcct gtctccgggt aaa                                  1353
```

<210> SEQ ID NO 227
<211> LENGTH: 470
<212> TYPE: PRT
<213> ORGANISM: Artificial Sequence
<220> FEATURE:
<223> OTHER INFORMATION: Humanized antibody sequence

<400> SEQUENCE: 227

```
Met Asp Trp Thr Trp Arg Ile Leu Phe Leu Val Ala Ala Ala Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Asp Phe Asn Ile
        35                  40                  45

Lys Asp Phe Tyr Leu His Trp Val Arg Gln Ala Pro Gly Gln Gly Leu
    50                  55                  60

Glu Trp Ile Gly Arg Ile Asp Pro Glu Asn Gly Asp Thr Leu Tyr Asp
65                  70                  75                  80

Pro Lys Phe Gln Asp Lys Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Glu Ala Asp Tyr Phe His Asp Gly Thr Ser Tyr
        115                 120                 125

Trp Tyr Phe Asp Val Trp Gly Arg Gly Thr Leu Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205
```

```
Leu Ser Ser Val Val Thr Val Pro Ser Ser Asn Phe Gly Thr Gln Thr
    210                 215                 220
Tyr Thr Cys Asn Val Asp His Lys Pro Ser Asn Thr Lys Val Asp Lys
225                 230                 235                 240
Thr Val Glu Arg Lys Cys Cys Val Glu Cys Pro Pro Cys Pro Ala Pro
                245                 250                 255
Pro Val Ala Gly Pro Ser Val Phe Leu Phe Pro Pro Lys Pro Lys Asp
            260                 265                 270
Thr Leu Met Ile Ser Arg Thr Pro Glu Val Thr Cys Val Val Val Asp
        275                 280                 285
Val Ser His Glu Asp Pro Glu Val Gln Phe Asn Trp Tyr Val Asp Gly
    290                 295                 300
Val Glu Val His Asn Ala Lys Thr Lys Pro Arg Glu Glu Gln Phe Asn
305                 310                 315                 320
Ser Thr Phe Arg Val Val Ser Val Leu Thr Val Val His Gln Asp Trp
                325                 330                 335
Leu Asn Gly Lys Glu Tyr Lys Cys Lys Val Ser Asn Lys Gly Leu Pro
            340                 345                 350
Ala Pro Ile Glu Lys Thr Ile Ser Lys Thr Lys Gly Gln Pro Arg Glu
        355                 360                 365
Pro Gln Val Tyr Thr Leu Pro Pro Ser Arg Glu Glu Met Thr Lys Asn
    370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Met Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
        435                 440                 445
Ser Val Met His Glu Ala Leu His Asn His Tyr Thr Gln Lys Ser Leu
    450                 455                 460
Ser Leu Ser Pro Gly Lys
465                 470

<210> SEQ ID NO 228
<211> LENGTH: 1410
<212> TYPE: DNA
<213> ORGANISM: Artificial Sequence
<220> FEATURE:
<223> OTHER INFORMATION: Humanized antibody sequence

<400> SEQUENCE: 228
atggactgga cctggaggat cctcttcttg gtggcagcag ccacaggagc ccactccgag      60
gtgcagctgg tgcagtctgg ggctgaggtg aagaagcctg gggcctcagt gaaggtctcc     120
tgcaaggctt ctgacttcaa cattaaagac ttctatctac actgggtgcg acaggcccct     180
ggacaagggc ttgagtggat tggaaggatt gatcctgaga atggtgatac tttatatgac     240
ccgaagttcc aggacaaggt caccatgacc acagacacgt ccaccagcac agcctacatg     300
gagctgagga gcctgagatc tgacgacacg gccgtgtatt actgtgcgag agaggcggat     360
tatttccacg atggtaccte ctactggtac ttcgatgtct ggggccgtgg caccctggtc     420
accgtctcta gtgcctccac caagggccca tcggtcttcc ccctggcgcc ctgctccagg     480
agcacctccg agagcacagc ggccctgggc tgcctggtca aggactactt ccccgaaccg     540
```

```
gtgacggtgt cgtggaactc aggcgctctg accagcggcg tgcacacctt cccagctgtc    600
ctacagtcct caggactcta ctccctcagc agcgtggtga ccgtgccctc agcaacttc     660 ggcacccaga cctacacctg caacgtagat cacaagccca gcaacaccaa ggtggacaag    720
acagttgagc gcaaatgttg tgtcgagtgc ccaccgtgcc cagcaccacc tgtggcagga    780
ccgtcagtct tcctcttccc cccaaaaccc aaggacaccc tcatgatctc ccggacccct    840
gaggtcacgt gcgtggtggt ggacgtgagc cacgaagacc ccgaggtcca gttcaactgg    900
tacgtggacg gcgtggaggt gcataatgcc aagacaaagc cacgggagga gcagttcaac    960
agcacgttcc gtgtggtcag cgtcctcacc gttgtgcacc aggactggct gaacggcaag    1020
gagtacaagt gcaaggtctc caacaaaggc ctcccagccc ccatcgagaa aaccatctcc    1080
aaaaccaaag ggcagccccg agaaccacag gtgtacaccc tgcccccatc ccgggaggag    1140
atgaccaaga accaggtcag cctgacctgc ctggtcaaag gcttctaccc cagcgacatc    1200
gccgtggagt gggagagcaa tgggcagccg gagaacaact acaagaccac acctcccatg    1260
ctggactccg acggctcctt cttcctctac agcaagctca ccgtggacaa gagcaggtgg    1320
cagcagggga acgtcttctc atgctccgtg atgcatgagg ctctgcacaa ccactacacg    1380
cagaagagcc tctccctgtc tccgggtaaa                                     1410
```

<210> SEQ ID NO 229
<211> LENGTH: 213
<212> TYPE: PRT
<213> ORGANISM: Artificial Sequence
<220> FEATURE:
<223> OTHER INFORMATION: Humanized antibody sequence

<400> SEQUENCE: 229

```
Asp Ile Gln Leu Thr Gln Ser Pro Ser Phe Leu Ser Ala Ser Val Gly
 1               5                  10                  15

Asp Arg Val Thr Ile Thr Cys Arg Ala Ser Ser Ile Ser Tyr Ile
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asp Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

Asn Arg Gly Glu Cys
    210

<210> SEQ ID NO 230
<211> LENGTH: 639
<212> TYPE: DNA
<213> ORGANISM: Artificial Sequence
<220> FEATURE:
<223> OTHER INFORMATION: Humanized antibody sequence

<400> SEQUENCE: 230

```
gacatccagt tgacccagtc tccatccttc ctgtctgcat ctgtaggaga cagagtcacc      60
atcacttgca gggccagctc aagtataagt tacatacact ggtatcagca aaaaccaggg     120
aaagccccta agctcctgat ctatgccaca tccaacctgg cttctggggt cccatcaagg     180
ttcagcggca gtggatctgg gacagaattc actctcacaa tcagcagcct gcagcctgaa     240
gattttgcaa cttattactg tcagcagtgg agtagtgacc cactcacgtt cggcggaggg     300
accaaggtgg agatcaaacg tacggtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgt                           639
```

<210> SEQ ID NO 231
<211> LENGTH: 235
<212> TYPE: PRT
<213> ORGANISM: Artificial Sequence
<220> FEATURE:
<223> OTHER INFORMATION: Humanized antibody sequence

<400> SEQUENCE: 231

Met Asp Met Arg Val Pro Ala Gln Leu Leu Gly Leu Leu Leu Leu Trp
1               5                   10                  15

Leu Pro Gly Ala Arg Cys Asp Ile Gln Leu Thr Gln Ser Pro Ser Phe
            20                  25                  30

Leu Ser Ala Ser Val Gly Asp Arg Val Thr Ile Thr Cys Arg Ala Ser
        35                  40                  45

Ser Ser Ile Ser Tyr Ile His Trp Tyr Gln Gln Lys Pro Gly Lys Ala
    50                  55                  60

Pro Lys Leu Leu Ile Tyr Ala Thr Ser Asn Leu Ala Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Glu Asp Phe Ala Thr Tyr Tyr Cys Gln Gln Trp
            100                 105                 110

Ser Ser Asp Pro Leu Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser

```
                     180                 185                 190
Thr Tyr Ser Leu Ser Ser Thr Leu Thr Leu Ser Lys Ala Asp Tyr Glu
        195                 200                 205
Lys His Lys Val Tyr Ala Cys Glu Val Thr His Gln Gly Leu Ser Ser
        210                 215                 220
Pro Val Thr Lys Ser Phe Asn Arg Gly Glu Cys
225                 230                 235

<210> SEQ ID NO 232
<211> LENGTH: 705
<212> TYPE: DNA
<213> ORGANISM: Artificial Sequence
<220> FEATURE:
<223> OTHER INFORMATION: Humanized antibody sequence

<400> SEQUENCE: 232
atggacatga gggtccccgc tcagctcctg gggctcctgc tgctctggct cccaggtgcc      60
agatgtgaca tccagttgac ccagtctcca tccttcctgt ctgcatctgt aggagacaga     120
gtcaccatca cttgcagggc cagctcaagt ataagttaca tacactggta tcagcaaaaa     180
ccagggaaag cccctaagct cctgatctat gccacatcca acctggcttc tggggtccca     240
tcaaggttca gcggcagtgg atctgggaca gaattcactc tcacaatcag cagcctgcag     300
cctgaagatt ttgcaactta ttactgtcag cagtggagta gtgacccact cacgttcggc     360
ggagggacca aggtggagat caaacgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactac gagaaacac aaagtctacg cctgcgaagt cacccatcag     660
ggcctgagct cgcccgtcac aaagagcttc aacaggggag agtgt                     705

<210> SEQ ID NO 233
<211> LENGTH: 447
<212> TYPE: PRT
<213> ORGANISM: Artificial Sequence
<220> FEATURE:
<223> OTHER INFORMATION: Humanized antibody sequence

<400> SEQUENCE: 233

Glu Val Gln Leu Val Gln Ser Gly Ala Glu Val Lys Lys Pro Gly Ala
1               5                   10                  15
Ser Val Lys Val Ser Cys Lys Ala Ser Gly Phe Asp Ile Lys Asp Tyr
            20                  25                  30
Tyr Ile His Trp Val Arg Gln Ala Pro Gly Gln Gly Leu Glu Trp Ile
        35                  40                  45
Gly Arg Val Asp Pro Asp Asn Gly Glu Thr Glu Phe Ala Pro Lys Phe
    50                  55                  60
Pro Gly Lys Val Thr Met Thr Thr Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Glu Asp Tyr Asp Gly Thr Tyr Thr Trp Phe Pro Tyr Trp Gly
            100                 105                 110
Gln Gly Thr Leu Val Thr Val Ser Ser Ala Ser Thr Lys Gly Pro Ser
        115                 120                 125
```

```
Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 234
<211> LENGTH: 1341
<212> TYPE: DNA
<213> ORGANISM: Artificial Sequence
<220> FEATURE:
<223> OTHER INFORMATION: Humanized antibody sequence

<400> SEQUENCE: 234
gaggtgcagc tggtgcagtc tggggctgag gtgaagaagc ctggggcctc agtgaaggtc      60
tcctgcaagg cttctggatt cgacattaag gactactata tacactgggt gcgacaggcc     120
cctggacaag gcttgagtg gatcggaagg gttgatcctg acaatggtga gactgaattt     180
gccccgaagt tccgggcaa ggtcaccatg accacagaca cgtccatcag cacagcctac     240
atggagctga gcaggctgag atctgacgac acggccgtgt attactgtgc gagagaagac     300
```

-continued

```
tacgatggta cctacacctg gtttccttat tggggccaag ggactctggt caccgtctct   360
agtgcctcca ccaagggccc atcggtcttc cccctggcgc cctgctccag gagcacctcc   420
gagagcacag cggccctggg ctgcctggtc aaggactact ccccgaacc ggtgacggtg   480
tcgtggaact caggcgctct gaccagcggc gtgcacacct tcccagctgt cctacagtcc   540
tcaggactct actccctcag cagcgtggtg accgtgccct ccagcaactt cggcacccag   600
acctacacct gcaacgtaga tcacaagccc agcaacacca aggtggacaa gacagttgag   660
cgcaaatgtt gtgtcgagtg cccaccgtgc ccagcaccac ctgtggcagg accgtcagtc   720
ttcctcttcc ccccaaaacc caaggacacc ctcatgatct cccggacccc tgaggtcacg   780
tgcgtggtgg tggacgtgag ccacgaagac cccgaggtcc agttcaactg gtacgtggac   840
ggcgtggagg tgcataatgc caagacaaag ccacgggagg agcagttcaa cagcacgttc   900
cgtgtggtca gcgtcctcac cgttgtgcac caggactggc tgaacggcaa ggagtacaag   960
tgcaaggtct ccaacaaagg cctcccagcc cccatcgaga aaaccatctc caaaaccaaa   1020
gggcagcccc gagaaccaca ggtgtacacc ctgcccccat cccgggagga gatgaccaag   1080
aaccaggtca gcctgacctg cctggtcaaa ggcttctacc ccagcgacat cgccgtggag   1140
tgggagagca atgggcagcc ggagaacaac tacaagacca cacctcccat gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa a   1341
```

<210> SEQ ID NO 235
<211> LENGTH: 466
<212> TYPE: PRT
<213> ORGANISM: Artificial Sequence
<220> FEATURE:
<223> OTHER INFORMATION: Humanized antibody sequence

<400> SEQUENCE: 235

```
Met Asp Trp Thr Trp Arg Ile Leu Phe Leu Val Ala Ala Ala Thr Gly
  1               5                  10                  15
Ala His Ser Glu Val Gln Leu Val Gln Ser Gly Ala Glu Val Lys Lys
             20                  25                  30
Pro Gly Ala Ser Val Lys Val Ser Cys Lys Ala Ser Gly Phe Asp Ile
         35                  40                  45
Lys Asp Tyr Tyr Ile His Trp Val Arg Gln Ala Pro Gly Gln Gly Leu
     50                  55                  60
Glu Trp Ile Gly Arg Val Asp Pro Asp Asn Gly Glu Thr Glu Phe Ala
 65                  70                  75                  80
Pro Lys Phe Pro Gly Lys Val Thr Met Thr Thr Asp Thr Ser Ile Ser
                 85                  90                  95
Thr Ala Tyr Met Glu Leu Ser Arg Leu Arg Ser Asp Asp Thr Ala Val
            100                 105                 110
Tyr Tyr Cys Ala Arg Glu Asp Tyr Asp Gly Thr Tyr Thr Trp Phe Pro
        115                 120                 125
Tyr Trp Gly Gln Gly Thr Leu Val Thr Val Ser Ser Ala Ser Thr Lys
    130                 135                 140
Gly Pro Ser Val Phe Pro Leu Ala Pro Cys Ser Arg Ser Thr Ser Glu
145                 150                 155                 160
Ser Thr Ala Ala Leu Gly Cys Leu Val Lys Asp Tyr Phe Pro Glu Pro
                165                 170                 175
```

```
Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200             205

Val Thr Val Pro Ser Ser Asn Phe Gly Thr Gln Thr Tyr Thr Cys Asn
            210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
            275                 280                 285

Asp Pro Glu Val Gln Phe Asn Trp Tyr Val Asp Gly Val Glu Val His
            290                 295                 300

Asn Ala Lys Thr Lys Pro Arg Glu Glu Gln Phe Asn Ser Thr Phe Arg
305                 310                 315                 320

Val Val Ser Val Leu Thr Val His Gln Asp Trp Leu Asn Gly Lys
            325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
            370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
            405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
            450                 455                 460

Gly Lys
465

<210> SEQ ID NO 236
<211> LENGTH: 1398
<212> TYPE: DNA
<213> ORGANISM: Artificial Sequence
<220> FEATURE:
<223> OTHER INFORMATION: Humanized antibody sequence

<400> SEQUENCE: 236
atggactgga cctggaggat cctcttcttg gtggcagcag ccacaggagc ccactccgag      60
gtgcagctgg tgcagtctgg ggctgaggtg aagaagcctg ggcctcagt gaaggtctcc     120 tgcaaggctt ctggattcga cattaaggac tactatatac actgggtgcg acaggccct     180 ggacaagggc ttgagtggat cggaaggggtt gatcctgaca atggtgagac tgaatttgcc    240
ccgaagttcc cggcaaggt caccatgacc acagacacgt ccatcagcac agcctacatg     300
gagctgagca ggctgagatc tgacgacacg gccgtgtatt actgtgcgag agaagactac    360
```

-continued

```
gatggtacct acacctggtt tccttattgg ggccaaggga ctctggtcac cgtctctagt      420
gcctccacca agggcccatc ggtcttcccc ctggcgccct gctccaggag cacctccgag      480
agcacagcgg ccctgggctg cctggtcaag gactacttcc ccgaaccggt gacggtgtcg      540
tggaactcag gcgctctgac cagcggcgtg cacaccttcc cagctgtcct acagtcctca      600
ggactctact ccctcagcag cgtggtgacc gtgccctcca gcaacttcgg cacccagacc      660
tacacctgca acgtagatca caagcccagc aacaccaagg tggacaagac agttgagcgc      720
aaatgttgtg tcgagtgccc accgtgccca gcaccacctg tggcaggacc gtcagtcttc      780
ctcttccccc caaaacccaa ggacaccctc atgatctccc ggacccctga ggtcacgtgc      840
gtggtggtgg acgtgagcca cgaagacccc gaggtccagt tcaactggta cgtggacggc      900
gtggaggtgc ataatgccaa gacaaagcca cgggaggagc agttcaacag cacgttccgt      960
gtggtcagcg tcctcaccgt tgtgcaccag gactggctga acggcaagga gtacaagtgc     1020
aaggtctcca acaaaggcct cccagccccc atcgagaaaa ccatctccaa aaccaaaggg     1080
cagccccgag aaccacaggt gtacaccctg cccccatccc gggaggagat gaccaagaac     1140
caggtcagcc tgacctgcct ggtcaaaggc ttctacccca gcgacatcgc cgtggagtgg     1200
gagagcaatg ggcagccgga gaacaactac aagaccacac ctcccatgct ggactccgac     1260
ggctccttct tcctctacag caagctcacc gtggacaaga gcaggtggca gcaggggaac     1320
gtcttctcat gctccgtgat gcatgaggct ctgcacaacc actacacgca gaagagcctc     1380
tccctgtctc cgggtaaa                                                   1398
```

<210> SEQ ID NO 237
<211> LENGTH: 7
<212> TYPE: PRT
<213> ORGANISM: Mus musculus

<400> SEQUENCE: 237

Gly Thr Ser Asn Leu Ala Ser
1               5

<210> SEQ ID NO 238
<211> LENGTH: 8
<212> TYPE: PRT
<213> ORGANISM: Mus musculus

<400> SEQUENCE: 238

Gln Gln Trp Thr Thr Thr Tyr Thr
1               5

<210> SEQ ID NO 239
<211> LENGTH: 11
<212> TYPE: PRT
<213> ORGANISM: Mus musculus

<400> SEQUENCE: 239

Arg Ala Ser Gln Asp Ile Ser Ser Tyr Leu Asn
1               5                   10

<210> SEQ ID NO 240
<211> LENGTH: 7
<212> TYPE: PRT
<213> ORGANISM: Mus musculus

<400> SEQUENCE: 240

Ser Thr Ser Arg Leu Asn Ser

```
<210> SEQ ID NO 241
<211> LENGTH: 8
<212> TYPE: PRT
<213> ORGANISM: Mus musculus

<400> SEQUENCE: 241

Gln Gln Asp Ile Lys His Pro Thr
 1               5

<210> SEQ ID NO 242
<211> LENGTH: 11
<212> TYPE: PRT
<213> ORGANISM: Mus musculus

<400> SEQUENCE: 242

Lys Ala Ser Gln Asp Val Phe Thr Ala Val Ala
 1               5                  10

<210> SEQ ID NO 243
<211> LENGTH: 7
<212> TYPE: PRT
<213> ORGANISM: Mus musculus

<400> SEQUENCE: 243

Trp Ala Ser Thr Arg His Thr
 1               5

<210> SEQ ID NO 244
<211> LENGTH: 9
<212> TYPE: PRT
<213> ORGANISM: Mus musculus

<400> SEQUENCE: 244

Gln Gln Tyr Ser Ser Tyr Pro Leu Thr
 1               5

<210> SEQ ID NO 245
<211> LENGTH: 5
<212> TYPE: PRT
<213> ORGANISM: Mus musculus

<400> SEQUENCE: 245

Asp Tyr Asn Met His
 1               5

<210> SEQ ID NO 246
<211> LENGTH: 17
<212> TYPE: PRT
<213> ORGANISM: Mus musculus

<400> SEQUENCE: 246

Glu Ile Asn Pro Asn Ser Gly Gly Ala Gly Tyr Asn Gln Lys Phe Lys
 1               5                  10                  15

Gly

<210> SEQ ID NO 247
<211> LENGTH: 14
<212> TYPE: PRT
<213> ORGANISM: Mus musculus

<400> SEQUENCE: 247

Leu Gly Tyr Asp Asp Ile Tyr Asp Asp Trp Tyr Phe Asp Val
```

<210> SEQ ID NO 248
<211> LENGTH: 5
<212> TYPE: PRT
<213> ORGANISM: Mus musculus

<400> SEQUENCE: 248

Asp Tyr Asn Met His
1               5

<210> SEQ ID NO 249
<211> LENGTH: 17
<212> TYPE: PRT
<213> ORGANISM: Mus musculus

<400> SEQUENCE: 249

Glu Ile Asn Pro Asn Ser Gly Gly Ser Gly Tyr Asn Gln Lys Phe Lys
1               5                   10                  15

Gly

<210> SEQ ID NO 250
<211> LENGTH: 14
<212> TYPE: PRT
<213> ORGANISM: Mus musculus

<400> SEQUENCE: 250

Leu Val Tyr Asp Gly Ser Tyr Glu Asp Trp Tyr Phe Asp Val
1               5                   10

<210> SEQ ID NO 251
<211> LENGTH: 5
<212> TYPE: PRT
<213> ORGANISM: Mus musculus

<400> SEQUENCE: 251

Asp Tyr Asn Met His
1               5

<210> SEQ ID NO 252
<211> LENGTH: 17
<212> TYPE: PRT
<213> ORGANISM: Mus musculus

<400> SEQUENCE: 252

Glu Ile Asn Pro Asn Ser Gly Gly Ala Gly Tyr Asn Gln Gln Phe Lys
1               5                   10                  15

Gly

<210> SEQ ID NO 253
<211> LENGTH: 14
<212> TYPE: PRT
<213> ORGANISM: Mus musculus

<400> SEQUENCE: 253

Leu Gly Tyr Val Gly Asn Tyr Glu Asp Trp Tyr Phe Asp Val
1               5                   10

<210> SEQ ID NO 254
<211> LENGTH: 5
<212> TYPE: PRT
<213> ORGANISM: Mus musculus

<400> SEQUENCE: 254

Asp Tyr Asn Met His
1               5

<210> SEQ ID NO 255
<211> LENGTH: 17
<212> TYPE: PRT
<213> ORGANISM: Mus musculus

<400> SEQUENCE: 255

Glu Ile Asn Pro Asn Ser Gly Gly Ala Gly Tyr Asn Gln Lys Phe Lys
1               5                   10                  15

Gly

<210> SEQ ID NO 256
<211> LENGTH: 14
<212> TYPE: PRT
<213> ORGANISM: Mus musculus

<400> SEQUENCE: 256

Leu Gly Tyr Asp Asp Ile Tyr Asp Asp Trp Tyr Phe Asp Val
1               5                   10

<210> SEQ ID NO 257
<211> LENGTH: 5
<212> TYPE: PRT
<213> ORGANISM: Mus musculus

<400> SEQUENCE: 257

Asp Tyr Asn Met His
1               5

<210> SEQ ID NO 258
<211> LENGTH: 17
<212> TYPE: PRT
<213> ORGANISM: Mus musculus

<400> SEQUENCE: 258

Glu Ile Asn Pro Asn Ser Gly Gly Ala Gly Tyr Asn Gln Lys Phe Lys
1               5                   10                  15

Gly

<210> SEQ ID NO 259
<211> LENGTH: 14
<212> TYPE: PRT
<213> ORGANISM: Mus musculus

<400> SEQUENCE: 259

Leu Gly Tyr Asp Asp Ile Tyr Asp Asp Trp Tyr Phe Asp Val
1               5                   10

<210> SEQ ID NO 260
<211> LENGTH: 5
<212> TYPE: PRT
<213> ORGANISM: Mus musculus

<400> SEQUENCE: 260

Asp Tyr Asn Met His
1               5

<210> SEQ ID NO 261
<211> LENGTH: 17
<212> TYPE: PRT
<213> ORGANISM: Mus musculus -continued

<400> SEQUENCE: 261

Glu Ile Asn Pro Asn Ser Gly Gly Ala Gly Tyr Asn Gln Lys Phe Lys
1               5                   10                  15
Gly

<210> SEQ ID NO 262
<211> LENGTH: 14
<212> TYPE: PRT
<213> ORGANISM: Mus musculus

<400> SEQUENCE: 262

Leu Gly Tyr Asp Asp Ile Tyr Asp Asp Trp Tyr Phe Asp Val
1               5                   10

<210> SEQ ID NO 263
<211> LENGTH: 5
<212> TYPE: PRT
<213> ORGANISM: Mus musculus

<400> SEQUENCE: 263

Asp Tyr Asn Met His
1               5

<210> SEQ ID NO 264
<211> LENGTH: 17
<212> TYPE: PRT
<213> ORGANISM: Mus musculus

<400> SEQUENCE: 264

Glu Ile Asn Pro Asn Ser Gly Gly Ser Gly Tyr Asn Gln Lys Phe Lys
1               5                   10                  15
Gly

<210> SEQ ID NO 265
<211> LENGTH: 14
<212> TYPE: PRT
<213> ORGANISM: Mus musculus

<400> SEQUENCE: 265

Leu Gly Tyr Tyr Gly Asn Tyr Glu Asp Trp Tyr Phe Asp Val
1               5                   10

<210> SEQ ID NO 266
<211> LENGTH: 5
<212> TYPE: PRT
<213> ORGANISM: Mus musculus

<400> SEQUENCE: 266

Asp Tyr Tyr Ile His
1               5

<210> SEQ ID NO 267
<211> LENGTH: 17
<212> TYPE: PRT
<213> ORGANISM: Mus musculus

<400> SEQUENCE: 267

Arg Ile Asp Pro Asp Asn Gly Glu Ser Thr Tyr Val Pro Lys Phe Gln
1               5                   10                  15
Gly

```
<210> SEQ ID NO 268
<211> LENGTH: 13
<212> TYPE: PRT
<213> ORGANISM: Mus musculus

<400> SEQUENCE: 268

Glu Gly Leu Asp Tyr Gly Asp Tyr Tyr Ala Val Asp Tyr
1               5                   10

<210> SEQ ID NO 269
<211> LENGTH: 5
<212> TYPE: PRT
<213> ORGANISM: Mus musculus

<400> SEQUENCE: 269

Asp Tyr Ile Met His
1               5

<210> SEQ ID NO 270
<211> LENGTH: 17
<212> TYPE: PRT
<213> ORGANISM: Mus musculus

<400> SEQUENCE: 270

Tyr Ile Asn Pro Tyr Asn Asp Asp Thr Glu Tyr Asn Glu Lys Phe Lys
1               5                   10                  15

Gly

<210> SEQ ID NO 271
<211> LENGTH: 11
<212> TYPE: PRT
<213> ORGANISM: Mus musculus

<400> SEQUENCE: 271

Ser Ile Tyr Tyr Tyr Asp Ala Pro Phe Ala Tyr
1               5                   10

<210> SEQ ID NO 272
<211> LENGTH: 5
<212> TYPE: PRT
<213> ORGANISM: Mus musculus

<400> SEQUENCE: 272

Asp Tyr Tyr Met His
1               5

<210> SEQ ID NO 273
<211> LENGTH: 17
<212> TYPE: PRT
<213> ORGANISM: Mus musculus

<400> SEQUENCE: 273

Arg Ile Asp Pro Glu Asn Gly Asp Ile Ile Tyr Asp Pro Lys Phe Gln
1               5                   10                  15

Gly

<210> SEQ ID NO 274
<211> LENGTH: 10
<212> TYPE: PRT
<213> ORGANISM: Mus musculus

<400> SEQUENCE: 274

Asp Ala Gly Asp Pro Ala Trp Phe Thr Tyr
1               5                   10
```

<210> SEQ ID NO 275
<211> LENGTH: 10
<212> TYPE: PRT
<213> ORGANISM: Mus musculus

<400> SEQUENCE: 275

Arg Ala Ser Ser Val Tyr Tyr Met His
 1               5                   10

<210> SEQ ID NO 276
<211> LENGTH: 7
<212> TYPE: PRT
<213> ORGANISM: Mus musculus

<400> SEQUENCE: 276

Ala Thr Ser Asn Leu Ala Ser
 1               5

<210> SEQ ID NO 277
<211> LENGTH: 9
<212> TYPE: PRT
<213> ORGANISM: Mus musculus

<400> SEQUENCE: 277

Gln Gln Trp Ser Ser Asp Pro Leu Thr
 1               5

<210> SEQ ID NO 278
<211> LENGTH: 12
<212> TYPE: PRT
<213> ORGANISM: Mus musculus

<400> SEQUENCE: 278

Ser Val Ser Ser Thr Ile Ser Ser Asn His Leu His
 1               5                   10

<210> SEQ ID NO 279
<211> LENGTH: 7
<212> TYPE: PRT
<213> ORGANISM: Mus musculus

<400> SEQUENCE: 279

Gly Thr Ser Asn Leu Ala Ser
 1               5

<210> SEQ ID NO 280
<211> LENGTH: 9
<212> TYPE: PRT
<213> ORGANISM: Mus musculus

<400> SEQUENCE: 280

Gln Gln Trp Ser Ser Tyr Pro Leu Thr
 1               5

<210> SEQ ID NO 281
<211> LENGTH: 10
<212> TYPE: PRT
<213> ORGANISM: Mus musculus

<400> SEQUENCE: 281

Arg Ala Ser Ser Ser Ile Ser Tyr Ile His
 1               5                   10

```
<210> SEQ ID NO 282
<211> LENGTH: 7
<212> TYPE: PRT
<213> ORGANISM: Mus musculus

<400> SEQUENCE: 282

Ala Thr Ser Asn Leu Ala Ser
 1               5

<210> SEQ ID NO 283
<211> LENGTH: 9
<212> TYPE: PRT
<213> ORGANISM: Mus musculus

<400> SEQUENCE: 283

Gln Gln Trp Ser Ser Asp Pro Leu Thr
 1               5

<210> SEQ ID NO 284
<211> LENGTH: 12
<212> TYPE: PRT
<213> ORGANISM: Mus musculus

<400> SEQUENCE: 284

Arg Ala Ser Ser Ser Val Thr Ser Ser Tyr Leu Asn
 1               5                  10

<210> SEQ ID NO 285
<211> LENGTH: 7
<212> TYPE: PRT
<213> ORGANISM: Mus musculus

<400> SEQUENCE: 285

Ser Thr Ser Asn Leu Ala Ser
 1               5

<210> SEQ ID NO 286
<211> LENGTH: 9
<212> TYPE: PRT
<213> ORGANISM: Mus musculus

<400> SEQUENCE: 286

Gln Gln Tyr Asp Phe Phe Pro Ser Thr
 1               5

<210> SEQ ID NO 287
<211> LENGTH: 5
<212> TYPE: PRT
<213> ORGANISM: Mus musculus

<400> SEQUENCE: 287

Asp Tyr Phe Ile His
 1               5

<210> SEQ ID NO 288
<211> LENGTH: 17
<212> TYPE: PRT
<213> ORGANISM: Mus musculus

<400> SEQUENCE: 288

Arg Leu Asp Pro Glu Asp Gly Glu Ser Asp Tyr Ala Pro Lys Phe Gln
 1               5                  10                  15

Asp
```

```
<210> SEQ ID NO 289
<211> LENGTH: 12
<212> TYPE: PRT
<213> ORGANISM: Mus musculus

<400> SEQUENCE: 289

Glu Asp Tyr Asp Gly Thr Tyr Thr Phe Phe Pro Tyr
1               5                   10

<210> SEQ ID NO 290
<211> LENGTH: 5
<212> TYPE: PRT
<213> ORGANISM: Mus musculus

<400> SEQUENCE: 290

Asp Phe Tyr Leu His
1               5

<210> SEQ ID NO 291
<211> LENGTH: 17
<212> TYPE: PRT
<213> ORGANISM: Mus musculus

<400> SEQUENCE: 291

Arg Ile Asp Pro Glu Asn Gly Asp Thr Leu Tyr Asp Pro Lys Phe Gln
1               5                   10                  15

Asp

<210> SEQ ID NO 292
<211> LENGTH: 16
<212> TYPE: PRT
<213> ORGANISM: Mus musculus

<400> SEQUENCE: 292

Glu Ala Asp Tyr Phe His Asp Gly Thr Ser Tyr Trp Tyr Phe Asp Val
1               5                   10                  15

<210> SEQ ID NO 293
<211> LENGTH: 5
<212> TYPE: PRT
<213> ORGANISM: Mus musculus

<400> SEQUENCE: 293

Asp Tyr Tyr Ile His
1               5

<210> SEQ ID NO 294
<211> LENGTH: 17
<212> TYPE: PRT
<213> ORGANISM: Mus musculus

<400> SEQUENCE: 294

Arg Val Asp Pro Asp Asn Gly Glu Thr Glu Phe Ala Pro Lys Phe Pro
1               5                   10                  15

Gly

<210> SEQ ID NO 295
<211> LENGTH: 12
<212> TYPE: PRT
<213> ORGANISM: Mus musculus

<400> SEQUENCE: 295

Glu Asp Tyr Asp Gly Thr Tyr Thr Trp Phe Pro Tyr
1               5                   10
```

<210> SEQ ID NO 296
<211> LENGTH: 5
<212> TYPE: PRT
<213> ORGANISM: Mus musculus

<400> SEQUENCE: 296

Asp Tyr Tyr Met Asn
1               5

<210> SEQ ID NO 297
<211> LENGTH: 17
<212> TYPE: PRT
<213> ORGANISM: Mus musculus

<400> SEQUENCE: 297

Asp Ile Asn Pro Tyr Asn Asp Asp Thr Thr Tyr Asn His Lys Phe Lys
1               5                   10                  15

Gly

<210> SEQ ID NO 298
<211> LENGTH: 11
<212> TYPE: PRT
<213> ORGANISM: Mus musculus

<400> SEQUENCE: 298

Glu Thr Ala Val Ile Thr Thr Asn Ala Met Asp
1               5                   10

<210> SEQ ID NO 299
<211> LENGTH: 130
<212> TYPE: PRT
<213> ORGANISM: Mus musculus

<400> SEQUENCE: 299

Met Asp Phe Gln Val Gln Ile Phe Ser Phe Met Leu Ile Ser Val Thr
1               5                   10                  15

Val Ile Leu Ser Ser Gly Glu Ile Val Leu Thr Gln Ser Pro Ala Leu
            20                  25                  30

Met Ala Ala Ser Pro Gly Glu Lys Val Thr Ile Thr Cys Ser Val Ser
        35                  40                  45

Ser Ser Ile Ser Ser Ser Asn Leu His Trp Ser Gln Gln Lys Ser Gly
    50                  55                  60

Thr Ser Pro Lys Leu Trp Ile Tyr Gly Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys Gln
            100                 105                 110

Gln Trp Thr Thr Thr Tyr Thr Phe Gly Ser Gly Thr Lys Leu Glu Leu
        115                 120                 125

Lys Arg
    130

<210> SEQ ID NO 300
<211> LENGTH: 390
<212> TYPE: DNA
<213> ORGANISM: Mus musculus

<400> SEQUENCE: 300

```
atggattttc aggtgcagat tttcagcttc atgctaatca gtgtcacagt catattgtcc    60
agtggagaaa ttgtgctcac ccagtctcca gcactcatgg ctgcatctcc aggggagaag   120
gtcaccatca cctgcagtgt cagctcgagt ataagttcca gcaacttaca ctggtcccag   180
cagaagtcag gaacctcccc caaactctgg atttatggca catccaacct tgcttctgga   240
gtccctgttc gcttcagtgg cagtggatct gggacctctt attctctcac aatcagcagc   300
atggaggctg aagatgctgc cacttattac tgtcaacagt ggactactac gtatacgttc   360
ggatcgggga ccaagctgga gctgaaacgt                                    390
```

<210> SEQ ID NO 301
<211> LENGTH: 141
<212> TYPE: PRT
<213> ORGANISM: Mus musculus

<400> SEQUENCE: 301

```
Met Gly Trp Asn Trp Ile Ile Phe Phe Leu Met Ala Val Val Thr Gly
  1               5                  10                  15
Val Asn Ser Glu Val Gln Leu Arg Gln Ser Gly Ala Asp Leu Val Lys
             20                  25                  30
Pro Gly Ala Ser Val Lys Leu Ser Cys Thr Ala Ser Gly Phe Asn Ile
         35                  40                  45
Lys Asp Tyr Tyr Ile His Trp Val Lys Gln Arg Pro Glu Gln Gly Leu
     50                  55                  60
Glu Trp Ile Gly Arg Ile Asp Pro Asp Asn Gly Glu Ser Thr Tyr Val
 65                  70                  75                  80
Pro Lys Phe Gln Gly Lys Ala Thr Ile Thr Ala Asp Thr Ser Ser Asn
                 85                  90                  95
Thr Ala Tyr Leu Gln Leu Arg Ser Leu Thr Ser Glu Asp Thr Ala Ile
            100                 105                 110
Tyr Tyr Cys Gly Arg Glu Gly Leu Asp Tyr Gly Asp Tyr Tyr Ala Val
        115                 120                 125
Asp Tyr Trp Gly Gln Gly Thr Ser Val Thr Val Ser Ser
    130                 135                 140
```

<210> SEQ ID NO 302
<211> LENGTH: 423
<212> TYPE: DNA
<213> ORGANISM: Mus musculus

<400> SEQUENCE: 302

```
atgggatgga actggatcat cttcttcctg atggcagtgg ttacaggggt caattcagag    60
gtgcagttgc ggcagtctgg ggcagacctt gtgaagccag ggcctcagt caagttgtcc    120 tgcacagctt ctggcttcaa cattaaagac tactatatac actgggtgaa gcagaggcct   180
gaacagggcc tggagtggat tggaaggatt gatcctgata atggtgaaag tacatatgtc   240
ccgaagttcc agggcaaggc cactataaca gcagacacat catccaacac agcctaccta   300
caactcagaa gcctgacatc tgaggacact gccatctatt attgtgggag agaggggctc   360
gactatggtg actactatgc tgtggactac tgggtcaag gaacctcggt cacagtctcg   420
agc                                                                423
```

<210> SEQ ID NO 303
<211> LENGTH: 130
<212> TYPE: PRT
<213> ORGANISM: Artificial Sequence
<220> FEATURE:

<223> OTHER INFORMATION: Humanized antibody sequence

<400> SEQUENCE: 303

Met Asp Met Arg Val Pro Ala Gln Leu Leu Gly Leu Leu Leu Leu Trp
1               5                   10                  15

Leu Pro Gly Ala Arg Cys Asp Ile Gln Leu Thr Gln Ser Pro Ser Phe
            20                  25                  30

Leu Ser Ala Ser Val Gly Asp Arg Val Thr Ile Thr Cys Ser Val Ser
        35                  40                  45

Ser Ser Ile Ser Ser Asn Leu His Trp Tyr Gln Gln Lys Pro Gly
    50                  55                  60

Lys Ala Pro Lys Leu Leu Ile Tyr Gly Thr Ser Asn Leu Ala Ser Gly
65                  70                  75                  80

Val Pro Ser Arg Phe Ser Gly Ser Gly Ser Gly Thr Glu Phe Thr Leu
                85                  90                  95

Thr Ile Ser Ser Leu Gln Pro Glu Asp Phe Ala Thr Tyr Tyr Cys Gln
            100                 105                 110

Gln Trp Thr Thr Thr Tyr Thr Phe Gly Gln Gly Thr Lys Leu Glu Ile
        115                 120                 125

Lys Arg
    130

<210> SEQ ID NO 304
<211> LENGTH: 390
<212> TYPE: DNA
<213> ORGANISM: Artificial Sequence
<220> FEATURE:
<223> OTHER INFORMATION: Humanized antibody sequence

<400> SEQUENCE: 304
atggatatgc gcgtgccggc gcagctgctg ggcctgctgc tgctgtggct gccgggcgcg      60
cgctgcgata ttcagctgac ccagagcccg agctttctga gcgcgagcgt gggcgatcgc     120
gtgaccatta cctgcagcgt gagcagcagc attagcagca gcaacctgca ttggtatcag     180
cagaaaccgg gcaaagcgcc gaaactgctg atttatggca ccagcaacct ggcgagcggc     240
gtgccgagcc gctttagcgg cagcggcagc ggcaccgaat ttaccctgac cattagcagc     300
ctgcagccgg aagattttgc gacctattat tgccagcagt ggaccaccac ctatacccttt    360
ggccagggca ccaaactgga aattaaacgt                                       390

<210> SEQ ID NO 305
<211> LENGTH: 141
<212> TYPE: PRT
<213> ORGANISM: Artificial Sequence
<220> FEATURE:
<223> OTHER INFORMATION: Humanized antibody sequence

<400> SEQUENCE: 305

Met Asp Trp Thr Trp Ser Ile Leu Phe Leu Val Ala Ala Pro Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Phe Asn Ile
        35                  40                  45

Lys Asp Tyr Tyr Ile His Trp Val Arg Gln Ala Pro Gly Gln Gly Leu
    50                  55                  60

Glu Trp Met Gly Arg Ile Asp Pro Asp Asn Gly Glu Thr Tyr Val
65                  70                  75                  80

```
Pro Lys Phe Gln Gly Arg Val Thr Met Thr Thr Asp Thr Ser Thr Ser
                85                  90                  95

Thr Ala Tyr Met Glu Leu Arg Ser Leu Arg Ser Asp Thr Ala Val
            100                 105                 110

Tyr Tyr Cys Ala Arg Glu Gly Leu Asp Tyr Gly Asp Tyr Tyr Ala Val
            115                 120                 125

Asp Tyr Trp Gly Gln Gly Thr Leu Val Thr Val Ser Ser
    130                 135                 140
```

<210> SEQ ID NO 306
<211> LENGTH: 423
<212> TYPE: DNA
<213> ORGANISM: Artificial Sequence
<220> FEATURE:
<223> OTHER INFORMATION: Humanized antibody sequence

<400> SEQUENCE: 306

```
atggattgga cctggagcat tctgtttctg gtggcggcgc cgaccggcgc gcatagcgaa      60
gtgcagctgg tgcagagcgg cgcggaagtg aaaaaaccgg gcgcgagcgt gaaagtgagc     120
tgcaaagcga gcggctttaa cattaaagat tattatattc attgggtgcg ccaggcgccg     180
ggccagggcc tggaatggat gggccgcatt gatccggata cggcgaaag cacctatgtg      240
ccgaaatttc agggccgcgt gaccatgacc accgatacca gcaccagcac cgcgtatatg     300
gaactgcgca gcctgcgcag cgatgatacc gcggtgtatt attgcgcgcg cgaaggcctg     360
gattatggcg attattatgc ggtggattat tggggccagg gcacccctggt gaccgtctcg    420
agc                                                                  423
```

<210> SEQ ID NO 307
<211> LENGTH: 127
<212> TYPE: PRT
<213> ORGANISM: Mus musculus

<400> SEQUENCE: 307

```
Met Met Ser Ser Ala Gln Phe Leu Gly Leu Leu Leu Leu Cys Phe Gln
  1               5                  10                  15

Gly Thr Arg Cys Asp Ile Gln Met Thr Gln Thr Thr Ser Ser Leu Ser
                20                  25                  30

Ala Ser Leu Gly Asp Arg Val Asn Ile Ser Cys Arg Ala Ser Gln Asp
            35                  40                  45

Ile Ser Ser Tyr Leu Asn Trp Tyr Gln Gln Lys Pro Asp Gly Thr Val
    50                  55                  60

Lys Leu Leu Ile Tyr Ser Thr Ser Arg Leu Asn Ser Gly Val Pro Ser
 65                 70                  75                  80

Arg Phe Ser Gly Ser Gly Ser Gly Thr Asp Tyr Ser Leu Thr Ile Ser
                85                  90                  95

Asn Leu Ala Gln Glu Asp Ile Ala Thr Tyr Phe Cys Gln Gln Asp Ile
            100                 105                 110

Lys His Pro Thr Phe Gly Gly Gly Thr Lys Leu Glu Leu Lys Arg
    115                 120                 125
```

<210> SEQ ID NO 308
<211> LENGTH: 381
<212> TYPE: DNA
<213> ORGANISM: Mus musculus

<400> SEQUENCE: 308

```
atgatgtcct ctgctcagtt ccttggtctc ctgttgctct gttttcaagg taccagatgt      60
gatatccaga tgacacagac tacatcctcc ctgtctgcct ctctgggaga cagagtcaac     120
atcagctgca gggcaagtca ggacattagc agttatttaa actggtatca gcagaaacca     180
gatggaactg ttaaactcct gatctactcc acatcaagat taaactcagg agtcccatca     240
aggttcagtg gcagtgggtc tgggacagat tattctctca ctattagcaa cctggcacaa     300
gaagatattg ccacttactt ttgccaacag gatattaagc atccgacgtt cggtggaggc     360
accaagttgg agctgaaacg t                                                381
```

<210> SEQ ID NO 309
<211> LENGTH: 139
<212> TYPE: PRT
<213> ORGANISM: Mus musculus

<400> SEQUENCE: 309

Met Glu Trp Ile Trp Ile Phe Leu Phe Leu Leu Ser Gly Thr Ala Gly
 1               5                  10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Phe Thr Phe
        35                  40                  45

Thr Asp Tyr Ile Met His Trp Val Lys Gln Lys Pro Gly Gln Gly Leu
    50                  55                  60

Glu Trp Ile Gly Tyr Ile Asn Pro Tyr Asn Asp Asp Thr Glu Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Asp Leu Ser Ser Leu Thr Ser Glu Gly Ser Ala Val
            100                 105                 110

Tyr Tyr Cys Ala Arg Ser Ile Tyr Tyr Tyr Asp Ala Pro Phe Ala Tyr
        115                 120                 125

Trp Gly Gln Gly Thr Leu Val Thr Val Ser Ser
    130                 135

<210> SEQ ID NO 310
<211> LENGTH: 417
<212> TYPE: DNA
<213> ORGANISM: Mus musculus

<400> SEQUENCE: 310

```
atggaatgga tctggatatt tctcttcctc ctgtcaggaa ctgcaggtgt ccactctgag      60
gtccagctgc agcagtctgg acctgagctg gtaaagcctg gggcttcagt gaagatgtcc     120
tgcaaggctt ctgggttcac attcactgac tacattatgc actgggtgaa gcagaagcct     180
gggcagggcc ttgagtggat tggatatatt aatccttaca atgatgatac tgaatacaat     240
gagaagttca aggcaaggc cacactgact tcagacaaat cctccagcac agcctacatg     300
gatctcagca gtctgacctc tgagggctct gcggtctatt actgtgcaag atcgatttat     360
tactacgatg ccccgtttgc ttactggggc caagggactc tggtcacagt ctcgagc       417
```

<210> SEQ ID NO 311
<211> LENGTH: 127
<212> TYPE: PRT
<213> ORGANISM: Artificial Sequence
<220> FEATURE:
<223> OTHER INFORMATION: Humanized antibody sequence

<400> SEQUENCE: 311

```
Met Met Ser Ser Ala Gln Phe Leu Gly Leu Leu Leu Cys Phe Gln
 1               5                  10                  15
Gly Thr Arg Cys Asp Ile Gln Met Thr Gln Ser Pro Ser Ser Leu Ser
            20                  25                  30
Ala Ser Val Gly Asp Arg Val Thr Ile Thr Cys Arg Ala Ser Gln Asp
        35                  40                  45
Ile Ser Ser Tyr Leu Asn Trp Tyr Gln Gln Lys Pro Gly Lys Ala Pro
    50                  55                  60
Lys Leu Leu Ile Tyr Ser Thr Ser Arg Leu Asn Ser Gly Val Pro Ser
65                  70                  75                  80
Arg Phe Ser Gly Ser Gly Ser Gly Thr Asp Phe Thr Leu Thr Ile Ser
                85                  90                  95
Ser Leu Gln Pro Glu Asp Phe Ala Thr Tyr Tyr Cys Gln Gln Asp Ile
            100                 105                 110
Lys His Pro Thr Phe Gly Gln Gly Thr Lys Val Glu Ile Lys Arg
        115                 120                 125
```

<210> SEQ ID NO 312
<211> LENGTH: 381
<212> TYPE: DNA
<213> ORGANISM: Artificial Sequence
<220> FEATURE:
<223> OTHER INFORMATION: Humanized antibody sequence

<400> SEQUENCE: 312

```
atgatgtcct ctgctcagtt ccttggtctc ctgttgctct gttttcaagg taccagatgt    60
gatatccaga tgacccagtc tccatcctcc ctgtctgcat ctgtaggtga ccgtgtcacc   120
atcacttgcc gcgcaagtca ggatattagc agctatttaa attggtatca gcagaaacca   180
gggaaagccc ctaagctcct gatctattct acttcccgtt tgaatagtgg ggtcccatca   240
cgcttcagtg gcagtggctc tgggacagat ttcactctca ccatcagcag tctgcaacct   300
gaagattttg caacttacta ctgtcaacag gatattaaac accctacgtt cggtcaaggc   360
accaaggtgg agatcaaacg t                                             381
```

<210> SEQ ID NO 313
<211> LENGTH: 139
<212> TYPE: PRT
<213> ORGANISM: Artificial Sequence
<220> FEATURE:
<223> OTHER INFORMATION: Humanized antibody sequence

<400> SEQUENCE: 313

```
Met Glu Trp Ile Trp Ile Phe Leu Phe Leu Leu Ser Gly Thr Ala Gly
 1               5                  10                  15
Val His Ser Glu Val Gln Leu Val Gln Ser Gly Ala Glu Val Lys Lys
            20                  25                  30
Pro Gly Ser Ser Val Lys Val Ser Cys Lys Ala Ser Gly Phe Thr Phe
        35                  40                  45
Thr Asp Tyr Ile Met His Trp Val Arg Gln Ala Pro Gly Gln Gly Leu
    50                  55                  60
Glu Trp Met Gly Tyr Ile Asn Pro Tyr Asn Asp Asp Thr Glu Tyr Asn
65                  70                  75                  80
Glu Lys Phe Lys Gly Arg Val Thr Ile Thr Ala Asp Lys Ser Thr Ser
                85                  90                  95
Thr Ala Tyr Met Glu Leu Ser Ser Leu Arg Ser Glu Asp Thr Ala Val
```

```
            100                 105                 110
Tyr Tyr Cys Ala Arg Ser Ile Tyr Tyr Asp Ala Pro Phe Ala Tyr
            115                 120                 125

Trp Gly Gln Gly Thr Leu Val Thr Val Ser Ser
130                 135
```

<210> SEQ ID NO 314
<211> LENGTH: 107
<212> TYPE: PRT
<213> ORGANISM: Mus musculus

<400> SEQUENCE: 314

```
Asp Ile Gln Met Thr Gln Thr Thr Ser Ser Leu Ser Ala Ser Leu Gly
1               5                   10                  15

Asp Arg Val Asn Ile Ser Cys Arg Ala Ser Gln Asp Ile Ser Ser Tyr
            20                  25                  30

Leu Asn Trp Tyr Gln Gln Lys Pro Asp Gly Thr Val Lys Leu Leu Ile
        35                  40                  45

Tyr Ser Thr Ser Arg Leu Asn Ser Gly Val Pro Ser Arg Phe Ser Gly
    50                  55                  60

Ser Gly Ser Gly Thr Asp Tyr Ser Leu Thr Ile Ser Asn Leu Ala Gln
65                  70                  75                  80

Glu Asp Ile Ala Thr Tyr Phe Cys Gln Gln Asp Ile Lys His Pro Thr
                85                  90                  95

Phe Gly Gly Gly Thr Lys Leu Glu Leu Lys Arg
            100                 105
```

<210> SEQ ID NO 315
<211> LENGTH: 128
<212> TYPE: PRT
<213> ORGANISM: Mus musculus

<400> SEQUENCE: 315

```
Met Lys Ser Gln Thr Gln Val Phe Val Tyr Met Leu Leu Trp Leu Ser
1               5                   10                  15

Gly Val Glu Gly Asp Ile Val Met Thr Gln Ser His Lys Phe Met Ser
            20                  25                  30

Thr Ser Val Gly Asp Arg Val Thr Ile Thr Cys Lys Ala Ser Gln Asp
        35                  40                  45

Val Phe Thr Ala Val Ala Trp Tyr Gln Gln Lys Pro Gly Gln Ser Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Asp Tyr Phe Cys Gln Gln Tyr Ser
            100                 105                 110

Ser Tyr Pro Leu Thr Phe Gly Ala Gly Thr Lys Leu Glu Leu Lys Arg
        115                 120                 125
```

<210> SEQ ID NO 316
<211> LENGTH: 381
<212> TYPE: DNA
<213> ORGANISM: Mus musculus

<400> SEQUENCE: 316

```
atgaagtcac agacccaggt ctttgtatac atgttgctgt ggttgtctgg tgttgaagga    60
```

```
gacattgtga tgacccagtc tcacaaattc atgtccacgt cagtaggaga cagggtcacc    120
atcacctgca aggccagtca ggatgtcttt actgctgtag cctggtatca acagaaacca    180
ggacaatctc ctaaactact gatttactgg gcatccaccc ggcacactgg agtccctgat    240
cgcttcacag gcagtggatc tgggacagat ttcactctca ccattagcaa tgtgcagtct    300
gaagacttgg cagattattt ctgtcaacaa tatagcagct atcctctcac gttcggtgct    360
gggaccaagt tggagctgaa a                                              381
```

<210> SEQ ID NO 317
<211> LENGTH: 138
<212> TYPE: PRT
<213> ORGANISM: Mus musculus

<400> SEQUENCE: 317

```
Met Gly Trp Asn Trp Ile Ile Phe Phe Leu Met Ala Val Val Thr Gly
 1               5                  10                  15

Val Asn Ser Glu Val Gln Leu Gln Gln Ser Gly Ala Glu Leu Val Arg
            20                  25                  30

Pro Gly Ala Leu Val Lys Leu Ser Cys Lys Ala Ser Gly Phe Asn Ile
        35                  40                  45

Lys Asp Tyr Tyr Met His Trp Val Lys Gln Arg Pro Glu Gln Gly Leu
    50                  55                  60

Glu Trp Ile Gly Arg Ile Asp Pro Glu Asn Gly Asp Ile Ile Tyr Asp
65                  70                  75                  80

Pro Lys Phe Gln Gly Lys Ala Ser Ile Thr Thr Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Tyr Asp Ala Gly Asp Pro Ala Trp Phe Thr Tyr Trp
        115                 120                 125

Gly Gln Gly Thr Leu Val Thr Val Ser Ser
    130                 135
```

<210> SEQ ID NO 318
<211> LENGTH: 411
<212> TYPE: DNA
<213> ORGANISM: Mus musculus

<400> SEQUENCE: 318

```
atgggatgga actggatcat cttcttcctg atggcagtgg ttacaggggt caattcagag    60
gttcagctgc agcagtctgg ggctgagctt gtgaggccag gggcttagt caagttgtcc    120 tgcaaagctt ctggcttcaa tattaaagac tactatatgc actgggtgaa gcagaggcct    180
gaacagggcc tggagtggat tggaaggatt gatcctgaga atggtgatat tatatatgac    240
ccgaagttcc agggcaaggc cagtataaca acagacacat cctccaacac agcctacctg    300
cagctcagca gcctgacgtc tgaggacact gccgtctatt actgtgctta cgatgctggt    360
gaccccgcct ggtttactta ctggggccaa gggactctgg tcaccgtctc g            411
```

<210> SEQ ID NO 319
<211> LENGTH: 130
<212> TYPE: PRT
<213> ORGANISM: Artificial Sequence
<220> FEATURE:
<223> OTHER INFORMATION: Humanized antibody sequence

<400> SEQUENCE: 319

```
Met Asp Met Arg Val Pro Ala Gln Leu Leu Gly Leu Leu Leu Leu Trp
 1               5                  10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Val Phe Thr Ala Val Ala Trp Tyr Gln Gln Lys Pro Gly Lys
    50                  55                  60

Ala Pro Lys Leu Leu Ile Tyr Trp Ala Ser Thr Arg His Thr Gly Val
 65                 70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Ser Ser Tyr Pro Leu Thr Phe Gly Gly Gly Thr Lys Val Glu Ile
        115                 120                 125

Lys Arg
    130

<210> SEQ ID NO 320
<211> LENGTH: 390
<212> TYPE: DNA
<213> ORGANISM: Artificial Sequence
<220> FEATURE:
<223> OTHER INFORMATION: Humanized antibody sequence

<400> SEQUENCE: 320
atggatatgc gcgtgccggc gcagctgctg ggcctgctgc tgctgtggct gcgcggcgcg      60
cgctgcgata tccagatgac ccagagcccg agcagcctga gcgcgagcgt gggcgatcgc     120
gtgaccatta cctgcaaagc gagccaggat gtgtttaccg cggtggcgtg gtatcagcag     180
aaaccgggca aagcgccgaa actgctgatt tattgggcga gcacccgcca taccggcgtg     240
ccgagtcgct ttagcggcag cggcagcggc accgatttta ccctgaccat tagcagcctg     300
cagccggaag attttgcgac ctattattgc cagcagtata gcagctatcc gctgaccttt     360
ggcggcggca ccaaagtgga aattaaacgt                                       390

<210> SEQ ID NO 321
<211> LENGTH: 138
<212> TYPE: PRT
<213> ORGANISM: Artificial Sequence
<220> FEATURE:
<223> OTHER INFORMATION: Humanized antibody sequence

<400> SEQUENCE: 321

Met Asp Trp Thr Trp Ser Ile Leu Phe Leu Val Ala Ala Pro Thr Gly
 1               5                  10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Phe Asn Ile
        35                  40                  45

Lys Asp Tyr Tyr Met His Trp Val Arg Gln Ala Pro Gly Gln Gly Leu
    50                  55                  60

Glu Trp Ile Gly Arg Ile Asp Pro Glu Asn Gly Asp Ile Ile Tyr Asp
 65                 70                  75                  80

Pro Lys Phe Gln Gly Arg Val Thr Met Thr Thr Asp Thr Ser Thr Ser
                85                  90                  95
```

```
Thr Ala Tyr Met Glu Leu Arg Ser Leu Arg Ser Asp Asp Thr Ala Val
            100                 105                 110
Tyr Tyr Cys Ala Tyr Asp Ala Gly Asp Pro Ala Trp Phe Thr Tyr Trp
            115                 120                 125
Gly Gln Gly Thr Leu Val Thr Val Ser Ser
            130                 135

<210> SEQ ID NO 322
<211> LENGTH: 414
<212> TYPE: DNA
<213> ORGANISM: Artificial Sequence
<220> FEATURE:
<223> OTHER INFORMATION: Humanized antibody sequence

<400> SEQUENCE: 322
atggattgga cctggagcat tctgtttctg gtggcggcgc cgaccggcgc gcatagcgaa     60
gtgcagctgg tgcagagcgg cgcggaagtg aaaaaaccgg gcgcgagcgt gaaagtgagc    120
tgcaaagcga gcggctttaa cattaaagat tattatatgc attgggtgcg ccaggcgccg    180
ggccagggcc tggaatggat cggccgcatt gatccggaaa acggcgatat tatttatgat    240
ccgaaatttc agggccgcgt gaccatgacc accgatacca gcaccagcac cgcgtatatg    300
gaactgcgca gcctgcgcag cgatgatacc gcggtgtatt attgcgcgta tgatgcgggc    360
gatccggcgt ggtttaccta ttggggccag ggcaccctgg tgaccgtctc gagc          414

<210> SEQ ID NO 323
<211> LENGTH: 106
<212> TYPE: PRT
<213> ORGANISM: Mus musculus

<400> SEQUENCE: 323

Thr Asp Ala Ala Pro Thr Val Ser Ile Phe Pro Pro Ser Ser Glu Gln
  1               5                  10                  15
Leu Thr Ser Gly Gly Ala Ser Val Val Cys Phe Leu Asn Asn Phe Tyr
             20                  25                  30
Pro Lys Asp Ile Asn Val Lys Trp Lys Ile Asp Gly Ser Glu Arg Gln
         35                  40                  45
Asn Gly Val Leu Asn Ser Trp Thr Asp Gln Asp Ser Lys Asp Ser Thr
     50                  55                  60
Tyr Ser Met Ser Ser Thr Leu Thr Leu Thr Lys Asp Glu Tyr Glu Arg
 65                  70                  75                  80
His Asn Ser Tyr Thr Cys Glu Ala Thr His Lys Thr Ser Thr Ser Pro
                 85                  90                  95
Ile Val Lys Ser Phe Asn Arg Asn Glu Cys
            100                 105

<210> SEQ ID NO 324
<211> LENGTH: 324
<212> TYPE: PRT
<213> ORGANISM: Mus musculus

<400> SEQUENCE: 324

Ala Lys Thr Thr Pro Pro Ser Val Tyr Pro Leu Ala Pro Gly Ser Ala
  1               5                  10                  15
Ala Gln Thr Asn Ser Met Val Thr Leu Gly Cys Leu Val Lys Gly Tyr
             20                  25                  30
Phe Pro Glu Pro Val Thr Val Thr Trp Asn Ser Gly Ser Leu Ser Ser
         35                  40                  45
```

```
Gly Val His Thr Phe Pro Ala Val Leu Gln Ser Asp Leu Tyr Thr Leu
 50                  55                  60

Ser Ser Ser Val Thr Val Pro Ser Ser Thr Trp Pro Ser Glu Thr Val
 65                  70                  75                  80

Thr Cys Asn Val Ala His Pro Ala Ser Ser Thr Lys Val Asp Lys Lys
                 85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 325
<211> LENGTH: 106
<212> TYPE: PRT
<213> ORGANISM: Homo sapiens

<400> SEQUENCE: 325

Thr Val Ala Ala Pro Ser Val Phe Ile Phe Pro Pro Ser Asp Glu Gln
  1               5                  10                  15

Leu Lys Ser Gly Thr Ala Ser Val Val Cys Leu Leu Asn Asn Phe Tyr
             20                  25                  30

Pro Arg Glu Ala Lys Val Gln Trp Lys Val Asp Asn Ala Leu Gln Ser
         35                  40                  45

Gly Asn Ser Gln Glu Ser Val Thr Glu Gln Asp Ser Lys Asp Ser Thr
     50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95
```

```
Val Thr Lys Ser Phe Asn Arg Gly Glu Cys
            100                 105

<210> SEQ ID NO 326
<211> LENGTH: 327
<212> TYPE: PRT
<213> ORGANISM: Homo sapiens

<400> SEQUENCE: 326

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 327
<211> LENGTH: 120
<212> TYPE: PRT
<213> ORGANISM: Mus musculus
```

<400> SEQUENCE: 327

Glu Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Asp Tyr
            20                  25                  30

Ile Met His Trp Val Lys Gln Lys Pro Gly Gln Gly Leu Glu Trp Ile
        35                  40                  45

Gly Tyr Ile Asn Pro Tyr Asn Asp Asp Thr Glu Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Asp Leu Ser Ser Leu Thr Ser Glu Gly Ser Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser
            115                 120

<210> SEQ ID NO 328
<211> LENGTH: 120
<212> TYPE: PRT
<213> ORGANISM: Mus musculus

<400> SEQUENCE: 328

Glu Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Asp Tyr
            20                  25                  30

Ile Met His Trp Val Lys Gln Lys Pro Gly Gln Gly Leu Glu Trp Ile
        35                  40                  45

Gly Tyr Ile Asn Pro Tyr Asn Asp Asp Thr Glu Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Asp Leu Ser Ser Leu Thr Ser Glu Gly Ser Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser
            115                 120

<210> SEQ ID NO 329
<211> LENGTH: 120
<212> TYPE: PRT
<213> ORGANISM: Mus musculus

<400> SEQUENCE: 329

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Asp Thr Glu Tyr Asn Glu Lys Phe
    50                  55                  60

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser
        115                 120

<210> SEQ ID NO 330
<211> LENGTH: 226
<212> TYPE: PRT
<213> ORGANISM: Mus musculus

<400> SEQUENCE: 330

Glu Val Gln Leu Gln Gln Ser Gly Pro Glu Leu Val Lys Pro Gly Ala
  1               5                  10                  15

Ser Val Lys Met Ser Cys Lys Ala Ser Gly Phe Thr Phe Thr Asp Tyr
                 20                  25                  30

Ile Met His Trp Val Lys Gln Lys Pro Gly Gln Gly Leu Glu Trp Ile
             35                  40                  45

Gly Tyr Ile Asn Pro Tyr Asn Asp Asp Thr Glu Tyr Asn Glu Lys Phe
         50                  55                  60

Lys Gly Lys Ala Thr Leu Thr Ser Asp Lys Ser Ser Ser Thr Ala Tyr
 65                  70                  75                  80

Met Asp Leu Ser Ser Leu Thr Ser Glu Gly Ser Ala Val Tyr Tyr Cys
                 85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser Thr Val Ala Ala Pro Ser Val Phe
        115                 120                 125

Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220

Glu Cys
225

<210> SEQ ID NO 331
<211> LENGTH: 447
<212> TYPE: PRT
<213> ORGANISM: Mus musculus

<400> SEQUENCE: 331

Glu Val Gln Leu Val Gln Ser Gly Ala Glu Val Lys Lys Pro Gly Ser
  1               5                  10                  15

Ser Val Lys Val Ser Cys Lys Ala Ser Gly Phe Thr Phe Thr Asp Tyr
                 20                  25                  30
```

-continued

```
Ile Met His Trp Val Arg Gln Ala Pro Gly Gln Gly Leu Glu Trp Met
        35                  40                  45
Gly Tyr Ile Asn Pro Tyr Asn Asp Asp Thr Glu Tyr Asn Glu Lys Phe
    50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Ile Tyr Tyr Asp Ala Pro Phe Ala Tyr Trp Gly Gln Gly
                100                 105                 110
Gly Thr Leu Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Lys Thr Tyr Thr Cys Asn Val Asp His Lys
            195                 200                 205
Pro Ser Asn Thr Lys Val Asp Lys Arg Val Glu Ser Lys Tyr Gly Pro
210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
                260                 265                 270
Val Gln Phe Asn Trp Tyr Val Asp Gly Val Glu Val His Asn Ala Lys
            275                 280                 285
Thr Lys Pro Arg Glu Glu Gln Phe Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Gln Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
                420                 425                 430
His Asn His Tyr Thr Gln Lys Ser Leu Ser Leu Ser Leu Gly Lys
            435                 440                 445
```

<210> SEQ ID NO 332
<211> LENGTH: 107
<212> TYPE: PRT
<213> ORGANISM: Mus musculus

<400> SEQUENCE: 332

Asp Ile Gln Met Thr Gln Ile Thr Ser Ser Leu Ser Ala Ser Leu Gly
1               5                   10                  15

Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Phe Tyr Thr Ser Arg Leu Leu Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Leu Glu Ile Lys
            100                 105

<210> SEQ ID NO 333
<211> LENGTH: 324
<212> TYPE: PRT
<213> ORGANISM: Mus musculus

<400> SEQUENCE: 333

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val

```
                225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
                260                 265                 270

Pro Ile Met Asp Thr Asp Gly Ser Tyr Phe Ile Tyr Ser Lys Leu Asn
                275                 280                 285

Val Gln Lys Ser Asn Trp Glu Ala Gly Asn Thr Phe Thr Cys Ser Val
        290                 295                 300

Leu His Glu Gly Leu His Asn His His Thr Glu Lys Ser Leu Ser His
305                 310                 315                 320

Ser Pro Gly Lys

<210> SEQ ID NO 334
<211> LENGTH: 213
<212> TYPE: PRT
<213> ORGANISM: Mus musculus

<400> SEQUENCE: 334

Asp Ile Gln Met Thr Gln Thr Thr Ser Ser Leu Ser Ala Ser Leu Gly
1               5                   10                  15

Asp Arg Val Asn Ile Ser Cys Arg Ala Ser Gln Asp Ile Ser Ser Tyr
            20                  25                  30

Leu Asn Trp Tyr Gln Gln Lys Pro Asp Gly Thr Val Lys Leu Leu Ile
        35                  40                  45

Tyr Ser Thr Ser Arg Leu Asn Ser Gly Val Pro Ser Arg Phe Ser Gly
    50                  55                  60

Ser Gly Ser Gly Thr Asp Tyr Ser Leu Thr Ile Ser Asn Leu Ala Gln
65                  70                  75                  80

Glu Asp Ile Ala Thr Tyr Phe Cys Gln Gln Asp Ile Lys His Pro Thr
                85                  90                  95

Phe Gly Gly Gly Thr Lys Leu Glu Leu Lys Arg Thr Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 335
<211> LENGTH: 444
<212> TYPE: PRT
<213> ORGANISM: Mus musculus

<400> SEQUENCE: 335

Glu Val Gln Leu Gln Gln Ser Gly Pro Glu Leu Val Lys Pro Gly Ala
1               5                   10                  15
```

-continued

```
Ser Val Lys Met Ser Cys Lys Ala Ser Gly Phe Thr Phe Thr Asp Tyr
            20                  25                  30

Ile Met His Trp Val Lys Gln Lys Pro Gly Gln Gly Leu Glu Trp Ile
            35                  40                  45

Gly Tyr Ile Asn Pro Tyr Asn Asp Asp Thr Glu Tyr Asn Glu Lys Phe
        50                  55                  60

Lys Gly Lys Ala Thr Leu Thr Ser Asp Lys Ser Ser Thr Ala Tyr
 65                  70                  75                  80

Met Asp Leu Ser Ser Leu Thr Ser Glu Gly Ser Ala Val Tyr Tyr Cys
                85                  90                  95

Ala Arg Ser Ile Tyr Tyr Asp Ala Pro Phe Ala Tyr Trp Gly Gln
            100                 105                 110

Gly Thr Leu Val Thr Val Ser Ser Ala Lys Thr Thr Pro Pro Ser Val
            115                 120                 125

Tyr Pro Leu Ala Pro Gly Ser Ala Ala Gln Thr Asn Ser Met Val Thr
            130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
            165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
            195                 200                 205

Ser Ser Thr Lys Val Asp Lys Lys Ile Val Pro Arg Asp Cys Gly Cys
        210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
            245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
        290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
            325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
            355                 360                 365

Phe Phe Pro Glu Asp Ile Thr Val Glu Trp Gln Trp Asn Gly Gln Pro
        370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
            405                 410                 415

Gly Asn Thr Phe Thr Cys Ser Val Leu His Glu Gly Leu His Asn His
            420                 425                 430
```

His Thr Glu Lys Ser Leu Ser His Ser Pro Gly Lys
        435                 440

<210> SEQ ID NO 336
<211> LENGTH: 108
<212> TYPE: PRT
<213> ORGANISM: Mus musculus

<400> SEQUENCE: 336

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Phe Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gly Gly Thr Lys Val Glu Ile Lys Arg
            100                 105

<210> SEQ ID NO 337
<211> LENGTH: 324
<212> TYPE: DNA
<213> ORGANISM: Mus musculus

<400> SEQUENCE: 337
gatatccaga tgacccagag cccgagcagc ctgagcgcga gcgtgggcga tcgcgtgacc      60
attacctgca aagcgagcca ggatgtgttt accgcggtgg cgtggtatca gcagaaaccg     120
ggcaaagcgc cgaaactgct gatttattgg gcgagcaccc gccataccgg cgtgccgagt     180
cgctttagcg gcagcggcag cggcaccgat tttaccctga ccattagcag cctgcagccg     240
gaagattttg cgacctatta ttgccagcag tatagcagct atccgctgac ctttggcggc     300
ggcaccaaag tggaaattaa acgt                                            324

<210> SEQ ID NO 338
<211> LENGTH: 119
<212> TYPE: PRT
<213> ORGANISM: Mus musculus

<400> SEQUENCE: 338

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Glu Trp Ile
        35                  40                  45

Gly Arg Ile Asp Pro Glu Asn Gly Asp Ile Ile Tyr Asp Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Tyr Asp Ala Gly Asp Pro Ala Trp Phe Thr Tyr Trp Gly Gln Gly

```
                  100                 105                 110
Thr Leu Val Thr Val Ser Ser
        115

<210> SEQ ID NO 339
<211> LENGTH: 357
<212> TYPE: DNA
<213> ORGANISM: Mus musculus

<400> SEQUENCE: 339
gaagtgcagc tggtgcagag cggcgcggaa gtgaaaaaac cgggcgcgag cgtgaaagtg      60
agctgcaaag cgagcggctt taacattaaa gattattata tgcattgggt gcgccaggcg     120
ccgggccagg gcctggaatg gatcggccgc attgatccgg aaaacggcga tattatttat     180
gatccgaaat ttcagggccg cgtgaccatg accaccgata ccagcaccag caccgcgtat     240
atggaactgc gcagcctgcg cagcgatgat accgcggtgt attattgcgc gtatgatgcg     300
ggcgatccgg cgtggtttac ctattgggc caggggcaccc tggtgaccgt ctcgagc       357

<210> SEQ ID NO 340
<211> LENGTH: 1395
<212> TYPE: DNA
<213> ORGANISM: Mus musculus

<400> SEQUENCE: 340
atggactgga cctggaggat cctcttcttg gtggcagcag ccacaggagc ccactccgag      60
gtgcagctgg tgcagtctgg ggctgaggtg aagaagcctg gtcctcggt gaaggtctcc     120 tgcaaggctt ctggttttac cttcaccgac tatattatgc actgggtgcg tcaggcccct     180
ggtcaagggc ttgagtggat gggctatatc aaccctata atgatgacac cgaatacaac     240
gagaagttca agggccgtgt cacgattacc gcggacaaat ccacgagcac agcctacatg     300
gagctgagca gcctgcgctc tgaggacacg gccgtgtatt actgtgcgcg ttcgatttat     360
tactacgatg ccccgtttgc ttactggggc caagggactc tggtcaccgt ctctagtgcc     420
tccaccaagg gcccatcggt cttccccctg gcgccctgct ccaggagcac ctccgagagc     480
acagcggccc tgggctgcct ggtcaaggac tacttccccg aaccggtgac ggtgtcgtgg     540
aactcaggcg ctctgaccag cggcgtgcac accttcccag ctgtcctaca gtcctcagga     600
ctctactccc tcagcagcgt ggtgaccgtg ccctccagca cttcggcac ccagacctac     660 acctgcaacg tagatcacaa gcccagcaac accaaggtgg acaagacagt tgagcgcaaa     720
tgttgtgtcg agtgcccacc gtgcccagca ccacctgtgg caggaccgtc agtcttcctc     780
ttccccccaa aacccaagga caccctcatg atctcccgga cccctgaggt cacgtgcgtg     840
gtggtggacg tgagccacga agaccccgag gtccagttca ctggtacgt ggacggcgtg     900 gaggtgcata atgccaagac aaagccacgg gaggagcagt tcaacagcac gttccgtgtg     960
gtcagcgtcc tcaccgttgt gcaccaggac tggctgaacg gcaaggagta caagtgcaag    1020
gtctccaaca aaggcctccc agcccccatc gagaaaacca tctccaaaac caaagggcag    1080
ccccgagaac acaggtgta caccctgccc ccatcccggg aggagatgac caagaaccag    1140
gtcagcctga cctgcctggt caaaggcttc taccccagcg acatcgccgt ggagtgggag    1200
agcaatgggc agccggagaa caactacaag accacacctc ccatgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
```

```
ctgtctccgg gtaaa                                                      1395
```

<210> SEQ ID NO 341
<211> LENGTH: 213
<212> TYPE: PRT
<213> ORGANISM: Mus musculus

<400> SEQUENCE: 341

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Ser Tyr
             20                  25                  30

Leu Asn Trp Tyr Gln Gln Lys Pro Gly Lys Ala Pro Lys Leu Leu Ile
         35                  40                  45

Tyr Ser Thr Ser Arg Leu Asn Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Ile Lys His Pro Thr
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 342
<211> LENGTH: 639
<212> TYPE: DNA
<213> ORGANISM: Mus musculus

<400> SEQUENCE: 342

```
gacatccaga tgacccagtc tccatcctcc ctgtctgcat ctgtaggtga ccgtgtcacc    60
atcacttgcc gcgcaagtca ggatattagc agctatttaa attggtatca gcagaaacca   120
gggaaagccc ctaagctcct gatctattct acttcccgtt tgaatagtgg ggtcccatca   180
cgcttcagtg gcagtggctc tgggacagat ttcactctca ccatcagcag tctgcaacct   240
gaagattttg caacttacta ctgtcaacag gatattaaac accctacgtt cggtcaaggc   300
accaaggtgg agatcaaacg tacggtggct gcaccatctg tcttcatctt cccgccatct   360
gatgagcagt tgaaatctgg aactgcctct gttgtgtgcc tgctgaataa cttctatccc   420
agagaggcca agtacagtg gaaggtggat aacgccctcc aatcgggtaa ctcccaggag   480
agtgtcacag agcaggacag caaggacagc acctacagcc tcagcagcac cctgacgctg   540
agcaaagcag actacgagaa acacaaagtc tacgcctgcg aagtcaccca tcagggcctg   600
```
agctcgcccg tcacaaagag cttcaacagg ggagagtgt                                  639

<210> SEQ ID NO 343
<211> LENGTH: 235
<212> TYPE: PRT
<213> ORGANISM: Mus musculus

<400> SEQUENCE: 343

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Ser Ser Tyr Leu Asn Trp Tyr Gln Gln Lys Pro Gly Lys
    50                  55                  60

Ala Pro Lys Leu Leu Ile Tyr Ser Thr Ser Arg Leu Asn Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Asp Ile Lys His Pro Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 344
<211> LENGTH: 705
<212> TYPE: DNA
<213> ORGANISM: Mus musculus

<400> SEQUENCE: 344
atggacatga gggtgcccgc tcagctcctg gggctcctgc tgctgtggct gagaggtgcc       60
agatgtgaca tccagatgac ccagtctcca tcctccctgt ctgcatctgt aggtgaccgt      120
gtcaccatca cttgccgcgc aagtcaggat attagcagct atttaaattg gtatcagcag      180
aaaccaggga agcccctaa gctcctgatc tattctactt cccgtttgaa tagtggggtc       240
ccatcacgct tcagtggcag tggctctggg acagatttca ctctcaccat cagcagtctg      300
caacctgaag attttgcaac ttactactgt caacaggata ttaaacaccc tacgttcggt      360
caaggcacca aggtggagat caaacgtacg gtggctgcac catctgtctt catcttcccg      420
ccatctgatg agcagttgaa atctggaact gcctctgttg tgtgcctgct gaataacttc      480

```
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca aagcagacta cgagaaacac aaagtctacg cctgcgaagt cacccatcag    660
ggcctgagct cgcccgtcac aaagagcttc aacaggggag agtgt                     705
```

<210> SEQ ID NO 345
<211> LENGTH: 446
<212> TYPE: PRT
<213> ORGANISM: Mus musculus
<400> SEQUENCE: 345

```
Glu Val Gln Leu Val Gln Ser Gly Ala Glu Val Lys Lys Pro Gly Ser
 1               5                  10                  15

Ser Val Lys Val Ser Cys Lys Ala Ser Gly Phe Thr Phe Thr Asp Tyr
             20                  25                  30

Ile Met His Trp Val Arg Gln Ala Pro Gly Gln Gly Leu Glu Trp Met
         35                  40                  45

Gly Tyr Ile Asn Pro Tyr Asn Asp Asp Thr Glu Tyr Asn Glu Lys Phe
     50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Tyr Asp Ala Pro Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335
```

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 346
<211> LENGTH: 1338
<212> TYPE: DNA
<213> ORGANISM: Mus musculus

<400> SEQUENCE: 346
gaggtgcagc tggtgcagtc tggggctgag gtgaagaagc ctgggtcctc ggtgaaggtc    60
tcctgcaagg cttctggttt taccttcacc gactatatta tgcactgggt gcgtcaggcc   120
cctggtcaag gcttgagtg gatgggctat atcaacccctt ataatgatga caccgaatac   180
aacgagaagt tcaagggccg tgtcacgatt accgcggaca atccacgag cacagcctac   240
atggagctga gcagcctgcg ctctgaggac acggccgtgt attactgtgc gcgttcgatt   300
tattactacg atgccccgtt tgcttactgg ggccaaggga ctctggtcac cgtctctagt   360
gcctccacca agggcccatc ggtcttcccc ctggcgccct gctccaggag cacctccgag   420
agcacagcgg ccctgggctg cctggtcaag gactacttcc ccgaaccggt gacggtgtcg   480
tggaactcag cgctctgac cagcggcgtg cacaccttcc cagctgtcct acagtcctca   540
ggactctact ccctcagcag cgtggtgacc gtgcctcca gcaacttcgg cacccagacc   600
tacacctgca acgtagatca caagcccagc aacaccaagg tggacaagac agttgagcgc   660
aaatgttgtg tcgagtgccc accgtgccca gcaccacctg tggcaggacc gtcagtcttc   720
ctcttccccc caaaacccaa ggacaccctc atgatctccc ggaccctga ggtcacgtgc   780
gtggtggtgg acgtgagcca cgaagacccc gaggtccagt tcaactggta cgtggacggc   840
gtggaggtgc ataatgccaa gacaaagcca cgggaggagc agttcaacag cacgttccgt   900
gtggtcagcg tcctcaccgt tgtgcaccag gactggctga acggcaagga gtacaagtgc   960
aaggtctcca acaaaggcct cccagccccc atcgagaaaa ccatctccaa aaccaaaggg  1020
cagccccgag aaccacaggt gtacaccctg cccccatccc gggaggagat gaccaagaac  1080
caggtcagcc tgacctgcct ggtcaaaggc ttctacccca gcgacatcgc cgtggagtgg  1140
gagagcaatg gcagccggaa gaacaactac aagaccacac tcccatgctg gactccgac   1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tccctgtctc cgggtaaa                                                 1338

<210> SEQ ID NO 347
<211> LENGTH: 465

<212> TYPE: PRT
<213> ORGANISM: Mus musculus

<400> SEQUENCE: 347

```
Met Asp Trp Thr Trp Arg Ile Leu Phe Leu Val Ala Ala Ala Thr Gly
1               5                   10                  15

Ala His Ser Glu Val Gln Leu Val Gln Ser Gly Ala Glu Val Lys Lys
            20                  25                  30

Pro Gly Ser Ser Val Lys Val Ser Cys Lys Ala Ser Gly Phe Thr Phe
        35                  40                  45

Thr Asp Tyr Ile Met His Trp Val Arg Gln Ala Pro Gly Gln Gly Leu
    50                  55                  60

Glu Trp Met Gly Tyr Ile Asn Pro Tyr Asn Asp Asp Thr Glu Tyr Asn
65                  70                  75                  80

Glu Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Ile Tyr Tyr Asp Ala Pro Phe Ala Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400
```

```
Ser Asn Gly Gln Pro Glu Asn Asn Tyr Lys Thr Thr Pro Pro Met Leu
            405                 410                 415

Asp Ser Asp Gly Ser Phe Phe Leu Tyr Ser Lys Leu Thr Val Asp Lys
        420                 425                 430

Ser Arg Trp Gln Gln Gly Asn Val Phe Ser Cys Ser Val Met His Glu
    435                 440                 445

Ala Leu His Asn His Tyr Thr Gln Lys Ser Leu Ser Leu Ser Pro Gly
        450                 455                 460

Lys
465

<210> SEQ ID NO 348
<211> LENGTH: 1395
<212> TYPE: DNA
<213> ORGANISM: Mus musculus

<400> SEQUENCE: 348
atggactgga cctggaggat cctcttcttg gtggcagcag ccacaggagc ccactccgag      60
gtgcagctgg tgcagtctgg ggctgaggtg aagaagcctg gtcctcggt gaaggtctcc     120 tgcaaggctt ctggttttac cttcaccgac tatattatgc actgggtgcg tcaggcccct     180
ggtcaagggc ttgagtggat gggctatatc aacccttata atgatgacac cgaatacaac     240
gagaagttca agggccgtgt cacgattacc gcggacaaat ccacgagcac agcctacatg     300
gagctgagca gcctgcgctc tgaggacacg gccgtgtatt actgtgcgcg ttcgatttat     360
tactacgatg ccccgtttgc ttactggggc caagggactc tggtcaccgt ctctagtgcc     420
tccaccaagg gcccatcggt cttccccctg gcgccctgct ccaggagcac ctccgagagc     480
acagcggccc tgggctgcct ggtcaaggac tacttccccg aaccggtgac ggtgtcgtgg     540
aactcaggcg ctctgaccag cggcgtgcac accttcccag ctgtcctaca gtcctcagga     600
ctctactccc tcagcagcgt ggtgaccgtg ccctccagca cttcggcac ccagacctac      660 acctgcaacg tagatcacaa gcccagcaac accaaggtgg acaagacagt tgagcgcaaa     720
tgttgtgtcg agtgcccacc gtgcccagca ccacctgtgg caggaccgtc agtcttcctc     780
ttccccccaa aacccaagga caccctcatg atctcccgga cccctgaggt cacgtgcgtg     840
gtggtggacg tgagccacga agaccccgag gtccagttca actggtacgt ggacggcgtg     900
gaggtgcata atgccaagac aaagccacgg gaggagcagt tcaacagcac gttccgtgtg     960
gtcagcgtcc tcaccgttgt gcaccaggac tggctgaacg gcaaggagta caagtgcaag    1020
gtctccaaca aaggcctccc agcccccatc gagaaaacca tctccaaaac caagggcag    1080 ccccgagaac acaggtgta cccctgcccc catcccggg aggagatgac caagaaccag      1140
gtcagcctga cctgcctggt caaaggcttc taccccagcg acatcgccgt ggagtgggag    1200
agcaatgggc agccggagaa caactacaag accacacctc ccatgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaa                                                     1395

<210> SEQ ID NO 349
<211> LENGTH: 417
<212> TYPE: DNA
<213> ORGANISM: Mus musculus

<400> SEQUENCE: 349
```

```
atggaatgga tctggatatt tctcttcctc ctgtcaggaa ctgcaggtgt ccactctgag      60
gtgcagctgg tgcagtctgg ggctgaggtg aagaagcctg gtcctcggt gaaggtctcc     120 tgcaaggctt ctggttttac cttcaccgac tatattatgc actgggtgcg tcaggccct     180 ggtcaaggc ttgagtggat ggctatatc aacccttata atgatgacac cgaatacaac     240
gagaagttca aggccgtgt cacgattacc gcggacaaat ccacgagcac agcctacatg     300
gagctgagca gcctgcgctc tgaggacacg gccgtgtatt actgtgcgcg ttcgatttat     360
tactacgatg ccccgtttgc ttactggggc caagggactc tggtcacagt ctcgagc       417
```

<210> SEQ ID NO 350
<211> LENGTH: 218
<212> TYPE: PRT
<213> ORGANISM: Mus musculus

<400> SEQUENCE: 350

```
Asp Ile Val Leu Thr Gln Ser Pro Ala Ser Leu Ala Val Ser Leu Gly
 1               5                  10                  15

Gln Arg Ala Thr Ile Ala Cys Lys Ala Ser Gln Ser Val Asp Tyr Asp
            20                  25                  30

Gly Thr Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Glu Ile Pro Ala
    50                  55                  60

Arg Phe Ser Gly Thr Gly Ser Gly Thr Asp Phe Thr Leu Asn Ile His
65                  70                  75                  80

Pro Val Glu Glu Glu Asp Ile Thr Thr Tyr Tyr Cys Gln Gln Ser Asn
                85                  90                  95

Glu Asp Pro Phe Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

<210> SEQ ID NO 351
<211> LENGTH: 15
<212> TYPE: PRT
<213> ORGANISM: Mus musculus

<400> SEQUENCE: 351

```
Lys Ala Ser Gln Ser Val Asp Tyr Asp Gly Thr Ser Tyr Met Asn
 1               5                  10                  15
```

<210> SEQ ID NO 352
<211> LENGTH: 7

```
<212> TYPE: PRT
<213> ORGANISM: Mus musculus

<400> SEQUENCE: 352

Ala Ala Ser Asn Leu Glu Ser
 1               5

<210> SEQ ID NO 353
<211> LENGTH: 9
<212> TYPE: PRT
<213> ORGANISM: Mus musculus

<400> SEQUENCE: 353

Gln Gln Ser Asn Glu Asp Pro Phe Thr
 1               5

<210> SEQ ID NO 354
<211> LENGTH: 657
<212> TYPE: DNA
<213> ORGANISM: Mus musculus

<400> SEQUENCE: 354
gacattgtgt tgacccagtc tccagcttct ttggctgtgt ctctagggca gagggccacc     60
atcgcctgca aggccagcca agtgttgat tatgatggta ctagttatat gaattggtac    120
caacagaaac caggacagcc acccaaactc ctcatctatg ctgcatccaa tctagaatct    180
gagatcccag ccaggtttag tggcactggg tctgggacag acttcaccct caacatccat    240
cctgtggagg aggaggatat cacaacctat tactgtcagc aaagtaatga ggatccgttc    300
acgttcggag gggggaccaa gttggaaata aaacgggctg atgctgcacc aactgtatcc    360
atcttcccac catccagtga gcagttaaca tctggaggtg cctcagtcgt gtgcttcttg    420
aacaacttct accccaaaga catcaatgtc aagtggaaga ttgatggcag tgaacgacaa    480
aatggcgtcc tgaacagttg gactgatcag gacagcaaag acagcaccta cagcatgagc    540
agcaccctca cgttgaccaa ggacgagtat gaacgacata cagctatac ctgtgaggcc     600 actcacaaga catcaacttc acccattgtc aagagcttca caggaatga gtgttag       657

<210> SEQ ID NO 355
<211> LENGTH: 238
<212> TYPE: PRT
<213> ORGANISM: Mus musculus

<400> SEQUENCE: 355

Met Glu Thr Asp Thr Ile Leu Leu Trp Val Leu Leu Leu Trp Val Pro
 1               5                  10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ala Cys Lys Ala Ser Gln Ser
            35                  40                  45

Val Asp Tyr Asp Gly Thr Ser Tyr Met Asn Trp Tyr Gln Gln Lys Pro
        50                  55                  60

Gly Gln Pro Pro Lys Leu Leu Ile Tyr Ala Ala Ser Asn Leu Glu Ser
 65                  70                  75                  80

Glu Ile Pro Ala Arg Phe Ser Gly Thr Gly Ser Gly Thr Asp Phe Thr
                85                  90                  95

Leu Asn Ile His Pro Val Glu Glu Glu Asp Ile Thr Thr Tyr Tyr Cys
                100                 105                 110

Gln Gln Ser Asn Glu Asp Pro Phe Thr Phe Gly Gly Gly Thr Lys Leu
```

```
                115                 120                 125
Glu Ile Lys Arg Ala Asp Ala Pro Thr Val Ser Ile Phe Pro Pro
            130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
                195                 200                 205

Glu Tyr Glu Arg His Asn Ser Tyr Thr Cys Glu Ala Thr His Lys Thr
            210                 215                 220

Ser Thr Ser Pro Ile Val Lys Ser Phe Asn Arg Asn Glu Cys
225                 230                 235

<210> SEQ ID NO 356
<211> LENGTH: 717
<212> TYPE: DNA
<213> ORGANISM: Mus musculus

<400> SEQUENCE: 356
atggagacag acacaatcct gctatgggtg ctgctgctct gggttccagg ctccactggt    60
gacattgtgt tgacccagtc tccagcttct ttggctgtgt ctctagggca gagggccacc   120
atcgcctgca aggccagcca aagtgttgat tatgatggta ctagttatat gaattggtac   180
caacagaaac caggacagcc acccaaactc ctcatctatg ctgcatccaa tctagaatct   240
gagatcccag ccaggtttag tggcactggg tctgggacag acttcaccct caacatccat   300
cctgtggagg aggaggatat acaacctat tactgtcagc aaagtaatga ggatccgttc   360
acgttcggag gggggaccaa gttggaaata aaacgggctg atgctgcacc aactgtatcc   420
atcttcccac catccagtga gcagttaaca tctggaggtg cctcagtcgt gtgcttcttg   480
aacaacttct accccaaaga catcaatgtc aagtggaaga ttgatggcag tgaacgacaa   540
aatggcgtcc tgaacagttg gactgatcag gacagcaaag acagcaccta cagcatgagc   600
agcaccctca cgttgaccaa ggacgagtat gaacgacata cagctatac ctgtgaggcc    660 actcacaaga catcaacttc acccattgtc aagagcttca caggaatga gtgttag       717

<210> SEQ ID NO 357
<211> LENGTH: 442
<212> TYPE: PRT
<213> ORGANISM: Mus musculus

<400> SEQUENCE: 357

Gln Val Gln Leu Gln Gln Pro Gly Thr Glu Leu Val Arg Pro Gly Thr
1               5                   10                  15

Ser Val Lys Leu Ser Cys Lys Ala Ser Gly Tyr Ile Phe Thr Thr Tyr
            20                  25                  30

Trp Met Asn Trp Val Lys Gln Arg Pro Gly Gln Gly Leu Glu Trp Ile
        35                  40                  45

Gly Met Ile His Pro Ser Ala Ser Glu Ile Arg Leu Asp Gln Lys Phe
    50                  55                  60

Lys Asp Lys Ala Thr Leu Thr Leu Asp Lys Ser Ser Ser Thr Ala Tyr
65                  70                  75                  80

Met His Leu Ser Gly Pro Thr Ser Val Asp Ser Ala Val Tyr Tyr Cys
```

```
                85                  90                  95
Ala Arg Ser Gly Glu Trp Gly Ser Met Asp Tyr Trp Gly Gln Gly Thr
            100                 105                 110

Ser Val Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Ile Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
        435                 440

<210> SEQ ID NO 358
<211> LENGTH: 5
<212> TYPE: PRT
<213> ORGANISM: Mus musculus

<400> SEQUENCE: 358

Thr Tyr Trp Met Asn
 1               5
```

<210> SEQ ID NO 359
<211> LENGTH: 17
<212> TYPE: PRT
<213> ORGANISM: Mus musculus

<400> SEQUENCE: 359

Met Ile His Pro Ser Ala Ser Glu Ile Arg Leu Asp Gln Lys Phe Lys
 1               5                  10                  15

Asp

<210> SEQ ID NO 360
<211> LENGTH: 9
<212> TYPE: PRT
<213> ORGANISM: Mus musculus

<400> SEQUENCE: 360

Ser Gly Glu Trp Gly Ser Met Asp Tyr
 1               5

<210> SEQ ID NO 361
<211> LENGTH: 1329
<212> TYPE: DNA
<213> ORGANISM: Mus musculus

<400> SEQUENCE: 361

| | |
|---|---:|
| caggtccaac tacagcagcc tgggactgag ctggtgaggc tggaacttc agtgaagttg | 60 |
| tcctgtaagg cttctggcta catcttcacc acctactgga tgaactgggt gaaacagagg | 120 |
| cctggacaag gccttgagtg gattggcatg attcatcctt ccgcaagtga aattaggttg | 180 |
| gatcagaaat tcaaggacaa ggccacattg actcttgaca atcctccag cacagcctat | 240 |
| atgcacctca gcggcccgac atctgtggat tctgcggtct attactgtgc aagatcaggg | 300 |
| gaatgggggt ctatggacta ctggggtcaa ggaacctcag tcaccgtctc ctcagccaaa | 360 |
| acgacacccc catctgtcta tccactggcc cctggatctg ctgcccaaac taactccatg | 420 |
| gtgaccctgg gatgcctggt caagggctat ttccctgagc cagtgacagt gacctggaac | 480 |
| tctggatccc tgtccagcgg tgtgcacacc ttcccagctg tcctgcagtc tgacctctac | 540 |
| actctgagca gctcagtgac tgtcccctcc agcacctggc ccagcgagac cgtcacctgc | 600 |
| aacgttgccc acccggccag cagcaccaag gtggacaaga aaattgtgcc cagggattgt | 660 |
| ggttgtaagc cttgcatatg tacagtccca gaagtatcat ctgtcttcat cttcccccca | 720 |
| aagcccaagg atgtgctcac cattactctg actcctaagg tcacgtgtgt tgtggtagac | 780 |
| atcagcaagg atgatcccga ggtccagttc agctggtttg tagatgatgt ggaggtgcac | 840 |
| acagctcaga cgcaaccccg ggaggagcag ttcaacagca ctttccgctc agtcagtgaa | 900 |
| cttcccatca tgcaccagga ctggctcaat ggcaaggagt tcaaatgcag ggtcaacagt | 960 |
| gcagctttcc ctgcccccat cgagaaaacc atctccaaaa ccaaaggcag accgaaggct | 1020 |
| ccacaggtgt acaccattcc acctcccaag gagcagatgg ccaaggataa agtcagtctg | 1080 |
| acctgcatga taacagactt cttccctgaa gacattactg tggagtggca gtggaatggg | 1140 |
| cagccagcgg agaactacaa gaacactcag cccatcatgg acacagatgg ctcttacttc | 1200 |
| atctacagca agctcaatgt gcagaagagc aactgggagg caggaaatac tttcacctgc | 1260 |
| tctgtgttac atgagggcct gcacaaccac catactgaga agagcctctc ccactctcct | 1320 |
| ggtaaatga | 1329 |

<210> SEQ ID NO 362
<211> LENGTH: 461
<212> TYPE: PRT
<213> ORGANISM: Mus musculus

<400> SEQUENCE: 362

```
Met Gly Trp Ser Ser Ile Ile Leu Phe Leu Val Ala Thr Ala Thr Gly
 1               5                  10                  15

Val His Ser Gln Val Gln Leu Gln Gln Pro Gly Thr Glu Leu Val Arg
            20                  25                  30

Pro Gly Thr Ser Val Lys Leu Ser Cys Lys Ala Ser Gly Tyr Ile Phe
        35                  40                  45

Thr Thr Tyr Trp Met Asn Trp Val Lys Gln Arg Pro Gly Gln Gly Leu
    50                  55                  60

Glu Trp Ile Gly Met Ile His Pro Ser Ala Glu Ile Arg Leu Asp
65                  70                  75                  80

Gln Lys Phe Lys Asp Lys Ala Thr Leu Thr Leu Asp Lys Ser Ser Ser
                85                  90                  95

Thr Ala Tyr Met His Leu Ser Gly Pro Thr Ser Val Asp Ser Ala Val
            100                 105                 110

Tyr Tyr Cys Ala Arg Ser Gly Glu Trp Gly Ser Met Asp Tyr Trp Gly
        115                 120                 125

Gln Gly Thr Ser Val Thr Val Ser Ser Ala Lys Thr Thr Pro Pro Ser
    130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Pro
        195                 200                 205

Ser Ser Thr Trp Pro Ser Glu Thr Val Thr Cys Asn Val Ala His Pro
    210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Pro Glu Val Gln
        275                 280                 285

Phe Ser Trp Phe Val Asp Asp Val Glu Val His Thr Ala Gln Thr Gln
    290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
        355                 360                 365

Lys Glu Gln Met Ala Lys Asp Lys Val Ser Leu Thr Cys Met Ile Thr
    370                 375                 380
```

| Asp | Phe | Phe | Pro | Glu | Asp | Ile | Thr | Val | Glu | Trp | Gln | Trp | Asn | Gly | Gln |
|---|---|---|---|---|---|---|---|---|---|---|---|---|---|---|---|
| 385 | | | | 390 | | | | 395 | | | | 400 | | | |

| Pro | Ala | Glu | Asn | Tyr | Lys | Asn | Thr | Gln | Pro | Ile | Met | Asp | Thr | Asp | Gly |
|---|---|---|---|---|---|---|---|---|---|---|---|---|---|---|---|
| | | | | 405 | | | | 410 | | | | | 415 | | |

| Ser | Tyr | Phe | Ile | Tyr | Ser | Lys | Leu | Asn | Val | Gln | Lys | Ser | Asn | Trp | Glu |
|---|---|---|---|---|---|---|---|---|---|---|---|---|---|---|---|
| | | | 420 | | | | 425 | | | | 430 | | | | |

| Ala | Gly | Asn | Thr | Phe | Thr | Cys | Ser | Val | Leu | His | Glu | Gly | Leu | His | Asn |
|---|---|---|---|---|---|---|---|---|---|---|---|---|---|---|---|
| | | 435 | | | | 440 | | | | 445 | | | | | |

| His | His | Thr | Glu | Lys | Ser | Leu | Ser | His | Ser | Pro | Gly | Lys |
|---|---|---|---|---|---|---|---|---|---|---|---|---|
| 450 | | | | | 455 | | | | 460 | | | |

<210> SEQ ID NO 363
<211> LENGTH: 1386
<212> TYPE: DNA
<213> ORGANISM: Mus musculus

<400> SEQUENCE: 363

```
atgggatgga gctctatcat cctcttcttg gtagcaacag ctacaggtgt ccactcccag      60
gtccaactac agcagcctgg gactgagctg gtgaggcctg gaacttcagt gaagttgtcc     120
tgtaaggctt ctggctacat cttcaccacc tactggatga actgggtgaa acagaggcct     180
ggacaaggcc ttgagtggat tggcatgatt catccttccg caagtgaaat taggttggat     240
cagaaattca aggacaaggc cacattgact cttgacaaat cctccagcac agcctatatg     300
cacctcagcg gcccgacatc tgtggattct gcggtctatt actgtgcaag atcaggggaa     360
tgggggtcta tggactactg gggtcaagga acctcagtca ccgtctcctc agccaaaacg     420
acacccccat ctgtctatcc actggcccct ggatctgctg cccaaactaa ctccatggtg     480
accctggat gcctggtcaa gggctatttc cctgagccag tgacagtgac ctggaactct     540
ggatccctgt ccagcggtgt gcacaccttc cagctgtcc tgcagtctga cctctacact     600
ctgagcagct cagtgactgt cccctccagc acctggccca cgagaccgt cacctgcaac     660
gttgcccacc cggccagcag caccaaggtg gacaagaaaa ttgtgcccag ggattgtggt     720
tgtaagcctt gcatatgtac agtcccagaa gtatcatctg tcttcatctt ccccccaaag     780
cccaaggatg tgctcaccat tactctgact cctaaggtca cgtgtgttgt ggtagacatc     840
agcaaggatg atcccgaggt ccagttcagc tggtttgtag atgatgtgga ggtgcacaca     900
gctcagacgc aaccccggga ggagcagttc aacagcactt tccgctcagt cagtgaactt     960
cccatcatgc accaggactg gctcaatggc aaggagttca aatgcagggt caacagtgca    1020
gctttccctg cccccatcga gaaaaccatc tccaaaacca aggcagacc gaaggctcca    1080
caggtgtaca ccattccacc tcccaaggag cagatggcca aggataaagt cagtctgacc    1140
tgcatgataa cagacttctt ccctgaagac attactgtgg agtggcagtg gaatgggcag    1200
ccagcggaga actacaagaa cactcagccc atcatggaca cagatggctc ttacttcatc    1260
tacagcaagc tcaatgtgca gaagagcaac tgggaggcag gaaatacttt cacctgctct    1320
gtgttacatg agggcctgca caaccaccat actgagaaga gcctctccca ctctcctggt    1380
aaatga                                                              1386
```

<210> SEQ ID NO 364
<211> LENGTH: 106
<212> TYPE: PRT
<213> ORGANISM: Mus musculus

<400> SEQUENCE: 364

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Ser Tyr
             20                  25                  30

Leu Asn Trp Tyr Gln Gln Lys Pro Gly Lys Ala Pro Lys Leu Leu Ile
         35                  40                  45

Tyr Ser Thr Ser Arg Leu Asn Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Ile Lys His Pro Thr
             85                  90                  95

Phe Gly Gln Gly Thr Lys Val Glu Ile Lys
            100                 105
```

<210> SEQ ID NO 365
<211> LENGTH: 318
<212> TYPE: DNA
<213> ORGANISM: Mus musculus

<400> SEQUENCE: 365

```
gacatccaga tgacccagtc tccatcctcc ctgtctgcat ctgtaggtga ccgtgtcacc    60
atcacttgcc gcgcaagtca ggatattagc agctatttaa attggtatca gcagaaacca   120
gggaaagccc ctaagctcct gatctattct acttcccgtt tgaatagtgg ggtcccatca   180
cgcttcagtg gcagtggctc tgggacagat ttcactctca ccatcagcag tctgcaacct   240
gaagattttg caacttacta ctgtcaacag gatattaaac accctacgtt cggtcaaggc   300
accaaggtgg agatcaaa                                                 318
```

<210> SEQ ID NO 366
<211> LENGTH: 120
<212> TYPE: PRT
<213> ORGANISM: Mus musculus

<400> SEQUENCE: 366

```
Glu Val Gln Leu Val Gln Ser Gly Ala Glu Val Lys Lys Pro Gly Ser
  1               5                  10                  15

Ser Val Lys Val Ser Cys Lys Ala Ser Gly Phe Thr Phe Thr Asp Tyr
             20                  25                  30

Ile Met His Trp Val Arg Gln Ala Pro Gly Gln Gly Leu Glu Trp Met
         35                  40                  45

Gly Tyr Ile Asn Pro Tyr Asn Asp Asp Thr Glu Tyr Asn Glu Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser
            115                 120
```

<210> SEQ ID NO 367
<211> LENGTH: 360
<212> TYPE: DNA
<213> ORGANISM: Mus musculus

<400> SEQUENCE: 367

```
gaggtgcagc tggtgcagtc tggggctgag gtgaagaagc ctgggtcctc ggtgaaggtc    60
tcctgcaagg cttctggttt taccttcacc gactatatta tgcactgggt gcgtcaggcc   120
cctggtcaag gcttgagtg gatgggctat atcaaccctt ataatgatga caccgaatac   180
aacgagaagt tcaagggccg tgtcacgatt accgcggaca aatccacgag cacagcctac   240
atggagctga gcagcctgcg ctctgaggac acggccgtgt attactgtgc gcgttcgatt   300
tattactacg atgccccgtt tgcttactgg ggccaaggga ctctggtcac cgtctctagt   360
```

<210> SEQ ID NO 368
<211> LENGTH: 108
<212> TYPE: PRT
<213> ORGANISM: Mus musculus

<400> SEQUENCE: 368

```
Asp Ile Gln Met Thr Gln Ser Pro Ser Ser Leu Ser Ala Ser Val Gly
 1               5                  10                  15
Asp Arg Val Thr Ile Thr Cys Lys Ala Ser Gln Asp Val Phe Thr Ala
            20                  25                  30
Val Ala Trp Tyr Gln Gln Lys Pro Gly Lys Ala Pro Lys Leu Leu Ile
        35                  40                  45
Tyr Trp Ala Ser Thr Arg His Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Ser Tyr Pro Leu
                85                  90                  95
Thr Phe Gly Gly Gly Thr Lys Val Glu Ile Lys Arg
            100                 105
```

<210> SEQ ID NO 369
<211> LENGTH: 324
<212> TYPE: DNA
<213> ORGANISM: Mus musculus

<400> SEQUENCE: 369

```
gatatccaga tgacccagag cccgagcagc ctgagcgcga gcgtgggcga tcgcgtgacc    60
attacctgca aagcgagcca ggatgtgttt accgcggtgg cgtggtatca gcagaaaccg   120
ggcaaagcgc cgaaactgct gatttattgg gcgagcaccc gccataccgg cgtgccgagt   180
cgctttagcg gcagcggcag cggcaccgat tttaccctga ccattagcag cctgcagccg   240
gaagattttg cgacctatta ttgccagcag tatagcagct atccgctgac ctttggcggc   300
ggcaccaaag tggaaattaa acgt                                          324
```

<210> SEQ ID NO 370
<211> LENGTH: 119
<212> TYPE: PRT
<213> ORGANISM: Mus musculus

<400> SEQUENCE: 370

```
Glu Val Gln Leu Val Gln Ser Gly Ala Glu Val Lys Lys Pro Gly Ala
 1               5                  10                  15
Ser Val Lys Val Ser Cys Lys Ala Ser Gly Phe Asn Ile Lys Asp Tyr
            20                  25                  30
Tyr Met His Trp Val Arg Gln Ala Pro Gly Gln Gly Leu Glu Trp Ile
        35                  40                  45
```

```
Gly Arg Ile Asp Pro Glu Asn Gly Asp Ile Ile Tyr Asp Pro Lys Phe
        50                   55                  60

Gln Gly Arg Val Thr Met Thr Thr Asp Thr Ser Thr Ser Thr Ala Tyr
 65                   70                  75                  80

Met Glu Leu Arg Ser Leu Arg Ser Asp Asp Thr Ala Val Tyr Tyr Cys
                 85                  90                  95

Ala Tyr Asp Ala Gly Asp Pro Ala Trp Phe Thr Tyr Trp Gly Gln Gly
            100                 105                 110

Thr Leu Val Thr Val Ser Ser
        115
```

<210> SEQ ID NO 371
<211> LENGTH: 357
<212> TYPE: DNA
<213> ORGANISM: Mus musculus

<400> SEQUENCE: 371

```
gaagtgcagc tggtgcagag cggcgcggaa gtgaaaaaac cgggcgcgag cgtgaaagtg     60
agctgcaaag cgagcggctt taacattaaa gattattata tgcattgggt gcgccaggcg    120
ccgggccagg gcctggaatg gatcggccgc attgatccgg aaaacggcga tattatttat    180
gatccgaaat ttcagggccg cgtgaccatg accaccgata ccagcaccag caccgcgtat    240
atggaactgc gcagcctgcg cagcgatgat accgcggtgt attattgcgc gtatgatgcg    300
ggcgatccgg cgtggtttac ctattggggc cagggcaccc tggtgaccgt ctcgagc       357
```

<210> SEQ ID NO 372
<211> LENGTH: 108
<212> TYPE: PRT
<213> ORGANISM: Mus musculus

<400> SEQUENCE: 372

```
Asp Ile Gln Leu Thr Gln Ser Pro Ser Phe Leu Ser Ala Ser Val Gly
  1               5                  10                  15

Asp Arg Val Thr Ile Thr Cys Ser Val Ser Ser Ser Ile Ser Ser Ser
             20                  25                  30

Asn Leu His Trp Tyr Gln Gln Lys Pro Gly Lys Ala Pro Lys Leu Leu
         35                  40                  45

Ile Tyr Gly Thr Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
 65                  70                  75                  80

Pro Glu Asp Phe Ala Thr Tyr Tyr Cys Gln Gln Trp Thr Thr Thr Tyr
                 85                  90                  95

Thr Phe Gly Gln Gly Thr Lys Leu Glu Ile Lys Arg
            100                 105
```

<210> SEQ ID NO 373
<211> LENGTH: 324
<212> TYPE: DNA
<213> ORGANISM: Mus musculus

<400> SEQUENCE: 373

```
gatattcagc tgacccagag cccgagcttt ctgagcgcga gcgtgggcga tcgcgtgacc     60
attacctgca gcgtgagcag cagcattagc agcagcaacc tgcattggta tcagcagaaa    120
ccgggcaaag cgccgaaact gctgatttat ggcaccagca acctggcgag cggcgtgccg    180
```

```
agccgcttta gcggcagcgg cagcggcacc gaatttaccc tgaccattag cagcctgcag    240
ccggaagatt ttgcgaccta ttattgccag cagtggacca ccacctatac ctttggccag    300
ggcaccaaac tggaaattaa acgt                                           324
```

<210> SEQ ID NO 374
<211> LENGTH: 122
<212> TYPE: PRT
<213> ORGANISM: Mus musculus

<400> SEQUENCE: 374

```
Glu Val Gln Leu Val Gln Ser Gly Ala Glu Val Lys Lys Pro Gly Ala
 1               5                  10                  15

Ser Val Lys Val Ser Cys Lys Ala Ser Gly Phe Asn Ile Lys Asp Tyr
            20                  25                  30

Tyr Ile His Trp Val Arg Gln Ala Pro Gly Gln Gly Leu Glu Trp Met
        35                  40                  45

Gly Arg Ile Asp Pro Asp Asn Gly Glu Ser Thr Tyr Val Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Gly Leu Asp Tyr Gly Asp Tyr Tyr Ala Val Asp Tyr Trp
               100                 105                 110

Gly Gln Gly Thr Leu Val Thr Val Ser Ser
           115                 120
```

<210> SEQ ID NO 375
<211> LENGTH: 366
<212> TYPE: DNA
<213> ORGANISM: Mus musculus

<400> SEQUENCE: 375

```
gaagtgcagc tggtgcagag cggcgcggaa gtgaaaaaac cgggcgcgag cgtgaaagtg     60
agctgcaaag cgagcggctt taacattaaa gattattata ttcattgggt gcgccaggcg    120
ccgggccagg gcctggaatg gatgggccgc attgatccgg ataacggcga aagcacctat    180
gtgccgaaat ttcagggccg cgtgaccatg accaccgata ccagcaccag caccgcgtat    240
atggaactgc gcagcctgcg cagcgatgat accgcggtgt attattgcgc gcgcgaaggc    300
ctggattatg gcgattatta tgcggtggat tattgggggcc agggcaccct ggtgaccgtc    360
tcgagc                                                              366
```

<210> SEQ ID NO 376
<211> LENGTH: 107
<212> TYPE: PRT
<213> ORGANISM: Mus musculus

<400> SEQUENCE: 376

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Leu Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Tyr
                85                  90                  95

Thr Phe Gly Gly Gly Thr Lys Val Glu Ile Lys
            100                 105

<210> SEQ ID NO 377
<211> LENGTH: 321
<212> TYPE: DNA
<213> ORGANISM: Mus musculus

<400> SEQUENCE: 377
gacatccaga tgacccagtc tccatcctcc ctctccgcat ccgtaggcga ccgcgtaacc      60
ataacatgta gagcatctca agatatttcc aactatttga attggtacca acaaaaaccc     120
ggcaaagcac ctaaactcct catttactat acatcaagac tcctctccgg cgttccatca     180
cgattctcag gctccggctc cggcacagat ttcacactca ctatttcctc cctccaacca     240
gaagattttg caacctatta ctgtcaacaa ggcgatacac tcccatacac attcggcggc     300
ggcacaaaag ttgaaattaa a                                              321

<210> SEQ ID NO 378
<211> LENGTH: 123
<212> TYPE: PRT
<213> ORGANISM: Mus musculus

<400> SEQUENCE: 378

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Met
            35                  40                  45

Gly Glu Ile Asn Pro Asn Ser Gly Gly Ala Gly Tyr Asn Gln Lys Phe
        50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser
        115                 120

<210> SEQ ID NO 379
<211> LENGTH: 369
<212> TYPE: DNA
<213> ORGANISM: Mus musculus

<400> SEQUENCE: 379
gaggtgcagc tggtgcagag cggcgccgag gtaaaaaaac caggagcaag cgttaaagtt      60
tcttgtaaag caagcggata cacatttaca gattacaaca tgcattgggt aagacaagcg     120
ccaggacaag gattggaatg gatgggcgaa attaaccceta atagtggagg agcaggctac     180
aatcaaaaat tcaagggag agttacaatg acaacagaca caagcacttc aacagcatat     240
atggaactgc gatcacttag aagcgacgat acagctgtat actattgcgc acgacttggg     300

```
tatgatgata tatatgatga ctggtatttc gatgtttggg gccagggaac aacagttacc    360
gtctctagt                                                            369
```

<210> SEQ ID NO 380
<211> LENGTH: 108
<212> TYPE: PRT
<213> ORGANISM: Mus musculus

<400> SEQUENCE: 380

```
Asp Ile Gln Leu Thr Gln Ser Pro Ser Phe Leu Ser Ala Ser Val Gly
 1               5                  10                  15

Asp Arg Val Thr Ile Thr Cys Arg Ala Ser Ser Ser Val Thr Ser Ser
            20                  25                  30

Tyr Leu Asn Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Tyr Asp Phe Phe Pro
                85                  90                  95

Ser Thr Phe Gly Gly Gly Thr Lys Val Glu Ile Lys
            100                 105
```

<210> SEQ ID NO 381
<211> LENGTH: 324
<212> TYPE: DNA
<213> ORGANISM: Mus musculus

<400> SEQUENCE: 381

```
gacatccagc tgacccagag ccccagcttc ctttccgcat ccgttggtga ccgagtaaca    60
atcacatgcc gcgcctcatc ttcagttaca tcttcttatc ttaattggta tcaacaaaaa   120
ccaggaaaag cacctaaact tcttatatac tctacatcta atctcgcatc aggagttccc   180
tctcgatttt caggatctgg atcaggcaca gaatttacac ttactatatc atcactccaa   240
ccagaagact cgccactta ttactgccaa caatacgatt tttttccaag cacattcgga    300
ggaggtacaa aagtagaaat caag                                           324
```

<210> SEQ ID NO 382
<211> LENGTH: 121
<212> TYPE: PRT
<213> ORGANISM: Mus musculus

<400> SEQUENCE: 382

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Arg Leu Glu Trp Met
        35                  40                  45

Gly Asp Ile Asn Pro Tyr Asn Asp Asp Thr Thr Tyr Asn His Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Glu Thr Ala Val Ile Thr Thr Asn Ala Met Asp Tyr Trp Gly
            100                 105                 110

Gln Gly Thr Thr Val Thr Val Ser Ser
        115                 120

<210> SEQ ID NO 383
<211> LENGTH: 363
<212> TYPE: DNA
<213> ORGANISM: Mus musculus

<400> SEQUENCE: 383
gaggtgcagc tggtgcagag cggcgccgag gtcaagaaac ctggagcaag cgtaaaggtt     60
agttgcaaag catctggata cacatttacc gactactaca tgaattgggt acgacaagcc    120
cctggacaaa gacttgaatg gatgggagac attaacccttt ataacgacga cactacatac    180
aatcataaat ttaaggaag agttacaatt acaagagata catccgcatc aaccgcctat    240
atggaacttt cctcattgag atctgaagac actgctgttt attactgtgc aagagaaact    300
gccgttatta ctactaacgc tatggattac tggggtcaag aaccactgt taccgtctct    360 agt                                                                  363

<210> SEQ ID NO 384
<211> LENGTH: 108
<212> TYPE: PRT
<213> ORGANISM: Mus musculus

<400> SEQUENCE: 384

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Thr Ile Ser Ser Asn
            20                  25                  30

His Leu His Trp Phe Gln Gln Lys Pro Gly Lys Ala Pro Lys Ser Leu
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Ser Tyr Pro
                85                  90                  95

Leu Thr Phe Gly Gly Gly Thr Lys Val Glu Ile Lys
            100                 105

<210> SEQ ID NO 385
<211> LENGTH: 324
<212> TYPE: DNA
<213> ORGANISM: Mus musculus

<400> SEQUENCE: 385
gacatccaga tgacccagtc tccatcctcc ctctcagcat ccgtaggcga tagagttaca     60
ataacatgca gcgtatcatc aactatatca tcaaatcatc ttcattggtt ccaacagaaa    120
cccggcaaag cacctaaatc acttatatac ggcacatcaa atctcgcatc aggcgttcct    180
tcaagatttt caggctctgg ctcaggcacc gactttactc ttacaatatc ctccctccaa    240
cccgaagact cgcaacccta ttactgtcaa caatggtcct catatccact cacatttggc    300
ggcggcacaa aagtagaaat taaa                                           324

<210> SEQ ID NO 386
<211> LENGTH: 125
<212> TYPE: PRT
<213> ORGANISM: Mus musculus

<400> SEQUENCE: 386

Glu Val Gln Leu Val Gln Ser Gly Ala Glu Val Lys Lys Pro Gly Ala
1               5                   10                  15

Ser Val Lys Val Ser Cys Lys Ala Ser Asp Phe Asn Ile Lys Asp Phe
            20                  25                  30

Tyr Leu His Trp Val Arg Gln Ala Pro Gly Gln Gly Leu Glu Trp Ile
        35                  40                  45

Gly Arg Ile Asp Pro Glu Asn Gly Asp Thr Leu Tyr Asp Pro Lys Phe
    50                  55                  60

Gln Asp Lys Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Asp Tyr Phe His Asp Gly Thr Ser Tyr Trp Tyr Phe
            100                 105                 110

Asp Val Trp Gly Arg Gly Thr Leu Val Thr Val Ser Ser
        115                 120                 125

<210> SEQ ID NO 387
<211> LENGTH: 375
<212> TYPE: DNA
<213> ORGANISM: Mus musculus

<400> SEQUENCE: 387
gaggtgcagc tggtgcagtc tggggctgag gtgaagaagc ctggggcctc agtgaaggtc      60
tcctgcaagg cttctgactt caacattaaa gacttctatc tacactgggt gcgacaggcc     120
cctggacaag gcttgagtg gattggaagg attgatcctg agaatggtga tactttatat      180
gacccgaagt tccaggacaa ggtcaccatg accacagaca cgtccaccag cacagcctac     240
atggagctga ggagcctgag atctgacgac acggccgtgt attactgtgc gagagaggcg     300
gattatttcc acgatggtac ctcctactgg tacttcgatg tctggggccg tggcaccctg     360
gtcaccgtct ctagt                                                      375

<210> SEQ ID NO 388
<211> LENGTH: 106
<212> TYPE: PRT
<213> ORGANISM: Mus musculus

<400> SEQUENCE: 388

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Ile Ser Tyr Ile
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asp Pro Leu Thr
                85                  90                  95

Phe Gly Gly Gly Thr Lys Val Glu Ile Lys
            100             105

<210> SEQ ID NO 389
<211> LENGTH: 318
<212> TYPE: DNA
<213> ORGANISM: Mus musculus

<400> SEQUENCE: 389
gacatccagt tgacccagtc tccatccttc ctgtctgcat ctgtaggaga cagagtcacc      60
atcacttgca gggccagctc aagtataagt tacatacact ggtatcagca aaaaccaggg    120
aaagccccta agctcctgat ctatgccaca tccaacctgg cttctggggt cccatcaagg    180
ttcagcggca gtggatctgg gacagaattc actctcacaa tcagcagcct gcagcctgaa    240
gattttgcaa cttattactg tcagcagtgg agtagtgacc cactcacgtt cggcggaggg    300
accaaggtgg agatcaaa                                                  318

<210> SEQ ID NO 390
<211> LENGTH: 121
<212> TYPE: PRT
<213> ORGANISM: Mus musculus

<400> SEQUENCE: 390

Glu Val Gln Leu Val Gln Ser Gly Ala Glu Val Lys Lys Pro Gly Ala
  1               5                  10                  15

Ser Val Lys Val Ser Cys Lys Ala Ser Gly Phe Asp Ile Lys Asp Tyr
             20                  25                  30

Tyr Ile His Trp Val Arg Gln Ala Pro Gly Gln Gly Leu Glu Trp Ile
         35                  40                  45

Gly Arg Val Asp Pro Asp Asn Gly Glu Thr Glu Phe Ala Pro Lys Phe
     50                  55                  60

Pro Gly Lys Val Thr Met Thr Thr Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Glu Asp Tyr Asp Gly Thr Tyr Thr Trp Phe Pro Tyr Trp Gly
            100                 105                 110

Gln Gly Thr Leu Val Thr Val Ser Ser
        115                 120

<210> SEQ ID NO 391
<211> LENGTH: 363
<212> TYPE: DNA
<213> ORGANISM: Mus musculus

<400> SEQUENCE: 391
gaggtgcagc tggtgcagtc tggggctgag gtgaagaagc ctggggcctc agtgaaggtc      60
tcctgcaagg cttctggatt cgacattaag gactactata cactgggt gcgacaggcc     120 cctggacaag ggcttgagtg gatcggaagg gttgatcctg acaatggtga gactgaattt    180
gccccgaagt tcccgggcaa ggtcaccatg accacagaca cgtccatcag cacagcctac    240
atggagctga gcaggctgag atctgacgac acggccgtgt attactgtgc gagagaagac    300
tacgatggta cctacacctg gtttccttat tggggccaag ggactctggt caccgtctct    360
agt                                                                  363

<210> SEQ ID NO 392

```
<211> LENGTH: 448
<212> TYPE: PRT
<213> ORGANISM: Artificial Sequence
<220> FEATURE:
<223> OTHER INFORMATION: Humanized antibody sequence

<400> SEQUENCE: 392
```

| Glu | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Asp | Tyr |
| | | | 20 | | | | | 25 | | | | | 30 | | |

| Asn | Met | His | Trp | Val | Arg | Gln | Ala | Pro | Gly | Gln | Gly | Leu | Glu | Trp | Met |
| | | 35 | | | | | 40 | | | | | 45 | | | |

| Gly | Glu | Ile | Asn | Pro | Asn | Ser | Gly | Ala | Gly | Tyr | Asn | Gln | Lys | Phe |
| 50 | | | | | 55 | | | | | 60 | | | | |

| Lys | Gly | Arg | Val | Thr | Met | Thr | Thr | Asp | Thr | Ser | Thr | Ser | Thr | Ala | Tyr |
| 65 | | | | | 70 | | | | 75 | | | | | 80 | |

| Met | Glu | Leu | Arg | Ser | Leu | Arg | Ser | Asp | Asp | Thr | Ala | Val | Tyr | Tyr | Cys |
| | | | | 85 | | | | | 90 | | | | | 95 | |

| Ala | Arg | Leu | Gly | Tyr | Asp | Asp | Ile | Tyr | Asp | Asp | Trp | Tyr | Phe | Asp | Val |
| | | | 100 | | | | | 105 | | | | | 110 | | |

| Trp | Gly | Gln | Gly | Thr | Thr | Val | Thr | Val | Ser | Ser | Ala | Ser | Thr | Lys | Gly |
| | | 115 | | | | | 120 | | | | | 125 | | | |

| Pro | Ser | Val | Phe | Pro | Leu | Ala | Pro | Cys | Ser | Arg | Ser | Thr | Ser | Glu | Ser |
| | 130 | | | | | 135 | | | | | 140 | | | | |

| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |

| Thr | Val | Ser | Trp | Asn | Ser | Gly | Ala | Leu | Thr | Ser | Gly | Val | His | Thr | Phe |
| | | | | 165 | | | | | 170 | | | | | 175 | |

| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |

| Thr | Val | Pro | Ser | Ser | Asn | Phe | Gly | Thr | Gln | Thr | Tyr | Thr | Cys | Asn | Val |
| | | 195 | | | | | 200 | | | | | 205 | | | |

| Asp | His | Lys | Pro | Ser | Asn | Thr | Lys | Val | Asp | Lys | Thr | Val | Glu | Arg | Lys |
| | 210 | | | | | 215 | | | | | 220 | | | | |

| Cys | Cys | Val | Glu | Cys | Pro | Pro | Cys | Pro | Ala | Pro | Pro | Val | Ala | Gly | Pro |
| 225 | | | | | 230 | | | | | 235 | | | | | 240 |

| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |

| Arg | Thr | Pro | Glu | Val | Thr | Cys | Val | Val | Val | Asp | Val | Ser | His | Glu | Asp |
| | | | 260 | | | | | 265 | | | | | 270 | | |

| Pro | Glu | Val | Gln | Phe | Asn | Trp | Tyr | Val | Asp | Gly | Val | Glu | Val | His | Asn |
| | | 275 | | | | | 280 | | | | | 285 | | | |

| Ala | Lys | Thr | Lys | Pro | Arg | Glu | Glu | Gln | Phe | Asn | Ser | Thr | Phe | Arg | Val |
| | 290 | | | | | 295 | | | | | 300 | | | | |

| Val | Ser | Val | Leu | Thr | Val | Val | His | Gln | Asp | Trp | Leu | Asn | Gly | Lys | Glu |
| 305 | | | | | 310 | | | | | 315 | | | | | 320 |

| Tyr | Lys | Cys | Lys | Val | Ser | Asn | Lys | Gly | Leu | Pro | Ala | Pro | Ile | Glu | Lys |
| | | | | 325 | | | | | 330 | | | | | 335 | |

| Thr | Ile | Ser | Lys | Thr | Lys | Gly | Gln | Pro | Arg | Glu | Pro | Gln | Val | Tyr | Thr |
| | | | 340 | | | | | 345 | | | | | 350 | | |

| Leu | Pro | Pro | Ser | Arg | Glu | Glu | Met | Thr | Lys | Asn | Gln | Val | Ser | Leu | Thr |
| | | 355 | | | | | 360 | | | | | 365 | | | |

| Cys | Leu | Val | Lys | Gly | Phe | Tyr | Pro | Ser | Asp | Ile | Ala | Val | Glu | Trp | Glu |
| | 370 | | | | | 375 | | | | | 380 | | | | |

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 393
<211> LENGTH: 446
<212> TYPE: PRT
<213> ORGANISM: Artificial Sequence
<220> FEATURE:
<223> OTHER INFORMATION: Humanized antibody sequence

<400> SEQUENCE: 393

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Arg Leu Glu Trp Met
        35                  40                  45

Gly Asp Ile Asn Pro Tyr Asn Asp Thr Thr Tyr Asn His Lys Phe
50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Thr Ala Val Ile Thr Thr Asn Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
            325                 330                 335

Ser Lys Thr Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly
    435                 440                 445

<210> SEQ ID NO 394
<211> LENGTH: 450
<212> TYPE: PRT
<213> ORGANISM: Artificial Sequence
<220> FEATURE:
<223> OTHER INFORMATION: Humanized antibody sequence

<400> SEQUENCE: 394

Glu Val Gln Leu Val Gln Ser Gly Ala Glu Val Lys Lys Pro Gly Ala
1               5                   10                  15

Ser Val Lys Val Ser Cys Lys Ala Ser Asp Phe Asn Ile Lys Asp Phe
            20                  25                  30

Tyr Leu His Trp Val Arg Gln Ala Pro Gly Gln Gly Leu Glu Trp Ile
        35                  40                  45

Gly Arg Ile Asp Pro Glu Asn Gly Asp Thr Leu Tyr Asp Pro Lys Phe
    50                  55                  60

Gln Asp Lys Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Asp Tyr Phe His Asp Gly Thr Ser Tyr Trp Tyr Phe
            100                 105                 110

Asp Val Trp Gly Arg Gly Thr Leu Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
        180                 185                 190

Val Val Thr Val Pro Ser Ser Asn Phe Gly Thr Gln Thr Tyr Thr Cys
    195                 200                 205

Asn Val Asp His Lys Pro Ser Asn Thr Lys Val Asp Lys Thr Val Glu
210                 215                 220

```
Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Phe
        290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 395
<211> LENGTH: 446
<212> TYPE: PRT
<213> ORGANISM: Artificial Sequence
<220> FEATURE:
<223> OTHER INFORMATION: Humanized antibody sequence

<400> SEQUENCE: 395

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Lys Asp Tyr
            20                  25                  30

Tyr Ile His Trp Val Arg Gln Ala Pro Gly Gln Gly Leu Glu Trp Ile
        35                  40                  45

Gly Arg Val Asp Pro Asp Asn Gly Glu Thr Glu Phe Ala Pro Lys Phe
    50                  55                  60

Pro Gly Lys Val Thr Met Thr Thr Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Glu Asp Tyr Asp Gly Thr Tyr Thr Trp Phe Pro Tyr Trp Gly
            100                 105                 110

Gln Gly Thr Leu Val Thr Val Ser Ser Ala Ser Thr Lys Gly Pro Ser
        115                 120                 125
```

```
Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 396
<211> LENGTH: 445
<212> TYPE: PRT
<213> ORGANISM: Artificial Sequence
<220> FEATURE:
<223> OTHER INFORMATION: Humanized antibody sequence

<400> SEQUENCE: 396

Glu Val Gln Leu Val Gln Ser Gly Ala Glu Val Lys Lys Pro Gly Ser
  1               5                  10                  15

Ser Val Lys Val Ser Cys Lys Ala Ser Gly Phe Thr Phe Thr Asp Tyr
                 20                  25                  30

Ile Met His Trp Val Arg Gln Ala Pro Gly Gln Gly Leu Glu Trp Met
             35                  40                  45
```

-continued

```
Gly Tyr Ile Asn Pro Tyr Asn Asp Asp Thr Glu Tyr Asn Glu Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Tyr Asp Ala Pro Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
            195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445
```

SCLEROSTIN-BINDING ANTIBODIES

RELATED APPLICATIONS

The present application is a divisional of U.S. patent application Ser. No. 11/411,003 (now issued as U.S. Pat. No. 7,592,429), filed Apr. 25, 2006, which claims the benefit of priority from U.S. Provisional Patent Application No. 60/792,645, filed Apr. 17, 2006, U.S. Provisional Patent Application No. 60/782,244, filed Mar. 13, 2006, U.S. Provisional Patent Application No. 60/776,847, filed Feb. 24, 2006 and U.S. Provisional Patent Application No. 60/677,583, filed May 3, 2005, under 35 U.S.C. §119. The foregoing patent applications are incorporated herein by reference in their entirety.

TECHNICAL FIELD

The present invention relates generally to epitopes of sclerostin protein, including human sclerostin protein, and binding agents (such as antibodies) capable of binding to sclerostin or fragments thereof

BACKGROUND OF THE INVENTION

Two or three distinct phases of changes to bone mass occur over the life of an individual (see Riggs, *West I Med.* 154:63-77 (1991)). The first phase occurs in both men and women and proceeds to attainment of a peak bone mass. This first phase is achieved through linear growth of the endochondral growth plates and radial growth due to a rate of periosteal apposition. The second phase begins around age 30 for trabecular bone (flat bones such as the vertebrae and pelvis) and about age 40 for cortical bone (e.g., long bones found in the limbs) and continues to old age. This phase is characterized by slow bone loss and occurs in both men and women. In women, a third phase of bone loss also occurs, most likely due to postmenopausal estrogen deficiencies. During this phase alone, women may lose an additional bone mass from the cortical bone and from the trabecular compartment (see Riggs, supra).

Loss of bone mineral content can be caused by a wide variety of conditions and may result in significant medical problems. For example, osteoporosis is a debilitating disease in humans and is characterized by marked decreases in skeletal bone mass and mineral density, structural deterioration of bone, including degradation of bone microarchitecture and corresponding increases in bone fragility (i.e., decreases in bone strength), and susceptibility to fracture in afflicted individuals. Osteoporosis in humans is generally preceded by clinical osteopenia (bone mineral density that is greater than one standard deviation but less than 2.5 standard deviations below the mean value for young adult bone), a condition found in approximately 25 million people in the United States. Another 7-8 million patients in the United States have been diagnosed with clinical osteoporosis (defined as bone mineral content greater than 2.5 standard deviations below that of mature young adult bone). The frequency of osteoporosis in the human population increases with age. Among Caucasians, osteoporosis is predominant in women who, in the United States, comprise 80% of the osteoporosis patient pool. The increased fragility and susceptibility to fracture of skeletal bone in the aged is aggravated by the greater risk of accidental falls in this population. Fractured hips, wrists, and vertebrae are among the most common injuries associated with osteoporosis. Hip fractures in particular are extremely uncomfortable and expensive for the patient, and for women, correlate with high rates of mortality and morbidity.

Although osteoporosis has been regarded as an increase in the risk of fracture due to decreased bone mass, few of the presently available treatments for skeletal disorders can increase the bone density of adults, and most of the presently available treatments work primarily by inhibiting further bone resorption rather than stimulating new bone formation. Estrogen is now being prescribed to retard bone loss. However, some controversy exists over whether patients gain any long-term benefit and whether estrogen has any effect on patients over 75 years old. Moreover, use of estrogen is believed to increase the risk of breast and endometrial cancer. Calcitonin, osteocalcin with vitamin K, or high doses of dietary calcium, with or without vitamin D, have also been suggested for postmenopausal women. High doses of calcium, however, often have undesired gastrointestinal side effects, and serum and urinary calcium levels must be continuously monitored (e.g., Khosla and Riggs, *Mayo Clin. Proc.* 70:978982, 1995).

Other current therapeutic approaches to osteoporosis include bisphosphonates (e.g., Fosamax™, Actonel™, Bonviva™, Zometa™, olpadronate, neridronate, skelid, bonefos), parathyroid hormone, calcilytics, calcimimetics (e.g., cinacalcet), statins, anabolic steroids, lanthanum and strontium salts, and sodium fluoride. Such therapeutics, however, are often associated with undesirable side effects (see Khosla and Riggs, supra).

Sclerostin, the product of the SOST gene, is absent in sclerosteosis, a skeletal disease characterized by bone overgrowth and strong dense bones (Brunkow et al., Am. J. Hum. Genet., 68:577-589, 2001; Balemans et al., Hum. Mol. Genet., 10:537-543, 2001). The amino acid sequence of human sclerostin is reported by Brunkow et al. ibid and is disclosed herein as SEQ ID NO:1.

BRIEF SUMMARY OF THE INVENTION

Disclosed herein are compositions and methods that can be used to increase at least one of bone formation, bone mineral density, bone mineral content, bone mass, bone quality and bone strength, and that therefore may be used to treat a wide variety of conditions in which an increase in at least one of bone formation, bone mineral density, bone mineral content, bone mass, bone quality and bone strength is desirable. The present invention also offers other related advantages described herein.

The invention relates to regions (epitopes) of human sclerostin recognized by the binding agents disclosed herein, methods of using these epitopes, and methods of making such epitopes.

The invention also relates to epitopes specific to the region of sclerostin identified as Loop 2, and binding agents which specifically bind to that region.

The invention also relates to epitopes specific to the cystine-knot region of sclerostin, and binding agents such as antibodies specifically binding to that region.

The invention relates to binding agents, such as antibodies, that specifically bind to sclerostin. The binding agents can be characterized by their ability to cross-block the binding of at least one antibody disclosed herein to sclerostin and/or to be cross-blocked from binding sclerostin by at least one antibody disclosed herein. The antibodies and other binding agents can also be characterized by their binding pattern to human sclerostin peptides in a "human sclerostin peptide epitope competition binding assay" as disclosed herein.

The invention relates to binding agents, such as antibodies, that can increase at least one of bone formation, bone mineral density, bone mineral content, bone mass, bone quality and bone strength in a mammal.

The invention relates to binding agents, such as antibodies, that can block the inhibitory effect of sclerostin in a cell based mineralization assay.

The invention further relates to polypeptide constructs comprising two, three, or four polypeptide fragments linked by at least one disulfide bond, representing a core region of the cystine-knot of sclerostin, and antibodies capable of specifically binding thereto.

The invention relates to methods of obtaining epitopes suitable for use as immunogens for generating, in mammals, binding agents, such as antibodies capable of binding specifically to sclerostin; in certain embodiments the binding agents generated are capable of neutralizing sclerostin activity in vivo.

The invention relates to a composition for eliciting an antibody specific for sclerostin when the composition is administered to an animal, the composition comprising a polypeptide having the amino acid sequence of SEQ ID NO:6, SEQ ID NO:63, SEQ ID NO:64, SEQ ID NO:65, SEQ ID NO:66, SEQ ID NO:67, SEQ ID NO:68, or SEQ ID NO:69.

The invention also relates to a composition for eliciting an antibody specific for sclerostin when the composition is administered to an animal, the composition comprising at least one polypeptide consisting essentially of the amino acid sequence of SEQ ID NO:2, SEQ ID NO:3, SEQ ID NO:4 or SEQ ID NO:5; the composition may comprise at least two or at least three of the amino acid sequences of SEQ ID NO:2, SEQ ID NO:3, SEQ ID NO:4 and SEQ ID NO:5, and the composition may comprise all four of the amino acid sequences of SEQ ID NO:2, SEQ ID NO:3, SEQ ID NO:4 and SEQ ID NO:5.

The invention further relates to a composition for eliciting an antibody specific for sclerostin when the composition is administered to an animal, the composition comprising a polypeptide having the amino acid sequences of SEQ ID NO:2, SEQ ID NO:3, SEQ ID NO:4 and SEQ ID NO:5, wherein SEQ ID NO:2 and 4 are joined by a disulfide bond at amino acid positions 57 and 111 with reference to SEQ ID NO:1, and SEQ ID NO:3 and 5 are joined by at least one of (a) a disulfide bond at amino acid positions 82 and 142 with reference to SEQ ID NO:1, and (b) a disulfide bond at amino acid positions 86 and 144 with reference to SEQ ID NO:1; the polypeptide may retain the tertiary structure of the corresponding polypeptide region of human sclerostin of SEQ ID NO:1.

The invention also relates to polypeptide T20.6 consisting essentially of a multiply truncated human sclerostin protein of SEQ ID NO:1, wherein amino acids 1-50, 65-72, 91-100, 118-137, and 150-190 of SEQ ID NO:1 are absent from the polypeptide; this polypeptide may be obtained by tryptic digestion of human sclerostin, and the protein may be isolated by HPLC fractionation.

The invention further relates to immunogenic portion T20.6 of human sclerostin comprising amino acids 51-64, 73-90, 101-117, and 138-149 of SEQ ID NO:1, wherein the immunogenic portion comprises at least one of:
(a) a disulfide bond between amino acids 57 and 111;
(b) a disulfide bond between amino acids 82 and 142; and
(c) a disulfide bond between amino acids 86 and 144;
the immunogenic portion may have at least two of these disulfide bonds; and the immunogenic portion may have all three disulfide bonds.

The invention further relates to an immunogenic portion T20.6 derivative of human sclerostin comprising amino acids 57-64, 73-86, 111-117, and 138-144 of SEQ ID NO:1, wherein the immunogenic portion comprises at least one of:
(a) a disulfide bond between amino acids 57 and 111;
(b) a disulfide bond between amino acids 82 and 142; and
(c) a disulfide bond between amino acids 86 and 144;
the immunogenic portion may have at least two of these disulfide bonds; and the immunogenic portion may have all three disulfide bonds.

The invention yet further relates to a polypeptide consisting essentially of a human sclerostin protein of SEQ ID NO:1 truncated at the C-terminal and N-terminal ends, wherein amino acids 1-85 and 112-190 of SEQ ID NO:1 are absent from the polypeptide.

The invention also relates to an immunogenic portion of human sclerostin, comprising amino acids 86-111 of SEQ ID NO:1; the immunogenic portion may consist essentially of contiguous amino acids CGPARLLPNAIGRGKWWRPSG-PDFRC (SEQ ID NO:6).

The invention further relates to an immunogenic portion of rat sclerostin, comprising amino acids 92-109 of SEQ ID NO:98; the immunogenic portion may consist essentially of contiguous amino acids PNAIGRVKWWRPNGPDFR (SEQ ID NO:96).

The invention still further relates to an immunogenic portion of rat sclerostin, comprising amino acids 99-120 of SEQ ID NO:98; the immunogenic portion may consist essentially of contiguous amino acids KWWRPNGPDFRCIP-DRYRAQRV (SEQ ID NO:97).

The invention relates to a method of producing an immunogenic portion of human sclerostin, comprising the steps of:
(a) treating human sclerostin to achieve complete tryptic digestion;
(b) collecting the tryptic digest sample having average molecular weight of 7,122.0 Daltons (theoretical mass 7121.5 Daltons) or retention time of about 20.6 minutes as determined by elution from a reverse-phase HPLC column with linear gradient from 0.05% trifluoroacetic acid to 90% acetonitrile in 0.05% TFA at a flow rate of 0.2 ml/min; and
(c) purifying the immunogenic portion.

The invention relates to a method of generating an antibody capable of specifically binding to sclerostin, comprising:
(a) immunizing an animal with a composition comprising a polypeptide of SEQ ID NO:6, SEQ ID NO:63, SEQ ID NO:64, SEQ ID NO:65, SEQ ID NO:66, SEQ ID NO:67, SEQ ID NO:68, SEQ ID NO:69, SEQ ID NO:96, or SEQ ID NO:97;
(b) collecting sera from the animal; and
(c) isolating from the sera an antibody capable of specifically binding to sclerostin.

The invention also relates to a method of generating an antibody capable of specifically binding to sclerostin, the method comprising:
(a) immunizing an animal with a composition comprising polypeptide T20.6 or a derivative of T20.6;
(b) collecting sera from the animal; and
(c) isolating from the sera an antibody capable of specifically binding to sclerostin.

The invention further relates to a method of detecting an anti-sclerostin antibody in a biological sample, comprising the steps of
(a) contacting the biological sample with a polypeptide consisting essentially of SEQ ID NO:6, SEQ ID NO:63, SEQ ID NO:64, SEQ ID NO:65, SEQ ID NO:66, SEQ ID NO:67, SEQ ID NO:68, SEQ ID NO:69, SEQ ID NO:96, or SEQ ID NO:97 under conditions allowing a complex to form between the antibody and the polypeptide; and (b) detecting the presence or absence of the complex, wherein the presence of the complex indicates that the biological sample contains an anti-sclerostin antibody.

The invention also relates to a method of detecting an anti-sclerostin antibody in a biological sample, comprising the steps of
(a) contacting the biological sample with polypeptide T20.6 or a derivative of T20.6 under conditions allowing a complex to form between the antibody and the polypeptide; and
(b) detecting the presence or absence of the complex, wherein the presence of the complex indicates that the biological sample contains an anti-sclerostin antibody.

The invention further relates to a sclerostin binding agent, such as an antibody, that cross-blocks the binding of at least one of antibodies Ab-A, Ab-B, Ab-C, or Ab-D to a sclerostin protein. The sclerostin binding agent may also be cross-blocked from binding to sclerostin by at least one of antibodies Ab-A, Ab-B, Ab-C, or Ab-D. The isolated antibody, or an antigen-binding fragment thereof, may be a polyclonal antibody, a monoclonal antibody, a humanized antibody, a human antibody, a chimeric antibody or the like.

The invention further relates to a sclerostin binding agent, such as an antibody, that is cross-blocked from binding to sclerostin by at least one of antibodies Ab-A, Ab-B, Ab-C, or Ab-D. The isolated antibody, or an antigen-binding fragment thereof, may be a polyclonal antibody, a monoclonal antibody, a humanized antibody, a human antibody, a chimeric antibody or the like.

The invention further relates to a sclerostin binding agent, such as an isolated antibody, that cross-blocks the binding of at least one of antibodies 1-24 (Ab-1 to Ab-24) to a sclerostin protein. The sclerostin binding agent may also be cross-blocked from binding to sclerostin by at least one of antibodies 1-24 (Ab-1 to Ab-24). The isolated antibody, or an antigen-binding fragment thereof, may be a polyclonal antibody, a monoclonal antibody, a humanized antibody, a human antibody, or a chimeric antibody.

The invention further relates to a sclerostin binding agent, such as an isolated antibody, that is cross-blocked from binding to sclerostin by at least one of antibodies 1-24 (Ab-1 to Ab-24); the isolated antibody, or an antigen-binding fragment thereof, may be a polyclonal antibody, a monoclonal antibody, a humanized antibody, a human antibody, or a chimeric antibody.

The invention further relates to a binding agent, such as an isolated antibody that exhibits a similar binding pattern to human sclerostin peptides in a "human sclerostin peptide epitope competition binding assay" as that exhibited by at least one of the antibodies Ab-A, Ab-B, Ab-C or Ab-D; the isolated antibody, or an antigen-binding fragment thereof, may be a polyclonal antibody, a monoclonal antibody, a humanized antibody, a human antibody, or a chimeric antibody.

The invention still further relates to a method for treating a bone disorder associated with at least one of low bone formation, low bone mineral density, low bone mineral content, low bone mass, low bone quality and low bone strength in a mammalian subject which comprises providing to a subject in need of such treatment an amount of an anti-sclerostin binding agent sufficient to increase at least one of bone formation, bone mineral density, bone mineral content, bone mass, bone quality and bone strength wherein the anti-sclerostin binding agent comprises an antibody, or sclerostin-binding fragment thereof.

The invention also relates to an isolated sclerostin polypeptide or fragments thereof, wherein the polypeptide contains 6 conserved cysteine residues and the fragments thereof comprise from 7 to 14 amino acids of SEQ ID NO:2; 8 to 17 amino acids of SEQ ID NO:3; 8 to 18 residues of SEQ ID NO:4; and 6 to 12 residues of SEQ ID NO:5, and the polypeptide or fragments thereof are stabilized by disulfide bonds between SEQ ID NO:2 and 4, and between SEQ ID NO:3 and 5; the polypeptide or fragments may comprise 10-14 amino acids of SEQ ID NO:2; 14 to 17 amino acids of SEQ ID NO:3; 13 to 18 amino acids of SEQ ID NO:4; and 8 to 12 residues of SEQ ID NO:5; and the polypeptide or fragments may comprise SEQ ID NO:2, SEQ ID NO:3, SEQ ID NO:4, and SEQ ID NO:5.

Provided herein are antibodies that specifically bind to human sclerostin. The antibodies are characterized by their ability to cross-block the binding of at least one antibody disclosed herein to human sclerostin and/or to be cross-blocked from binding human sclerostin by at least one antibody disclosed herein.

Also provided is an isolated antibody, or an antigen-binding fragment thereof, that can increase at least one of bone formation, bone mineral density, bone mineral content, bone mass, bone quality and bone strength in a mammal.

Also provided in an isolated antibody, or an antigen-binding fragment thereof, that can block the inhibitory effect of sclerostin in a cell based mineralization assay.

Also provided is a binding agent, such as an antibody, that specifically binds to human sclerostin and has at least one CDR sequence selected from SEQ ID NOs: 39, 40, 41, 42, 43, 44, 45, 46, 47, 48, 49, 50, 51, 52, 53, 54, 55, 56, 57, 58, 59, 60, 61, 62, 78, 79, 80, 81, 99, 100, 101, 102, 103, 104, 105, 106, 107, 108, 109, 110, 111, 112, 113, 114, 115, 116, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 351, 352, 353, 358, 359, and 360, and variants thereof, wherein the antibody or antigen-binding fragment thereof neutralizes sclerostin.

Also provided is a binding agent, such as an antibody, that specifically binds to human sclerostin and has at least one CDR sequence selected from SEQ ID NOs:39, 40, 41, 42, 43, 44, 45, 46, 47, 48, 49, 50, 51, 52, 53, 54, 55, 56, 57, 58, 59, 60, 61, 62, 78, 79, 80, 81, 99, 100, 101, 102, 103, 104, 105, 106, 107, 108, 109, 110, 111, 112, 113, 114, 115, 116, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 351, 352, 353, 358, 359, and 360, and variants thereof.

Also provided are regions of human sclerostin which are important for the in vivo activity of the protein.

These and other aspects of the present invention will become apparent upon reference to the following detailed description and attached drawings. All references disclosed herein are hereby incorporated by reference in their entireties as if each was incorporated individually.

BRIEF DESCRIPTION OF THE DRAWINGS

FIG. 1 depicts the amino acid sequences of the mature form (signal peptides cleaved off) of the light chain (FIG. 1A) (SEQ ID NO:23) and heavy chain (FIG. 1B) (SEQ ID NO:27) for the anti-human sclerostin and anti-mouse sclerostin antibody Ab-A.

FIG. 2 depicts the amino acid sequences of the mature form (signal peptides cleaved off) of the light chain (FIG. 2A) (SEQ ID NO:31) and heavy chain (FIG. 2B) (SEQ ID NO:35) for the anti-human sclerostin and anti-mouse sclerostin antibody Ab-B.

FIG. 3 depicts the amino acid sequences of the mature form (signal peptides cleaved off) of the light chain (FIG. 3A) (SEQ ID NO:15) and heavy chain (FIG. 3B) (SEQ ID NO:19) for the anti-human sclerostin and anti-mouse sclerostin antibody Ab-C.

FIG. 4 depicts the amino acid sequences of the mature form (signal peptides cleaved off) of the light chain (FIG. 4A) (SEQ ID NO:7) and heavy chain (FIG. 4B) (SEQ ID NO:11) for the anti-human sclerostin and anti-mouse sclerostin antibody Ab-D.

FIG. 8 depicts the amino acid sequence of the mature form (signal peptide cleaved off) of human sclerostin (SEQ ID NO:1). Also depicted is the nucleotide sequence of the human sclerostin coding region that encodes the mature form of human sclerostin (SEQ ID No: 1). The eight cysteines are numbered C1 through C8. The cystine-knot is formed by three disulfide bonds (C1-C5; C3-C7; C4-C8). C2 and C6 also form a disulfide bond, however this disulfide is not part of the cystine-knot.

FIG. 11 depicts sequence and mass information for the isolated human sclerostin disulfide linked peptides generated by trypsin digestion. Seq. pos.=sequence position relative to SEQ ID NO: 1. Obs.=observed. Observed mass was determined by ESI-LC-MS analysis.

FIG. 12 depicts sequence and mass information for the isolated human sclerostin peptides generated by AspN digestion. The AspN22.7-23.5 peptide contains the 4 disulfide bonds. Seq. pos.=sequence position relative to SEQ ID NO: 1. Obs.=observed. Observed mass was determined by ESI-LC-MS analysis.

FIG. 19A shows sequence of the Loop 2 epitope for binding of Ab-A and Ab-B to human sclerostin (SEQ ID NO:6). FIG. 19B shows sequence, disulfide bonding and schematic of the T20.6 epitope for binding of Ab-C and Ab-D to human sclerostin (SEQ ID NO:2-5).

FIG. 20A shows digestion of the human sclerostin Ab-D complex. FIG. 20B shows digestion of human sclerostin alone. The T19.2, T20, T20.6 and T21-22 peptide peaks are indicated.

FIG. 21 shows the sequence, disulfide bonding and schematic of the "T20.6 derivative 1 (cystine-knot+4 arms)" epitope for binding of Ab-D to human sclerostin. (SEQ ID NO:70-73).

DETAILED DESCRIPTION

Figure 5:
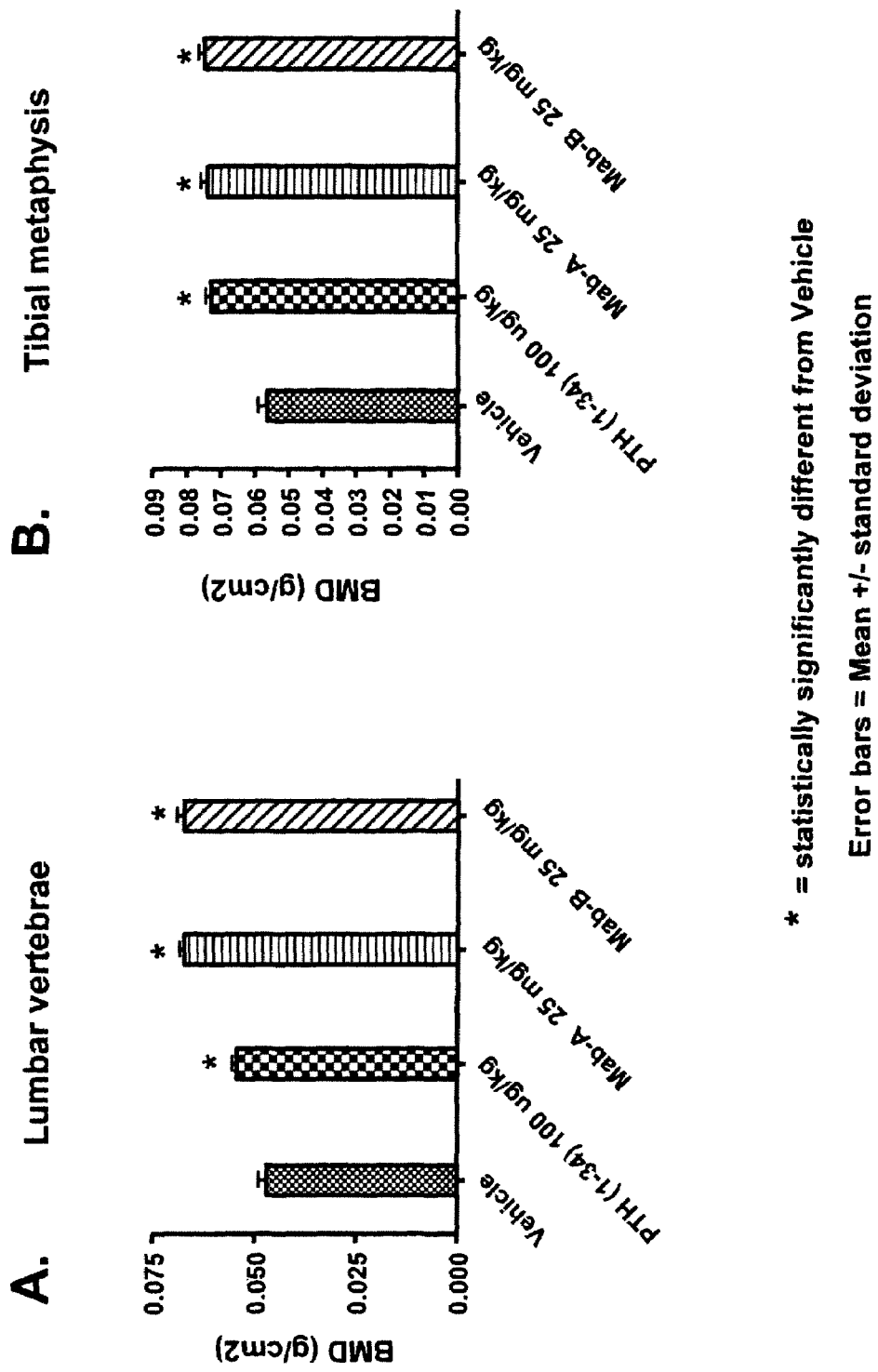
FIG. 5 depicts bone mineral density in mice measured at two skeletal sites (lumbar vertebrae (FIG. 5A) and tibial metaphysis (FIG. 5B)) after 3 weeks of treatment with vehicle, PTH (1-34), Ab-A or Ab-B.

The present invention relates to regions of the human sclerostin protein that contain epitopes recognized by antibodies that also bind to full-length sclerostin, and methods of making and using these epitopes. The invention also provides binding agents (such as antibodies) that specifically bind to sclerostin or portions of sclerostin, and methods for using such binding agents. The binding agents are useful to block or impair binding of human sclerostin to one or more ligand.

Recombinant human sclerostin/SOST is commercially available from R&D Systems (Minneapolis, Minn., USA; 2006 cat# 1406-ST-025). Additionally, recombinant mouse sclerostin/SOST is commercially available from R&D Systems (Minneapolis, Minn., USA; 2006 cat# 1589-ST-025). Research grade sclerostin binding monoclonal antibodies are commercially available from R&D Systems (Minneapolis, Minn., USA; mouse monoclonal: 2006 cat# MAB1406; rat monoclonal: 2006 cat# MAB1589). U.S. Pat. Nos. 6,395,511 and 6,803,453, and U.S. Patent Publications 20040009535 and 20050106683 refer to anti-sclerostin antibodies generally.

As used herein, the term human sclerostin is intended to include the protein of SEQ ID NO:1 and allelic variants thereof. Sclerostin can be purified from 293T host cells that have been transfected by a gene encoding sclerostin by elution of filtered supernatant of host cell culture fluid using a Heparin HP column, using a salt gradient. The preparation and further purification using cation exchange chromatography are described in Examples 1 and 2.

Binding agents of the invention are preferably antibodies, as defined herein. The term "antibody" refers to an intact antibody, or a binding fragment thereof. An antibody may comprise a complete antibody molecule (including polyclonal, monoclonal, chimeric, humanized, or human versions having full length heavy and/or light chains), or comprise an antigen binding fragment thereof. Antibody fragments include F(ab')$_2$, Fab, Fab', F$_v$, Fc, and Fd fragments, and can be incorporated into single domain antibodies, single-chain antibodies, maxibodies, minibodies, intrabodies, diabodies, triabodies, tetrabodies, v-NAR and bis-scFv (See e.g., Hollinger and Hudson, 2005, Nature Biotechnology, 23, 9, 1126-1136). Antibody polypeptides are also disclosed in U.S. Pat. No. 6,703,199, including fibronectin polypeptide monobodies. Other antibody polypeptides are disclosed in U.S. Patent Publication 2005/0238646, which are single-chain polypeptides.

Antigen binding fragments derived from an antibody can be obtained, for example, by proteolytic hydrolysis of the antibody, for example, pepsin or papain digestion of whole antibodies according to conventional methods. By way of example, antibody fragments can be produced by enzymatic cleavage of antibodies with pepsin to provide a 5S fragment termed F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., *Arch. Biochem. Biophys.* 89:230, 1960; Porter, *Biochem. J.* 73:119, 1959; Edelman et al., in *Methods in Enzymology* 1:422 (Academic Press 1967); and by Andrews, S. M. and Titus, J. A. in *Current Protocols in Immunology* (Coligan J. E., et al., eds), John Wiley & Sons, New York (2003). pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

An antibody fragment may also be any synthetic or genetically engineered protein. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker (scFv proteins).

Another form of an antibody fragment is a peptide comprising one or more complementarity determining regions (CDRs) of an antibody. CDRs (also termed "minimal recognition units", or "hypervariable region") can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., *Methods: A Companion to Methods in Enzymology* 2:106, 1991; Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression of Antibodies," in *Monoclonal Antibodies: Principles and Applications*, Birch et al., (eds.), page 137 (Wiley-Liss, Inc. 1995)).

Thus, in one embodiment, the binding agent comprises at least one CDR as described herein. The binding agent may comprise at least two, three, four, five or six CDR's as described herein. The binding agent further may comprise at least one variable region domain of an antibody described herein. The variable region domain may be of any size or amino acid composition and will generally comprise at least one CDR sequence responsible for binding to human sclerostin, for example CDR-H1, CDR-H2, CDR-H3 and/or the light chain CDRs specifically described herein and which is adjacent to or in frame with one or more framework sequences. In general terms, the variable (V) region domain may be any suitable arrangement of immunoglobulin heavy (V$_H$) and/or light (V$_L$) chain variable domains. Thus, for example, the V region domain may be monomeric and be a V$_H$ or V$_L$ domain, which is capable of independently binding human sclerostin with an affinity at least equal to $1 \times 10^{-7}$M or less as described below. Alternatively, the V region domain may be dimeric and contain $V_H$-$V_H$, $V_H$-$V_L$, or $V_L$-$V_L$, dimers. The V region dimer comprises at least one $V_H$ and at least one $V_L$ chain that may be non-covalently associated (hereinafter referred to as $F_V$). If desired, the chains may be covalently coupled either directly, for example via a disulfide bond between the two variable domains, or through a linker, for example a peptide linker, to form a single chain $F_V$ (sc$F_V$).

The variable region domain may be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly a $V_L$ domain may be linked to a $C_K$ domain or a fragment thereof. In this way, for example, the antibody may be a Fab fragment wherein the antigen binding domain contains associated $V_H$ and $V_L$ domains covalently linked at their C-termini to a CH1 and $C_K$ domain, respectively. The CH1 domain may be extended with further amino acids, for example to provide a hinge region or a portion of a hinge region domain as found in a Fab' fragment, or to provide further domains, such as antibody CH2 and CH3 domains.

As described herein, binding agents comprise at least one of these CDRs. For example, one or more CDR may be incorporated into known antibody framework regions (IgG1, IgG2, etc.), or conjugated to a suitable vehicle to enhance the half-life thereof. Suitable vehicles include, but are not limited to Fc, polyethylene glycol (PEG), albumin, transferrin, and the like. These and other suitable vehicles are known in the art. Such conjugated CDR peptides may be in monomeric, dimeric, tetrameric, or other form. In one embodiment, one or more water-soluble polymer is bonded at one or more specific position, for example at the amino terminus, of a binding agent.

In certain preferred embodiments, a binding agent comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative binding agent comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

It will be appreciated that a binding agent of the present invention may have at least one amino acid substitution, providing that the binding agent retains binding specificity. Therefore, modifications to the binding agent structures are encompassed within the scope of the invention. These may include amino acid substitutions, which may be conservative or non-conservative, that do not destroy the sclerostin binding capability of a binding agent. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position.

Non-conservative substitutions may involve the exchange of a member of one class of amino acids or amino acid mimetics for a member from another class with different physical properties (e.g. size, polarity, hydrophobicity, charge). Such substituted residues may be introduced into regions of the human antibody that are homologous with non-human antibodies, or into the non-homologous regions of the molecule.

Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974), Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3): 377-87 (1997); Sippi et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-4358 (1987)), and "evolutionary linkage" (See Holm, supra (1999), and Brenner, supra (1997)).

In certain embodiments, variants of binding agents include glycosylation variants wherein the number and/or type of glycosylation site has been altered compared to the amino acid sequences of a parent polypeptide. In certain embodiments, variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the art at the time such substitutions are desired. In certain embodiments, amino acid substitutions can be used to identify important residues of antibodies to sclerostin, or to increase or decrease the affinity of the antibodies to sclerostin described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

In certain embodiments, binding agents of the invention may be chemically bonded with polymers, lipids, or other moieties.

The binding agents may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendramisat domains may be used (See e.g., Nygren and Uhlen, 1997, Current Opinion in Structural Biology, 7, 463-469).

In preferred embodiments, it will be appreciated that the binding agents of the invention include the humanized antibodies described herein. Humanized antibodies such as those described herein can be produced using techniques known to those skilled in the art (Zhang, W., et al., *Molecular Immunology.* 42(12):1445-1451, 2005; Hwang W. et al., *Methods.* 36(1):35-42, 2005; Dall'Acqua W F, et al., *Methods* 36(1): 43-60, 2005; and Clark, M., *Immunology Today.* 21(8):397-402, 2000).

Additionally, one skilled in the art will recognize that suitable binding agents include portions of these antibodies, such as one or more of CDR-H1, CDR-H2, CDR-H3, CDR-L1, CDR-L2 and CDR-L3 as specifically disclosed herein. At least one of the regions of CDR-H1, CDR-H2, CDR-H3, CDR-L1, CDR-L2 and CDR-L3 may have at least one amino acid substitution, provided that the binding agent retains the binding specificity of the non-substituted CDR. The non-CDR portion of the binding agent may be a non-protein molecule, wherein the binding agent cross-blocks the binding of an antibody disclosed herein to sclerostin and/or neutralizes sclerostin. The non-CDR portion of the binding agent may be a non-protein molecule in which the binding agent exhibits a similar binding pattern to human sclerostin peptides in a "human sclerostin peptide epitope competition binding assay" as that exhibited by at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24, and/or neutralizes sclerostin. The non-CDR portion of the binding agent may be composed of amino acids, wherein the binding agent is a recombinant binding protein or a synthetic peptide, and the recombinant binding protein cross-blocks the binding of an antibody disclosed herein to sclerostin and/or neutralizes sclerostin. The non-CDR portion of the binding agent may be composed of amino acids, wherein the binding agent is a recombinant binding protein, and the recombinant binding protein exhibits a similar binding pattern to human sclerostin peptides in the human sclerostin peptide epitope competition binding assay (described hereinbelow) as that exhibited by at least one of the antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24, and/or neutralizes sclerostin.

Where an antibody comprises one or more of CDR-H1, CDR-H2, CDR-H3, CDR-L1, CDR-L2 and CDR-L3 as described above, it may be obtained by expression from a host cell containing DNA coding for these sequences. A DNA coding for each CDR sequence may be determined on the basis of the amino acid sequence of the CDR and synthesized together with any desired antibody variable region framework and constant region DNA sequences using oligonucleotide synthesis techniques, site-directed mutagenesis and polymerase chain reaction (PCR) techniques as appropriate. DNA coding for variable region frameworks and constant regions is widely available to those skilled in the art from genetic sequences databases such as GenBank®. Each of the above-mentioned CDRs will be typically located in a variable region framework at positions 31-35 (CDR-H1), 50-65 (CDR-H2) and 95-102 (CDR-H3) of the heavy chain and positions 24-34 (CDR-L1), 50-56 (CDR-L2) and 89-97 (CDR-L3) of the light chain according to the Kabat numbering system (Kabat et al., 1987 in *Sequences of Proteins of Immunological Interest*, U.S. Department of Health and Human Services, NIH, USA).

Once synthesized, the DNA encoding an antibody of the invention or fragment thereof may be propagated and expressed according to any of a variety of well-known procedures for nucleic acid excision, ligation, transformation, and transfection using any number of known expression vectors. Thus, in certain embodiments expression of an antibody fragment may be preferred in a prokaryotic host, such as *Escherichia coli* (see, e.g., Pluckthun et al., 1989 *Methods Enzymol.* 178:497-515). In certain other embodiments, expression of the antibody or a fragment thereof may be preferred in a eukaryotic host cell, including yeast (e.g., *Saccharomyces cerevisiae, Schizosaccharomyces pombe*, and *Pichia pastoris*), animal cells (including mammalian cells) or plant cells. Examples of suitable animal cells include, but are not limited to, myeloma (such as a mouse NSO line), COS, CHO, or hybridoma cells. Examples of plant cells include tobacco, corn, soybean, and rice cells.

One or more replicable expression vectors containing DNA encoding an antibody variable and/or constant region may be prepared and used to transform an appropriate cell line, for example, a non-producing myeloma cell line, such as a mouse NSO line or a bacteria, such as *E. coli*, in which production of the antibody will occur. In order to obtain efficient transcription and translation, the DNA sequence in each vector should include appropriate regulatory sequences, particularly a promoter and leader sequence operatively linked to the variable domain sequence. Particular methods for producing antibodies in this way are generally well-known and routinely used. For example, basic molecular biology procedures are described by Maniatis et al. (*Molecular Cloning, A Laboratory Manual*, 2nd ed., Cold Spring Harbor Laboratory, New York, 1989; see also Maniatis et al, 3rd ed., Cold Spring Harbor Laboratory, New York, (2001)). DNA sequencing can be performed as described in Sanger et al. (PNAS 74:5463, (1977)) and the Amersham International plc sequencing handbook, and site directed mutagenesis can be carried out according to methods known in the art (Kramer et al., *Nucleic Acids Res.* 12:9441, (1984); Kunkel *Proc. Natl. Acad. Sci. USA* 82:488-92 (1985); Kunkel et al., *Methods in Enzymol.* 154:367-82 (1987); the Anglian Biotechnology Ltd handbook). Additionally, numerous publications describe techniques suitable for the preparation of antibodies by manipulation of DNA, creation of expression vectors, and transformation and culture of appropriate cells (Mountain A and Adair, J R in *Biotechnology and Genetic Engineering Reviews* (ed. Tombs, M P, 10, Chapter 1, 1992, Intercept, Andover, UK); "Current Protocols in Molecular Biology", 1999, F. M. Ausubel (ed.), Wiley Interscience, New York).

Where it is desired to improve the affinity of antibodies according to the invention containing one or more of the above-mentioned CDRs can be obtained by a number of affinity maturation protocols including maintaining the CDRs (Yang et al., *J. Mol. Biol.*, 254, 392-403, 1995), chain shuffling (Marks et al., *Bio/Technology*, 10, 779-783, 1992), use of mutation strains of *E. coli*. (Low et al., *J. Mol. Biol.*, 250, 350-368, 1996), DNA shuffling (Patten et al., *Curr. Opin. Biotechnol.*, 8, 724-733, 1997), phage display (Thompson et al., *J. Mol. Biol.*, 256, 7-88, 1996) and sexual PCR (Crameri, et al., *Nature*, 391, 288-291, 1998). All of these methods of affinity maturation are discussed by Vaughan et al. (*Nature Biotechnology*, 16, 535-539, 1998).

Other antibodies according to the invention may be obtained by conventional immunization and cell fusion procedures as described herein and known in the art. Monoclonal antibodies of the invention may be generated using a variety of known techniques. In general, monoclonal antibodies that bind to specific antigens may be obtained by methods known to those skilled in the art (see, for example, Kohler et al., *Nature* 256:495, 1975; Coligan et al. (eds.), *Current Protocols in Immunology*, 1:2.5.12.6.7 (John Wiley & Sons 1991); U.S. Pat. Nos. RE 32,011, 4,902,614, 4,543,439, and 4,411,993; *Monoclonal Antibodies, Hybridomas: A New Dimension in Biological Analyses*, Plenum Press, Kennett, McKearn, and Bechtol (eds.) (1980); and *Antibodies: A Laboratory Manual*, Harlow and Lane (eds.), Cold Spring Harbor Laboratory Press (1988); Picksley et al., "Production of monoclonal antibodies against proteins expressed in *E. coli*," in *DNA Cloning 2: Expression Systems*, 2nd Edition, Glover et al. (eds.), page 93 (Oxford University Press 1995)). Antibody fragments may be derived therefrom using any suitable standard technique such as proteolytic digestion, or optionally, by proteolytic digestion (for example, using papain or pepsin) followed by mild reduction of disulfide bonds and alkylation. Alternatively, such fragments may also be generated by recombinant genetic engineering techniques as described herein.

Monoclonal antibodies can be obtained by injecting an animal, for example, a rat, hamster, a rabbit, or preferably a mouse, including for example a transgenic or a knock-out, as known in the art, with an immunogen comprising human sclerostin of SEQ ID NO:1, or a fragment thereof, according to methods known in the art and described herein. The presence of specific antibody production may be monitored after the initial injection and/or after a booster injection by obtaining a serum sample and detecting the presence of an antibody that binds to human sclerostin or peptide using any one of several immunodetection methods known in the art and described herein. From animals producing the desired antibodies, lymphoid cells, most commonly cells from the spleen or lymph node, are removed to obtain B-lymphocytes. The B lymphocytes are then fused with a drug-sensitized myeloma cell fusion partner, preferably one that is syngeneic with the immunized animal and that optionally has other desirable properties (e.g., inability to express endogenous Ig gene products, e.g., P3×63-Ag 8.653 (ATCC No. CRL 1580); NSO, SP20) to produce hybridomas, which are immortal eukaryotic cell lines. The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells but not unfused myeloma cells. A preferred selection media is HAT (hypoxanthine, aminopterin, thymidine). After a sufficient time, usually about one to two weeks, colonies of cells are observed. Single colonies are isolated, and antibodies produced by the cells may be tested for binding activity to human sclerostin, using any one of a variety of immunoassays known in the art and described herein. The hybridomas are cloned (e.g., by limited dilution cloning or by soft agar plaque isolation) and positive clones that produce an antibody specific to sclerostin are selected and cultured. The monoclonal antibodies from the hybridoma cultures may be isolated from the supernatants of hybridoma cultures. An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, Vol. 10, pages 79-104 (The Humana Press, Inc. 1992)). Monoclonal antibodies may be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anticonstant region (light chain or heavy chain) antibody, an anti-idiotype antibody, and a TGF-beta binding protein, or fragment or variant thereof.

An antibody of the present invention may also be a human monoclonal antibody. Human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B cells, fusion of spleen cells from immunized transgenic mice carrying inserted human immunoglobulin genes, isolation from human immunoglobulin V region phage libraries, or other procedures as known in the art and based on the disclosure herein. For example, human monoclonal antibodies may be obtained from transgenic mice that have been engineered to produce specific human antibodies in response to antigenic challenge. Methods for obtaining human antibodies from transgenic mice are described, for example, by Green et al., *Nature Genet.* 7:13, 1994; Lonberg et al., *Nature* 368:856, 1994; Taylor et al., *Int. Immun.* 6:579, 1994; U.S. Pat. No. 5,877,397; Bruggemann et al., 1997 *Curr. Opin. Biotechnol.* 8:455-58; Jakobovits et al., 1995 *Ann. N.Y. Acad. Sci.* 764: 525-35. In this technique, elements of the human heavy and light chain locus are introduced into strains of mice derived from embryonic stem cell lines that contain targeted disruptions of the endogenous heavy chain and light chain loci (see also Bruggemann et al., *Curr. Opin. Biotechnol.* 8:455-58 (1997)). For example, human immunoglobulin transgenes may be mini-gene constructs, or transloci on yeast artificial chromosomes, which undergo B cell-specific DNA rearrangement and hypermutation in the mouse lymphoid tissue. Human monoclonal antibodies may be obtained by immunizing the transgenic mice, which may then produce human antibodies specific for sclerostin. Lymphoid cells of the immunized transgenic mice can be used to produce human antibody-secreting hybridomas according to the methods described herein. Polyclonal sera containing human antibodies may also be obtained from the blood of the immunized animals.

Another method for generating human antibodies of the invention includes immortalizing human peripheral blood cells by EBV transformation. See, e.g., U.S. Pat. No. 4,464,456. Such an immortalized B cell line (or lymphoblastoid cell line) producing a monoclonal antibody that specifically binds to sclerostin can be identified by immunodetection methods as provided herein, for example, an ELISA, and then isolated by standard cloning techniques. The stability of the lymphoblastoid cell line producing an anti-sclerostin antibody may be improved by fusing the transformed cell line with a murine myeloma to produce a mouse-human hybrid cell line according to methods known in the art (see, e.g., Glasky et al., *Hybridoma* 8:377-89 (1989)). Still another method to generate human monoclonal antibodies is in vitro immunization, which includes priming human splenic B cells with human sclerostin, followed by fusion of primed B cells with a heterohybrid fusion partner. See, e.g., Boerner et al., 1991 *J. Immunol.* 147:86-95.

In certain embodiments, a B cell that is producing an anti-human sclerostin antibody is selected and the light chain and heavy chain variable regions are cloned from the B cell according to molecular biology techniques known in the art (WO 92/02551; U.S. Pat. No. 5,627,052; Babcook et al., *Proc. Natl. Acad. Sci. USA* 93:7843-48 (1996)) and described herein. B cells from an immunized animal may be isolated from the spleen, lymph node, or peripheral blood sample by selecting a cell that is producing an antibody that specifically binds to sclerostin. B cells may also be isolated from humans, for example, from a peripheral blood sample. Methods for detecting single B cells that are producing an antibody with the desired specificity are well known in the art, for example, by plaque formation, fluorescence-activated cell sorting, in vitro stimulation followed by detection of specific antibody, and the like. Methods for selection of specific antibody-producing B cells include, for example, preparing a single cell suspension of B cells in soft agar that contains human sclerostin. Binding of the specific antibody produced by the B cell to the antigen results in the formation of a complex, which may be visible as an immunoprecipitate. After the B cells producing the desired antibody are selected, the specific antibody genes may be cloned by isolating and amplifying DNA or mRNA according to methods known in the art and described herein.

An additional method for obtaining antibodies of the invention is by phage display. See, e.g., Winter et al., 1994 *Annu. Rev. Immunol.* 12:433-55; Burton et al, 1994 *Adv. Immunol.* 57:191-280. Human or murine immunoglobulin variable region gene combinatorial libraries may be created in phage vectors that can be screened to select Ig fragments (Fab, $F_v$, sFv, or multimers thereof) that bind specifically to TGF-beta binding protein or variant or fragment thereof. See, e.g., U.S. Pat. No. 5,223,409; Huse et al., 1989 *Science* 246: 1275-81; Sastry et al., *Proc. Natl. Acad. Sci. USA* 86:5728-32 (1989); Alting-Mees et al, *Strategies in Molecular Biology* 3:1-9 (1990); Kang et al., 1991 *Proc. Natl. Acad. Sci. USA* 88:4363-66; Hoogenboom et al, 1992 *J. Molec. Biol.* 227: 381-388; Schlebusch et al, 1997 *Hybridoma* 16:47-52 and references cited therein. For example, a library containing a plurality of polynucleotide sequences encoding Ig variable region fragments may be inserted into the genome of a filamentous bacteriophage, such as M13 or a variant thereof, in frame with the sequence encoding a phage coat protein. A fusion protein may be a fusion of the coat protein with the light chain variable region domain and/or with the heavy chain variable region domain. According to certain embodiments, immunoglobulin Fab fragments may also be displayed on a phage particle (see, e.g., U.S. Pat. No. 5,698,426).

Heavy and light chain immunoglobulin cDNA expression libraries may also be prepared in lambda phage, for example, using λImmunoZap™ (H) and λImmunoZap™ (L) vectors (Stratagene, La Jolla, Calif.). Briefly, mRNA is isolated from a B cell population, and used to create heavy and light chain immunoglobulin cDNA expression libraries in the λImmunoZap(H) and λImmunoZap(L) vectors. These vectors may be screened individually or co-expressed to form Fab fragments or antibodies (see Huse et al, supra; see also Sastry et al, supra). Positive plaques may subsequently be converted to a non-lytic plasmid that allows high level expression of monoclonal antibody fragments from *E. coli*.

In one embodiment, in a hybridoma the variable regions of a gene expressing a monoclonal antibody of interest are amplified using nucleotide primers. These primers may be synthesized by one of ordinary skill in the art, or may be purchased from commercially available sources. (See, e.g., Stratagene (La Jolla, Calif.), which sells primers for mouse and human variable regions including, among others, primers for $V_{Ha}$, $V_{Hb}$, $V_{Hc}$, $V_{Hd}$, $C_{H1}$, $V_L$ and $C_L$ regions.) These primers may be used to amplify heavy or light chain variable regions, which may then be inserted into vectors such as ImmunoZAP™ H or ImmunoZAP™ L (Stratagene), respectively. These vectors may then be introduced into *E. coli*, yeast, or mammalian-based systems for expression. Large amounts of a single-chain protein containing a fusion of the $V_H$ and $V_L$ domains may be produced using these methods (see Bird et al., *Science* 242:423-426, 1988).

Once cells producing antibodies according to the invention have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

Preferably the binding agents specifically bind to sclerostin. As with all binding agents and binding assays, one of skill in this art recognizes that the various moieties to which a binding agent should not detectably bind in order to be therapeutically effective and suitable would be exhaustive and impractical to list. Therefore, for a binding agent disclosed herein, the term "specifically binds" refers to the ability of a binding agent to bind to sclerostin, preferably human sclerostin, with greater affinity than it binds to an unrelated control protein. Preferably the control protein is hen egg white lysozyme. Preferably the binding agents bind to sclerostin with an affinity that is at least, 50, 100, 250, 500, 1000, or 10,000 times greater than the affinity for a control protein. A binding agent may have a binding affinity for human sclerostin of less than or equal to $1\times10^{-7}$M, less than or equal to $1\times10^{-8}$M, less than or equal to $1\times10^{-9}$M, less than or equal to $1\times10^{-7}$M, less than or equal to $1\times10^{-8}$ M, or less than or equal to $1\times10^{-12}$ M.

Affinity may be determined by an affinity ELISA assay. In certain embodiments, affinity may be determined by a BIAcore assay. In certain embodiments, affinity may be determined by a kinetic method. In certain embodiments, affinity may be determined by an equilibrium/solution method. Such methods are described in further detail herein or known in the art.

Sclerostin binding agents of the present invention preferably modulate sclerostin function in the cell-based assay described herein and/or the in vivo assay described herein and/or bind to one or more of the epitopes described herein and/or cross-block the binding of one of the antibodies described in this application and/or are cross-blocked from binding sclerostin by one of the antibodies described in this application. Accordingly such binding agents can be identified using the assays described herein.

In certain embodiments, binding agents are generated by first identifying antibodies that bind to one more of the epitopes provided herein and/or neutralize in the cell-based and/or in vivo assays described herein and/or cross-block the antibodies described in this application and/or are cross-blocked from binding sclerostin by one of the antibodies described in this application. The CDR regions from these antibodies are then used to insert into appropriate biocompatible frameworks to generate sclerostin binding agents. The non-CDR portion of the binding agent may be composed of amino acids, or may be a non-protein molecule. The assays described herein allow the characterization of binding agents. Preferably the binding agents of the present invention are antibodies as defined herein.

It will be understood by one skilled in the art that some proteins, such as antibodies, may undergo a variety of post-translational modifications. The type and extent of these modifications often depends on the host cell line used to express the protein as well as the culture conditions. Such modifications may include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705:129-134, 1995).

Antibodies referred to as Ab-A, Ab-B, Ab-C, Ab-D and Ab-1 are described below. "HC" refers to the heavy chain and "LC" refers to the light chain. For some antibodies below, the CDRs are box shaded and the constant (C) regions are shown in bold italics.

Ab-D

Figure 18:
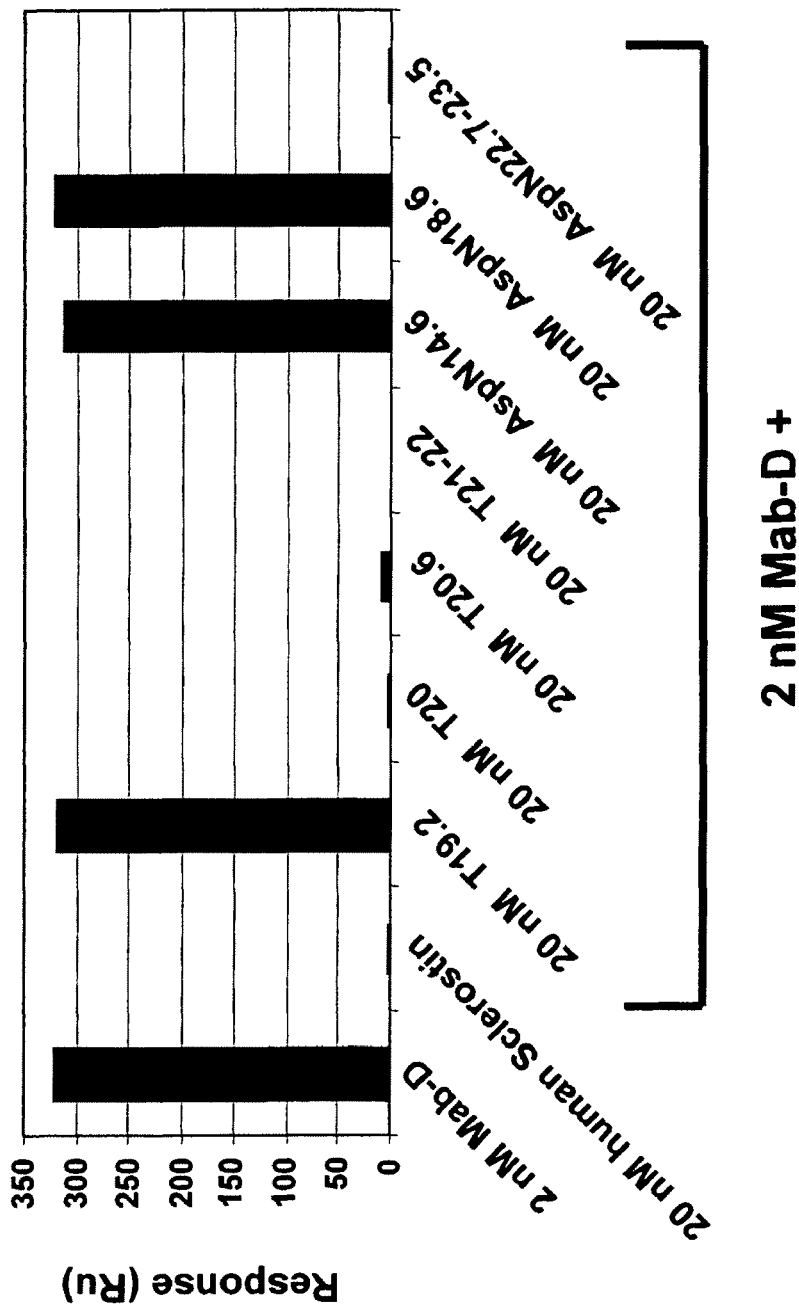
FIG. 18 shows the resonance unit (Ru) signal from Biacore-based "human sclerostin peptide epitope competition binding assay." Relative Mab binding to various human sclerostin-peptides (in solution) versus Mab binding to intact mature form human sclerostin (immobilized on Biacore chip) was assessed. Data shown is for Ab-D. Human sclerostin peptides used were T19.2, T20, T20.6, T21-22, AspN14.6, AspN18.6 and AspN22.7-23.5.

Antibody D (also referred to herein as Ab-D and Mab-D) is a mouse antibody which exhibits high affinity binding to sclerostin. The BIAcore binding pattern of Ab-D is shown in FIG. 18.

The amino acid sequence of the mature form (signal peptide removed) of Ab-D light chain:

```
  1 DVQMIQSPSS LSASLGDIVT MTCQASQGTS INLNWFQQKP GKAPKLLIYG
 51 SSNLEDGVPS RFSGSRYGTD FTLTISSLED EDLATYFCLQ HSYLPYTFGG
101 GTKLEIKRAD AAPTVSIFPP SSEQLTSGGA SVVCFLNNFY PKDINVKWKI
151 DGSERQNGVL NSWTDQDSKD STYSMSSTLT LTKDEYERHN SYTCEATHKT
201 STSPIVKSFN RNEC
```

Nucleic acid sequence encoding the mature form (signal peptide removed) of Ab-D LC is as follows:

```
                                  (SEQ ID NO: 8)
  1 GATGTCCAGA TGATTCAGTC TCCATCCTCC
    CTGTCTGCAT CTTTGGGAGA
 51 CATAGTCACC ATGACTTGCC AGGCAAGTCA
    GGGCACTAGC ATTAATTTAA
101 ACTGGTTTCA GCAAAAACCA GGGAAGGCTC
    CTAAGCTCCT GATCTATGGT
151 TCAAGCAACT TGGAAGATGG GGTCCCATCA
    AGGTTCAGTG GCAGTAGATA
201 TGGGACAGAT TTCACTCTCA CCATCAGCAG
    CCTGGAGGAT GAAGATCTGG
251 CAACTTATTT CTGTCTACAA CATAGTTATC
    TCCCGTACAC GTTCGGAGGG
301 GGGACCAAGC TGGAAATAAA ACGGGCTGAT
    GCTGCACCAA CTGTATCCAT
351 CTTCCCACCA TCCAGTGAGC AGTTAACATC
    TGGAGGTGCC TCAGTCGTGT
401 GCTTCTTGAA CAACTTCTAC CCCAAAGACA
    TCAATGTCAA GTGGAAGATT
451 GATGGCAGTG AACGACAAAA TGGCGTCCTG
    AACAGTTGGA CTGATCAGGA
501 CAGCAAAGAC AGCACCTACA GCATGAGCAG
    CACCCTCACG TTGACCAAGG
551 ACGAGTATGA ACGACATAAC AGCTATACCT
    GTGAGGCCAC TCACAAGACA
601 TCAACTTCAC CCATTGTCAA GAGCTTCAAC
    AGGAATGAGT GTTAG
```

The amino acid sequence of Ab-D LC including signal peptide is as follows:

```
                                  (SEQ ID NO: 9)
  1 MNTRAPAEFL GFLLLWFLGA RCDVQMIQSP
    SSLSASLGDI VTMTCQASQG
 51 TSINLNWFQQ KPGKAPKLLI YGSSNLEDGV
    PSRFSGSRYG TDFTLTISSL
101 EDEDLATYFC LQHSYLPYTF GGGTKLEIKR
    ADAAPTVSIF PPSSEQLTSG
151 GASVVCFLNN FYPKDINVKW KIDGSERQNG
    VLNSWTDQDS KDSTYSMSST
201 LTLTKDEYER HNSYTCEATH KTSTSPIVKS
    FNRNEC
```

(SEQ ID NO: 7)

Nucleic acid sequence of Ab-D LC including signal peptide encoding sequence:

```
                                  (SEQ ID NO: 10)
  1 ATGAACACGA GGGCCCCTGC TGAGTTCCTT
    GGGTTCCTGT TGCTCTGGTT
 51 TTTAGGTGCC AGATGTGATG TCCAGATGAT
    TCAGTCTCCA TCCTCCCTGT
101 CTGCATCTTT GGGAGACATA GTCACCATGA
    CTTGCCAGGC AAGTCAGGGC
151 ACTAGCATTA ATTTAAACTG GTTTCAGCAA
    AAACCAGGGA AGGCTCCTAA
201 GCTCCTGATC TATGGTTCAA GCAACTTGGA
    AGATGGGTC CCATCAAGGT
251 TCAGTGGCAG TAGATATGGG ACAGATTTCA
    CTCTCACCAT CAGCAGCCTG
301 GAGGATGAAG ATCTGGCAAC TTATTTCTGT
    CTACAACATA GTTATCTCCC
351 GTACACGTTC GGAGGGGGGA CCAAGCTGGA
    AATAAAACGG GCTGATGCTG
401 CACCAACTGT ATCCATCTTC CCACCATCCA
    GTGAGCAGTT AACATCTGGA
451 GGTGCCTCAG TCGTGTGCTT CTTGAACAAC
    TTCTACCCCA AAGACATCAA
501 TGTCAAGTGG AAGATTGATG GCAGTGAACG
    ACAAAATGGC GTCCTGAACA
551 GTTGGACTGA TCAGGACAGC AAAGACAGCA
    CCTACAGCAT GAGCAGCACC
601 CTCACGTTGA CCAAGGACGA GTATGAACGA
    CATAACAGCT ATACCTGTGA
651 GGCCACTCAC AAGACATCAA CTTCACCCAT
    TGTCAAGAGC TTCAACAGGA
701 ATGAGTGTTA G
```

The amino acid sequence of the mature form (signal peptide removed) of Ab-D HC heavy chain is as follows:

(SEQ ID NO: 11)

```
  1 EVQLQQSGPE LVTPGASVKI SCKASGYTFT DHYMSWVKQS HGKSLEWIGD
 51 INPYSGETTY NQKFKGTATL TVDKSSSIAY MEIRGLTSED SAVYYCARDD
101 YDASPFAYWG QGTLVTVSAA KTTPPSVYPL APGSAAQTNS MVTLGCLVKG
151 YFPEPVTVTW NSGSLSSGVH TFPAVLQSDL YTLSSSVTVP SSTWPSETVT
201 CNVAHPASST KVDKKIVPRD CGCKPCICTV PEVSSVFIFP PKPKDVLTIT
251 LTPKVTCVVV DISKDDPEVQ FSWFVDDVEV HTAQTQPREE QFNSTFRSVS
301 ELPIMHQDWL NGKEFKCRVN SPAFPAPIEK TISKTKGRPK APQVYTIPPP
351 KEQMAKDKVS LTCMITDFFP EDITVEWQWN GQPAENYKNT QPIMDTDGSY
401 FIYSKLNVQK SNWEAGNTFT CSVLHEGLHN HHTEKSLSHS PGK
```

The nucleic acid sequence encoding the mature form (signal peptide removed) of Ab-D HC is:

(SEQ ID NO: 12)

```
   1 GAGGTCCAGC TGCAACAGTC TGGACCTGAA
     CTGGTGACGC CTGGGGCTTC
  51 AGTGAAGATA TCTTGTAAGG CTTCTGGATA
     CACATTCACT GACCACTACA
 101 TGAGCTGGGT GAAGCAGAGT CATGGAAAAA
     GCCTTGAGTG GATTGGAGAT
 151 ATTAATCCCT ATTCTGGTGA AACTACCTAC
     AACCAGAAGT TCAAGGGCAC
 201 GGCCACATTG ACTGTAGACA AGTCTTCCAG
     TATAGCCTAC ATGGAGATCC
 251 GCGGCCTGAC ATCTGAGGAC TCTGCAGTCT
     ATTACTGTGC AAGAGATGAT
 301 TACGACGCCT CTCCGTTTGC TTACTGGGGC
     CAAGGGACTC TGGTCACTGT
 351 CTCTGCAGCC AAAACGACAC CCCCATCTGT
     CTATCCACTG GCCCCTGGAT
 401 CTGCTGCCCA AACTAACTCC ATGGTGACCC
     TGGGATGCCT GGTCAAGGGC
 451 TATTTCCCTG AGCCAGTGAC AGTGACCTGG
     AACTCTGGAT CCCTGTCCAG
 501 CGGTGTGCAC ACCTTCCCAG CTGTCCTGCA
     GTCTGACCTC TACACTCTGA
 551 GCAGCTCAGT GACTGTCCCC TCCAGCACCT
     GGCCCAGCGA GACCGTCACC
 601 TGCAACGTTG CCCACCCGGC CAGCAGCACC
     AAGGTGGACA AGAAAATTGT
 651 GCCCAGGGAT TGTGGTTGTA AGCCTTGCAT
     ATGTACAGTC CCAGAAGTAT
 701 CATCTGTCTT CATCTTCCCC CCAAAGCCCA
     AGGATGTGCT CACCATTACT
 751 CTGACTCCTA AGGTCACGTG TGTTGTGGTA
     GACATCAGCA AGGATGATCC
 801 CGAGGTCCAG TTCAGCTGGT TTGTAGATGA
     TGTGGAGGTC CACACAGCTC
 851 AGACGCAACC CCGGGAGGAG CAGTTCAACA
     GCACTTTCCG CTCAGTCAGT
 901 GAACTTCCCA TCATGCACCA GGACTGGCTC
     AATGGCAAGG AGTTCAAATG
 951 CAGGGTCAAC AGTCCAGCTT TCCCTGCCCC
     CATCGAGAAA ACCATCTCCA
1001 AAACCAAAGG CAGACCGAAG GCTCCACAGG
     TGTACACCAT TCCACCTCCC
1051 AAGGAGCAGA TGGCCAAGGA TAAAGTCAGT
     CTGACCTGCA TGATAACAGA
1101 CTTCTTCCCT GAAGACATTA CTGTGGAGTG
     GCAGTGGAAT GGGCAGCCAG
1151 CGGAGAACTA CAAGAACACT CAGCCCATCA
     TGGACACAGA TGGCTCTTAC
1201 TTCATCTACA GCAAGCTCAA TGTGCAGAAG
     AGCAACTGGG AGGCAGGAAA
1251 TACTTTCACC TGCTCTGTGT TACATGAGGG
     CCTGCACAAC CACCATACTG
1301 AGAAGAGCCT CTCCCACTCT CCTGGTAAAT
     GA
```

The amino acid sequence of Ab-D HC including signal peptide is:

(SEQ ID NO: 13)

```
  1 MRCRWIFLFL LSGTAGVLSE VQLQQSGPEL
    VTPGASVKIS CKASGYTFTD
 51 HYMSWVKQSH GKSLEWIGDI NPYSGETTYN
    QKFKGTATLT VDKSSSIAYM
101 EIRGLTSEDS AVYYCARDDY DASPFAYWGQ
    GTLVTVSAAK TTPPSVYPLA
151 PGSAAQTNSM VTLGCLVKGY FPEPVTVTWN
    SGSLSSGVHT FPAVLQSDLY
201 TLSSSVTVPS STWPSETVTC NVAHPASSTK
    VDKKIVPRDC GCKPCICTVP
251 EVSSVFIFPP KPKDVLTITL TPKVTCVVVD
    ISKDDPEVQF SWFVDDVEVH
301 TAQTQPREEQ FNSTFRSVSE LPIMHQDWLN
    GKEFKCRVNS PAFPAPIEKT
351 ISKTKGRPKA PQVYTIPPPK EQMAKDKVSL
    TCMITDFFPE DITVEWQWNG
401 QPAENYKNTQ PIMDTDGSYF IYSKLNVQKS
    NWEAGNTFTC SVLHEGLHNH
451 HTEKSLSHSP GK
```

The nucleic acid sequence of Ab-D HC including signal peptide encoding sequence is:

(SEQ ID NO: 14)

```
   1  ATGAGATGCA GGTGGATCTT TCTCTTTCTC
      CTGTCAGGAA CTGCAGGTGT
  51  CCTCTCTGAG GTCCAGCTGC AACAGTCTGG
      ACCTGAACTG GTGACGCCTG
 101  GGGCTTCAGT GAAGATATCT TGTAAGGCTT
      CTGGATACAC ATTCACTGAC
 151  CACTACATGA GCTGGGTGAA GCAGAGTCAT
      GGAAAAAGCC TTGAGTGGAT
 201  TGGAGATATT AATCCCTATT CTGGTGAAAC
      TACCTACAAC CAGAAGTTCA
 251  AGGGCACGGC CACATTGACT GTAGACAAGT
      CTTCCAGTAT AGCCTACATG
 301  GAGATCCGCG GCCTGACATC TGAGGACTCT
      GCAGTCTATT ACTGTGCAAG
 351  AGATGATTAC GACGCCTCTC CGTTTGCTTA
      CTGGGGCCAA GGGACTCTGG
 401  TCACTGTCTC TGCAGCCAAA ACGACACCCC
      CATCTGTCTA TCCACTGGCC
 451  CCTGGATCTG CTGCCCAAAC TAACTCCATG
      GTGACCCTGG GATGCCTGGT
 501  CAAGGGCTAT TTCCCTGAGC CAGTGACAGT
      GACCTGGAAC TCTGGATCCC
 551  TGTCCAGCGG TGTGCACACC TTCCCAGCTG
      TCCTGCAGTC TGACCTCTAC
 601  ACTCTGAGCA GCTCAGTGAC TGTCCCCTCC
      AGCACCTGGC CCAGCGAGAC
 651  CGTCACCTGC AACGTTGCCC ACCCGGCCAG
      CAGCACCAAG GTGGACAAGA
 701  AAATTGTGCC CAGGGATTGT GGTTGTAAGC
      CTTGCATATG TACAGTCCCA
 751  GAAGTATCAT CTGTCTTCAT CTTCCCCCCA
      AAGCCCAAGG ATGTGCTCAC
 801  CATTACTCTG ACTCCTAAGG TCACGTGTGT
      TGTGGTAGAC ATCAGCAAGG
 851  ATGATCCCGA GGTCCAGTTC AGCTGGTTTG
      TAGATGATGT GGAGGTGCAC
 901  ACAGCTCAGA CGCAACCCCG GGAGGAGCAG
      TTCAACAGCA CTTTCCGCTC
 951  AGTCAGTGAA CTTCCCATCA TGCACCAGGA
      CTGGCTCAAT GGCAAGGAGT
1001  TCAAATGCAG GGTCAACAGT CCAGCTTTCC
      CTGCCCCCAT CGAGAAAACC
1051  ATCTCCAAAA CCAAAGGCAG ACCGAAGGCT
      CCACAGGTGT ACACCATTCC
1101  ACCTCCCAAG GAGCAGATGG CCAAGGATAA
      AGTCAGTCTG ACCTGCATGA
1151  TAACAGACTT CTTCCCTGAA GACATTACTG
      TGGAGTGGCA GTGGAATGGG
1201  CAGCCAGCGG AGAACTACAA GAACACTCAG
      CCCATCATGG ACACAGATGG
1251  CTCTTACTTC ATCTACAGCA AGCTCAATGT
      GCAGAAGAGC AACTGGGAGG
1301  CAGGAAATAC TTTCACCTGC TCTGTGTTAC
      ATGAGGGCCT GCACAACCAC
1351  CATACTGAGA AGAGCCTCTC CCACTCTCCT
      GGTAAATGA
```

The CDR (complementarity determining region) sequences in the variable region of the heavy chain of Ab-D are as follows:

| CDR-H1: | DHYMS | (SEQ ID NO: 39) |
| CDR-H2: | DINPYSGETTYNQKFKG | (SEQ ID NO: 40) |
| CDR-H3: | DDYDASPFAY | (SEQ ID NO: 41) |

The light chain variable region CDR sequences of Ab-D are:

| CDR-L1: | QASQGTSINLN | (SEQ ID NO: 42) |
| CDR-L2: | GSSNLED | (SEQ ID NO: 43) |
| CDR-L3: | LQHSYLPYT | (SEQ ID NO: 44) |

Ab-C

Figure 17:
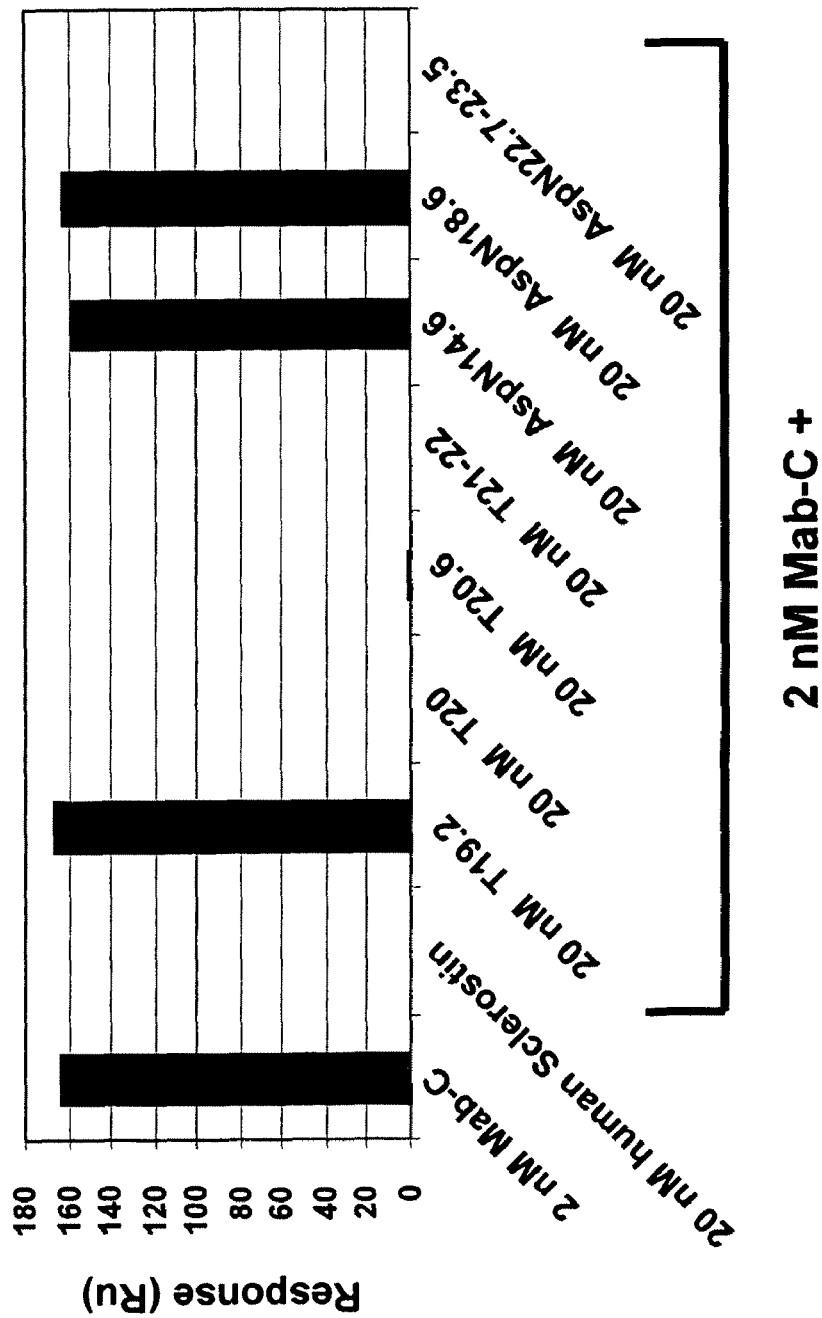
FIG. 17 shows the resonance unit (Ru) signal from the Biacore-based "human sclerostin peptide epitope competition binding assay." Relative Mab binding to various human sclerostin-peptides (in solution) versus Mab binding to intact mature form human sclerostin (immobilized on Biacore chip) was assessed. Data shown is for Ab-C. Human sclerostin peptides used were T19.2, T20, T20.6, T21-22, AspN14.6, AspN18.6 and AspN22.7-23.5.

Antibody C (also referred to herein as Ab-C and Mab-C) is a mouse antibody which exhibits high affinity binding to sclerostin. The BIAcore binding pattern of Ab-C is shown in FIG. 17. The amino acid sequence of the mature form (signal peptide removed) of Ab-C Light Chain is as follows:

(SEQ ID NO: 15)

```
  1 DIVLTQSPAS LTVSLGLRAT ISCKASQSVD YDGDSYMNWY QQKPGQPPKL
 51 LIYAASNLES GIPARFSGNG SGTDFTLNIH PVEEEDAVTY YCQQSNEDPW
101 TFGGGTKLEI KRADAAPTVS IFPPSSEQLT SGGASVVCFL NNFYPKDINV
151 KWKIDGSERQ NGVLNSWTDQ DSKDSTYSMS STLTLTKDEY ERHNSYTCEA
201 THKTSTSPIV KSFNRNEC
```

The nucleic acid sequence encoding the mature form (signal peptide removed) of Ab-C LC is:

(SEQ ID NO: 16)
```
  1  GACATTGTGC TGACCCAATC TCCAGCTTCT
     TTGACTGTGT CTCTAGGCCT
 51  GAGGGCCACC ATCTCCTGCA AGGCCAGCCA
     AAGTGTTGAT TATGATGGTG
101  ATAGTTATAT GAACTGGTAC CAGCAGAAAC
     CAGGACAGCC ACCCAAACTC
151  CTCATCTATG CTGCATCCAA TCTAGAATCT
     GGGATCCCAG CCAGGTTTAG
201  TGGCAATGGG TCTGGGACAG ACTTCACCCT
     CAACATCCAT CCTGTGGAGG
251  AGGAGGATGC TGTAACCTAT TACTGTCAAC
     AAAGTAATGA GGATCCGTGG
301  ACGTTCGGTG GAGGCACCAA GCTGGAAATC
     AAACGGGCTG ATGCTGCACC
351  AACTGTATCC ATCTTCCCAC CATCCAGTGA
     GCAGTTAACA TCTGGAGGTG
401  CCTCAGTCGT GTGCTTCTTG AACAACTTCT
     ACCCCAAAGA CATCAATGTC
451  AAGTGGAAGA TTGATGGCAG TGAACGACAA
     AATGGCGTCC TGAACAGTTG
501  GACTGATCAG GACAGCAAAG ACAGCACCTA
     CAGCATGAGC AGCACCCTCA
551  CGTTGACCAA GGACGAGTAT GAACGACATA
     ACAGCTATAC CTGTGAGGCC
601  ACTCACAAGA CATCAACTTC ACCCATTGTC
     AAGAGCTTCA ACAGGAATGA
651  GTGTTAG
```

The amino acid sequence of Ab-C LC including signal peptide is:

(SEQ ID NO: 17)
```
  1  METDTILLWV LLLWVPGSTG DIVLTQSPAS
     LTVSLGLRAT ISCKASQSVD
 51  YDGDSYMNWY QQKPGQPPKL LIYAASNLES
     GIPARFSGNG SGTDFTLNIH
101  PVEEEDAVTY YCQQSNEDPW TFGGGTKLEI
     KRADAAPTVS IFPPSSEQLT
```

-continued
```
151  SGGASVVCFL NNFYPKDINV KWKIDGSERQ
     NGVLNSWTDQ DSKDSTYSMS
201  STLTLTKDEY ERHNSYTCEA THKTSTSPIV
     KSFNRNEC
```

The nucleic acid sequence of Ab-C LC including signal peptide encoding sequence is:

(SEQ ID NO: 18)
```
  1  ATGGAGACAG ACACAATCCT GCTATGGGTG
     CTGCTGCTCT GGGTTCCAGG
 51  CTCCACTGGT GACATTGTGC TGACCCAATC
     TCCAGCTTCT TTGACTGTGT
101  CTCTAGGCCT GAGGGCCACC ATCTCCTGCA
     AGGCCAGCCA AAGTGTTGAT
151  TATGATGGTG ATAGTTATAT GAACTGGTAC
     CAGCAGAAAC CAGGACAGCC
201  ACCCAAACTC CTCATCTATG CTGCATCCAA
     TCTAGAATCT GGGATCCCAG
251  CCAGGTTTAG TGGCAATGGG TCTGGGACAG
     ACTTCACCCT CAACATCCAT
301  CCTGTGGAGG AGGAGGATGC TGTAACCTAT
     TACTGTCAAC AAAGTAATGA
351  GGATCCGTGG ACGTTCGGTG GAGGCACCAA
     GCTGGAAATC AAACGGGCTG
401  ATGCTGCACC AACTGTATCC ATCTTCCCAC
     CATCCAGTGA GCAGTTAACA
451  TCTGGAGGTG CCTCAGTCGT GTGCTTCTTG
     AACAACTTCT ACCCCAAAGA
501  CATCAATGTC AAGTGGAAGA TTGATGGCAG
     TGAACGACAA AATGGCGTCC
551  TGAACAGTTG GACTGATCAG GACAGCAAAG
     ACAGCACCTA CAGCATGAGC
601  AGCACCCTCA CGTTGACCAA GGACGAGTAT
     GAACGACATA ACAGCTATAC
651  CTGTGAGGCC ACTCACAAGA CATCAACTTC
     ACCCATTGTC AAGAGCTTCA
701  ACAGGAATGA GTGTTAG
```

Ab-C Heavy Chain

The amino acid sequence of the mature form (signal peptide removed) of Ab-C HC is:

(SEQ ID NO: 19)
```
  1  EVQLQQSGPE LVKPGTSVKM SCKASGYTFT DCYMNWVKQS HGKSLEWIGD
 51  INPFNGGTTY NQKFKGKATL TVDKSSSTAY MQLNSLTSDD SAVYYCARSH
101  YYFDGRVPWD AMDYWGQGTS VTVSSAKTTP PSVYPLAPGS AAQTNSMVTL
151  GCLVKGYFPE PVTVTWNSGS LSSGVHTFPA VLQSDLYTLS SSVTVPSSTW
201  PSETVTCNVA HPASSTKVDK KIVPRDCGCK PCICTVPEVS SVFIFPPKPK
251  DVLTITLTPK VTCVVVDISK DDPEVQFSWF VDDVEVHTAQ TQPREEQFNS
301  TFRSVSELPI MHQDWLNGKE FKCRVNSAAF PAPIEKTISK TKGRPKAPQV
351  YTIPPPKEQM AKDKVSLTCM ITDFFPEDIT VEWQWNGQPA ENYKNTQPIM
401  DTDGSYFIYS KLNVQKSNWE AGNTFTCSVL HEGLHNHHTE KSLSHSPGK
```

The nucleic acid sequence encoding the mature form (signal peptide removed) of Ab-C HC is as follows:

(SEQ ID NO: 20)

```
   1  GAGGTCCAGC TGCAACAATC TGGACCTGAG
      CTGGTGAAGC CTGGGACTTC
  51  AGTGAAGATG TCCTGTAAGG CTTCTGGATA
      CACATTCACT GACTGCTACA
 101  TGAACTGGGT GAAGCAGAGC CATGGGAAGA
      GCCTTGAATG GATTGGAGAT
 151  ATTAATCCTT TCAACGGTGG TACTACCTAC
      AACCAGAAGT TCAAGGGCAA
 201  GGCCACATTG ACTGTAGACA AATCCTCCAG
      CACAGCCTAC ATGCAGCTCA
 251  ACAGCCTGAC ATCTGACGAC TCTGCAGTCT
      ATTACTGTGC AAGATCCCAT
 301  TATTACTTCG ATGGTAGAGT CCCTTGGGAT
      GCTATGGACT ACTGGGGTCA
 351  AGGAACCTCA GTCACCGTCT CCTCAGCCAA
      AACGACACCC CCATCTGTCT
 401  ATCCACTGGC CCCTGGATCT GCTGCCCAAA
      CTAACTCCAT GGTGACCCTG
 451  GGATGCCTGG TCAAGGGCTA TTTCCCTGAG
      CCAGTGACAG TGACCTGGAA
 501  CTCTGGATCC CTGTCCAGCG GTGTGCACAC
      CTTCCCAGCT GTCCTGCAGT
 551  CTGACCTCTA CACTCTGAGC AGCTCAGTGA
      CTGTCCCCTC CAGCACCTGG
 601  CCCAGCGAGA CCGTCACCTG CAACGTTGCC
      CACCCGGCCA GCAGCACCAA
 651  GGTGGACAAG AAAATTGTGC CCAGGGATTG
      TGGTTGTAAG CCTTGCATAT
 701  GTACAGTCCC AGAAGTATCA TCTGTCTTCA
      TCTTCCCCCC AAAGCCCAAG
 751  GATGTGCTCA CCATTACTCT GACTCCTAAG
      GTCACGTGTG TTGTGGTAGA
 801  CATCAGCAAG GATGATCCCG AGGTCCAGTT
      CAGCTGGTTT GTAGATGATG
 851  TGGAGGTGCA CACAGCTCAG ACGCAACCCC
      GGGAGGAGCA GTTCAACAGC
 901  ACTTTCCGCT CAGTCAGTGA ACTTCCCATC
      ATGCACCAGG ACTGGCTCAA
 951  TGGCAAGGAG TTCAAATGCA GGGTCAACAG
      TGCAGCTTTC CCTGCCCCCA
1001  TCGAGAAAAC CATCTCCAAA ACCAAAGGCA
      GACCGAAGGC TCCACAGGTG
1051  TACACCATTC CACCTCCCAA GGAGCAGATG
      GCCAAGGATA AAGTCAGTCT
1101  GACCTGCATG ATAACAGACT TCTTCCCTGA
      AGACATTACT GTGGAGTGGC
1151  AGTGGAATGG GCAGCCAGCG GAGAACTACA
      AGAACACTCA GCCCATCATG
1201  GACACAGATG GCTCTTACTT CATCTACAGC
      AAGCTCAATG TGCAGAAGAG
```

-continued

```
1251  CAACTGGGAG GCAGGAAATA CTTTCACCTG
      CTCTGTGTTA CATGAGGGCC
1301  TGCACAACCA CCATACTGAG AAGAGCCTCT
      CCCACTCTCC TGGTAAATGA
```

The amino acid sequence of Ab-C HC including signal peptide is:

(SEQ ID NO: 21)

```
   1  MGWNWIFLFL LSGTAGVYSE VQLQQSGPEL
      VKPGTSVKMS CKASGYTFTD
  51  CYMNWVKQSH GKSLEWIGDI NPFNGGTTYN
      QKFKGKATLT VDKSSSTAYM
 101  QLNSLTSDDS AVYYCARSHY YFDGRVPWDA
      MDYWGQGTSV TVSSAKTTPP
 151  SVYPLAPGSA AQTNSMVTLG CLVKGYFPEP
      VTVTWNSGSL SSGVHTFPAV
 201  LQSDLYTLSS SVTVPSSTWP SETVTCNVAH
      PASSTKVDKK IVPRDCGCKP
 251  CICTVPEVSS VFIFPPKPKD VLTITLTPKV
      TCVVVDISKD DPEVQFSWFV
 301  DDVEVHTAQT QPREEQFNST FRSVSELPIM
      HQDWLNGKEF KCRVNSAAFP
 351  APIEKTISKT KGRPKAPQVY TIPPPKEQMA
      KDKVSLTCMI TDFFPEDITV
 401  EWQWNGQPAE NYKNTQPIMD TDGSYFIYSK
      LNVQKSNWEA GNTFTCSVLH
 451  EGLHNHHTEK SLSHSPGK
```

The nucleic acid sequence of Ab-C HC including signal peptide encoding sequence is:

(SEQ ID NO: 22)

```
   1  ATGGGATGGA ACTGGATCTT TCTCTTCCTC
      TTGTCAGGAA CTGCAGGTGT
  51  CTACTCTGAG GTCCAGCTGC AACAATCTGG
      ACCTGAGCTG GTGAAGCCTG
 101  GGACTTCAGT GAAGATGTCC TGTAAGGCTT
      CTGGATACAC ATTCACTGAC
 151  TGCTACATGA ACTGGGTGAA GCAGAGCCAT
      GGGAAGAGCC TTGAATGGAT
 201  TGGAGATATT AATCCTTTCA ACGGTGGTAC
      TACCTACAAC CAGAAGTTCA
 251  AGGGCAAGGC CACATTGACT GTAGACAAAT
      CCTCCAGCAC AGCCTACATG
 301  CAGCTCAACA GCCTGACATC TGACGACTCT
      GCAGTCTATT ACTGTGCAAG
 351  ATCCCATTAT TACTTCGATG GTAGAGTCCC
      TTGGGATGCT ATGGACTACT
 401  GGGGTCAAGG AACCTCAGTC ACCGTCTCCT
      CAGCCAAAAC GACACCCCCA
 451  TCTGTCTATC CACTGGCCCC TGGATCTGCT
      GCCCAAACTA ACTCCATGGT
 501  GACCCTGGGA TGCCTGGTCA AGGGCTATTT
      CCCTGAGCCA GTGACAGTGA
```

-continued

```
551  CCTGGAACTC TGGATCCCTG TCCAGCGGTG
     TGCACACCTT CCCAGCTGTC
601  CTGCAGTCTG ACCTCTACAC TCTGAGCAGC
     TCAGTGACTG TCCCCTCCAG
651  CACCTGGCCC AGCGAGACCG TCACCTGCAA
     CGTTGCCCAC CCGGCCAGCA
701  GCACCAAGGT GGACAAGAAA ATTGTGCCCA
     GGGATTGTGG TTGTAAGCCT
751  TGCATATGTA CAGTCCCAGA AGTATCATCT
     GTCTTCATCT TCCCCCCAAA
801  GCCCAAGGAT GTGCTCACCA TTACTCTGAC
     TCCTAAGGTC ACGTGTGTTG
851  TGGTAGACAT CAGCAAGGAT GATCCCGAGG
     TCCAGTTCAG CTGGTTTGTA
901  GATGATGTGG AGGTGCACAC AGCTCAGACG
     CAACCCCGGG AGGAGCAGTT
951  CAACAGCACT TTCCGCTCAG TCAGTGAACT
     TCCCATCATG CACCAGGACT
1001 GGCTCAATGG CAAGGAGTTC AAATGCAGGG
     TCAACAGTGC AGCTTTCCCT
```

-continued

CDR-H3: SHYYFDGRVPWDAMDY (SEQ ID NO: 47)

The light chain variable region CDR sequences of Ab-C are:

CDR-L1: KASQSVDYDGDSYMN (SEQ ID NO: 48)

CDR-L2: AASNLES (SEQ ID NO: 49)

CDR-L3: QQSNEDPWT (SEQ ID NO: 50)

Figure 15:
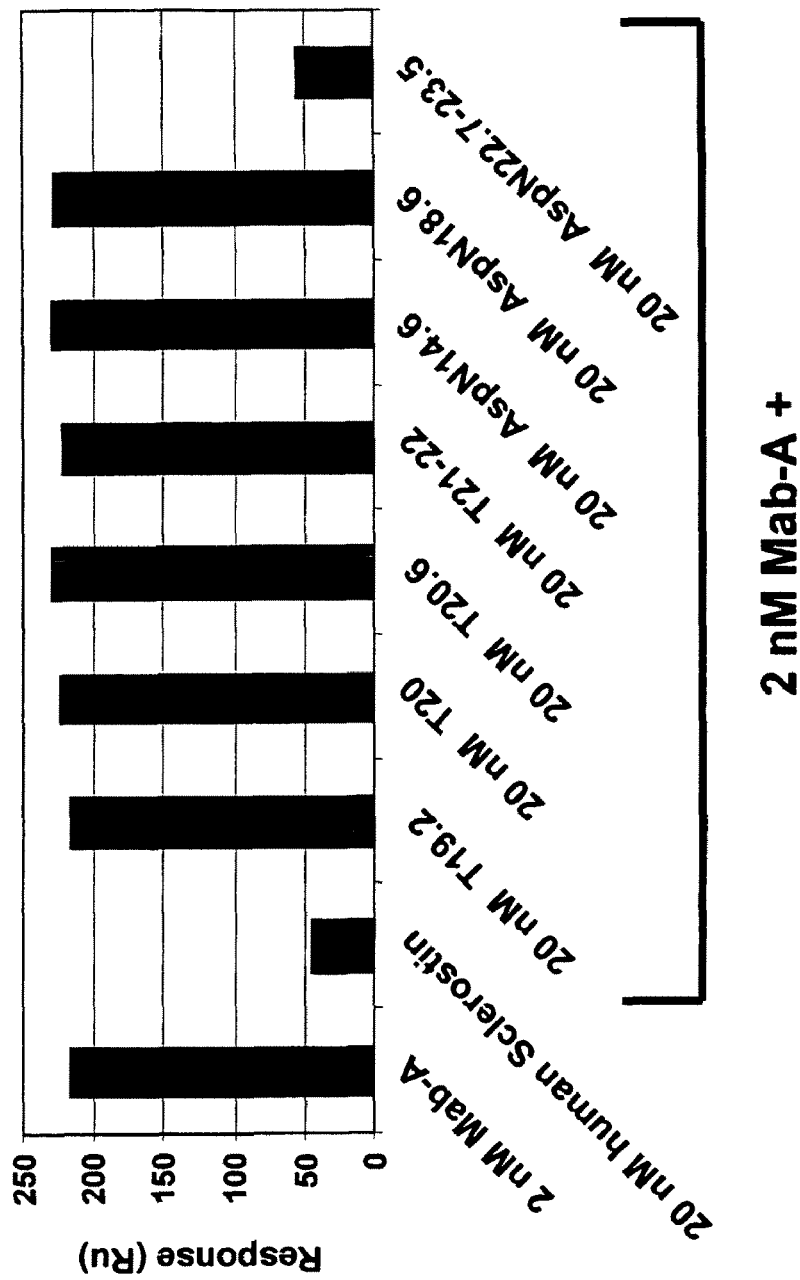
FIG. 15 shows the resonance unit (Ru) signal from the Biacore-based "human sclerostin peptide epitope competition binding assay." Relative Mab binding to various human sclerostin-peptides (in solution) versus Mab binding to intact mature form human sclerostin (immobilized on Biacore chip) was assessed. Data shown is for Ab-A. Human sclerostin peptides used were T19.2, T20, T20.6, T21-22, AspN14.6, AspN18.6 and AspN22.7-23.5.

Antibody A (also referred to herein as Ab-A and Mab-A) is a rabbit-mouse chimeric antibody which exhibits high affinity binding to sclerostin. The BIAcore binding pattern of Ab-A is shown in FIG. 15.

Ab-A Light Chain

The amino acid sequence of the mature form (signal peptide removed) of Ab-A LC:

(SEQ ID NO: 23)
```
  1 AQVLTQTPAS VSAAVGGTVT INCQSSQSVY DNNWLAWFQQ KPGQPPKLLI
 51 YDASDLASGV PSRFSGSGSG TQFTLTISGV QCADAATYYC QGAYNDVIYA
101 FGGGTEVVVK RTDAAPTVSI FPPSSEQLTS GGASVVCFLN NFYPKDINVK
151 WKIDGSERQN GVLNSWTDQD SKDSTYSMSS TLTLTKDEYE RHNSYTCEAT
201 HKTSTSPIVK SFNRNEC
```

-continued

```
1051 GCCCCCATCG AGAAAACCAT CTCCAAAACC
     AAAGGCAGAC CGAAGGCTCC
1101 ACAGGTGTAC ACCATTCCAC CTCCCAAGGA
     GCAGATGGCC AAGGATAAAG
1151 TCAGTCTGAC CTGCATGATA ACAGACTTCT
     TCCCTGAAGA CATTACTGTG
1201 GAGTGGCAGT GGAATGGGCA GCCAGCGGAG
     AACTACAAGA ACACTCAGCC
1251 CATCATGGAC ACAGATGGCT CTTACTTCAT
     CTACAGCAAG CTCAATGTGC
1301 AGAAGAGCAA CTGGGAGGCA GGAAATACTT
     TCACCTGCTC TGTGTTACAT
1351 GAGGGCCTGC ACAACCACCA TACTGAGAAG
     AGCCTCTCCC ACTCTCCTGG
1401 TAAATGA
```

The CDR (complementarity determining region) sequences in the variable region of the heavy chain of Ab-C are as follows:

CDR-H1: DCYMN (SEQ ID NO: 45)

CDR-H2: DINPFNGGTTYNQKFKG (SEQ ID NO: 46)

The nucleic acid sequence encoding the mature form (signal peptide removed) of Ab-A LC:

(SEQ ID NO: 24)
```
  1 GCGCAAGTGC TGACCCAGAC TCCAGCCTCC
    GTGTCTGCAG CTGTGGGAGG
 51 CACAGTCACC ATCAATTGCC AGTCCAGTCA
    GAGTGTTTAT GATAACAACT
101 GGTTAGCCTG GTTTCAGCAG AAACCAGGGC
    AGCCTCCCAA GCTCCTGATT
151 TATGATGCAT CCGATCTGGC ATCTGGGGTC
    CCATCGCGGT TCAGTGGCAG
201 TGGATCTGGG ACACAGTTCA CTCTCACCAT
    CAGCGGCGTG CAGTGTGCCG
251 ATGCTGCCAC TTACTACTGT CAAGGCGCTT
    ATAATGATGT TATTTATGCT
301 TTCGGCGGAG GGACCGAGGT GGTGGTCAAA
    CGTACGGATG CTGCACCAAC
351 TGTATCCATC TTCCCACCAT CCAGTGAGCA
    GTTAACATCT GGAGGTGCCT
401 CAGTCGTGTG CTTCTTGAAC AACTTCTACC
    CCAAAGACAT CAATGTCAAG
451 TGGAAGATTG ATGGCAGTGA ACGACAAAAT
    GGCGTCCTGA ACAGTTGGAC
```

```
501  TGATCAGGAC AGCAAAGACA GCACCTACAG
     CATGAGCAGC ACCCTCACGT
551  TGACCAAGGA CGAGTATGAA CGACATAACA
     GCTATACCTG TGAGGCCACT
601  CACAAGACAT CAACTTCACC CATTGTCAAG
     AGCTTCAACA GGAATGAGTG
651  TTAG
```

The amino acid sequence of Ab-A LC including signal peptide is:

```
                                     (SEQ ID NO: 25)
  1  MDTRAPTQLL GLLLLWLPGA TFAQVLTQTP
     ASVSAAVGGT VTINCQSSQS
 51  VYDNNWLAWF QQKPGQPPKL LIYDASDLAS
     GVPSRFSGSG SGTQFTLTIS
101  GVQCADAATY YCQGAYNDVI YAFGGGTEVV
     VKRTDAAPTV SIFPPSSEQL
151  TSGGASVVCF LNNFYPKDIN VKWKIDGSER
     QNGVLNSWTD QDSKDSTYSM
201  SSTLTLTKDE YERHNSYTCE ATHKTSTSPI
     VKSFNRNEC
```

The nucleic acid sequence of Ab-A LC including signal peptide encoding sequence is:

```
                                     (SEQ ID NO: 26)
  1  ATGGACACGA GGGCCCCCAC TCAGCTGCTG
     GGGCTCCTGC TGCTCTGGCT
 51  CCCAGGTGCC ACATTTGCGC AAGTGCTGAC
     CCAGACTCCA GCCTCCGTGT
101  CTGCAGCTGT GGGAGGCACA GTCACCATCA
     ATTGCCAGTC CAGTCAGAGT
151  GTTTATGATA ACAACTGGTT AGCCTGGTTT
     CAGCAGAAAC CAGGGCAGCC
201  TCCCAAGCTC CTGATTTATG ATGCATCCGA
     TCTGGCATCT GGGGTCCCAT
251  CGCGGTTCAG TGGCAGTGGA TCTGGGACAC
     AGTTCACTCT CACCATCAGC
301  GGCGTGCAGT GTGCCGATGC TGCCACTTAC
     TACTGTCAAG GCGCTTATAA
351  TGATGTTATT TATGCTTTCG GCGGAGGGAC
     CGAGGTGGTG GTCAAACGTA
401  CGGATGCTGC ACCAACTGTA TCCATCTTCC
     CACCATCCAG TGAGCAGTTA
451  ACATCTGGAG GTGCCTCAGT CGTGTGCTTC
     TTGAACAACT TCTACCCCAA
501  AGACATCAAT GTCAAGTGGA AGATTGATGG
     CAGTGAACGA CAAAATGGCG
551  TCCTGAACAG TTGGACTGAT CAGGACAGCA
     AAGACAGCAC CTACAGCATG
601  AGCAGCACCC TCACGTTGAC CAAGGACGAG
     TATGAACGAC ATAACAGCTA
651  TACCTGTGAG GCCACTCACA AGACATCAAC
     TTCACCCATT GTCAAGAGCT
701  TCAACAGGAA TGAGTGTTAG
```

The amino acid sequence of the mature form (signal peptide removed) of Ab-A HC is:

```
                                     (SEQ ID NO: 27)
  1  QSLEESGGRL VTPGTPLTLT CTASGFSLSS YWMNWVRQAP GEGLEWIGTI
 51  DSGGRTDYAS WAKGRFTISR TSTTMDLKMT SLTTGDTARY FCARNWNLWG
101  QGTLVTVSSA STKGPSVYPL APGSAAQTNS MVTLGCLVKG YFPEPVTVTW
151  NSGSLSSGVH TFPAVLQSDL YTLSSSVTVP SSTWPSETVT CNVAHPASST
201  KVDKKIVPRD CGCKPCICTV PEVSSVFIFP PKPKDVLTIT LIPKVTCVVV
251  DISKDDPEVQ FSWFVDDVEV HTAQTQPREE QFNSTFRSVS ELPIMHQDWL
301  NGKEFKCRVN SAAFPAPIEK TISKTKGRPK APQVYTIPPP KEQMAKDKVS
351  LTCMITDFFP EDITVEWQWN GQPAENYKNT QPIMNTNGSY FVYSKLNVQK
401  SNWEAGNTFT CSVLHEGLHN HHTEKSLSHS PGK
```

The nucleic acid sequence encoding the mature form (signal peptide removed) of Ab-A HC:

```
                                     (SEQ ID NO: 28)
  1  CAGTCGCTGG AGGAGTCCGG GGGTCGCCTG
     GTCACGCCTG GGACACCCCT
 51  GACACTCACC TGCACAGCCT CTGGATTCTC
     CCTCAGTAGT TATTGGATGA
101  ACTGGGTCCG CCAGGCTCCA GGGGAGGGGC
     TGGAATGGAT CGGAACCATT
151  GATTCTGGTG GTAGGACGGA CTACGCGAGC
     TGGGCAAAAG GCCGATTCAC
201  CATCTCCAGA ACCTCGACTA CGATGGATCT
     GAAAATGACC AGTCTGACGA
251  CCGGGGACAC GGCCCGTTAT TTCTGTGCCA
     GAAATTGGAA CTTGTGGGGC
301  CAAGGCACCC TCGTCACCGT CTCGAGCGCT
     TCTACAAAGG GCCCATCTGT
351  CTATCCACTG GCCCCTGGAT CTGCTGCCCA
     AACTAACTCC ATGGTGACCC
```

-continued

```
 401    TGGGATGCCT GGTCAAGGGC TATTTCCCTG
        AGCCAGTGAC AGTGACCTGG
 451    AACTCTGGAT CCCTGTCCAG CGGTGTGCAC
        ACCTTCCCAG CTGTCCTGCA
 501    GTCTGACCTC TACACTCTGA GCAGCTCAGT
        GACTGTCCCC TCCAGCACCT
 551    GGCCCAGCGA GACCGTCACC TGCAACGTTG
        CCCACCCGGC CAGCAGCACC
 601    AAGGTGGACA AGAAAATTGT GCCCAGGGAT
        TGTGGTTGTA AGCCTTGCAT
 651    ATGTACAGTC CCAGAAGTAT CATCTGTCTT
        CATCTTCCCC CCAAAGCCCA
 701    AGGATGTGCT CACCATTACT CTGACTCCTA
        AGGTCACGTG TGTTGTGGTA
 751    GACATCAGCA AGGATGATCC CGAGGTCCAG
        TTCAGCTGGT TTGTAGATGA
 801    TGTGGAGGTG CACACAGCTC AGACGCAACC
        CCGGGAGGAG CAGTTCAACA
 851    GCACTTTCCG CTCAGTCAGT GAACTTCCCA
        TCATGCACCA GGACTGGCTC
 901    AATGGCAAGG AGTTCAAATG CAGGGTCAAC
        AGTGCAGCTT TCCCTGCCCC
 951    CATCGAGAAA ACCATCTCCA AAACCAAAGG
        CAGACCGAAG GCTCCACAGG
1001    TGTACACCAT TCCACCTCCC AAGGAGCAGA
        TGGCCAAGGA TAAAGTCAGT
1051    CTGACCTGCA TGATAACAGA CTTCTTCCCT
        GAAGACATTA CTGTGGAGTG
1101    GCAGTGGAAT GGGCAGCCAG CGGAGAACTA
        CAAGAACACT CAGCCCATCA
1151    TGGACACAGA TGGCTCTTAC TTCGTCTACA
        GCAAGCTCAA TGTGCAGAAG
1201    AGCAACTGGG AGGCAGGAAA TACTTTCACC
        TGCTCTGTGT TACATGAGGG
1251    CCTGCACAAC CACCATACTG AGAAGAGCCT
        CTCCCACTCT CCTGGTAAAT
1301    GA
```

The amino acid sequence of the Ab-A HC including signal peptide is:

```
                               (SEQ ID NO: 29)
  1    METGLRWLLL VAVLKGVHCQ SLEESGGRLV
       TPGTPLTLTC TASGFSLSSY
 51    WMNWVRQAPG EGLEWIGTID SGGRTDYASW
       AKGRFTISRT STTMDLKMTS
101    LTTGDTARYF CARNWNLWGQ GTLVTVSSAS
       TKGPSVYPLA PGSAAQTNSM
151    VTLGCLVKGY FPEPVTVTWN SGSLSSGVHT
       FPAVLQSDLY TLSSSVTVPS
201    STWPSETVTC NVAHPASSTK VDKKIVPRDC
       GCKPCICTVP EVSSVFIFPP
251    KPKDVLTITL TPKVTCVVVD ISKDDPEVQF
       SWFVDDVEVH TAQTQPREEQ
301    FNSTFRSVSE LPIMHQDWLN GKEFKCRVNS
       AAFPAPIEKT ISKTKGRPKA
351    PQVYTIPPPK EQMAKDKVSL TCMITDFFPE
       DITVEWQWNG QPAENYKNTQ
401    PIMNTNGSYF VYSKLNVQKS NWEAGNTFTC
       SVLHEGLHNH HTEKSLSHSP
451    GK
```

The nucleic acid sequence of Ab-A HC including signal peptide encoding sequence:

```
                               (SEQ ID NO: 30)
   1    ATGGAGACTG GGCTGCGCTG GCTTCTCCTG
        GTCGCTGTGC TCAAAGGTGT
  51    CCACTGTCAG TCGCTGGAGG AGTCCGGGGG
        TCGCCTGGTC ACGCCTGGGA
 101    CACCCCTGAC ACTCACCTGC ACAGCCTCTG
        GATTCTCCCT CAGTAGTTAT
 151    TGGATGAACT GGGTCCGCCA GGCTCCAGGG
        GAGGGGCTGG AATGGATCGG
 201    AACCATTGAT TCTGGTGGTA GGACGGACTA
        CGCGAGCTGG GCAAAAGGCC
 251    GATTCACCAT CTCCAGAACC TCGACTACGA
        TGGATCTGAA AATGACCAGT
 301    CTGACGACCG GGACACGGC CCGTTATTTC
        TGTGCCAGAA ATTGGAACTT
 351    GTGGGGCCAA GGCACCCTCG TCACCGTCTC
        GAGCGCTTCT ACAAAGGGCC
 401    CATCTGTCTA TCCACTGGCC CCTGGATCTG
        CTGCCCAAAC TAACTCCATG
 451    GTGACCCTGG GATGCCTGGT CAAGGGCTAT
        TTCCCTGAGC CAGTGACAGT
 501    GACCTGGAAC TCTGGATCCC TGTCCAGCGG
        TGTGCACACC TTCCCAGCTG
 551    TCCTGCAGTC TGACCTCTAC ACTCTGAGCA
        GCTCAGTGAC TGTCCCCTCC
 601    AGCACCTGGC CCAGCGAGAC CGTCACCTGC
        AACGTTGCCC ACCCGGCCAG
 651    CAGCACCAAG GTGGACAAGA AAATTGTGCC
        CAGGGATTGT GGTTGTAAGC
 701    CTTGCATATG TACAGTCCCA GAAGTATCAT
        CTGTCTTCAT CTTCCCCCCA
 751    AAGCCCAAGG ATGTGCTCAC CATTACTCTG
        ACTCCTAAGG TCACGTGTGT
 801    TGTGGTAGAC ATCAGCAAGG ATGATCCCGA
        GGTCCAGTTC AGCTGGTTTG
 851    TAGATGATGT GGAGGTGCAC ACAGCTCAGA
        CGCAACCCCG GGAGGAGCAG
 901    TTCAACAGCA CTTTCCGCTC AGTCAGTGAA
        CTTCCCATCA TGCACCAGGA
 951    CTGGCTCAAT GGCAAGGAGT TCAAATGCAG
        GGTCAACAGT GCAGCTTTCC
1001    CTGCCCCCAT CGAGAAAACC ATCTCCAAAA
        CCAAAGGCAG ACCGAAGGCT
```

```
1051    CCACAGGTGT ACACCATTCC ACCTCCCAAG
        GAGCAGATGG CCAAGGATAA

1101    AGTCAGTCTG ACCTGCATGA TAACAGACTT
        CTTCCCTGAA GACATTACTG

1151    TGGAGTGGCA GTGGAATGGG CAGCCAGCGG
        AGAACTACAA GAACACTCAG

1201    CCCATCATGG ACACAGATGG CTCTTACTTC
        GTCTACAGCA AGCTCAATGT

1251    GCAGAAGAGC AACTGGGAGG CAGGAAATAC
        TTTCACCTGC TCTGTGTTAC

1301    ATGAGGGCCT GCACAACCAC CATACTGAGA
        AGAGCCTCTC CCACTCTCCT

1351    GGTAAATGA
```

The CDR (complementarity determining region) sequences in the variable region of the heavy chain of Ab-A are as follows:

```
CDR-H1:    SYWMN              (SEQ ID NO: 51)
CDR-H2:    TIDSGGRTDYASWAKG   (SEQ ID NO: 52)
CDR-H3:    NWNL               (SEQ ID NO: 53)
```

The light chain variable region CDR sequences of Ab-A are:

```
CDR-L1:    QSSQSVYDNNWLA      (SEQ ID NO: 54)
CDR-L2:    DASDLAS            (SEQ ID NO: 55)
CDR-L3:    QGAYNDVIYA         (SEQ ID NO: 56)
```

Ab-A was humanized, and is referred to as Antibody 1 (also referred to herein as Ab-1), having the following sequences:

The nucleic acid sequence of the Ab-1 LC variable region including signal peptide encoding sequence is

```
ATGGACACGAGGGCCCCCACTCAGCTG    (SEQ ID NO: 74)

CTGGGGCTCCTGCTGCTCTGGCTCCCA

GGTGCCACATTTGCTCAAGTTCTGACC

CAGAGTCCAAGCAGTCTCTCCGCCAGC

GTAGGCGATCGTGACTATTACCTGTCA

ATCTAGTCAGAGCGTGTATGATAACAA

TTGGCTGGCGTGGTACCAGAAAAACCG
```

```
GGCAAAGCCCCGAAGCTGCTCATCTAT

GACGCGTCCGATCTGGCTAGCGGTGTG

CCAAGCCGTTTCAGTGGCAGTGGCAGC

GGTACTGACTTTACCCTCACAATTTCG

TCTCTCCAGCCGGAAGATTTCGCCACT

TACTATTGTCAAGGTGCTTACAACGAT

GTGATTTATGCCTTCGGTCAGGGCACT

AAAGTAGAAATCAAACGT
```

The amino acid sequence of Ab-1 LC variable region including signal peptide is:

(SEQ ID NO: 75)

MDTRAPTQLLGLLLLWLPGATFAQVLTQSPSSLSASVGDRVTITCQSSQSVYDNNWLA
WYQQKPGKAPKLLIYDASDLASGVPSRFSGSGSGTFDTLTISSLQPEDFATYYCQGAYN
DVIYAFGQGTKVEIKR

The nucleic acid sequence of Ab-1 HC variable region including signal peptide encoding sequence is:

```
ATGGAGACTGGGCTGCGCTGGCTTCTC    (SEQ ID NO: 76)

CTGGTCGCTGTGCTCAAAGGTGTCCAC

TGTGAGGTGCAGCTGTTGGAGTCTGGA

GGCGGGCTTGTCCAGCCTGGAGGGAGC

CTGCGTCTCTCTTGTGCAGCAAGCGGC

TTCAGCTTATCCTCTTACTGGATGAAT

TGGGTGCGGCAGGCACCTGGGAAGGGC

CTGGAGTGGGTGGGCACCATTGATTCC

GGAGGCCGTACAGACTACGCGTCTTGG

GCAAAGGGCCGTTTCACCATTTCCCGC

GACAACTCCAAAAATACCATGTACCTC

CAGATGAACTCTCTCCGCGCAGAGGAC

ACAGCACGTTACTGTGCACGCAACTGG

AATCTGTGGGGTCAAGGTACTCTTGTA

ACAGTCTCGAGC
```

Amino acid sequence of Ab-1 HC variable region including signal peptide (SEQ ID NO: 77)

```
METGLRWLLLVAVLKGVHCEVQLLESGGGLVQPGGSLRLSCAASGFSLSSYWMNWVR
QAPGKGLEWVGTIDSGGRIDYASWAKGRFTISRDNSKNTMYLQMNSLRAEDTARYYC
ARNWNLWGQGTLVTVSS
```

The CDR (complementarity determining region) sequences in the variable region of the heavy chain of Ab-1 are as follows:

| | | |
|---|---|---|
| CDR-H1: | SYWMN | (SEQ ID NO: 51) |
| CDR-H2: | TIDSGGRTDYASWAKG | (SEQ ID NO: 52) |
| CDR-H3: | NWNL | (SEQ ID NO: 53) |

The light chain variable region CDR sequences of Ab-1 are:

| | | |
|---|---|---|
| CDR-L1: | QSSQSVYDNNWLA | (SEQ ID NO: 54) |
| CDR-L2: | DASDLAS | (SEQ ID NO: 55) |
| CDR-L3: | QGAYNDVIYA | (SEQ ID NO: 56) |

Ab-B

Figure 16:
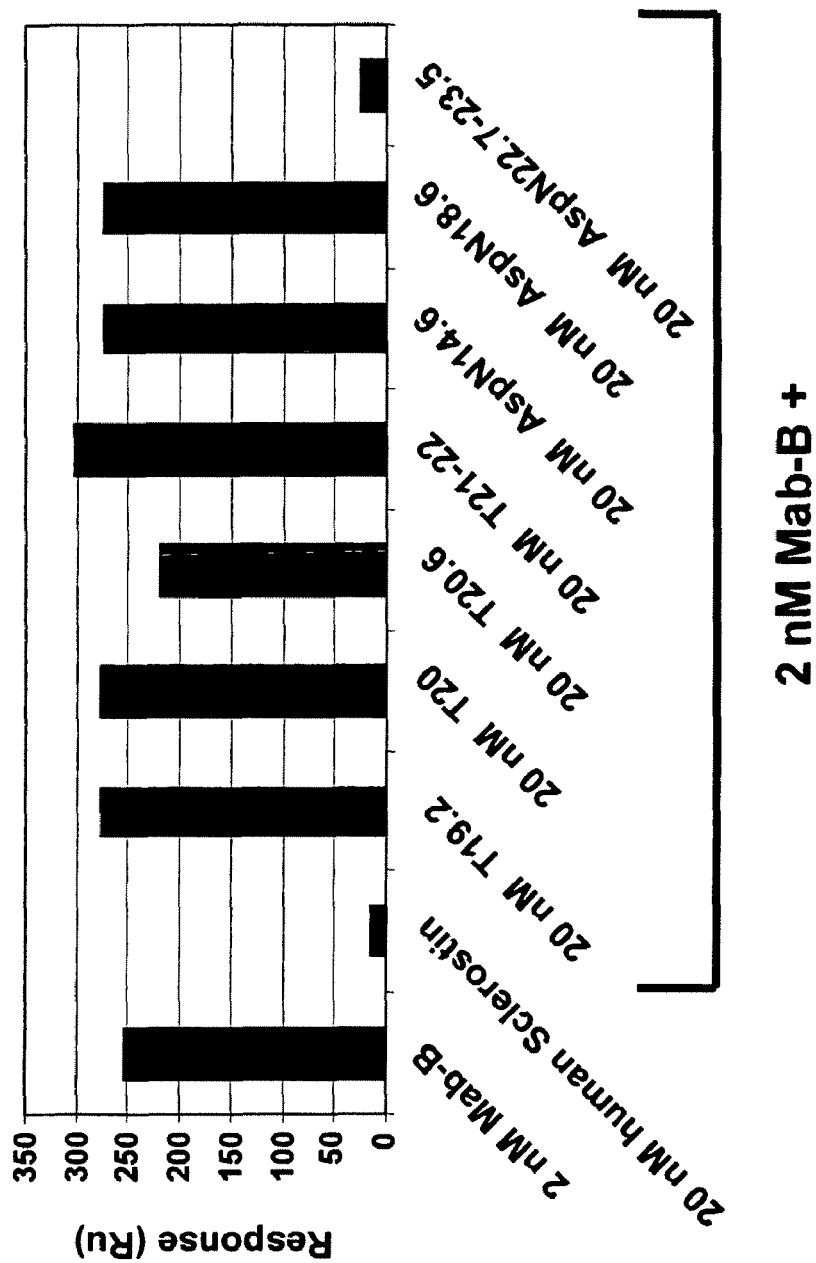
FIG. 16 shows the resonance unit (Ru) signal from the Biacore-based "human sclerostin peptide epitope competition binding assay." Relative Mab binding to various human sclerostin-peptides (in solution) versus Mab binding to intact mature form human sclerostin (immobilized on Biacore chip) was assessed. Data shown is for Ab-B. Human sclerostin peptides used were T19.2, T20, T20.6, T21-22, AspN14.6, AspN18.6 and AspN22.7-23.5.

Antibody B (also referred to herein as Ab-B and Mab-B) is a mouse antibody which exhibits high affinity binding to sclerostin. The BIAcore binding pattern of Ab-B is shown in FIG. 16.

Ab-B Light Chain

The amino acid sequence of the mature form (signal peptide removed) of the Ab-B LC is:

```
  1 QIVLTQSPTI VSASPGEKVT LICSASSSVS FVDWFQQKPG TSPKRWIYRT
 51 SNLGFGVPAR FSGGGSGTSH SLTISRMEAE DAATYYCQQR STYPPTFGAG
101 TKLELKRADA APTVSIFPPS SEQLTSGGAS VVCFLNNFYP KDINVKWKID
151 GSERQNGVLN SWTDQDSKDS TYSMSSTLTL TKDEYERHNS YTCEATHKTS
201 TSPIVKSFNR NEC
```

The nucleic acid sequence encoding the mature form (signal peptide removed) of Ab-B LC is:

```
                                              (SEQ ID NO: 32)
  1    CAAATTGTTC TCACCCAGTC TCCAACAATC
       GTGTCTGCAT CTCCAGGGGA
 51    GAAGGTCACC CTAATCTGCA GTGCCAGTTC
       AAGTGTAAGT TTCGTGGACT
101    GGTTCCAGCA GAAGGCAGGC ACTTCTCCCA
       AACGCTGGAT TTACAGAACA
151    TCCAACCTGG GTTTTGGAGT CCCTGCTCGC
       TTCAGTGGCG GTGGATCTGG
201    GACCTCTCAC TCTCTCACAA TCAGCCGAAT
       GGAGGCTGAA GATGCTGCCA
251    CTTATTACTG CCAGCAAAGG AGTACTTACC
       CACCCACGTT CGGTGCTGGG
301    ACCAAGCTGG AACTGAAACG GGCTGATGCT
       GCACCAACTG TATCCATCTT
351    CCCACCATCC AGTGAGCAGT TAACATCTGG
       AGGTGCCTCA GTCGTGTGCT
401    TCTTGAACAA CTTCTACCCC AAAGACATCA
       ATGTCAAGTG GAAGATTGAT
451    GGCAGTGAAC GACAAAATGG CGTCCTGAAC
       AGTTGGACTG ATCAGGACAG
501    CAAAGACAGC ACCTACAGCA TGAGCAGCAC
       CCTCACGTTG ACCAAGGACG
551    AGTATGAACG ACATAACAGC TATACCTGTG
       AGGCCACTCA CAAGAGATCA
601    ACTTCACCCA TTGTCAAGAG CTTCAACAGG
       AATGAGTGTT AG
```

The amino acid sequence of Ab-B LC including signal peptide is:

```
                                              (SEQ ID NO: 33)
  1    MHFQVQIFSF LLISASVIVS RGQIVLTQSP
       TIVSASPGEK VTLICSASSS
 51    VSFVDWFQQK PGTSPKRWIY RTSNLGFGVP
       ARFSGGGSGT SHSLTISRME (SEQ ID NO: 31)

101    AEDAATYYCQ QRSTYPPTFG AGTKLELKRA
       DAAPTVSIFP PSSEQLTSGG
151    ASVVCFLNNF YPKDINVKWK IDGSERQNGV
       LNSWTDQDSK DSTYSMSSTL
201    TLTKDEYERH NSYTCEATHK TSTSPIVKSF
       NRNEC
```

The nucleic acid sequence of Ab-B LC including signal peptide encoding sequence is:

```
                                              (SEQ ID NO: 34)
  1    ATGCATTTTC AAGTGCAGAT TTTCAGCTTC
       CTGCTAATCA GTGCCTCAGT
 51    CATAGTGTCC AGAGGGCAAA TTGTTCTCAC
       CCAGTCTCCA ACAATCGTGT
101    CTGCATCTCC AGGGGAGAAG GTCACCCTAA
       TCTGCAGTGC CAGTTCAAGT
```

```
151  GTAAGTTTCG TGGACTGGTT CCAGCAGAAG
     CCAGGCACTT CTCCCAAACG

201  CTGGATTTAC AGAACATCCA ACCTGGGTTT
     TGGAGTCCCT GCTCGCTTCA

251  GTGGCGGTGG ATCTGGGACC TCTCACTCTC
     TCACAATCAG CCGAATGGAG

301  GCTGAAGATG CTGCCACTTA TTACTGCCAG
     CAAAGGAGTA CTTACCCACC

351  CACGTTCGGT GCTGGGACCA AGCTGGAACT
     GAAACGGGCT GATGCTGCAC

401  CAACTGTATC CATCTTCCCA CCATCCAGTG
     AGCAGTTAAC ATCTGGAGGT

451  GCCTCAGTCG TGTGCTTCTT GAACAACTTC
     TACCCCAAAG ACATCAATGT

501  CAAGTGGAAG ATTGATGGCA GTGAACGACA
     AAATGGCGTC CTGAACAGTT

551  GGACTGATCA GGACAGCAAA GACAGCACCT
     ACAGCATGAG CAGCACCCTC

601  ACGTTGACCA AGGACGAGTA TGAACGACAT
     AACAGCTATA CCTGTGAGGC

651  CACTCACAAG ACATCAACTT CACCCATTGT
     CAAGAGCTTC AACAGGAATG

701  AGTGTTAG
```

Ab-B Heavy Chain

The amino acid sequence of the mature form (signal peptide removed) of Ab-B HC:

(SEQ ID NO: 35)

```
  1 QVTLKESGPG ILQPSQTLSL TCSFSGFSLS TSGMGVGWIR HPSGKNLEWL
 51 AHIWWDDVKR YNPVLKSRLT ISKDTSNSQV FLKIANVDTA DTATYYCARI
101 EDFDYDEEYY AMDYWGQGTS VIVSSAKTTP PSVYPLAPGS AAQTNSMVTL
151 GCLVKGYFPE PVTVTWNSGS LSSGVHTFPA VLQSDLYTLS SSVTVPSSTW
201 PSETVTCNVA HPASSTKVDK KIVPRDCGCK PCICTVPEVS SVFIFPPKPK
251 DVLTITLTPK VTCVVVDISK DDPEVQFSWF VDDVEVHTAQ TQPREEQFNS
301 TFRSVSELPI MHQDWLNGKE FKCRVNSAAF PAPIEKTISK TKGRPKAPQV
351 YTIPPPKEQM AKDKVSLTCM ITDFFPEDIT VEWQWNGQPA ENYKNTQPIM
401 DTDGSYFVYS KLNVQKSNWE AGNTFTCSVL HEGLHNHHTE KSLSHSPGK
```

The nucleic acid sequence encoding the mature form (signal peptide removed) of Ab-B HC:

(SEQ ID NO: 36)

```
   1 CAGGTTACTC TGAAAGAGTC TGGCCCTGGG
     ATATTGCAGC CCTCCCAGAC

51 CCTCAGTCTG ACTTGTTCTT CTCTGGGTT
     TTCACTGAGC ACTTCTGGTA

101 TGGGTGTAGG CTGGATTCGT CACCCATCAG
     GGAAGAATCT GGAGTGGCTG

151 GCACACATTT GGTGGGATGA TGTCAAGCGC
     TATAACCCAG TCCTGAAGAG

201 CCGACTGACT ATCTCCAAGG ATACCTCCAA
     CAGCCAGGTA TTCCTCAAGA

251 TCGCCAATGT GGACACTGCA GATACTGCCA
     CATACTACTG TGCTCGAATA

301 GAGGACTTTG ATTACGACGA GGAGTATTAT
     GCTATGGACT ACTGGGGTCA

351 AGGAACCTCA GTCATCGTCT CCTCAGCCAA
     AACGACACCC CCATCTGTCT

401 ATCCACTGGC CCCTGGATCT GCTGCCCAAA
     CTAACTCCAT GGTGACCCTG

451 GGATGCCTGG TCAAGGGCTA TTTCCCTGAG
     CCAGTGACAG TGACCTGGAA

501 CTCTGGATCC CTGTCCAGCG GTGTGCACAC
     CTTCCCAGCT GTCCTGCAGT

551 CTGACCTCTA CACTCTGAGC AGCTCAGTGA
     CTGTCCCCTC CAGCACCTGG

601 CCCAGCGAGA CCGTCACCTG CAACGTTGCC
     CACCCGGCCA GCAGCACCAA

651 GGTGGACAAG AAAATTGTGC CCAGGGATTG
     TGGTTGTAAG CCTTGCATAT

701 GTACAGTCCC AGAAGTATCA TCTGTCTTCA
     TCTTCCCCCC AAAGCCCAAG

751 GATGTGCTCA CCATTACTCT GACTCCTAAG
     GTCACGTGTG TTGTGGTAGA

801 CATCAGCAAG GATGATCCCG AGGTCCAGTT
     CAGCTGGTTT GTAGATGATG

851 TGGAGGTGCA CACAGCTCAG ACGCAACCCC
     GGGAGGAGCA GTTCAACAGC

901 ACTTTCCGCT CAGTCAGTGA ACTTCCCATC
     ATGCACCAGG ACTGGCTCAA

951 TGGCAAGGAG TTCAAATGCA GGGTCAACAG
     TGCAGCTTTC CCTGCCCCCA

1001 TCGAGAAAAC CATCTCCAAA ACCAAAGGCA
     GACCGAAGGC TCCACAGGTG

1051 TACACCATTC CACCTCCCAA GGAGCAGATG
     GCCAAGGATA AAGTCAGTCT

1101 GACCTGCATG ATAACAGACT TCTTCCCTGA
     AGACATTACT GTGGAGTGGC

1151 AGTGGAATGG GCAGCCAGCG GAGAACTACA
     AGAACACTCA GCCCATCATG

1201 GACACAGATG GCTCTTACTT CGTCTACAGC
     AAGCTCAATG TGCAGAAGAG
```

-continued

```
1251    CAACTGGGAG GCAGGAAATA CTTTCACCTG
        CTCTGTGTTA CATGAGGGCC

1301    TGCACAACCA CCATACTGAG AAGAGCCTCT
        CCCACTCTCC TGGTAAATGA
```

The amino acid sequence of Ab-B HC including signal peptide:

```
                                    (SEQ ID NO: 37)
  1    MGRLTSSFLL LIVPAYVLSQ VTLKESGPGI
       LQPSQTLSLT CSFSGFSLST

51    SGMGVGWIRH PSGKNLEWLA HIWWDDVKRY
       NPVLKSRLTI SKDTSNSQVF

101    LKIANVDTAD TATYYCARIE DFDYDEEYYA
       MDYWGQGTSV IVSSAKTTPP

151    SVYPLAPGSA AQTNSMVTLG CLVKGYFPEP
       VTVTWNSGSL SSGVHTFPAV

201    LQSDLYTLSS SVTVPSSTWP SETVTCNVAH
       PASSTKVDKK IVPRDCGCKP

251    CICTVPEVSS VFIFPPKPKD VLTITLTPKV
       TCVVVDISKD DPEVQFSWFV

301    DDVEVHTAQT QPREEQFNST FRSVSELPIM
       HQDWLNGKEF KCRVNSAAFP

351    APIEKTISKT KGRPKAPQVY TIPPPKEQMA
       KDKVSLTCMI TDFFPEDITV

401    EWQWNGQPAE NYKNTQPIMD TDGSYFVYSK
       LNVQKSNWEA GNTFTCSVLH

451    EGLHNHHTEK SLSHSPGK
```

The nucleic acid sequence of Ab-B HC including signal peptide encoding sequence:

```
                                    (SEQ ID NO: 38)
  1    ATGGGCAGGC TTACTTCTTC ATTCCTGCTA
       CTGATTGTCC CTGCATATGT

51    CCTGTCCCAG GTTACTCTGA AAGAGTCTGG
       CCCTGGGATA TTGCAGCCCT

101    CCCAGACCCT CAGTCTGACT TGTTCTTTCT
       CTGGGTTTTC ACTGAGCACT

151    TCTGGTATGG GTGTAGGCTG GATTCGTCAC
       CCATCAGGGA AGAATCTGGA

201    GTGGCTGGCA CACATTTGGT GGGATGATGT
       CAAGCGCTAT AACCCAGTCC

251    TGAAGAGCCG ACTGACTATC TCCAAGGATA
       CCTCCAACAG CCAGGTATTC

301    CTCAAGATCG CCAATGTGGA CACTGCAGAT
       ACTGCCACAT ACTACTGTGC

351    TCGAATAGAG GACTTTGATT ACGACGAGGA
       GTATTATGCT ATGGACTACT

401    GGGGTCAAGG AACCTCAGTC ATCGTCTCCT
       CAGCCAAAAC GACACCCCCA

451    TCTGTCTATC CACTGGCCCC TGGATCTGCT
       GCCCAAACTA ACTCCATGGT

501    GACCCTGGGA TGCCTGGTCA AGGGCTATTT
       CCCTGAGCCA GTGACAGTGA

551    CCTGGAACTC TGGATCCCTG TCCAGCGGTG
       TGCACACCTT CCCAGCTGTC

601    CTGCAGTCTG ACCTCTACAC TCTGAGCAGC
       TCAGTGACTG TCCCCTCCAG

651    CACCTGGCCC AGCGAGACCG TCACCTGCAA
       CGTTGCCCAC CCGGCCAGCA

701    GCACCAAGGT GGACAAGAAA ATTGTGCCCA
       GGGATTGTGG TTGTAAGCCT

751    TGCATATGTA CAGTCCCAGA AGTATCATCT
       GTCTTCATCT TCCCCCCAAA

801    GCCCAAGGAT GTGCTCACCA TTACTCTGAC
       TCCTAAGGTC ACGTGTGTTG

851    TGGTAGACAT CAGCAAGGAT GATCCCGAGG
       TCCAGTTCAG CTGGTTTGTA

901    GATGATGTGG AGGTGCACAC AGCTCAGACG
       CAACCCCGGG AGGAGCAGTT

951    CAACAGCACT TTCCGCTCAG TCAGTGAACT
       TCCCATCATG CACCAGGACT

1001   GGCTCAATGG CAAGGAGTTC AAATGCAGGG
       TCAACAGTGC AGCTTTCCCT

1051   GCCCCCATCG AGAAACCAT CTCCAAAACC
       AAAGGCAGAC CGAAGGCTCC

1101   ACAGGTGTAC ACCATTCCAC CTCCCAAGGA
       GCAGATGGCC AAGGATAAAG

1151   TCAGTCTGAC CTGCATGATA ACAGACTTCT
       TCCCTGAAGA CATTACTGTG

1201   GAGTGGCAGT GGAATGGGCA GCCAGCGGAG
       AACTACAAGA ACACTCAGCC

1251   CATCATGGAC ACAGATGGCT CTTACTTCGT
       CTACAGCAAG CTCAATGTGC

1301   AGAAGAGCAA CTGGGAGGCA GGAAATACTT
       TCACCTGCTC TGTGTTACAT

1351   GAGGGCCTGC ACAACCACCA TACTGAGAAG
       AGCCTCTCCC ACTCTCCTGG

1401   TAAATGA
```

The CDR (complementarity determining region) sequences in the variable region of the heavy chain of Ab-B are as follows:

```
CDR-H1:    TSGMGVG              (SEQ ID NO: 57)

CDR-H2:    HIWWDDVKRYNPVLKS     (SEQ ID NO: 58)

CDR-H3:    EDFDYDEEYYAMDY       (SEQ ID NO: 59)
```

The light chain variable region CDR sequences of Ab-B are:

```
CDR-L1:    SASSSVSFVD           (SEQ ID NO: 60)

CDR-L2:    RTSNLGF              (SEQ ID NO: 61)

CDR-L3:    QQRSTYPPT            (SEQ ID NO: 62)
```

Antibodies disclosed herein bind to regions of human sclerostin which are important for the in vivo activity of the protein. Binding of an antibody to sclerostin can be correlated with increases in, for example, the bone mineral density achieved by use of the antibody in vivo such as described in Examples 5 and 9 (mice) and Example 12 (monkey). Increases in at least one of bone formation, bone mineral content, bone mass, bone quality and bone strength can also be achieved by use of the antibody in vivo such as described in Examples 5 and 9 (mice) and Example 12 (monkey). Since the binding of an antibody to sclerostin is primarily determined by its CDR sequences, an antibody for practicing the invention may be generated with all or some of the disclosed CDR sequences in an appropriate framework, wherein the antibody retains the ability to bind specifically to sclerostin, and can be expected to achieve increases in, for example, bone mineral density. Such antibodies are useful in the treatment of human or animal conditions that are caused by, associated with, or result in at least one of low bone formation, low bone mineral density, low bone mineral content, low bone mass, low bone quality and low bone strength. Methods of constructing and expressing antibodies and fragments thereof comprising CDR's of the present invention are known to those of skill in the art.

The present invention therefore relates in one embodiment to an isolated antibody, including Ab-A, or an antigen binding fragment thereof, which specifically binds to sclerostin and wherein the variable domain of the heavy chain comprises at least one CDR having the sequences given in SEQ ID NO:51 for CDR-H1, SEQ ID NO:52 for CDR-H2 and SEQ ID NO:53 for CDR-H3. The antibody or antigen binding fragment thereof may comprise a heavy chain variable domain in which the CDRs consist of at least one of the peptides of SEQ ID NO:51 for CDR-H1, SEQ ID NO:52 for CDR-H2 and SEQ ID NO:53 for CDR-H3.

When in antibodies of the invention a light chain is present the light chain may be any suitable complementary chain and may in particular be selected from a light chain wherein the variable domain comprises at least one CDR having the sequences given in SEQ ID NO:54 for CDR-L1, SEQ ID NO:55 for CDR-L2 and SEQ ID NO:56 for CDR-L3. The antibody or antigen binding fragment thereof may comprise a light chain variable domain in which the CDRs consist of at least one of the peptides of SEQ ID NO:54 for CDR-L1, SEQ ID NO:55 for CDR-L2 and SEQ ID NO:56 for CDR-L3.

The present invention further relates to an isolated antibody, including Ab-B, or an antigen binding fragment hereof, which specifically binds to sclerostin and wherein the variable domain of the heavy chain comprises at least one CDR having the sequences given in SEQ ID NO:57 for CDR-H1, SEQ ID NO:58 for CDR-H2 and SEQ ID NO:59 for CDR-H3. The antibody or antigen binding fragment thereof may comprise a heavy chain variable domain in which the CDRs consist of at least one of the peptides of SEQ ID NO:57 for CDR-H1, SEQ ID NO:58 for CDR-H2 and SEQ ID NO:59 for CDR-H3.

When in antibodies of the invention a light chain is present the light chain may be any suitable complementary chain and may in particular be selected from a light chain wherein the variable domain comprises at least one CDR having the sequences given in SEQ ID NO:60 for CDR-L1, SEQ ID NO:61 for CDR-L2 and SEQ ID NO:62 for CDR-L3. The antibody or antigen binding fragment thereof may comprise a light chain variable domain in which the CDRs consist of at least one of the peptides of SEQ ID NO:60 for CDR-L1, SEQ ID NO:61 for CDR-L2 and SEQ ID NO:62 for CDR-L3.

The present invention still further relates to an isolated antibody, including Ab-C, or an antigen binding fragment hereof, which specifically binds to sclerostin and wherein the variable domain of the heavy chain comprises at least one CDR having the sequences given in SEQ ID NO:45 for CDR-H1, SEQ ID NO:46 for CDR-H2 and SEQ ID NO:47 for CDR-H3. The antibody or antigen binding fragment thereof may comprise a heavy chain variable domain in which the CDRs consist of at least one of the peptides of SEQ ID NO:45 for CDR-H1, SEQ ID NO:46 for CDR-H2 and SEQ ID NO:47 for CDR-H3.

When in antibodies of the invention a light chain is present the light chain may be any suitable complementary chain and may in particular be selected from a light chain wherein the variable domain comprises at least one CDR having the sequences given in SEQ ID NO:48 for CDR-L1, SEQ ID NO:49 for CDR-L2 and SEQ ID NO:50 for CDR-L3. The antibody or antigen binding fragment thereof may comprise a light chain variable domain in which the CDRs consist of at least one of the peptides of SEQ ID NO:48 for CDR-L1, SEQ ID NO:49 for CDR-L2 and SEQ ID NO:50 for CDR-L3.

The present invention also relates to an isolated antibody, including Ab-D, or an antigen binding fragment hereof, which specifically binds to sclerostin and wherein the variable domain of the heavy chain comprises at least one CDR having the sequences given in SEQ ID NO:39 for CDR-H1, SEQ ID NO:40 for CDR-H2 and SEQ ID NO:41 for CDR-H3. The antibody or antigen binding fragment thereof may comprise a heavy chain variable domain in which the CDRs consist of at least one of the peptides of SEQ ID NO:39 for CDR-H1, SEQ ID NO:40 for CDR-H2 and SEQ ID NO:41 for CDR-H3.

When in antibodies of the invention a light chain is present the light chain may be any suitable complementary chain and may in particular be selected from a light chain wherein the variable domain comprises at least one CDR having the sequences given in SEQ ID NO:42 for CDR-L1, SEQ ID NO:43 for CDR-L2 and SEQ ID NO:44 for CDR-L3. The antibody or antigen binding fragment thereof may comprise a light chain variable domain in which the CDRs consist of at least one of the peptides of SEQ ID NO:42 for CDR-L1, SEQ ID NO:43 for CDR-L2 and SEQ ID NO:44 for CDR-L3.

Additional anti-sclerostin antibodies are described below. For some of the amino acid sequences the complementarity-determining regions (CDRs) are boxed-shaded and the constant regions are in bold-italics.

Ab-2

The sequences of the Antibody 2 (also referred to as Ab-2) LC and HC are as follows:

Ab-2 Light Chain:

Amino acid sequence of the mature form (signal peptide removed) of the Ab-2 LC:

(SEQ ID NO: 117)

```
  1 QIVLSQSPAI LSTSPGEKVT MTCRASSSVY YMHWYQQKPG SSPKPWIYAT
 51 SNLASGVPVR FSGSGSGTSY SLTITRVEAE DAATYYCQQW SSDPLTFGAG
101 TKLELKRADA APTVSIFPPS SEQLTSGGAS VVCFLNNFYP KDINVKWKID
151 GSERQNGVLN SWTDQDSKDS TYSMSSTLTL TKDEYERHNS YTCEATHKTS
201 TSPIVKSFNR NEC
```

Nucleic acid sequence encoding the mature form (signal peptide removed) of the Ab-2 LC:

(SEQ ID NO: 118)
```
  1  CAAATTGTTC TCTCCCAGTC TCCAGCAATC
     CTGTCTACAT CTCCAGGGGA
 51  GAAGGTCACA ATGACTTGCA GGGCCAGCTC
     AAGTGTATAT TACATGCACT
101  GGTACCAGCA GAAGCCAGGA TCCTCCCCCA
     AACCCTGGAT TTATGCCACA
151  TCCAACCTGG CTTCTGGAGT CCCTGTTCGC
     TTCAGTGGCA GTGGGTCTGG
201  GACCTCTTAC TCTCTCACAA TCACCAGAGT
     GGAGGCTGAA GATGCTGCCA
251  CTTATTACTG CCAGCAGTGG AGTAGTGACC
     CACTCACGTT CGGTGCTGGG
301  ACCAAGCTGG AGCTGAAACG GGCTGATGCT
     GCACCAACTG TATCCATCTT
351  CCCACCATCC AGTGAGCAGT TAACATCTGG
     AGGTGCCTCA GTCGTGTGCT
401  TCTTGAACAA CTTCTACCCC AAAGACATCA
     ATGTCAAGTG GAAGATTGAT
451  GGCAGTGAAC GACAAAATGG CGTCCTGAAC
     AGTTGGACTG ATCAGGACAG
501  CAAAGACAGC ACCTACAGCA TGAGCAGCAC
     CCTCACGTTG ACCAAGGACG
551  AGTATGAACG ACATAACAGC TATACCTGTG
     AGGCCACTCA CAAGACATCA
601  ACTTCACCCA TTGTCAAGAG CTTCAACAGG
     AATGAGTGTT AG
```

Amino acid sequence of the Ab-2 LC including signal peptide:

(SEQ ID NO: 119)
```
  1  MDFQVQIFSF LLISASVIMS RGQIVLSQSP
     AILSTSPGEK VTMTCRASSS
 51  VYYMHWYQQK PGSSPKPWIY ATSNLASGVP
     VRFSGSGSGT SYSLTITRVE
101  AEDAATYYCQ QWSSDPLTFG AGTKLELKRA
     DAAPTVSIFP PSSEQLTSGG
```

```
151  ASVVCFLNNF YPKDINVKWK IDGSERQNGV
     LNSWTDQDSK DSTYSMSSTL
201  TLTKDEYERH NSYTCEATHK TSTSPIVKSF
     NRNEC
```

Nucleic acid sequence of the Ab-2 LC including signal peptide encoding sequence:

(SEQ ID NO: 120)
```
  1  ATGGATTTTC AAGTGCAGAT TTTCAGCTTC
     CTGCTAATCA GTGCTTCAGT
 51  CATTATGTCC AGGGGACAAA TTGTTCTCTC
     CCAGTCTCCA GCAATCCTGT
101  CTACATCTCC AGGGGAGAAG GTCACAATGA
     CTTGCAGGGC CAGCTCAAGT
151  GTATATTACA TGCACTGGTA CCAGCAGAAG
     CCAGGATCCT CCCCCAAACC
201  CTGGATTTAT GCCACATCCA ACCTGGCTTC
     TGGAGTCCCT GTTCGCTTCA
251  GTGGCAGTGG GTCTGGGACC TCTTACTCTC
     TCACAATCAC CAGAGTGGAG
301  GCTGAAGATG CTGCCACTTA TTACTGCCAG
     CAGTGGAGTA GTGACCCACT
351  CACGTTCGGT GCTGGGACCA AGCTGGAGCT
     GAAACGGGCT GATGCTGCAC
401  CAACTGTATC CATCTTCCCA CCATCCAGTG
     AGCAGTTAAC ATCTGGAGGT
451  GCCTCAGTCG TGTGCTTCTT GAACAACTTC
     TACCCCAAAG ACATCAATGT
501  CAAGTGGAAG ATTGATGGCA GTGAACGACA
     AAATGGCGTC CTGAACAGTT
551  GGACTGATCA GGACAGCAAA GACAGCACCT
     ACAGCATGAG CAGCACCCTC
601  ACGTTGACCA AGGACGAGTA TGAACGACAT
     AACAGCTATA CCTGTGAGGC
651  CACTCACAAG ACATCAACTT CACCCATTGT
     CAAGAGCTTC AACAGGAATG
701  AGTGTTAG
```

Ab-2 Heavy Chain

Amino acid sequence of the mature form (signal peptide removed) of the Ab-2 HC:

(SEQ ID NO: 121)
```
  1  EVQVQQSGPE LVKPGASVKL SCTASGFNIK DYFIHWVKQR PEQGLEWIGR
 51  LDPEDGESDY APKFQDKAIM TADTSSNTAY LQLRSLTSED TAIYYCERED
101  YDGTYTFPFY WGQGTLVTVS AAKTTPPSVY PLAPGSAAQT NSMVTLGCLV
151  KGYFPEPVTV TWNSGSLSSG VHTFPAVLQS DLYTLSSSVT VPSSTWPSET
201  VTCNVAHPAS STKVDKKIVP RDCGCKPCIC TVPEVSSVFI FPPKPKDVLT
251  ITLTPKVTCV VVDISKDDPE VQFSWFVDDV EVHTAQTQPR EEQFNSTFRS
301  VSELPIMHQD WLNGKEFKCR VNSAAFPAPI EKTISKTKGR PKAPQVYTIP
351  PPKEQMAKDK VSLTCMITDF FPEDITVEWQ WNGQPAENYK NTQPIMDTDG
401  SYFIYSKLNV QKSNWEAGNT FTCSVLHEGL HNHHTEKSLS HSPGK
```

Nucleic acid sequence encoding the mature form (signal peptide removed) of the Ab-2 HC:

(SEQ ID NO: 122)

```
   1   GAGGTTCAGG TGCAGCAGTC TGGGCCAGAA
       CTTGTGAAGC CAGGGGCCTC
  51   AGTCAAGTTG TCCTGCACAG CTTCTGGCTT
       CAACATTAAA GACTACTTTA
 101   TACACTGGGT GAAGCAGAGG CCTGAACAGG
       GCCTGGAGTG GATTGGAAGG
 151   CTTGATCCTG AGGATGGTGA AAGTGATTAT
       GCCCCGAAGT TCCAGGACAA
 201   GGCCATTATG ACAGCAGACA CATCATCCAA
       CACAGCCTAT CTTCAGCTCA
 251   GAAGCCTGAC ATCTGAGGAC ACTGCCATCT
       ATTATTGTGA GAGAGAGGAC
 301   TACGATGGTA CCTACACCTT TTTTCCTTAC
       TGGGGCCAAG GGACTCTGGT
 351   CACTGTCTCT GCAGCCAAAA CGACACCCCC
       ATCTGTCTAT CCACTGGCCC
 401   CTGGATCTGC TGCCCAAACT AACTCCATGG
       TGACCCTGGG ATGCCTGGTC
 451   AAGGGCTATT TCCCTGAGCC AGTGACAGTG
       ACCTGGAACT CTGGATCCCT
 501   GTCCAGCGGT GTGCACACCT TCCCAGCTGT
       CCTGCAGTCT GACCTCTACA
 551   CTCTGAGCAG CTCAGTGACT GTCCCCTCCA
       GCACCTGGCC CAGCGAGACC
 601   GTCACCTGCA ACGTTGCCCA CCCGGCCAGC
       AGCACCAAGG TGGACAAGAA
 651   AATTGTGCCC AGGGATTGTG GTTGTAAGCC
       TTGCATATGT ACAGTCCCAG
 701   AAGTATCATC TGTCTTCATC TTCCCCCCAA
       AGCCCAAGGA TGTGCTCACC
 751   ATTACTCTGA CTCCTAAGGT CACGTGTGTT
       GTGGTAGACA TCAGCAAGGA
 801   TGATCCCGAG GTCCAGTTCA GCTGGTTTGT
       AGATGATGTG GAGGTGCACA
 851   CAGCTCAGAC GCAACCCCGG GAGGAGCAGT
       TCAACAGCAC TTTTCGCTCA
 901   GTCAGTGAAC TTCCCATCAT GCACCAGGAC
       TGGCTCAATG GCAAGGAGTT
 951   CAAATGCAGG GTCAACAGTG CAGCTTTCCC
       TGCCCCCATC GAGAAAACCA
1001   TCTCCAAAAC CAAAGGCAGA CCGAAGGCTC
       CACAGGTGTA CACCATTCCA
1051   CCTCCCAAGG AGCAGATGGC CAAGGATAAA
       GTCAGTCTGA CCTGCATGAT
1101   AACAGACTTC TTCCCTGAAG ACATTACTGT
       GGAGTGGCAG TGGAATGGGC
1151   AGCCAGCGGA GAACTACAAG AACACTCAGC
       CCATCATGGA CACAGATGGC
1201   TCTTACTTCA TCTACAGCAA GCTCAATGTG
       CAGAAGAGCA ACTGGGAGGC
1251   AGGAAATACT TTCACCTGCT CTGTGTTACA
       TGAGGGCCTG CACAACCACC
1301   ATACTGAGAA GAGCCTCTCC CACTCTCCTG
       GTAAATGA
```

Amino acid sequence of the Ab-2 HC including signal peptide:

(SEQ ID NO: 123)

```
  1   MKCSWVIFFL MAVVTGVNSE VQVQQSGPEL
      VKPGASVKLS CTASGFNIKD
 51   YFIHWVKQRP EQGLEWIGRL DPEDGESDYA
      PKFQDKAIMT ADTSSNTAYL
101   QLRSLTSEDT AIYYCEREDY DGTYTFFPYW
      GQGTLVTVSA AKTTPPSVYP
151   LAPGSAAQTN SMVTLGCLVK GYFPEPVTVT
      WNSGSLSSGV HTFPAVLQSD
201   LYTLSSSVTV PSSTWPSETV TCNVAHPASS
      TKVDKKIVPR DCGCKPCICT
251   VPEVSSVFIF PPKPKDVLTI TLTPKVTCVV
      VDISKDDPEV QFSWFVDDVE
301   VHTAQTQPRE EQFNSTFRSV SELPIMHQDW
      LNGKEFKCRV NSAAFPAPIE
351   KTISKTKGRP KAPQVYTIPP PKEQMAKDKV
      SLTCMITDFF PEDITVEWQW
401   NGQPAENYKN TQPIMDTDGS YFIYSKLNVQ
      KSNWEAGNTF TCSVLHEGLH
451   NHHTEKSLSH SPGK
```

Nucleic acid sequence of the Ab-2 HC including signal peptide encoding sequence:

(SEQ ID NO: 124)

```
   1   ATGAAATGCA GCTGGGTCAT CTTCTTCCTG
       ATGGCAGTGG TTACAGGGGT
  51   CAATTCAGAG GTTCAGGTGC AGCAGTCTGG
       GCCAGAACTT GTGAAGCCAG
 101   GGGCCTCAGT CAAGTTGTCC TGCACAGCTT
       CTGGCTTCAA CATTAAAGAC
 151   TACTTTATAC ACTGGGTGAA GCAGAGGCCT
       GAACAGGGCC TGGAGTGGAT
 201   TGGAAGGCTT GATCCTGAGG ATGGTGAAAG
       TGATTATGCC CCGAAGTTCC
 251   AGGACAAGGC CATTATGACA GCAGACACAT
       CATCCAACAC AGCCTATCTT
 301   CAGCTCAGAA GCCTGACATC TGAGGACACT
       GCCATCTATT ATTGTGAGAG
 351   AGAGGACTAC GATGGTACCT ACACCTTTTT
       TCCTTACTGG GGCCAAGGGA
 401   CTCTGGTCAC TGTCTCTGCA GCCAAAACGA
       CACCCCCATC TGTCTATCCA
 451   CTGGCCCCTG GATCTGCTGC CCAAACTAAC
       TCCATGGTGA CCCTGGGATG
 501   CCTGGTCAAG GGCTATTTCC CTGAGCCAGT
       GACAGTGACC TGGAACTCTG
```

```
551   GATCCCTGTC CAGCGGTGTG CACACCTTCC
      CAGCTGTCCT GCAGTCTGAC
601   CTCTACACTC TGAGCAGCTC AGTGACTGTC
      CCCTCCAGCA CCTGGCCCAG
651   CGAGACCGTC ACCTGCAACG TTGCCCACCC
      GGCCAGCAGC ACCAAGGTGG
701   ACAAGAAAAT TGTGCCCAGG GATTGTGGTT
      GTAAGCCTTG CATATGTACA
751   GTCCCAGAAG TATCATCTGT CTTCATCTTC
      CCCCCAAAGC CCAAGGATGT
801   GCTCACCATT ACTCTGACTC CTAAGGTCAC
      GTGTGTTGTG GTAGACATCA
851   GCAAGGATGA TCCCGAGGTC CAGTTCAGCT
      GGTTTGTAGA TGATGTGGAG
901   GTGCACACAG CTCAGACGCA ACCCCGGGAG
      GAGCAGTTCA ACAGCACTTT
951   CCGCTCAGTC AGTGAACTTC CCATCATGCA
      CCAGGACTGG CTCAATGCA
1001  AGGAGTTCAA ATGCAGGGTC AACAGTGCAG
      CTTTCCCTGC CCCCATCGAG
1051  AAAACCATCT CCAAAACCAA AGGCAGACCG
      AAGGCTCCAC AGGTGTACAC
1101  CATTCCACCT CCCAAGGAGC AGATGGCCAA
      GGATAAAGTC AGTCTGACCT
1151  GCATGATAAC AGACTTCTTC CCTGAAGACA
      TTACTGTGGA GTGGCAGTGG
1201  AATGGGCAGC CAGCGGAGAA CTACAAGAAC
      ACTCAGCCCA TCATGGACAC
1251  AGATGGCTCT TACTTCATCT ACAGCAAGCT
      CAATGTGCAG AAGAGCAACT
1301  GGGAGGCAGG AAATACTTTC ACCTGCTCTG
      TGTTACATGA GGGCCTGCAC
1351  AACCACCATA CTGAGAAGAG CCTCTCCCAC
      TCTCCTGGTA AATGA
```

Ab-3

The sequences of the Antibody 3 (also referred to herein as Ab3) LC and HC are as follows:

Ab-3 Light Chain

Amino acid sequence of the mature form (signal peptide removed) of the Ab-3 LC:

(SEQ ID NO: 125)
```
1   EIVLTQSPAL MAASPGEKVT ITCSVSSTIS SNHLHWFQQK SDTSPKPWIY
51  GTSNLASGVP VRFSGSGSGT SYSLTISSME AEDAATYYCQ QWSSYPLTFG
101 AGTKLELRRA DAAPTVSIFP PSSEQLTSGG ASVVCFLNNF YPKDINVKWK
151 IDGSERQNGV LNSWTDQDSK DSTYSMSSTL TLTKDEYERH NSYTCEATHK
201 TSTSPIVKSF NRNEC
```

Nucleic acid sequence encoding the mature form (signal peptide removed) of the Ab-3 LC:

(SEQ ID NO: 126)
```
1   GAAATTGTGC TCACCCAGTC TCCAGCACTC
    ATGGCTGCAT CTCCGGGGGA
51  GAAGGTCACC ATCACCTGCA GTGTCAGTTC
    AACTATAAGT TCCAACCACT
101 TGCACTGGTT CCAGCAGAAG TCAGACACCT
    CCCCCAAACC CTGGATTTAT
151 GGCACATCCA ACCTGGCTTC TGGAGTCCCT
    GTTCGCTTCA GTGGCAGTGG
201 ATCTGGGACC TCTTATTCTC TCACAATCAG
    CAGCATGGAG GCTGAGGATG
251 CTGCCACTTA TTACTGTCAA CAGTGGAGTA
    GTTACCCACT CACGTTCGGC
301 GCTGGGACCA AGCTGGAGCT GAGACGGGCT
    GATGCTGCAC CAACTGTATC
351 CATCTTCCCA CCATCCAGTG AGCAGTTAAC
    ATCTGGAGGT GCCTCAGTCG
401 TGTGCTTCTT GAACAACTTC TACCCCAAAG
    ACATCAATGT CAAGTGGAAG
451 ATTGATGGCA GTGAACGACA AAATGGCGTC
    CTGAACAGTT GGACTGATCA
501 GGACAGCAAA GACAGCACCT ACAGCATGAG
    CAGCACCCTC ACGTTGACCA
551 AGGACGAGTA TGAACGACAT AACAGCTATA
    CCTGTGAGGC CACTCACAAG
601 ACATCAACTT CACCCATTGT CAAGAGCTTC
    AACAGGAATG AGTGTTAG
```

Amino acid sequence of the Ab-3 LC including signal peptide:

(SEQ ID NO: 127)
```
1   MDFHVQIFSF MLISVTVILS SGEIVLTQSP
    ALMAASPGEK VTITCSVSST
51  ISSNHLHWFQ QKSDTSPKPW IYGTSNLASG
    VPVRFSGSGS GTSYSLTISS
101 MEAEDAATYY CQQWSSYPLT FGAGTKLELR
    RADAAPTVSI FPPSSEQLTS
151 GGASVVCFLN NFYPKDINVK WKIDGSERQN
    GVLNSWTDQD SKDSTYSMSS
201 TLTLTKDEYE RHNSYTCEAT HKTSTSPIVK
    SFNRNEC
```

Nucleic acid sequence of the Ab-3 LC including signal peptide encoding sequence:

(SEQ ID NO: 128)

```
  1  ATGGATTTTC ATGTGCAGAT TTTCAGCTTC
     ATGCTAATCA GTGTCACAGT
 51  CATTTTGTCC AGTGGAGAAA TTGTGCTCAC
     CCAGTCTCCA GCACTCATGG
101  CTGCATCTCC GGGGGAGAAG GTCACCATCA
     CCTGCAGTGT CAGTTCAACT
151  ATAAGTTCCA ACCACTTGCA CTGGTTCCAG
     CAGAAGTCAG ACACCTCCCC
201  CAAACCCTGG ATTTATGGCA CATCCAACCT
     GGCTTCTGGA GTCCCTGTTC
251  GCTTCAGTGG CAGTGGATCT GGGACCTCTT
     ATTCTCTCAC AATCAGCAGC
301  ATGGAGGCTG AGGATGCTGC CACTTATTAC
     TGTCAACAGT GGAGTAGTTA
351  CCCACTCACG TTCGGCGCTG GGACCAAGCT
     GGAGCTGAGA CGGGCTGATG
401  CTGCACCAAC TGTATCCATC TTCCCACCAT
     CCAGTGAGCA GTTAACATCT
451  GGAGGTGCCT CAGTCGTGTG CTTCTTGAAC
     AACTTCTACC CCAAAGACAT
501  CAATGTCAAG TGGAAGATTG ATGGCAGTGA
     ACGACAAAAT GGCGTCCTGA
551  ACAGTTGGAC TGATCAGGAC AGCAAAGACA
     GCACCTACAG CATGAGCAGC
601  ACCCTCACGT TGACCAAGGA CGAGTATGAA
     CGACATAACA GCTATACCTG
651  TGAGGCCACT CACAAGACAT CAACTTCACC
     CATTGTCAAG AGCTTCAACA
701  GGAATGAGTG TTAG
```

Ab-3 Heavy Chain

Amino acid sequence of the mature form (signal peptide removed) of the Ab-3 HC:

(SEQ ID NO: 129)

```
  1  EVQLQQSGAE LVRPGALVKL SCTASDFNIK DYFLHWMRQR PEQGLDWIGR
 51  IDPENGDTLY DPKFQDKATL TTDTSSNTAY LQLSGLTSET TAVYYCSREA
101  DYEHDGTSYW YFDVWGAGTT ITVSSAKTTP PSVYPLAPGS AAQTNSMVTL
151  GCLVKGYFPE PVTVTWNSGS LSSGVHTFPA VLQSDLYTLS SSVTVPSSTW
201  PSETVTCNVA HPASSTKVDK KIVPRDCGCK PCICTVPEVS SVFIFPPKPK
251  DVLTITLTPK VTCVVVDISK DDPEVQFSWF VDDVEVHTAQ TQPREEQFNS
301  TFRSVSELPI MHQDWLNGKE FKCRVNSAAF PAPIEKTISK TKGRPKAPQV
351  YTIPPPKEQM AKDKVSLTCM ITDFFPEDIT VEWQWNGQPA ENYKNTQPIM
401  DTDGSYFIYS KLNVQKSNWE AGNTFTCSVL HEGLHNHHTE KSLSHSPGK
```

Nucleic acid sequence encoding the mature form (signal peptide removed) of the Ab-3 HC:

(SEQ ID NO: 130)

```
  1  GAGGTTCAGC TGCAGCAGTC TGGGGCTGAA
     CTTGTGAGGC CAGGGGCCTT
 51  AGTCAAGTTG TCCTGCACAG CTTCTGACTT
     CAACATTAAA GACTTCTATC
101  TACACTGGAT GAGGCAGCGG CCTGAACAGG
     GCCTGGACTG GATTGGAAGG
151  ATTGATCCTG AGAATGGTGA TACTTTATAT
     GACCCGAAGT TCCAGGACAA
201  GGCCACTCTT ACAACAGACA CATCCTCCAA
     CACAGCCTAC CTGCAGCTCA
251  GCGGCCTGAC ATCTGAGACC ACTGCCGTCT
     ATTACTGTTC TAGAGAGGCG
301  GATTATTTCC ACGATGGTAC CTCCTACTGG
     TACTTCGATG TCTGGGGCGC
351  AGGGACCACA ATCACCGTCT CCTCAGCCAA
     AACGACACCC CCATCTGTCT
401  ATCCACTGGC CCCTGGATCT GCTGCCCAAA
     CTAACTCCAT GGTGACCCTG
451  GGATGCCTGG TCAAGGGCTA TTTCCCTGAG
     CCAGTGACAG TGACCTGGAA
501  CTCTGGATCC CTGTCCAGCG GTGTGCACAC
     CTTCCCAGCT GTCCTGCAGT
551  CTGACCTCTA CACTCTGAGC AGCTCAGTGA
     CTGTCCCCTC CAGCACCTGG
601  CCCAGCGAGA CCGTCACCTG CAACGTTGCC
     CACCCGGCCA GCAGCACCAA
651  GGTGGACAAG AAAATTGTGC CCAGGGATTG
     TGGTTGTAAG CCTTGCATAT
701  GTACAGTCCC AGAAGTATCA TCTGTCTTCA
     TCTTCCCCCC AAAGCCCAAG
751  GATGTGCTCA CCATTACTCT GACTCCTAAG
     GTCACGTGTG TTGTGGTAGA
801  CATCAGCAAG GATGATCCCG AGGTCCAGTT
     CAGCTGGTTT GTAGATGATG
851  TGGAGGTGCA CACAGCTCAG ACGCAACCCC
     GGGAGGAGCA GTTCAACAGC
901  ACTTTCCGCT CAGTCAGTGA ACTTCCCATC
     ATGCACCAGG ACTGGCTCAA
951  TGGCAAGGAG TTCAAATGCA GGGTCAACAG
     TGCAGCTTTC CCTGCCCCCA
1001 TCGAGAAAAC CATCTCCAAA ACCAAAGGCA
     GACCGAAGGC TCCACAGGTG
1051 TACACCATTC CACCTCCCAA GGAGCAGATG
     GCCAAGGATA AAGTCAGTCT
```

```
1101    GACCTGCATG ATAACAGACT TCTTCCCTGA
        AGACATTACT GTGGAGTGGC
1151    AGTGGAATGG GCAGCCAGCG GAGAACTACA
        AGAACACTCA GCCCATCATG
1201    GACACAGATG GCTCTTACTT CATCTACAGC
        AAGCTCAATG TGCAGAAGAG
1251    CAACTGGAG GCAGGAAATA CTTTCACCTG
        CTCTGTGTTA CATGAGGGCC
1301    TGCACAACCA CCATACTGAG AAGAGCCTCT
        CCCACTCTCC TGGTAAATGA
```

Amino acid sequence of the Ab-3 HC including signal peptide:

```
                                    (SEQ ID NO: 131)
  1    MKCSWVIFFL MAVVTGVNSE VQLQQSGAEL
       VRPGALVKLS CTASDFNIKD
 51    FYLHWMRQRP EQGLDWIGRI DPENGDTLYD
       PKFQDKATLT TDTSSNTAYL
101    QLSGLTSETT AVYYCSREAD YFHDGTSYWY
       FDVWGAGTTI TVSSAKTTPP
151    SVYPLAPGSA AQTNSMVTLG CLVKGYFPEP
       VTVTWNSGSL SSGVHTFPAV
201    LQSDLYTLSS SVTVPSSTWP SETVTCNVAH
       PASSTKVDKK IVPRDCGCKP
251    CICTVPEVSS VFIFPPKPKD VLTITLTPKV
       TCVVVDISKD DPEVQFSWFV
301    DDVEVHTAQT QPREEQFNST FRSVSELPIM
       HQDWLNGKEF KCRVNSAAFP
351    APIEKTISKT KGRPKAPQVY TIPPPKEQMA
       KDKVSLTCMI TDFFPEDITV
401    EWQWNGQPAE NYKNTQPIMD TDGSYFIYSK
       LNVQKSNWEA GNTFTCSVLH
451    EGLHNHHTEK SLSHSPGK
```

Nucleic acid sequence of the Ab-3 HC including signal peptide encoding sequence:

```
                                    (SEQ ID NO: 132)
  1    ATGAAATGCA GCTGGGTCAT CTTCTTCCTG
       ATGGCAGTGG TTACAGGGGT
 51    CAATTCAGAG GTTCAGCTGC AGCAGTCTGG
       GGCTGAACTT GTGAGGCCAG
101    GGGCCTTAGT CAAGTTGTCC TGCACAGCTT
       CTGACTTCAA CATTAAAGAC
151    TTCTATCTAC ACTGGATGAG GCAGCGGCCT
       GAACAGGGCC TGGACTGGAT
201    TGGAAGGATT GATCCTGAGA ATGGTGATAC
       TTTATATGAC CCGAAGTTCC
251    AGGACAAGGC CACTCTTACA ACAGACACAT
       CCTCCAACAC AGCCTACCTG
301    CAGCTCAGCG GCCTGACATC TGAGACCACT
       GCCGTCTATT ACTGTTCTAG
351    AGAGGCGGAT TATTTCCACG ATGGTACCTC
       CTACTGGTAC TTCGATGTCT
401    GGGGCGCAGG GACCACAATC ACCGTCTCCT
       CAGCCAAAAC GACACCCCCA
451    TCTGTCTATC CACTGGCCCC TGGATCTGCT
       GCCCAAACTA ACTCCATGGT
501    GACCCTGGGA TGCCTGGTCA AGGGCTATTT
       CCCTGAGCCA GTGACAGTGA
551    CCTGGAACTC TGGATCCCTG TCCAGCGGTG
       TGCACACCTT CCCAGCTGTC
601    CTGCAGTCTG ACCTCTACAC TCTGAGCAGC
       TCAGTGACTG TCCCCTCCAG
651    CACCTGGCCC AGCGAGACCG TCACCTGCAA
       CGTTGCCCAC CCGGCCAGCA
701    GCACCAAGGT GGACAAGAAA ATTGTGCCCA
       GGGATTGTGG TTGTAAGCCT
751    TGCATATGTA CAGTCCCAGA AGTATCATCT
       GTCTTCATCT TCCCCCCAAA
801    GCCCAAGGAT GTGCTCACCA TTACTCTGAC
       TCCTAAGGTC ACGTGTGTTG
851    TGGTAGACAT CAGCAAGGAT GATCCCGAGG
       TCCAGTTCAG CTGGTTTGTA
901    GATGATGTGG AGGTGCACAC AGCTCAGACG
       CAACCCCGGG AGGAGCAGTT
951    CAACAGCACT TTCCGCTCAG TCAGTGAACT
       TCCCATCATG CACCAGGACT
1001   GGCTCAATGG CAAGGAGTTC AAATGCAGGG
       TCAACAGTGC AGCTTTCCCT
1051   GCCCCCATCG AGAAAACCAT CTCCAAAACC
       AAAGGCAGAC CGAAGGCTCC
1101   ACAGGTGTAC ACCATTCCAC CTCCCAAGGA
       GCAGATGGCC AAGGATAAAG
1151   TCAGTCTGAC CTGCATGATA ACAGACTTCT
       TCCCTGAAGA CATTACTGTG
1201   GAGTGGCAGT GGAATGGGCA GCCAGCGGAG
       AACTACAAGA ACACTCAGCC
1251   CATCATGGAC ACAGATGGCT CTTACTTCAT
       CTACAGCAAG CTCAATGTGC
1301   AGAAGAGCAA CTGGGAGGCA GGAAATACTT
       TCACCTGCTC TGTGTTACAT
1351   GAGGGCCTGC ACAACCACCA TACTGAGAAG
       AGCCTCTCCC ACTCTCCTGG
1401   TAAATGA
```

Ab-4

The sequences of the Antibody 4 (also referred to herein as Ab-4) LC and HC are as follows:

Ab-4 Light Chain:

Amino acid sequence of the mature form (signal peptide removed) of the Ab-4 LC:

```
  1 DIQMTQITSS LSASLGDRVS ISCRASQDIS NYLNWYQQKP DGTFKLLIFY
 51 TSRLLSGVPS RFSGSGSGTD YSLTIYNLEQ EDFATYFCQQ GDTLPYTFGG
101 GTKLEIKRAD AAPTVSIFPP SSEQLTSGGA SVVCFLNNFY PKDINVKWKI
151 DGSERQNGVL NSWTDQDSKD STYSMSSTLT LTKDEYERHN SYTCEATHKT
201 STSPIVKSFN RNEC
```

(SEQ ID NO: 133)

Nucleic acid sequence encoding the mature form (signal peptide removed) of the Ab-4 LC:

(SEQ ID NO: 134)
```
  1  GATATCCAGA TGACACAGAT TACATCCTCC
     CTGTCTGCCT CTCTGGGAGA
 51  CAGGGTCTCC ATCAGTTGCA GGGCAAGTCA
     AGACATTAGC AATTATTTAA
101  ACTGGTATCA GCAGAAACCA GATGGAACTT
     TTAAACTCCT TATCTTCTAC
151  ACATCAAGAT TACTCTCAGG AGTCCCATCA
     AGGTTCAGTG GCAGTGGGTC
201  TGGAACAGAT TATTCTCTCA CCATTTACAA
     CCTGGAGCAA GAAGATTTTG
251  CCACTTACTT TTGCCAACAG GGAGATACGC
     TTCCGTACAC TTTCGGAGGG
301  GGGACCAAGC TGGAAATAAA ACGGGCTGAT
     GCTGCACCAA CTGTATCCAT
351  CTTCCCACCA TCCAGTGAGC AGTTAACATC
     TGGAGGTGCC TCAGTCGTGT
401  GCTTCTTGAA CAACTTCTAC CCCAAAGACA
     TCAATGTCAA GTGGAAGATT
451  GATGGCAGTG AACGACAAAA TGGCGTCCTG
     AACAGTTGGA CTGATCAGGA
501  CAGCAAAGAC AGCACCTACA GCATGAGCAG
     CACCCTCACG TTGACCAAGG
551  ACGAGTATGA ACGACATAAC AGCTATACCT
     GTGAGGCCAC TCACAAGACA
601  TCAACTTCAC CCATTGTCAA GAGCTTCAAC
     AGGAATGAGT GTTAG
```

Amino acid sequence of the Ab-4 LC including signal peptide:

(SEQ ID NO: 135)
```
  1  MMSSAQFLGL LLLCFQGTRC DIQMTQITSS
     LSASLGDRVS ISCRASQDIS
 51  NYLNWYQQKP DGTFKLLIFY TSRLLSGVPS
     RFSGSGSGTD YSLTIYNLEQ
101  EDFATYFCQQ GDTLPYTFGG GTKLEIKRAD
     AAPTVSIFPP SSEQLTSGGA
151  SVVCFLNNFY PKDINVKWKI DGSERQNGVL
     NSWTDQDSKD STYSMSSTLT
201  LTKDEYERHN SYTCEATHKT STSPIVKSFN
     RNEC
```

Nucleic acid sequence of the Ab-4 LC including signal peptide encoding sequence:

(SEQ ID NO: 136)
```
  1  ATGATGTCCT CTGCTCAGTT CCTTGGTCTC
     CTGTTGCTCT GTTTTCAAGG
 51  TACCAGATGT GATATCCAGA TGACACAGAT
     TACATCCTCC CTGTCTGCCT
101  CTCTGGGAGA CAGGGTCTCC ATCAGTTGCA
     GGGCAAGTCA AGACATTAGC
151  AATTATTTAA ACTGGTATCA GCAGAAACCA
     GATGGAACTT TTAAACTCCT
201  TATCTTCTAC ACATCAAGAT TACTCTCAGG
     AGTCCCATCA AGGTTCAGTG
251  GCAGTGGGTC TGGAACAGAT TATTCTCTCA
     CCATTTACAA CCTGGAGCAA
301  GAAGATTTTG CCACTTACTT TTGCCAACAG
     GGAGATACGC TTCCGTACAC
351  TTTCGGAGGG GGGACCAAGC TGGAAATAAA
     ACGGGCTGAT GCTGCACCAA
401  CTGTATCCAT CTTCCCACCA TCCAGTGAGC
     AGTTAACATC TGGAGGTGCC
451  TCAGTCGTGT GCTTCTTGAA CAACTTCTAC
     CCCAAAGACA TCAATGTCAA
501  GTGGAAGATT GATGGCAGTG AACGACAAAA
     TGGCGTCCTG AACAGTTGGA
551  CTGATCAGGA CAGCAAAGAC AGCACCTACA
     GCATGAGCAG CACCCTCACG
601  TTGACCAAGG ACGAGTATGA ACGACATAAC
     AGCTATACCT GTGAGGCCAC
651  TCACAAGACA TCAACTTCAC CCATTGTCAA
     GAGCTTCAAC AGGAATGAGT
701  GTTAG
```

Ab-4 Heavy Chain:

Amino acid sequence of the mature form (signal peptide removed) of the Ab-4 HC:

```
  1 EVQLQQSGPE LMKPGASVKM SCKASGYTFT DYNMHWVKQN QGKTLEWIGE
 51 INPNSGGAGY NQKFKGKATL TVDKSSTTAY MELRSLTSED SAVYYCARLG
101 YDDLYDDWYF DVWGAGTTVT VSSAKTTPPS VYPLAPGSAA QTNSMVTLGC
151 LVKGYFPEPV TVTWNSGSLS SGVHTFPAVL QSDLYTLSSS VTVPSSTWPS
201 ETVTCNVAHP ASSTKVDKKI VPRDCGCKPC ICTVPEVSSV FIFPPKPKDV
251 LTITLTPKVT CVVVDISKDD PEVQFSWFVD DVEVHTAQTQ PREEQFNSTF
301 RSVSELPIMH QDWLNGKEFK CRVNSAAFPA PIEKTISKTK GRPKAPQVYT
351 IPPPKEQMAK DKVSLTCMIT DFFPEDITVE WQWNGQPAEN YKNTQPIMDT
401 DGSYFIYSKL NVQKSNWEAG NTFTCSVLHE GLHNHHTEKS LSHSPGK
```

(SEQ ID NO: 137)

Nucleic acid sequence encoding the mature form (signal peptide removed) of the Ab-4 HC:

```
                              (SEQ ID NO: 138)
   1  GAGGTCCAAC TGCAACAGTC TGGACCTGAA
      CTAATGAAGC CTGGGGCTTC
  51  AGTGAAGATG TCCTGCAAGG CTTCTGGATA
      TACATTCACT GACTACAACA
 101  TGCACTGGGT GAAGCAGAAC CAAGGAAAGA
      CCCTAGAGTG GATAGGAGAA
 151  ATTAATCCTA ACAGTGGTGG TGCTGGCTAC
      AACCAGAAGT TCAAGGGCAA
 201  GGCCACATTG ACTGTAGACA AGTCCTCCAC
      CACAGCCTAC ATGGAGCTCC
 251  GCAGCCTGAC ATCTGAGGAC TCTGCAGTCT
      ATTACTGTGC AAGATTGGGC
 301  TACGATGATA TCTACGACGA CTGGTACTTC
      GATGTCTGGG GCGCAGGGAC
 351  CACGGTCACC GTCTCCTCAG CCAAAACGAC
      ACCCCCATCT GTCTATCCAC
 401  TGGCCCCTGG ATCTGCTGCC CAAACTAACT
      CCATGGTGAC CCTGGGATGC
 451  CTGGTCAAGG GCTATTTCCC TGAGCCAGTG
      ACAGTGACCT GGAACTCTGG
 501  ATCCCTGTCC AGCGGTGTGC ACACCTTCCC
      AGCTGTCCTG CAGTCTGACC
 551  TCTACACTCT GAGCAGCTCA GTGACTGTCC
      CCTCCAGCAC CTGGCCCAGC
 601  GAGACCGTCA CCTGCAACGT TGCCCACCCG
      GCCAGCAGCA CCAAGGTGGA
 651  CAAGAAAATT GTGCCCAGGG ATTGTGGTTG
      TAAGCCTTGC ATATGTACAG
 701  TCCCAGAAGT ATCATCTGTC TTCATCTTCC
      CCCCAAAGCC CAAGGATGTG
 751  CTCACCATTA CTCTGACTCC TAAGGTCACG
      TGTGTTGTGG TAGACATCAG
 801  CAAGGATGAT CCCGAGGTCC AGTTCAGCTG
      GTTTGTAGAT GATGTGGAGG
 851  TGCACACAGC TCAGACGCAA CCCCGGGAGG
      AGCAGTTCAA CAGCACTTTC
 901  CGCTCAGTCA GTGAACTTCC CATCATGCAC
      CAGGACTGGC TCAATGGCAA
 951  GGAGTTCAAA TGCAGGGTCA ACAGTGCAGC
      TTTCCCTGCC CCCATCGAGA
```

```
           -continued
1001  AAACCATCTC CAAAACCAAA GGCAGACCGA
      AGGCTCCACA GGTGTACACC
1051  ATTCCACCTC CCAAGGAGCA GATGGCCAAG
      GATAAAGTCA GTCTGACCTG
1101  CATGATAACA GACTTCTTCC CTGAAGACAT
      TACTGTGGAG TGGCAGTGGA
1151  ATGGGCAGCC AGCGGAGAAC TACAAGAACA
      CTCAGCCCAT CATGGACACA
1201  GATGGCTCTT ACTTCATCTA CAGCAAGCTC
      AATGTGCAGA AGAGCAACTG
1251  GGAGGCAGGA AATACTTTCA CCTGCTCTGT
      GTTACATGAG GGCCTGCACA
1301  ACCACCATAC TGAGAAGAGC CTCTCCCACT
      CTCCTGGTAA ATGA
```

Amino acid sequence of the Ab-4 HC including signal peptide:

```
                              (SEQ ID NO: 139)
   1  MGWSWTFLFL LSGTAGVLSE VQLQQSGPEL
      MKPGASVKMS CKASGYTFTD
  51  YNMHWVKQNQ GKTLEWIGEI NPNSGGAGYN
      QKFKGKATLT VDKSSTTAYM
 101  ELRSLTSEDS AVYYCARLGY DDIYDDWYFD
      VWGAGTTVTV SSAKTTPPSV
 151  YPLAPGSAAQ TNSMVTLGCL VKGYFPEPVT
      VTWNSGSLSS GVHTFPAVLQ
 201  SDLYTLSSSV TVPSSTWPSE TVTCNVAHPA
      SSTKVDKKIV PRDCGCKPCI
 251  CTVPEVSSVF IFPPKPKDVL TITLTPKVTC
      VVVDISKDDP EVQFSWFVDD
 301  VEVHTAQTQP REEQFNSTFR SVSELPIMHQ
      DWLNGKEFKC RVNSAAFPAP
 351  IEKTISKTKG RPKAPQVYTI PPPKEQMAKD
      KVSLTCMITD FFPEDITVEW
 401  QWNGQPAENY KNTQPIMDTD GSYFIYSKLN
      VQKSNWEAGN TFTCSVLHEG
 451  LHNHHTEKSL SHSPGK
```

Nucleic acid sequence of the Ab-4 HC including signal peptide encoding sequence:

```
                              (SEQ ID NO: 140)
   1  ATGGGATGGA GCTGGACCTT TCTCTTCCTC
      CTGTCAGGAA CTGCAGGTGT
```

```
 51  CCTCTCTGAG GTCCAACTGC AACAGTCTGG
     ACCTGAACTA ATGAAGCCTG
101  GGGCTTCAGT GAAGATGTCC TGCAAGGCTT
     CTGGATATAC ATTCACTGAC
151  TACAACATGC ACTGGGTGAA GCAGAACCAA
     GGAAAGACCC TAGAGTGGAT
201  AGGAGAAATT AATCCTAACA GTGGTGGTGC
     TGGCTACAAC CAGAAGTTCA
251  AGGGCAAGGC CACATTGACT GTAGACAAGT
     CCTCCACCAC AGCCTACATG
301  GAGCTCCGCA GCCTGACATC TGAGGACTCT
     GCAGTCTATT ACTGTGCAAG
351  ATTGGGCTAC GATGATATCT ACGACGACTG
     GTACTTCGAT GTCTGGGGCG
401  CAGGGACCAC GGTCACCGTC TCCTCAGCCA
     AAACGACACC CCCATCTGTC
451  TATCCACTGG CCCCTGGATC TGCTGCCCAA
     ACTAACTCCA TGGTGACCCT
501  GGGATGCCTG GTCAAGGGCT ATTTCCCTGA
     GCCAGTGACA GTGACCTGGA
551  ACTCTGGATC CCTGTCCAGC GGTGTGCACA
     CCTTCCCAGC TGTCCTGCAG
601  TCTGACCTCT ACACTCTGAG CAGCTCAGTG
     ACTGTCCCCT CCAGCACCTG
651  GCCCAGCGAG ACCGTCACCT GCAACGTTGC
     CCACCCGGCC AGCAGCACCA
701  AGGTGGACAA GAAAATTGTG CCCAGGGATT
     GTGGTTGTAA GCCTTGCATA
751  TGTACAGTCC CAGAAGTATC ATCTGTCTTC
     ATCTTCCCCC CAAAGCCCAA
801  GGATGTGCTC ACCATTACTC TGACTCCTAA
```

-continued
```
     GGTCACGTGT GTTGTGGTAG
851  ACATCAGCAA GGATGATCCC GAGGTCCAGT
     TCAGCTGGTT TGTAGATGAT
901  GTGGAGGTGC ACACAGCTCA GACGCAACCC
     CGGGAGGAGC AGTTCAACAG
951  CACTTTCCGC TCAGTCAGTG AACTTCCCAT
     CATGCACCAG GACTGGCTCA
1001 ATGGCAAGGA GTTCAAATGC AGGGTCAACA
     GTGCAGCTTT CCCTGCCCCC
1051 ATCGAGAAAA CCATCTCCAA AACCAAAGGC
     AGACCGAAGG CTCCACAGGT
1101 GTACACCATT CCACCTCCCA AGGAGCAGAT
     GGCCAAGGAT AAAGTCAGTC
1151 TGACCTGCAT GATAACAGAC TTCTTCCCTG
     AAGACATTAC TGTGGAGTGG
1201 CAGTGGAATG GGCAGCCAGC GGAGAACTAC
     AAGAACACTC AGCCCATCAT
1251 GGACACAGAT GGCTCTTACT TCATCTACAG
     CAAGCTCAAT GTGCAGAAGA
1301 GCAACTGGGA GGCAGGAAAT ACTTTCACCT
     GCTCTGTGTT ACATGAGGGC
1351 CTGCACAACC ACCATACTGA GAAGAGCCTC
     TCCCACTCTC CTGGTAAATG
1401 A
```

Ab-4 was humanized to generate Ab-5.

Ab-5

The sequences of the Antibody 5 (also referred to herein as Ab-5) LC and HC are as follows:

Ab-5 Light Chain:

Amino acid sequence of the mature form (signal peptide removed) of the Ab-5 LC:

(SEQ ID NO: 141)
```
  1 DIQMTQSPSS LSASVGDRVT ITCRASQDIS NYLNWYQQKP GKAPKLLIYY
 51 TSRLHSGVPS RFSGSGSGTD FTLTISSLQP EDFATYYCQQ GDTLPYTFGG
101 GTKVEIKRTV AAPSVFIFPP SDEQLKSGTA SVVCLLNNFY PREAKVQWKV
151 DNALQSGNSQ ESVTEQDSKD STYSLSSTLT LSKADYEKHK VYACEVTHQG
201 LSSPVTKSFN RGEC
```

Nucleic acid sequence encoding the mature form (signal peptide removed) of the Ab-5 LC:

(SEQ ID NO: 142)
```
  1  GACATCCAGA TGACCCAGTC TCCATCCTCC
     CTCTCCGCAT CCGTAGGCGA
 51  CCGCGTAACC ATAACATGTA GAGCATCTCA
     AGATATTTCC AACTATTTGA
101  ATTGGTACCA ACAAAAACCC GGCAAAGCAC
     CTAAACTCCT CATTTACTAT
```

```
151 ACATCAAGAC TCCTCTCCGG CGTTCCATCA
    CGATTCTCAG GCTCCGGCTC
201 CGGCACAGAT TTCACACTCA CTATTTCCTC
    CCTCCAACCA GAAGATTTTG
251 CAACCTATTA CTGTCAACAA GGCGATACAC
    TCCCATACAC ATTCGGCGGC
301 GGCACAAAAG TTGAAATTAA ACGTACGGTG
    GCTGCACCAT CTGTCTTCAT
351 CTTCCCGCCA TCTGATGAGC AGTTGAAATC
    TGGAACTGCC TCTGTTGTGT
401 GCCTGCTGAA TAACTTCTAT CCCAGAGAGG
    CCAAAGTACA GTGGAAGGTG
451 GATAACGCCC TCCAATCGGG TAACTCCCAG
    GAGAGTGTCA CAGAGCAGGA
501 CAGCAAGGAC AGCACCTACA GCCTCAGCAG
    CACCCTGACG CTGAGCAAAG
551 CAGACTACGA GAAACACAAA GTCTACGCCT
    GCGAAGTCAC CCATCAGGGC
601 CTGAGCTCGC CCGTCACAAA GAGCTTCAAC
    AGGGGAGAGT GT
```

Amino acid sequence of the Ab-5 LC including signal peptide:

```
                                    (SEQ ID NO: 143)
  1 MDMRVPAQLL GLLLLWLRGA RCDIQMTQSP
    SSLSASVGDR VTITCRASQD
 51 ISNYLNWYQQ KPGKAPKLLI YYTSRLLSGV
    PSRFSGSGSG TDFTLTISSL
101 QPEDFATYYC QQGDTLPYTF GGGTKVEIKR
    TVAAPSVFIF PPSDEQLKSG
151 TASVVCLLNN FYPREAKVQW KVDNALQSGN
    SQESVTEQDS KDSTYSLSST
201 LTLSKADYEK HKVYACEVTH QGLSSPVTKS
    FNRGEC
```

Nucleic acid sequence of the Ab-5 LC including signal peptide encoding sequence:

```
                                    (SEQ ID NO: 144)
  1 ATGGACATGA GGGTCCCCGC TCAGCTCCTG
    GGGCTCCTGC TACTCTGGCT
 51 CCGAGGTGCC AGATGTGACA TCCAGATGAC
    CCAGTCTCCA TCCTCCCTCT
101 CCGCATCCGT AGGCGACCGC GTAACCATAA
    CATGTAGAGC ATCTCAAGAT
151 ATTTCCAACT ATTTGAATTG GTACCAACAA
    AAACCCGGCA AAGCACCTAA
201 ACTCCTCATT TACTATACAT CAAGACTCCT
    CTCCGGCGTT CCATCACGAT
251 TCTCAGGCTC CGGCTCCGGC ACAGATTTCA
    CACTCACTAT TTCCTCCCTC
301 CAACCAGAAG ATTTTGCAAC CTATTACTGT
    CAACAAGGCG ATACACTCCC
351 ATACACATTC GGCGGCGGCA CAAAAGTTGA
    AATTAAACGT ACGGTGGCTG
401 CACCATCTGT CTTCATCTTC CCGCCATCTG
    ATGAGCAGTT GAAATCTGGA
451 ACTGCCTCTG TTGTGTGCCT GCTGAATAAC
    TTCTATCCCA GAGAGGCCAA
501 AGTACAGTGG AAGGTGGATA ACGCCCTCCA
    ATCGGGTAAC TCCCAGGAGA
551 GTGTCACAGA GCAGGACAGC AAGGACAGCA
    CCTACAGCCT CAGCAGCACC
601 CTGACGCTGA GCAAAGCAGA CTACGAGAAA
    CACAAAGTCT ACGCCTGCGA
651 AGTCACCCAT CAGGGCCTGA GCTCGCCCGT
    CACAAAGAGC TTCAACAGGG
701 GAGAGTGT
```

Ab-5 Heavy Chain:

Amino acid sequence of the mature form (signal peptide removed) of the Ab-5 HC:

```
                                    (SEQ ID NO: 145)
  1 EVQLVQSGAE VKKPGASVKV SCKASGYTFT DYNMHWVRQA PGQGLEWMGE
 51 INPNSGGAGY NQKFKGRVTM TTDTSTSTAY MELRSLRSDD TAVYYCARLG
101 YDDIYDDWYF DVWGQGTTVT VSSASTKGPS VFPLAPCSRS TSESTAALGC
151 LVKDYFPEPV TVSWNSGALT SGVHTFPAVL QSSGLYSLSS VVTVPSSNFG
201 TQTYTCNVDH KPSNTKVDKT VERKCCVECP PCPAPPVAGP SVFLFPPKPK
251 DTLMISRTPE VTCVVVDVSH EDPEVQFNWY VDGVEVHNAK TKPREEQFNS
301 TFRVVSVLTV VHQDWLNGKE YKCKVSNKGL PAPIEKTISK TKGQPREPQV
351 YTLPPSREEM TKNQVSLTCL VKGFYPSDIA VEWESNGQPE NNYKTTPPML
401 DSDGSFFLYS KLTVDKSRWQ QGNVFSCSVM HEALHNHYTQ KSLSLSPGK
```

Amino acid sequence of the mature form (signal peptide removed) of the Ab-5 HC without carboxy-terminal lysine:

(SEQ ID NO: 392)

```
  1 EVQLVQSGAE VKKPGASVKV SCKASGYTFT DYNMHWVRQA PGQGLEWMGE
 51 INPNSGGAGY NQKFKGRVTM TTDTSTSTAY MELRSLRSDD TAVYYCARLG
101 YDDIYDDWYF DVWGQGTTVT VSSASTKGPS VFPLAPCSRS TSESTAALGC
151 LVKDYFPEPV TVSWNSGALT SGVHTFPAVL QSSGLYSLSS VVTVPSSNFG
201 TQTYTCNVDH KPSNTKVDKT VERKCCVECP PCPAPPVAGP SVFLFPPKPK
251 DTLMISRTPE VTCVVVDVSH EDPEVQFNWY VDGVEVHNAK TKPREEQFNS
301 TFRVVSVLTV VHQDWLNGKE YKCKVSNKGL PAPIEKTISK TKGQPREPQV
351 YTLPPSREEM TKNQVSLTCL VKGFYPSDIA VEWESNGQPE NNYKTTPPML
401 DSDGSFFLYS KLTVDKSRWQ QGNVFSCSVM HEALHNHYTQ KSLSLSPS
```

Nucleic acid sequence encoding the mature form (signal peptide removed) of the Ab-5 HC:

(SEQ ID NO: 146)

```
   1 GAGGTGCAGC TGGTGCAGAG CGGCGCCGAG
     GTAAAAAAAC CAGGAGCAAG
  51 CGTTAAAGTT TCTTGTAAAG CAAGCGGATA
     TACATTTACA GATTACAACA
 101 TGCATTGGGT AAGACAAGCG CCAGGACAAG
     GATTGGAATG GATGGGCGAA
 151 ATTAACCCTA ATAGTGGAGG AGCAGGCTAC
     AATCAAAAAT TCAAAGGGAG
 201 AGTTACAATG ACAACAGACA CAAGCACTTC
     AACAGCATAT ATGGAACTGC
 251 GATCACTTAG AAGCGACGAT ACAGCTGTAT
     ACTATTGCGC ACGACTTGGG
 301 TATGATGATA TATATGATGA CTGGTATTTC
     GATGTTTGGG GCCAGGGAAC
 351 AACAGTTACC GTCTCTAGTG CCTCCACCAA
     GGGCCCATCG GTCTTCCCCC
 401 TGGCGCCCTG CTCCAGGAGC ACCTCCGAGA
     GCACAGCGGC CCTGGGCTGC
 451 CTGGTCAAGG ACTACTTCCC CGAACCGGTG
     ACGGTGTCGT GGAACTCAGG
 501 CGCTCTGACC AGCGGCGTGC ACACCTTCCC
     AGCTGTCCTA CAGTCCTCAG
 551 GACTCTACTC CCTCAGCAGC GTGGTGACCG
     TGCCCTCCAG CAACTTCGGC
 601 ACCCAGACCT ACACCTGCAA CGTAGATCAC
     AAGCCCAGCA ACACCAAGGT
 651 GGACAAGACA GTTGAGCGCA AATGTTGTGT
     CGAGTGCCCA CCGTGCCCAG
 701 CACCACCTGT GGCAGGACCG TCAGTCTTCC
     TCTTCCCCCC AAAACCCAAG
 751 GACACCCTCA TGATCTCCCG GACCCCTGAG
     GTCACGTGCG TGGTGGTGGA
 801 CGTGAGCCAC GAAGACCCCG AGGTCCAGTT
     CAACTGGTAC GTGGACGGCG
 851 TGGAGGTGCA TAATGCCAAG ACAAAGCCAC
     GGGAGGAGCA GTTCAACAGC
 901 ACGTTCCGTG TGGTCAGCGT CCTCACCGTT
     GTGCACCAGG ACTGGCTGAA
 951 CGGCAAGGAG TACAAGTGCA AGGTCTCCAA
     CAAAGGCCTC CCAGCCCCCA
1001 TCGAGAAAAC CATCTCCAAA ACCAAAGGGC
     AGCCCCGAGA ACCACAGGTG
1051 TACACCCTGC CCCCATCCCG GGAGGAGATG
     ACCAAGAACC AGGTCAGCCT
1101 GACCTGCCTG GTCAAGGCT TCTACCCCAG
     CGACATCGCC GTGGAGTGGG
1151 AGAGCAATGG GCAGCCGGAG AACAACTACA
     AGACCACACC TCCCATGCTG
1201 GACTCCGACG GCTCCTTCTT CCTCTACAGC
     AAGCTCACCG TGGACAAGAG
1251 CAGGTGGCAG CAGGGGAACG TCTTCTCATG
     CTCCGTGATG CATGAGGCTC
1301 TGCACAACCA CTACACGCAG AAGAGCCTCT
     CCCTGTCTCC GGGTAAA
```

Amino acid sequence of the Ab-5 HC including signal peptide:

(SEQ ID NO: 147)

```
  1 MDWTWRILFL VAAATGAHSE VQLVQSGAEV
    KKPGASVKVS CKASGYTFTD
 51 YNMHWVRQAP GQGLEWMGEI NPNSGGAGYN
    QKFKGRVTMT TDTSTSTAYM
101 ELRSLRSDDT AVYYCARLGY DDIYDDWYFD
    VWGQGTTVTV SSASTKGPSV
151 FPLAPCSRST SESTAALGCL VKDYFPEPVT
    VSWNSGALTS GVHTFPAVLQ
201 SSGLYSLSSV VTVPSSNFGT QTYTCNVDHK
    PSNTKVDKTV ERKCCVECPP
251 CPAPPVAGPS VFLFPPKPKD TLMISRTPEV
    TCVVVDVSHE DPEVQFNWYV
301 DGVEVHNAKT KPREEQFNST FRVVSVLTVV
    HQDWLNGKEY KCKVSNKGLP
351 APIEKTISKT KGQPREPQVY TLPPSREEMT
    KNQVSLTCLV KGFYPSDIAV
401 EWESNGQPEN NYKTTPPMLD SDGSFFLYSK
    LTVDKSRWQQ GNVFSCSVMH
451 EALHNHYTQK SLSLSPGK
```

Nucleic acid sequence of the Ab-5 HC including signal peptide encoding sequence:

(SEQ ID NO: 148)

```
   1  ATGGACTGGA CCTGGAGGAT CCTCTTCTTG
      GTGGCAGCAG CCACAGGAGC
  51  CCACTCCGAG GTGCAGCTGG TGCAGAGCGG
      CGCCGAGGTA AAAAAACCAG
 101  GAGCAAGCGT TAAAGTTTCT TGTAAAGCAA
      GCGGATATAC ATTTACAGAT
 151  TACAACATGC ATTGGGTAAG ACAAGCGCCA
      GGACAAGGAT TGGAATGGAT
 201  GGGCGAAATT AACCCTAATA GTGGAGGAGC
      AGGCTACAAT CAAAAATTCA
 251  AAGGGAGAGT TACAATGACA ACAGACACAA
      GCACTTCAAC AGCATATATG
 301  GAACTGCGAT CACTTAGAAG CGACGATACA
      GCTGTATACT ATTGCGCACG
 351  ACTTGGGTAT GATGATATAT ATGATGACTG
      GTATTTCGAT GTTTGGGGCC
 401  AGGGAACAAC AGTTACCGTC TCTAGTGCCT
      CCACCAAGGG CCCATCGGTC
 451  TTCCCCCTGG CGCCCTGCTC CAGGAGCACC
      TCCGAGAGCA CAGCGGCCCT
 501  GGGCTGCCTG GTCAAGGACT ACTTCCCCGA
      ACCGGTGACG GTGTCGTGGA
```

-continued

```
 551  ACTCAGGCGC TCTGACCAGC GGCGTGCACA
      CCTTCCCAGC TGTCCTACAG
 601  TCCTCAGGAC TCTACTCCCT CAGCAGCGTG
      GTGACCGTGC CCTCCAGCAA
 651  CTTCGGCACC CAGACCTACA CCTGCAACGT
      AGATCACAAG CCCAGCAACA
 701  CCAAGGTGGA CAAGACAGTT GAGCGCAAAT
      GTTGTGTCGA GTGCCCACCG
 751  TGCCCAGCAC CACCTGTGGC AGGACCGTCA
      GTCTTCCTCT TCCCCCCAAA
 801  ACCCAAGGAC ACCCTCATGA TCTCCCGGAC
      CCCTGAGGTC ACGTGCGTGG
 851  TGGTGGACGT GAGCCACGAA GACCCCGAGG
      TCCAGTTCAA CTGGTACGTG
 901  GACGGCGTGG AGGTGCATAA TGCCAAGACA
      AAGCCACGGG AGGAGCAGTT
 951  CAACAGCACG TTCCGTGTGG TCAGCGTCCT
      CACCGTTGTG CACCAGGACT
1001  GGCTGAACGG CAAGGAGTAC AAGTGCAAGG
      TCTCCAACAA AGGCCTCCCA
```

-continued

```
1051  GCCCCCATCG AGAAAACCAT CTCCAAAACC
      AAAGGGCAGC CCCGAGAACC
1101  ACAGGTGTAC ACCCTGCCCC CATCCCGGGA
      GGAGATGACC AAGAACCAGG
1151  TCAGCCTGAC CTGCCTGGTC AAAGGCTTCT
      ACCCCAGCGA CATCGCCGTG
1201  GAGTGGGAGA GCAATGGGCA GCCGGAGAAC
      AACTACAAGA CCACACCTCC
1251  CATGCTGGAC TCCGACGGCT CCTTCTTCCT
      CTACAGCAAG CTCACCGTGG
1301  ACAAGAGCAG GTGGCAGCAG GGGAACGTCT
      TCTCATGCTC CGTGATGCAT
1351  GAGGCTCTGC ACAACCACTA CACGCAGAAG
      AGCCTCTCCC TGTCTCCGGG
1401  TAAA
```

Ab-5 Variable Domains:

Ab-5 light chain variable domain amino acid sequence (without signal sequence):

(SEQ ID NO: 376)

```
  1  DIQMTQSPSS LSASVGDRVT ITCRASQDIS NYLNWYQQKP GKAPKLLIYY
 51  TSRLLSGVPS RFSGSGSGTD FTLTISSLQP EDFATYYCQQ GDTLPYTFGG
101  GTKVEIK
```

Ab-5 light chain variable domain DNA sequence (without signal sequence):

(SEQ ID NO: 377)

```
  1  GACATCCAGA TGACCCAGTC TCCATCCTCC
     CTCTCCGCAT CCGTAGGCGA
 51  CCGCGTAACC ATAACATGTA GAGCATCTCA
     AGATATTTCC AACTATTTGA
101  ATTGGTACCA ACAAAAACCC GGCAAAGCAC
     CTAAACTCCT CATTTACTAT
151  ACATCAAGAC TCCTCTCCGG CGTTCCATCA
     CGATTCTCAG GCTCCGGCTC
201  CGGCACAGAT TTCACACTCA CTATTTCCTC
     CCTCCAACCA GAAGATTTTG
251  CAACCTATTA CTGTCAACAA GGCGATACAC
     TCCCATACAC ATTCGGCGGC
301  GGCACAAAAG TTGAAATTAA A
```

Ab-5 heavy chain variable domain amino acid sequence (without signal sequence):

```
  1 EVQLVQSGAE VKKPGASVKV SCKASGYTFT DYNMHWVRQA PGQGLEWMGE
 51 INPNSGGAGY NQKFKGRVTM TTDTSTSTAY MELRSLRSDD TAVYYCARLG
101 YDDIYDDWYF DVWGQGTTVT VSS
```

Ab-5 heavy chain variable domain DNA sequence (without signal sequence):

```
                              (SEQ ID NO: 379)
  1   GAGGTGCAGC TGGTGCAGAG CGGCGCCGAG
      GTAAAAAAAC CAGGAGCAAG
 51   CGTTAAAGTT TCTTGTAAAG CAAGCGGATA
      TACATTTACA GATTACAACA
101   TGCATTGGGT AAGACAAGCG CCAGGACAAG
      GATTGGAATG GATGGGCGAA
151   ATTAACCCTA ATAGTGGAGG AGCAGGCTAC
      AATCAAAAAT TCAAAGGGAG
201   AGTTACAATG ACAACAGACA CAAGCACTTC
      AACAGCATAT ATGGAACTGC
251   GATCACTTAG AAGCGACGAT ACAGCTGTAT
      ACTATTGCGC ACGACTTGGG
301   TATGATGATA TATATGATGA CTGGTATTTC
      GATGTTTGGG GCCAGGGAAC
351   AACAGTTACC GTCTCTAGT
```

The CDR (complementarity determining region) sequences in the variable region of the heavy chain of Ab-5 are as follows:

```
CDR-H1:   DYNMH              (SEQ ID NO: 245)
CDR-H2:   EINPNSGGAGYNQKFKG  (SEQ ID NO: 246)
CDR-H3:   LGYDDIYDDWYFDV     (SEQ ID NO: 247)
```

The light chain variable region CDR sequences of Ab-5 are:

```
CDR-L1:   RASQDISNYLN   (SEQ ID NO: 78)
CDR-L2:   YTSRLLS       (SEQ ID NO: 79)
CDR-L3:   QQGDTLPYT     (SEQ ID NO: 80)
```

Ab-6

The sequences of the Antibody 6 (also referred to herein as Ab-6) LC and HC are as follows:

Ab-6 Light Chain:

Amino acid sequence of the mature form (signal peptide removed) of the Ab-6 LC:

```
                                            (SEQ ID NO: 149)
  1 DIQMTQTTSS LSASLGDRVT ISCRASQDIS NYLNWFQQKP DGTLKLLIFY
 51 TSRLHSGVPS RFSGSGSGTD YSLTISNLEQ EDIATYFCQQ GDTLPYTFGG
101 GTKLEIRRAD AAPTVSIFPP SSEQLTSGGA SVVCFLNNFY PKDINVKWKI
151 DGSERQNGVL NSWTDQDSKD STYSMSSTLT LTKDEYERHN SYTCEATHKT
201 STSPIVKSFN RNEC
```

Nucleic acid sequence encoding the mature form (signal peptide removed) of the Ab-6 LC:

```
                              (SEQ ID NO: 378)
  1   GATATCCAGA TGACACAGAC TACATCCTCC
      CTGTCTGCCT CTCTGGGAGA
 51   CAGAGTCACC ATCAGTTGCA GGGCAAGTCA
      GGACATTAGC AATTATTTAA
101   ACTGGTTTCA GCAGAAACCA GATGGAACTC
      TTAAACTCCT GATCTTTCTAC
151   ACATCAAGAT TACACTCAGG AGTTCCATCA
      AGGTTCAGTG GCAGTGGGTC
201   TGGAACAGAT TATTCTCTCA CCATTAGCAA
      CCTGGAGCAA GAAGATATTG
251   CCACTTACTT TTGCCAACAG GGTGATACGC
      TTCCGTACAC GTTCGGGGGG
301   GGGACCAAGC TGGAAATAAG ACGGGCTGAT
      GCTGCACCAA CTGTATCCAT
351   CTTCCCACCA TCCAGTGAGC AGTTAACATC
      TGGAGGTGCC TCAGTCGTGT
401   GCTTCTTGAA CAACTTCTAC CCCAAAGACA
      TCAATGTCAA GTGGAAGATT
451   GATGGCAGTG AACGACAAAA TGGCGTCCTG
      AACAGTTGGA CTGATCAGGA
501   CAGCAAAGAC AGCACCTACA GCATGAGCAG
      CACCCTCACG TTGACCAAGG
551   ACGAGTATGA ACGACATAAC AGCTATACCT
      GTGAGGCCAC TCACAAGACA
601   TCAACTTCAC CCATTGTCAA GAGCTTCAAC
      AGGAATGAGT GTTAG
```

Amino acid sequence of the Ab-6 LC including signal peptide:

```
                                            (SEQ ID NO: 151)
  1 MMSSAQFLGL LLLCFQGTRC DIQMTQTTSS
    LSASLGDRVT ISCRASQDIS
 51 NYLNWFQQKP DGTLKLLIFY TSRLHSGVPS
    RFSGSGSGTD YSLTISNLEQ
```

```
101    EDIATYFCQQ GDTLPYTFGG GTKLEIRRAD
       AAPTVSIFPP SSEQLTSGGA

151    SVVCFLNNFY PKDINVKWKI DGSERQNGVL
       NSWTDQDSKD STYSMSSTLT

201    LTKDEYERHN SYTCEATHKT STSPIVKSFN
       RNEC
```

Nucleic acid sequence of the Ab-6 LC including signal peptide encoding sequence:

```
                                   (SEQ ID NO: 152)
  1    ATGATGTCCT CTGCTCAGTT CCTTGGTCTC
       CTGTTGCTCT GTTTTCAAGG

51    TACCAGATGT GATATCCAGA TGACACAGAC
       TACATCCTCC CTGTCTGCCT

101    CTCTGGGAGA CAGAGTCACC ATCAGTTGCA
       GGGCAAGTCA GGACATTAGC

151    AATTATTTAA ACTGGTTTCA GCAGAAACCA
       GATGGAACTC TTAAACTCCT

201    GATCTTCTAC ACATCAAGAT TACACTCAGG
       AGTTCCATCA AGGTTCAGTG

251    GCAGTGGGTC TGGAACAGAT TATTCTCTCA
       CCATTAGCAA CCTGGAGCAA

301    GAAGATATTG CCACTTACTT TTGCCAACAG
       GGTGATACGC TTCCGTACAC

351    GTTCGGGGGG GGGACCAAGC TGGAAATAAG
       ACGGGCTGAT GCTGCACCAA

401    CTGTATCCAT CTTCCCACCA TCCAGTGAGC
       AGTTAACATC TGGAGGTGCC

451    TCAGTCGTGT GCTTCTTGAA CAACTTCTAC
       CCCAAAGACA TCAATGTCAA

501    GTGGAAGATT GATGGCAGTG AACGACAAAA
       TGGCGTCCTG AACAGTTGGA

551    CTGATCAGGA CAGCAAAGAC AGCACCTACA
       GCATGAGCAG CACCCTCACG

601    TTGACCAAGG ACGAGTATGA ACGACATAAC
       AGCTATACCT GTGAGGCCAC

651    TCACAAGACA TCAACTTCAC CCATTGTCAA
       GAGCTTCAAC AGGAATGAGT

701    GTTAG
```

Ab-6 Heavy Chain:

Amino acid sequence of the mature form (signal peptide removed) of the Ab-6 HC:

Nucleic acid sequence encoding the mature form (signal peptide removed) of the Ab-6 HC:

```
                                   (SEQ ID NO: 154)
  1    GAGGTCCAGC TGCAACAGTC TGGACCTGAA
       CTAATGAAGC CTGGGGCTTC

51    AGTGAAGATG TCCTGCAAGG CTTCTGGATA
       CACATTCACT GACTACAACA

101    TGCACTGGGT GAAACAGAAC CAAGGAAAGA
       GCCTAGAGTG GATAGGAGAA

151    ATTAATCCTA ACAGTGGTGG TAGTGGCTAC
       AACCAAAAGT TCAAAGGCAA

201    GGCCACATTG ACTGTAGACA AGTCTTCCAG
       CACAGCCTAC ATGGAGCTCC

251    GCAGCCTGAC ATCTGAGGAC TCTGCAGTCT
       ATTACTGTGC AAGATTGGTC

301    TACGATGGCA GCTACGAGGA CTGGTACTTC
       GATGTCTGGG GCGCAGGGAC

351    CACGGTCACC GTCTCCTCAG CCAAAACGAC
       ACCCCCATCT GTCTATCCAC

401    TGGCCCCTGG ATCTGCTGCC CAAACTAACT
       CCATGGTGAC CCTGGGATGC

451    CTGGTCAAGG GCTATTTCCC TGAGCCAGTG
       ACAGTGACCT GGAACTCTGG

501    ATCCCTGTCC AGCGGTGTGC ACACCTTCCC
       AGCTGTCCTG CAGTCTGACC

551    TCTACACTCT GAGCAGCTCA GTGACTGTCC
       CCTCCAGCAC CTGGCCCAGC

601    GAGACCGTCA CCTGCAACGT TGCCCACCCG
       GCCAGCAGCA CCAAGGTGGA

651    CAAGAAAATT GTGCCCAGGG ATTGTGGTTG
       TAAGCCTTGC ATATGTACAG

701    TCCCAGAAGT ATCATCTGTC TTCATCTTCC
       CCCCAAAGCC CAAGGATGTG

751    CTCACCATTA CTCTGACTCC TAAGGTCACG
       TGTGTTGTGG TAGACATCAG

801    CAAGGATGAT CCCGAGGTCC AGTTCAGCTG
       GTTTGTAGAT GATGTGGAGG

851    TGCACACAGC TCAGACGCAA CCCCGGGAGG
       AGCAGTTCAA CAGCACTTTC

901    CGCTCAGTCA GTGAACTTCC CATCATGCAC
       CAGGACTGGC TCAATGGCAA

951    GGAGTTCAAA TGCAGGGTCA ACAGTGCAGC
       TTTCCCTGCC CCCATCGAGA
```

```
                                   (SEQ ID NO: 153)
  1    EVQLQQSGPE LMKPGASVKM SCKASGYTFT DYNMHWVKQN QGKSLEWIGE
 51    INPNSGGSGY NQKFKGKATL TVDKSSSTAY MELRSLTSED SAVYYCARLV
101    YDGSYEDWYF DVWGAGTTVT VSSAKTTPPS VYPLAPGSAA QTNSMVTLGC
151    LVKGYFPEPV TVTWNSGSLS SGVHTFPAVL QSDLYTLSSS VTVPSSTWPS
201    ETVTCNVAHP ASSTKVDKKI VPRDCGCKPC ICTVPEVSSV FIFPPKPKDV
251    LTITLTPKVT CVVVDISKDD PEVQFSWFVD DVEVHTAQTQ PREEQFNSTF
301    RSVSELPIMH QDWLNGKEFK CRVNSAAFPA PIEKTISKTK GRPKAPQVYT
351    IPPPKEQMAK DKVSLTCMIT DFFPEDITVE WQQNGQPAEN YKNTQPIMDT
401    DGSYFIYSKL NVQKSNWEAG NTFTCSVLHE GLHNHHTEKS LSHSPGK
```

```
1001  AAACCATCTC CAAAACCAAA GGCAGACCGA
      AGGCTCCACA GGTGTACACC

1051  ATTCCACCTC CCAAGGAGCA GATGGCCAAG
      GATAAAGTCA GTCTGACCTG

1101  CATGATAACA GACTTCTTCC CTGAAGACAT
      TACTGTGGAG TGGCAGTGGA

1151  ATGGGCAGCC AGCGGAGAAC TACAAGAACA
      CTCAGCCCAT CATGGACACA

1201  GATGGCTCTT ACTTCATCTA CAGCAAGCTC
      AATGTGCAGA AGAGCAACTG

1251  GGAGGCAGGA AATACTTTCA CCTGCTCTGT
      GTTACATGAG GGCCTGCACA

1301  ACCACCATAC TGAGAAGAGC CTCTCCCACT
      CTCCTGGTAA ATGA
```

Amino acid sequence of the Ab-6 HC including signal peptide:

```
                                    (SEQ ID NO: 155)
  1   MGWSWTFLFL LSGTAGVLSE VQLQQSGPEL
      MKPGASVKMS CKASGYTFTD

51   YNMHWVKQNQ GKSLEWIGEI NPNSGGSGYN
      QKFKGKATLT VDKSSSTAYM

101   ELRSLTSEDS AVYYCARLVY DGSYEDWYFD
      VWGAGTTVTV SSAKTTPPSV

151   YPLAPGSAAQ TNSMVTLGCL VKGYFPEPVT
      VTWNSGSLSS GVHTFPAVLQ

201   SDLYTLSSSV TVPSSTWPSE TVTCNVAHPA
      SSTKVDKKIV PRDCGCKPCI

251   CTVPEVSSVF IFPPKPKDVL TITLTPKVTC
      VVVDISKDDP EVQFSWFVDD

301   VEVHTAQTQP REEQFNSTFR SVSELPIMHQ
      DWLNGKEFKC RVNSAAFPAP

351   IEKTISKTKG RPKAPQVYTI PPPKEQMAKD
      KVSLTCMITD FFPEDITVEW

401   QWNGQPAENY KNTQPIMDTD GSYFIYSKLN
      VQKSNWEAGN TFTCSVLHEG

451   LHNHHTEKSL SHSPGK
```

Nucleic acid sequence of the Ab-6 HC including signal peptide encoding sequence:

```
                                    (SEQ ID NO: 156)
  1   ATGGGATGGA GCTGGACCTT TCTCTTCCTC
      CTGTCAGGAA CTGCAGGTGT

51   CCTCTCTGAG GTCCAGCTGC AACAGTCTGG
      ACCTGAACTA ATGAAGCCTG

101   GGGCTTCAGT GAAGATGTCC TGCAAGGCTT
      CTGGATACAC ATTCACTGAC

151   TACAACATGC ACTGGGTGAA ACAGAACCAA
      GGAAAGAGCC TAGAGTGGAT

201   AGGAGAAATT AATCCTAACA GTGGTGGTAG
      TGGCTACAAC CAAAAGTTCA

251   AAGGCAAGGC CACATTGACT GTAGACAAGT
      CTTCCAGCAC AGCCTACATG

301   GAGCTCCGCA GCCTGACATC TGAGGACTCT
      GCAGTCTATT ACTGTGCAAG

351   ATTGGTCTAC GATGGCAGCT ACGAGGACTG
      GTACTTCGAT GTCTGGGGCG

401   CAGGGACCAC GGTCACCGTC TCCTCAGCCA
      AAACGACACC CCCATCTGTC

451   TATCCACTGG CCCCTGGATC TGCTGCCCAA
      ACTAACTCCA TGGTGACCCT

501   GGGATGCCTG GTCAAGGGCT ATTTCCCTGA
      GCCAGTGACA GTGACCTGGA

551   ACTCTGGATC CCTGTCCAGC GGTGTGCACA
      CCTTCCCAGC TGTCCTGCAG

601   TCTGACCTCT ACACTCTGAG CAGCTCAGTG
      ACTGTCCCCT CCAGCACCTG

651   GCCCAGCGAG ACCGTCACCT GCAACGTTGC
      CCACCCGGCC AGCAGCACCA

701   AGGTGGACAA GAAAATTGTG CCCAGGGATT
      GTGGTTGTAA GCCTTGCATA

751   TGTACAGTCC AGAAGTATC ATCTGTCTTC
      ATCTTCCCCC CAAAGCCCAA

801   GGATGTGCTC ACCATTACTC TGACTCCTAA
      GGTCACGTGT GTTGTGGTAG

851   ACATCAGCAA GGATGATCCC GAGGTCCAGT
      TCAGCTGGTT TGTAGATGAT

901   GTGGAGGTGC ACACAGCTCA GACGCAACCC
      CGGGAGGAGC AGTTCAACAG

951   CACTTTCCGC TCAGTCAGTG AACTTCCCAT
      CATGCACCAG GACTGGCTCA

1001  ATGGCAAGGA GTTCAAATGC AGGGTCAACA
      GTGCAGCTTT CCCTGCCCCC

1051  ATCGAGAAAA CCATCTCCAA AACCAAAGGC
      AGACCGAAGG CTCCACAGGT

1101  GTACACCATT CCACCTCCCA AGGAGCAGAT
      GGCCAAGGAT AAAGTCAGTC

1151  TGACCTGCAT GATAACAGAC TTCTTCCCTG
      AAGACATTAC TGTGGAGTGG

1201  CAGTGGAATG GGCAGCCAGC GGAGAACTAC
      AAGAACACTC AGCCCATCAT

1251  GGACACAGAT GGCTCTTACT TCATCTACAG
      CAAGCTCAAT GTGCAGAAGA

1301  GCAACTGGGA GGCAGGAAAT ACTTTCACCT
      GCTCTGTGTT ACATGAGGGC

1351  CTGCACAACC ACCATACTGA AGAGCCTC
      TCCCACTCTC CTGGTAAATG

1401  A
```

Ab-7

The sequences of the Antibody 7 (also referred to herein as Ab-7) LC and HC are as follows:

Ab-7 Light Chain:

Amino acid sequence of the mature form (signal peptide removed) of the Ab-7 LC:

```
  1 DIQMTQTTSS LSASLGDRVT ICCRASQVIT NYLYWYQQKP DGTFKLLIYY
 51 TSRLHSGVPS RFSGSGSGTD YSLTISNLEQ EDIATYFCQQ GDTLPYTFGG
101 GTKLEIKRAD AAPTVSIFPP SSEQLTSGGA SVVCFLNNFY PKDINVKWKI
151 DGSERQNGVL NSWTDQDSKD STYSMSSTLT LTKDEYERHN SYTCEATHKT
201 STSPIVKSFN RNEC
```
(SEQ ID NO: 157)

Nucleic acid sequence encoding the mature form (signal peptide removed) of the Ab-7 LC:

(SEQ ID NO: 158)
```
  1   GATATCCAGA TGACACAGAC TACATCCTCC
      CTGTCTGCCT CTCTGGGAGA
 51   CAGAGTCACC ATCTGTTGCA GGGCAAGTCA
      GGTCATTACC AATTATTTAT
101   ACTGGTATCA GCAGAAACCA GATGGAACTT
      TTAAACTCCT GATCTACTAC
151   ACATCAAGAT TACACTCAGG AGTCCCATCA
      AGGTTCAGTG GCAGTGGGTC
201   TGGAACAGAT TATTCTCTCA CCATTAGCAA
      CCTGGAACAG GAAGATATTG
251   CCACTTACTT TTGCCAACAG GGTGATACGC
      TTCCGTACAC GTTCGGAGGG
301   GGGACCAAGC TGGAAATAAA ACGGGCTGAT
      GCTGCACCAA CTGTATCCAT
351   CTTCCCACCA TCCAGTGAGC AGTTAACATC
      TGGAGGTGCC TCAGTCGTGT
401   GCTTCTTGAA CAACTTCTAC CCCAAAGACA
      TCAATGTCAA GTGGAAGATT
451   GATGGCAGTG AACGACAAAA TGGCGTCCTG
      AACAGTTGGA CTGATCAGGA
501   CAGCAAAGAC AGCACCTACA GCATGAGCAG
      CACCCTCACG TTGACCAAGG
551   ACGAGTATGA ACGACATAAC AGCTATACCT
      GTGAGGCCAC TCACAAGACA
601   TCAACTTCAC CCATTGTCAA GAGCTTCAAC
      AGGAATGAGT GT
```

Amino acid sequence of the Ab-7 LC including signal peptide:

(SEQ ID NO: 159)
```
  1   MMSSAQFLGL LLLCFQGTRC DIQMTQTTSS
      LSASLGDRVT ICCRASQVIT
 51   NYLYWYQQKP DGTFKLLIYY TSRLHSGVPS
      RFSGSGSGTD YSLTISNLEQ
101   EDIATYFCQQ GDTLPYTFGG GTKLEIKRAD
      AAPTVSIFPP SSEQLTSGGA
151   SVVCFLNNFY PKDINVKWKI DGSERQNGVL
      NSWTDQDSKD STYSMSSTLT
201   LTKDEYERHN SYTCEATHKT STSPIVKSFN
      RNEC
```

Nucleic acid sequence of the Ab-7 LC including signal peptide encoding sequence:

(SEQ ID NO: 160)
```
  1   ATGATGTCCT CTGCTCAGTT CCTTGGTCTC
      CTGTTGCTCT GTTTTCAAGG
 51   TACCAGATGT GATATCCAGA TGACACAGAC
      TACATCCTCC CTGTCTGCCT
101   CTCTGGGAGA CAGAGTCACC ATCTGTTGCA
      GGGCAAGTCA GGTCATTACC
151   AATTATTTAT ACTGGTATCA GCAGAAACCA
      GATGGAACTT TTAAACTCCT
201   GATCTACTAC ACATCAAGAT TACACTCAGG
      AGTCCCATCA AGGTTCAGTG
251   GCAGTGGGTC TGGAACAGAT TATTCTCTCA
      CCATTAGCAA CCTGGAACAG
301   GAAGATATTG CCACTTACTT TTGCCAACAG
      GGTGATACGC TTCCGTACAC
351   GTTCGGAGGG GGGACCAAGC TGGAAATAAA
      ACGGGCTGAT GCTGCACCAA
401   CTGTATCCAT CTTCCCACCA TCCAGTGAGC
      AGTTAACATC TGGAGGTGCC
451   TCAGTCGTGT GCTTCTTGAA CAACTTCTAC
      CCCAAAGACA TCAATGTCAA
501   GTGGAAGATT GATGGCAGTG AACGACAAAA
      TGGCGTCCTG AACAGTTGGA
551   CTGATCAGGA CAGCAAAGAC AGCACCTACA
      GCATGAGCAG CACCCTCACG
601   TTGACCAAGG ACGAGTATGA ACGACATAAC
      AGCTATACCT GTGAGGCCAC
651   TCACAAGACA TCAACTTCAC CCATTGTCAA
      GAGCTTCAAC AGGAATGAGT
701   GT
```

Ab-7 Heavy Chain:

Amino acid sequence of the mature form (signal peptide removed) of the Ab-7 HC:

(SEQ ID NO: 161)

```
  1 EVQLQQSGPE LMKPGASVKM SCKASGYTFT DYNMHWMKQN QGKSLEWIGE
 51 INPNSGGAGY NQQFKGKATL TVDKSSRTAY MELRSLTSED SAVYYCARLG
101 YVGNYEDWYF DVWGAGTTVT VSSAKTTPPS VYPLAPGSAA QTNSMVTLGC
151 LVKGYFPEPV TVTWNSGSLS SGVHTFPAVL QSDLYTLSSS VTVPSSTWPS
201 ETVTCNVAHP ASSTKVDKKI VPRDCGCKPC ICTVPEVSSV FIFPPKPKDV
251 LTITLTPKVT CVVVDISKDD PEVQFSWFVD DVEVHTAQTQ PREEQFNSTF
301 RSVSELPIMH QDWLNGKEFK CRVNSAAFPA PIEKTISKTK GRPKAPQVYT
351 IPPPKEQMAK DKVSLTCMIT DFFPEDITVE WQWNGQPAEN YKNTQPIMDT
401 DGSYFIYSKL NVQKSNWEAG NTFTCSVLHE GLHNHHTEKS LSHSPGK
```

Nucleic acid sequence encoding the mature form (signal peptide removed) of the Ab-7 HC:

```
                                          (SEQ ID NO: 162)
   1    GAGGTCCAGC TGCAACAGTC TGGACCTGAA
        CTAATGAAGC CTGGGGCTTC
  51    AGTGAAGATG TCCTGCAAGG CTTCTGGATA
        CACATTCACT GACTACAACA
 101    TGCACTGGAT GAAGCAGAAC CAAGGAAAGA
        GCCTAGAATG GATAGGAGAA
 151    ATTAATCCTA ACAGTGGTGG TGCTGGCTAC
        AACCAGCAGT TCAAAGGCAA
 201    GGCCACATTG ACTGTAGACA AGTCCTCCAG
        GACAGCCTAC ATGGAGCTCC
 251    GCAGCCTGAC ATCTGAGGAC TCTGCAGTCT
        ATTACTGTGC AAGATTGGGC
 301    TACGTTGGTA ATTACGAGGA CTGGTACTTC
        GATGTCTGGG GCGCAGGGAC
 351    CACGGTCACC GTCTCCTCAG CCAAAACGAC
        ACCCCCATCT GTCTATCCAC
 401    TGGCCCCTGG ATCTGCTGCC CAAACTAACT
        CCATGGTGAC CCTGGGATGC
 451    CTGGTCAAGG GCTATTTCCC TGAGCCAGTG
        ACAGTGACCT GGAACTCTGG
 501    ATCCCTGTCC AGCGGTGTGC ACACCTTCCC
        AGCTGTCCTG CAGTCTGACC
 551    TCTACACTCT GAGCAGCTCA GTGACTGTCC
        CCTCCAGCAC CTGGCCCAGC
 601    GAGACCGTCA CCTGCAACGT TGCCCACCCG
        GCCAGCAGCA CCAAGGTGGA
 651    CAAGAAAATT GTGCCCAGGG ATTGTGGTTG
        TAAGCCTTGC ATATGTACAG
 701    TCCCAGAAGT ATCATCTGTC TTCATCTTCC
        CCCCAAAGCC CAAGGATGTG
 751    CTCACCATTA CTCTGACTCC TAAGGTCACG
        TGTGTTGTGG TAGACATCAG
 801    CAAGGATGAT CCCGAGGTCC AGTTCAGCTG
        GTTTGTAGAT GATGTGGAGG
 851    TGCACACAGC TCAGACGCAA CCCCGGGAGG
        AGCAGTTCAA CAGCACTTTC
 901    CGCTCAGTCA GTGAACTTCC CATCATGCAC
        CAGGACTGGC TCAATGGCAA
 951    GGAGTTCAAA TGCAGGGTCA ACAGTGCAGC
        TTTCCCTGCC CCCATCGAGA
1001    AAACCATCTC CAAAACCAAA GGCAGACCGA
        AGGCTCCACA GGTGTACACC
1051    ATTCCACCTC CCAAGGAGCA GATGGCCAAG
        GATAAAGTCA GTCTGACCTG
1101    CATGATAACA GACTTCTTCC CTGAAGACAT
        TACTGTGGAG TGGCAGTGGA
1151    ATGGGCAGCC AGCGGAGAAC TACAAGAACA
        CTCAGCCCAT CATGGACACA
1201    GATGGCTCTT ACTTCATCTA CAGCAAGCTC
        AATGTGCAGA AGAGCAACTG
1251    GGAGGCAGGA AATACTTTCA CCTGCTCTGT
        GTTACATGAG GGCCTGCACA
1301    ACCACCATAC TGAGAAGAGC CTCTCCCACT
        CTCCTGGTAA A
```

Amino acid sequence of the Ab-7 HC including signal peptide:

```
                                          (SEQ ID NO: 163)
  1    MGWSWTFLFL LSGTAGVLSE VQLQQSGPEL
       MKPGASVKMS CKASGYTFTD
 51    YNMHWMKQNQ GKSLEWIGEI NPNSGGAGYN
       QQFKGKATLT VDKSSRTAYM
101    ELRSLTSEDS AVYYCARLGY VGNYEDWYFD
       VWGAGTTVTV SSAKTTPPSV
151    YPLAPGSAAQ TNSMVTLGCL VKGYFPEPVT
       VTWNSGSLSS GVHTFPAVLQ
201    SDLYTLSSSV TVPSSTWPSE TVTCNVAHPA
       SSTKVDKKIV PRDCGCKPCI
251    CTVPEVSSVF IFPPKPKDVL TITLTPKVTC
       VVVDISKDDP EVQFSWFVDD
301    VEVHTAQTQP REEQFNSTFR SVSELPIMHQ
       DWLNGKEFKC RVNSAAFPAP
351    IEKTISKTKG RPKAPQVYTI PPPKEQMAKD
       KVSLTCMITD FFPEDITVEW
401    QWNGQPAENY KNTQPIMDTD GSYFIYSKLN
       VQKSNWEAGN TFTCSVLHEG
451    LHNHHTEKSL SHSPGK
```

Nucleic acid sequence of the Ab-7 HC including signal peptide encoding sequence:

```
                                          (SEQ ID NO: 164)
   1    ATGGGATGGA GCTGGACCTT TCTCTTCCTC
        CTGTCAGGAA CTGCAGGTGT
```

-continued

```
  51  CCTCTCTGAG GTCCAGCTGC AACAGTCTGG
      ACCTGAACTA ATGAAGCCTG
 101  GGGCTTCAGT GAAGATGTCC TGCAAGGCTT
      CTGGATACAC ATTCACTGAC
 151  TACAACATGC ACTGGATGAA GCAGAACCAA
      GGAAAGAGCC TAGAATGGAT
 201  AGGAGAAATT AATCCTAACA GTGGTGGTGC
      TGGCTACAAC CAGCAGTTCA
 251  AAGGCAAGGC CACATTGACT GTAGACAAGT
      CCTCCAGGAC AGCCTACATG
 301  GAGCTCCGCA GCCTGACATC TGAGGACTCT
      GCAGTCTATT ACTGTGCAAG
 351  ATTGGGCTAC GTTGGTAATT ACGAGGACTG
      GTACTTCGAT GTCTGGGGCG
 401  CAGGGACCAC GGTCACCGTC TCCTCAGCCA
      AAACGACACC CCCATCTGTC
 451  TATCCACTGG CCCCTGGATC TGCTGCCCAA
      ACTAACTCCA TGGTGACCCT
 501  GGGATGCCTG GTCAAGGGCT ATTTCCCTGA
      GCCAGTGACA GTGACCTGGA
 551  ACTCTGGATC CCTGTCCAGC GGTGTGCACA
      CCTTCCCAGC TGTCCTGCAG
 601  TCTGACCTCT ACACTCTGAG CAGCTCAGTG
      ACTGTCCCCT CCAGCACCTG
 651  GCCCAGCGAG ACCGTCACCT GCAACGTTGC
      CCACCCGGCC AGCAGCACCA
```

-continued

```
 701  AGGTGGACAA GAAAATTGTG CCCAGGGATT
      GTGGTTGTAA GCCTTGCATA
 751  TGTACAGTCC CAGAAGTATC ATCTGTCTTC
      ATCTTCCCCC CAAAGCCCAA
 801  GGATGTGCTC ACCATTACTC TGACTCCTAA
      GGTCACGTGT GTTGTGGTAG
 851  ACATCAGCAA GGATGATCCC GAGGTCCAGT
      TCAGCTGGTT TGTAGATGAT
 901  GTGGAGGTGC ACACAGCTCA GACGCAACCC
      CGGGAGGAGC AGTTCAACAG
 951  CACTTTCCGC TCAGTCAGTG AACTTCCCAT
      CATGCACCAG GACTGGCTCA
1001  ATGGCAAGGA GTTCAAATGC AGGGTCAACA
      GTGCAGCTTT CCCTGCCCCC
1051  ATCGAGAAAA CCATCTCCAA AACCAAGGC
      AGACCGAAGG CTCCACAGGT
1101  GTACACCATT CCACCTCCCA AGGAGGAGAT
      GGCCAAGGAT AAAGTCAGTC
1151  TGACCTGCAT GATAACAGAC TTCTTCCCTG
      AAGACATTAC TGTGGAGTGG
1201  CAGTGGAATG GGCAGCCAGC GGAGAACTAC
      AAGAACACTC AGCCCATCAT
1251  GGACACAGAT GGCTCTTACT TCATCTACAG
      CAAGCTCAAT GTGCAGAAGA
1301  GCAACTGGGA GGCAGGAAAT ACTTTCACCT
      GCTCTGTGTT ACATGAGGGC
1351  CTGCACAACC ACCATACTGA GAAGAGCCTC
      TCCCACTCTC CTGGTAAA
```

Ab-8

The sequences of the Antibody 8 (also referred to herein as Ab-8) LC and HC are as follows:

Ab-8 Light Chain:

Amino acid sequence of the mature form (signal peptide removed) of the Ab-8 LC:

(SEQ ID NO: 165)

```
  1  DIQMTQTTSS LSASLGDRVS ISCRASQDIS NYLNWYQQKP DGTFKLLIFY
 51  TSRLHSGVPS RFSGSGSGTD YSLTIYNLEQ EDFATYFCQQ GDTLPYTFGG
101  GTKLEIKRAD AAPTVSIFPP SSEQLTSGGA SVVCFLNNFY PKDINVKWKI
151  DGSERQNGVL NSWTDQDSKD STYSMSSTLT LTKDEYERHN SYTCEATHKT
201  STSPIVKSFN RNEC
```

Nucleic acid sequence encoding the mature form (signal peptide removed) of the Ab-8 LC:

(SEQ ID NO: 166)

```
  1  GATATCCAGA TGACACAGAC TACATCCTCC
     CTGTCTGCCT CTCTGGGAGA
 51  CAGGGTCTCC ATCAGTTGCA GGGCAAGTCA
     AGACATTAGC AATTATTTAA
101  ACTGGTATCA GCAGAAACCA GATGGAACTT
     TTAAACTCCT TATCTTCTAC
151  ACATCAAGAT TACTCTCAGG AGTCCCATCA
     AGGTTCAGTG GCAGTGGGTC
201  TGGAACAGAT TATTCTCTCA CCATTTACAA
     CCTGGAGCAA GAAGATTTTG
251  CCACTTACTT TTGCCAACAG GGAGATACGC
     TTCCGTACAC TTTCGGAGGG
301  GGGACCAAAC TGGAAATAAA ACGGGCTGAT
     GCTGCACCAA CTGTATCCAT
```

```
351  CTTCCCACCA TCCAGTGAGC AGTTAACATC
     TGGAGGTGCC TCAGTCGTGT

401  GCTTCTTGAA CAACTTCTAC CCCAAAGACA
     TCAATGTCAA GTGGAAGATT

451  GATGGCAGTG AACGACAAAA TGGCGTCCTG
     AACAGTTGGA CTGATCAGGA

501  CAGCAAAGAC AGCACCTACA GCATGAGCAG
     CACCCTCACG TTGACCAAGG

551  ACGAGTATGA ACGACATAAC AGCTATACCT
     GTGAGGCCAC TCACAAGACA

601  TCAACTTCAC CCATTGTCAA GAGCTTCAAC
     AGGAATGAGT GTTAG
```

Amino acid sequence of the Ab-8 LC including signal peptide:

```
                                    (SEQ ID NO: 167)
  1  MMSSAQFLGL LLLCFQGTRC DIQMTQTTSS
     LSASLGDRVS ISCRASQDIS
 51  NYLNWYQQKP DGTFKLLIFY TSRLLSGVPS
     RFSGSGSGTD YSLTIYNLEQ
101  EDFATYFCQQ GDTLPYTFGG GTKLEIKRAD
     AAPTVSIFPP SSEQLTSGGA
151  SVVCFLNNFY PKDINVKWKI DGSERQNGVL
     NSWTDQDSKD STYSMSSTLT
201  LTKDEYERHN SYTCEATHKT STSPIVKSFN
     RNEC
```

Nucleic acid sequence of the Ab-8 LC including signal peptide encoding sequence:

```
                                    (SEQ ID NO: 168)
  1  ATGATGTCCT CTGCTCAGTT CCTTGGTCTC
     CTGTTGCTCT GTTTTCAAGG
 51  TACCAGATGT GATATCCAGA TGACACAGAC
     TACATCCTCC CTGTCTGCCT
101  CTCTGGGAGA CAGGGTCTCC ATCAGTTGCA
     GGGCAAGTCA AGACATTAGC
151  AATTATTTAA ACTGGTATCA GCAGAAACCA
     GATGGAACTT TTAAACTCCT
201  TATCTTCTAC ACATCAAGAT TACTCTCAGG
     AGTCCCATCA AGGTTCAGTG
251  GCAGTGGGTC TGGAACAGAT TATTCTCTCA
     CCATTTACAA CCTGGAGCAA
301  GAAGATTTTG CCACTTACTT TTGCCAACAG
     GGAGATACGC TTCCGTACAC
351  TTTCGGAGGG GGGACCAAAC TGGAAATAAA
     ACGGGCTGAT GCTGCACCAA
401  CTGTATCCAT CTTCCCACCA TCCAGTGAGC
     AGTTAACATC TGGAGGTGCC
451  TCAGTCGTGT GCTTCTTGAA CAACTTCTAC
     CCCAAAGACA TCAATGTCAA
501  GTGGAAGATT GATGGCAGTG AACGACAAAA
     TGGCGTCCTG AACAGTTGGA
551  CTGATCAGGA CAGCAAAGAC AGCACCTACA
     GCATGAGCAG CACCCTCACG
601  TTGACCAAGG ACGAGTATGA ACGACATAAC
     AGCTATACCT GTGAGGCCAC
651  TCACAAGACA TCAACTTCAC CCATTGTCAA
     GAGCTTCAAC AGGAATGAGT
701  GTTAG
```

Ab-8 Heavy Chain:

Amino acid sequence of the mature form (signal peptide removed) of the Ab-8 HC:

```
                                    (SEQ ID NO: 169)
  1  EVQLQQSGPE LMKPGASVKM SCKASGYTFT DYNMHWVKQN QGKTLDWIGE
 51  INPNSGGAGY NQKFKGKATL TVDKSSTTAY MELRSLTSED SAVYYCARLG
101  YDDIYDDWYF DVWGAGTTVT VSSAKTTPPS VYPLAPGSAA QTNSMVTLGC
151  LVKGYFPEPV TVTWNSGSLS SGVHTFPAVL QSDLYTLSSS VTVPSSTWPS
201  ETVTCNVAHP ASSTKVDKKI VPRDCGCKPC ICTVPEVSSV FIFPPKPKDV
251  LTITLTPKVT CVVVDISKDD PEVQFSWFVD DVEVHTAQTQ PREEQFNSTF
301  RSVSELPIMH QDWLNGKEFK CRVNSAAFPA PIEKTISKTK GRPKAPQVYT
351  IPPPKEQMAK DKVSLTCMIT DFFPEDITVE WQWNGQPAEN YKNTQPIMDT
401  DGSYFIYSKL NVQKSNWEAG NTFTCSVLHE GLHNHHTEKS LSHSPGK
```

Nucleic acid sequence encoding the mature form (signal peptide removed) of the Ab-8 HC:

```
                                    (SEQ ID NO: 170)
  1  GAGGTCCAAC TGCAACAGTC TGGACCTGAA
     CTAATGAAGC CTGGGGCTTC
 51  AGTGAAGATG TCCTGCAAGG CTTCTGGATA
     TACATTCACT GACTACAACA
101  TGCACTGGGT GAAGCAGAAC CAAGGAAAGA
     CCCTAGACTG GATAGGAGAA
151  ATTAATCCTA ACAGTGGTGG TGCTGGCTAC
     AACCAGAAGT TCAAGGGCAA
201  GGCCACATTG ACTGTAGACA AGTCCTCCAC
     CACAGCCTAC ATGGAGCTCC
```

-continued

```
 251   GCAGCCTGAC ATCTGAGGAC TCTGCAGTCT
       ATTACTGTGC AAGATTGGGC

301   TACGATGATA TCTACGACGA CTGGTACTTC
       GATGTCTGGG GCGCAGGGAC

351   CACGGTCACC GTCCTCAG CCAAAACGAC
       ACCCCCATCT GTCTATCCAC

401   TGGCCCCTGG ATCTGCTGCC CAAACTAACT
       CCATGGTGAC CCTGGGATGC

451   CTGGTCAAGG GCTATTTCCC TGAGCCAGTG
       ACAGTGACCT GGAACTCTGG

501   ATCCCTGTCC AGCGGTGTGC ACACCTTCCC
       AGCTGTCCTG CAGTCTGACC

551   TCTACACTCT GAGCAGCTCA GTGACTGTCC
       CCTCCAGCAC CTGGCCCAGC

601   GAGACCGTCA CCTGCAACGT TGCCCACCCG
       GCCAGCAGCA CCAAGGTGGA

651   CAAGAAAATT GTGCCCAGGG ATTGTGGTTG
       TAAGCCTTGC ATATGTACAG

701   TCCCAGAAGT ATCATCTGTC TTCATCTTCC
       CCCCAAAGCC CAAGGATGTG

751   CTCACCATTA CTCTGACTCC TAAGGTCACG
       TGTGTTGTGG TAGACATCAG

801   CAAGGATGAT CCCGAGGTCC AGTTCAGCTG
       GTTTGTAGAT GATGTGGAGG

851   TGCACACAGC TCAGACGCAA CCCCGGGAGG
       AGCAGTTCAA CAGCACTTTC

901   CGCTCAGTCA GTGAACTTCC CATCATGCAC
       CAGGACTGGC TCAATGGCAA

951   GGAGTTCAAA TGCAGGGTCA ACAGTGCAGC
       TTTCCCTGCC CCCATCGAGA

1001   AAACCATCTC CAAAACCAAA GGCAGACCGA
       AGGCTCCACA GGTGTACACC

1051   ATTCCACCTC CAAGGAGCA GATGGCCAAG
       GATAAAGTCA GTCTGACCTG

1101   CATGATAACA GACTTCTTCC CTGAAGACAT
       TACTGTGGAG TGGCAGTGGA

1151   ATGGGCAGCC AGCGGAGAAC TACAAGAACA
       CTCAGCCCAT CATGGACACA

1201   GATGGCTCTT ACTTCATCTA CAGCAAGCTC
       AATGTGCAGA AGAGCAACTG

1251   GGAGGCAGGA AATACTTTCA CCTGCTCTGT
       GTTACATGAG GGCCTGCACA

1301   ACCACCATAC TGAGAAGAGC CTCTCCCACT
       CTCCTGGTAA ATGA
```

Amino acid sequence of the Ab-8 HC including signal peptide:

```
                                      (SEQ ID NO: 171)
   1   MGWSWTFLFL LSGTAGVLSE VQLQQSGPEL
       MKPGASVKMS CKASGYTFTD

51   YNMHWVKQNQ GKTLDWIGEI NPNSGGAGYN
       QKFKGKATLT VDKSSTTAYM

101   ELRSLTSEDS AVYYCARLGY DDIYDDWYFD
       VWGAGTTVTV SSAKTTPPSV
```

```
 151   YPLAPGSAAQ TNSMVTLGCL VKGYFPEPVT
       VTWNSGSLSS GVHTFPAVLQ

201   SDLYTLSSSV TVPSSTWPSE TVTCNVAHPA
       SSTKVDKKIV PRDCGCKPCI

251   CTVPEVSSVF IFPPKPKDVL TITLTPKVTC
       VVVDISKDDP EVQFSWFVDD

301   VEVHTAQTQP REEQFNSTFR SVSELPIMHQ
       DWLNGKEFKC RVNSAAFPAP

351   IEKTISKTKG RPKAPQVYTI PPPKEQMAKD
       KVSLTCMITD FFPEDITVEW

401   QWNGQPAENY KNTQPIMDTD GSYFIYSKLN
       VQKSNWEAGN TFTCSVLHEG

451   LHNHHTEKSL SHSPGK
```

Nucleic acid sequence of the Ab-8 HC including signal peptide encoding sequence:

```
                                      (SEQ ID NO: 172)
   1   ATGGGATGGA GCTGGACCTT TCTCTTCCTC
       CTGTCAGGAA CTGCAGGTGT

51   CCTCTCTGAG GTCCAACTGC AACAGTCTGG
       ACCTGAACTA ATGAAGCCTG

101   GGGCTTCAGT GAAGATGTCC TGCAAGGCTT
       CTGGATATAC ATTCACTGAC

151   TACAACATGC ACTGGGTGAA GCAGAACCAA
       GGAAAGACCC TAGACTGGAT

201   AGGAGAAATT AATCCTAACA GTGGTGGTGC
       TGGCTACAAC CAGAAGTTCA

251   AGGGCAAGGC CACATTGACT GTAGACAAGT
       CCTCCACCAC AGCCTACATG

301   GAGCTCCGCA GCCTGACATC TGAGGACTCT
       GCAGTCTATT ACTGTGCAAG

351   ATTGGGCTAC GATGATATCT ACGACGACTG
       GTACTTCGAT GTCTGGGGCG

401   CAGGGACCAC GGTCACCGTC TCCTCAGCCA
       AAACGACACC CCCATCTGTC

451   TATCCACTGG CCCCTGGATC TGCTGCCCAA
       ACTAACTCCA TGGTGACCCT

501   GGGATGCCTG GTCAAGGGCT ATTTCCCTGA
       GCCAGTGACA GTGACCTGGA

551   ACTCTGGATC CCTGTCCAGC GGTGTGCACA
       CCTTCCCAGC TGTCCTGCAG

601   TCTGACCTCT ACACTCTGAG CAGCTCAGTG
       ACTGTCCCCT CCAGCACCTG

651   GCCCAGCGAG ACCGTCACCT GCAACGTTGC
       CCACCCGGCC AGCAGCACCA

701   AGGTGGACAA GAAAATTGTG CCCAGGGATT
       GTGGTTGTAA GCCTTGCATA

751   TGTACAGTCC CAGAAGTATC ATCTGTCTTC
       ATCTTCCCCC CAAAGCCCAA

801   GGATGTGCTC ACCATTACTC TGACTCCTAA
       GGTCACGTGT GTTGTGGTAG

851   ACATCAGCAA GGATGATCCC GAGGTCCAGT
       TCAGCTGGTT TGTAGATGAT
```

```
 901    GTGGAGGTGC ACACAGCTCA GACGCAACCC
        CGGGAGGAGC AGTTCAACAG

951    CACTTTCCGC TCAGTCAGTG AACTTCCCAT
        CATGCACCAG GACTGGCTCA

1001    ATGGCAAGGA GTTCAAATGC AGGGTCAACA
        GTGCAGCTTT CCCTGCCCCC

1051    ATCGAGAAAA CCATCTCCAA AACCAAAGGC
        AGACCGAAGG CTCCACAGGT

1101    GTACACCATT CCACCTCCCA AGGAGCAGAT
        GGCCAAGGAT AAAGTCAGTC

1151    TGACCTGCAT GATAACAGAC TTCTTCCCTG
        AAGACATTAC TGTGGAGTGG

1201    CAGTGGAATG GGCAGCCAGC GGAGAACTAC
        AAGAACACTC AGCCCATCAT

1251    GGACACAGAT GGCTCTTACT TCATCTACAG
        CAAGCTCAAT GTGCAGAAGA

1301    GCAACTGGGA GGCAGGAAAT ACTTTCACCT
        GCTCTGTGTT ACATGAGGGC

1351    CTGCACAACC ACCATACTGA AAGAGCCTC
        TCCCACTCTC CTGGTAAATG

1401    A
```

Ab-9

The sequences of the Antibody 9 (also referred to herein as Ab-9) LC and HC are as follows:

Ab-9 Light Chain:

Amino acid sequence of the mature form (signal peptide removed) of the Ab-9 LC:

```
  1 DIQMTQITSS LSASLGDRVS ISCRASQDIS NYLNWYQQKP DGTFKLLIFY
 51 TSRLFSGVPS RFSGSGSGTD YSLTIYNLEQ EDFATYFCQQ GDTLPYTFGG
101 GTKVEIKRAD AAPTVSIFPP SSEQLTSGGA SVVCFLNNFY PKDINVKWKI
151 DGSERQNGVL NSWTDQDSKD STYSMSSTLT LTKDEYERHN SYTCEATHKT
201 STSPIVKSFN RNEC
```

(SEQ ID NO: 173)

Nucleic acid sequence encoding the mature form (signal peptide removed) of the Ab-9 LC:

```
                                           (SEQ ID NO: 174)
  1   GATATCCAGA TGACACAGAT TACATCCTCC
      CTGTCTGCCT CTCTGGGAGA

51   CAGGGTCTCC ATCAGTTGCA GGGCAAGTCA
      AGACATTAGC AATTATTTAA

101   ATTGGTATCA GCAGAAACCA GATGGAACTT
      TTAAACTCCT TATCTTCTAC

151   ACATCAAGAT TATTTTCAGG AGTCCCATCA
      AGGTTCAGTG GCAGTGGGTC

201   TGGAACAGAT TATTCTCTCA CCATTTACAA
      CCTGGAGCAA GAAGATTTTG

251   CCACTTACTT TTGCCAACAG GGAGATACGC
      TTCCGTACAC TTTCGGAGGG

301   GGGACCAAGG TGGAAATAAA ACGGGCTGAT
      GCTGCACCAA CTGTATCCAT
```

```
 351    CTTCCCACCA TCCAGTGAGC AGTTAACATC
        TGGAGGTGCC TCAGTCGTGT

401    GCTTCTTGAA CAACTTCTAC CCCAAAGACA
        TCAATGTCAA GTGGAAGATT

451    GATGGCAGTG AACGACAAAA TGGCGTCCTG
        AACAGTTGGA CTGATCAGGA

501    CAGCAAAGAC AGCACCTACA GCATGAGCAG
        CACCCTCACG TTGACCAAGG

551    ACGAGTATGA ACGACATAAC AGCTATACCT
        GTGAGGCCAC TCACAAGACA

601    TCAACTTCAC CCATTGTCAA GAGCTTCAAC
        AGGAATGAGT GT
```

Amino acid sequence of the Ab-9 LC including signal peptide:

```
                                           (SEQ ID NO: 175)
  1   MMSSAQFLGL LLLCFQGTRC DIQMTQITSS
      LSASLGDRVS ISCRASQDIS

51   NYLNWYQQKP DGTFKLLIFY TSRLFSGVPS
      RFSGSGSGTD YSLTIYNLEQ

101   EDFATYFCQQ GDTLPYTFGG GTKVEIKRAD
      AAPTVSIFPP SSEQLTSGGA

151   SVVCFLNNFY PKDINVKWKI DGSERQNGVL
      NSWTDQDSKD STYSMSSTLT

201   LTKDEYERHN SYTCEATHKT STSPIVKSFN
      RNEC
```

Nucleic acid sequence of the Ab-9 LC including signal peptide encoding sequence:

```
                                           (SEQ ID NO: 176)
  1   ATGATGTCCT CTGCTCAGTT CCTTGGTCTC
      CTGTTGCTCT GTTTTCAAGG

51   TACCAGATGT GATATCCAGA TGACACAGAT
      TACATCCTCC CTGTCTGCCT

101   CTCTGGGAGA CAGGGTCTCC ATCAGTTGCA
      GGGCAAGTCA AGACATTAGC

151   AATTATTTAA ATTGGTATCA GCAGAAACCA
      GATGGAACTT TTAAACTCCT

201   TATCTTCTAC ACATCAAGAT TATTTTCAGG
      AGTCCCATCA AGGTTCAGTG

251   GCAGTGGGTC TGGAACAGAT TATTCTCTCA
      CCATTTACAA CCTGGAGCAA

301   GAAGATTTTG CCACTTACTT TTGCCAACAG
      GGAGATACGC TTCCGTACAC
```

-continued

```
351  TTTCGGAGGG GGGACCAAGG TGGAAATAAA
     ACGGGCTGAT GCTGCACCAA
401  CTGTATCCAT CTTCCCACCA TCCAGTGAGC
     AGTTAACATC TGGAGGTGCC
451  TCAGTCGTGT GCTTCTTGAA CAACTTCTAC
     CCCAAAGACA TCAATGTCAA
501  GTGGAAGATT GATGGCAGTG AACGACAAAA
     TGGCGTCCTG AACAGTTGGA
551  CTGATCAGGA CAGCAAAGAC AGCACCTACA
     GCATGAGCAG CACCCTCACG
601  TTGACCAAGG ACAGTGATGA ACGACATAAC
     AGCTATACCT GTGAGGCCAC
651  TCACAAGACA TCAACTTCAC CCATTGTCAA
     GAGCTTCAAC AGGAATGAGT
701  GT
```

Ab-9 Heavy Chain:

Amino acid sequence of the mature form (signal peptide removed) of the Ab-9 HC:

```
  1 EVQLQQSGPE LMKPGTSVKM SCKASGYTFT DYNMHWVKQT QGKTLEWIGE
 51 INPNSGGAGY NQKFKGKATL TVDKSSTTAY MELRSLTSED SAVYYCAKLG
101 YDDIYDDWYF DVWGAGTTVT VSSAKTTAPS VYPLAPVCGD TTGSSVTLGC
151 LVKGYFPEPV TLTWNSGSLS SDVHTFPALL QSGLYTLSSS VTVTTWPSQT
201 ITCNVAHPAS STKVDKKIEP RGSPTHKPCP PCPAPNLLGG PSVFIFPPKI
251 KDVLMISLSP MVTCVVVDVS EDDPDVHVSW FVNNVEVHTA QTQTHREDYN
301 STIRVVSALP IQHQDWMSGK EFKCKVNNKA LPAPIERTIS KPKGPVRAPQ
351 VYVLPPPEEE MTKKQVTLTC MITDFMPEDI YVEWTNNGQT ELNYKNTEPV
401 LDSDGSYFMY SKLRVEKKNW VERNSYSCSV VHEGLHNHHT TKSFSRTPGK
```

Nucleic acid sequence encoding the mature form (signal peptide removed) of the Ab-9 HC:

(SEQ ID NO: 178)

```
   1  GAGGTCCAAC TGCAACAGTC TGGACCTGAA
      CTAATGAAGC CTGGGACTTC
  51  AGTGAAGATG TCCTGCAAGG CTTCTGGATA
      TACATTCACT GACTACAACA
 101  TGCACTGGGT GAAGCAGACC CAAGGAAAGA
      CCCTAGAGTG GATAGGAGAA
 151  ATTAATCCTA ACAGTGGTGG TGCTGGCTAC
      AACCAGAAGT TCAAGGGCAA
 201  GGCCACATTG ACTGTAGACA AGTCCTCCAC
      CACAGCCTAC ATGGAGCTCC
 251  GCAGCCTGAC ATCTGAGGAC TCTGCAGTCT
      ATTACTGTGC AAAATTGGGC
 301  TACGATGATA TCTACGACGA CTGGTATTTC
      GATGTCTGGG GCGCAGGGAC
 351  CACGGTCACC GTCTCCTCAG CCAAAACAAC
      AGCCCCATCG GTCTATCCAC
 401  TGGCCCCTGT GTGTGGAGAT ACAACTGGCT
      CCTCGGTGAC TCTAGGATGC
 451  CTGGTCAAGG GTTATTTCCC TGAGCCAGTG
      ACCTTGACCT GGAACTCTGG
 501  ATCCCTGTCC AGTGATGTGC ACACCTTCCC
      AGCTCTCCTG CAGTCTGGCC
 551  TCTACACCCT CAGCAGCTCA GTGACTGTAA
      CCACCTGGCC CAGCCAGACC
 601  ATCACCTGCA ATGTGGCCCA CCCGGCAAGC
      AGCACCAAAG TGGACAAGAA
 651  AATTGAGCCC AGAGGGTCCC CAACACATAA
      ACCCTGTCCT CCATGCCCAG
 701  CTCCTAACCT CTTGGGTGGA CCATCCGTCT
      TCATCTTCCC TCCAAAGATC
 751  AAGGATGTAC TCATGATCTC CCTGAGCCCC
      ATGGTCACGT GTGTGGTGGT
 801  GGATGTGAGC GAGGATGACC CAGATGTCCA
      TGTCAGCTGG TTCGTGAACA
 851  ACGTGGAAGT ACACACAGCT CAGACACAAA
      CCCATAGAGA GGATTACAAC
 901  AGTACTATCC GGGTGGTCAG TGCCCTCCCC
```

(SEQ ID NO: 177)

-continued

```
      ATCCAGCACC AGGACTGGAT
 951  GAGTGGCAAG GAGTTCAAAT GCAAGGTCAA
      CAACAAAGCC CTCCCAGCGC
1001  CCATCGAGAG AACCATCTCA AAACCCAAAG
      GGCCAGTAAG AGCTCCACAG
1051  GTATATGTCT TGCCTCCACC AGAAGAAGAG
      ATGACTAAGA AACAGGTCAC
1101  TCTGACCTGC ATGATCACAG ACTTCATGCC
      TGAAGACATT TACGTGGAGT
1151  GGACCAACAA CGGGCAAACA GAGCTAAACT
      ACAAGAACAC TGAACCAGTC
1201  CTGGACTCTG ATGGTTCTTA CTTCATGTAC
      AGCAAGCTGA GAGTGGAAAA
1251  GAAGAACTGG GTGGAAAGAA ATAGCTACTC
      CTGTTCAGTG GTCCACGAGG
1301  GTCTGCACAA TCACCACACG ACTAAGAGCT
      TCTCCCGGAC TCCGGGTAAA
```

Amino acid sequence of the Ab-9 HC including signal peptide:

(SEQ ID NO: 179)

```
  1  MGWSWTFLFL LSGTAGVLSE VQLQQSGPEL
     MKPGTSVKMS CKASGYTFTD
```

```
 51     YNMHWVKQTQ GKTLEWIGEI NPNSGGAGYN
        QKFKGKATLT VDKSSTTAYM

101     ELRSLTSEDS AVYYCAKLGY DDIYDDWYFD
        VWGAGTTVTV SSAKTTAPSV

151     YPLAPVCGDT TGSSVTLGCL VKGYFPEPVT
        LTWNSGSLSS DVHTFPALLQ

201     SGLYTLSSSV TVTTWPSQTI TCNVAHPASS
        TKVDKKIEPR GSPTHKPCPP

251     CPAPNLLGGP SVFIFPPKIK DVLMISLSPM
        VTCVVVDVSE DDPDVHVSWF

301     VNNVEVHTAQ TQTHREDYNS TIRVVSALPI
        QHQDWMSGKE FKCKVNNKAL

351     PAPIERTISK PKGPVRAPQV YVLPPPEEEM
        TKKQVTLTCM ITDFMPEDIY

401     VEWTNNGQTE LNYKNTEPVL DSDGSYFMYS
        KLRVEKKNWV ERNSYSCSVV

451     HEGLHNHHTT KSFSRTPGK
```

Nucleic acid sequence of the Ab-9 HC including signal peptide encoding sequence:

```
                                   (SEQ ID NO: 180)
   1    ATGGGATGGA GCTGGACCTT TCTCTTCCTC
        CTGTCAGGAA CTGCAGGTGT

51    CCTCTCTGAG GTCCAACTGC AACAGTCTGG
        ACCTGAACTA ATGAAGCCTG

101    GGACTTCAGT GAAGATGTCC TGCAAGGCTT
        CTGGATATAC ATTCACTGAC

151    TACAACATGC ACTGGGTGAA GCAGACCCAA
        GGAAAGACCC TAGAGTGGAT

201    AGGAGAAATT AATCCTAACA GTGGTGGTGC
        TGGCTACAAC CAGAAGTTCA

251    AGGGCAAGGC CACATTGACT GTAGACAAGT
        CCTCCACCAC AGCCTACATG

301    GAGCTCCGCA GCCTGACATC TGAGGACTCT
        GCAGTCTATT ACTGTGCAAA

351    ATTGGGCTAC GATGATATCT ACGACGACTG
        GTATTTCGAT GTCTGGGGCG

401    CAGGGACCAC GGTCACCGTC TCCTCAGCCA
        AAACAACAGC CCCATCGGTC

451    TATCCACTGG CCCCTGTGTG TGGAGATACA
        ACTGGCTCCT CGGTGACTCT

501    AGGATGCCTG GTCAAGGGTT ATTTCCCTGA
        GCCAGTGACC TTGACCTGGA

551    ACTCTGGATC CCTGTCCAGT GATGTGCACA
        CCTTCCCAGC TCTCCTGCAG

601    TCTGGCCTCT ACACCCTCAG CAGCTCAGTG
        ACTGTAACCA CCTGGCCCAG

651    CCAGACCATC ACCTGCAATG TGGCCCACCC
        GGCAAGCAGC ACCAAAGTGG
```

```
 701    ACAAGAAAAT TGAGCCCAGA GGGTCCCCAA
        CACATAAACC CTGTCCTCCA

751    TGCCCAGCTC CTAACCTCTT GGGTGGACCA
        TCCGTCTTCA TCTTCCCTCC

801    AAAGATCAAG GATGTACTCA TGATCTCCCT
        GAGCCCCATG GTCACGTGTG

851    TGGTGGTGGA TGTGAGCGAG GATGACCCAG
        ATGTCCATGT CAGCTGGTTC

901    GTGAACAACG TGGAAGTACA CACAGCTCAG
        ACACAAACCC ATAGAGAGGA

951    TTACAACAGT ACTATCCGGG TGGTCAGTGC
        CCTCCCCATC CAGCACCAGG

1001    ACTGGATGAG TGGCAAGGAG TTCAAATGCA
        AGGTCAACAA CAAAGCCCTC

1051    CCAGCGCCCA TCGAGAGAAC CATCTCAAAA
        CCCAAAGGGC CAGTAAGAGC

1101    TCCACAGGTA TATGTCTTGC CTCCACCAGA
        AGAAGAGATG ACTAAGAAAC

1151    AGGTCACTCT GACCTGCATG ATCACAGACT
        TCATGCCTGA AGACATTTAC

1201    GTGGAGTGGA CCAACAACGG GCAAACAGAG
        CTAAACTACA AGAACACTGA

1251    ACCAGTCCTG GACTCTGATG GTTCTTACTT
        CATGTACAGC AAGCTGAGAG

1301    TGGAAAAGAA GAACTGGGTG GAAAGAAATA
        GCTACTCCTG TTCAGTGGTC

1351    CACGAGGGTC TGCACAATCA CCACACGACT
        AAGAGCTTCT CCCGGACTCC

1401    GGGTAAA
```

Ab-10

The sequences of the Antibody 10 (also referred to herein as Ab-10) LC and HC are as follows:

Ab-10 Light Chain:

Amino acid sequence of the mature form (signal peptide removed) of the Ab-10 LC:

```
  1 DIQMTQTTSS LSASLGDRVS ISCRASQDIS NYLNWYQQKP DGTFKLLIFY
 51 TSRLLSGVPS RFSGSGSGTD YSLTIYNLEQ EDFATYFCQQ GDTLPYTFGG
101 GTKLEIKRAD AAPTVSIFPL SSEQLTSGGA SVVCFLNNFY PKDINVKWKI
151 DGSERQNGVL NSWTDQDSKD STYSMSSTLT LTKDEYERHN SYTCEATHKT
201 STSPIVKSFN RNEC
```
(SEQ ID NO: 181)

Nucleic acid sequence encoding the mature form (signal peptide removed) of the Ab-10 LC:

(SEQ ID NO: 182)
```
  1 GATATCCAGA TGACACAGAC TACATCCTCC
    CTGTCTGCCT CTCTGGGAGA
 51 CAGGGTCTCC ATCAGTTGCA GGGCAAGTCA
    AGACATTAGC AATTATTTAA
101 ACTGGTATCA GCAGAAACCA GATGGAACTT
    TTAAACTCCT TATCTTCTAC
151 ACATCAAGAT TACTCTCAGG AGTCCCATCA
    AGGTTCAGTG GCAGTGGGTC
201 TGGAACAGAT TATTCTCTCA CCATTTACAA
    CCTGGAGCAA GAAGATTTTG
251 CCACTTACTT TTGCCAACAG GGAGATACGC
    TTCCGTACAC TTTCGGAGGG
301 GGGACCAAAC TGGAAATAAA ACGGGCTGAT
    GCTGCACCAA CTGTATCCAT
351 CTTCCCACTA TCCAGTGAGC AGTTAACATC
    TGGAGGTGCC TCAGTCGTGT
401 GCTTCTTGAA CAACTTCTAC CCCAAAGACA
    TCAATGTCAA GTGGAAGATT
451 GATGGCAGTG AACGACAAAA TGGCGTCCTG
    AACAGTTGGA CTGATCAGGA
501 CAGCAAAGAC AGCACCTACA GCATGAGCAG
    CACCCTCACG TTGACCAAGG
551 ACGAGTATGA ACGACATAAC AGCTATACCT
    GTGAGGCCAC TCACAAGACA
601 TCAACTTCAC CCATTGTCAA GAGCTTCAAC
    AGGAATGAGT GTTAG
```

Amino acid sequence of the Ab-10 LC including signal peptide:

(SEQ ID NO: 183)
```
  1 MMSSAQFLGL LLLCFQGTRG DIQMTQTTSS
    LSASLGDRVS ISCRASQDIS
 51 NYLNWYQQKP DGTFKLLIFY TSRLLSGVPS
    RFSGSGSGTD YSLTIYNLEQ
101 EDFATYFCQQ GDTLPYTFGG GTKLEIKRAD
    AAPTVSIFPL SSEQLTSGGA
151 SVVCFLNNFY PKDINVKWKI DGSERQNGVL
    NSWTDQDSKD STYSMSSTLT
201 LTKDEYERHN SYTCEATHKT STSPIVKSFN
    RNEC
```

Nucleic acid sequence of the Ab-10 LC including signal peptide encoding sequence:

(SEQ ID NO: 184)
```
  1 ATGATGTCCT CTGCTCAGTT CCTTGGTCTC
    CTGTTGCTCT GTTTTCAAGG
 51 TACCAGATGT GATATCCAGA TGACACAGAC
    TACATCCTCC CTGTCTGCCT
101 CTCTGGGAGA CAGGGTCTCC ATCAGTTGCA
    GGGCAAGTCA AGACATTAGC
151 AATTATTTAA ACTGGTATCA GCAGAAACCA
    GATGGAACTT TTAAACTCCT
201 TATCTTCTAC ACATCAAGAT TACTCTCAGG
    AGTCCCATCA AGGTTCAGTG
251 GCAGTGGGTC TGGAACAGAT TATTCTCTCA
    CCATTTACAA CCTGGAGCAA
301 GAAGATTTTG CCACTTACTT TTGCCAACAG
    GGAGATACGC TTCCGTACAC
351 TTTCGGAGGG GGGACCAAAC TGGAAATAAA
    ACGGGCTGAT GCTGCACCAA
401 CTGTATCCAT CTTCCCACTA TCCAGTGAGC
    AGTTAACATC TGGAGGTGCC
451 TCAGTCGTGT GCTTCTTGAA CAACTTCTAC
    CCCAAAGACA TCAATGTCAA
501 GTGGAAGATT GATGGCAGTG AACGACAAAA
    TGGCGTCCTG AACAGTTGGA
551 CTGATCAGGA CAGCAAAGAC AGCACCTACA
    GCATGAGCAG CACCCTCACG
601 TTGACCAAGG ACGAGTATGA ACGACATAAC
    AGCTATACCT GTGAGGCCAC
651 TCACAAGACA TCAACTTCAC CCATTGTCAA
    GAGCTTCAAC AGGAATGAGT
701 GTTAG
```

Ab-10 Heavy Chain:

Amino acid sequence of the mature form (signal peptide removed) of the Ab-10 HC:

(SEQ ID NO: 185)

```
  1 EVQLQQSGPE LMKPGASVKM SCKASGYTFT DYNMHWVKQN QGKTLEWIGE
 51 INPNSGGAGY NQKFKGKATL TVDKSSTTAY MELRSLTSED SAVYYCARLG
101 YDDIYDDWYF DVWGAGTTVT VSSAKTTPPS VYPLAPGSAA QTNSMVTLGC
151 LVKGYFPEPV TVTWNSGSLS SGVHTFPAVL QSDLYTLSSS VTVPSSTWPS
201 ETVTCNVAHP ASSTKVDKKI VPRDCGCKPC ICTVPEVSSV FIFPPKPKDV
251 LTITLTPKVT CVVVDISKDD PEVQFSWFVD DVEVHTAQTQ PREEQFNSTF
301 RSVSELPIMH QDWLNGKEFK CRVNSAAFPA PIEKTISKTK GRPKAPQVYT
351 IPPPKEQMAK DKVSLTCMIT DFFPEDITVE WQWNGQPAEN YKNTQPIMDT
401 DGSYFIYSKL NVQKSNWEAG NTFTCSVLHE GLHNHHTEKS LSHSPGK
```

Nucleic acid sequence encoding the mature form (signal peptide removed) of the Ab-10 HC:

```
                                      (SEQ ID NO: 186)
  1   GAGGTCCAAC TGCAACAGTC TGGACCTGAA
      CTAATGAAGC CTGGGGCTTC
 51   AGTGAAGATG TCCTGCAAGG CTTCTGGATA
      TACATTCACT GACTACAACA
101   TGCACTGGGT GAAGCAGAAC CAAGGAAAGA
      CCCTAGAATG GATAGGAGAA
151   ATTAATCCTA ACAGTGGTGG TGCTGGCTAC
      AACCAGAAGT TCAAGGGCAA
201   GGCCACATTG ACTGTAGACA AGTCCTCCAC
      CACAGCCTAC ATGGAGCTCC
251   GCAGCCTGAC ATCTGAGGAC TCTGCAGTCT
      ATTACTGTGC AAGATTGGGC
301   TACGATGATA TCTACGACGA CTGGTACTTC
      GATGTCTGGG GCGCAGGGAC
351   CACGGTCACC GTCTCCTCAG CCAAAACGAC
      ACCCCCATCT GTCTATCCAC
401   TGGCCCCTGG ATCTGCTGCC CAAACTAACT
      CCATGGTGAC CCTGGGATGC
451   CTGGTCAAGG GCTATTTCCC TGAGCCAGTG
      ACAGTGACCT GGAACTCTGG
501   ATCCCTGTCC AGCGGTGTGC ACACCTTCCC
      AGCTGTCCTG CAGTCTGACC
551   TCTACACTCT GAGCAGCTCA GTGACTGTCC
      CCTCCAGCAC CTGGCCCAGC
601   GAGACCGTCA CCTGCAACGT TGCCCACCCG
      GCCAGCAGCA CCAAGGTGGA
651   CAAGAAAATT GTGCCCAGGG ATTGTGGTTG
      TAAGCCTTGC ATATGTACAG
701   TCCCAGAAGT ATCATCTGTC TTCATCTTCC
      CCCCAAAGCC CAAGGATGTG
751   CTCACCATTA CTCTGACTCC TAAGGTCACG
      TGTGTTGTGG TAGACATCAG
801   CAAGGATGAT CCCGAGGTCC AGTTCAGCTG
      GTTTGTAGAT GATGTGGAGG
851   TGCACACAGC TCAGACGCAA CCCCGGGAGG
      AGCAGTTCAA CAGCACTTTC
901   CGCTCAGTCA GTGAACTTCC CATCATGCAC
      CAGGACTGGC TCAATGGCAA
951   GGAGTTCAAA TGCAGGGTCA ACAGTGCAGC
      TTTCCCTGCC CCCATCGAGA
1001  AAACCATCTC CAAAACCAAA GGCAGACCGA
      AGGCTCCACA GGTGTACACC
1051  ATTCCACCTC CCAAGGAGCA GATGGCCAAG
      GATAAAGTCA GTCTGACCTG
1101  CATGATAACA GACTTCTTCC CTGAAGACAT
      TACTGTGGAG TGGCAGTGGA
1151  ATGGGCAGCC AGCGGAGAAC TACAAGAACA
      CTCAGCCCAT CATGGACACA
1201  GATGGCTCTT ACTTCATCTA CAGCAAGCTC
      AATGTGCAGA AGAGCAACTG
1251  GGAGGCAGGA AATACTTTCA CCTGCTCTGT
      GTTACATGAG GGCCTGCACA
1301  ACCACCATAC TGAGAAGAGC CTCTCCCACT
      CTCCTGGTAA ATGA
```

Amino acid sequence of the Ab-10 HC including signal peptide:

```
                                      (SEQ ID NO: 187)
  1   MGWSWTFLFL LSGTAGVLSE VQLQQSGPEL
      MKPGASVKMS CKASGYTFTD
 51   YNMHWVKQNQ GKTLEWIGEI NPNSGGAGYN
      QKFKGKATLT VDKSSTTAYM
101   ELRSLTSEDS AVYYCARLGY DDIYDDWYFD
      VWGAGTTVTV SSAKTTPPSV
151   YPLAPGSAAQ TNSMVTLGCL VKGYFPEPVT
      VTWNSGSLSS GVHTFPAVLQ
201   SDLYTLSSSV TVPSSTWPSE TVTCNVAHPA
      SSTKVDKKIV PRDCGCKPCI
251   CTVPEVSSVF IFPPKPKDVL TITLTPKVTC
      VVVDISKDDP EVQFSWFVDD
301   VEVHTAQTQP REEQFNSTFR SVSELPIMHQ
      DWLNGKEFKC RVNSAAFPAP
351   IEKTISKTKG RPKAPQVYTI PPPKEQMAKD
      KVSLTCMITD FFPEDITVEW
401   QWNGQPAENY KNTQPIMDTD GSYFIYSKLN
      VQKSNWEAGN TFTCSVLHEG
451   LHNHHTEKSL SHSPGK
```

Nucleic acid sequence of the Ab-10 HC including signal peptide encoding sequence:

```
                                      (SEQ ID NO: 188)
  1   ATGGGATGGA GCTGGACCTT TCTCTTCCTC
      CTGTCAGGAA CTGCAGGTGT
```

-continued

```
  51  CCTCTCTGAG GTCCAACTGC AACAGTCTGG
      ACCTGAACTA ATGAAGCCTG
 101  GGGCTTCAGT GAAGATGTCC TGCAAGGCTT
      CTGGATATAC ATTCACTGAC
 151  TACAACATGC ACTGGGTGAA GCAGAACCAA
      GGAAAGACCC TAGAATGGAT
 201  AGGAGAAATT AATCCTAACA GTGGTGGTGC
      TGGCTACAAC CAGAAGTTCA
 251  AGGGCAAGGC CACATTGACT GTAGACAAGT
      CCTCCACCAC AGCCTACATG
 301  GAGCTCCGCA GCCTGACATC TGAGGACTCT
      GCAGTCTATT ACTGTGCAAG
 351  ATTGGGCTAC GATGATATCT ACGACGACTG
      GTACTTCGAT GTCTGGGGCG
 401  CAGGGACCAC GGTCACCGTC TCCTCAGCCA
      AAACGACACC CCCATCTGTC
 451  TATCCACTGG CCCCTGGATC TGCTGCCCAA
      ACTAACTCCA TGGTGACCCT
 501  GGGATGCCTG GTCAAGGGCT ATTTCCCTGA
      GCCAGTGACA GTGACCTGGA
 551  ACTCTGGATC CCTGTCCAGC GGTGTGCACA
      CCTTCCCAGC TGTCCTGCAG
 601  TCTGACCTCT ACACTCTGAG CAGCTCAGTG
      ACTGTCCCCT CCAGCACCTG
 651  GCCCAGCGAG ACCGTCACCT GCAACGTTGC
      CCACCCGGCC AGCAGCACCA
```

-continued

```
 701  AGGTGGACAA GAAAATTGTG CCCAGGGATT
      GTGGTTGTAA GCCTTGCATA
 751  TGTACAGTCC CAGAAGTATC ATCTGTCTTC
      ATCTTCCCCC CAAAGCCCAA
 801  GGATGTGCTC ACCATTACTC TGACTCCTAA
      GGTCACGTGT GTTGTGGTAG
 851  ACATCAGCAA GGATGATCCC GAGGTCCAGT
      TCAGCTGGTT TGTAGATGAT
 901  GTGGAGGTGC ACACAGCTCA GACGCAACCC
      CGGGAGGAGC AGTTCAACAG
 951  CACTTTCCGC TCAGTCAGTG AACTTCCCAT
      CATGCACCAG GACTGGCTCA
1001  ATGGCAAGGA GTTCAAATGC AGGGTCAACA
      GTGCAGCTTT CCCTGCCCCC
```

-continued

```
1051  ATCGAGAAAA CCATCTCCAA AACCAAAGGC
      AGACCGAAGG CTCCACAGGT
1101  GTACACCATT CCACCTCCCA AGGAGCAGAT
      GGCCAAGGAT AAAGTCAGTC
1151  TGACCTGCAT GATAACAGAC TTCTTCCCTG
      AAGACATTAC TGTGGAGTGG
1201  CAGTGGAATG GGCAGCCAGC GGAGAACTAC
      AAGAACACTC AGCCCATCAT
1251  GGACACAGAT GGCTCTTACT TCATCTACAG
      CAAGCTCAAT GTGCAGAAGA
1301  GCAACTGGGA GGCAGGAAAT ACTTTCACCT
      GCTCTGTGTT ACATGAGGGC
1351  CTGCACAACC ACCATACTGA GAAGAGCCTC
      TCCCACTCTC CTGGTAAATG
1401  A
```

Ab-11

The sequences of the Antibody 11 (also referred to herein as Ab-11) LC and HC are as follows:

Ab-11 Light Chain:

Amino acid sequence of the mature form (signal peptide removed) of the Ab-11 LC:

(SEQ ID NO: 189)
```
  1  QIVLSQSPAF LSVSPGDKVT MTCRASSSIS YIHWFQQKPG SSPRSWIYAT
 51  SNLASGVPGR FSGSGSGTSY SLTISRVEAE DAATYYCQQW SSDPLTFGAG
101  TKLELKRADA APTVSIFPPS SEQLTSGGAS VVCFLNNFYP KDINVKWKID
151  GSERQNGVLN SWTDQDSKDS TYSMSSTLTL TKDEYERHNS YTCEATHKTS
201  TSPIVKSFNR NEC
```

Nucleic acid sequence encoding the mature form (signal peptide removed) of the Ab-11 LC:

(SEQ ID NO: 190)
```
  1  CAAATTGTTC TCTCCCAGTC TCCAGCATTC
     CTGTCTGTAT CTCCAGGGGA
 51  TAAGGTCACA ATGACTTGCA GGGCCAGCTC
     AAGTATAAGT TACATACACT
101  GGTTTCAGCA GAAGCCAGGA TCCTCCCCCA
     GATCCTGGAT TTATGCCACA
151  TCCAACCTGG CTTCTGGAGT CCCTGGTCGC
     TTCAGTGGCA GTGGGTCTGG
201  GACCTCTTAC TCTCTCACAA TCAGCAGAGT
     GGAGGCTGAG GATGCTGCCA
251  CTTATTACTG CCAGCAGTGG AGTAGTGACC
     CACTCACGTT CGGTGCTGGG
```

-continued

```
301  ACCAAGCTGG AGCTGAAACG GGCTGATGCT
     GCACCAACTG TATCCATCTT

351  CCCACCATCC AGTGAGCAGT TAACATCTGG
     AGGTGCCTCA GTCGTGTGCT

401  TCTTGAACAA CTTCTACCCC AAAGACATCA
     ATGTCAAGTG GAAGATTGAT

451  GGCAGTGAAC GACAAAATGG CGTCCTGAAC
     AGTTGGACTG ATCAGGACAG

501  CAAAGACAGC ACCTACAGCA TGAGCAGCAC
     CCTCACGTTG ACCAAGGACG

551  AGTATGAACG ACATAACAGC TATACCTGTG
     AGGCCACTCA CAAGACATCA

601  ACTTCACCCA TTGTCAAGAG CTTCAACAGG
     AATGAGTGTT AG
```

Amino acid sequence of the Ab-11 LC including signal peptide:

```
                                    (SEQ ID NO: 191)
  1  MDFQVQIFSF LLISASVIMS RGQIVLSQSP
     AFLSVSPGDK VTMTCRASSS

51  ISYIHWFQQK PGSSPRSWIY ATSNLASGVP
     GRFSGSGSGT SYSLTISRVE

101  AEDAATYYCQ QWSSDPLTFG AGTKLELKRA
     DAAPTVSIFP PSSEQLTSGG

151  ASVVCFLNNF YPKDINVKWK IDGSERQNGV
     LNSWTDQDSK DSTYSMSSTL

201  TLTKDEYERH NSYTCEATHK TSTSPIVKSF
     NRNEC
```

Nucleic acid sequence of the Ab-11 LC including signal peptide encoding sequence:

```
                                    (SEQ ID NO: 192)
  1  ATGGATTTTC AAGTGCAGAT TTTCAGCTTC
     CTGCTAATCA GTGCTTCAGT

51  CATAATGTCC AGAGGACAAA TTGTTCTCTC
     CCAGTCTCCA GCATTCCTGT

101  CTGTATCTCC AGGGGATAAG GTCACAATGA
     CTTGCAGGGC CAGCTCAAGT

151  ATAAGTTACA TACACTGGTT TCAGCAGAAG
     CCAGGATCCT CCCCCAGATC

201  CTGGATTTAT GCCACATCCA ACCTGGCTTC
     TGGAGTCCCT GGTCGCTTCA
```

-continued

```
251  GTGGCAGTGG GTCTGGGACC TCTTACTCTC
     TCACAATCAG CAGAGTGGAG

301  GCTGAGGATG CTGCCACTTA TTACTGCCAG
     CAGTGGAGTA GTGACCCACT

351  CACGTTCGGT GCTGGGACCA AGCTGGAGCT
     GAAACGGGCT GATGCTGCAC

401  CAACTGTATC CATCTTCCCA CCATCCAGTG
     AGCAGTTAAC ATCTGGAGGT

451  GCCTCAGTCG TGTGCTTCTT GAAGAACTTC
     TACCCCAAAG ACATCAATGT

501  CAAGTGGAAG ATTGATGGCA GTGAACGACA
     AAATGGCGTC CTGAACAGTT

551  GGACTGATCA GGACAGCAAA GACAGCACCT
     ACAGCATGAG CAGCACCCTC

601  ACGTTGACCA AGGACGAGTA TGAACGACAT
     AACAGCTATA CCTGTGAGGC

651  CACTCACAAG ACATCAACTT CACCCATTGT
     CAAGAGCTTC AACAGGAATG

701  AGTGTTAG
```

Ab-11 Heavy Chain:

Amino acid sequence of the mature form (signal peptide removed) of the Ab-11 HC:

```
                                    (SEQ ID NO: 193)
  1  EVQLQQSGAD LVQPGASVKV SCTASGFDIK DYYIHWMKQR PDQGLEWIGR
 51  VDPDNGETEF APKFPGKATF TTDTSSNTAY LQLRGLTSED TAIYYCGRED
101  YDGTYTWFPY WGQGTLVTVS AAKTTPPSVY PLAPGSAAQT NSMVTLGCLV
151  KGYFPEPVTV TWNSGSLSSG VHTFPAVLQS DLYTLSSSVT VPSSTWPSET
201  VTCNVAHPAS STKVDKKIVP RDCGCKPCIC TVPEVSSVFI FPPKPKDVLT
251  ITLTPKVTCV VVDISKDDPE VQFSWFVDDV EVHTAQTQPR EEQFNSTFRS
301  VSELPIMHQD WLNGKEFKCR VNSAAFPAPI EKTISKTKGR PKAPQVYTIP
351  PPKEQMAKDK VSLTCMITDF FPEDITVEWQ WNGQPAENYK NTQPIMDTDG
401  SVFIYSKLNV QKSNWEAGNT FTCSVLHEGL HNHHTEKSLS HSPGK
```

Nucleic acid sequence encoding the mature form (signal peptide removed) of the Ab-11 HC:

```
                                    (SEQ ID NO: 194)
  1  GAAGTTCAGC TGCAACAGTC TGGGGCAGAC
     CTTGTGCAGC CAGGGGCCTC

51  AGTCAAGGTG TCCTGCACAG CTTCTGGCTT
     CGACATTAAG GACTACTATA

101  TACACTGGAT GAAACAGAGG CCTGACCAGG
     GCCTGGAGTG GATTGGAAGG

151  GTTGATCCTG ACAATGGTGA GACTGAATTT
     GCCCCGAAGT TCCCGGGCAA
```

```
201   GGCCACTTTT ACAACAGACA CATCCTCCAA
      CACAGCCTAC CTACAACTCA
251   GAGGCCTGAC ATCTGAGGAC ACTGCCATCT
      ATTACTGTGG GAGAGAAGAC
301   TACGATGGTA CCTACACCTG GTTTCCTTAT
      TGGGGCCAAG GGACTCTGGT
351   CACTGTCTCT GCAGCCAAAA CGACACCCCC
      ATCTGTCTAT CCACTGGGCC
401   CTGGATCTGC TGCCCAAACT AACTCCATGG
      TGACCCTGGG ATGCCTGGTC
451   AAGGGCTATT TCCCTGAGCC AGTGACAGTG
      ACCTGGAACT CTGGATCCCT
501   GTCCAGCGGT GTGCACACCT TCCCAGCTGT
      CCTGCAGTCT GACCTCTACA
551   CTCTGAGCAG CTCAGTGACT GTCCCCTCCA
      GCACCTGGCC CAGCGAGACC
601   GTCACCTGCA ACGTTGCCCA CCCGGCCAGC
      AGCACCAAGG TGGACAAGAA
651   AATTGTGCCC AGGGATTGTG GTTGTAAGCC
      TTGCATATGT ACAGTCCCAG
701   AAGTATCATC TGTCTTCATC TTCCCCCCAA
      AGCCCAAGGA TGTGCTCACC
751   ATTACTCTGA CTCCTAAGGT CACGTGTGTT
      GTGGTAGACA TCAGCAAGGA
801   TGATCCCGAG GTCCAGTTCA GCTGGTTTGT
      AGATGATGTG GAGGTGCACA
851   CAGCTCAGAC GCAACCCCGG GAGGAGCAGT
      TCAACAGCAC TTTCCGCTCA
901   GTCAGTGAAC TTCCCATCAT GCACCAGGAC
      TGGCTCAATG GCAAGGAGTT
951   CAAATGCAGG GTCAACAGTG CAGCTTTCCC
      TGCCCCCATC GAGAAAACCA
1001  TCTCCAAAAC CAAAGGCAGA CCGAAGGCTC
      CACAGGTGTA CACCATTCCA
1051  CCTCCCAAGG AGCAGATGGC CAAGGATAAA
      GTCAGTCTGA CCTGCATGAT
1101  AACAGACTTC TTCCCTGAAG ACATTACTGT
      GGAGTGGCAG TGGAATGGGC
1151  AGCCAGCGGA GAACTACAAG AACACTCAGC
      CCATCATGGA CACAGATGGC
1201  TCTTACTTCA TCTACAGCAA GCTCAATGTG
      CAGAAGAGCA ACTGGGAGGC
1251  AGGAAATACT TTCACCTGCT CTGTGTTACA
      TGAGGGCCTG CACAACCACC
1301  ATACTGAGAA GAGCCTCTCC CACTCTCCTG
      GTAAATGA
```

Amino acid sequence of the Ab-11 HC including signal peptide:

```
                                    (SEQ ID NO: 195)
1     MKCSWVIFFL MAVVTGVNSE VQLQQSGADL
      VQPGASVKVS CTASGFDIKD
51    YYIHWMKQRP DQGLEWIGRV DPDNGETEFA
      PKFPGKATFT TDTSSNTAYL
101   QLRGLTSEDT AIYYCGREDY DGTYTWFPYW
      GQGTLVTVSA AKTTPPSVYP
151   LAPGSAAQTN SMVTLGCLVK GYFPEPVTVT
      WNSGSLSSGV HTFPAVLQSD
201   LYTLSSSVTV PSSTWPSETV TCNVAHPASS
      TKVDKKIVPR DCGCKPCICT
251   VPEVSSVFIF PPKPKDVLTI TLTPKVTCVV
      VDISKDDPEV QFSWFVDDVE
301   VHTAQTQPRE EQFNSTFRSV SELPIMHQDW
      LNGKEFKCRV NSAAFPAPIE
351   KTISKTKGRP KAPQVYTIPP PKEQMAKDKV
      SLTCMITDFF PEDITVEWQW
401   NGQPAENYKN TQPIMDTDGS YFIYSKLNVQ
      KSNWEAGNTF TCSVLHEGLH
451   NHHTEKSLSH SPGK
```

Nucleic acid sequence of the Ab-11 HC including signal peptide encoding sequence:

```
                                    (SEQ ID NO: 196)
1     ATGAAATGCA GCTGGGTCAT CTTCTTCCTG
      ATGGCAGTGG TTACAGGGGT
51    CAATTCAGAA GTTCAGCTGC AACAGTCTGG
      GGCAGACCTT GTGCAGCCAG
101   GGGCCTCAGT CAAGGTGTCC TGCACAGCTT
      CTGGCTTCGA CATTAAGGAC
151   TACTATATAC ACTGGATGAA ACAGAGGCCT
      GACCAGGGCC TGGAGTGGAT
201   TGGAAGGGTT GATCCTGACA ATGGTGAGAC
      TGAATTTGCC CCGAAGTTCC
251   CGGGCAAGGC CACTTTTACA ACAGACACAT
      CCTCCAACAC AGCCTACCTA
301   CAACTCAGAG GCCTGACATC TGAGGACACT
      GCCATCTATT ACTGTGGGAG
351   AGAAGACTAC GATGGTACCT ACACCTGGTT
      TCCTTATTGG GGCCAAGGGA
401   CTCTGGTCAC TGTCTCTGCA GCCAAAACGA
      CACCCCCATC TGTCTATCCA
451   CTGGCCCCTG GATCTGCTGC CCAAACTAAC
      TCCATGGTGA CCCTGGGATG
501   CCTGGTCAAG GGCTATTTCC CTGAGCCAGT
      GACAGTGACC TGGAACTCTG
551   GATCCCTGTC CAGCGGTGTG CACACCTTCC
      CAGCTGTCCT GCAGTCTGAC
601   CTCTACACTC TGAGCAGCTC AGTGACTGTC
      CCCTCCAGCA CCTGGCCCAG
651   CGAGACCGTC ACCTGCAACG TTGCCCACCC
      GGCCAGCAGC ACCAAGGTGG
701   ACAAGAAAAT TGTGCCCAGG GATTGTGGTT
      GTAAGCCTTG CATATGTACA
751   GTCCCAGAAG TATCATCTGT CTTCATCTTC
      CCCCCAAAGC CAAGGATGTG
801   GCTCACCATT ACTCTGACTC CTAAGGTCAC
      GTGTGTTGTG GTAGACATCA
```

```
 851    GCAAGGATGA TCCCGAGGTC CAGTTCAGCT
        GGTTTGTAGA TGATGTGGAG

901    GTGCACACAG CTCAGACGCA ACCCCGGGAG
        GAGCAGTTCA ACAGCACTTT

951    CCGCTCAGTC AGTGAACTTC CCATCATGCA
        CCAGGACTGG CTCAATGGCA

1001    AGGAGTTCAA ATGCAGGGTC AACAGTGCAG
        CTTTCCCTGC CCCCATCGAG

1051    AAAACCATCT CCAAAACCAA AGGCAGACCG
        AAGGCTCCAC AGGTGTACAC

1101    CATTCCACCT CCCAAGGAGC AGATGGCCAA
        GGATAAAGTC AGTCTGACCT

1151    GCATGATAAC AGACTTCTTC CCTGAAGACA
        TTACTGTGGA GTGGCAGTGG

1201    AATGGGCAGC CAGCGGAGAA CTACAAGAAC
        ACTCAGCCCA TCATGGACAC

1251    AGATGGCTCT TACTTCATCT ACAGCAAGCT
        CAATGTGCAG AAGAGCAACT

1301    GGGAGGCAGG AAATACTTTC ACCTGCTCTG
        TGTTACATGA GGGCCTGCAC

1351    AACCACCATA CTGAGAAGAG CCTCTCCCAC
        TCTCCTGGTA AATGA
```

Ab-12

The sequences of the Antibody 12 (also referred to herein as Ab-12) LC and HC are as follows:

Ab-12 Light Chain:

Amino acid sequence of the mature form (signal peptide removed) of the Ab-12 LC:

```
                                          (SEQ ID NO: 197)
  1 DLQMTQTTSS LSASLGDRVT ISCRASQDIS NYLNWYQQKP DGTVKLLIFY
 51 TSTLQSGVPS RFSGSGSGTN YSLTITNLEQ DDAATYFCQQ GDTLPYTFGG
101 GTKLEIKRAD AAPTVSIFPP SSEQLTSGGA SVVCFLNNFY PKDINVKWKI
151 DGSERQNGVL NSWTDQDSKD STYSMSSTLT LTKDEYERHN SYTCEATHKT
201 STSPIVKSFN RNEC
```

Nucleic acid sequence encoding the mature form (signal peptide removed) of the Ab-12 LC:

```
                         (SEQ ID NO: 198)
  1   GATCTCCAGA TGACACAGAC TACTTCCTCC
      CTGTCTGCCT CTCTGGGAGA

51   CAGAGTCACC ATCAGTTGCA GGGCAAGTCA
      GGACATTAGC AATTATTTAA

101   ACTGGTATCA GCAGAAACCA GATGGAACTG
      TTAAGCTCCT GATCTTCTAC

151   ACATCAACAT TACAGTCAGG AGTCCCATCG
      AGGTTCAGTG GCAGTGGGTC

201   TGGAACAAAT TATTCTCTCA CCATTACCAA
      CCTGGAGCAA GATGATGCTG

251   CCACTTACTT TTGCCAACAG GGTGATACGC
      TTCCGTACAC GTTCGGAGGG
```

```
                         -continued
301   GGGACCAAGC TGGAAATAAA ACGGGCTGAT
      GCTGCACCAA CTGTATCCAT

351   CTTCCCACCA TCCAGTGAGC AGTTAACATC
      TGGAGGTGCC TCAGTCGTGT

401   GCTTCTTGAA CAACTTCTAC CCCAAAGACA
      TCAATGTCAA GTGGAAGATT

451   GATGGCAGTG AACGACAAAA TGGCGTCCTG
      AACAGTTGGA CTGATCAGGA

501   CAGCAAAGAC AGCACCTACA GCATGAGCAG
      CACCCTCACG TTGACCAAGG

551   ACGAGTATGA ACGACATAAC AGCTATACCT
      GTGAGGCCAC TCACAAGACA

601   TCAACTTCAC CCATTGTCAA GAGCTTCAAC
      AGGAATGAGT GTTAG
```

Amino acid sequence of the Ab-12 LC including signal peptide:

```
                                          (SEQ ID NO: 199)
  1   MMSSAQFLGL LLLCFQGSRC DLQMTQTTSS
      LSASLGDRVT ISCRASQDIS

51   NYLNWYQQKP DGTVKLLIFY TSTLQSGVPS
      RFSGSGSGTN YSLTITNLEQ

101   DDAATYFCQQ GDTLPYTFGG GTKLEIKRAD
      AAPTVSIFPP SSEQLTSGGA

151   SVVCFLNNFY PKDINVKWKI DGSERQNGVL
      NSWTDQDSKD STYSMSSTLT

201   LTKDEYERHN SYTCEATHKT STSPIVKSFN
      RNEC
```

Nucleic acid sequence of the Ab12 LC including signal peptide encoding sequence:

```
                         (SEQ ID NO: 200)
  1   ATGATGTCCT CTGCTCAGTT CCTTGGTCTC
      CTGTTGCTCT GTTTTCAAGG

51   TTCCAGATGT GATCTCCAGA TGACACAGAC
      TACTTCCTCC CTGTCTGCCT

101   CTCTGGGAGA CAGAGTCACC ATCAGTTGCA
      GGGCAAGTCA GGACATTAGC

151   AATTATTTAA ACTGGTATCA GCAGAAACCA
      GATGGAACTG TTAAGCTCCT

201   GATCTTCTAC ACATCAACAT TACAGTCAGG
      AGTCCCATCG AGGTTCAGTG

251   GCAGTGGGTC TGGAACAAAT TATTCTCTCA
      CCATTACCAA CCTGGAGCAA
```

Ab-12 Heavy Chain:

Amino acid sequence of the mature form (signal peptide removed) of the Ab-12 HC:

(SEQ ID NO: 201)

```
  1 EVQLQQSGPE LMKPGASVKM SCKASGYTFT DYNMHWNKQN QGKSLEWIGE
 51 INPNSGGSGY NQKFKGKATL TVDKSSSTAY MELRSLTSED SAVYYCARLG
101 YYGNYEDWYF DVWGAGTTVT VSSAKTTPPS VYPLAPGSAA QTNSMVTLGC
151 LVKGYFPEPV TVTWNSGSLS SGVHTFPAVL QSDLYTLSSS VTVPSSTWPS
201 ETVTCNVAHP ASSTKVDKKI VPRDCGCKPC ICTVPEVSSV FIFPPKPKDV
251 LTITLTPKVT CVVVDISKDD PEVQFSWFVD DVEVHTAQTQ PREEQFNSTF
301 RSVSELPIMH QDWLNGKEFK CRVNSAAFPA PIEKTISKTK GRPKAPQVYT
351 IPPPKEQMAK DKVSLTCMIT DFFPEDITVE WQWNGQPAEN YKNTQPIMDT
401 DGSYFIYSKL NVQKSNWEAG NTFTCSVLHE GLHNHHTEKS LSHSPGK
```

Nucleic acid sequence encoding the mature form (signal peptide removed) of the Ab-12 HC:

(SEQ ID NO: 202)

```
   1 GAGGTCCAGT TGCAACAGTC TGGACCTGAA
     CTAATGAAGC CTGGGGCTTC
  51 AGTGAAGATG TCCTGCAAGG CTTCTGGATA
     CACATTCACT GACTACAACA
 101 TGCACTGGAT GAAGCAGAAC CAAGGAAAGA
     GCCTAGAGTG GATAGGAGAG
 151 ATTAATCCTA ACAGTGGTGG TTCTGGTTAC
     AACCAGAAGT TCAAAGGCAA
 201 GGCCACATTG ACTGTAGACA AGTCCTCCAG
     CACAGCCTAC ATGGAGCTCC
 251 GCAGCCTGAC ATCTGAGGAC TCTGCAGTCT
     ATTACTGTGC AAGATTGGGC
 301 TACTATGGTA ACTACGAGGA CTGGTATTTC
     GATGTCTGGG GCGCAGGGAC
 351 CACGGTCACC GTCTCCTCTG CCAAAACGAC
     ACCCCCATCT GTCTATCCAC
 401 TGGCCCCTGG ATCTGCTGCC CAAACTAACT
     CCATGGTGAC CCTGGGATGC
 451 CTGGTCAAGG GCTATTTCCC TGAGCCAGTG
     ACAGTGACCT GGAACTCTGG
 501 ATCCCTGTCC AGCGGTGTGC ACACCTTCCC
     AGCTGTCCTG CAGTCTGACC
 551 TCTACACTCT GAGCAGCTCA GTGACTGTCC
     CCTCCAGCAC CTGGCCCAGC
 601 GAGACCGTCA CCTGCAACGT TGCCCACCCG
     GCCAGCAGCA CCAAGGTGGA
 651 CAAGAAAATT GTGCCCAGGG ATTGTGGTTG
     TAAGCCTTGC ATATGTACAG
 701 TCCCAGAAGT ATCATCTGTC TTCATCTTCC
     CCCCAAAGCC CAAGGATGTG
 751 CTCACCATTA CTCTGACTCC TAAGGTCACG
     TGTGTTGTGG TAGACATCAG
 801 CAAGGATGAT CCCGAGGTCC AGTTCAGCTG
     GTTTGTAGAT GATGTGGAGG
 851 TGCACACAGC TCAGACGCAA CCCCGGGAGG
     AGCAGTTCAA CAGCACTTTC
 901 CGCTCAGTCA GTGAACTTCC CATCATGCAC
     CAGGACTGGC TCAATGGCAA
 951 GGAGTTCAAA TGCAGGGTCA ACAGTGCAGC
     TTTCCCTGCC CCCATCGAGA
1001 AAACCATCTC CAAAACCAAA GGCAGACCGA
     AGGCTCCACA GGTGTACACC
1051 ATTCCACCTC CCAAGGAGCA GATGGCCAAG
     GATAAAGTCA GTCTGACCTG
1101 CATGATAACA GACTTCTTCC CTGAAGACAT
     TACTGTGGAG TGGCAGTGGA
1151 ATGGGCAGCC AGCGGAGAAC TACAAGAACA
     CTCAGCCCAT CATGGACACA
1201 GATGGCTCTT ACTTCATCTA CAGCAAGCTC
     AATGTGCAGA AGAGCAACTG
1251 GGAGGCAGGA AATACTTTCA CCTGCTCTGT
     GTTACATGAG GGCCTGCACA
1301 ACCACCATAC TGAGAAGAGC CTCTCCCACT
     CTCCTGGTAA ATGA
```

Amino acid sequence of the Ab-12 HC including signal peptide:

(SEQ ID NO: 203)

```
  1  MGWSWTFLFL LSGTSGVLSE VQLQQSGPEL
     MKPGASVKMS CKASGYTFTD
 51  YNMHWMKQNQ GKSLEWIGEI NPNSGGSGYN
     QKFKGKATLT VDKSSSTAYM
101  ELRSLTSEDS AVYYCARLGY YGNYEDWYFD
     VWGAGTTVTV SSAKTTPPSV
151  YPLAPGSAAQ TNSMVTLGCL VKGYFPEPVT
     VTWNSGSLSS GVHTFPAVLQ
201  SDLYTLSSSV TVPSSTWPSE TVTCNVAHPA
     SSTKVDKKIV PRDCGCKPCI
251  CTVPEVSSVF IFPPKPKDVL TITLTPKVTC
     VVVDISKDDP EVQFSWFVDD
301  VEVHTAQTQP REEQFNSTFR SVSELPIMHQ
     DWLNGKEFKC RVNSAAFPAP
351  IEKTISKTKG RPKAPQVYTI PPPKEQMAKD
     KVSLTCMITD FFPEDITVEW
401  QWNGQPAENY KNTQPIMDTD GSYFIYSKLN
     VQKSNWEAGN TFTCSVLHEG
451  LHNHHTEKSL SHSPGK
```

Nucleic acid sequence of the Ab-12 HC including signal peptide encoding sequence:

(SEQ ID NO: 204)

```
   1  ATGGGATGGA GCTGGACCTT TCTCTTCCTC
      CTGTCAGGAA CTTCGGGTGT
  51  CCTCTCTGAG GTCCAGTTGC AACAGTCTGG
      ACCTGAACTA ATGAAGCCTG
 101  GGGCTTCAGT GAAGATGTCC TGCAAGGCTT
      CTGGATACAC ATTCACTGAC
 151  TACAACATGC ACTGGATGAA GCAGAACCAA
      GGAAAGAGCC TAGAGTGGAT
 201  AGGAGAGATT AATCCTAACA GTGGTGGTTC
      TGGTTACAAC CAGAAGTTCA
 251  AAGGCAAGGC CACATTGACT GTAGACAAGT
      CCTCCAGCAC AGCCTACATG
 301  GAGCTCCGCA GCCTGACATC TGAGGACTCT
      GCAGTCTATT ACTGTGCAAG
 351  ATTGGGCTAC TATGGTAACT ACGAGGACTG
      GTATTTCGAT GTCTGGGGCG
 401  CAGGGACCAC GGTCACCGTC TCCTCTGCCA
      AAACGACACC CCCATCTGTC
 451  TATCCACTGG CCCCTGGATC TGCTGCCCAA
      ACTAACTCCA TGGTGACCCT
 501  GGGATGCCTG GTCAAGGGCT ATTTCCCTGA
      GCCAGTGACA GTGACCTGGA
 551  ACTCTGGATC CCTGTCCAGC GGTGTGCACA
      CCTCCCAGC TGTCCTGCAG
 601  TCTGACCTCT ACACTCTGAG CAGCTCAGTG
      ACTGTCCCCT CCAGCACCTG
 651  GCCCAGCGAG ACCGTCACCT GCAACGTTGC
      CCACCCGGCC AGCAGCACCA
 701  AGGTGGACAA GAAAATTGTG CCCAGGGATT
      GTGGTTGTAA GCCTTGCATA
 751  TGTACAGTCC CAGAAGTATC ATCTGTCTTC
      ATCTTCCCCC CAAAGCCCAA
 801  GGATGTGCTC ACCATTACTC TGACTCCTAA
      GGTCACGTGT GTTGTGGTAG
 851  ACATCAGCAA GGATGATCCC GAGGTCCAGT
      TCAGCTGGTT TGTAGATGAT
 901  GTGGAGGTGC ACACAGCTCA GACGCAACCC
      CGGGAGGAGC AGTTCAACAG
 951  CACTTTCCGC TCAGTCAGTG AACTTCCCAT
      CATGCACCAG GACTGGCTCA
1001  ATGGCAAGGA GTTCAAATGC AGGGTCAACA
      GTGCAGCTTT CCCTGCCCCC
1051  ATCGAGAAAA CCATCTCCAA AACCAAGGGC
      AGACCGAAGG CTCCACAGGT
1101  GTACACCATT CCACCTCCCA AGGAGCAGAT
      GGCCAAGGAT AAAGTCAGTC
1151  TGACCTGCAT GATAACAGAC TTCTTCCCTG
      AAGACATTAC TGTGGAGTGG
1201  CAGTGGAATG GGCAGCCAGC GGAGAACTAC
      AAGAACACTC AGCCCATCAT
1251  GGACACAGAT GGCTCTTACT TCATCTACAG
      CAAGCTCAAT GTGCAGAAGA
1301  GCAACTGGGA GGCAGGAAAT ACTTTCACCT
      GCTCTGTGTT ACATGAGGGC
1351  CTGCACAACC ACCATACTGA GAAGAGCCTC
      TCCCACTCTC CTGGTAAATG
1401  A
```

Ab-13

The sequences of the Antibody 13 (also referred to herein as Ab-13) LC and HC are as follows:

Ab-13 Light Chain:

Amino acid sequence of the mature form (signal peptide removed) of the Ab-13 LC:

(SEQ ID NO: 205)

```
  1 QIVLTQSPAI MSASPGEKVT MTCRASSSVT SSYLNWYQQK PGSSPKLWIY
 51 STSNLASGVP ARFSGSGSGT SYSLTISSVE AEDAATYYCQ QYDFFPSTFG
101 GGTKLEIKRA DAAPTVSIFP PSSEQLTSGG ASVVCFLNNF YPKDINVKWK
151 IDGSERQNGV LNSWTDQDSK DSTYSMSSTL TLTKDEYERH NSYTCEATHK
201 TSTSPIVKSF NRNEC
```

Nucleic acid sequence encoding the mature form (signal peptide removed) of the Ab-13 LC:

(SEQ ID NO: 206)

```
  1 CAGATTGTTC TCACCCAGTC TCCAGCAATC
    ATGTCTGCAT CTCCAGGGGA
 51 GAAGGTCACC ATGACCTGCA GGGCCAGCTC
    AAGTGTAACT TCCAGTTACT
101 TGAACTGGTA CCAGCAGAAG CCAGGATCTT
    CCCCCAAACT CTGGATTTAT
151 AGCACATCCA ACCTGGCTTC AGGAGTCCCA
    GCTCGCTTCA GTGGCAGTGG
201 GTCTGGGACC TCTTACTCTC TCACAATCAG
    CAGTGTGGAG GCTGAGGATG
251 CTGCCACTTA TTACTGCCAG CAGTATGATT
    TTTTCCCATC GACGTTCGGT
301 GGAGGCACCA AGCTGGAAAT CAAGCGGGCT
    GATGCTGCAC CAACTGTATC
351 CATCTTCCCA CCATCCAGTG AGCAGTTAAC
    ATCTGGAGGT GCCTCAGTCG
401 TGTGCTTCTT GAACAACTTC TACCCCAAAG
    ACATCAATGT CAAGTGGAAG
451 ATTGATGGCA GTGAACGACA AAATGGCGTC
    CTGAACAGTT GGACTGATCA
501 GGACAGCAAA GACAGCACCT ACAGCATGAG
    CAGCACCCTC ACGTTGACCA
551 AGGACGAGTA TGAACGACAT AACAGCTATA
    CCTGTGAGGC CACTCACAAG
601 ACATCAACTT CACCCATCGT CAAGAGCTTC
    AACAGGAATG AGTGT
```

Amino acid sequence of the Ab-13 LC including signal peptide:

(SEQ ID NO: 207)

```
  1 MDSQVQIFSF LLISALVKMS RGQIVLTQSP
    AIMSASPGEK VTMTCRASSS
 51 VTSSYLNWYQ QKPGSSPKLW IYSTSNLASG
    VPARFSGSGS GTSYSLTISS
101 VEAEDAATYY CQQYDFFPST FGGGTKLEIK
    RADAAPTVSI FPPSSEQLTS
151 GGASVVCFLN NFYPKDINVK WKIDGSERQN
    GVLNSWTDQD SKDSTYSMSS
201 TLTLTKDEYE RHNSYTCEAT HKTSTSPIVK
    SFNRNEC
```

Nucleic acid sequence of the Ab-13 LC including signal peptide encoding sequence:

(SEQ ID NO: 208)

```
  1 ATGGATTCTC AAGTGCAGAT TTTCAGCTTC
    CTTCTAATCA GTGCCTTAGT
 51 CAAAATGTCC AGAGGACAGA TTGTTCTCAC
    CCAGTCTCCA GCAATCATGT
101 CTGCATCTCC AGGGGAGAAG GTCACCATGA
    CCTGCAGGGC CAGCTCAAGT
151 GTAACTTCCA GTTACTTGAA CTGGTACCAG
    CAGAAGCCAG GATCTTCCCC
201 CAAACTCTGG ATTTATAGCA CATCCAACCT
    GGCTTCAGGA GTCCCAGCTC
251 GCTTCAGTGG CAGTGGGTCT GGGACCTCTT
    ACTCTCTCAC AATCAGCAGT
301 GTGGAGGCTG AGGATGCTGC CACTTATTAC
    TGCCAGCAGT ATGATTTTTT
351 CCCATCGACG TTCGGTGGAG GCACCAAGCT
    GGAAATCAAG CGGGCTGATG
401 CTGCACCAAC TGTATCCATC TTCCCACCAT
    CCAGTGAGCA GTTAACATCT
451 GGAGGTGCCT CAGTCGTGTG CTTCTTGAAC
    AACTTCTACC CCAAAGACAT
501 CAATGTCAAG TGGAAGATTG ATGGCAGTGA
    ACGACAAAAT GGCGTCCTGA
551 ACAGTTGGAC TGATCAGGAC AGCAAAGACA
    GCACCTACAG CATGAGCAGC
601 ACCCTCACGT TGACCAAGGA CGAGTATGAA
    CGACATAACA GCTATACCTG
651 TGAGGCCACT CACAAGACAT CAACTTCACC
    CATCGTCAAG AGCTTCAACA
701 GGAATGAGTG T
```

Ab-13 Heavy Chain:

Amino acid sequence of the mature form (signal peptide removed) of the Ab-13 HC:

```
  1 EVQLQQSGPE LVKPGASVKM SCKASGYTFT DYYMNWVKQS HGESLEWIGD
 51 INPYNDDTTY NHKFKGKATL TVDKSSNTAY MQLNSLTSED SAVYYCARET
101 AVITTNAMDY WGQGTSVTVS SAKTTPPSVY PLAPGSAAQT NSMVTLGCLV
151 KGYFPEPVTV TWNSGSLSSG VHTFPAVLQS DLYTLSSSVT VPSSTWPSET
201 VTCNVAHPAS STKVDKKIVP RDCGCKPCIC TVPEVSSVFI FPPKPKDVLT
251 ITLTPKVTCV VVDISKDDPE VQFSWFVDDV EVHTAQTQPR EEQFNSTFRS
301 VSELPIMHQD WLNGKEFKCR VNSAAFPAPI EKTISKTKGR PKAPQVYTIP
351 PPKEQMAKDK VSLTCMITDF FPEDITVEWQ WNGQPAENYK NTQPIMDTDG
401 SYFIYSKLNV QKSNWEAGNT FTCSVLHEGL HNHHTEKSLS HSPGK
```

(SEQ ID NO: 209)

Nucleic acid sequence encoding the mature form (signal peptide removed) of the Ab-13 HC:

```
                                              (SEQ ID NO: 210)
    1      GAGGTCCAGC TGCAACAATC TGGACCTGAG
           CTGGTGAAGC CTGGGGCTTC
   51      AGTGAAGATG TCCTGTAAGG CTTCTGGATA
           CACATTCACT GACTACTACA
  101      TGAACTGGGT GAAGCAGAGC CATGGAGAGA
           GCCTTGAGTG GATTGGAGAT
  151      ATTAATCCTT ACAACGATGA TACTACCTAC
           AACCACAAGT TCAAGGGCAA
  201      GGCCACATTG ACTGTAGACA AATCCTCCAA
           CACAGCCTAC ATGCAGCTCA
  251      ACAGCCTGAC ATCTGAGGAC TCTGCAGTCT
           ATTACTGTGC AAGAGAGACG
  301      GCCGTTATTA CTACGAATGC TATGGACTAC
           TGGGGTCAAG GAACCTCAGT
  351      CACCGTCTCC TCAGCCAAAA CGACACCCCC
           ATCTGTCTAT CCACTGGCCC
  401      CTGGATCTGC TGCCCAAACT AACTCCATGG
           TGACCCTGGG ATGCCTGGTC
  451      AAGGGCTATT TCCCTGAGCC AGTGACAGTG
           ACCTGGAACT CTGGATCCCT
  501      GTCCAGCGGT GTGCACACCT TCCCAGCTGT
           CCTGCAGTCT GACCTCTACA
  551      CTCTGAGCAG CTCAGTGACT GTCCCCTCCA
           GCACCTGGCC CAGCGAGACC
  601      GTCACCTGCA ACGTTGCCCA CCCGGCCAGC
           AGCACCAAGG TGGACAAGAA
  651      AATTGTGCCC AGGGATTGTG GTTGTAAGCC
           TTGCATATGT ACAGTCCCAG
  701      AAGTATCATC TGTCTTCATC TTCCCCCCAA
           AGCCCAAGGA TGTGCTCACC
  751      ATTACTCTGA CTCCTAAGGT CACGTGTGTT
           GTGGTAGACA TCAGCAAGGA
  801      TGATCCCGAG GTCCAGTTCA GCTGGTTTGT
           AGATGATGTG GAGGTGCACA
  851      CAGCTCAGAC GCAACCCCGG GAGGAGCAGT
           TCAACAGCAC TTTCCGCTCA
  901      GTCAGTGAAC TTCCCATCAT GCACCAGGAC
           TGGCTCAATG GCAAGGAGTT
  951      CAAATGCAGG GTCAACAGTG CAGCTTTCCC
           TGCCCCCATC GAGAAAACCA
```

-continued

```
 1001      TCTCCAAAAC CAAAGGCAGA CCGAAGGCTC
           CACAGGTGTA CACCATTCCA
 1051      CCTCCCAAGG AGCAGATGGC CAAGGATAAA
           GTCAGTCTGA CCTGCATGAT
 1101      AACAGACTTC TTCCCTGAAG ACATTACTGT
           GGAGTGGCAG TGGAATGGGC
 1151      AGCCAGCGGA GAACTACAAG AACACTCAGC
           CCATCATGGA CACAGATGGC
 1201      TCTTACTTCA TCTACAGCAA GCTCAATGTG
           CAGAAGAGCA ACTGGGAGGC
 1251      AGGAAATACT TTCACCTGCT CTGTGTTACA
           TGAGGGCCTG CACAACCACC
 1301      ATACTGAGAA GAGCCTCTCC CACTCTCCTG
           GTAAA
```

Amino acid sequence of the Ab-13 HC including signal peptide:

```
                                              (SEQ ID NO: 211)
    1      MGWNWIFLFL LSGTAGVYSE VQLQQSGPEL
           VKPGASVKMS CKASGYTFTD
   51      YYMNWVKQSH GESLEWIGDI NPYNDDTTYN
           HKFKGKATLT VDKSSNTAYM
  101      QLNSLTSEDS AVYYCARETA VITTNAMDYW
           GQGTSVTVSS AKTTPPSVYP
  151      LAPGSAAQTN SMVTLGCLVK GYFPEPVTVT
           WNSGSLSSGV HTFPAVLQSD
  201      LYTLSSSVTV PSSTWPSETV TCNVAHPASS
           TKVDKKIVPR DCGCKPCICT
  251      VPEVSSVFIF PPKPKDVLTI TLTPKVTCVV
           VDISKDDPEV QFSWFVDDVE
  301      VHTAQTQPRE EQFNSTFRSV SELPIMHQDW
           LNGKEFKCRV NSAAFPAPIE
  351      KTISKTKGRP KAPQVYTIPP PKEQMAKDKV
           SLTCMITDFF PEDITVEWQW
  401      NGQPAENYKN TQPIMDTDGS YFIYSKLNVQ
           KSNWEAGNTF TCSVLHEGLH
  451      NHHTEKSLSH SPGK
```

Nucleic acid sequence of the Ab-13 HC including signal peptide encoding sequence:

```
                                              (SEQ ID NO: 212)
    1      ATGGGATGGA ACTGGATCTT TCTCTTCCTC
           TTGTCAGGAA CTGCAGGTGT
```

-continued

```
 51  CTACTCTGAG GTCCAGCTGC AACAATCTGG
     ACCTGAGCTG GTGAAGCCTG
101  GGGCTTCAGT GAAGATGTCC TGTAAGGCTT
     CTGGATACAC ATTCACTGAC
151  TACTACATGA ACTGGGTGAA GCAGAGCCAT
     GGAGAGAGCC TTGAGTGGAT
201  TGGAGATATT AATCCTTACA ACGATGATAC
     TACCTACAAC CACAAGTTCA
251  AGGGCAAGGC CACATTGACT GTAGACAAAT
     CCTCCAACAC AGCCTACATG
301  CAGCTCAACA GCCTGACATC TGAGGACTCT
     GCAGTCTATT ACTGTGCAAG
351  AGAGACGGCC GTTATTACTA CGAATGCTAT
     GGACTACTGG GGTCAAGGAA
401  CCTCAGTCAC CGTCTCCTCA GCCAAAACGA
     CACCCCCATC TGTCTATCCA
451  CTGGCCCCTG GATCTGCTGC CCAAACTAAC
     TCCATGGTGA CCCTGGGATG
501  CCTGGTCAAG GGCTATTTCC CTGAGCCAGT
     GACAGTGACC TGGAACTCTG
551  GATCCCTGTC CAGCGGTGTG CACACCTTCC
     CAGCTGTCCT GCAGTCTGAC
601  CTCTACACTC TGAGCAGCTC AGTGACTGTC
     CCCTCCAGCA CCTGGCCCAG
```

-continued

```
651  CGAGACCGTC ACCTGCAACG TTGCCCACCC
     GGCCAGCAGC ACCAAGGTGG
701  ACAAGAAAAT TGTGCCCAGG GATTGTGGTT
     GTAAGCCTTG CATATGTACA
751  GTCCCAGAAG TATCATCTGT CTTCATCTTC
     CCCCCAAAGC CCAAGGATGT
801  GCTCACCATT ACTCTGACTC CTAAGGTCAC
     GTGTGTTGTG GTAGACATCA
851  GCAAGGATGA TCCCGAGGTC CAGTTCAGCT
     GGTTTGTAGA TGATGTGGAG
901  GTGCACACAG CTCAGACGCA ACCCCGGGAG
     GAGCAGTTCA ACAGCACTTT
951  CCGCTCAGTC AGTGAACTTC CCATCATGCA
     CCAGGACTGG CTCAATGCA
1001 AGGAGTTCAA ATGCAGGGTC AACAGTGCAG
     CTTTCCCTGC CCCCATCGAG
1051 AAAACCATCT CCAAAACCAA AGGCAGACCG
     AAGGCTCCAC AGGTGTACAC
1101 CATTCCACCT CCCAAGGAGC AGATGGCCAA
     GGATAAAGTC AGTCTGACCT
1151 GCATGATAAC AGACTTCTTC CCTGAAGACA
     TTACTGTGGA GTGGCAGTGG
1201 AATGGGCAGC CAGCGGAGAA CTACAAGAAC
     ACTCAGCCCA TCATGGACAC
1251 AGATGGCTCT TACTTCATCT ACAGCAAGCT
     CAATGTGCAG AAGAGCAACT
1301 GGGAGGCAGG AAATACTTTC ACCTGCTCTG
     TGTTACATGA GGGCCTGCAC
1351 AACCACCATA CTGAGAAGAG CCTCTCCCAC
     TCTCCTGGTA AA
```

Ab-13 was humanized to generate Ab-14.

The sequences of the Antibody 14 (also referred to herein as Ab-14) LC and HC are as follows:

Ab-14 Light Chain:

Amino acid sequence of the mature form (signal peptide removed) of the Ab-14 LC:

(SEQ ID NO: 213)
```
  1 DIQLTQSPSF LSASVGDRVT ITCRASSSVT SSYLNWYQQK PGKAPKLLIY
 51 STSNLASGVP SRFSGSGSGT EFTLTISSLQ PEDFATYYCQ QYDFFPSTFG
101 GGTKVEIKRT VAAPSVFIFP PSDEQLKSGT ASVVCLLNNF YPREAKVQWK
151 VDNALQSGNS QESVTEQDSK DSTYSLSSTL TLSKADYEKH KVYACEVTHQ
201 GLSSPVTKSF NRGEC
```

Nucleic acid sequence encoding the mature form (signal peptide removed) of the Ab-14 LC:

(SEQ ID NO: 214)
```
  1 GACATCCAGC TGACCCAGAG CCCCAGCTTC
    CTTTCCGCAT CCGTTGGTGA
 51 CCGAGTAACA ATCACATGCC GCGCCTCATC
    TTCAGTTACA TCTTCTTATC
101 TTAATTGGTA TCAACAAAAA CCAGGAAAAG
    CACCTAAACT TCTTATATAC
151 TCTACATCTA ATCTCGCATC AGGAGTTCCC
    TCTCGATTTT CAGGATCTGG
201 ATCAGGCACA GAATTTACAC TTACTATATC
    ATCACTCCAA CCAGAAGACT
251 TCGCCACTTA TTACTGCCAA CAATACGATT
    TTTTTCCAAG CACATTCGGA
301 GGAGGTACAA AAGTAGAAAT CAAGCGTACG
    GTGGCTGCAC CATCTGTCTT
```

```
351  CATCTTCCCG CCATCTGATG AGCAGTTGAA
     ATCTGGAACT GCCTCTGTTG
401  TGTGCCTGCT GAATAACTTC TATCCCAGAG
     AGGCCAAAGT ACAGTGGAAG
451  GTGGATAACG CCCTCCAATC GGGTAACTCC
     CAGGAGAGTG TCACAGAGCA
501  GGACAGCAAG GACAGCACCT ACAGCCTCAG
     CAGCACCCTG ACGCTGAGCA
551  AAGCAGACTA CGAGAAACAC AAAGTCTACG
     CCTGCGAAGT CACCCATCAG
601  GGCCTGAGCT CGCCCGTCAC AAAGAGCTTC
     AACAGGGGAG AGTGT
```

Amino acid sequence of the Ab-14 LC including signal peptide:

```
                                    (SEQ ID NO: 215)
  1  MDMRVPAQLL GLLLLWLPGA RCDIQLTQSP
     SFLSASVGDR VTITCRASSS
 51  VTSSYLNWYQ QKPGKAPKLL IYSTSNLASG
     VPSRFSGSGS GTEFTLTISS
101  LQPEDFATYY CQQYDFFPST FGGGTKVEIK
     RTVAAPSVFI FPPSDEQLKS
151  GTASVVCLLN NFYPREAKVQ WKVDNALQSG
     NSQESVTEQD SKDSTYSLSS
201  TLTLSKADYE KHKVYACEVT HQGLSSPVTK
     SFNRGEC
```

Nucleic acid sequence of the Ab-14 LC including signal peptide encoding sequence:

```
                                    (SEQ ID NO: 216)
  1  ATGGACATGA GGGTCCCCGC TCAGCTCCTG
     GGGCTCCTGC TACTCTGGCT
 51  CCCAGGTGCC AGATGTGACA TCCAGCTGAC
     CCAGAGCCCC AGCTTCCTTT
101  CCGCATCCGT TGGTGACCGA GTAACAATCA
     CATGCCGCGC CTCATCTTCA
151  GTTACATCTT CTTATCTTAA TTGGTATCAA
     CAAAAACCAG GAAAAGCACC
201  TAAACTTCTT ATATACTCTA CATCTAATCT
     CGCATCAGGA GTTCCCTCTC
251  GATTTTCAGG ATCTGGATCA GGCACAGAAT
     TTACACTTAC TATATCATCA
301  CTCCAACCAG AAGACTTCGC CACTTATTAC
     TGCCAACAAT ACGATTTTTT
351  TCCAAGCACA TTCGGAGGAG GTACAAAAGT
     AGAAATCAAG CGTACGGTGG
401  CTGCACCATC TGTCTTCATC TTCCCGCCAT
     CTGATGAGCA GTTGAAATCT
451  GGAACTGCCT CTGTTGTGTG CCTGCTGAAT
     AACTTCTATC CCAGAGAGGC
501  CAAAGTACAG TGGAAGGTGG ATAACGCCCT
     CCAATCGGGT AACTCCCAGG
551  AGAGTGTCAC AGAGCAGGAC AGCAAGGACA
     GCACCTACAG CCTCAGCAGC
601  ACCCTGACGC TGAGCAAAGC AGACTACGAG
     AAACACAAAG TCTACGCCTG
651  CGAAGTCACC CATCAGGGCC TGAGCTCGCC
     CGTCACAAAG AGCTTCAACA
701  GGGGAGAGTG T
```

Ab-14 Heavy Chain:

Amino acid sequence of the mature form (signal peptide removed) of the Ab-14 HC:

```
                                    (SEQ ID NO: 217)
  1  EVQLVQSGAE VKKPGASVKV SCKASGYTFT DYYMNWVRQA PGQRLEWMGD
 51  INPYNDDTTY NHKFKGRVTI TRDTSASTAY MELSSLRSED TAVYYCARET
101  AVITTNAMDY WGQGTTVTVS SASTKGPSVF PLAPCSRSTS ESTAALGCLV
151  KDYFPEPVTV SWNSGALTSG VHTFPAVLQS SGLYSLSSVV TVPSSNFGTQ
201  TYTCNVDHKP SNTKVDKTVE RKCCVECPPC PAPPVAGPSV FLFPPKPKDT
251  LMISRTPEVT CVVVDVSHED PEVQFNWYVD GVEVHNAKTK PREEQFNSTF
301  RVVSVLTVVH QDWLNGKEYK CKVSNKGLPA PIEKTISKTK GQPREPQVYT
351  LPPSREEMTK NQVSLTCLVK GFYPSDIAVE WESNGQPENN YKTTPPMLDS
401  DGSFFLYSKL TVDKSRWQQG NVFSCSVMHE ALHNHYTQKS LSLSPGK
```

Amino acid sequence of the mature form (signal peptide removed) of the Ab-14 HC without carboxy-terminal lysine:

(SEQ ID NO: 393)

```
  1 EVQLVQSGAE VKKPGASVKV SCKASGYTFT DYYMNWVRQA PGQRLEWMGD
 51 INPYNDDTTY NHKFKGRVTI TRDTSASTAY MELSSLRSED TAVYYCARET
101 AVITTNAMDY WGQGTTVTVS SASTKGPSVF PLAPCSRSTS ESTAALGCLV
151 KDYFPEPVTV SWNSGALTSG VHTFPAVLQS SGLYSLSSVV TVPSSNFGTQ
201 TYTCNVDHKP SNTKVDKTVE RKCCVECPPC PAPPVAGPSV FLFPPKPKDT
251 LMISRTPEVT CVVVDVSHED PEVQFNWYVD GVEVHNAKTK PREEQFNSTF
301 RVVSVLTVVH QDWLNGKEYK CKVSNKGLPA PIEKTISKTK GQPREPQVYT
351 LPPSREEMTK NQVSLTCLVK GFYPSDIAVE WESNGQPENN YKTTPPMLDS
401 DGSFFLYSKL TVDKSRWQQG NVFSCSVMHE ALHNHYTQKS LSLSPG
```

Nucleic acid sequence encoding the mature form (signal peptide removed) of the Ab-14 HC:

(SEQ ID NO: 218)

```
   1 GAGGTGCAGC TGGTGCAGAG CGGCGCCGAG
     GTCAAGAAAC CTGGAGCAAG
  51 CGTAAAGGTT AGTTGCAAAG CATCTGGATA
     CACATTTACC GACTACTACA
 101 TGAATTGGGT ACGACAAGCC CCTGGACAAA
     GACTTGAATG GATGGGAGAC
 151 ATTAACCCTT ATAACGACGA CACTACATAC
     AATCATAAAT TTAAAGGAAG
 201 AGTTACAATT ACAAGAGATA CATCCGCATC
     AACCGCCTAT ATGGAACTTT
 251 CCTCATTGAG ATCTGAAGAC ACTGCTGTTT
     ATTACTGTGC AAGAGAAACT
 301 GCCGTTATTA CTACTAACGC TATGGATTAC
     TGGGGTCAAG GAACCACTGT
 351 TACCGTCTCT AGTGCCTCCA CCAAGGGCCC
     ATCGGTCTTC CCCCTGGCGC
 401 CCTGCTCCAG GAGCACCTCC GAGAGCACAG
     CGGCCCTGGG CTGCCTGGTC
 451 AAGGACTACT TCCCCGAACC GGTGACGGTG
     TCGTGGAACT CAGGCGCTCT
 501 GACCAGCGGC GTGCACACCT TCCCAGCTGT
     CCTACAGTCC TCAGGACTCT
 551 ACTCCCTCAG CAGCGTGGTG ACCGTGCCCT
     CCAGCAACTT CGGCACCCAG
 601 ACCTACACCT GCAACGTAGA TCACAAGCCC
     AGCAACACCA AGGTGGACAA
 651 GACAGTTGAG CGCAAATGTT GTGTCGAGTG
     CCCACCGTGC CCAGCACCAC
 701 CTGTGGCAGG ACCGTCAGTC TTCCTCTTCC
     CCCCAAAACC CAAGGACACC
 751 CTCATGATCT CCCGGACCCC TGAGGTCACG
     TGCGTGGTGG TGGACGTGAG
 801 CCACGAAGAC CCCGAGGTCC AGTTCAACTG
     GTACGTGGAC GGCGTGGAGG
 851 TGCATAATGC CAAGACAAAG CCACGGGAGG
     AGCAGTTCAA CAGCACGTTC
 901 CGTGTGGTCA GCGTCCTCAC CGTTGTGCAC
     CAGGACTGGC TGAACGGCAA
 951 GGAGTACAAG TGCAAGGTCT CCAACAAAGG
     CCTCCCAGCC CCCATCGAGA
1001 AAACCATCTC CAAAACCAAA GGGCAGCCCC
     GAGAACCACA GGTGTACACC
1051 CTGCCCCCAT CCCGGGAGGA GATGACCAAG
     AACCAGGTCA GCCTGACCTG
1101 CCTGGTCAAA GGCTTCTACC CCAGCGACAT
     CGCCGTGGAG TGGGAGAGCA
1151 ATGGGCAGCC GGAGAACAAC TACAAGACCA
     CACCTCCCAT GCTGGACTCC
1201 GACGGCTCCT TCTTCCTCTA CAGCAAGCTC
     ACCGTGGACA AGAGCAGGTG
1251 GCAGCAGGGG AACGTCTTCT CATGCTCCGT
     GATGCATGAG GCTCTGCACA
1301 ACCACTACAC GCAGAAGAGC CTCTCCCTGT
     CTCCGGGTAA A
```

Amino acid sequence of the Ab-14 HC including signal peptide:

(SEQ ID NO: 219)

```
  1 MDWTWRILFL VAAATGAHSE VQLVQSGAEV
    KKPGASVKVS CKASGYTFTD
 51 YYMNWVRQAP GQRLEWMGDI NPYNDDTTYN
    HKFKGRVTIT RDTSASTAYM
101 ELSSLRSEDT AVYYCARETA VITTNAMDYW
    GQGTTVTVSS ASTKGPSVFP
151 LAPCSRSTSE STAALGCLVK DYFPEPVTVS
    WNSGALTSGV HTFPAVLQSS
201 GLYSLSSVVT VPSSNFGTQT YTCNVDHKPS
    NTKVDKTVER KCCVECPPCP
251 APPVAGPSVF LFPPKPKDTL MISRTPEVTC
    VVVDVSHEDP EVQFNWYVDG
301 VEVHNAKTKP REEQFNSTFR VVSVLTVVHQ
    DWLNGKEYKC KVSNKGLPAP
351 IEKTISKTKG QPREPQVYTL PPSREEMTKN
    QVSLTCLVKG FYPSDIAVEW
401 ESNGQPENNY KTTPPMLDSD GSFFLYSKLT
    VDKSRWQQGN VFSCSVMHEA
451 LHNHYTQKSL SLSPGK
```

Nucleic acid sequence of the Ab-14 HC including signal peptide encoding sequence:

(SEQ ID NO: 220)

```
   1 ATGGACTGGA CCTGGAGGAT CCTCTTCTTG
     GTGGCAGCAG CCACAGGAGC
  51 CCACTCCGAG GTGCAGCTGG TGCAGAGCGG
     CGCCGAGGTC AAGAAACCTG
 101 GAGCAAGCGT AAAGGTTAGT TGCAAAGCAT
     CTGGATACAC ATTTACCGAC
 151 TACTACATGA ATTGGGTACG ACAAGCCCCT
     GGACAAAGAC TTGAATGGAT
 201 GGGAGACATT AACCCTTATA ACGACGACAC
     TACATACAAT CATAAATTTA
 251 AAGGAAGAGT TACAATTACA AGAGATACAT
     CCGCATCAAC CGCCTATATG
 301 GAACTTTCCT CATTGAGATC TGAAGACACT
     GCTGTTTATT ACTGTGCAAG
 351 AGAAACTGCC GTTATTACTA CTAACGCTAT
     GGATTACTGG GGTCAAGGAA
 401 CCACTGTTAC CGTCTCTAGT GCCTCCACCA
     AGGGCCCATC GGTCTTCCCC
 451 CTGGCGCCCT GCTCCAGGAG CACCTCCGAG
     AGCACAGCGG CCCTGGGCTG
 501 CCTGGTCAAG GACTACTTCC CCGAACCGGT
     GACGGTGTCG TGGAACTCAG
 551 GCGCTCTGAC CAGCGGCGTG CACACCTTCC
     CAGCTGTCCT ACAGTCCTCA
 601 GGACTCTACT CCCTCAGCAG CGTGGTGACC
     GTGCCCTCCA GCAACTTCGG
 651 CACCCAGACC TACACCTGCA ACGTAGATCA
     CAAGCCCAGC AACACCAAGG
 701 TGGACAAGAC AGTTGAGCGC AAATGTTGTG
     TCGAGTGCCC ACCGTGCCCA
 751 GCACCACCTG TGGCAGGACC GTCAGTCTTC
     CTCTTCCCCC CAAAACCCAA
 801 GGACACCCTC ATGATCTCCC GGACCCCTGA
     GGTCACGTGC GTGGTGGTGG
```

-continued

```
1051 ATCGAGAAAA CCATCTCCAA AACCAAAGGG
     CAGCCCCGAG AACCACAGGT
1101 GTACACCCTG CCCCCATCCC GGGAGGAGAT
     GACCAAGAAC CAGGTCAGCC
1151 TGACCTGCCT GGTCAAAGGC TTCTACCCCA
     GCGACATCGC CGTGGAGTGG
1201 GAGAGCAATG GGCAGCCGGA GAACAACTAC
     AAGACCACAC CTCCCATGCT
1251 GGACTCCGAC GGCTCCTTCT TCCTCTACAG
     CAAGCTCACC GTGGACAAGA
1301 GCAGGTGGCA GCAGGGGAAC GTCTTCTCAT
     GCTCCGTGAT GCATGAGGCT
1351 CTGCACAACC ACTACACGCA GAAGAGCCTC
     TCCCTGTCTC CGGGTAAA
```

The CDR sequences in the variable region of the heavy chain of Ab-14 are:

```
CDR-H1:  DYYMN            (SEQ ID NO: 296)
CDR-H2:  DINPYNDDTTYNHKFKG (SEQ ID NO: 297)
CDR-H3:  ETAVITTNAMD      (SEQ ID NO: 298)
```

The light chain variable region CDR sequences of Ab-14 are:

```
CDR-L1:  RASSSVTSSYLN     (SEQ ID NO: 284)
CDR-L2:  STSNLAS          (SEQ ID NO: 285)
CDR-L3:  QQYDFFPST        (SEQ ID NO: 286)
```

Ab-14 Variable Domains:

Ab-14 light chain variable domain amino acid sequence (without signal sequence):

(SEQ ID NO: 380)
```
  1 DIQLTQSPSF LSASVGDRVT ITCRASSSVT SSYLNWYQQK PGKAPKLLIY
 51 STSNLASGVP SRFSGSGSGT EFTLTISSLQ PEDFATYYCQ QYDFFPSTFG
101 GGTKVEIK
```

-continued

```
 851 ACGTGAGCCA CGAAGACCCC GAGGTCCAGT
     TCAACTGGTA CGTGGACGGC
 901 GTGGAGGTGC ATAATGCCAA GACAAAGCCA
     CGGGAGGAGC AGTTCAACAG
 951 CACGTTCCGT GTGGTCAGCG TCCTCACCGT
     TGTGCACCAG GACTGGCTGA
1001 ACGGCAAGGA GTACAAGTGC AAGGTCTCCA
     ACAAAGGCCT CCCAGCCCCC
```

Ab-14 light chain variable domain DNA sequence (without signal sequence):

(SEQ ID NO: 381)
```
  1 GACATCCAGC TGACCCAGAG CCCCAGCTTC
    CTTTCCGCAT CCGTTGGTGA
 51 CCGAGTAACA ATCACATGCC GCGCCTCATC
    TTCAGTTACA TCTTCTTATC
101 TTAATTGGTA TCAACAAAAA CCAGGAAAAG
    CACCTAAACT TCTTATATAC
```

-continued

```
151   TCTACATCTA ATCTCGCATC AGGAGTTCCC
      TCTCGATTTT CAGGATCTGG

201   ATCAGGCACA GAATTTACAC TTACTATATC
      ATCACTCCAA CCAGAAGACT

251   TCGCCACTTA TTACTGCCAA CAATACGATT
      TTTTTCCAAG CACATTCGGA

301   GGAGGTACAA AAGTAGAAAT CAAG
```

Ab-14 heavy chain variable domain amino acid sequence (without signal sequence):

(SEQ ID NO: 382)

```
  1 EVQLVQSGAE VKKPGASVKV SCKASGYTFT DYYMNWVRQA PGQRLEWMGD
 51 INPYNDDTIY NHKFKGRVTI TRDTSASTAY MELSSLRSED TAVYYCARET
101 AVITTNAMDY WGQGTTVTVS S
```

Ab-14 heavy chain variable domain DNA sequence (without signal sequence):

(SEQ ID NO: 383)

```
  1   GAGGTGCAGC TGGTGCAGAG CGGCGCCGAG
      GTCAAGAAAC CTGGAGCAAG

51   CGTAAAGGTT AGTTGCAAAG CATCTGGATA
      CACATTTACC GACTACTACA

101   TGAATTGGGT ACGACAAGCC CCTGGACAAA
      GACTTGAATG GATGGGAGAC

151   ATTAACCCTT ATAACGACGA CACTACATAC
      AATCATAAAT TTAAAGGAAG

201   AGTTACAATT ACAAGAGATA CATCCGCATC
      AACCGCCTAT ATGGAACTTT

251   CCTCATTGAG ATCTGAAGAC ACTGCTGTTT
      ATTACTGTGC AAGAGAAACT

301   GCCGTTATTA CTACTAACGC TATGGATTAC
      TGGGGTCAAG GAACCACTGT

351   TACCGTCTCT AGT
```

Ab-3 was humanized to generate Ab-15.

Ab-15

The sequences of the Antibody 15 (also referred to herein as Ab-15) LC and HC are as follows:

Ab-15 Light Chain:

Amino acid sequence of the mature form (signal peptide removed) of the Ab-15 LC:

(SEQ ID NO: 221)

```
  1 DIQMTQSPSS LSASVGDRVT ITCSVSSTIS SNHLHWFQQK PGKAPKSLIY
 51 GTSNLASGVP SRFSGSGSGT DFTLTISSLQ PEDFATYYCQ QWSSYPLTFG
101 GGTKVEIKRT VAAPSVFIFP PSDEQLKSGT ASVVCLLNNF YPREAKVQWK
151 VDNALQSGNS QESVTEQDSK DSTYSLSSTL TLSKADYEKH KVYACEVTHQ
201 GLSSPVTKSF NRGEC
```

Nucleic acid sequence encoding the mature form (signal peptide removed) of the Ab-15 LC:

(SEQ ID NO: 222)

```
  1   GACATCCAGA TGACCCAGTC TCCATCCTCC
      CTCTCAGCAT CCGTAGGCGA

51   TAGAGTTACA ATAACATGCA GCGTATCATC
      AACTATATCA TCAAATCATC

101   TTCATTGGTT CCAACAGAAA CCCGGCAAAG
      CACCTAAATC ACTTATATAC
```

-continued

```
151   GGCACATCAA ATCTCGCATC AGGCGTTCCT
      TCAAGATTTT CAGGCTCTGG

201   CTCAGGCACC GACTTTACTC TTACAATATC
      CTCCCTCCAA CCCGAAGACT

251   TCGCAACCTA TTACTGTCAA CAATGGTCCT
      CATATCCACT CACATTTGGC

301   GGCGGCACAA AAGTAGAAAT TAAACGTACG
      GTGGCTGCAC CATCTGTCTT

351   CATCTTCCCG CCATCTGATG AGCAGTTGAA
      ATCTGGAACT GCCTCTGTTG

401   TGTGCCTGCT GAATAACTTC TATCCCAGAG
      AGGCCAAAGT ACAGTGGAAG

451   GTGGATAACG CCCTCCAATC GGGTAACTCC
      CAGGAGAGTG TCACAGAGCA

501   GGACAGCAAG GACAGCACCT ACAGCCTCAG
      CAGCACCCTG ACGCTGAGCA

551   AAGCAGACTA CGAGAAACAC AAAGTCTACG
      CCTGCGAAGT CACCCATCAG

601   GGCCTGAGCT CGCCCGTCAC AAAGAGCTTC
      AACAGGGGAG AGTGT
```

Amino acid sequence of the Ab-15 LC including signal peptide:

(SEQ ID NO: 223)

```
  1 MDMRVPAQLL GLLLLWLRGA RCDIQMTQSP
    SSLSASVGDR VTITCSVSST
```

```
 51    ISSNHLHWFQ QKPGKAPKSL IYGTSNLASG
       VPSRFSGSGS GTDFTLTISS
101    LQPEDFATYY CQQWSSYPLT FGGGTKVEIK
       RTVAAPSVFI FPPSDEQLKS
151    GTASVVCLLN NFYPREAKVQ WKVDNALQSG
       NSQESVTEQD SKDSTYSLSS
201    TLTLSKADYE KHKVYACEVT HQGLSSPVTK
       SFNRGEC
```

Nucleic acid sequence of the Ab-15 LC including signal peptide encoding sequence:

```
                                    (SEQ ID NO: 224)
  1    ATGGACATGA GGGTCCCCGC TCAGCTCCTG
       GGGCTCCTGC TACTCTGGCT
 51    CCGAGGTGCC AGATGTGACA TCCAGATGAC
       CCAGTCTCCA TCCTCCCTCT
101    CAGCATCCGT AGGCGATAGA GTTACAATAA
       CATGCAGCGT ATCATCAACT
151    ATATCATCAA ATCATCTTCA TTGGTTCCAA
       CAGAAACCCG GCAAAGCACC
201    TAAATCACTT ATATACGGCA CATCAAATCT
       CGCATCAGGC GTTCCTTCAA
251    GATTTTCAGG CTCTGGCTCA GGCACCGACT
       TTACTCTTAC AATATCCTCC
301    CTCCAACCCG AAGACTTCGC AACCTATTAC
       TGTCAACAAT GGTCCTCATA
```

```
351    TCCACTCACA TTTGGCGGCG GCACAAAAGT
       AGAAATTAAA CGTACGGTGG
401    CTGCACCATC TGTCTTCATC TTCCCGCCAT
       CTGATGAGCA GTTGAAATCT
451    GGAACTGCCT CTGTTGTGTG CCTGCTGAAT
       AACTTCTATC CCAGAGAGGC
501    CAAAGTACAG TGGAAGGTGG ATAACGCCCT
       CCAATCGGGT AACTCCCAGG
551    AGAGTGTCAC AGAGCAGGAC AGCAAGGACA
       GCACCTACAG CCTCAGCAGC
601    ACCCTGACGC TGAGCAAAGC AGACTACGAG
       AAACACAAAG TCTACGCCTG
651    CGAAGTCACC CATCAGGGCC TGAGCTCGCC
       CGTCACAAAG AGCTTCAACA
701    GGGGAGAGTG T
```

Ab-15 Heavy Chain

Amino acid sequence of the mature form (signal peptide removed) of Ab-15 HC.

```
                                    (SEQ ID NO: 225)
  1    EVQLVQSGAE VKKPGASVKV SCKASDFNIK DFYLHWVRQA PGQGLEWIGR
 51    IDPENGDTLY DPKFQDKVTM TTDTSTSTAY MELRSLRSDD TAVYYCAREA
101    DYFHDGTSYW YFDVWGRGTL VTVSSASTKG PSVFPLAPCS RSTSESTAAL
151    GCLVKDYFPE PVTVSWNSGA LTSGVHTFPA VLQSSGLYSL SSVVTVPSSN
201    FGTQTYTCNV DHKPSNTKVD KTVERKCCVE CPPCPAPPVA GPSVFLFPPK
251    PKDTLMISRT PEVTCVVVDV SHEDPEVQFN WYVDGVEVHN AKTKPREEQF
301    NSTFRVVSVL TVVHQDWLNG KEYKCKVSNK GLPAPIEKTI SKTKGQPREP
351    QVYTLPPSRE EMTKNQVSLT CLVKGFYPSD LAVEWESNQO PENNYKTTPP
401    MLDSDGSFFL YSKLTVDKSR WQQGNVFSCS VMHEALHNHY TQKSLSLSPG
451    K
```

Amino acid sequence of the mature form (signal peptide removed) of Ab-15 HC without carboxy-terminal lysine:

```
                                    (SEQ ID NO: 394)
  1    EVQLVQSGAE VKKPGASVKV SCKASDFNIK DFYLHWVRQA PGQGLEWIGR
 51    IDPENGDTLY DPKFQDKVTM TTDTSTSTAY MELRSLRSDD TAVYYCAREA
101    DYFHDGTSYW YFDVWGRGTL VTVSSASTKG PSVFPLAPCS RSTSESTAAL
151    GCLVKDYFPE PVTVSWNSGA LTSGVHTFPA VLQSSGLYSL SSVVTVPSSN
201    FGTQTYTCNV DHKPSNTKVD KTVERKCCVE CPPCPAPPVA GPSVFLFPPK
251    PKDTLMISRT PEVTCVVVDV SHEDPEVQFN WYVDGVEVHN AKTKPREEQF
301    NSTFRVVSVL TVVHQDWLNG KEYKCKVSNK GLPAPIEKTI SKTKGQPREP
351    QVYTLPPSRE EMTKNQVSLT CLVKGFYPSD LAVEWESNQO PENNYKTTPP
401    MLDSDGSFFL YSKLTVDKSR WQQGNVFSCS VMHEALHNHY TQKSLSLSPG
451
```

Nucleic acid sequence encoding the mature form (signal peptide removed) of the Ab-15 HC:

(SEQ ID NO: 226)

```
   1  GAGGTGCAGC TGGTGCAGTC TGGGGCTGAG
      GTGAAGAAGC CTGGGGCCTC
  51  AGTGAAGGTC TCCTGCAAGG CTTCTGACTT
      CAACATTAAA GACTTCTATC
 101  TACACTGGGT GCGACAGGCC CCTGGACAAG
      GGCTTGAGTG GATTGGAAGG
 151  ATTGATCCTG AGAATGGTGA TACTTTATAT
      GACCCGAAGT TCCAGGACAA
 201  GGTCACCATG ACCACAGACA CGTCCACCAG
      CACAGCCTAC ATGGAGCTGA
 251  GGAGCCTGAG ATCTGACGAC ACGGCCGTGT
      ATTACTGTGC GAGAGAGGCG
 301  GATTATTTCC ACGATGGTAC CTCCTACTGG
      TACTTCGATG TCTGGGGCCG
 351  TGGCACCCTG GTCACCGTCT CTAGTGCCTC
      CACCAAGGGC CCATCGGTCT
 401  TCCCCCTGGC GCCCTGCTCC AGGAGCACCT
      CCGAGAGCAC AGCGGCCCTG
 451  GGCTGCCTGG TCAAGGACTA CTTCCCCGAA
      CCGGTGACGG TGTCGTGGAA
 501  CTCAGGCGCT CTGACCAGCG GCGTGCACAC
      CTTCCCAGCT GTCCTACAGT
 551  CCTCAGGACT CTACTCCCTC AGCAGCGTGG
      TGACCGTGCC CTCCAGCAAC
 601  TTCGGCACCC AGACCTACAC CTGCAACGTA
      GATCACAAGC CCAGCAACAC
 651  CAAGGTGGAC AAGACAGTTG AGCGCAAATG
      TTGTGTCGAG TGCCCACCGT
 701  GCCCAGCACC ACCTGTGCA GGACCGTCAG
      TCTTCCTCTT CCCCCCAAAA
 751  CCCAAGGACA CCCTCATGAT CTCCCGGACC
      CCTGAGGTCA CGTGCGTGGT
 801  GGTGGACGTG AGCCACGAAG ACCCCGAGGT
      CCAGTTCAAC TGGTACGTGG
 851  ACGGCGTGGA GGTGCATAAT GCCAAGACAA
      AGCCACGGGA GGAGCAGTTC
 901  AACAGCACGT TCCGTGTGGT CAGCGTCCTC
      ACCGTTGTGC ACCAGGACTG
 951  GCTGAACGGC AAGGAGTACA AGTGCAAGGT
      CTCCAACAAA GGCCTCCCAG
1001  CCCCCATCGA GAAAACCATC TCCAAAACCA
      AAGGGCAGCC CCGAGAACCA
1051  CAGGTGTACA CCCTGCCCCC ATCCCGGGAG
      GAGATGACCA AGAACCAGGT
1101  CAGCCTGACC TGCCTGGTCA AAGGCTTCTA
      CCCCAGCGAC ATCGCCGTGG
1151  AGTGGGAGAG CAATGGGCAG CCGGAGAACA
      ACTACAAGAC CACACCTCCC
1201  ATGCTGGACT CCGACGGCTC CTTCTTCCTC
      TACAGCAAGC TCACCGTGGA
1251  CAAGAGCAGG TGGCAGCAGG GGAACGTCTT
      CTCATGCTCC GTGATGCATG
1301  AGGCTCTGCA CAACCACTAC ACGCAGAAGA
      GCCTCTCCCT GTCTCCGGGT
1351  AAA
```

Amino acid sequence of the Ab-15 HC including signal peptide:

(SEQ ID NO: 227)

```
   1  MDWTWRILFL VAAATGAHSE VQLVQSGAEV
      KKPGASVKVS CKASDFNIKD
  51  FYLHWVRQAP GQGLEWIGRI DPENGDTLYD
      PKFQDKVTMT TDTSTSTAYM
 101  ELRSLRSDDT AVYYCAREAD YFHDGTSYWY
      FDVWGRGTLV TVSSASTKGP
 151  SVFPLAPCSR STSESTAALG CLVKDYFPEP
      VTVSWNSGAL TSGVHTFPAV
 201  LQSSGLYSLS SVVTVPSSNF GTQTYTCNVD
      HKPSNTKVDK TVERKCCVEC
 251  PPCPAPPVAG PSVFLFPPKP KDTLMISRTP
      EVTCVVVDVS HEDPEVQFNW
 301  YVDGVEVHNA KTKPREEQFN STFRVVSVLT
      VVHQDWLNGK EYKCKVSNKG
 351  LPAPIEKTIS KTKGQPREPQ VYTLPPSREE
      MTKNQVSLTC LVKGFYPSDI
 401  AVEWESNGQP ENNYKTTPPM LDSDGSFFLY
      SKLTVDKSRW QQGNVFSCSV
 451  MHEALHNHYT QKSLSLSPGK
```

Nucleic acid sequence of the Ab-15 HC including signal peptide encoding sequence:

(SEQ ID NO: 228)

```
   1  ATGGACTGGA CCTGGAGGAT CCTCTTCTTG
      GTGGCAGCAG CCACAGGAGC
  51  CCACTCCGAG GTGCAGCTGG TGCAGTCTGG
      GGCTGAGGTG AAGAAGCCTG
 101  GGGCCTCAGT GAAGGTCTCC TGCAAGGCTT
      CTGACTTCAA CATTAAAGAC
 151  TTCTATCTAC ACTGGGTGCG ACAGGCCCCT
      GGACAAGGGC TTGAGTGGAT
 201  TGGAAGGATT GATCCTGAGA ATGGTGATAC
      TTTATATGAC CCGAAGTTCC
 251  AGGACAAGGT CACCATGACC ACAGACACGT
      CCACCAGCAC AGCCTACATG
 301  GAGCTGAGGA GCCTGAGATC TGACGACACG
      GCCGTGTATT ACTGTGCGAG
 351  AGAGGCGGAT TATTTCCACG ATGGTACCTC
      CTACTGGTAC TTCGATGTCT
 401  GGGGCCGTGG CACCCTGGTC ACCGTCTCTA
      GTGCCTCCAC CAAGGGCCCA
 451  TCGGTCTTCC CCCTGGCGCC CTGCTCCAGG
      AGCACCTCCG AGAGCACAGC
```

```
-continued
 501   GGCCCTGGGC TGCCTGGTCA AGGACTACTT
       CCCCGAACCG GTGACGGTGT

551   CGTGGAACTC AGGCGCTCTG ACCAGCGGCG
       TGCACACCTT CCCAGCTGTC

601   CTACAGTCCT CAGGACTCTA CTCCCTCAGC
       AGCGTGGTGA CCGTGCCCTC

651   CAGCAACTTC GGCACCCAGA CCTACACCTG
       CAACGTAGAT CACAAGCCCA

701   GCAACACCAA GGTGGACAAG ACAGTTGAGC
       GCAAATGTTG TGTCGAGTGC

751   CCACCGTGCC CAGCACCACC TGTGGCAGGA
       CCGTCAGTCT TCCTCTTCCC

801   CCCAAAACCC AAGGACACCC TCATGATCTC
       CCGGACCCCT GAGGTCACGT

851   GCGTGGTGGT GGACGTGAGC CACGAAGACC
       CCGAGGTCCA GTTCAACTGG

901   TACGTGGACG GCGTGGAGGT GCATAATGCC
       AAGACAAAGC CACGGGAGGA

951   GCAGTTCAAC AGCACGTTCC GTGTGGTCAG
       CGTCCTCACC GTTGTGCACC

1001   AGGACTGGCT GAACGGCAAG GAGTACAAGT
       GCAAGGTCTC CAACAAAGGC
```

```
-continued
1051   CTCCCAGCCC CCATCGAGAA AACCATCTCC
       AAAACCAAAG GGCAGCCCCG

1101   AGAACCACAG GTGTACACCC TGCCCCCATC
       CCGGGAGGAG ATGACCAAGA

1151   ACCAGGTCAG CCTGACCTGC CTGGTCAAAG
       GCTTCTACCC CAGCGACATC

1201   GCCGTGGAGT GGGAGAGCAA TGGGCAGCCG
       GAGAACAACT ACAAGACCAC

1251   ACCTCCCATG CTGGACTCCG ACGGCTCCTT
       CTTCCTCTAC AGCAAGCTCA

1301   CCGTGGACAA GAGCAGGTGG CAGCAGGGGA
       ACGTCTTCTC ATGCTCCGTG

1351   ATGCATGAGG CTCTGCACAA CCACTACACG
       CAGAAGAGCC TCTCCCTGTC

1401   TCCGGGTAAA
```

The CDR sequences in the variable region of the heavy chain of Ab-15 are:

| | | |
|---|---|---|
| CDR-H1: | DFYLH | (SEQ ID NO: 290) |
| CDR-H2: | RIDPENGDTLYDPKFQD | (SEQ ID NO: 291) |
| CDR-H3: | EADYFHDGTSYWYFDV | (SEQ ID NO: 292) |

The light chain variable region CDR sequences of Ab-15 are:

| | | |
|---|---|---|
| CDR-L1: | SVSSTISSNHLH | (SEQ ID NO: 278) |
| CDR-L2: | GTSNLAS | (SEQ ID NO: 279) |
| CDR-L3: | QQWSSYPLT | (SEQ ID NO: 280) |

Ab-15 Variable Domains:

Ab-15 light chain variable domain amino acid sequence (without signal sequence):

(SEQ ID NO: 384)
```
  1 DIQMTQSPSS LSASVGDRVT ITCSVSSTIS SNHLHWFQQK PGKAPKSLIY
 51 GTSNLASGVP SRFSGSGSGT DFTLTISSLQ PEDFATYYCQ QWSSYPLTFG
101 GGTKVEIK
```

Ab-15 light chain variable domain DNA sequence (without signal sequence):

(SEQ ID NO: 385)
```
  1   GACATCCAGA TGACCCAGTC TCCATCCTCC
      CTCTCAGCAT CCGTAGGCGA
 51   TAGAGTTACA ATAACATGCA GCGTATCATC
      AACTATATCA TCAAATCATC
101   TTCATTGGTT CCAACAGAAA CCCGGCAAAG
      CACCTAAATC ACTTATATAC
151   GGCACATCAA ATCTCGCATC AGGCGTTCCT
      TCAAGATTTT CAGGCTCTGG
201   CTCAGGCACC GACTTTACTC TTACAATATC
      CTCCCTCCAA CCCGAAGACT
251   TCGCAACCTA TTACTGTCAA CAATGGTCCT
      CATATCCACT CACATTTGGC
301   GGCGGCACAA AAGTAGAAAT TAAA
```

Ab-15 heavy chain variable domain amino acid sequence (without signal sequence):

(SEQ ID NO: 386)
```
  1 EVQLVQSGAE VKKPGASVKV SCKASDFNIK DFYLHWVRQA PGQGLEWIGR
 51 IDPENGDTLY DPKFQDKVTM TTDTSTSTAY MELRSLRSDD TAVYYCAREA
101 DYFHDGTSYW YFDVWGRGTL VTVSS
```

Ab-15 heavy chain variable domain DNA sequence (without signal sequence):

```
                                      (SEQ ID NO: 387)
  1    GAGGTGCAGC TGGTGCAGTC TGGGGCTGAG
       GTGAAGAAGC TGGGGCCTC

51    AGTGAAGGTC TCCTGCAAGG CTTCTGACTT
       CAACATTAAA GACTTCTATC

101    TACACTGGGT GCGACAGGCC CCTGGACAAG
       GGCTTGAGTG GATTGGAAGG

151    ATTGATCCTG AGAATGGTGA TACTTTATAT
       GACCCGAAGT TCCAGGACAA

201    GGTCACCATG ACCACAGACA CGTCCACCAG
       CACAGCCTAC ATGGAGCTGA

251    GGAGCCTGAG ATCTGACGAC ACGGCCGTGT
       ATTACTGTGC GAGAGAGGCG

301    GATTATTTCC ACGATGGTAC CTCCTACTGG
       TACTTCGATG TCTGGGGCCA

351    TGGCACCCTG GTCACCGTCT CTAGT
```

Ab-11 was humanized to generate Ab-16.

Ab-16

The sequences of the Antibody 16 (also referred to herein as Ab-16) LC and HC are as follows:

Ab-16 Light Chain:

Amino acid sequence of the mature form (signal peptide removed) of the Ab-16 LC:

```
                                     (SEQ ID NO: 229)
  1 DIQLTQSPSF LSASVGDRVT ITCRASSSIS YIHWYQQKPG KAPKLLIYAT
 51 SNLASGVPSR FSGSGSGTEF TLTISSLQPE DFATYYCQQW SSDPLTFGGG
101 TKVEIKRTVA APSVFIFPPS DEQLKSGTAS VVCLLNNFYP REAKVQWKVD
151 NALQSGNSQE SVTEQDSKDS TYSLSSTLTL SKADYEKHKV YACEVTHQGL
201 SSPVTKSFNR GEC
```

Nucleic acid sequence encoding the mature form (signal peptide removed) of the Ab-16 LC:

```
                                      (SEQ ID NO: 230)
  1    GACATCCAGT TGACCCAGTC TCCATCCTTC
       CTGTCTGCAT CTGTAGGAGA

51    CAGAGTCACC ATCACTTGCA GGGCCAGCTC
       AAGTATAAGT TACATACACT

101    GGTATCAGCA AAAACCAGGG AAAGCCCCTA
       AGCTCCTGAT CTATGCCACA

151    TCCAACCTGG CTTCTGGGGT CCCATCAAGG
       TTCAGCGGCA GTGGATCTGG

201    GACAGAATTC ACTCTCACAA TCAGCAGCCT
       GCAGCCTGAA GATTTTGCAA

251    CTTATTACTG TCAGCAGTGG AGTAGTGACC
       CACTCACGTT CGGCGGAGGG

301    ACCAAGGTGG AGATCAAACG TACGGTGGCT
       GCACCATCTG TCTTCATCTT

351    CCCGCCATCT GATGAGCAGT TGAAATCTGG
       AACTGCCTCT GTTGTGTGCC
```

```
401    TGCTGAATAA CTTCTATCCC AGAGAGGCCA
       AAGTACAGTG GAAGGTGGAT

451    AACGCCCTCC AATCGGGTAA CTCCCAGGAG
       AGTGTCACAG AGCAGGACAG

501    CAAGGACAGC ACCTACAGCC TCAGCAGCAC
       CCTGACGCTG AGCAAAGCAG

551    ACTACGAAA ACACAAAGTC TACGCCTGCG
       AAGTCACCCA TCAGGGCCTG

601    AGCTCGCCCG TCACAAAGAG CTTCAACAGG
       GGAGAGTGT
```

Amino acid sequence of the Ab-16 LC including signal peptide:

```
                                     (SEQ ID NO: 231)
  1    MDMRVPAQLL GLLLLWLPGA RCDIQLTQSP
       SFLSASVGDR VTITCRASSS

51    ISYIHWYQQK PGKAPKLLIY ATSNLASGVP
       SRFSGSGSGT EFTLTISSLQ

101    PEDFATYYCQ QWSSDPLTFG GGTKVEIKRT
       VAAPSVFIFP PSDEQLKSGT

151    ASVVCLLNNF YPREAKVQWK VDNALQSGNS
       QESVTEQDSK DSTYSLSSTL

201    TLSKADYEKH KVYACEVTHQ GLSSPVTKSF
       NRGEC
```

Nucleic acid sequence of the Ab-16 LC including signal peptide encoding sequence:

```
                                      (SEQ ID NO: 232)
  1    ATGGACATGA GGGTCCCCGC TCAGCTCCTG
       GGGCTCCTGC TGCTCTGGCT

51    CCCAGGTGCC AGATGTGACA TCCAGTTGAC
       CCAGTCTCCA TCCTTCCTGT

101    CTGCATCTGT AGGAGACAGA GTCACCATCA
       CTTGCAGGGC CAGCTCAAGT

151    ATAAGTTACA TACACTGGTA TCAGCAAAAA
       CCAGGGAAAG CCCCTAAGCT

201    CCTGATCTAT GCCACATCCA ACCTGGCTTC
       TGGGGTCCCA TCAAGGTTCA

251    GCGGCAGTGG ATCTGGGACA GAATTCACTC
       TCACAATCAG CAGCCTGCAG

301    CCTGAAGATT TTGCAACTTA TTACTGTCAG
       CAGTGGAGTA GTGACCCACT

351    CACGTTCGGC GGAGGGACCA AGGTGGAGAT
       CAAACGTACG GTGGCTGCAC
```

```
                    -continued
401    CATCTGTCTT CATCTTCCCG CCATCTGATG
       AGCAGTTGAA ATCTGGAACT

451    GCCTCTGTTG TGTGCCTGCT GAATAACTTC
       TATCCCAGAG AGGCCAAAGT

501    ACAGTGGAAG GTGGATAACG CCCTCCAATC
       GGGTAACTCC CAGGAGAGTG

551    TCACAGAGCA GGACAGCAAG GACAGCACCT
       ACAGCCTCAG CAGCACCCTG

601    ACGCTGAGCA AAGCAGACTA CGAGAAACAC
       AAAGTCTACG CCTGCGAAGT

651    CACCCATCAG GGCCTGAGCT CGCCCGTCAC
       AAAGAGCTTC AACAGGGGAG

701    AGTGT
```

Ab-16 Heavy Chain:

Amino acid sequence of the mature form (signal peptide removed) of the Ab-16 HC:

```
  1  EVQLVQSGAE VKKPGASVKV SCKASGFDIK DYYIHWVRQA PGQGLEWIGR
 51  VDPDNGETEF APKFPGKVTM TTDTSISTAY MELSRLRSDD TAVYYCARED
101  YDGTYTWFPY WGOGTLVTVS SASTKGPSVF PLAPCSRSTS ESTAALGCLV
151  KDYFPEPVTV SWNSGALTSG VHTFPAVLQS SGLYSLSSVV TVPSSNFGTQ
201  TYTCNVDHKP SNTKVDKTVE RKCCVECPPC PAPPVAGPSV FLFPPKPKDT
251  LMISRTPEVT CVVVDVSHED PEVQFNWYVD GVEVHNAKTK PREEQFNSTF
301  RVVSVLTVVH QDWLNGKEYK CKVSNKGLPA PIEKTISKTK GQPREPQVYT
351  LPPSREEMTK NQVSLTCLVK GFYPSDIAVE WESNGQPENN YKTTPPMLDS
401  DGSFFLYSKL TVDKSRWQQG NVFSCSVMHE ALHNHYTQKS LSLSPGK
```

(SEQ ID NO: 233)

Amino acid sequence of the mature form (signal peptide removed) of the Ab-16 HC without carboxy-terminal lysine:

```
  1  EVQLVQSGAE VKKPGASVKV SCKASGFDIK DYYIHWVRQA PGQGLEWIGR
 51  VDPDNGETEF APKFPGKVTM TTDTSISTAY MELSRLRSDD TAVYYCARED
101  YDGTYTWFPY WGOGTLVTVS SASTKGPSVF PLAPCSRSTS ESTAALGCLV
151  KDYFPEPVTV SWNSGALTSG VHTFPAVLQS SGLYSLSSVV TVPSSNFGTQ
201  TYTCNVDHKP SNTKVDKTVE RKCCVECPPC PAPPVAGPSV FLFPPKPKDT
251  LMISRTPEVT CVVVDVSHED PEVQFNWYVD GVEVHNAKTK PREEQFNSTF
301  RVVSVLTVVH QDWLNGKEYK CKVSNKGLPA PIEKTISKTK GQPREPQVYT
351  LPPSREEMTK NQVSLTCLVK GFYPSDIAVE WESNGQPENN YKTTPPMLDS
401  DGSFFLYSKL TVDKSRWQQG NVFSCSVMHE ALHNHYTQKS LSLSPG
```

(SEQ ID NO: 395)

Nucleic acid sequence encoding the mature form (signal peptide removed) of the Ab-16 HC:

```
                                          (SEQ ID NO: 234)
  1    GAGGTGCAGC TGGTGCAGTC TGGGGCTGAG
       GTGAAGAAGC CTGGGGCCTC

51    AGTGAAGGTC TCCTGCAAGG CTTCTGGATT
       CGACATTAAG GACTACTATA

101    TACACTGGGT GCGACAGGCC CCTGGACAAG
       GGCTTGAGTG GATCGGAAGG

151    GTTGATCCTG ACAATGGTGA GACTGAATTT
       GCCCCGAAGT TCCCGGGCAA

201    GGTCACCATG ACCACAGACA CGTCCATCAG
       CACAGCCTAC ATGGAGCTGA

251    GCAGGCTGAG ATCTGACGAC ACGGCCGTGT
       ATTACTGTGC GAGAGAAGAC

301    TACGATGGTA CCTACACCTG GTTTCCTTAT
       TGGGGCCAAG GGACTCTGGT

351    CACCGTCTCT AGTGCCTCCA CCAAGGGCCC
       ATCGGTCTTC CCCCTGGCGC

401    CCTGCTCCAG GAGCACCTCC GAGAGCACAG
       CGGCCCTGGG CTGCCTGGTC

451    AAGGACTACT TCCCCGAACC GGTGACGGTG
       TCGTGGAACT CAGGCGCTCT

501    GACCAGCGGC GTGCACACCT TCCCAGCTGT
       CCTACAGTCC TCAGGACTCT

551    ACTCCCTCAG CAGCGTGGTG ACCGTGCCCT
       CCAGCAACTT CGGCACCCAG

601    ACCTACACCT GCAACGTAGA TCACAAGCCC
       AGCAACACCA AGGTGGACAA

651    GACAGTTGAG CGCAAATGTT GTGTCGAGTG
       CCCACCGTGC CCAGCACCAC

701    CTGTGGCAGG ACCGTCAGTC TTCCTCTTCC
       CCCCAAAACC CAAGGACACC

751    CTCATGATCT CCCGGACCCC TGAGGTCACG
       TGCGTGGTGG TGGACGTGAG

801    CCACGAAGAC CCCGAGGTCC AGTTCAACTG
       GTACGTGGAC GGCGTGGAGG

851    TGCATAATGC CAAGACAAAG CCACGGGAGG
       AGCAGTTCAA CAGCACGTTC
```

```
      -continued
 901  CGTGTGGTCA GCGTCCTCAC CGTTGTGCAC
      CAGGACTGGC TGAACGGCAA

951  GGAGTACAAG TGCAAGGTCT CCAACAAAGG
      CCTCCCAGCC CCCATCGAGA

1001  AAACCATCTC CAAAACCAAA GGGCAGCCCC
      GAGAACCACA GGTGTACACC

1051  CTGCCCCCAT CCCGGGAGGA GATGACCAAG
      AACCAGGTCA GCCTGACCTG

1101  CCTGGTCAAA GGCTTCTACC CCAGCGACAT
      CGCCGTGGAG TGGGAGAGCA

1151  ATGGGCAGCC GGAGAACAAC TACAAGACCA
      CACCTCCCAT GCTGGACTCC

1201  GACGGCTCCT TCTTCCTCTA CAGCAAGCTC
      ACCGTGGACA AGAGCAGGTG

1251  GCAGCAGGGG AACGTCTTCT CATGCTCCGT
      GATGCATGAG GCTCTGCACA

1301  ACCACTACAC GCAGAAGAGC CTCTCCCTGT
      CTCCGGGTAA A
```

Amino acid sequence of the Ab-16 HC including signal peptide:

```
                                        (SEQ ID NO: 235)
  1   MDWTWRILFL VAAATGAHSE VQLVQSGAEV
      KKPGASVKVS CKASGFDIKD

51   YYIHWVRQAP GQGLEWIGRV DPDNGETEFA
      PKFPGKVTMT TDTSISTAYM

101   ELSRLRSDDT AVYYCAREDY DGTYTWFPYW
      GQGTLVTVSS ASTKGPSVFP

151   LAPCSRSTSE STAALGCLVK DYFPEPVTVS
      WNSGALTSGV HTFPAVLQSS

201   GLYSLSSVVT VPSSNFGTQT YTCNVDHKPS
      NTKVDKTVER KCCVECPPCP

251   APPVAGPSVF LFPPKPKDTL MISRTPEVTC
      VVVDVSHEDP EVQFNWYVDG

301   VEVHNAKTKP REEQFNSTFR VVSVLTVVHQ
      DWLNGKEYKC KVSNKGLPAP

351   IEKTISKTKG QPREPQVYTL PPSREEMTKN
      QVSLTCLVKG FYPSDIAVEW

401   ESNGQPENNY KTTPPMLDSD GSFFLYSKLT
      VDKSRWQQGN VFSCSVMHEA

451   LHNHYTQKSL SLSPGK
```

Nucleic acid sequence of the Ab-16 HC including signal peptide encoding sequence:

```
                                        (SEQ ID NO: 236)
  1   ATGGACTGGA CCTGGAGGAT CCTCTTCTTG
      GTGGCAGCAG CCACAGGAGC

51   CCACTCCGAG GTGCAGCTGG TGCAGTCTGG
      GGCTGAGGTG AAGAAGCCTG

101   GGGCCTCAGT GAAGGTCTCC TGCAAGGCTT
      CTGGATTCGA CATTAAGGAC

151   TACTATATAC ACTGGGTGCG ACAGGCCCCT
      GGACAAGGGC TTGAGTGGAT

201  CGGAAGGGTT GATCCTGACA ATGGTGAGAC
      TGAATTTGCC CCGAAGTTCC

251  CGGGCAAGGT CACCATGACC ACAGACACGT
      CCATCAGCAC AGCCTACATG

301  GAGCTGAGCA GGCTGAGATC TGACGACACG
      GCCGTGTATT ACTGTGCGAG

351  AGAAGACTAC GATGGTACCT ACACCTGGTT
      TCCTTATTGG GGCCAAGGGA

401  CTCTGGTCAC CGTCTCTAGT GCCTCCACCA
      AGGGCCCATC GGTCTTCCCC

451  CTGGCGCCCT GCTCCAGGAG CACCTCCGAG
      AGCACAGCGG CCCTGGGCTG

501  CCTGGTCAAG GACTACTTCC CCGAACCGGT
      GACGGTGTCG TGGAACTCAG

551  GCGCTCTGAC CAGCGGCGTG CACACCTTCC
      CAGCTGTCCT ACAGTCCTCA

601  GGACTCTACT CCCTCAGCAG CGTGGTGACC
      GTGCCCTCCA GCAACTTCGG

651  CACCCAGACC TACACCTGCA ACGTAGATCA
      CAAGCCCAGC AACACCAAGG

701  TGGACAAGAC AGTTGAGCGC AAATGTTGTG
      TCGAGTGCCC ACCGTGCCCA

751  GCACCACCTG TGGCAGGACC GTCAGTCTTC
      CTCTTCCCCC CAAAACCCAA

801  GGACACCCTC ATGATCTCCC GGACCCCTGA
      GGTCACGTGC GTGGTGGTGG

851  ACGTGAGCCA CGAAGACCCC GAGGTCCAGT
      TCAACTGGTA CGTGGACGGC

901  GTGGAGGTGC ATAATGCCAA GACAAAGCCA
      CGGGAGGAGC AGTTCAACAG

951  CACGTTCCGT GTGGTCAGCG TCCTCACCGT
      TGTGCACCAG GACTGGCTGA

1001  ACGGCAAGGA GTACAAGTGC AAGGTCTCCA
      ACAAAGGCCT CCCAGCCCCC

1051  ATCGAGAAAA CCATCTCCAA AACCAAGGG
      CAGCCCCGAG AACCACAGGT

1101  GTACACCCTG CCCCCATCCC GGGAGGAGAT
      GACCAAGAAC CAGGTCAGCC

1151  TGACCTGCCT GGTCAAAGGC TTCTACCCCA
      GCGACATCGC CGTGGAGTGG

1201  GAGAGCAATG GGCAGCCGGA GAACAACTAC
      AAGACCACAC CTCCCATGCT

1251  GGACTCCGAC GGCTCCTTCT TCCTCTACAG
      CAAGCTCACC GTGGACAAGA

1301  GCAGGTGGCA GCAGGGGAAC GTCTTCTCAT
      GCTCCGTGAT GCATGAGGCT

1351  CTGCACAACC ACTACACGCA GAAGAGCCTC
      TCCCTGTCTC CGGGTAAA
```

The CDR sequences in the variable region of the heavy chain of Ab-16 are:

| | | |
|---|---|---|
| CDR-H1: | DYYIH | (SEQ ID NO: 293) |
| CDR-H2: | RVDPDNGETEFAPKFPG | (SEQ ID NO: 294) |
| CDR-H3: | EDYDGTYTWFPY | (SEQ ID NO: 295) |

The light chain variable region CDR sequences of Ab-16 are:

```
CDR-L1:     RASSSISYIH      (SEQ ID NO: 281)
CDR-L2:     ATSNLAS         (SEQ ID NO: 282)
CDR-L3:     QQWSSDPLT       (SEQ ID NO: 283)
```

Ab-16 Variable Domains:

Ab-16 light chain variable domain amino acid sequence (without signal sequence):

(SEQ ID NO: 388)

```
  1 DIQLTQSPSF LSASVGDRVT ITCRASSSIS YIHWYQQKPG KAPKLLIYAT
 51 SNLASGVPSR FSGSGSGTEF TLTISSLQPE DFATYYCQQW SSDPLTFGGG
101 TKVEIK
```

Ab-16 light chain variable domain DNA sequence (without signal sequence):

(SEQ ID NO: 389)

```
  1  GACATCCAGT TGACCCAGTC TCCATCCTTC
     CTGTCTGCAT CTGTAGGAGA
 51  CAGAGTCACC ATCACTTGCA GGGCCAGCTC
     AAGTATAAGT TACATACACT
101  GGTATCAGCA AAAACCAGGG AAAGCCCCTA
     AGCTCCTGAT CTATGCCACA
151  TCCAACCTGG CTTCTGGGGT CCCATCAAGG
     TTCAGCGGCA GTGGATCTGG
201  GACAGAATTC ACTCTCACAA TCAGCAGCCT
     GCAGCCTGAA GATTTTGCAA
251  CTTATTACTG TCAGCAGTGG AGTAGTGACC
     CACTCACGTT CGGCGGAGGG
301  ACCAAGGTGG AGATCAAA
```

Ab-16 heavy chain variable domain amino acid sequence (without signal sequence):

(SEQ ID NO: 390)

```
  1 EVQLVQSGAE VKKPGASVKV SCKASGFDIK DYYIHWVRQA PGQGLEWIGR
 51 VDPDNGETEF APKFPGKVTM TTDTSISTAY MELSRLRSDD TAVYYCARED
101 YDGTYTWFPY WGQGTLVTVS S
```

Ab-16 heavy chain variable domain DNA sequence (without signal sequence):

(SEQ ID NO: 391)

```
  1  GAGGTGCAGC TGGTGCAGTC TGGGGCTGAG
     GTGAAGAAGC CTGGGGCCTC
 51  AGTGAAGGTC TCCTGCAAGG CTTCTGGATT
     CGACATTAAG GACTACTATA
101  TACACTGGGT GCGACAGGCC CCTGGACAAG
     GGCTTGAGTG GATCGGAAGG
151  GTTGATCCTG ACAATGGTGA GACTGAATTT
     GCCCCGAAGT TCCCGGGCAA
201  GGTCACCATG ACCACAGACA CGTCCATCAG
     CACAGCCTAC ATGGAGCTGA
251  GCAGGCTGAG ATCTGACGAC ACGGCCGTGT
     ATTACTGTGC GAGAGAAGAC
301  TACGATGGTA CCTACACCTG GTTTCCTTAT
     TGGGGCCAAG GGACTCTGGT
351  CACCGTCTCT AGT
```

Additional antibodies are referred to herein as Antibodies 17-22 (also referred to herein as Ab-17, Ab-18, Ab-19, Ab-20, Ab-21, and Ab-22). The Kappa Constant region for all VK regions of Ab-17, Ab-19, and Ab-21 is as follows:

TDAAPTVSIFPPSSEQLTSGGASVVCFLNNFYP     (SEQ ID NO: 323)

KDINVKWKIDSERQNGVLNSWTDQDSKDSTY

SMSSTLTLTKDEYERHNSYTCEATHKTSTSPIVK

SFNRNEC

The Heavy Constant Region for all VH regions of antibodies 17, 19 and 21 is as follows:

AKTTPPSVYPLAPGSAAQTNSMVTLGCLVKGYF     (SEQ ID NO: 324)

PEPVTVTWNSGSLSSGVHTFPAVLQSDLYTLSS

SVTVPSSTWPSETVTCNVAHPASSTKVDKKIVP

RDCGCKPCICTVPEVSSVFIFPPKPKDVLTITLT

PKVTCVVVDISKDDPEVQFSWFVDDVEVHTAQT

QPREEQFNSTFRSVSELPIMHQDWLNGKEFKCR

VNSAAFPAPIEKTISKTKGRPKAPQVYTIPPPKE

QMAKDKVSLTCMITDFFPEDITVEWQWNGQPAE

NYKNTQPIMDTDGSYFVYSKLNVQKSNWEAGNT

FTCSVLHEGLHNHHTEKSLSHSPGK

In the following antibody amino acid sequences, the boxed-shaded amino acids represent complement-determining regions (CDRs) and the underlined amino acids represent signal peptide.

Ab-17

Amino acid sequence of the Ab-17 LC including signal peptide:

(SEQ ID NO: 299)

MDFQVQIFSFMLISVTVILSSGEIVLTQSPALMAASPGEKVTITCSVSSISSSNLHWSQQK
SGTSPKLWIYGTSNLASGVPVRFSGSGSGTSYSLTISSMEAEDAATYYCQQWTTTYTFGS
GTKLELKR

Nucleic acid sequence of the Ab-17 LC including signal peptide:

ATGGATTTTCAGGTGCAGATTTTCAGCTTCATG (SEQ ID NO: 300)

CTAATCAGTGTCACAGTCATATTGTCCAGTGGA

GAAATTGTGCTCACCCAGTCTCCAGCACTCATG

GCTGCATCTCCAGGGGAGAAGGTCACCATCACC

TGCAGTGTCAGCTCGAGTATAAGTTCCAGCAAC

TTACACTGGTCCCAGCAGAAGTCAGGAACCTCC

CCCAAACTCTGGATTTATGGCACATCCAACCTTG

CTTCTGGAGTCCCTGTTCGCTTCAGTGGCAGTGG

ATCTGGGACCTCTTATTCTCTCACAATCAGCAGC

ATGGAGGCTGAAGATGCTGCCACTTATTACTGTC

AACAGTGGACTACTACGTATACGTTCGGATCGGG

GACCAAGCTGGAGCTGAAACGT

Amino acid sequence of the Ab-17 HC including signal peptide:

MGWNWIIFFLMAVVTGVNSEVQLRQSGADLVKPGASVKLSCTASGFNIKDYYIHWVKQ
RPEQGLEWIGRIDPDNGESTYVPKFQGKATITADTSSNTAYLQLRSLTSEDTAIYYCGRE
GLDYGDYYAVDYWGQGTSVTVSS

Nucleic acid sequence of the Ab-17 HC including signal peptide:

ATGGGATGGAACTGGATCATCTTCTTCCTGATG (SEQ ID NO: 302)

GCAGTGGTTACAGGGGTCAATTCAGAGGTGCAG

TTGCGGCAGTCTGGGGCAGACCTTGTGAAGCCA

GGGGCCTCAGTCAAGTTGTCCTGCACAGCTTCT

-continued

GGCTTCAACATTAAAGACTACTATATACACTGGG

TGAAGCAGAGGCCTGAACAGGGCCTGGAGTGGA

TTGGAAGGATTGATCCTGATAATGGTGAAAGTAC

ATATGTCCCGAAGTTCCAGGGCAAGGCCACTAT

AACAGCAGACACATCATCCAACACAGCCTACCT

ACAACTCAGAAGCCTGACATCTGAGGACACTGC

CATCTATTATTGTGGGAGAGAGGGGCTCGACTAT

GGTGACTACTATGCTGTGGACTACTGGGGTCAAG

GAACCTCGGTCACAGTCTCGAGC

Ab-17 was humanized to generate Ab-18.

Ab-18

Amino acid sequence of the Ab-18 LC including signal peptide:

(SEQ ID NO: 301)

(SEQ ID NO: 303)

MDMRVPAQLLGLLLLWLPGARCDIQLTQSPSFLSASVGDRVTITCSVSSISSSNLHWYQ
QKPGKAPKLLIYGTSNLASGVPSRFSGSGSGTEFTLTISSLQPEDFATYYCQQWTTTYTFG
QGTKLEIKR

Nucleic acid sequence of the Ab-18 LC including signal peptide:

ATGGATATGCGCGTGCCGGCGCAGCTGCTGGGC (SEQ ID NO: 304)
CTGCTGCTGCTGTGGCTGCCGGGCGCGCGCTGC
GATATTCAGCTGACCCAGAGCCCGAGCTTTCTG
AGCGCGAGCGTGGGCGATCGCGTGACCATTACC
TGCAGCGTGAGCAGCAGCATTAGCAGCAGCAAC
CTGCATTGGTATCAGCAGAAACCGGGCAAAGCG

-continued

CCGAAACTGCTGATTTATGGCACCAGCAACCTG
GCGAGCGGCGTGCCGAGCCGCTTTAGCGGCAGC
GGCAGCGGCACCGAATTTACCCTGACCATTAGC
AGCCTGCAGCCGGAAGATTTTGCGACCTATTATT
GCCAGCAGTGGACCACCACCTATACCTTTGGCC
AGGGCACCAAACTGGAAATTAAACGT

Amino acid sequence of the Ab-18 HC including signal peptide:

(SEQ ID NO: 305)
MDWTWSILFLVAAPTGAHSEVQLVQSGAEVKKPGASVKVSCKASGFNIKDYYIHWVR
QAPGQGLEWMGRIDPDNGESTYVPKFQGRVTMTTDTSTSTAYMELRSLRSDDTAVYYC
AREGLDYGDYYAVDYWGQGTLVTVSS

Nucleic acid sequence of the Ab-18 HC including signal peptide:

ATGGATTGGACCTGGAGCATTCTGTTTCTGGTG (SEQ ID NO: 306)
GCGGCGCCGACCGGCGCGCATAGCGAAGTGCAG
CTGGTGCAGAGCGGCGCGGAAGTGAAAAAACCGG
GCGCGAGCGTGAAAGTGAGCTGCAAAGCGAGCG
GCTTTAACATTAAAGATTATTATATTCATTGGGT
GCGCCAGGCGCCGGGCCAGGGCCTGGAATGGAT
GGGCCGCATTGATCCGGATAACGGCGAAAGCAC
CTATGTGCCGAAATTTCAGGGCCGCGTGACCATG
ACCACCGATACCAGCACCAGCACCGCGTATATGG
AACTGCGCAGCCTGCGCAGCGATGATACCGCGGT
GTATTATTGCGCGCGCGAAGGCCTGGATTATGG
CGATTATTATGCGGTGGATTATTGGGGCCAGGGC
ACCCTGGTGACCGTCTCGAGC

Ab-18 light chain variable domain amino acid sequence (without signal sequence):

(SEQ ID NO: 368)
DIQLTQSPSFLSASVGDRVTITCSVSSSISSSNLHWYGGKPGKAPKLLIYGTSNLASGVPS
RFSGSGSGTEFTLTISSLQPEDFATYYCQQWTTTYTFGQGTKLEIKR

Ab-18 light chain variable domain DNA sequence (without signal sequence):

GATATTCAGCTGACCCAGAGCCCGAGCTTTCTG  (SEQ ID NO: 369)
AGCGCGAGCGTGGGCGATCGCGTGACCATTACC
TGCAGCGTGAGAGCAGCATTAGCAGCAGCAACC
TGCATTGGTATCAGCAGAAACCGGGCAAAGCGCC
GAAACTGCTGATTTATGGCACCAGCAACCTGGCG

-continued
AGCGGCGTGCCGAGCCGCTTTAGCGGCAGCGGC
AGCGGCACCGAATTTACCCTGACCATTAGCAGCC
TGCAGCCGGAAGATTTTGCGACCTATTATTGCCA
GCAGTGGACCACCACCTATACCTTTGGCCAGGGC
ACCAAACTGGAAATTAAACGT Ab-18 heavy chain variable domain amino acid sequence (without signal sequence):

(SEQ ID NO: 370)
EVQLVQSGAEVKKPGASVKVSCKASGFNIKDYYIHWVRQAPGQGLEWNGRIDPDNGE
STYVPKFQGRVTMTTDTSTSTAYMELRSLRSDDTAVYYCAREGLDYGDYYAVDYWGQ
GTLVTVSS

Ab-18 heavy chain variable domain DNA sequence (without signal sequence):

GAAGTGCAGCTGGTGCAGAGCGGCGCGGAAGTG  (SEQ ID NO: 371)
AAAAAACCGGGCGCGAGCGTGAAAGTGAGCTGCA
AAGCGAGCGGCTTTAACATTAAAGATTATTATAT
TCATTGGGTGCGCCAGGCGCCGGGCCAGGGCCT
GGAATGGATGGGCCGCATTGATCCGGATAACGG
CGAAAGCACCTATGTGCCGAAATTTCAGGGCCG
CGTGACCATGACCACCGATACCAGCACCAGCAC
CGCGTATATGGAACTGCGCAGCCTGCGCAGCGAT
GATACCGCGGTGTATTATTGCGCGCGCGAAGGCC
TGGATTATGGCGATTATTATGCGGTGGATTATTG
GGGCCAGGGCACCCTGGTGACCGTCTCGAGC

Ab-19

Amino acid sequence of the Ab-19 LC including signal peptide:

(SEQ ID NO: 307)
MMSSAQFLGLLLLCFQGTRCDIQMTQTTSSLSASLGDRVNISCRASQDISSYLNWYQQK
PDGTVKLLIYSTSRLHSGVPSRFSGSGSGTDYSLTISNLAQEDIATYFCQQDIKHPTFGGG
TKLELKR

Nucleic acid sequence of the Ab-19 LC including signal peptide:

ATGATGTCCTCTGCTCAGTTCCTTGGTCTCCTG (SEQ ID NO: 308)
TTGCTCTGTTTTCAAGGTACCAGATGTGATATCC
AGATGACACAGACTACATCCTCCCTGTCTGCCT
CTCTGGGAGACAGAGTCAACATCAGCTGCAGGG
CAAGTCAGGACATTAGCAGTTATTTAAACTGGTA
TCAGCAGAAACCAGATGGAACTGTTAAACTCCT

-continued
GATCTACTCCACATCAAGATTAAACTCAGGAGT
CCCATCAAGTTCAGTGGCAGTGGGTCTGGGACA
GATTATTCTCTCACTATTAGCAACCTGGCACAAG
AAGATATTGCCACTTACTTTTGCCAACAGGATAT
TAAGCATCCGACGTTCGGTGGAGGCACCAAGTT
GGAGCTGAAACGT Amino acid sequence of the Ab-19 HC including signal peptide:

(SEQ ID NO: 309)

MEWIWIFLFLLSGTAGVHSEVQLQQSGPELVKPGASVKMSCKASGFTFTDYIMHWVKQ
KPGQGLEWIGVINPYNDDTEYNEKFKGKATLTSDKSSSTAYMDLSSTSEGSAVYYCAR
SIYYDAPFAYWGQGTLVTVSS

Nucleic acid sequence of the Ab-19 HC including signal peptide:

ATGGAATGGATCTGGATATTTCTCTTCCTCCTG (SEQ ID NO: 310)
TCAGGAACTGCAGGTGTCCACTCTGAGGTCCAG
CTGCAGCAGTCTGGACCTGAGCTGGTAAAGCCT
GGGGCTTCAGTGAAGATGTCCTGCAAGGCTTCTG
GGTTCACATTCACTGACTACATTATGCACTGGGT
GAAGCAGAAGCCTGGGCAGGGCCTTGAGTGGATT
GGATATATTAATCCTTACAATGATGATACTGAAT
ACAATGAGAAGTTCAAAGGCAAGGCCACACTGAC
TTCAGACAAATCCTCCAGCACAGCCTACATGGAT
CTCAGCAGTCTGACCTCTGAGGGCTCTGCGGTCT
ATTACTGTGCAAGATCGATTTATTACTACGATGC
CCCGTTTGCTTACTGGGGCCAAGGGACTCTGGTC
ACAGTCTCGAGC

Ab-19 was humanized to generate Antibody 20 (also referred to herein as Ab-20) and Antibody 23 (also referred to herein as Ab-23).

Ab-20

IgG4 Version

Amino acid sequence of the Ab-20 LC including signal peptide:

(SEQ ID NO: 311)

MMSSAQFLGLLLLCFQGTRCDIQMTQSPSSLSASVGDRVTITCRASQDISSYLNWYQQK
PGKAPKLLIYSTSRLNSGVPSRFSGSGSGTDFTLTISSLQPEDFATYYCQQDIKHPTFGQG
TKVEIKR

Nucleic acid sequence of the Ab-20 LC including signal peptide:

ATGATGTCCTCTGCTCAGTTCCTTGGTCTCCTG    (SEQ ID NO: 312)
TTGCTCTGTTTTCAAGGTACCAGATGTGATATCC
AGATGACCCAGTCTCCATCCTCCCTGTCTGCATC
TGTAGGTGACCGTGTCACCATCACTTGCCGCGC
AAGTCAGGATATTAGCAGCTATTTAAATTGGTAT
CAGCAGAAACCAGGGAAAGCCCCTAAGCTCCTG

-continued
ATCTATTCTACTTCCCGTTTGAATAGTGGGGTCC
CATCACGCTTCAGTGGCAGTGGCTCTGGGACAGA
TTTCACTCTCACCATCAGCAGTCTGCAACCTGAA
GATTTTGCAACTTACTACTGTCAACAGGATATTA
AACACCCTACGTTCGGTCAAGGCACCAAGGTGG
AGATCAAACGT Amino acid sequence of the Ab-20 HC including signal peptide:

(SEQ ID NO: 313)
MEWIWIFLFLLSGTAGVHSEVQLVQSGAEVKKPGSSVKVSCKASGFTFTDYIMHWVRQ
APGQGLEWMGYINPYNDDTEYNEKFKGRVTITADKSTSTAYMELSSLRSEDTAVYYCA
RSIYYYDAPPAYWGQGTLVTVSS

Nucleic acid sequence of the Ab-20 HC including signal peptide:

ATGGAATGGATCTGGATATTTCTCTTCCTCCTG    (SEQ ID NO: 349)
TCAGGAACTGCAGGTGTCCACTCTGAGGTGCAG
CTGGTGCAGTCTGGGGCTGAGGTGAAGAAGCCT
GGGTCCTCGGTGAAGGTCTCCTGCAAGGCTTCTG
GTTTTACCTTCACCGACTATATTATGCACTGGGT
GCGTCAGGCCCCTGGTCAAGGGCTTGAGTGGATG
GGCTATATCAACCCTTATAATGATGACACCGAAT
ACAACGAGAAGTTCAAGGGCCGTGTCACGATTAC
CGCGGACAAATCCACGAGCACAGCCTACATGGA
GCTGAGCAGCCTGCGCTCTGAGGACACGGCCGT
GTATTACTGTGCGCGTTCGATTTATTACTACGAT
GCCCCGTTTGCTTACTGGGGCCAAGGGACTCTG
GTCACAGTCTCGAGC

Ab-23

IgG2 Version

Light Chain:

Amino acid sequence of the mature form (signal peptide removed) of the Ab-23 LC:

(SEQ ID NO: 341)
```
  1 DIQMTQSPSS LSASVGDRVT ITCRASQDIS SYLNWYQQKP GKAPKLLIYS
 51 TSRLHSGVPS RFSGSGSGTD FTLTISSLQP EDFATYYCQQ DIKHPTFGQG
101 TKVEIKRTVA APSVFIFPPS DEQLKSGTAS VVCLLNNFYP REAKVQWKVD
151 NALQSGNSQE SVTEQDSKDS TYSLSSTLTL SKADYEKHKV YACEVTHQGL
201 SSPVTKSFNR GEC
```

Nucleic acid sequence encoding the mature form (signal peptide removed) of the Ab-23 LC:

```
                                          (SEQ ID NO: 342)
  1   GACATCCAGA TGACCCAGTC TCCATCCTCC
      CTGTCTGCAT CTGTAGGTGA

51   CCGTGTCACC ATCAGTTGCC GCGCAAGTCA
      GGATATTAGC AGCTATTTAA

101   ATTGGTATCA GCAGAAACCA GGGAAAGCCC
      CTAAGCTCCT GATCTATTCT

151   ACTTCCCGTT TGAATAGTGG GGTCCCATCA
      CGCTTCAGTG GCAGTGGCTC

201   TGGGACAGAT TTCACTCTCA CCATCAGCAG
      TCTGCAACCT GAAGATTTTG

251   CAACTTACTA CTGTCAACAG GATATTAAAC
      ACCCTACGTT CGGTCAAGGC

301   ACCAAGGTGG AGATCAAACG TACGGTGGCT
      GCACCATCTG TCTTCATCTT

351   CCCGCCATCT GATGAGCAGT TGAAATCTGG
      AACTGCCTCT GTTGTGTGCC

401   TGCTGAATAA CTTCTATCCC AGAGAGGCCA
      AAGTACAGTG GAAGGTGGAT

451   AACGCCCTCC AATCGGGTAA CTCCCAGGAG
      AGTGTCACAG AGGAGGACAG

501   CAAGGACAGC ACCTACAGCC TCAGCAGCAC
      CCTGACGCTG AGCAAAGCAG

551   ACTACGAGAA ACACAAAGTC TACGCCTGCG
      AAGTCACCCA TCAGGGCCTG

601   AGCTCGCCCG TCACAAAGAG CTTCAACAGG
      GGAGAGTGT
```

Amino acid sequence of the Ab-23 LC including signal peptide:

```
                                          (SEQ ID NO: 343)
  1   MDMRVPAQLL GLLLLWLRGA RCDIQMTQSP
      SSLSASVGDR VTITCRASQD

51   ISSYLNWYQQ KPGKAPKLLI YSTSRLNSGV
      PSRFSGSGSG TDFTLTISSL

101   QPEDFATYYC QQDIKHPTFG QGTKVEIKRT
      VAAPSVFIFP PSDEQLKSGT

151   ASVVCLLNNF YPREAKVQWK VDNALQSGNS
      QESVTEQDSK DSTYSLSSTL

201   TLSKADYEKH KVYACEVTHQ GLSSPVTKSF
      NRGEC
```

Nucleic acid sequence of the Ab-23 LC including signal peptide encoding sequence:

```
                                          (SEQ ID NO: 344)
  1   ATGGACATGA GGGTGCCCGC TCAGCTCCTG
      GGGCTCCTGC TGCTGTGGCT

51   GAGAGGTGCC AGATGTGACA TCCAGATGAC
      CCAGTCTCCA TCCTCCCTGT

101   CTGCATCTGT AGGTGACCGT GTCACCATCA
      CTTGCCGCGC AAGTCAGGAT

151   ATTAGCAGCT ATTTAAATTG GTATCAGCAG
      AAACCAGGGA AAGCCCCTAA

201   GCTCCTGATC TATTCTACTT CCCGTTTGAA
      TAGTGGGGTC CCATCACGCT

251   TCAGTGGCAG TGGCTCTGGG ACAGATTTCA
      CTCTCACCAT CAGCAGTCTG

301   CAACCTGAAG ATTTTGCAAC TTACTACTGT
      CAACAGGATA TTAAACACCC

351   TACGTTCGGT CAAGGCACCA AGGTGGAGAT
      CAAACGTACG GTGGCTGCAC

401   CATCTGTCTT CATCTTCCCG CCATCTGATG
      AGCAGTTGAA ATCTGGAACT

451   GCCTCTGTTG TGTGCCTGCT GAATAACTTC
      TATCCCAGAG AGGCCAAAGT

501   ACAGTGGAAG GTGGATAACG CCCTCCAATC
      GGGTAACTCC CAGGAGAGTG

551   TCACAGAGCA GGACAGCAAG GACAGCACCT
      ACAGCCTCAG CAGCACCCTG

601   ACGCTGAGCA AAGCAGACTA CGAGAAACAC
      AAAGTCTACG CCTGCGAAGT

651   CACCCATCAG GGCCTGAGCT CGCCCGTCAC
      AAAGAGCTTC AACAGGGGAG

701   AGTGT
```

Heavy Chain:

Amino acid sequence of the mature form (signal peptide removed) of the Ab-23 HC:

```
                                          (SEQ ID NO: 345)
  1   EVQLVQSGAE VKKPGSSVKV SCKASGFTFT DYIMHWVRQA PGQGLEWMGY
 51   INPYNDDTEY NEKFKGRVTI TADKSTSTAY MELSSLRSED TAVYYCARSI
101   YYYDAFFAYW GQGTLVTVSS ASTKGPSVFP LAPCSRSTSE STAALGCLVK
151   DYFPEPVTVS WNSGALTSGV HTFPAVLQSS GLYSLSSVVT VPSSNFGTQT
201   TYCNVDHKPS NTKVDKTVER KCCVECPPCP APPVAGPSVF LFPPKPKDTL
251   MISRTPEVTC VVVDVSHEDP EVQFNWYVDG VEVHNAKTKP REEQFNSTFR
301   VVSVLTVVHQ DWLNGKEYKC KVSNKGLPAP IEKTISKTKG QPREPQVTYL
351   PPSREEMTKN QVSLTCLVKG FYPSDLAVEW ESNGQPENNY KTTPPMLDSD
401   GSFFYLSKLT VDKSRWQQGN VFSCVMHEAL HNHYTQKSLS LSPGK
```

Amino acid sequence of the mature form (signal peptide removed) of the Ab-23 HC without carboxy-terminal lysine:

(SEQ ID NO: 396)

```
  1 EVQLVQSHAE VKKPGSSVKV SCKASGFTFT DYIMHWVRQA PGQGLEWMGY
 51 INPYNDDTEY NEKFKGRVTI TADKSTSTAY MELSSLRSED TAVYYCARSI
101 YYDAPFAYW GQGTLVTVSS ASTKGPSVFP LAPCSRSTSE STAALGCLVK
151 DYFPEPVTVS WNSGALTSGV HTFPAVLQSS GLYSLSSVVT VPSSNFGTQT
201 YTCNVDHKPS NTKVDKTVER KCCVECPPCP APPVAGPSVF LFPPKPKDTL
251 MISRTPEVTC VVVDVSHEDP EVQFNWYVDG VEVHNAKTKP REEQFNSTFR
301 VVSVLTVVHQ DWLNGKEYKC KVSNKGLPAP IEKTISKTKG QPREPQVYTL
351 PPSREEMTKN QVSLTCLVKG FYPSDIAVEW ESNGQPENNY KTTPPMLDSD
401 GSFFLYSKLT VDKSRWQQGN VFSCSVMHEA LHNHYTQKSL SLSPG
```

Nucleic acid sequence encoding the mature form (signal peptide removed) of the Ab-23 HC:

(SEQ ID NO: 346)

```
   1 GAGGTGCAGC TGGTGCAGTC TGGGGCTGAG
     GTGAAGAAGC CTGGGTCCTC
  51 GGTGAAGGTC TCCTGCAAGG CTTCTGGTTT
     TACCTTCACC GACTATATTA
 101 TGCACTGGGT GCGTCAGGCC CCTGGTCAAG
     GGCTTGAGTG GATGGGCTAT
 151 ATCAACCCTT ATAATGATGA CACCGAATAC
     AACGAGAAGT TCAAGGGCCG
 201 TGTCACGATT ACCGCGGACA AATCCACGAG
     CACAGCCTAC ATGGAGCTGA
 251 GCAGCCTGCG CTCTGAGGAC ACGGCCGTGT
     ATTACTGTGC GCGTTCGATT
 301 TATTACTACG ATGCCCCGTT TGCTTACTGG
     GGCCAAGGGA CTCTGGTCAC
 351 CGTCTCTAGT GCCTCCACCA AGGGCCCATC
     GGTCTTCCCC CTGGCGCCCT
 401 GCTCCAGGAG CACCTCCGAG AGCACAGCGG
     CCCTGGGCTG CCTGGTCAAG
 451 GACTACTTCC CCGAACCGGT GACGGTGTCG
     TGGAACTCAG GCGCTCTGAC
 501 CAGCGGCGTG CACACCTTCC CAGCTGTCCT
     ACAGTCCTCA GGACTCTACT
 551 CCCTCAGCAG CGTGGTGACC GTGCCCTCCA
     GCAACTTCGG CACCCAGACC
 601 TACACCTGCA ACGTAGATCA CAAGCCCAGC
     AACACCAAGG TGGACAAGAC
 651 AGTTGAGCGC AAATGTTGTG TCGAGTGCCC
     ACCGTGCCCA GCACCACCTG
 701 TGGGAGGACC GTCAGTCTTC CTCTTCCCCC
     CAAAACCCAA GGACACCCTC
 751 ATGATCTCCC GGACCCCTGA GGTCACGTGC
     GTGGTGGTGG ACGTGAGGCA
 801 CGAAGACCCC GAGGTCCAGT TCAACTGGTA
     CGTGGACGGC GTGGAGGTGC
 851 ATAATGCCAA GACAAAGCCA CGGGAGGAGC
     AGTTCAACAG CACGTTCCGT
 901 GTGGTCAGCG TCCTCACCGT TGTGCACCAG
     GACTGGCTGA ACGGCAAGGA
 951 GTACAAGTGC AAGGTCTCCA ACAAAGGCCT
     CCCAGCCCCC ATCGAGAAAA
1001 CCATCTCCAA AACCAAAGGG CAGCCCCGAG
     AACCACAGGT GTACACCCTG
1051 CCCCCATCCC GGGAGGAGAT GACCAAGAAC
     CAGGTCAGCC TGACCTGCCT
1101 GGTCAAAGGC TTCTACCCCA GCGACATCGC
     CGTGGAGTGG GAGAGCAATG
1151 GGCAGCCGGA GAACAACTAC AAGACCACAC
     CTCCCATGCT GGACTCCGAC
1201 GGCTCCTTCT TCCTCTACAG CAAGCTCACC
     GTGGACAAGA GCAGGTGGCA
1251 GCAGGGGAAC GTCTTCTCAT GCTCCGTGAT
     GCATGAGGCT CTGCACAACC
1301 ACTACACGCA GAAGAGCCTC TCCCTGTCTC
     CGGGTAAA
```

Amino acid sequence of the Ab-23 HC including signal peptide:

(SEQ ID NO: 347)

```
  1 MDWTWRILFL VAAATGAHSE VQLVQSGAEV
    KKPGSSVKVS CKASGFTFTD
 51 YIMHWVRQAP GQGLEWMGYI NPYNDDTEYN
    EKFKGRVTIT ADKSTSTAYM
101 ELSSLRSEDT AVYYCARSIY YYDAPFAYWG
    QGTLVTVSSA STKGPSVFPL
151 APCSRSTSES TAALGCLVKD YFPEPVTVSW
    NSGALTSGVH TFPAVLQSSG
201 LYSLSSVVTV PSSNFGTQTY TCNVDHKPSN
    TKVDKTVERK CCVECPPCPA
251 PPVAGPSVFL FPPKPKDTLM ISRTPEVTCV
    VVDVSHEDPE VQFNWYVDGV
301 EVHNAKTKPR EEQFNSTFRV VSVLTVVHQD
    WLNGKEYKCK VSNKGLPAPI
351 EKTISKTKGQ PREPQVYTLP PSREEMTKNQ
    VSLTCLVKGF YPSDIAVEWE
401 SNGQPENNYK TTPPMLDSDG SFFLYSKLTV
    DKSRWQQGNV FSCSVMHEAL
451 HNHYTQKSLS LSPGK
```

Nucleic acid sequence of the Ab-23 HC including signal peptide encoding sequence:

```
                                          (SEQ ID NO: 348)
   1    ATGGACTGGA CCTGGAGGAT CCTCTTCTTG
        GTGGCAGCAG CCACAGGAGC
  51    CCACTCCGAG GTGCAGCTGG TGCAGTCTGG
        GGCTGAGGTG AAGAAGCCTG
 101    GGTCCTCGGT GAAGGTCTCC TGCAAGGCTT
        CTGGTTTTAC CTTCACCGAC
 151    TATATTATGC ACTGGGTGCG TCAGGCCCCT
        GGTCAAGGGC TTGAGTGGAT
 201    GGGCTATATC AACCCTTATA ATGATGACAC
        CGAATACAAC GAGAAGTTCA
 251    AGGGCCGTGT CACGATTACC GCGGACAAAT
        CCACGAGCAC AGCCTACATG
 301    GAGCTGAGCA GCCTGCGCTC TGAGGACACG
        GCCGTGTATT ACTGTGCGCG
 351    TTCGATTTAT TACTACGATG CCCCGTTTGC
        TTACTGGGGC CAAGGGACTC
 401    TGGTCACCGT CTCTAGTGCC TCCACCAAGG
        GCCCATCGGT CTTCCCCCTG
 451    GCGCCCTGCT CCAGGAGCAC CTCCGAGAGC
        ACAGCGGCCC TGGGCTGCCT
 501    GGTCAAGGAC TACTTCCCCG AACCGGTGAC
        GGTGTCGTGG AACTCAGGCG
 551    CTCTGACCAG CGGCGTGCAC ACCTTCCCAG
        CTGTCCTACA GTCCTCAGGA
 601    CTCTACTCCC TCAGCAGCGT GGTGACCGTG
        CCCTCCAGCA ACTTCGGCAC
 651    CCAGACCTAC ACCTGCAACG TAGATCACAA
        GCCCAGCAAC ACCAAGGTGG
 701    ACAAGACAGT TGAGCGCAAA TGTTGTGTCG
        AGTGCCCACC GTGCCCAGCA
 751    CCACCTGTGG CAGGACCGTC AGTCTTCCTC
        TTCCCCCCAA AACCCAAGGA
 801    CACCCTCATG ATCTCCCGGA CCCCTGAGGT
        CACGTGCGTG GTGGTGGACG
 851    TGAGCCACGA AGACCCCGAG GTCCAGTTCA
        ACTGGTACGT GGACGGCGTG
 901    GAGGTGCATA ATGCCAAGAC AAAGCCACGG
        GAGGAGCAGT TCAACAGCAC
 951    GTTCCGTGTG GTCAGCGTCC TCACCGTTGT
        GCACCAGGAC TGGCTGAACG
1001    GCAAGGAGTA CAAGTGCAAG GTCTCCAACA
        AAGGCCTCCC AGCCCCCATC
1051    GAGAAAACCA TCTCCAAAAC CAAAGGGCAG
        CCCCGAGAAC CACAGGTGTA
1101    CACCCTGCCC CCATCCCGGG AGGAGATGAC
        CAAGAACCAG GTCAGCCTGA
1151    CCTGCCTGGT CAAAGGCTTC TACCCCAGCG
        ACATCGCCGT GGAGTGGGAG
1201    AGCAATGGGC AGCCGGAGAA CAACTACAAG
        ACCACACCTC CCATGCTGGA
1251    CTCCGACGGC TCCTTCTTCC TCTACAGCAA
        GCTCACCGTG GACAAGAGCA
1301    GGTGGCAGCA GGGGAACGTC TTCTCATGCT
        CCGTGATGCA TGAGGCTCTG
1351    CACAACCACT ACACGCAGAA GAGCCTCTCC
        CTGTCTCCGG GTAAA
```

The CDR (complementarity determining region) sequences in the variable region of the heavy chain of Ab-23 are as follows:

```
CDR-H1:    DYIMH              (SEQ ID NO: 269)
CDR-H2:    YINPYNDDTEYNEKFKG
           (SEQ ID NO: 270)
CDR-H3:    SIYYYDAPFAY (SEQ ID
           NO: 271)
```

The light chain variable region CDR sequences of Ab-23 are:

```
CDR-L1:    RASQDISSYLN    (SEQ ID NO: 239)
CDR-L2:    STSRLNS        (SEQ ID NO: 240)
CDR-L3:    QQDIKHPT       (SEQ ID NO: 241)
```

Ab-23 Variable Domains:

Ab-23 light chain variable domain amino acid sequence (without signal sequence):

```
DIQMTQSPSS LSASVGDRVT ITCRASQDISS   (SEQ ID NO: 364)
YLNWYQQKP GKAPKLLIYSTSRLNSGVPS RF
SGSGSGTD FTLTISSLQPEDFATYYCQQ DIK
HPTFGQGTKVEIK
```

Ab-23 light chain variable domain DNA sequence (without signal sequence):

```
GACATCCAGATGACCCAGTCTCCATCCTCCCTG   (SEQ ID NO: 365)
TCTGCATCTGTAGGTGACCGTGTCACC ATCAC
TTGCC GCGCAAGTCA GGATATTAGC AGCTA
TTTAAATTGGTATCAGCAGAAACCA GGGAAAGC
CC CTAAGCTCCT GATCTATTCTACTTCCCGTT
TGAATAGTGG GGTCCCATCA CGCTTCAGTG G
CAGTGGCTCTGGGACAGAT TTCACTCTCA CC
ATCAGCAG TCTGCAACCT GAAGATTTTGCAAC
TTACTA CTGTCAACAG GATATTAAAC ACCCT
ACGTT CGGTCAAGGCACCAAGGTGG AGATC
AAA
```

Ab-23 heavy chain variable domain amino acid sequence (without signal sequence):

EVQLVQSGAE VKKPGSSVKV SCKASGFTFT D (SEQ ID NO: 366)
YIMHWVRQA PGQGLEWMGYINPYNDDTEY NEK
FKGRVTI TADKSTSTAY MELSSLRSED TAVY
YCARSIYYYDAPFAYW GQGTLVTVSS

Ab-23 heavy chain variable domain DNA sequence (without signal sequence):

GAGGTGCAGCTGGTGCAGTCTGGGGCTGAGGTG   (SEQ ID NO: 367)
AAGAAGCCTGGGTCCTCGGTGAAGGTC TCCTG
CAAGG CTTCTGGTTT TACCTTCACC GACTAT
ATTATGCACTGGGT GCGTCAGGCC CCTGGTC
AAG GGCTTGAGTG GATGGGCTATATCAACCCT
T ATAATGATGA CACCGAATAC AACGAGAAGT

-continued

TCAAGGGCCGTGTCACGATT ACCGCGGACA AA

TCCACGAG CACAGCCTAC ATGGAGCTGAGCAG

CCTGCG CTCTGAGGAC ACGGCCGTGT ATTAC

TGTGC GCGTTCGATTTATTACTACG ATGCCCC

GTT TGCTTACTGG GGCCAAGGGACTCTGGTCA

CCGTCTCTAGT

Ab-21

Amino acid sequence of the Ab-21 LC including signal peptide:

(SEQ ID NO: 315)
MKSQTQVFVYMLLWLSGVEGDIVMTQSHKFMSTSVGDRVTITCKASQDVFTAVAWYQ
QKPGQSPKLLIYWASTRHTGVPDRFTGSGSGTDFTLTISNVQSEDLADYFCQQYSSYPLT
FGAGTKLELKR

Nucleic acid sequence of the Ab-21 LC including signal peptide:

ATGAAGTCACAGACCCAGGTCTTTGTATACATG   (SEQ ID NO: 316)
TTGCTGTGGTTGTCTGGTGTTGAAGGAGACATTG
TGATGACCCAGTCTCACAAATTCATGTCCACGT
CAGTAGGAGACAGGGTCACCATCACCTGCAAGG
CCAGTCAGGATGTCTTTACTGCTGTAGCCTGGTA
TCAACAGAAACCAGGACAATCTCCTAAACTACT
GATTTACTGGGCATCCACCCGGCACACTGGAGT
CCCTGATCGCTTCACAGGCAGTGGATCTGGGAC
AGATTTCACTCTCACCATTAGCAATGTGCAGTCT
GAAGACTTGGCAGATTATTTCTGTCAACAATATA
GCAGCTATCCTCTCACGTTCGGTGCTGGGACCA
AGTTGGAGCTGAAACGT

Amino acid sequence of the Ab-21 HC including signal peptide:

(SEQ ID NO: 317)
MGWNWIIFFLMAVVTGVNSEVQLQQSGAELVRPGALVKLSCKASGFNIKDYYMHWVK
QRPEQGLEWIGRIDPENGDIIYDPKFQGKASITTDTSSNTAYLQLSSTSEDTAVYYCAYD
AGDPAWFTYWGQGTLVTVSS

Nucleic acid sequence of the Ab-21 HC including signal peptide:

ATGGGATGGAACTGGATCATCTTCTTCCTGATG   (SEQ ID NO: 318)
GCAGTGGTTACAGGGGTCAATTCAGAGGTTCAG
CTGCAGCAGTCTGGGGCTGAGCTTGTGAGGCCA
GGGGCCTTAGTCAAGTTGTCCTGCAAAGCTTCTG
GCTTCAATATTAAAGACTACTATATGCACTGGGT
GAAGCAGAGGCCTGAACAGGGCCTGGAGTGGAT
TGGAAGGATTGATCCTGAGAATGGTGATATTATA
TATGACCCGAAGTTCCAGGGCAAGGCCAGTATAA
CAACAGACACATCCTCCAACACAGCCTACCTGC
AGCTCAGCAGCCTGACGTCTGAGGACACTGCCGT
CTATTACTGTGCTTACGATGCTGGTGACCCCGCC

Ab-21 was humanized to yield Ab-22.

Ab-22

Amino acid sequence of the Ab-22 LC including signal peptide:

MDMRVPAQLLGLLLLWLRGARCDIQMTQSPSSLSASVGDRVTITCKASQDVETAVAWY
QQKPGKAPKLLIYWASTRHTGVPSRFSGSGSGTDFTLTISSLQPEDFATYYCQQYSSYPL
TFGGGTKVEIKR (SEQ ID NO: 319)

Nucleic acid sequence of the Ab-22 LC including signal peptide:

ATGGATATGCGCGTGCCGGCGCAGCTGCTGGGC (SEQ ID NO: 320)

CTGCTGCTGCTGTGGCTGCGCGGCGCGCGCTGC

GATATCCAGATGACCCAGAGCCCGAGCAGCCTG

AGCGCGAGCGTGGGCGATCGCGTGACCATTACC

TGCAAAGCGAGCCAGGATGTGTTTACCGCGGTG

GCGTGGTATCAGCAGAAACCGGGCAAAGCGCCG

AAACTGCTGATTTATTGGGCGAGCACCCGCCATA

CCGGCGTGCCGAGTCGCTTTAGCGGCAGCGGCA

GCGGCACCGATTTTACCCTGACCATTAGCAGCCT

GCAGCCGGAAGATTTTGCGACCTATTATTGCCAG

CAGTATAGCAGCTATCCGCTGACCTTTGGCGGCG

GCACCAAAGTGGAAATTAAACGT

Amino acid sequence of the Ab-22 HC including signal peptide:

MDWTWSILFVAAPTGAHSEVQLVQSGAEVKKPGASVKVSCKASGFNIKDYYMHWVR
QAPGQGLEWIGRIDPENGDITYDPKFQGRVTMTTDTSTSTAYMELRSLRSDDTAVYYCA
YDAGDPAWFTYWGQGTLVTVSS (SEQ ID NO: 321)

Nucleic acid sequence of the Ab-22 HC including signal peptide:

ATGGATTGGACCTGGAGCATTCTGTTTCTGGTG (SEQ ID NO: 322)

GCGGCGCCGACCGGCGCGCATAGCGAAGTGCAG

CTGGTGCAGAGCGGCGCGGAAGTGAAAAAACCGG

GCGCGAGCGTGAAAGTGAGCTGCAAAGCGAGCGG

CTTTAACATTAAAGATTATTATATGCATTGGGTG

CGCCAGGCGCCGGGCCAGGGCCTGGAATGGATC

GGCCGCATTGATCCGGAAAACGGCGATATTATTT

ATGATCCGAAATTTCAGGGCCGCGTGACCATGAC

CACCGATACCAGCACCAGCACCGCGTATATGGAA

CTGCGCAGCCTGCGCAGCGATGATACCGCGGTGT

ATTATTGCGCGTATGATGCGGGCGATCCGGCGTG

GTTTACCTATTGGGGCCAGGGCACCCTGGTGACC

GTCTCGAGC

Ab-22 light chain variable domain amino acid sequence (without signal sequence):

DIQMTQSPSS LSASVGDRVT ITCKASQDVF   (SEQ ID NO: 336)

TAVAWYQQKP GKAPKLLIYW ASTRHTGVPS

RFSGSGSGTD FTLTISSLQP EDFATYYCQQ

YSSYPLTFGG GTKVEIKR

Ab-22 light chain variable domain DNA sequence (without signal sequence):

GATATCCAGATGACCCAGAGCCCGAGC        (SEQ ID NO: 337)

AGCCTGAGCGCGAGCGTGGGCGATCGCGT

GACCATTACCTGCAAAGCGAGCCAGGA

TGTGTTTACCGCGGTGGCGTGGTATCAGC

AGAAACCGGGCAAAGCGCCGAAACTGC

TGATTATTGGGCGAGCACCCGCCATACC

GGCGTGCCGAGTCGCTTTAGCGGCAGC

GGCAGCGGCACCGATTTTACCCTGACCATT

AGCAGCCTGCAGCCGGAAGATTTTGCG

ACCTATTATTGCCAGCAGTATAGCAGCTAT

```
-continued
CCGCTGACCTTTGGCGGCGGCACCAAA
GTGGAAATTAAACGT
```

Ab-22 heavy chain variable domain amino acid sequence (without signal sequence):

```
EVQLVQSGAEVKKPGASVKVSCKASGFNIKDYY    (SEQ ID NO: 338)
MHWVRQAPGQGLEWIGRIDPENGDIIYDPKFQGR
VTMTTDTSTSTAYMELRSLRSDDTAVYYCAYDA
GDPAWFTYWGQGTLVTSS
```

Ab-22 heavy chain variable domain DNA sequence (without signal sequence):

```
GAAGTGCAGCTGGTGCAGAGCGGCGCGGAAGTGA  (SEQ ID NO: 339)
AAAAACCGGGCGCGAGCGTGAAAGTGAGCTGCAA
AGCGAGCGGCTTTAACATTAAAGATTATTATATG
CATTGGGTGCGCCAGGCGCCGGGCCAGGGCCTGG
AATGGATCGGCCGCATTGATCCGGAAAACGGCGA
TATTATTTATGATCCGAAATTTCAGGGCCGCGTG
ACCATGACCACCGATACCAGCACCAGCACCGCGT
ATATGGAACTGCGCAGCCTGCGCAGCGATGATA
```

```
                -continued
CCGCGGTGTATTATTGCGCGTATGATGCGGGCG
ATCCGGCGTGGTTTACCTATTGGGGCCAGGGC
ACCCTGGTGACCGTCTCGAGC.
```

For Ab-18, Ab-20, and Ab-22, the light chain human kappa constant region is as follows:

```
TVAAPSVFIFPPSDEQLKSGTASVVCLLNNFYP    (SEQ ID NO: 325)
REAKVQWKVDNALQSGNSQESVTEQDSKDSTY
SLSSTLTLSKADYEKHKVYACEVTHQGLSSPV
TKSFNRGEC*
``` and the heavy chain human gamma-4 constant region is as follows:

```
ASTKGPSVFPLAPCSRSTSESTAALGCLVKDYFP   (SEQ ID NO: 326)
EPVTVSWNSGALTSGVHTFPAVLQSSGLYSLSS
VVTVPSSSLGTKTYTCNVDHKPSNTKVDKRVES
KYGPPCPPCPAPEFLGGPSVFLFPPKPKDTLMI
SRTPEVTCVVVDVSQEDPEVQFNWYVDGVEV
HNAKTKPREEQFNSTYRVVSVLTVLHQDWLNG
KEYKCKVSNKGLPSSIEKTISKAKGQPREPQVY
TLPPSQEEMTKNQVSLTCLVKGFYPSDIAVEWES
NGQPENNYKTTPPVLDSDGSFFLYSRLTVDKSR
WQEGNVFSCSVMHEALHNHYTQKSLSLSLGK*
```

The hinge region contains the Ser-241-Pro mutation to improve hinge stability (Angal S et al, (1993), Mol Immunol, 30(1), 105-108).

Ab-24

The sequences of Antibody 24 (also referred to herein as Ab-24) LC and HC are as follows:

Light Chain:

Amino acid sequence of the mature form (signal peptide removed) of the Ab-24 LC:

(SEQ ID NO: 350)
```
  1 DIVLTQSPAS LAVSLGQRAT IACKASQSVD YDGTSYMNWY QQKPGQPPKL
 51 LIYAASNLES EIPARFSGTG SGTDFTLNIH PVEEDITTY YCQQSNEDPF
101 TFGGGTKLEI KRADAAPTVS IFPPSSEQLT SGGASVVCFL NNFYPKDINV
151 KWKIDGSERQ NGVLNSWTDQ DSKDSTYSMS STLTLTDKEY ERHNSYTCEA
201 THKTSTSPIV KSFNREC
```

Nucleic acid sequence encoding the mature form (signal peptide removed) of the Ab-24 LC:

(SEQ ID NO: 354)
```
  1    GACATTGTGT TGACCCAGTC TCCAGCTTCT
       TTGGCTGTGT CTCTAGGGCA
 51    GAGGGCCACC ATCGCCTGCA AGGCCAGCCA
       AAGTGTTGAT TATGATGGTA
101    CTAGTTATAT GAATTGGTAC CAACAGAAAC
       CAGGACAGCC ACCCAAACTC
151    CTCATCTATG CTGCATCCAA TCTAGAATCT
       GAGATCCCAG CCAGGTTTAG
201    TGGCACTGGG TCTGGGACAG ACTTCACCCT
       CAACATCCAT CCTGTGGAGG
251    AGGAGGATAT CACAACCTAT TACTGTCAGC
       AAAGTAATGA GGATCCGTTC
301    ACGTTCGGAG GGGGGACCAA GTTGGAAATA
       AAACGGGCTG ATGCTGCACC
```

```
351    AACTGTATCC ATCTTCCCAC CATCCAGTGA
       GCAGTTAACA TCTGGAGGTG
401    CCTCAGTCGT GTGCTTCTTG AACAACTTCT
       ACCCCAAAGA CATCAATGTC
451    AAGTGGAAGA TTGATGGCAG TGAACGACAA
       AATGGCGTCC TGAACAGTTG
501    GACTGATCAG GACAGCAAAG ACAGCACCTA
       CAGCATGAGC AGCACCCTCA
551    CGTTGACCAA GGACGAGTAT GAACGACATA
       ACAGCTATAC CTGTGAGGCC
601    ACTCACAAGA CATCAACTTC ACCCATTGTC
       AAGAGCTTCA ACAGGAATGA
651    GTGTTAG
```

Amino acid sequence of the Ab-24 LC including signal peptide:

```
                                    (SEQ ID NO: 355)
  1    METDTILLWV LLLWVPGSTG DIVLTQSPAS
       LAVSLGQRAT IACKASQSVD
 51    YDGTSYMNWY QQKPGQPPKL LIYAASNLES
       EIPARFSGTG SGTDFTLNIH
101    PVEEEDITTY YCQQSNEDPF TFGGGTKLEI
       KRADAAPTVS IFPPSSEQLT
151    SGGASVVCFL NNFYPKDINV KWKIDGSERQ
       NGVLNSWTDQ DSKDSTYSMS
201    STLTLTKDEY ERHNSYTCEA THKTSTSPIV
       KSFNRNEC
```

Nucleic acid sequence of the Ab-24 LC including signal peptide encoding sequence:

```
                                    (SEQ ID NO: 356)
  1    ATGGAGACAG ACACAATCCT GCTATGGGTG
       CTGCTGCTCT GGGTTCCAGG
 51    CTCCACTGGT GACATTGTGT TGACCCAGTC
       TCCAGCTTCT TTGGCTGTGT
101    CTCTAGGGCA GAGGGCCACC ATCGCCTGCA
       AGGCCAGCCA AAGTGTTGAT
151    TATGATGGTA CTAGTTATAT GAATTGGTAC
       CAACAGAAAC CAGGACAGCC
201    ACCCAAACTC CTCATCTATG CTGCATCCAA
       TCTAGAATCT GAGATCCCAG
251    CCAGGTTTAG TGGCACTGGG TCTGGGACAG
       ACTTCACCCT CAACATCCAT
301    CCTGTGGAGG AGGAGGATAT CACAACCTAT
       TACTGTCAGC AAAGTAATGA
351    GGATCCGTTC ACGTTCGGAG GGGGGACCAA
       GTTGGAAATA AAACGGGCTG
401    ATGCTGCACC AACTGTATCC ATCTTCCCAC
       CATCCAGTGA GCAGTTAACA
451    TCTGGAGGTG CCTCAGTCGT GTGCTTCTTG
       AACAACTTCT ACCCCAAAGA
501    CATCAATGTC AAGTGGAAGA TTGATGGCAG
       TGAACGACAA AATGGCGTCC
551    TGAACAGTTG GACTGATCAG GACAGCAAAG
       ACAGCACCTA CAGCATGAGC
601    AGCACCCTCA CGTTGACCAA GGACGAGTAT
       GAACGACATA ACAGCTATAC
651    CTGTGAGGCC ACTCACAAGA CATCAACTTC
       ACCCATTGTC AAGAGCTTCA
701    ACAGGAATGA GTGTTAG
```

Ab-24 Heavy Chain:

Amino acid sequence of the mature form (signal peptide removed) of the Ab-24 HC:

```
                                    (SEQ ID NO: 357)
  1    QVQLQQPGTE LVRPGTSVKL SCKASGYIFT TYNMNWVKQR PGQGLEWIGM
 51    IHPSASEIRL DQKFKDKATL TLDKSSSTAY MHLSGPTSVD SAVYYCARSG
101    EWGSMDYWGQ GTSVTVSSAK TTPPSVYPLA PGSAAQTNSM VTLGCLVKGY
151    FPEPVTVTWN SGSLSSGVHT FPAVLQSDLT LSSSVTVPSA STWPSETVTC
201    NVAHPASSTK VDKKIVPRDC GCKPCICTVP EVSSVFIFPP KPKDVLTITL
251    TPKVTCVVVD ISKDDPEVQF SWFVDDVEVH TAQTQPREEQ FNSTFRSVSE
301    LIPMHQDWLN GKEFKCRVNS AAFPAPIEKT ISKTKGRPKA PQVYTIPPPK
351    EQMAKDVSKL TCMITDFFPE DITVEWQWNG QPAENYKNTQ PIMDTDGSYF
401    IYSKLNVQKS NWEAGNTFTC SVLHEGLHNH HTEKSLSHSP GK
```

Nucleic acid sequence encoding the mature form (signal peptide removed) of the Ab-24 HC:

```
                                    (SEQ ID NO: 361)
  1    CAGGTCCAAC TACAGCAGCC TGGGACTGAG
       CTGGTGAGGC CTGGAACTTC
 51    AGTGAAGTTG TCCTGTAAGG CTTCTGGCTA
       CATCTTCACC ACCTACTGGA
101    TGAACTGGGT GAAACAGAGG CCTGGACAAG
       GCCTTGAGTG GATTGGCATG
151    ATTCATCCTT CCGCAAGTGA AATTAGGTTG
       GATCAGAAAT TCAAGGACAA
```

```
201   GGCCACATTG ACTCTTGACA AATCCTCCAG
      CACAGCCTAT ATGCACCTCA

251   GCGGCCCGAC ATCTGTGGAT TCTGCGGTCT
      ATTACTGTGC AAGATCAGGG

301   GAATGGGGGT CTATGGACTA CTGGGGTCAA
      GGAACCTCAG TCACCGTCTC

351   CTCAGCCAAA ACGACACCCC CATCTGTCTA
      TCCACTGGCC CCTGGATCTG

401   CTGCCCAAAC TAACTCCATG GTGACCCTGG
      GATGCCTGGT CAAGGGCTAT

451   TTCCCTGAGC CAGTGACAGT GACCTGGAAC
      TCTGGATCCC TGTCCAGCGG

501   TGTGCACACC TTCCCAGCTG TCCTGCAGTC
      TGACCTCTAC ACTCTGAGCA

551   GCTCAGTGAC TGTCCCCTCC AGCACCTGGC
      CCAGCGAGAC CGTCACCTGC

601   AACGTTGCCC ACCCGGCCAG CAGCACCAAG
      GTGGACAAGA AAATTGTGCC

651   CAGGGATTGT GGTTGTAAGC CTTGCATATG
      TACAGTCCCA GAAGTATCAT

701   CTGTCTTCAT CTTCCCCCCA AAGCCCAAGG
      ATGTGCTCAC CATTACTCTG

751   ACTCCTAAGG TCACGTGTGT TGTGGTAGAC
      ATCAGCAAGG ATGATCCCGA

801   GGTCCAGTTC AGCTGGTTTG TAGATGATGT
      GGAGGTGCAC ACAGCTCAGA

851   CGCAACCCCG GGAGGAGCAG TTCAACAGCA
      CTTTCCGCTC AGTCAGTGAA

901   CTTCCCATCA TGCACCAGGA CTGGCTCAAT
      GGCAAGGAGT TCAAATGCAG

951   GGTCAACAGT GCAGCTTTCC CTGCCCCCAT
      CGAGAAAACC ATCTCCAAAA

1001  CCAAAGGCAG ACCGAAGGCT CCACAGGTGT
      ACACCATTCC ACCTCCCAAG

1051  GAGCAGATGG CCAAGGATAA AGTCAGTCTG
      ACCTGCATGA TAACAGACTT

1101  CTTCCCTGAA GACATTACTG TGGAGTGGCA
      GTGGAATGGG CAGCCAGCGG

1151  AGAACTACAA GAACACTCAG CCCATCATGG
      ACACAGATGG CTCTTACTTC

1201  ATCTACAGCA AGCTCAATGT GCAGAAGAGC
      AACTGGGAGG CAGGAAATAC

1251  TTTCACCTGC TCTGTGTTAC ATGAGGGCCT
      GCACAACCAC CATACTGAGA

1301  AGAGCCTCTC CCACTCTCCT GGTAAATGA
```

Amino acid sequence of the Ab-24 HC including signal peptide:

```
                                  (SEQ ID NO: 362)
  1   MGWSSIILFL VATATGVHSQ VQLQQPGTEL
      VRPGTSVKLS CKASGYIFTT

51   YWMNWVKQRP GQGLEWIGMI HPSASEIRLD
      QKFKDKATLT LDKSSSTAYM

101   HLSGPTSVDS AVYYCARSGE WGSMDYWGQG
      TSVTVSSAKT TPPSVYPLAP

151   GSAAQTNSMV TLGCLVKGYF PEPVTVTWNS
      GSLSSGVHTF PAVLQSDLYT

201   LSSSVTVPSS TWPSETVTCN VAHPASSTKV
      DKKIVPRDCG CKPCICTVPE

251   VSSVFIFPPK PKDVLTITLT PKVTCVVVDI
      SKDDPEVQFS WFVDDVEVHT

301   AQTQPREEQF NSTFRSVSEL PIMHQDWLNG
      KEFKCRVNSA AFPAPIEKTI

351   SKTKGRPKAP QVYTIPPPKE QMAKDKVSLT
      CMITDFFPED ITVEWQWNGQ

401   PAENYKNTQP IMDTDGSYFI YSKLNVQKSN
      WEAGNTFTCS VLHEGLHNHH

451   TEKSLSHSPG K
```

Nucleic acid sequence of the Ab-24 HC including signal peptide encoding sequence:

```
                                  (SEQ ID NO: 363)
  1   ATGGGATGGA GCTCTATCAT CCTCTTCTTG
      GTAGCAACAG CTACAGGTGT

51   CCACTCCCAG GTCCAACTAC AGCAGCCTGG
      GACTGAGCTG GTGAGGCCTG

101   GAACTTCAGT GAAGTTGTCC TGTAAGGCTT
      CTGGCTACAT CTTCACCACC

151   TACTGGATGA ACTGGGTGAA ACAGAGGCCT
      GGACAAGGCC TTGAGTGGAT

201   TGGCATGATT CATCCTTCCG CAAGTGAAAT
      TAGGTTGGAT CAGAAATTCA

251   AGGACAAGGC CACATTGACT CTTGACAAAT
      CCTCCAGCAC AGCCTATATG

301   CACCTCAGCG GCCCGACATC TGTGGATTCT
      GCGGTCTATT ACTGTGCAAG

351   ATCAGGGGAA TGGGGGTCTA TGGACTACTG
      GGGTCAAGGA ACCTCAGTCA

401   CCGTCTCCTC AGCCAAAACG ACACCCCCAT
      CTGTCTATCC ACTGGCCCCT

451   GGATCTGCTG CCCAAACTAA CTCCATGGTG
      ACCCTGGGAT GCCTGGTCAA

501   GGGCTATTTC CCTGAGCCAG TGACAGTGAC
      CTGGAACTCT GGATCCCTGT

551   CCAGCGGTGT GCACACCTTC CCAGCTGTCC
      TGCAGTCTGA CCTCTACACT

601   CTGAGCAGCT CAGTGACTGT CCCCTCCAGC
      ACCTGGCCCA GCGAGACCGT

651   CACCTGCAAC GTTGCCCACC CGGCCAGCAG
      CACCAAGGTG GACAAGAAAA

701   TTGTGCCCAG GGATTGTGGT TGTAAGCCTT
      GCATATGTAC AGTCCCAGAA

751   GTATCATCTG TCTTCATCTT CCCCCCAAAG
      CCCAAGGATG TGCTCACCAT

801   TACTCTGACT CCTAAGGTCA CGTGTGTTGT
      GGTAGACATC AGCAAGGATG
```

```
 851   ATCCCGAGGT CCAGTTCAGC TGGTTTGTAG
       ATGATGTGGA GGTGCACACA

901   GCTCAGACGC AACCCCGGGA GGAGCAGTTC
       AACAGCACTT TCCGCTCAGT

951   CAGTGAACTT CCCATCATGC ACCAGGACTG
       GCTCAATGGC AAGGAGTTCA

1001   AATGCAGGGT CAACAGTGCA GCTTTCCCTG
       CCCCCATCGA GAAAACCATC

1051   TCCAAAACCA AAGGCAGACC GAAGGCTCCA
       CAGGTGTACA CCATTCCACC

1101   TCCCAAGGAG CAGATGGCCA AGGATAAAGT
       CAGTCTGACC TGCATGATAA

1151   CAGACTTCTT CCCTGAAGAC ATTACTGTGG
       AGTGGCAGTG GAATGGGCAG

1201   CCAGCGGAGA ACTACAAGAA CACTCAGCCC
       ATCATGGACA CAGATGGCTC

1251   TTACTTCATC TACAGCAAGC TCAATGTGCA
       GAAGAGCAAC TGGGAGGCAG

1301   GAAATACTTT CACCTGCTCT GTGTTACATG
       AGGGCCTGCA CAACCACCAT

1351   ACTGAGAAGA GCCTCTCCCA CTCTCCTGGT
       AAATGA
```

The CDR sequences in the variable region of the light chain of Ab-24 are as follows:

```
CDR-L1:   KASQSVDYDGTSYMN    (SEQ ID NO: 351)
CDR-L2:   AASNLES            (SEQ ID NO: 352)
CDR-L3:   QQSNEDPFT          (SEQ ID NO: 353)
```

The CDR sequences in the variable region of the heavy chain of Ab-24 are as follows:

```
CDR-H1:   TYWMN              (SEQ ID NO: 358)
CDR-H2:   MIHPSASEIRLDQKFKD  (SEQ ID NO: 359)
CDR-H3:   SGEWGSMDY          (SEQ ID NO: 360)
```

Table 1 below provides the SEQ ID NOs and amino acid sequences of the CDR's of Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24. L1, L2, and L3 refer to light chain CDR's 1, 2, and 3, and H1, H2, and H3 refer to heavy chain CDR's 1, 2, and 3 according to the Kabat numbering system (Kabat et al., 1987 in *Sequences of Proteins of immunological Interest*, U.S. Department of Health and Human Services, NIH, USA).

TABLE 1

| SEQ ID NO | DESCRIPTION | AMINO ACID SEQUENCE |
|---|---|---|
| 54 | Ab-A and Ab-1 CDR-L1 | QSSQSVYDNNWLA |
| 55 | Ab-A and Ab-1 CDR-L2 | DASDLAS |
| 56 | Ab-A and Ab-1 CDR-L3 | QGAYNDVIYA |
| 51 | Ab-A and Ab-1 CDR-H1 | SYWMN |
| 52 | Ab-A and Ab-1 CDR-H2 | TIDSGGRTDYASWAKG |
| 53 | Ab-A and Ab-1 CDR-H3 | NWNL |
| 60 | Ab-B CDR-L1 | SASSSVSFVD |
| 61 | Ab-B CDR-L2 | RTSNLGF |
| 62 | Ab-B CDR-L3 | QQRSTYPPT |
| 57 | Ab-B CDR-H1 | TSGMGVG |
| 58 | Ab-B CDR-H2 | HIWWDDVKRYNPVLKS |
| 59 | Ab-B CDR-H3 | EDFDYDEEYYAMDY |
| 48 | Ab-C CDR-L1 | KASQSVDYDGDSYMN |
| 49 | Ab-C CDR-L2 | AASNLES |
| 50 | Ab-C CDR-L3 | QQSNEDPWT |
| 45 | Ab-C CDR-H1 | DCYMN |
| 46 | Ab-C CDR-H2 | DINPPNGGTTYNQKFKG |
| 47 | Ab-C CDR-H3 | SHYYFDGRVPWDAMDY |
| 42 | Ab-D CDR-L1 | QASQGTSINLN |
| 43 | Ab-D CDR-L2 | GSSNLED |
| 44 | Ab-D CDR-L3 | LQHSYLPYT |
| 39 | Ab-D CDR-H1 | DHYMS |
| 40 | Ab-D CDR-H2 | DINPYSGETTYNQKFKG |
| 41 | Ab-D CDR-H3 | DDYDASPFAY |
| 275 | Ab-2 CDR-L1 | RASSSVYYMH |
| 276 | Ab-2 CDR-L2 | ATSNLAS |
| 277 | Ab-2 CDR-L3 | QQWSSDPLT |
| 287 | Ab-2 CDR-H1 | DYFIH |
| 288 | Ab-2 CDR-H2 | RLDPEDGESDYAPKFQD |
| 289 | Ab-2 CDR-H3 | EDYDGTYTFFPY |
| 278 | Ab-3 and Ab-15 CDR-L1 | SVSSTISSNHLH |
| 279 | Ab-3 and Ab-15 CDR-L2 | GTSNLAS |
| 280 | Ab-3 and Ab-15 CDR-L3 | QQWSSYPLT |
| 290 | Ab-3 and Ab-15 CDR-H1 | DFYLH |
| 291 | Ab-3 and Ab-15 CDR-H2 | RIDPENGDTLYDPKFQD |
| 292 | Ab-3 and Ab-15 CDR-H3 | EADYFHDGTSYWYFDV |
| 78 | Ab-4 and Ab-5 CDR-L1 | RASQDISNYLN |
| 79 | Ab-4 and Ab-5 CDR-L2 | YTSRLLS |
| 80 | Ab-4 and Ab-5 CDR-L3 | QQGDTLPYT |
| 245 | Ab-4 and Ab-5 CDR-H1 | DYNMH |

TABLE 1-continued

| SEQ ID NO | DESCRIPTION | AMINO ACID SEQUENCE |
|---|---|---|
| 246 | Ab-4 and Ab-5 CDR-H2 | EINPNSGGAGYNQKFKG |
| 247 | Ab-4 and Ab-5 CDR-H3 | LGYDDIYDDWYFDV |
| 81 | Ab-6 CDR-L1 | RASQDISNYLN |
| 99 | Ab-6 CDR-L2 | YTSRLHS |
| 100 | Ab-6 CDR-L3 | QQGDTLPYT |
| 248 | Ab-6 CDR-H1 | DYNMH |
| 249 | Ab-6 CDR-H2 | EINPNSGGSGYNQKFKG |
| 250 | Ab-6 CDR-H3 | LVYDGSYEDWYFDV |
| 101 | Ab-7 CDR-L1 | RASQVITNYLY |
| 102 | Ab-7 CDR-L2 | YTSRLHS |
| 103 | Ab-7 CDR-L3 | QQGDTLPYT |
| 251 | Ab-7 CDR-H1 | DYNMH |
| 252 | Ab-7 CDR-H2 | EINPNSGGAGYNQQFKG |
| 253 | Ab-7 CDR-H3 | LGYVGNYEDWYFDV |
| 104 | Ab-8 CDR-L1 | RASQDISNYLN |
| 105 | Ab-8 CDR-L2 | YTSRLLS |
| 106 | Ab-8 CDR-L3 | QQGDTLPYT |
| 254 | Ab-8 CDR-H1 | DYNMH |
| 255 | Ab-8 CDR-H2 | EINPNSGGAGYNQKFKG |
| 256 | Ab-8 CDR-H3 | LGYDDIYDDWYFDV |
| 107 | Ab-9 CDR-L1 | RASQDISNYLN |
| 108 | Ab-9 CDR-L2 | YTSRLFS |
| 109 | Ab-9 CDR-L3 | QQGDTLPYT |
| 257 | Ab-9 CDR-H1 | DYNMH |
| 258 | Ab-9 CDR-H2 | EINPNSGGAGYNQKFKG |
| 259 | Ab-9 CDR-H3 | LGYDDIYDDWYFDV |
| 110 | Ab-10 CDR-L1 | RASQDISNYLN |
| 111 | Ab-10 CDR-L2 | YTSRLLS |
| 112 | Ab-10 CDR-L3 | QQGDTLPYT |
| 260 | Ab-10 CDR-H1 | DYNMH |
| 261 | Ab-10 CDR-H2 | EINPNSGGAGYNQKFKG |
| 262 | Ab-10 CDR-H3 | LGYDDIYDDWYFDV |
| 281 | Ab-11 and Ab-16 CDR-L1 | RASSSISYIH |
| 282 | Ab-11 and Ab-16 CDR-L2 | ATSNLAS |
| 283 | Ab-11 and Ab-16 CDR-L3 | QQWSSDPLT |
| 293 | Ab-11 and Ab-16 CDR-H1 | DYYIH |
| 294 | Ab-11 and Ab-16 CDR-H2 | RVDPDNGETEFAPKFPG |
| 295 | Ab-11 and Ab-16 CDR-H3 | EDYDGTYTWFPY |
| 113 | Ab-12 CDR-L1 | RASQDISNYLN |
| 114 | Ab-12 CDR-L2 | YTSTLQS |
| 115 | Ab-12 CDR-L3 | QQGDTLPYT |
| 263 | Ab-12 CDR-H1 | DYNMH |
| 264 | Ab-12 CDR-H2 | EINPNSGGSGYNQKFKG |
| 265 | Ab-12 CDR-H3 | LGYYGNYEDWYFDV |
| 284 | Ab-13 and Ab-14 CDR-L1 | RASSSVTSSYLN |
| 285 | Ab-13 and Ab-14 CDR-L2 | STSNLAS |
| 286 | Ab-13 and Ab-14 CDR-L3 | QQYDFFPST |
| 296 | Ab-13 and Ab-14 CDR-H1 | DYYMN |
| 297 | Ab-13 and Ab-14 CDR-H2 | DINPYNDDTTYNHKFKG |
| 298 | Ab-13 and Ab-14 CDR-H3 | ETAVITTNAMD |
| 116 | Ab-17 and Ab-18 CDR-L1 | SVSSSISSSNLH |
| 237 | Ab-17 and Ab-18 CDR-L2 | GTSNLAS |
| 238 | Ab-17 and Ab-18 CDR-L3 | QQWTTTYT |
| 266 | Ab-17 and Ab-18 CDR-H1 | DYYIH |
| 267 | Ab-17 and Ab-18 CDR-H2 | RIDPDNGESTYVPKFQG |
| 268 | Ab-17 and Ab-18 CDR-H3 | EGLDYGDYYAVDY |
| 239 | Ab-19, Ab-20 and Ab-23 CDR-L1 | RASQDISSYLN |
| 240 | Ab-19, Ab-20 and Ab-23 CDR-L2 | STSRLNS |
| 241 | Ab-19, Ab-20 and Ab-23 CDR-L3 | QQDIKHPT |
| 269 | Ab-19, Ab-20 and Ab-23 CDR-H1 | DYIMH |
| 270 | Ab-19, Ab-20 and Ab-23 CDR-H2 | YINPYNDDTEYNEKFKG |
| 271 | Ab-19, Ab-20 and Ab-23 CDR-H3 | SIYYYDAPFAY |
| 242 | Ab-21 and Ab-22 CDR-L1 | KASQDVFTAVA |
| 243 | Ab-21 and Ab-22 CDR-L2 | WASTRHT |
| 244 | Ab-21 and Ab-22 CDR-L3 | QQYSSYPLT |
| 272 | Ab-21 and Ab-22 CDR-H1 | DYYMH |
| 273 | Ab-21 and Ab-22 CDR-H2 | RIDPENGDIIYDPKFQG |
| 274 | Ab-21 and Ab-22 CDR-H3 | DAGDPAWFTY |
| 351 | Ab-24 CDR-L1 | KASQSVDYDGTSYMN |
| 352 | Ab-24 CDR-L2 | AASNLES |
| 353 | Ab-24 CDR-L3 | QQSNEDPFT |
| 358 | Ab-24 CDR-H1 | TYWMN |
| 359 | Ab-24 CDR-H2 | MIHPSASEIRLDQKFKD |
| 360 | Ab-24 CDR-H3 | SGEWGSMDY |

An oligopeptide or polypeptide is within the scope of the invention if it has an amino acid sequence that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to least one of the CDR's of Table 1 above; and/or to a CDR of a sclerostin binding agent that cross-blocks the binding of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24 to sclerostin, and/or is cross-blocked from binding to sclerostin by at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24; and/or to a CDR of a sclerostin binding agent wherein the binding agent can block the inhibitory effect of sclerostin in a cell based mineralization assay (i.e. a sclerostin neutralizing binding agent); and/or to a CDR of a sclerostin binding agent that binds to a Loop 2 epitope; and/or to a CDR of a sclerostin binding agent that binds to a T20.6 epitope; and/or to a CDR of a sclerostin binding agent that binds to a "T20.6 derivative (cystine-knot+4 arms)" epitope.

Sclerostin binding agent polypeptides and antibodies are within the scope of the invention if they have amino acid sequences that are at least 85%, 86%, 87%, 88%, 89%, 90%, 91%, 92%, 93%, 94%, 95%, 96%, 97%, 98% or 99% identical to a variable region of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24, and cross-block the binding of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24 to sclerostin, and/or are cross-blocked from binding to sclerostin by at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24; and/or can block the inhibitory effect of sclerostin in a cell based mineralization assay (i.e. a sclerostin neutralizing binding agent); and/or bind to a Loop 2 epitope; and/or bind to a T20.6 epitope; and/or bind to a "T20.6 derivative (cystine-knot+4 arms)" epitope.

Polynucleotides encoding sclerostin binding agents are within the scope of the invention if they have polynucleotide sequences that are at least 85%, 86%, 87%, 88%, 89%, 90%, 91%, 92%, 93%, 94%, 95%, 96%, 97%, 98% or 99% identical to a polynucleotide encoding a variable region of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24, and wherein the encoded sclerostin binding agents cross-block the binding of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24 to sclerostin, and/or are cross-blocked from binding to sclerostin by at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24; and/or can block the inhibitory effect of sclerostin in a cell based mineralization assay (i.e. a sclerostin neutralizing binding agent); and/or bind to a Loop 2 epitope; and/or bind to a T20.6 epitope; and/or bind to a "T20.6 derivative (cystine-knot+4 arms)" epitope.

Antibodies according to the invention may have a binding affinity for human sclerostin of less than or equal to $1 \times 10^{-7}$ M, less than or equal to $1 \times 10^{-8}$ M, less than or equal to $1 \times 10^{-9}$ M, less than or equal to $1 \times 10^{-10}$ M, less than or equal to $1 \times 10^{-1}$ M, or less than or equal to $1 \times 10^{-12}$ M.

The affinity of a binding agent such as an antibody or binding partner, as well as the extent to which a binding agent (such as an antibody) inhibits binding, can be determined by one of ordinary skill in the art using conventional techniques, for example those described by Scatchard et al (*Ann. N.Y. Acad. Sci.* 51:660-672 (1949)) or by surface plasmon resonance (SPR; BIAcore, Biosensor, Piscataway, N.J.). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al., *Cancer Res.* 53:2560-65 (1993)).

An antibody according to the present invention may belong to any immunoglobin class, for example IgG, IgE, IgM, IgD, or IgA. It may be obtained from or derived from an animal, for example, fowl (e.g., chicken) and mammals, which includes but is not limited to a mouse, rat, hamster, rabbit, or other rodent, cow, horse, sheep, goat, camel, human, or other primate. The antibody may be an internalizing antibody. Production of antibodies is disclosed generally in U.S. Patent Publication No. 2004/0146888 A1.

Characterization Assays

In the methods described above to generate antibodies according to the invention, including the manipulation of the specific Ab-A, Ab-B, Ab-C, Ab-D, and Antibody 1-24 (Ab-1 to Ab-24) CDRs into new frameworks and/or constant regions, appropriate assays are available to select the desired antibodies or binding agents (i.e. assays for determining binding affinity to sclerostin; cross-blocking assays; Biacore-based "human sclerostin peptide epitope competition binding assay;" MC3T3-E1 cell based assay; in vivo assays).

Epitope Binding Assays

Figure 9:
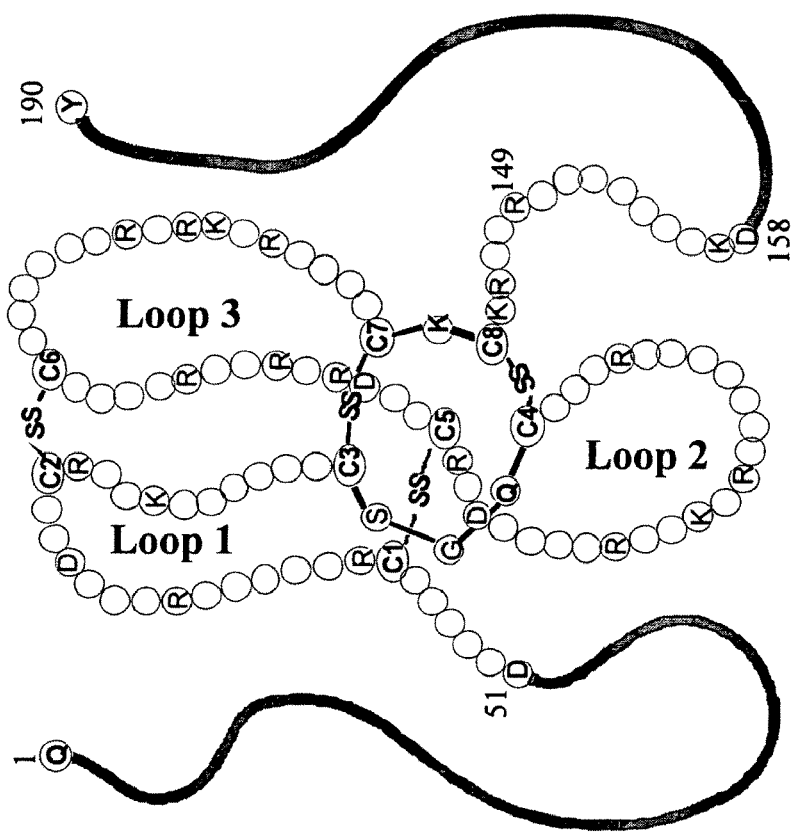
FIG. 9 depicts a schematic of the basic structure of human sclerostin. There is an N-terminal arm (from the first Q to C1) and a C-terminal arm (from C8 to the terminal Y). In between these arms there is the cystine-knot structure (formed by three disulfides: C1-C5; C3-C7; C4-C8) and three loops which are designated Loop 1, Loop 2 and Loop 3. The distal regions of Loop 1 and Loop 3 are linked by the C2-C6 disulfide. Potential trypsin cleavage sites are indicated (arginine=R and lysine=K). Some of the potential AspN cleavage sites are indicated (only aspartic acid (D) residues are shown).

Mature form human sclerostin is a 190 amino acid glycoprotein with a cystine-knot structure (FIGS. 8 and 9). In addition to the cystine-knot structure, the protein is characterized as having three loops designated as Loop 1, Loop 2 and Loop 3. Human sclerostin was subjected to proteolytic digestion to produce fragments. Briefly, using different proteases, including trypsin, aspN, and lysC, fragments with various cleavage sites and sizes were generated. The sequences and mass for various human sclerostin peptides were determined. Antibody protection was evaluated to determine the effect on accessibility for proteolysis, including clipped site masking and peptide shifting. Finally, a BIAcore-based "human sclerostin peptide epitope competition assay" was performed.

Figure 13:
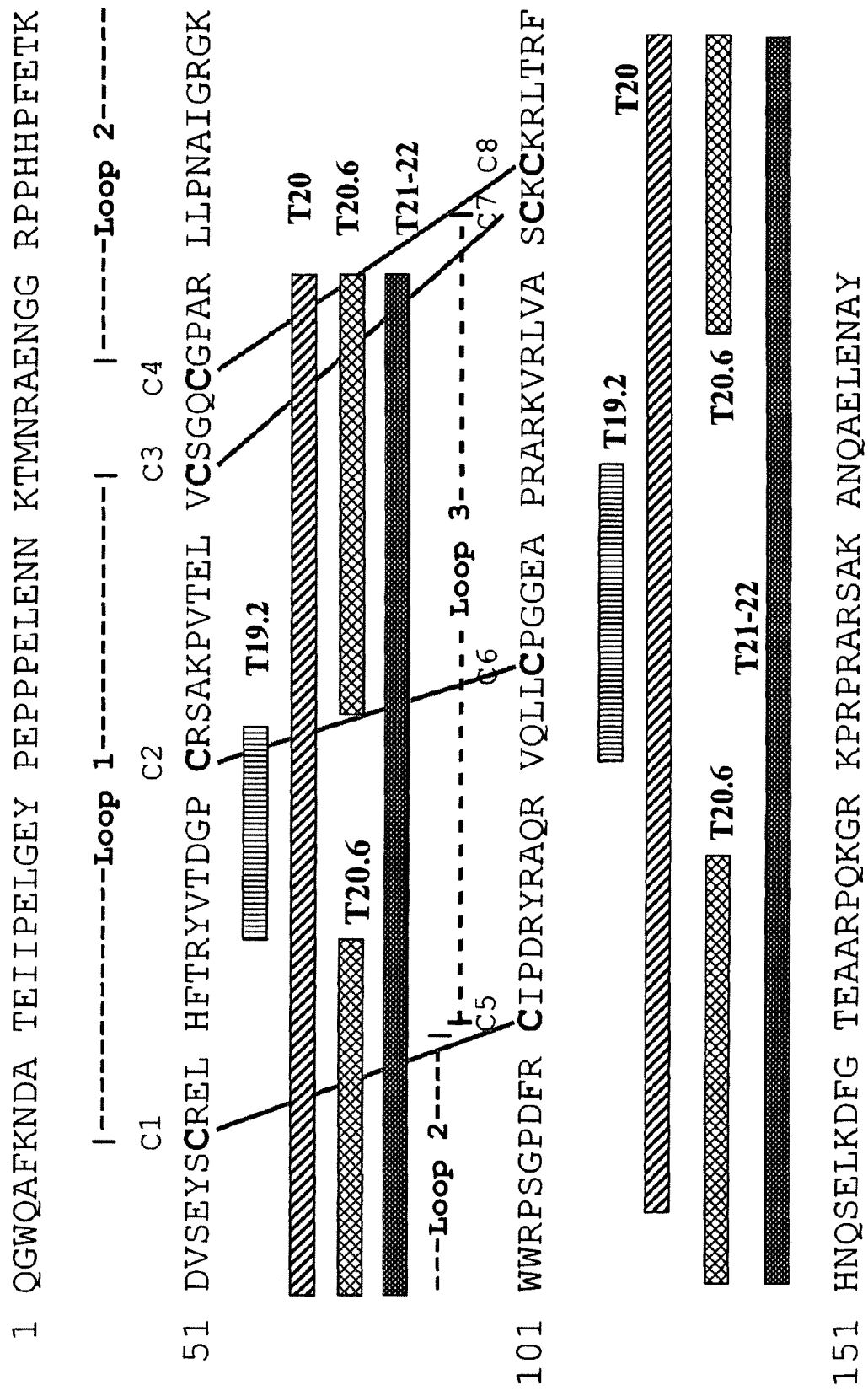
FIG. 13 shows a linear schematic of four human sclerostin peptides (T19.2, T20, T20.6 and T21-22) generated by trypsin digestion.

Exposure of sclerostin to trypsin cleavage resulted in a pattern of peptide fragments as summarized in FIG. 13. The fragments are referred to as T19.2, T20, T20.6, and T21-22. As shown schematically in FIG. 19B, the T20.6 epitope is a complex of four separate peptide sequences which are joined by the three disulfide bonds of the cystine-knot region. Two of the peptides are joined by two disulfide bonds. The other two peptides are linked by one disulfide bond that, schematically, bisects the first two polypeptides.

The T20.6 epitope that was generated by trypsin digestion retains the cystine-knot structure of the native polypeptide and is recognized by antibodies Ab-C and Ab-D. A derivative of epitope T20.6 consists of the cystine-knot region and amino acids 58-64, 73-81, 112-117 and 138-141 in sequence position with reference to SEQ ID NO:1. This derivative epitope is shown in FIG. 21. An epitope comprising the cystine-knot region may have one or more amino acids that is present in the T20.6 epitope (FIG. 19B) but not present in the T20.6 derivative epitope (FIG. 21).

Another epitope-containing region was identified in the Loop 2 region of human sclerostin (FIG. 19A) and is recognized by antibodies Ab-A and Ab-B. A Loop 2 epitope comprises amino acids 86-111 of SEQ ID NO:1 (C4 GPARLLP-NAIGRGKWWRPSGPDFRC5, SEQ ID NO:6). Sterically, with reference to full-length sclerostin of SEQ ID NO:1, the Loop 2-containing structure is defined at one end by a disulfide bond between cysteine at position 86 (C4) and cysteine at position 144 (C8), and at the other end by a disulfide bond between cysteine at position 111 (C5) and cysteine at position 57 (C1).

The peptides generated by aspN cleavage of human sclerostin are shown in FIG. 12. In the Figure, these peptides are designated as AspN14.6, AspN18.6, and AspN22.7-23.5, and are also referred to herein as N14.6, N18.6, and N22.7-23.5, respectively.

One group of antibodies exhibits a specific pattern of binding to certain epitopes as evidenced by a Biacore-based "human sclerostin peptide epitope competition binding assay." Briefly, the antibody is preincubated with the epitope to be tested, at concentrations that will saturate the epitope-binding sites on the antibody. The antibody is then exposed to sclerostin bound to a chip surface. After the appropriate incubation and washing procedures, a pattern of competitive binding is established. As shown in FIG. 18, exemplary antibody Ab-D bound to sclerostin molecules attached to the surface of the chip. Preincubation of antibody Ab-D with sclerostin decreased the binding of the antibody to the sclerostin on the chip to close to zero. Preincubation with a peptide consisting of epitope T19.2 showed that T19.2 did not compete with sclerostin for antibody binding. However, preincubation with any one of the epitopes designated T20, T20.6, T21-22, or N22.7-23.5 abolished a large proportion of the binding of antibody to sclerostin on the chip. In contrast, preincubation of the antibody with any one of the epitopes designated T19.2, N14.6 or N18.6 did not abolish the ability of the antibody to bind to sclerostin. A second exemplary antibody with this binding profile (FIG. 17) is Ab-C.

Antibody Ab-D therefore is exemplary and representative of a group of antibodies that bind to the epitopes T20, T20.6, T21-22, and N22.7-23.5, and have minimal detectable binding to epitopes T19.2, N14.6 and N18.6, as measured by the ability to block antibody binding to sclerostin. Antibodies having this characteristic binding pattern may or may not share amino acid sequence in one or more regions of the antibody molecule. Antibody similarity is determined functionally such as by the ability to bind to sclerostin following preincubation with each of the epitopes described above. Antibodies that exhibit a binding pattern similar or identical to that of antibody Ab-D are included in the invention. By "similar to" is meant, for example, the antibody will exhibit binding to each of the polypeptides T20, T20.6, T21-22 and N22.7-23.5 whereby this binding will specifically compete out at least 50% of the antibody's binding to sclerostin that would otherwise occur in the absence of preincubation with sclerostin or a sclerostin peptide. The antibody will also exhibit little or no detectable binding to polypeptides T19.2, N14.6 and N18.6, resulting in a reduction of 30% or less of the binding that would occur in the absence of preincubation with sclerostin or a sclerostin peptide.

For example, without being bound by a particular mechanism, the antibody binding pattern of FIG. 18 suggests that the epitope space to which antibody Ab-D and other antibodies having the epitope binding pattern of Ab-D bind consists of a polypeptide comprising the cystine-knot region of sclerostin.

Figure 19:
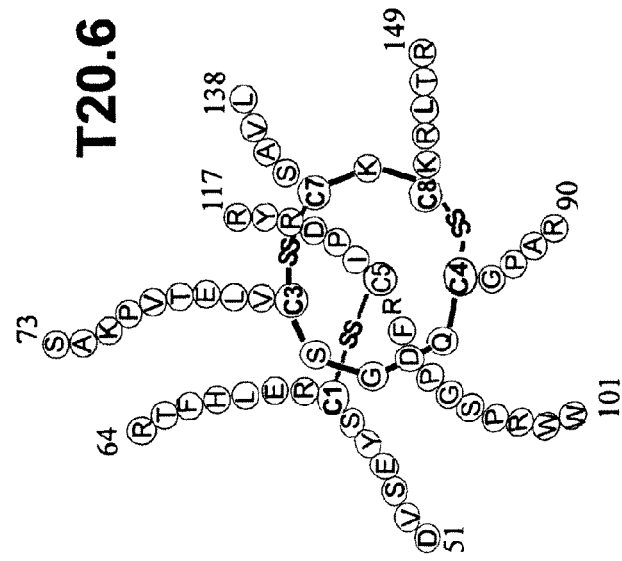
FIG. 19 shows two Mab binding epitopes of human sclerostin.

Thus, as disclosed herein and with reference to FIG. 19B, an exemplary T20.6 epitope comprises four peptide chains attached via three separate disulfide bonds. Peptide chain SAKPVTELVC3SGQC4GPAR (SEQ ID NO:3) is attached to peptide chain LVASC7KC8KRLTR (SEQ ID NO:5) by disulfide bonds from C3 to C7, and from C4 to C8. Peptide chain DVSEYSC1RELHFTR (SEQ ID NO:2) is attached to peptide chain WWRPSGPDFRC51PDRYR (SEQ ID NO:4) by a disulfide bond from C1 to C5. The polypeptides of SEQ ID NOs:3 and 5 remain associated with the polypeptides of SEQ ID NOs:2 and 4 through a steric construct whereby the C1-C5 bond crosses the plane of the C4-C8 and C3-C7 bonds and is located between them, as illustrated in FIG. 19B.

As disclosed herein and with reference to FIG. 21, an exemplary derivative epitope of T20.6 comprises four peptide chains attached via three separate disulfide bonds. Peptide chain SAKPVTELVC3SGQC4 (SEQ ID NO:70) is attached to peptide chain LVASC7KC8 (SEQ ID NO:71) by disulfide bonds from C3 to C7, and from C4 to C8. Peptide chain C1RELHFTR (SEQ ID NO:72) is attached to peptide chain C51PDRYR (SEQ ID NO:73) by a disulfide bond from C1 to C5. The polypeptides of SEQ ID NOs:70 and 71 remain associated with the polypeptides of SEQ ID NOs:72 and 73 through a steric construct whereby the C1-C5 bond crosses the plane of the C4-C8 and C3-C7 bonds and is located between them, as illustrated in FIG. 21.

Antibody Ab-A is exemplary and representative of a second group of antibodies that have a characteristic binding pattern to human sclerostin peptides that is distinct from that obtained for antibodies Ab-C and Ab-D. Ab-A and the group of antibodies it represents bind to the N22.7-23.5 epitope and have minimal detectable binding to epitopes T19.2, T20, T20.6, T21-22, N14.6 or N18.6, as measured by the ability to block antibody binding to sclerostin (FIG. 15). A second exemplary antibody with this binding profile (FIG. 16) is Ab-B. Antibodies having this characteristic binding pattern may or may not share amino acid sequence in one or more regions of the antibody molecule. Antibody similarity is determined functionally such as by the ability to bind to sclerostin following preincubation with each of the epitopes described above. Antibodies that exhibit a binding pattern similar or identical to that of antibody Ab-A are included in the invention. By "similar to" is meant, for example, the antibody will exhibit binding to the N22.7-23.5 polypeptide whereby this binding will specifically compete out at least 50% of the antibody's binding to sclerostin that would otherwise occur in the absence of preincubation with sclerostin or a sclerostin peptide. The antibody will also exhibit little or no detectable binding to polypeptides T19.2, T20, T20.6, T21-22, N14.6 and N18.6, resulting in a reduction of 30% or less of the binding that would occur in the absence of preincubation with sclerostin or a sclerostin peptide.

For example, without being bound by a particular mechanism, the antibody binding pattern of FIG. 15 suggests that the epitope space to which antibody Ab-A and other antibodies having the epitope binding pattern of Ab-A bind consists of a polypeptide comprising the Loop 2 region of sclerostin. Thus, as disclosed herein and with reference to FIG. 19A, the Loop 2 region can be described as a linear peptide, but it acquires a tertiary structure when it is present in native sclerostin or a cystine-knot-containing portion of sclerostin in which the native disulfide bond structure is maintained. The linear or tertiary structure of the Loop 2 epitope can affect antibody binding thereto, as discussed in the Examples. A Loop 2 region can comprise the following amino acid sequence: C4 GPARLLPNAIGRGKWWRPSGPDFRC5 (SEQ ID NO:6). "C4" refers to a cysteine residue located at position 86 with reference to SEQ ID NO:1. "C5" refers to a cysteine residue located at position 111 with reference to SEQ ID NO:1. In native sclerostin protein, C4 is linked to a cysteine at position 144 (C8) by a disulfide bond, and C5 is linked to a cysteine at position 57 (C1) by a disulfide bond. Epitopes derived from the Loop 2 region include CGPARLLP-NAIGRGKWWRPS (SEQ ID NO:63); GPARLLP-NAIGRGKWWRPSG (SEQ ID NO:64); PARLLP-NAIGRGKWWRPSGP (SEQ ID NO:65); ARLLPNAIGRGKWWRPSGPD (SEQ ID NO:66); RLLP-NAIGRGKWWRPSGPDF (SEQ ID NO:67); LLP-NAIGRGKWWRPSGPDFR (SEQ ID NO:68); and LPNAIGRGKWWRPSGPDFRC (SEQ ID NO:69)

Cross-Blocking Assays

The terms "cross-block", "cross-blocked" and "cross-blocking" are used interchangeably herein to mean the ability of an antibody or other binding agent to interfere with the binding of other antibodies or binding agents to sclerostin.

The extent to which an antibody or other binding agent is able to interfere with the binding of another to sclerostin, and therefore whether it can be said to cross-block according to the invention, can be determined using competition binding assays. One particularly suitable quantitative assay uses a Biacore machine which can measure the extent of interactions using surface plasmon resonance technology. Another suitable quantitative cross-blocking assay uses an ELISA-based approach to measure competition between antibodies or other binding agents in terms of their binding to sclerostin.

Biacore Cross-Blocking Assay

The following generally describes a suitable Biacore assay for determining whether an antibody or other binding agent cross-blocks or is capable of cross-blocking according to the invention. For convenience reference is made to two antibodies, but it will be appreciated that the assay can be used with any of the sclerostin binding agents described herein. The Biacore machine (for example the Biacore 3000) is operated in line with the manufacturer's recommendations.

Thus in one cross-blocking assay, sclerostin is coupled to a CM5 Biacore chip using standard amine coupling chemistry to generate a sclerostin-coated surface. Typically 200-800 resonance units of sclerostin would be coupled to the chip (an amount that gives easily measurable levels of binding but that is readily saturable by the concentrations of test reagent being used).

The two antibodies (termed A* and B*) to be assessed for their ability to cross-block each other are mixed at a one to one molar ratio of binding sites in a suitable buffer to create the test mixture. When calculating the concentrations on a binding site basis the molecular weight of an antibody is assumed to be the total molecular weight of the antibody divided by the number of sclerostin binding sites on that antibody.

The concentration of each antibody in the test mix should be high enough to readily saturate the binding sites for that antibody on the sclerostin molecules captured on the Biacore chip. The antibodies in the mixture are at the same molar concentration (on a binding basis) and that concentration would typically be between 1.00 and 1.5 micromolar (on a binding site basis).

Separate solutions containing antibody A* alone and antibody B* alone are also prepared. Antibody A* and antibody B* in these solutions should be in the same buffer and at the same concentration as in the test mix.

The test mixture is passed over the sclerostin-coated Biacore chip and the total amount of binding recorded. The chip is then treated in such a way as to remove the bound antibodies without damaging the chip-bound sclerostin. Typically this is done by treating the chip with 30 mM HCl for 60 seconds.

The solution of antibody A* alone is then passed over the sclerostin-coated surface and the amount of binding recorded. The chip is again treated to remove all of the bound antibody without damaging the chip-bound sclerostin.

The solution of antibody B* alone is then passed over the sclerostin-coated surface and the amount of binding recorded.

The maximum theoretical binding of the mixture of antibody A* and antibody B* is next calculated, and is the sum of the binding of each antibody when passed over the sclerostin surface alone. If the actual recorded binding of the mixture is less than this theoretical maximum then the two antibodies are cross-blocking each other.

Thus, in general, a cross-blocking antibody or other binding agent according to the invention is one which will bind to sclerostin in the above Biacore cross-blocking assay such that during the assay and in the presence of a second antibody or other binding agent of the invention the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two antibodies or binding agents in combination.

The Biacore assay described above is a primary assay used to determine if antibodies or other binding agents cross-block each other according to the invention. On rare occasions particular antibodies or other binding agents may not bind to sclerostin coupled via amine chemistry to a CM5 Biacore chip (this usually occurs when the relevant binding site on sclerostin is masked or destroyed by the coupling to the chip). In such cases cross-blocking can be determined using a tagged version of Sclerostin, for example N-terminal His-tagged Sclerostin (R & D Systems, Minneapolis, Minn., USA; 2005 cat#1406-ST-025). In this particular format, an anti-His antibody would be coupled to the Biacore chip and then the His-tagged Sclerostin would be passed over the surface of the chip and captured by the anti-His antibody. The cross blocking analysis would be carried out essentially as described above, except that after each chip regeneration cycle, new His-tagged sclerostin would be loaded back onto the anti-His antibody coated surface. In addition to the example given using N-terminal His-tagged Sclerostin, C-terminal His-tagged sclerostin could alternatively be used. Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin).

ELISA-Based Cross-Blocking Assay

The following generally describes an ELISA assay for determining whether an anti-sclerostin antibody or other sclerostin binding agent cross-blocks or is capable of cross-blocking according to the invention. For convenience, reference is made to two antibodies (Ab-X and Ab-Y), but it will be appreciated that the assay can be used with any of the sclerostin binding agents described herein.

The general principal of the assay is to have an anti-sclerostin antibody coated onto the wells of an ELISA plate. An excess amount of a second, potentially cross-blocking, anti-sclerostin antibody is added in solution (i.e. not bound to the ELISA plate). A limited amount of sclerostin is then added to the wells. The coated antibody and the antibody in solution compete for binding of the limited number of sclerostin molecules. The plate is washed to remove sclerostin that has not been bound by the coated antibody and to also remove the second, solution phase antibody as well as any complexes formed between the second, solution phase antibody and sclerostin. The amount of bound sclerostin is then measured using an appropriate sclerostin detection reagent. An antibody in solution that is able to cross-block the coated antibody will be able to cause a decrease in the number of sclerostin molecules that the coated antibody can bind relative to the number of sclerostin molecules that the coated antibody can bind in the absence of the second, solution phase, antibody.

This assay is described in more detail further below for Ab-X and Ab-Y. In the instance where Ab-X is chosen to be the immobilized antibody, it is coated onto the wells of the ELISA plate, after which the plates are blocked with a suitable blocking solution to minimize non-specific binding of reagents that are subsequently added. An excess amount of Ab-Y is then added to the ELISA plate such that the moles of Ab-Y sclerostin binding sites per well are at least 10 fold higher than the moles of Ab-X sclerostin binding sites that were used, per well, during the coating of the ELISA plate. Sclerostin is then added such that the moles of sclerostin added per well are at least 25-fold lower than the moles of Ab-X sclerostin binding sites that were used for coating each well. Following a suitable incubation period the ELISA plate is washed and a sclerostin detection reagent is added to measure the amount of sclerostin specifically bound by the coated anti-sclerostin antibody (in this case Ab-X). The background signal for the assay is defined as the signal obtained in wells with the coated antibody (in this case Ab-X), second solution phase antibody (in this case Ab-Y), sclerostin buffer only (i.e. no sclerostin) and sclerostin detection reagents. The positive control signal for the assay is defined as the signal obtained in wells with the coated antibody (in this case Ab-X), second solution phase antibody buffer only (i.e. no second solution phase antibody), sclerostin and sclerostin detection reagents. The ELISA assay needs to be run in such a manner so as to have the positive control signal be at least 6 times the background signal.

To avoid any artifacts (e.g. significantly different affinities between Ab-X and Ab-Y for sclerostin) resulting from the choice of which antibody to use as the coating antibody and which to use as the second (competitor) antibody, the cross-blocking assay needs to be run in two formats:

1) format 1 is where Ab-X is the antibody that is coated onto the ELISA plate and Ab-Y is the competitor antibody that is in solution and 2) format 2 is where Ab-Y is the antibody that is coated onto the ELISA plate and Ab-X is the competitor antibody that is in solution.

Ab-X and Ab-Y are defined as cross-blocking if, either in format 1 or in format 2, the solution phase anti-sclerostin antibody is able to cause a reduction of between 60% and 100%, specifically between 70% and 100%, and more specifically between 80% and 100%, of the sclerostin detection signal (i.e. the amount of sclerostin bound by the coated antibody) as compared to the sclerostin detection signal obtained in the absence of the solution phase anti-sclerostin antibody (i.e. the positive control wells).

An example of such an ELISA-based cross blocking assay can be found in Example 7 ("ELISA-based cross-blocking assay").

Cell Based Neutralization Assay

Mineralization by osteoblast-lineage cells in culture, either primary cells or cell lines, is used as an in vitro model of bone formation. Mineralization takes from about one to six weeks to occur beginning with the induction of osteoblast-lineage cell differentiation by one or more differentiation agents. The overall sequence of events involves cell proliferation, differentiation, extracellular matrix production, matrix maturation and finally deposition of mineral, which refers to crystallization and/or deposition of calcium phosphate. This sequence of events starting with cell proliferation and differentiation, and ending with deposition of mineral is referred to herein as mineralization. Measurement of calcium (mineral) is the output of the assay.

MC3T3-E1 cells (Sudo H, Kodama H-A, Amagai Y, Yamamoto S, Kasai S. 1983. *In vitro differentiation and calcification in a new clonal osteogenic cell line derived from newborn mouse calvaria*. J. Cell Biol. 96:191-198) and subclones of the original cell line can form mineral in culture upon growth in the presence of differentiating agents. Such subclones include MC3T3-E1-BF (Smith E, Redman R, Logg C, Coetzee G, Kasahara N, Frenkel B. 2000. *Glucocorticoids inhibit developmental stage-specific osteoblast cell cycle*. J. Biol. Chem. 275:19992-20001). For both the MC3T3-E1-BF subclone as well as the original MC3T3-E1 cells, sclerostin can inhibit one or more of the sequence of events leading up to and including mineral deposition (i.e. sclerostin inhibits mineralization). Anti-sclerostin antibodies that are able to neutralize sclerostin's inhibitory activity allow for mineralization of the culture in the presence of sclerostin such that there is a statistically significant increase in deposition of calcium phosphate (measured as calcium) as compared to the amount of calcium measured in the sclerostin-only (i.e. no antibody) treatment group. The antibodies used in the cell based mineralization assay experiments shown in FIGS. 22, 23 and 24 have molecular weights of about 145 Kd and have 2 sclerostin binding sites per antibody molecule.

When running the assay with the goal of determining whether a particular anti-sclerostin antibody or anti-sclerostin binding agent can neutralize sclerostin (i.e., is a sclerostin neutralizing antibody or derivative thereof, or is a sclerostin neutralizing binding agent), the amount of sclerostin used in the assay needs to be the minimum amount of sclerostin that causes at least a 70%, statistically significant, reduction in deposition of calcium phosphate (measured as calcium) in the sclerostin-only group, as compared to the amount of calcium measured in the no sclerostin group. An anti-sclerostin neutralizing antibody or an anti-sclerostin neutralizing binding agent is defined as one that causes a statistically significant increase in deposition of calcium phosphate (measured as calcium) as compared to the amount of calcium measured in the sclerostin-only (i.e. no antibody, no binding agent) treatment group. To determine whether an anti-sclerostin antibody or an anti-sclerostin binding agent is neutralizing or not, the amount of anti-sclerostin antibody or anti-sclerostin binding agent used in the assay needs to be such that there is an excess of moles of sclerostin binding sites per well as compared to the number of moles of sclerostin per well. Depending on the potency of the antibody, the fold excess that may be required can be 24, 18, 12, 6, 3, or 1.5, and one of skill is familiar with the routine practice of testing more than one concentration of binding agent. For example, a very potent anti-sclerostin neutralizing antibody or anti-sclerostin neutralizing binding agent will be able to neutralize sclerostin even when there is less than a 6-fold excess of moles of sclerostin binding sites per well as compared to the number of moles of sclerostin per well. A less potent anti-sclerostin neutralizing antibody or anti-sclerostin neutralizing binding agent will be able to neutralize sclerostin only at a 12, 18 or 24 fold excess. Sclerostin binding agents within this full range of potencies are suitable as neutralizing sclerostin binding agents. Exemplary cell based mineralization assays are described in detail in Example 8.

Anti-sclerostin antibodies and derivatives thereof that can neutralize human sclerostin, and sclerostin binding agents that can neutralize human sclerostin may be of use in the treatment of human conditions/disorders that are caused by, associated with, or result in at least one of low bone formation, low bone mineral density, low bone mineral content, low bone mass, low bone quality and low bone strength.

In Vivo Neutralization Assay

Increases in various parameters associated with, or that result from, the stimulation of new bone formation can be measured as an output from in vivo testing of sclerostin binding agents in order to identify those binding agents that are able to neutralize sclerostin and thus able to cause stimulation of new bone formation. Such parameters include various serum anabolic markers [e.g. osteocalcin, PINP (n-terminal propeptide of type I procollagen)], histomorphometric markers of bone formation (e.g. osteoblast surface/bone surface; bone formation rate/bone surface; trabecular thickness), bone mineral density, bone mineral content, bone mass, bone quality and bone strength. A sclerostin neutralizing binding agent is defined as one capable of causing a statistically significant increase, as compared to vehicle treated animals, in any parameter associated with, or that results from, the stimulation of new bone formation. Such in vivo testing can be performed in any suitable mammal (e.g. mouse, rat, monkey). An example of such in vivo testing can be found in Example 5 ("In vivo testing of anti-sclerostin monoclonal antibodies").

Although the amino acid sequence of sclerostin is not 100% identical across mammalian species (e.g. mouse sclerostin is not 100% identical to human sclerostin), it will be appreciated by one skilled in the art that a sclerostin binding agent that can neutralize, in vivo, the sclerostin of a certain species (e.g. mouse) and that also can bind human sclerostin in vitro is very likely to be able to neutralize human sclerostin in vivo. Thus, such a human sclerostin binding agent (e.g. anti-human sclerostin antibody) may be of use in the treatment of human conditions/disorders that are caused by, associated with, or result in at least one of low bone formation, low bone mineral density, low bone mineral content, low bone mass, low bone quality and low bone strength. Mice in which homologous recombination had been used to delete the mouse sclerostin gene and insert the human sclerostin gene in its place (i.e. human sclerostin gene knock-in mice or human SOST knock-in mice) would be an example of an additional in vivo system.

Pharmaceutical compositions are provided, comprising one of the above-described binding agents such as at least one of antibody Ab-A, Ab-B, Ab-C, Ab-D and Ab-1 to Ab-24 to human sclerostin, along with a pharmaceutically or physiologically acceptable carrier, excipient, or diluent. Pharmaceutical compositions and methods of treatment are disclosed in copending application Ser. No. 10/868,497, filed Jun. 16, 2004, which claims priority to Ser. No. 60/478,977, both of which are incorporated by reference herein.

The development of suitable dosing and treatment regimens for using the particular compositions described herein in a variety of treatment regimens, including e.g., subcutaneous, oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein subcutaneously, parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, *Remington's Pharmaceutical Sci-* ences, 15th ed., pp. 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, *Trends Biotechnol.* 16(7):307-21, 1998; Takakura, *Nippon Rinsho* 56(3): 691-95, 1998; Chandran et al., *Indian J. Exp. Biol.* 35(8):801-09, 1997; Margalit, *Crit. Rev. Ther. Drug Carrier Syst.* 12(2-3):233-61, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety). The use of liposomes does not appear to be associated with autoimmune responses or unacceptable toxicity after systemic delivery. In certain embodiments, liposomes are formed from phospholipids that are dispersed in an aqueous medium and spontaneously form multilamellar concentric bilayer vesicles (also termed multilamellar vesicles (MLVs)).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., *Drug Dev. Ind. Pharm.* 24(12):1113-28, 1998). To avoid side effects due to intracellular polymeric overloading, such ultrafine particles (sized around 0.1 µm) may be designed using polymers able to be degraded in vivo. Such particles can be made as described, for example, by Couvreur et al., *Crit. Rev. Ther. Drug Carrier Syst.* 5(1):1-20, 1988; zur Muhlen et al., *Eur. J. Pharm. Biopharm.* 45(2):149-55, 1998; Zambaux et al., *J. Controlled Release* 50(1-3):3140, 1998; and U.S. Pat. No. 5,145,684.

In addition, pharmaceutical compositions of the present invention may be placed within containers, along with packaging material that provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) that may be necessary to reconstitute the pharmaceutical composition.

The dose administered may range from 0.01 mg/kg to 100 mg/kg of body weight. As will be evident to one of skill in the art, the amount and frequency of administration will depend, of course, on such factors as the nature and severity of the indication being treated, the desired response, the condition of the patient, and so forth. Typically, the compositions may be administered by a variety of techniques, as noted above.

Increases in bone mineral content and/or bone mineral density may be determined directly through the use of X-rays (e.g., Dual Energy X-ray Absorptometry or "DEXA"), or by inference through the measurement of 1) markers of bone formation and/or osteoblast activity, such as, but not limited to, osteoblast specific alkaline phosphatase, osteocalcin, type 1 procollagen C' propeptide (PICP), total alkaline phosphatase (see Comier, *Curr. Opin. in Rheu.* 7:243 (1995)) and serum procollagen 1 N-terminal propeptide (P1NP) and/or 2) markers of bone resorption and/or osteoclast activity including, but not limited to, pyridinoline, deoxypryridinoline, N-telopeptide, urinary hydroxyproline, plasma tartrate-resistant acid phosphatases, and galactosyl hydroxylysine; (see Comier, id); serum TRAP 5b (tartrate-resistant acid phosphatase isoform 5b) and serum cross-linked C-telopeptide (sCTXI). The amount of bone mass may also be calculated from body weights or by using other methods (see Guinness-Hey, *Metab. Bone Dis. Relat. Res.* 5:177-181, 1984). Animals and particular animal models are used in the art for testing the effect of the compositions and methods of the invention on, for example, parameters of bone loss, bone resorption, bone formation, bone strength or bone mineralization that mimic conditions of human disease such as osteoporosis and osteopenias. Examples of such models include the ovariectomized rat model (Kalu, D. N., *The ovariectomized rat model of postmenopausal bone loss. Bone and Mineral* 15:175-192 (1991); Frost, H. M. and Jee, W. S. S. *On the rat model of human osteopenias and osteoporosis. Bone and Mineral* 18:227-236 (1992); and Jee, W. S. S. and Yao, W., *Overview: animal models of osteopenia and osteoporosis. J. Musculoskel. Neuron. Interact.* 1:193-207 (2001)).

Particular conditions which may be treated by the compositions of the present invention include dysplasias, wherein growth or development of bone is abnormal and a wide variety of causes of osteopenia, osteoporosis and bone loss. Representative examples of such conditions include achondroplasia, cleidocranial dysostosis, enchondromatosis, fibrous dysplasia, Gaucher's Disease, hypophosphatemic rickets, Marfan's syndrome, multiple hereditary exotoses, neurofibromatosis, osteogenesis imperfecta, osteopetrosis, osteopoikilosis, sclerotic lesions, pseudoarthrosis, and pyogenic osteomyelitis, periodontal disease, anti-epileptic drug induced bone loss, primary and secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, fabry disease, turner syndrome, Down Syndrome, Klinefelter Syndrome, leprosy, Perthes' Disease, adolescent idiopathic scoliosis, infantile onset multi-system inflammatory disease, Winchester Syndrome, Menkes Disease, Wilson's Disease, ischemic bone disease (such as Legg-Calve-Perthes disease, regional migratory osteoporosis), anemic states, conditions caused by steroids, glucocorticoid-induced bone loss, heparin-induced bone loss, bone marrow disorders, scurvy, malnutrition, calcium deficiency, idiopathic osteopenia or osteoporosis, congenital osteopenia or osteoporosis, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, fibrous dysplasia, chemotherapy associated bone loss, tumor induced bone loss, cancer-related bone loss, hormone ablative bone loss, multiple myeloma, drug-induced bone loss, anorexia nervosa, disease associated facial bone loss, disease associated cranial bone loss, disease associated bone loss of the jaw, disease associated bone loss of the skull, and bone loss associated with space travel. Further conditions relate to bone loss associated with aging, including facial bone loss associated with aging, cranial bone loss associated with aging, jaw bone loss associated with aging, and skull bone loss associated with aging.

Compositions of the present invention may also be useful for improving outcomes in orthopedic procedures, dental procedures, implant surgery, joint replacement, bone grafting, bone cosmetic surgery and bone repair such as fracture healing, nonunion healing, delayed union healing and facial reconstruction. One or more compositions may be administered before, during and/or after the procedure, replacement, graft, surgery or repair.

The invention also provides a diagnostic kit comprising at least one anti-sclerostin binding agent according to the present invention. The binding agent may be an antibody. In addition, such a kit may optionally comprise one or more of the following:
  (1) instructions for using the one or more binding agent(s) for screening, diagnosis, prognosis, therapeutic monitoring or any combination of these applications;
  (2) a labeled binding partner to the anti-sclerostin binding agent(s);
  (3) a solid phase (such as a reagent strip) upon which the anti-sclerostin binding agent(s) is immobilized; and
  (4) a label or insert indicating regulatory approval for screening, diagnostic, prognostic or therapeutic use or any combination thereof.

If no labeled binding partner to the binding agent(s) is provided, the binding agent(s) itself can be labeled with one or more of a detectable marker(s), e.g. a chemiluminescent, enzymatic, fluorescent, or radioactive moiety.

The following examples are offered by way of illustration, and not by way of limitation.

EXAMPLES

Example 1

Recombinant Expression of Sclerostin

Recombinant human sclerostin/SOST is commercially available from R&D Systems (Minneapolis, Minn., USA; 2006 cat# 1406-ST-025). Additionally, recombinant mouse sclerostin/SOST is commercially available from R&D Systems (Minneapolis, Minn., USA; 2006 cat# 1589-ST-025).

Alternatively, the different species of sclerostin can be expressed transiently in serum-free suspension adapted 293T or 293EBNA cells. Transfections can be performed as 500 mL or 1 L cultures. The following reagents and materials are available from Gibco BRL (now Invitrogen, Carlsbad, Calif.). Catalog numbers are listed in parentheses: serum-free DMEM (21068-028); DMEM/F12 (3:1) (21068/11765); 1× Insulin-Transferrin-Selenium Supplement (51500-056); 1× Pen Strep Glut (10378-016); 2 mM 1-Glutamine (25030-081); 20 mM HEPES (15630-080); 0.01% Pluronic F68 (24040-032). Briefly, the cell inoculum ($5.0–10.0 \times 10^5$ cells/mL×culture volume) is centrifuged at 2,500 RPM for 10 minutes at 4° C. to remove the conditioned medium.

The cells are resuspended in serum-free DMEM and centrifuged again at 2,500 RPM for 10 minutes at 4° C. After aspirating the wash solution, the cells are resuspended in growth medium [DMEM/F12 (3:1)+1× Insulin-Transferrin-Selenium Supplement+1× Pen Strep Glut+2 mM L-Glutamine+20 mM HEPES+0.01% Pluronic F68] in a 1 L or 3 L spinner flask culture. The spinner flask culture is maintained on magnetic stir plate at 125 RPM which is placed in a humidified incubator maintained at 37° C. and 5% $CO_2$. The mammalian expression plasmid DNA (e.g. pcDNA3.1, pCEP4, Invitrogen Life Technologies, Carlsbad, Calif.), containing the complete coding region (and stop codon) of sclerostin with a Kozak consensus sequence (e.g., CCACC) directly 5' of the start site ATG, is complexed to the transfection reagent in a 50 mL conical tube.

The DNA-transfection reagent complex can be prepared in 5-10% of the final culture volume in serum-free DMEM or OPTI-MEM. The transfection reagents that can be used for this purpose include X-tremeGene RO-1539 (Roche Applied Science, Indianapolis, Ind.), FuGene6 (Roche Applied Science, Indianapolis, Ind.), Lipofectamine 2000 (Invitrogen, Carlsbad, Calif.) and 293fectin (Invitrogen, Carlsbad, Calif.). 1-5 µg plasmid DNA/mL culture is first added to serum-free DMEM, followed by 1-5 µl transfection reagent/mL culture. The complexes can be incubated at room temperature for approximately 10-30 minutes and then added to the cells in the spinner flask. The transfection/expression can be performed for 4-7 days, after which the conditioned medium (CM) is harvested by centrifugation at 4,000 RPM for 60 minutes at 4° C.

Example 2

Purification of Recombinant Sclerostin

Recombinant sclerostin was purified from mammalian host cells as follows. All purification processes were carried out at room temperature. One purification scheme was used to purify various species of sclerostin, including murine and human sclerostin. The purification scheme used affinity chromatography followed by cation exchange chromatography.

Heparin Chromatograph

The mammalian host cell conditioned medium (CM) was centrifuged in a Beckman J6-M1 centrifuge at 4000 rpm for 1 hour at 4° C. to remove cell debris. The CM supernatant was then filtered through a sterile 0.2 µm filter. (At this point the sterile filtered CM may be optionally stored frozen until purification.) If the CM was frozen, it was thawed at the following temperatures, or combination thereof: 4° C., room temperature or warm water. Following thawing the CM was filtered through a sterile 0.2 µm filter and optionally concentrated by tangential flow ultrafiltration (TFF) using a 10 kD molecular weight cut-off membrane. The CM concentrate was filtered through a sterile 0.2 µm filter and then loaded onto a Heparin High Performance (Heparin HP) column (GE Healthcare, formerly Amersham Biosciences) equilibrated in PBS. Alternatively, the filtered CM supernatant may be loaded directly onto the Heparin HP column equilibrated in PBS.

After loading, the Heparin HP column was washed with PBS until the absorbance at 280 nm of the flow-through returned to baseline (i.e., absorbance measured before loading CM supernatant). The sclerostin was then eluted from the column using a linear gradient from 150 mM to 2M sodium chloride in PBS. The absorbance at 280 nm of the eluate was monitored and fractions containing protein were collected. The fractions were then assayed by Coomassie-stained SDS-PAGE to identify fractions containing a polypeptide that migrates at the size of glycosylated sclerostin. The appropriate fractions from the column were combined to make the Heparin HP pool.

Cation Exchange Chromatography

The sclerostin eluted from the Heparin HP column was further purified by cation exchange chromatography using SP High Performance (SPHP) chromatography media (GE Healthcare, formerly Amersham Biosciences). The Heparin HP pool was buffer exchanged into PBS by dialysis using 10,000 MWCO membranes (Pierce Slide-A-Lyzer). The dialyzed Heparin HP pool was then loaded onto an SPHP column equilibrated in PBS. After loading, the column was washed with PBS until the absorbance at 280 nm of the flow-through returned to baseline. The sclerostin was then eluted from the SPHP column using a linear gradient from 150 mM to 1 M sodium chloride in PBS. The absorbance at 280 nm of the eluate was monitored and the eluted sclerostin was collected in fractions. The fractions were then assayed by Coomassie-stained SDS-PAGE to identify fractions containing a polypeptide that migrates at the size of glycosylated sclerostin. The appropriate fractions from the column were combined to make the SPHP pool.

Formulation

Following purification, the SPHP pool was formulated in PBS by dialysis using 10,000 MWCO membranes (Pierce Slide-A-Lyzer). If concentration of sclerostin was necessary, a centrifugal device (Amicon Centricon or Centriprep) with a 10,000 MWCO membrane was used. Following formulation the sclerostin was filtered through a sterile 0.2 µm filter and stored at 4° C. or frozen.

Example 3

Peptide Biding ELISA

A series of overlapping peptides (each peptide being approximately 20-25 amino acids long) were synthesized based on the known amino acid sequence of rat sclerostin (SEQ ID NO:98). The peptides were designed such that they all contained a reduced cysteine residue; an additional cysteine was included at the C-terminus of each peptide which did not already contain one in its sequence. This enabled the peptides to be bound to the assay plates by covalent coupling, using commercially available sulfhydryl binding plates (Costar), at a concentration of 1 µg/ml, in phosphate buffered saline (PBS: pH 6.5) containing 1 mM EDTA. Following incubation for 1 hour at room temperature, the plates were washed three times with PBS containing 0.5% Tween 20. The plates were blocked by incubation with a PBS solution containing 0.5% fish skin gelatin (Sigma) for 30 minutes at room temperature and then washed three times in PBS containing 0.5% Tween 20.

Antibodies to be tested were diluted to 1 µg/ml in PBS containing 0.5% fish skin gelatin and incubated with the peptide-coated plates for 1 hour at room temperature. Excess antibody was removed by three washes with PBS, 0.5% Tween 20. The plates were then incubated with an appropriate secondary antibody conjugated to horseradish peroxidase (diluted appropriately in PBS containing 0.5% Tween 20) and capable of binding to the antibody of interest. The plates were then washed three times: once with PBS containing 0.5% Tween 20, and twice with PBS. Finally the plates were incubated with a horseradish peroxidase chromogenic substrate (TMB-Stable Stop, RDI) for 5 minutes at room temperature, the color development was stopped with acid, and the plates' optical density measured at 450 nm.

Materials

Costar's Sulfhydryl Binding Plates (VWR # 29442-278)
Coating Buffer: 1×PBS PH 6.5+1 mM EDTA
Blocking Buffer: 1×PBS+0.5% Fish Skin Gelatin (PBS from CS; FSG from Sigma# G 7765)
Wash Buffer: 1×PBS+0.5% Tween 20
Rat Sclerostin peptides
Antibody Samples Transient Ab, Purified recombinant Ab, rabbit Serum, etc.
Appropriate secondary Ab: Goat-anti-Rabbit/Mouse-HRP (Jackson Immuno Research, 115-036-072)
TMB-Stable Stop (RDI# RDI-TMBSX-1 L)
0.5M HCl Methods were as Follows:
1. Coat plates with 100 µL/well of rat sclerostin peptide diluted in 1×PBS PH 6.5+1 mM EDTA at 1 µg/ml. Incubate plates 1 hour at room temperature. (Plates should be used within 30 minutes of opening).
2. Wash plates 3× with wash buffer.
3. Block plates with 200 µl/well blocking buffer. Incubate plates 30 minutes at room temp.
4. Repeat washing as described in (2).
5. Incubate plates with 50 µl/well of samples diluted in blocking buffer—Serum titers starting at 1:100; Transient Recombinant Ab use neat; Purified recombinant Ab use at 1 µg/ml (all samples run in duplicates). Incubate plates 1 h at room temp.
6. Wash plates as described in (2).
7. Incubate plates with 50 µl/well of appropriate Secondary Antibody (HRP labeled) diluted 1:1600 in Blocking Buffer. Incubate plates 1 hour at room temperature.
8. Wash plates 1× wash buffer, 2×PBS
9. Incubate plates with 50 µl/well of TMB, 5 minutes at room temp.
10. Stop reaction with 50 µl/well 0.5M HCl.
11. Read plates at 450 nm wavelength.

The following peptides sequences were screened as described above:

| | |
|---|---|
| QGWQAFKNDATEIIPGLREYPEPP | (SEQ ID NO: 82) |
| TEIIPGLREYPEPPQELENN | (SEQ ID NO: 83) |
| PEPPQELENNQTMNRAENGG | (SEQ ID NO: 84) |
| ENGGRPPHHPYDTKDVSEYS | (SEQ ID NO: 85) |
| CRELHYTRFVTDGP | (SEQ ID NO: 86) |
| CRELHYTRFVTDGPSRSAKPVTELV | (SEQ ID NO: 87) |
| CRSAKPVTELVSSGQSGPRARLL | (SEQ ID NO: 88) |
| CGPARLLPNAIGRVKWWRPNGPDFR | (SEQ ID NO: 89) |
| RAQRVQLLCPGGAAPRSRKV | (SEQ ID NO: 90) |
| PGGAAPRSRKVRLVAS | (SEQ ID NO: 91) |
| KRLTRFHNQSELKDFGPETARPQ | (SEQ ID NO: 92) |
| IPDRYAQRVQLLSPGG | (SEQ ID NO: 93) |
| SELKDFGPETARPQKGRKPRPRAR | (SEQ ID NO: 94) |
| KGRKPRPRARGAKANQAELENAY | (SEQ ID NO: 95) |
| PNAIGRVKWWRPNGPDFR | (SEQ ID NO: 96) |
| KWWRPNGPDFRCIPDRYAQRV. | (SEQ ID NO: 97) |

A high-affinity neutralizing antibody (Ab-19) bound to two overlapping peptide sequences: PNAIGRVKWWRP-NGPDFR (SEQ ID NO:96) and KWWRPNGPDFRCIP-DRYRAQRV (SEQ ID NO:97).

This procedure allows the recognition of epitopes for antibodies that react with apparent linear epitopes. Peptides that contain all or part of the antibody binding site will bind antibody and thus be detected.

Example 4

Identification of Human Sclerostin Epitopes

Sclerostin Structure

Mature form (signal peptide removed) human sclerostin is a 190 amino acid protein (FIG. 8). FIG. 9 shows a schematic of the general structure of sclerostin with an N-terminal arm (from the N-terminal Q to Cysteine1) and a C-terminal arm (from Cysteine8 to the terminal Y). Sandwiched in between these two arms there is the cystine-knot structure and three loops which are designated Loop1, Loop2 and Loop 3. The four disulfide bonds in sclerostin are Cys1 at sequence position 57 linked to Cys5 at sequence position 111 (referred to as C1-C5), Cys2 at sequence position 71 linked to Cys6 at sequence position 125 (referred to as C2-C6), Cys3 at sequence position 82 linked to Cys7 at sequence position 142 (referred to as C3-C7), Cys4 at sequence position 86 linked to Cys8 at sequence position 144 (referred to as C4-C8). The eight-membered ring structure is formed via C3-C7 and C4-C8 disulfide bonding. This ring structure, together with the C1-C5 disulfide bond penetrating through the ring, forms a typical cystine-knot. C2-C6, which is not part of the cystine-knot, brings two large loop structures, loop 1 (residues 57 to 82) and loop 3 (residues 111 to 142) close together. Loop 2 goes from C4 (residue 86) to C5 (residue 111).

Experimental

The general approach for characterizing the epitopes bound by anti-sclerostin monoclonal antibodies involved fragmenting human Sclerostin into peptides with different proteases, determining the sequence of the various human sclerostin peptides, isolating these peptides and testing each of them for their ability to bind to a particular monoclonal antibody using a Biacore-based "human sclerostin peptide epitope competition binding assay.". The resulting data permitted the location of the binding epitope to be determined.

The peptide digests were subjected to HPLC peptide mapping; the individual peaks were collected, and the peptides identified and mapped by matrix assisted laser desorption mass spectrometry (MALDI-MS) and electrospray ionization LC-MS (ESI-LC-MS) analyses and/or by N-terminal sequencing. All HPLC analyses for these studies were performed using a reverse-phase C8 column (2.1 mm i.d.×15 cm length). HPLC peptide mapping was performed with a linear gradient from 0.05% trifloroacetic acid (mobile phase A) to 90% acetonitrile in 0.05% trifluoroacetic acid. Columns were developed over 50 minutes at a flow rate of 0.2 ml/min.

Trypsin and AspN Endoproteinase Digestions

Mature form human sclerostin was digested with trypsin, which cleaves after arginine and lysine, or with AspN. About 200 μg of sclerostin at 0.5-1.0 mg/ml was incubated in PBS (pH 7.2) for 20 hrs at 37° C. with 8 μg of either trypsin or AspN.

Trypsin Digestion

Figure 10:
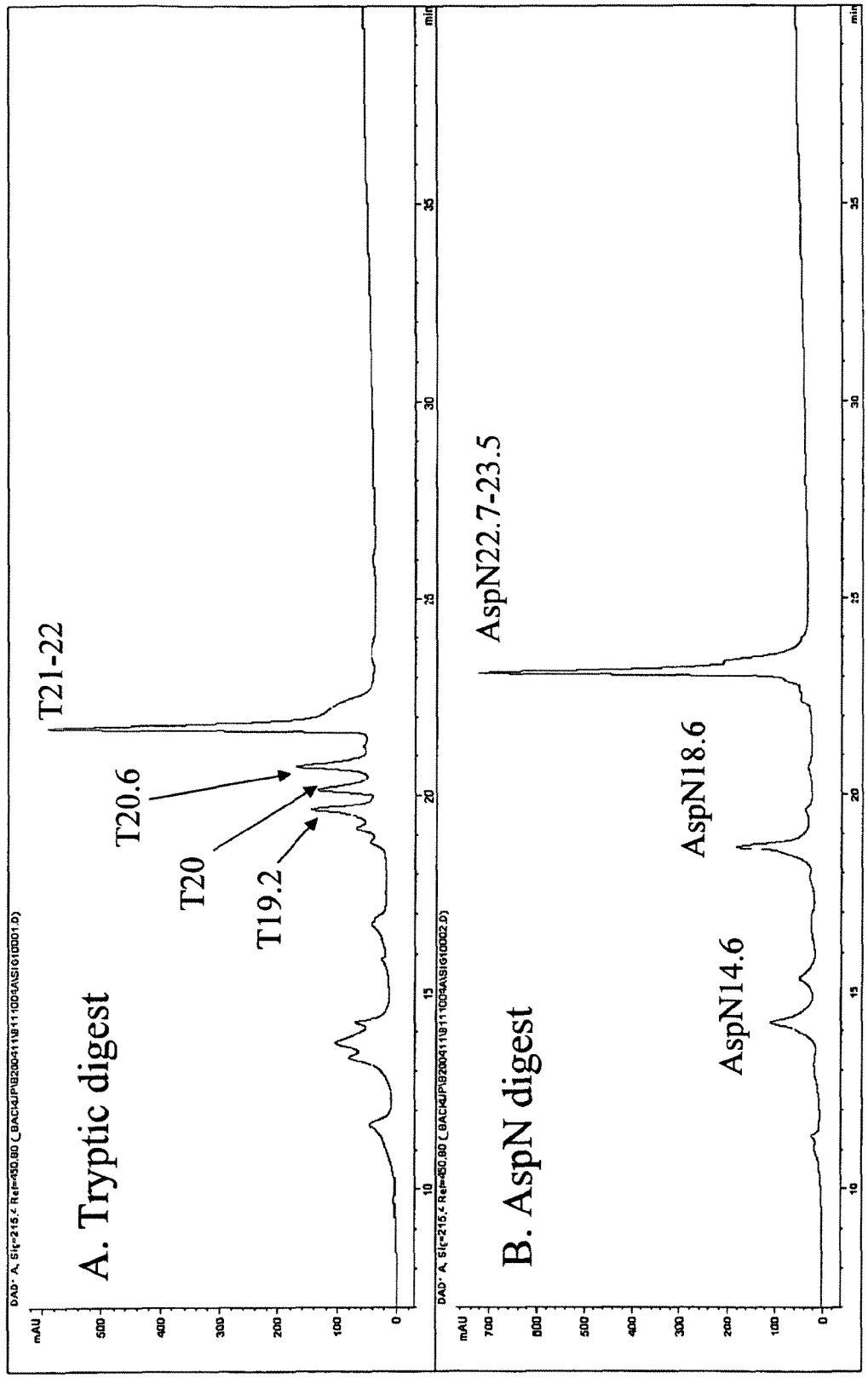
FIG. 10 depicts the HPLC peptide maps of human sclerostin after digestion with either trypsin or AspN. The human sclerostin peptides generated by trypsin digestion are indicated (T19.2, T20, T20.6 and T21-22) as are the human sclerostin peptides generated by AspN digestion (AspN14.6, AspN18.6 and AspN22.7-23.5).

HPLC chromatography of the trypsin digests yielded several major peaks (FIG. 10A). Sequence analysis was conducted on the peptide peaks recovered from HPLC after trypsin digestion. On-line ESI LC-MS analysis of the peptide digest was also performed to determine the precise mass of the peptides that were separated by HPLC. The identity of the peptides present in the peptide peaks was thus determined (FIG. 11). FIG. 13 shows the alignment of various peptide sequences (T19.2, T20, T20.6, T21-22) along the sclerostin sequence. The number following each T (e.g., T19.2) reflects the retention time. T19.2 contains two peptides (one from loop 1 and one from loop 3) linked by the C2-C6 disulfide bond. T20 contains two peptides held together by the cystine-knot structure, with intact loops 1 and 3 held together by the C2-C6 disulfide and with most of loop 2 absent. T20.6 contains four sequences held together by the cystine-knot structure, but is missing part of loop 1 and 3 (the T19.2 part) and is missing most of loop 2. T21-22 is almost identical to T20 but has 3 additional amino acids in the loop 2 region.

AspN Digestion

Figure 14:
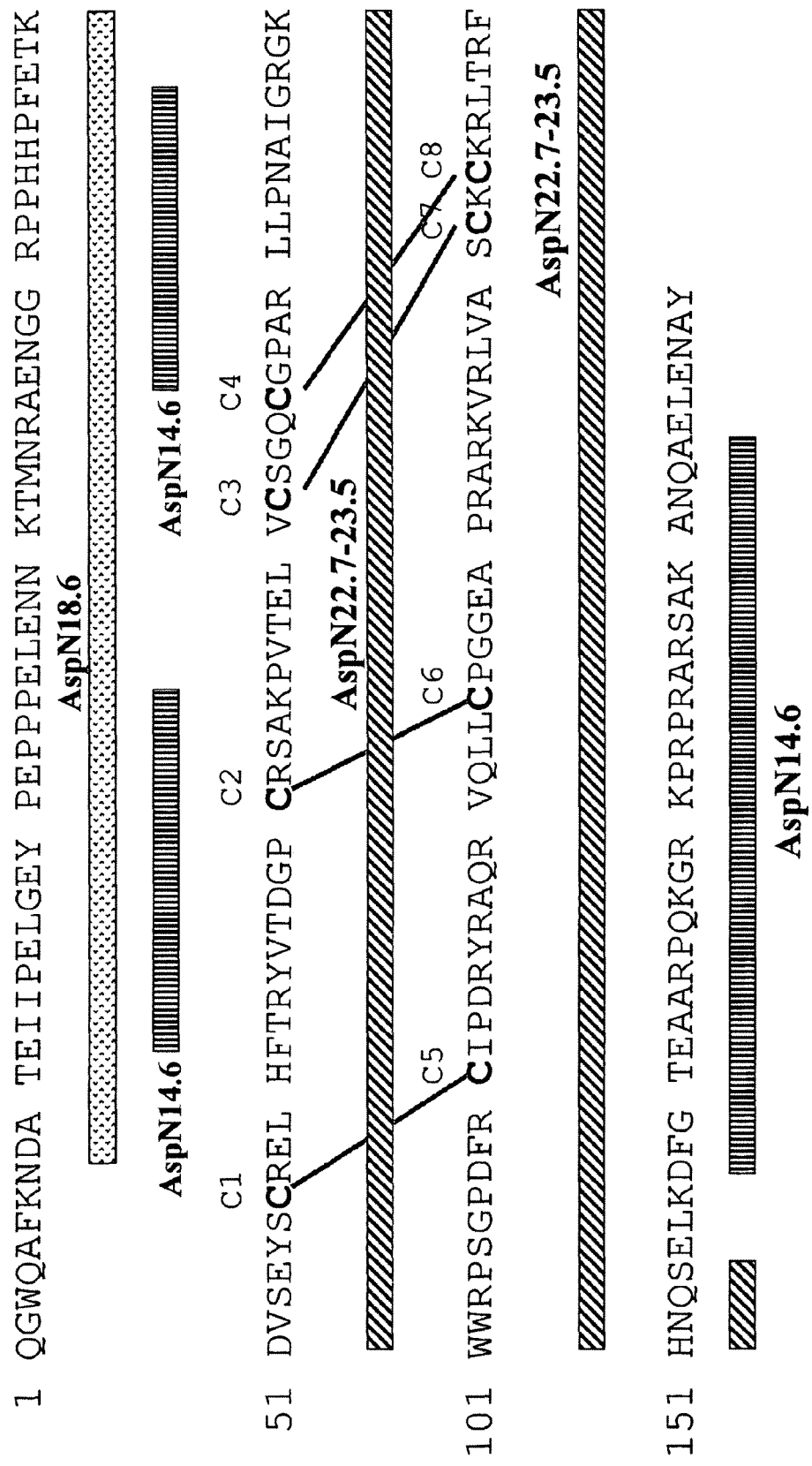
FIG. 14 shows a linear schematic of five human sclerostin peptides (AspN14.6, AspN18.6 and AspN22.7-23.5) generated by AspN digestion. The AspN14.6 HPLC peak is composed of three peptides not linked by any disulfide bonds.

HPLC chromatography of the AspN digests yielded several major peaks (FIG. 10B). Sequence analysis was conducted on the peptide peaks recovered from HPLC. On-line ESI LC-MS analysis of the peptide digest was also performed to determine the precise mass of the peptides that were separated by HPLC. The identity of the peptides present in the peptide peaks from the AspN digestion was thus determined (FIG. 12). FIG. 14 shows the alignment of various peptide sequences (AspN14.6, AspN18.6, AspN22.7-23.5) along the sclerostin sequence. The number following each AspN (e.g. AspN18.6) reflects the retention time. AspN14.6 contains three short peptides from both the N- and C-terminal arms of sclerostin, while AspN18.6 is a larger peptide from the N-terminal arm of sclerostin. AspN22.7-23.5 contains a single peptide fragment of 104 amino acids the encompasses all eight cysteines (the four disulfide bonds), the cystine-knot and all of loops 1, 2 and 3.

The strategy for characterizing the epitopes was to use these various trypsin and AspN generated human sclerostin peptides and determine which peptides could still be bound by the various Antibodies (Ab-A, Ab-B, Ab-C and Ab-D). Specifically this was tested in a Biacore-based "human sclerostin peptide epitope competition binding assay" where the binding of a particular monoclonal antibody to human sclerostin immobilized on the Biacore chip was determine in the presence or absence of each of the various isolated trypsin and AspN HPLC peptide fractions. In the absence of any competing peptides, the particular monoclonal antibody was able to bind the human sclerostin on the chip and produce a resonance unit, $R^U$, response. Preincubation of the particular monoclonal antibody with intact human sclerostin in solution, followed by testing of binding to the chip, demonstrated that the binding of the Mab to human sclerostin in solution prevented the binding of the Mab to the human sclerostin on the chip, thus validating the general principal of this competition assay.

This general procedure was repeated individually for each peptide. A robust RU response was taken to indicate that the particular peptide being tested could not bind the Mab in solution (hence the Mab was free to bind the human sclerostin that had been immobilized on the chip). Conversely, the absence of a robust RU response indicated that the Mab was able to bind the sclerostin peptide in solution. These binding patterns, couple with the known identity of the various sclerostin peptides, were used to determine the epitopes of sclerostin that were bound by anti-sclerostin antibodies Ab-A, Ab-B, Ab-C and Ab-D.

Biacore-Based Human Sclerostin Peptide Epitope Competition Binding Assay

Preparation of Human Sclerostin Surface:

Immobilization of mature form human sclerostin to a BIAcore sensor chip (CM5) surface was performed according to manufacturer's instructions. Briefly, carboxyl groups on the sensor chip surfaces were activated by injecting 60 μL of a mixture containing 0.2 M N-ethyl-N'-(dimethylaminopropyl) carbodiimide (EDC) and 0.05 M N-hydroxysuccinimide (NHS). Human sclerostin was diluted in 10 mM sodium acetate, pH 4.0 at a concentration of 20 μg/mL followed by injecting over the activated CM5 surface. Excess reactive groups on the surfaces were deactivated by injecting 60 μL of 1 M ethanolamine. Final immobilized levels were ~5000 resonance units (RU) for the human sclerostin surface. A blank, mock-coupled reference surface was also prepared on the sensor chips.

Binding Specificity Analysis:

1× Phosphate-buffered saline without calcium chloride or magnesium chloride was from Gibco/Invitrogen, Carlsbad, Calif. Bovine serum albumin, fraction V, IgG-free was from Sigma-Aldrich, St. Louis, Mo. Each Mab (2 nM) was separately incubated with 20 nM human sclerostin or a particular human sclerostin peptide (note: there are 3 unlinked peptides in AspN14.6) in sample buffer (1×PBS+0.005% P-20+0.1 mg/mL BSA) before injection over the immobilized human sclerostin surface. The flow rate for sample injection was 5 μL/min followed by surface regeneration using 1 M NaCl in 8 mM Glycine, pH 2.0 at 30 μL/min for 30 seconds. The data was analyzed using BIAevaluation 3.2, and is presented in FIG. 15 (Ab-A), FIG. 16 (Ab-B), FIG. 17 (Ab-C) and FIG. 18 (Ab-D).

Loop 2 and T20.6 Epitopes:

The sclerostin peptide binding pattern for two representative antibodies (Ab-A and Ab-B) were virtually identical (FIG. 15 and FIG. 16) and showed that both of these Antibodies could only bind the AspN22.7-23.5 peptide. The unique difference between AspN22.7-23.5 and all the other sclerostin peptides is that AspN22.7-23.5 contains an intact loop 2. This shows that Ab-A and Ab-B bind the loop 2 region of sclerostin thus defining the loop 2 epitope (FIG. 19A). The sclerostin peptide binding pattern for Ab-C and Ab-D were virtually identical to each other (FIG. 17 and FIG. 18) but completely distinct from that found for Ab-A and Ab-B. Of the peptides tested in this Example, the most diminutive peptide that Ab-C and Ab-D could bind to was the T20.6 peptide. This result defines the T20.6 epitope (FIG. 19B).

Protease Protection Assay:

The general principle of this assay is that binding of a Mab to sclerostin can result in protection of certain specific protease cleavage sites and this information can be used to determine the region of sclerostin to where the Mab binds.

Figure 20:
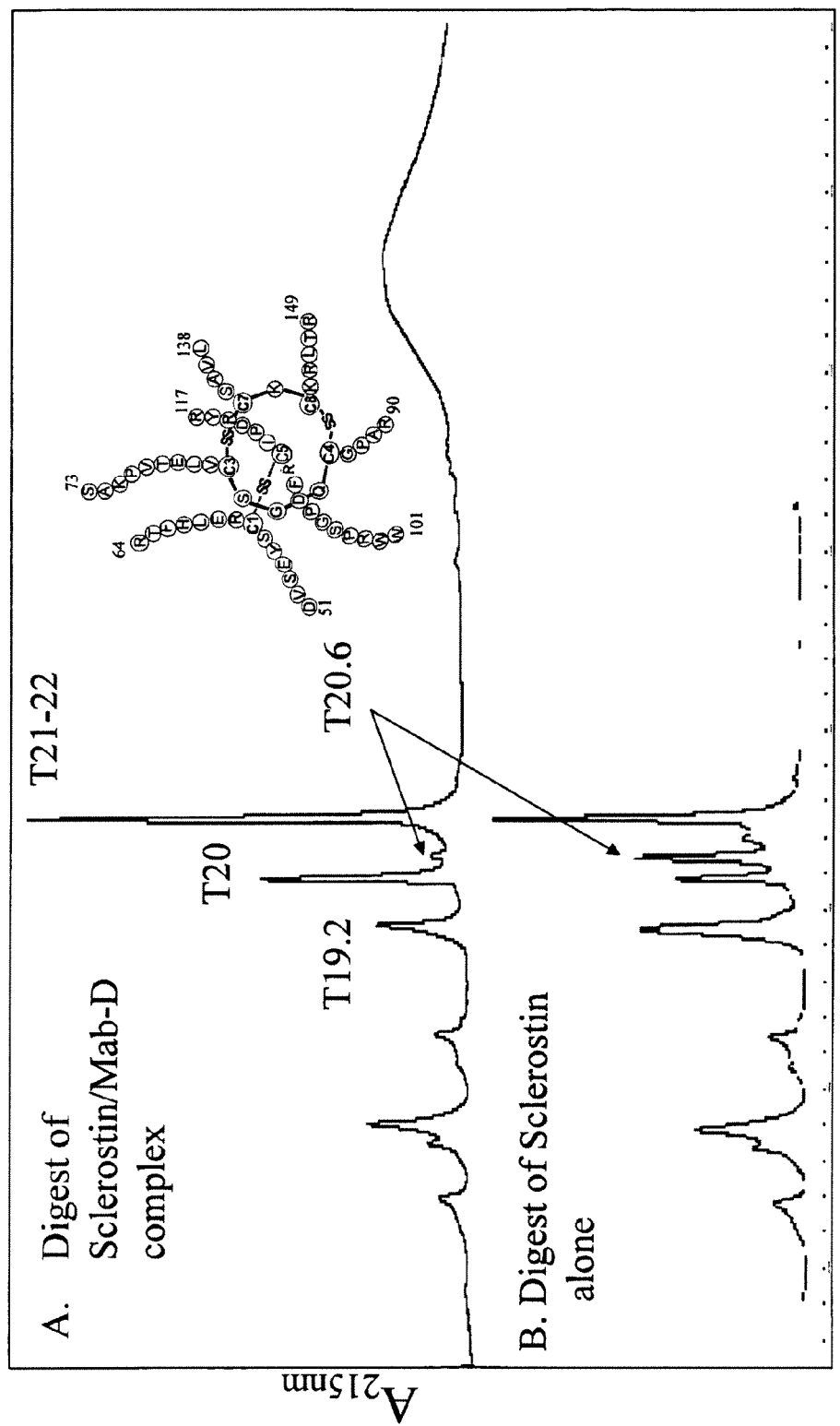
FIG. 20 depicts the HPLC peptide maps of human sclerostin after digestion with trypsin.

"T20.6 Derivative 1 (Cystine-Knot+4 Arms)" Epitope:

FIG. 20 shows the HPLC peptide maps for a human sclerostin Ab-D complex (FIG. 20A: human sclerostin was preincubated at a 1:1 molar ratio with Ab-D prior to digestion with trypsin as described above) and human sclerostin alone (FIG. 20B: human sclerostin was digested with trypsin as described above). The peptide peaks of T19.2 and T20.6 in FIG. 20A showed a clear reduction in their respective peak height, as compared to FIG. 20B. This reduction in peak heights was accompanied by an increase in peak height for peptides T20 and T21-22. These data indicate that basic amino acid residues in loop 1 and loop 3, which in the absence of Ab-D were cleaved by trypsin to generate peptides T19.2 and T20.6, were resistant to cleavage by trypsin when Ab-D was prebound to sclerostin. The presence of T20, T20.6 and T21-22 indicates that loop 2 was still cleaved efficiently when Ab-D was prebound to sclerostin. These data indicate that Ab-D bound on the loop 1 and loop 3 side of the T20.6 epitope thus defining the smaller "T20.6 derivative 1 (cystine-knot+4 arms)" epitope shown in FIG. 21.

Example 5

In Vivo Testing of Anti-Sclerostin Monoclonal Antibodies in Mice

Four week-old BDF1 male mice were obtained from Charles River Laboratories (Raleigh, N.C.) and housed in clean caging, five animals per cage. Room temperature was maintained between 68 and 72° F., and relative humidity was maintained between 34 and 73%. The laboratory housing the cages had a 12-hour light/dark cycle and met all AAALAC specifications. Clinical observations of all mice on study occurred once daily.

Figure 6:
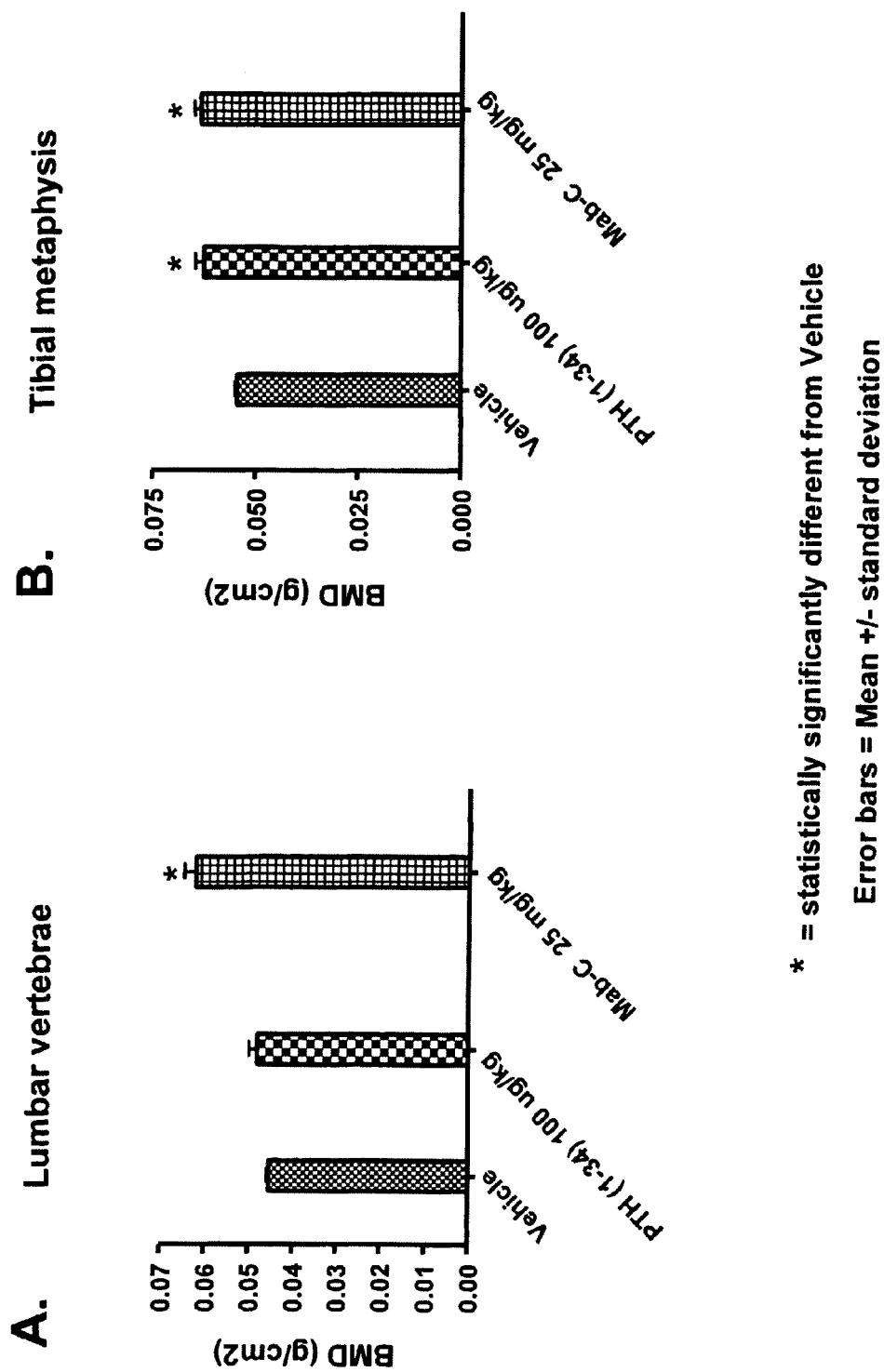
FIG. 6 shows bone mineral density in mice measured at two skeletal sites (lumbar vertebrae (FIG. 6A) and tibial metaphysic (FIG. 6B)) after 2 weeks of treatment with vehicle, PTH (1-34) or Ab-C.
Figure 7:
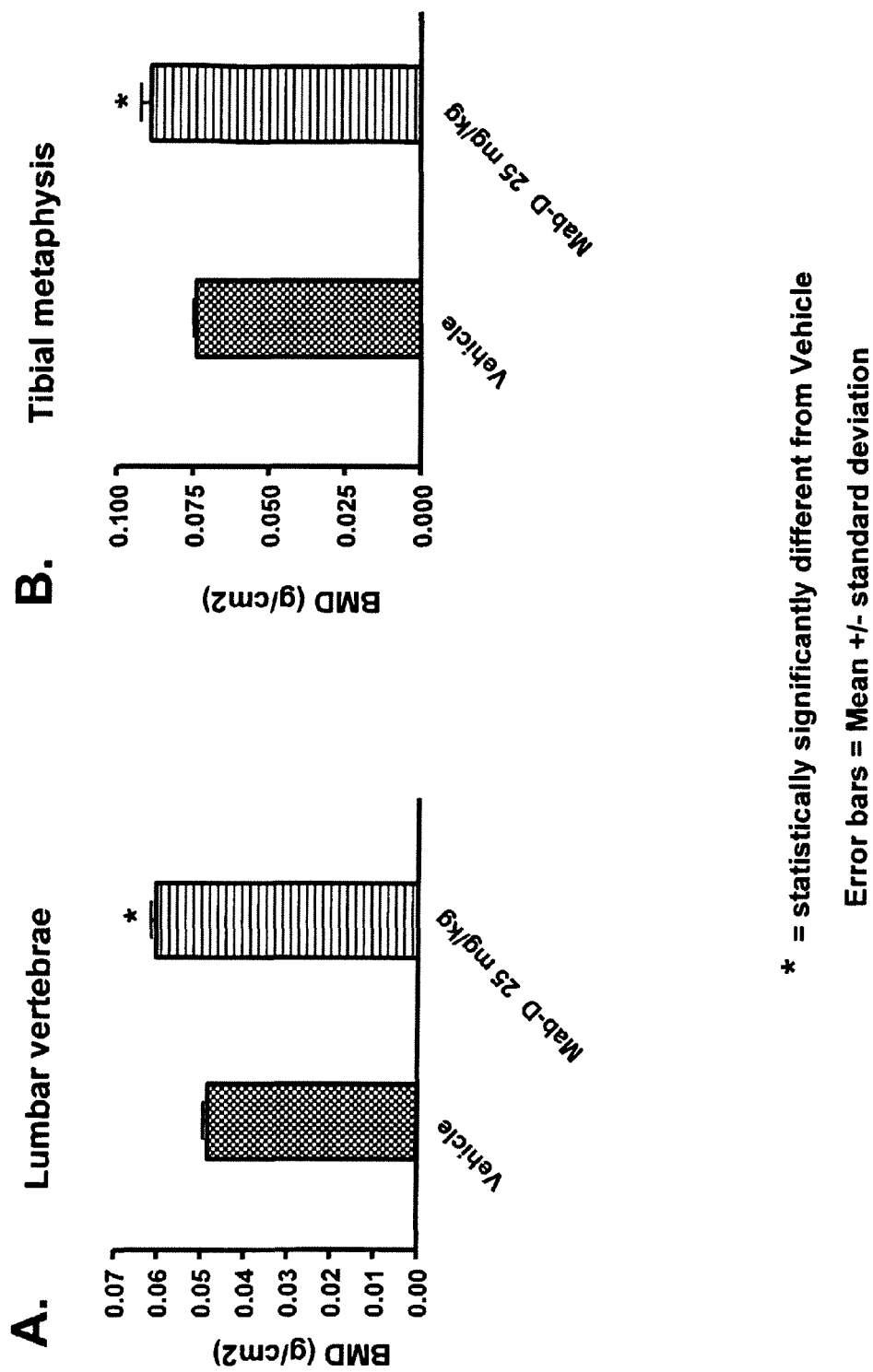
FIG. 7 depicts bone mineral density in mice measured at two skeletal sites (lumbar vertebrae (FIG. 7A) and tibial metaphysic (FIG. 7B)) after 3 weeks of treatment with vehicle or Ab-D.

Purified anti-sclerostin monoclonal antibodies (Ab-A FIG. 1; Ab-B FIG. 2; Ab-C FIG. 3; Ab-D FIG. 4) were diluted in sterile Dulbecco's phosphate buffered saline. Mice were injected with anti-sclerostin Antibodies or PBS vehicle subcutaneously at 21 μl per gram body weight, two times per week (Monday and Thursday) at 25 mg/kg. Human PTH (1-34) was diluted in PTH buffer (0.001 N HCl, 0.15 M NaCl, 2% BSA), and dosed subcutaneously at 21 μl per gram body weight five times per week (Monday, Tuesday, Wednesday, Thursday, Friday) at 100 μg/kg as a positive control (FIGS. 5 and 6). Number of mice per group was N=5 in FIGS. 5 and 6, and N=6 in FIG. 7.

PIXImus in Vivo Bone Densitometry

Bone mineral density (BMD) was determined weekly at the proximal tibial metaphysis and lumbar vertebrae by peripheral Dual Energy X-ray Absorptometry (PDEXA) with the PIXImus2 system from GE/Lunar Medical Systems, Madison, Wis. A 25 mm² region of interest (ROI) was placed to include the proximal articular surface, the epiphysis, and the proximal end on the metaphysis of the tibia. A region of interest (ROI) was placed to include the lumbar vertebrae (L1-L5). The proximal tibia and lumbar regions were analyzed to determine total bone mineral density. Group means were reported±Standard Deviation and compared to the vehicle treatment group for statistical analysis.

Statistical Analysis

Statistical analysis was performed with a Dunnett's and Tukey-Kramer (using MS Excel and JMP v. 5.0. for the BMD data). Group means for each data set were considered significantly different when the P value was less than 0.05 (P<0.05).

Sclerostin Neutralizing Activity of Antibodies

The statistically significant increases in BMD as compared to vehicle seen for each of Ab-A (FIG. 5), Ab-B (FIG. 5), Ab-C (FIG. 6) and Ab-D (FIG. 7) demonstrates that these four antibodies are sclerostin neutralizing antibodies. Furthermore this data shows that, for anti-sclerostin antibodies that bind mouse sclerostin, treatment and analysis of mice as described above can be used to identify sclerostin neutralizing antibodies.

Example 6

Screening Assay for Antibodies that Block Binding of an Antibody to Human Sclerostin Human sclerostin was coupled to a CM5 Biacore chip using standard amine coupling chemistry to generate a sclerostin coated surface. 300 resonance units of sclerostin were coupled to the surface.

The antibodies to be tested were diluted to a concentration of 200 ug/ml in HBS-EP buffer (being 10 mM HEPES pH 7.4, 150 mM NaCl, 3 mM EDTA, 0.005% (v/v) Surfactant P20) and then mixed in a one to one molar ratio (on a binding site basis) to generate the test mixture. This test mixture thus contained each antibody at a concentration of 100 ug/ml (1.3 um on a binding site basis). Separate solutions containing each of the antibodies in the test mix alone were also prepared. These solutions contained the individual antibodies in HBS-EP buffer at a concentration of 100 ug/ml (1.3 um on a binding site basis).

20 µL of the test mixture was passed over the sclerostin-coated chip at a flow rate of 10 µL/min and the amount of binding recorded. The chip was then treated with two 60 second pulses of 30 mM HCl to remove all of the bound antibody. A solution containing only one of the antibodies of the test mixture (at 1.3 µM in the same buffer as the test mixture on a binding site basis) was then passed over the chip in the same manner as the test mixture and the amount of binding recorded. The chip was again treated to remove all of the bound antibody and finally a solution containing the other antibody from the test mixture alone (at 1.3 µM in the same buffer as the test mixture on a binding site basis) was passed over the chip and the amount of binding recorded.

The table below show the results from cross-blocking assays on a range of different antibodies. The values in each square of the table represent the amount of binding (in RU) seen when the antibodies (at 1.3 µM on a binding site basis) or buffer indicated in the top row of the table were mixed with the antibodies (at 1.3 uM on a binding site basis) or buffer indicated in the first column of the table.

|        | Buffer | Ab-4   | Ab-13  | Ab-A   | Ab-3  | Ab-19  |
|--------|--------|--------|--------|--------|-------|--------|
| Buffer | −0.5   | 693    | 428.5  | 707.3  | 316.1 | 649.9  |
| Ab-4   | 687.7  | 795.1  | 1018.2 | 860.5  | 869.3 | 822.5  |
| Ab-13  | 425.6  | 1011.3 | 442.7  | 1108.4 | 431.9 | 1042.4 |
| Ab-A   | 692.4  | 833.1  | 1080.4 | 738.5  | 946.2 | 868.1  |
| Ab-3   | 305.5  | 845.1  | 428.2  | 952.2  | 344.4 | 895.7  |
| Ab-19  | 618.1  | 788.6  | 1022.5 | 863.3  | 891.5 | 658.7  |

Using the mean binding value (in RU) for each combination of antibodies in the above table (since each combination appears twice) it is possible to calculate the percentage of the theoretical binding shown by each combination of antibodies. The theoretical binding being calculated as the sum of the average values for the components of each test mixture when assayed alone (i.e., antibody and buffer).

|        | Buffer | | | | | |
|--------|--------|-------|-------|------|------|-------|
|        | Buffer | Ab-4  | Ab-13 | Ab-A | Ab-3 | Ab-19 |
| Ab-4   |        |       | 90.75 | 60.45 | 85.4 | 60.75 |
| Ab-13  |        |       |       | 96.9 | 58.0 | 97.0  |
| Ab-A   |        |       |       |      | 93.5 | 65.0  |
| Ab-3   |        |       |       |      |      | 94.4  |
| Ab-19  |        |       |       |      |      |       |

From the above data it is clear that Ab-4, Ab-A and Ab-19 cross-block each other. Similarly Ab-13 and Ab-3 cross block each other.

Example 7

ELISA-Based Cross-Blocking Assay

Liquid volumes used in this example would be those typically used in 96-well plate ELISAs (e.g. 50-200 µl/well). Ab-X and Ab-Y, in this example are assumed to have molecular weights of about 145 Kd and to have 2 sclerostin binding sites per antibody molecule. An anti-sclerostin antibody (Ab-X) is coated (e.g. 50µ of 1 µg/ml) onto a 96-well ELISA plate [e.g. Corning 96 Well EIA/RIA Flat Bottom Microplate (Product #3590), Corning Inc., Acton, Mass.] for at least one hour. After this coating step the antibody solution is removed, the plate is washed once or twice with wash solution (e.g., PBS and 0.05% Tween 20) and is then blocked using an appropriate blocking solution (e.g., PBS, 1% BSA, 1% goat serum and 0.5% Tween 20) and procedures known in the art. Blocking solution is then removed from the ELISA plate and a second anti-sclerostin antibody (Ab-Y), which is being tested for it's ability to cross-block the coated antibody, is added in excess (e.g. 50 µl of 10 µg/ml) in blocking solution to the appropriate wells of the ELISA plate. Following this, a limited amount (e.g. 50 µl of 10 µg/ml) of sclerostin in blocking solution is then added to the appropriate wells and the plate is incubated for at least one hour at room temperature while shaking. The plate is then washed 2-4 times with wash solution. An appropriate amount of a sclerostin detection reagent [e.g., biotinylated anti-sclerostin polyclonal antibody that has been pre-complexed with an appropriate amount of a streptavidin-horseradish peroxidase (HRP) conjugate] in blocking solution is added to the ELISA plate and incubated for at least one hour at room temperature. The plate is then washed at least 4 times with wash solution and is developed with an appropriate reagent [e.g. HRP substrates such as TMB (colorimetric) or various HRP luminescent substrates]. The background signal for the assay is defined as the signal obtained in wells with the coated antibody (in this case Ab-X), second solution phase antibody (in this case Ab-Y), sclerostin buffer only (i.e. no sclerostin) and sclerostin detection reagents. The positive control signal for the assay is defined as the signal obtained in wells with the coated antibody (in this case Ab-X), second solution phase antibody buffer only (i.e. no second solution phase antibody), sclerostin and sclerostin detection reagents. The ELISA assay needs to be run in such a manner so as to have the positive control signal be at least 6 times the background signal.

To avoid any artifacts (e.g. significantly different affinities between Ab-X and Ab-Y for sclerostin) resulting from the choice of which antibody to use as the coating antibody and which to use as the second (competitor) antibody, the cross-blocking assay needs to be run in two formats:

1) format 1 is where Ab-X is the antibody that is coated onto the ELISA plate and Ab-Y is the competitor antibody that is in solution and 2) format 2 is where Ab-Y is the antibody that is coated onto the ELISA plate and Ab-X is the competitor antibody that is in solution.

Ab-X and Ab-Y are defined as cross-blocking if, either in format 1 or in format 2, the solution phase anti-sclerostin antibody is able to cause a reduction of between 60% and 100%, specifically between 70% and 100%, and more specifically between 80% and 100%, of the sclerostin detection signal (i.e. the amount of sclerostin bound by the coated antibody) as compared to the sclerostin detection signal obtained in the absence of the solution phase anti-sclerostin antibody (i.e. the positive control wells).

In the event that a tagged version of sclerostin is used in the ELISA, such as a N-terminal His-tagged Sclerostin (R&D Systems, Minneapolis, Minn., USA; 2005 cat# 1406-ST-025) then an appropriate type of sclerostin detection reagent would include an HRP labeled anti-H is antibody. In addition to using N-terminal His-tagged Sclerostin, one could also use C-terminal His-tagged Sclerostin. Furthermore, various other tags and tag binding protein combinations that are known in the art could be used in this ELISA-based cross-blocking assay (e.g., HA tag with anti-HA antibodies; FLAG tag with anti-FLAG antibodies; biotin tag with streptavidin).

Example 8

Cell Based Mineralization Assay for Identifying Agents Able to Antagonize Sclerostin Activity Introduction Mineralization by osteoblast-lineage cells in culture, either primary cells or cell lines, is used as an in vitro model of bone formation. Mineralization takes from about one to six weeks to occur beginning with the induction of osteoblast-lineage cell differentiation by one or more differentiation agents. The overall sequence of events involves cell proliferation, differentiation, extracellular matrix production, matrix maturation and finally deposition of mineral, which refers to crystallization and/or deposition of calcium phosphate. This sequence of events starting with cell proliferation and differentiation, and ending with deposition of mineral is referred to herein as mineralization. Measurement of calcium (mineral) is the output of the assay.

Deposition of mineral has a strong biophysical characteristic, in that once mineral "seeds" begin to form, the total amount of mineral that will be deposited in the entire culture can sometimes be deposited quite rapidly, such as within a few days thereafter. The timing and extent of mineral deposition in culture is influenced, in part, by the particular osteoblast-lineage cells/cell-line being used, the growth conditions, the choice of differentiation agents and the particular lot number of serum used in the cell culture media. For osteoblast-lineage cell/cell-line mineralization cultures, at least eight to fifteen serum lots from more than one supplier should be tested in order to identify a particular serum lot that allows for mineralization to take place.

MC3T3-E1 cells (Sudo H et al., *In vitro differentiation and calcification in a new clonal osteogenic cell line derived from newborn mouse calvaria*. J. Cell Biol. 96:191-198) and sub-clones of the original cell line can form mineral in culture upon growth in the presence of differentiating agents. Such subclones include MC3T3-E1-BF (Smith E, Redman R. Logg C, Coetzee G, Kasahara N, Frenkel B. 2000. *Glucocorticoids inhibit developmental stage-specific osteoblast cell cycle*. J Biol Chem 275:19992-20001).

Identification of Sclerostin Neutralizing Antibodies

MC3T3-E1-BF cells were used for the mineralization assay. Ascorbic acid and B-glycerophosphate were used to induce MC3T3-E1-BF cell differentiation leading to mineral deposition. The specific screening protocol, in 96-well format, involved plating cells on a Wednesday, followed by seven media changes (as described further below) over a 12-day period with most of the mineral deposition taking place in the final approximately eighteen hours (e.g. Sunday night through Monday). For any given treatment, 3 wells were used (N=3). The specific timing, and extent, of mineral deposition may vary depending, in part, on the particular serum lot number being used. Control experiments will allow such variables to be accounted for, as is well know in the art of cell culture experimentation generally.

Figure 22:
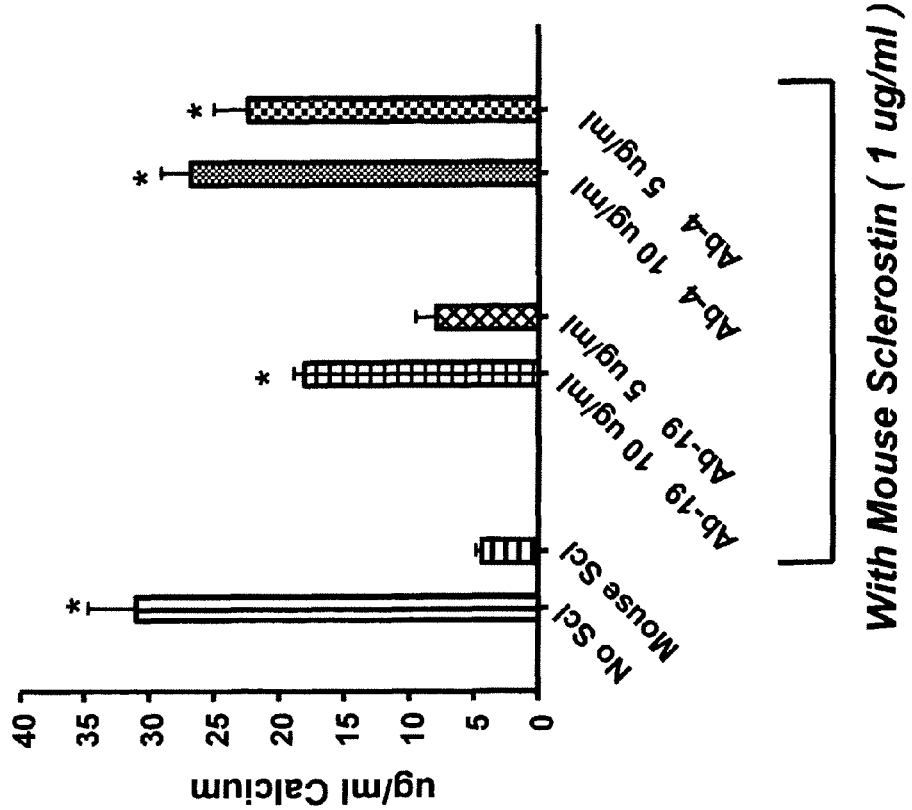
FIG. 22 shows results from the MC3T3-E1-BF osteoblast cell line mineralization assay used for identifying anti-sclerostin neutralizing Mabs. Mouse sclerostin (Scl) was used at 1 μg/ml. Monoclonal antibodies were used at 10 and 5 μg/ml. Extent of mineralization (various types of insoluble calcium phosphate) was quantitated by measuring calcium.

In this assay system sclerostin inhibited one or more of the sequence of events leading up to and including mineral deposition (i.e., sclerostin inhibited mineralization). Anti-sclerostin antibodies that were able to neutralize sclerostin's inhibitory activity allowed for mineralization of the culture in the presence of sclerostin such that there was a statistically significant increase in deposition of calcium phosphate (measured as calcium) as compared to the amount of calcium measured in the sclerostin-only (i.e., no antibody) treatment group. For statistical analysis (using MS Excel and JMP) a 1-way-ANOVA followed by Dunnett's comparison was used to determine differences between groups. Group means for each data set were considered significantly different when the P value was less than 0.05 (P<0.05). A representative result from running this assay is shown in FIG. 22. In the absence of recombinant mouse sclerostin, the sequence of events leading up to and including mineral deposition proceeded normally. Calcium levels in each treatment group are shown as means±Standard Error of the Mean (SEM). In this exemplary experiment calcium levels from the calcium assay were ~31 µg/ml. However, addition of recombinant mouse sclerostin caused inhibition of mineralization, and calcium was reduced by ~85%. Addition of anti-sclerostin monoclonal antibody Ab-19 or Ab-4 along with the recombinant sclerostin resulted in a statistically significant increase in mineral deposition, as compared to the sclerostin-only group, because the inhibitory activity of sclerostin was neutralized by either antibody. The results from this experiment indicate that Ab-19 and Ab-4 are sclerostin neutralizing monoclonal antibodies (Mabs).

Figure 23:
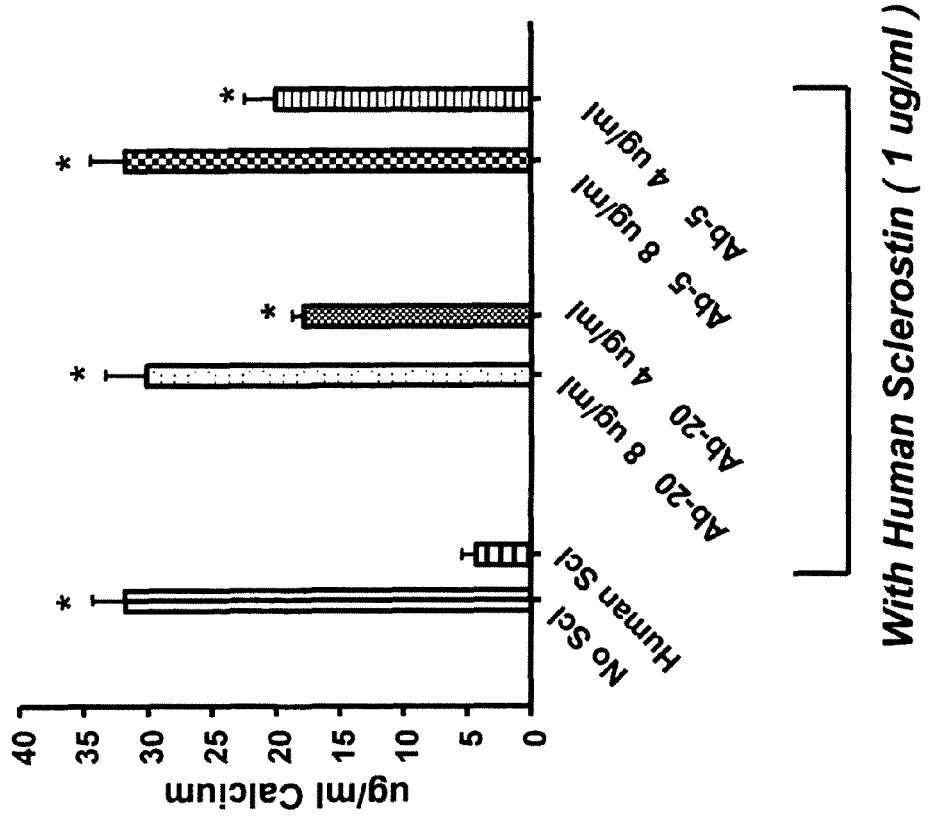
FIG. 23 depicts results from the MC3T3-E1-BF osteoblast cell line mineralization assay used for identifying anti-sclerostin neutralizing Mabs. Human sclerostin (Scl) was used at 1 μg/ml. Monoclonal antibodies were used at 8 and 4 μg/ml. Extent of mineralization (various types of insoluble calcium phosphate) was quantitated by measuring calcium.

FIG. 23 shows a very similar result using recombinant human sclerostin and two humanized anti-sclerostin Mabs.

Figure 24:
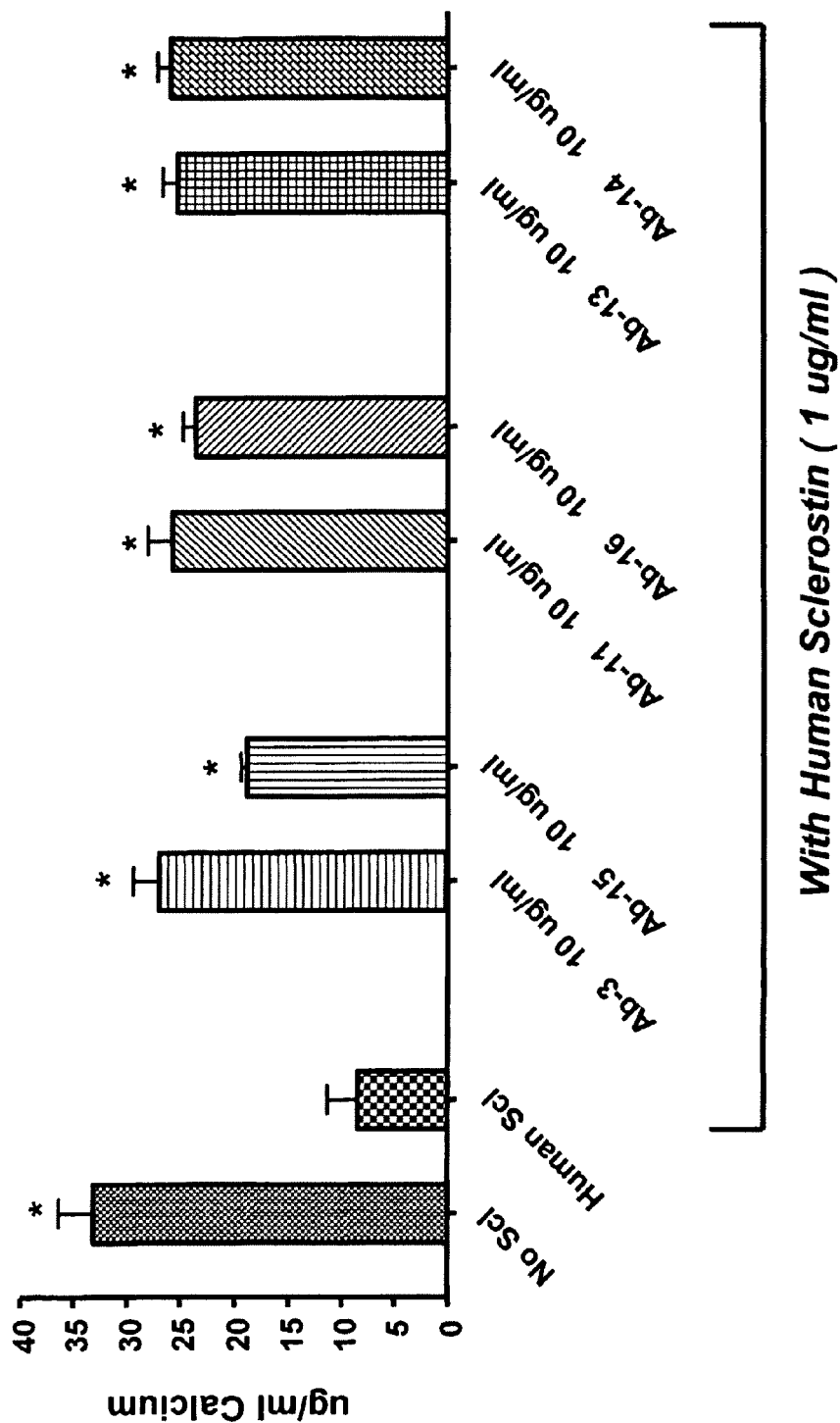
FIG. 24 shows results from the MC3T3-E1-BF osteoblast cell line mineralization assay used for identifying anti-sclerostin neutralizing Mabs. Human sclerostin (Scl) was used at 1 μg/ml. Monoclonal antibodies were used at 10 μg/ml. Extent of mineralization (various types of insoluble calcium phosphate) was quantitated by measuring calcium.

FIG. 24 also shows a very similar result using recombinant human sclerostin and mouse and humanized anti-sclerostin Mabs as indicated.

The antibodies used for the experiments shown in FIGS. 22, 23 and 24 have molecular weights of about 145 Kd and have 2 sclerostin binding sites per antibody molecule.

A detailed MC3T3-E1-BF cell culture protocol is described below.

| Reagents and Medias | | |
| --- | --- | --- |
| Reagents | Company | Catalog # |
| Alpha-MEM | Gibco-Invitrogen | 12571-048 |
| Ascorbic acid | Sigma | A4544 |
| Beta-glycerophosphate | Sigma | G6376 |
| 100X PenStrepGlutamine | Gibco-Invitrogen | 10378-016 |
| Dimethylsulphoxide (DMSO) | Sigma | D5879 or D2650 |
| Fetal bovine serum (FBS) | Cansera | CS-C08-500 (lot # SF50310) |
| or Fetal bovine serum (FBS) | TerraCell Int. | CS-C08-1000A (lot # SF-20308) |

Alpha-MEM is usually manufactured with a 1 year expiration date. Alpha-MEM that was not older than 6-months post-manufacture date was used for the cell culture.

Expansion Medium (Alpha-MEM/10% FBS/PenStrepGlu) was prepared as follows: A 500 ml bottle of FBS was thawed and filter sterilized through a 0.22 micron filter.

100 mls of this FBS was added to 1 liter of Alpha-MEM followed by the addition of 10 mls of 100× PenStrepGlutamine. Unused FBS was aliquoted and refrozen for later use.

Differentiation Medium (Alpha-MEM/10% FBS/PenStrep-Glu, +50 µg/ml ascorbic acid, +10 mM beta-glycerophosphate) was prepared as follows:

100 mls of Differentiation Medium was prepared by supplementing 100 mls of Expansion Medium with ascorbic acid and beta-glycerophosphate as follows:

| | Stock conc (see below) | Volume | Final Conc. |
| --- | --- | --- | --- |
| Ascorbic acid | 10 mg/ml | 0.5 mls | 100 µg/ml (50 µg/ml + 50 µg/ml) |
| β-glycerophosphate | 1 M | 1.0 mls | 10 mM |

Differentiation Medium was made by supplementing Expansion Medium only on the day that the Differentiation media was going to be used for cell culture. The final concentration of ascorbic acid in Differentiation medium is 100 µg/ml because Alpha-MEM already contains 50 µg/ml ascorbic acid. Ascorbic acid stock solution (10 mg/ml) was made and aliquoted for freezing at −80° C. Each aliquot was only used once (i.e. not refrozen). Beta-glycerophosphate stock solution (1 M) was made and aliquoted for freezing at −20° C. Each aliquot was frozen and thawed a maximum of 5 times before being discarded.

Cell Culture for expansion of MC3T3-E1-BF cells.

Cell culture was performed at 37° C. and 5% $CO_2$. A cell bank was generated for the purposes of screening for sclerostin neutralizing antibodies. The cell bank was created as follows:

One vial of frozen MC3T3-E1-BF cells was thawed by agitation in a 37° C. water bath. The thawed cells were put into 10 mls of Expansion Medium (Alpha-MEM/10% FBS/PenStrepGlu) in a 50 ml tube and gently spun down for 5 minutes. The cells were then resuspended in 4 mls of Alpha-MEM/10% FBS/PenStrepGlu. After determining the number of cells using trypan blue and hemacytometer, $1 \times 10^6$ cells were plated in 50 mls Alpha-MEM/10% FBS/PenStrepGlu media in one T175 flask.

When this passage was confluent (at approximately 7 days), the cells were trypsinized with trypsin/EDTA (0.05% Trypsin; 0.53 mM EDTA), gently spun down for 5 minutes and then resuspended in 5 mls Alpha-MEM/10% FBS/PenStrepGlu. After determining the number of cells using trypan blue and hemacytometer, cells were plated at $1 \times 10^6$ cells in 50 mls Alpha-MEM/10% FBS/PenStrepGlu media per one T175 flask. The number of T175 flasks used for plating at this point depended upon the total cell number available and the desired number of flasks that were to be taken forward to the next passage. Extra cells were frozen down at $1-2 \times 10^6$ live cells/ml in 90% FBS/10% DMSO.

When this passage was confluent (about 3-4 days), the cells were trypsinized with trypsin/EDTA (0.05% Trypsin; 0.53 mM EDTA), gently spun down for 5 minutes and then resuspended in 5 mls Alpha-MEM/10% FBS/PenStrepGlu. After determining the number of cells using trypan blue and hemacytometer, cells were plated at $1 \times 10^6$ cells in 50 mls Alpha-MEM/10% FBS/PenStrepGlu media per one T175 flask. The number of T175 flasks used for plating at this point depended upon the total cell number available and the desired number of flasks that were to be taken forward to the next passage. Extra cells were frozen down at $1-2 \times 10^6$ live cells/ml in 90% FBS/10% DMSO.

When this passage was confluent (about 3-4 days), the cells were trypsinized with trypsin/EDTA (0.05% Trypsin; 0.53 mM EDTA), gently spun down for 5 minutes and then resuspended in 5 mls Alpha-MEM/10% FBS/PenStrepGlu. After determining the number of cells using trypan blue and hemacytometer, cells were plated at $1 \times 10^6$ cells in 50 mls Alpha-MEM/10% FBS/PenStrepGlu media per one T175 flask. The number of T175 flasks used for plating at this point depended upon the total cell number available and the desired number of flasks that were to be taken forward to the next passage. Extra cells were frozen down at $1-2 \times 10^6$ live cells/ml in 90% FBS/10% DMSO.

When this passage was confluent (about 3-4 days), the cells were trypsinized with trypsin/EDTA (0.05% Trypsin; 0.53 mM EDTA), gently spun down for 5 minutes and then resuspended in 5 mls Alpha-MEM/10% FBS/PenStrepGlu. After determining the number of cells using trypan blue and hemacytometer, the cells were frozen down at $1-2 \times 10^6$ live cells/ml in 90% FBS/10% DMSO. This "final passage" of frozen cells was the passage that was used for the screening assay.

Cell Culture for Mineralizing MC3T3-E1-BF Cells.

Cell culture was performed at 37° C. and 5% $CO_2$. It is desirable to minimize temperature and % $CO_2$ fluctuations during the mineralization cell culture procedure. This can be achieved by minimizing the time that plates spend out of the incubator during feeding and also by minimizing the number of times the incubator door is opened and closed during the mineralization cell culture procedure. In this regard having a tissue culture incubator that is dedicated exclusively for the mineralization cell culture (and thus not opened and closed more than is necessary) can be helpful.

An appropriate number of "final passage" vials prepared as described above were thawed by agitation in a 37° C. water bath. The thawed cells were put into 10 mls of Expansion Medium (Alpha-MEM/10% FBS/PenStrepGlu) in a 50 ml tube and gently spun down for 5 minutes. The cells were then resuspended in 4 mls of Alpha-MEM/10% FBS/PenStrepGlu. After determining the number of cells by trypan blue and hemacytometer, 2500 cells were plated in 200 microliters of Expansion media per well on collagen I coated 96-well plates (Becton Dickinson Labware, cat #354407).

To avoid a mineralization plate-edge effect, cells were not plated in the outermost row/column all the way around the plate. Instead 200 microliters of PBS was added to these wells.

Exemplary Cell Culture Procedure

In the following procedure, the starting day for plating the cells is indicated to be a Wednesday. If a different day of the week is used as the starting day for plating the cells, that day will trigger the daily schedule for removing and adding media during the entire process as indicated below. For example, if the cells are plated on a Tuesday, media should not be removed and added on the first Friday and Saturday, nor on the second Friday and Saturday. With a Tuesday start, the plates would be prepared for the calcium assay on the final Sunday.

Cells were plated on a Wednesday at 2500 cells in 200 µl of Expansion media.

On Thursday all of the Expansion media was removed and 200 µl of Differentiation Media was added.

On Friday 100 µl of media was removed and 100 µl of fresh Differentiation Media was added.

On Monday 100 µl of media was removed and 100 µl of fresh Differentiation Media was added.

On Tuesday 1001 of media was removed and 100 µl of fresh Differentiation Media was added.

On Wednesday 100 µl of media was removed and 100 µl of fresh Differentiation Media was added.

On Thursday 100 µl of media was removed and 100 µl of fresh Differentiation Media was added.

On Friday 100 µl of media was removed and 100 µl of fresh Differentiation Media was added.

On the following Monday plates were prepared for the calcium assay as follows:

Plates were washed once with 10 mM Tris, HCl pH 7-8.

Working under a fume hood, 200 µl of 0.5 N HCl was added per well. Plates were then frozen at −80° C.

Just prior to measuring calcium, the plates were freeze-thawed twice, and then trituration with a multichannel pipette was used to disperse the contents of the plate. The contents of the plate was then allowed to settle at 4° C. for 30 minutes at which point an appropriate amount of supernatant was removed for measuring calcium using a commercially available calcium kit. An exemplary and not-limiting kit is Calcium (CPC) Liquicolor, Cat. No. 0150-250, Stanbio Laboratory, Boerne, Tex.

In this cell based assay, sclerostin inhibits one or more of the sequence of events leading up to and including mineral deposition (i.e. sclerostin inhibits mineralization). Thus, in experiments where sclerostin was included in the particular cell culture experiment, the recombinant sclerostin was added to the media starting on the first Thursday and every feeding day thereafter. In cases where an anti-sclerostin monoclonal antibody (Mab) was being tested for the ability to neutralize sclerostin, i.e. allow for mineralization by neutralizing sclerostin's ability to inhibit mineralization, the Mab was added to the media starting on the first Thursday and every feeding day thereafter. According to the protocol, this was accomplished as follows: the Mab was preincubated with the recombinant sclerostin in Differentiation media for 45-60 minutes at 37° C. and then this media was used for feeding the cells.

Described above is a 12-day mineralization protocol for MC3T3-E1-BF cells. Using the same reagents and feeding protocol, the original MC3T3-E1 cells (Sudo H, Kodama H-A, Amagai Y, Yamamoto S, Kasai S. 1983. *In vitro differentiation and calcification in a new clonal osteogenic cell line derived from newborn mouse calvaria*. J Cell Biol 96:191-198) which we obtained from the RIKEN Cell Bank (RCB 1126, RIKEN BioResource Center 3-1-1 Koyadai, Tsukubashi, Ibaraki 305-0074 Japan) took longer to mineralize (20 days total for mineralization) than the MC3T3-E1-BF cells. Mineralization of the original MC3T3-E1 cells was inhibited by recombinant sclerostin and this inhibition was blocked using a sclerostin neutralizing antibody.

Example 9

Anti-Sclerostin Antibody Protects from Inflammation-Induced Bone Loss in the Cd4 CD45RB$^{HI}$ Transfer Model of Colitis in SCID Mice Summary of Model Injection of the CD45RB$^{high}$ subset of CD4+ T cells into C.B-17 scid mice results in chronic intestinal inflammation with characteristics similar to those of human inflammatory bowel disease (IBD). Diarrhea and wasting disease is noted 3-5 weeks after cell transfer with severe leukocyte infiltration into the colon accompanied by epithelial cell hyperplasia and granuloma formation. C.B-17 scid mice which receive the reciprocal subset of CD4+ cells, those which express CD45RB$^{low}$, do not exhibit colitis and have a weight gain indistinguishable from uninjected scid mice. In addition to colitis symptoms, the CD4+ CD45RB$^{high}$ T cell transfer model of colitis is accompanied by a reduction in bone mineral density (BMD), thought to be primarily through inflammatory mechanisms rather than dietary malabsorption (Byrne, F. R. et al., Gut 54:78-86, 2005).

Induction of Colitis and Inflammation-Induced Bone Loss

Spleens were taken from female balb/c mice and disrupted through a 70 µm cell strainer. The CD4+ population was then enriched by negative selection with Dynabeads using antibodies against B220, MAC-1, CD8 and I-A$^d$. The enriched population was then stained with FITC conjugated anti-CD4 and PE conjugated anti-CD45RB and fractionated into CD4+ CD45RB$^{high}$ and CD4+ CD45RB$^{low}$ populations by two-color sorting on a Moflo (Dakocytomation). The CD45RB$^{high}$ and CD45RB$^{low}$ populations were defined as the brightest staining 40% and the dullest staining 20% of CD4+ cells respectively. $5 \times 10^5$ cells were then injected i.p. into C.B-17 scid mice on day 0 and the development of colitis was monitored through the appearance of soft stools or diarrhea and weight loss. Bone mineral density measurements were taken at the termination of the study (day 88).

Effect of Anti-Sclerostin Treatment on Colitis Symptoms and BMD

Ab-A IgG was dosed at 10 mg/kg s.c. from the day prior to CD4+ CD45RB$^{high}$ cell transfer and compared with mice which received the negative control antibody 101.4 also dosed at 10 mg/kg s.c. The antibodies were dosed weekly thereafter. A group of mice which received non-pathogenic CD4+ CD45RB$^{low}$ cells and were dosed with 10 mg/kg 101.4 was studied as a control. At the termination of the study (day 88) the bone mineral density was measured and sections of the colon taken for analysis of cell infiltration and assessment of histological damage.

a) No Effect on Colitis Symptoms

Typical colitis symptoms such as weight loss and infiltration of inflammatory cells into the colon were unaffected by treatment with Ab-A. Similarly there was no improvement of histological damage to the colon after treatment with Ab-A.

b) Inhibition of Inflammation-Induced Loss of Bone Mineral Density.

Figure 25:
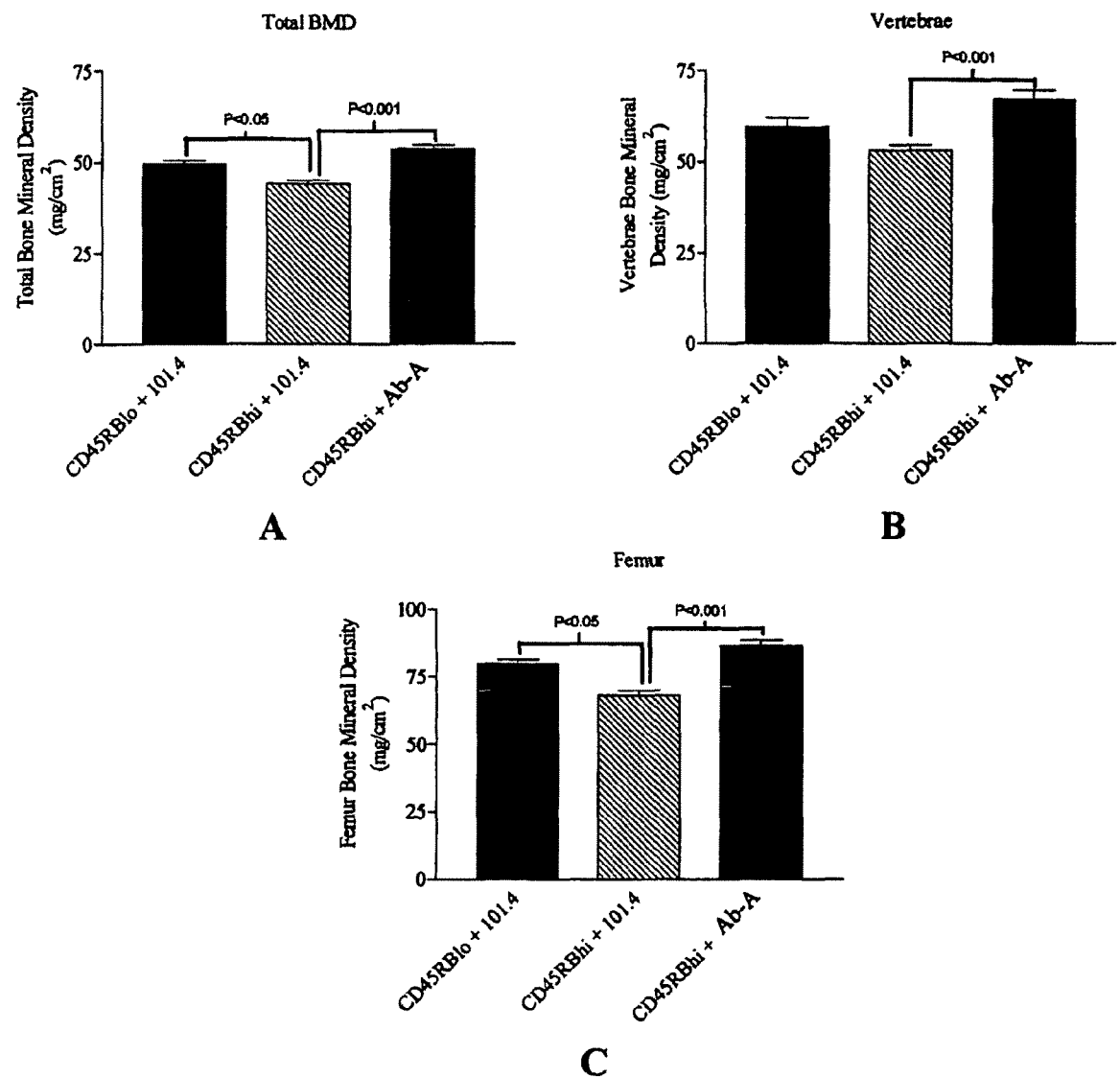
FIG. 25 depicts results from an inflammation-induced bone loss SCID mouse model. Ab-A treatment protected mice from inflammation-related bone loss associated with colitis when measured as total bone mineral density (FIG. 25A), vertebral bone density (FIG. 25B), and femur bone density (FIG. 25C).

On day 88 after transfer of cells into C.B-17 scid mice, the bone mineral density was measured (total BMD, vertebrae BMD and femur BMD). In comparison to control mice which received CD4+ CD45RB$^{low}$ non-pathogenic cells, mice which received CD4+ CD45RB$^{high}$ T cells and the negative control antibody 101.4 had reduced bone mineral density, as shown in FIG. 25. In contrast, no reduction in BMD was noted after treatment with Ab-A. Total, vertebrae and femur measurements of BMD were significantly higher in mice receiving CD4+ CD45RB$^{high}$ T cells and treated with Ab-A than mice receiving CD4+ CD45RB$^{high}$ T cells and treated with 101.4 ($P<0.001$ by Bonferroni multiple comparison test).

Example 10

KinExA-Based Determination of Affinity ($K_D$) of Anti-Sclerostin Antibodies for Human Sclerostin The affinity of several anti-sclerostin antibodies to human sclerostin was assessed by a solution equilibrium binding analysis using KinExA® 3000 (Sapidyne Instruments Inc., Boise, Id.). For these measurements, Reacti-Gel 6× beads (Pierce, Rockford, Ill.) were pre-coated with 40 µg/ml human sclerostin in 50 mM Na$_2$CO$_3$, pH 9.6 at 4° C. overnight. The beads were then blocked with 1 mg/ml BSA in 1 M Tris-HCl, pH 7.5 at 4° C. for two hours. 10 µM, 30 µM, or 100 µM of the antibody was mixed with various concentrations of human sclerostin, ranging in concentration from 0.1 µM to 1 nM, and equilibrated at room temperature for over 8 hours in PBS with 0.1 mg/ml BSA and 0.005% P20. The mixtures were then passed over the human sclerostin coated beads. The amount of bead-bound anti-sclerostin antibody was quantified using fluorescent Cy5-labeled goat anti-mouse-IgG or fluorescent Cy5-labeled goat anti-human-IgG antibodies (Jackson Immuno Research, West Grove, Pa.) for the mouse or human antibody samples, respectively. The amount of fluorescent signal measured was proportional to the concentration of free anti-sclerostin antibody in each reaction mixture at equilibrium. The dissociation equilibrium constant ($K_D$) was obtained from nonlinear regression of the competition curves using a n-curve one-site homogeneous binding model provided in the KinExA Pro software. Results of the KinExA assays for the selected antibodies are summarized in the table below.

| Antibodies | Antigen | $K_D$ (pM) | 95% confidence interval |
|---|---|---|---|
| Ab-13 | Human Sclerostin | 0.6 | 0.4~0.8 pM |
| Ab-4 | Human Sclerostin | 3 | 1.8~4 pM |
| Ab-19 | Human Sclerostin | 3 | 1.7~4 pM |
| Ab-14 | Human Sclerostin | 1 | 0.5~2 pM |

-continued

| Antibodies | Antigen | $K_D$ (pM) | 95% confidence interval |
|---|---|---|---|
| Ab-5 | Human Sclerostin | 6 | 4.3~8 pM |
| Ab-23 | Human Sclerostin | 4 | 2.1~8 pM |

Example 11

Biacore Method for Determining the Affinity of Humanised Anti-Sclerostin Antibodies for Human Sclerostin The BIAcore technology monitors the binding between biomolecules in real time and without the requirement for labelling. One of the interactants, termed the ligand, is either immobilised directly or captured on the immobilised surface while the other, termed the analyte, flows in solution over the captured surface. The sensor detects the change in mass on the sensor surface as the analyte binds to the ligand to form a complex on the surface. This corresponds to the association process. The dissociation process is monitored when the analyte is replaced by buffer. In the affinity BIAcore assay, the ligand is the anti-sclerostin antibody and the analyte is sclerostin.

Instrument

Biacore® 3000, Biacore AB, Uppsala, Sweden

Sensor Chip

CM5 (research grade) Catalogue Number: BR-1001-14, Biacore AB, Uppsala, Sweden. Chips were stored at 4° C.

BIAnormalising Solution

70% (w/w) Glycerol. Part of BIAmaintenance Kit Catalogue Number: BR-1002-51, Biacore AB, Uppsala, Sweden. The BIAmaintenance kit was stored at 4° C.

Amine Coupling Kit

Catalogue Number: BR-1000-50, Biacore AB, Uppsala, Sweden.

Ethyl-3-(3-dimethylaminopropyl) carbodiimide hydrochloride (EDC). Made up to 75 mg/mL in distilled water and stored in 200 µL aliquots at −70° C.

N-Hydroxysuccinimide (NHS). Made up to 11.5 mg/mL in distilled water and stored in 200 µL aliquots at −70° C.

1 M Ethanolamine hydrochloride-NaOH pH 8.5. Stored in 200 µL aliquots at −70° C.

Buffers

Running buffer for immobilising capture antibody: HBS-EP (being 0.01 M HEPES pH 7.4, 0.15 M NaCl, 3 mM EDTA, 0.005% Surfactant P20). Catalogue Number: BR-1001-88, Biacore AB, Uppsala, Sweden. Buffer stored at 4° C.

Immobilisation buffer: Acetate 5.0 (being 10 mM sodium acetate pH 5.0). Catalogue number: BR-1003-51, Biacore AB, Uppsala, Sweden. Buffer stored at 4° C.

Running buffer for binding assay: HBS-EP (being 0.01 M HEPES pH 7.4, 0.15 M NaCl, 3 mM EDTA, 0.005% Surfactant P20, Catalogue Number: BR-1001-88, Biacore AB, Uppsala, Sweden) with CM-Dextran added at 1 mg/mL (Catalogue Number 27560, Fluka BioChemika, Buchs, Switzerland). Buffer stored at 4° C.

Ligand Capture

Affinipure F(ab')₂ fragment goat anti-human IgG, Fc fragment specific. Jackson ImmunoResearch Inc (Pennsylvania, USA) Catalogue number: 109-006-098. Reagent stored at 4° C.

Ligand

Humanised anti-human sclerostin antibodies Ab5, Ab14 and Ab20.

Analyte

Recombinant human sclerostin. Aliquots stored at −70° C. and thawed once for each assay.

Regeneration Solution 40 mM HCl prepared by dilution with distilled water from an 11.6 M stock solution (BDH, Poole, England. Catalogue number: 101254H).

5 mM NaOH prepared by dilution with distilled water from a 50 mM stock solution. Catalogue number: BR-1003-58, Biacore AB, Uppsala, Sweden.

Assay Method

The assay format was capture of the anti-sclerostin antibody by immobilised anti-human IgG-Fc then titration of the sclerostin over the captured surface.

An example of the procedure is given below:

BIA (Biamolecular Interaction Analysis) was performed using a BIAcore 3000 (BIAcore AB). Affinipure F(ab')₂ Fragment goat anti-human IgG, Fc fragment specific (Jackson ImmunoResearch) was immobilised on a CM5 Sensor Chip via amine coupling chemistry to a capture level of 4000 response units (RUs). HBS-EP buffer (10 mM HEPES pH 7.4, 0.15 M NaCl, 3 mM EDTA, 0.005% Surfactant P20, BIAcore AB) containing 1 mg/mL CM-Dextran was used as the running buffer with a flow rate of 10 µl/min. A 10 µl injection of the anti-sclerostin antibody at ~5 µg/mL was used for capture by the immobilised anti-human IgG-Fc. Antibody capture levels were typically 100-200 RU. Sclerostin was titrated over the captured anti-sclerostin antibody at various concentrations at a flow rate of 30 µL/min. The surface was regenerated by two 10 µL injections of 40 mM HCl, followed by a 5 µL injection of 5 mM NaOH at a flowrate of 10 µL/min.

Background subtraction binding curves were analysed using the BIAevaluation software (version 3.2) following standard procedures. Kinetic parameters were determined from the fitting algorithm.

The kinetic data and calculated dissociation constants are given in Table 2.

TABLE 2

Affinity of anti-sclerostin antibodies for sclerostin

| Antibody | ka (1/Ms) | kd (1/s) | Kd (pM) |
|---|---|---|---|
| Ab-5 | 1.78E+06 | 1.74E−04 | 97.8 |
| Ab-14 | 3.30E+06 | 4.87E−06 | 1.48 |
| Ab-20 | 2.62E+06 | 4.16E−05 | 15.8 |

Example 12

In Vivo Testing of Anti-Sclerostin Monoclonal Antibodies in Cynomolgous Monkeys

Thirty-three, approximately 3-5 year old, female cynomolgus monkeys (*Macaca fascicularis*) were used in this 2-month study. The study contained 11 groups:

Group 1: vehicle (N=4)

Group 2: Ab-23 (N=2, dose 3 mg/kg)

Group 3: Ab-23 (N=3, dose 10 mg/kg)

Group 4: Ab-23 (N=3, dose 30 mg/kg)

Group 5: Ab-5 (N=3, dose 3 mg/kg)

Group 6: Ab-5 (N=3, dose 10 mg/kg)

Group 7: Ab-5 (N=3, dose 30 mg/kg)

Group 8: Ab-14 (N=3, dose 3 mg/kg)

Group 9: Ab-14 (N=3, dose 10 mg/kg)

Group 10: Ab-14 (N=3, dose 30 mg/kg)

Group 11: Parathyroid Hormone (1-34) [PTH (1-34)] (N=3, dose 10 ug/kg)

All dosing was subcutaneous. PTH (1-34) was dosed everyday, monoclonal antibodies (Mabs) were dosed twice (first dose at the beginning of the study and second dose at the one month time point). For assessment of bone parameters (e.g. bone mineral density) pQCT (peripheral quantitative computed tomography) and DXA (dual energy X-ray absorptiometry) scans were performed prior to the beginning of the study (to obtain baseline values) and after a month (prior to the second dose of Mab) and finally at the end of the study (2-month time point) at which point the monkeys were necropsied for further analysis (e.g. histomorphometric analysis). Animals were fluorochrome labeled (days 14, 24, 47, and 57) for dynamic histomorphometry. Serum was collected at various time points during the study [day 1 pre-dose (the day of the first Mab dose), day 1 twelve hours post-dose, day 2, day 3, day 5, day 7, day 14, day 21, day 28, day 29 twelve hours post-dose (day 29 was the day of the second and final Mab dose), day 30, day 31, day 33, day 35, day 42, day 49 and day 56].

Three bone-related serum biomarkers were measured using commercially available kits:

Osteocalcin (OC) (DSL Osteocalcin Radioimmunoassay Kit; Diagnostic Systems Laboratories, Inc., Webster, Tex., USA)

N-terminal Propeptide of Type I Procollagen (P1NP) (P1NP Radioimmunoassay Kit; Orion Diagnostica, Espoo, Finland)

C-telopeptide fragments of collagen type 1 a1 chains (sCTXI) (Serum CrossLaps® ELISA; Nordic Bioscience Diagnostics A/S, Herlev, Denmark).

pQCT and DXA scans yielded data on various bone parameters (including bone mineral density (BMD) and bone mineral content) across numerous skeletal sites (including tibial metaphysis and diaphysis, radial metaphysis and diaphysis, femur neck, lumbar vertebrae). Analysis of this bone data (percent change from baseline for each animal) and the anabolic (OC, P1NP) serum biomarker data (percent change from baseline for each animal) revealed statistically significant increases, versus the vehicle group, in some parameters at some of the time points and doses for each Mab. This bone parameter data, serum biomarker data, as well as the histomorphometric data, indicated that each of the 3 Mabs (Ab-23, Ab-5 and Ab-14) was able to neutralize sclerostin in cynomolgous monkeys. This activity was most robust for Ab-23 and Ab-5, particularly at the highest dose (30 mg/kg), with a clear increase in bone formation (anabolic effect) as well as net gains in bone (e.g. BMD). Statistically significant increases in bone parameters and anabolic histomorphometric parameters were also found for the positive control group (PTH (1-34)).

Serum bone formation markers (P1NP, osteocalcin) were increased (p<0.05 vs vehicle (VEH)) at various time points and doses, but particularly in the 30 mg/kg groups for Ab-23 and Ab-5. Histomorphometric analysis revealed dramatic increases (p<0.05 vs VEH) in bone formation rates in cancellous bone at lumbar vertebra and proximal tibia (up to 5-fold increase), as well as at the endocortical surface of the femur midshaft (up to 10-fold increase) at the higher doses of Ab-23 and Ab-5. Trabecular thickness was increased with high dose Ab-23 and Ab-5 in lumbar vertebrae (>60%, p<0.05 vs VEH). By study end (2 months), areal BMD, as percent change from baseline, was increased (p<0.05 vs VEH) at the femur neck, ultra-distal radius (Ab-23, 30 mg/kg), and lumbar vertebrae (Ab-5, 30 mg/kg). The increases in areal BMD at the lumbar vertebrae were accompanied by increases in vertebral strength (97% increase in vertebral maximal load for Ab-23, 30 mg/kg; p<0.05 vs VEH); baseline values for lumbar areal BMD prior to Mab dosing were statistically similar across all groups. In summary, short-term administration of sclerostin-neutralizing Mabs in cynomolgous monkeys resulted, in part, in increases in bone formation, BMD and vertebral bone strength.

From the foregoing, although specific embodiments of the invention have been described herein for purposes of illustration, various modifications may be made without deviating from the spirit and scope of the invention. Accordingly, the invention is not limited except as by the appended claims. All publications, published patent applications, and patent documents disclosed herein are hereby incorporated by reference.

What is claimed is:

1. An isolated antibody or fragment thereof that binds sclerostin of SEQ ID NO: 1 with a dissociation constant of less than or equal to $1\times10^{-7}$ M, comprising six CDRs, CDR-H1, CDR-H2, CDR-H3, CDR-L1, CDR-L2 and CDR-L3, wherein CDR-H1 has the sequence given in SEQ ID NO: 269, CDR-H2 has the sequence given in SEQ ID NO: 270, CDR-H3 has the sequence given in SEQ ID NO: 271, CDR-L1 has the sequence given in SEQ ID NO: 239, CDR-L2 has the sequence given in SEQ ID NO: 240 and CDR-L3 has the sequence given in SEQ ID NO: 241.

2. The isolated antibody or fragment thereof of claim 1 comprising a heavy chain wherein said heavy chain comprises the variable region amino acid sequence given in SEQ ID NO: 366.

3. The isolated antibody or fragment thereof of claim 1 comprising a light chain wherein said light chain comprises the variable region amino acid sequence given in SEQ ID NO: 364.

4. The isolated antibody or fragment thereof of claim 1 comprising both a heavy chain and a light chain wherein the heavy chain comprises the variable region amino acid sequence given in SEQ ID NO: 366 and the light chain comprises the variable region amino acid sequence given in SEQ ID NO: 364.

5. The isolated antibody or fragment thereof of claim 1 comprising a heavy chain wherein said heavy chain comprises the variable region amino acid sequence given in SEQ ID NO: 327.

6. The isolated antibody or fragment thereof of claim 1 comprising a light chain wherein said light chain comprises the variable region amino acid sequence given in SEQ ID NO: 314.

7. The isolated antibody or fragment thereof of claim 1 comprising both a heavy chain and a light chain wherein the heavy chain comprises a the variable region amino acid sequence given in SEQ ID NO: 327 and the light chain comprises the variable region amino acid sequence given in SEQ ID NO: 314.

8. The isolated antibody or fragment thereof of any one of claims 1-7, wherein the antibody or fragment thereof is a human antibody, humanized antibody, or chimeric antibody.

9. The isolated antibody or fragment thereof of any one of claims 1-7, wherein the antibody or fragment thereof is a monoclonal antibody.

10. The isolated antibody or fragment thereof of any one of claims 1-7, which is an antibody fragment.

11. The isolated antibody fragment of claim 10, comprising an $F(ab')_2$, Fab, Fab', Fv, Fc, or Fd antibody fragment.

12. The isolated antibody or fragment thereof of any one of claims 1-7 which comprises a light chain and/or heavy chain constant region.

13. The isolated antibody or fragment thereof of claim 12, which comprises an IgG4 or an IgG2 constant region.

14. The isolated antibody or fragment thereof of claim 1, which is an antibody comprising a heavy chain comprising a polypeptide having the sequence provided in SEQ ID NO: 335, and a light chain comprising a polypeptide having the sequence provided in SEQ ID NO: 334.

15. The isolated antibody or fragment thereof of claim 1, which is an antibody comprising a heavy chain comprising a polypeptide having the sequence provided in SEQ ID NO: 331, and a light chain comprising a polypeptide comprising the sequences provided in SEQ ID NO: 341.

16. The isolated antibody or fragment thereof of claim 1, which is an antibody comprising a heavy chain comprising a polypeptide having the sequence provided in SEQ ID NO: 345 or 396, and a light chain comprising a polypeptide having the sequence provided in SEQ ID NO: 341.

17. The isolated antibody of claim 1 that binds sclerostin of SEQ ID NO: 1 with a dissociation constant of less than or equal to $1\times10^{-8}$ M.

18. An isolated sclerostin-binding antibody having heavy chains of the sequence of SEQ ID NO: 335, and light chains of the sequence of SEQ ID NO: 334.

19. An isolated sclerostin-binding antibody having heavy chains of the sequence of SEQ ID NO: 331, and light chains of the sequence of SEQ ID NO: 341.

20. An isolated sclerostin-binding antibody having heavy chains of the sequence of SEQ ID NO: 345, and light chains of the sequence of SEQ ID NO:341.

21. An isolated sclerostin-binding antibody having heavy chains of the sequence of SEQ ID NO: 396, and light chains of the sequence of SEQ ID NO: 341.

22. The isolated antibody or fragment thereof according to any one of claims 1-7 and 14-21 to which one or more effector or reporter molecule(s) is attached.

23. A pharmaceutical composition comprising the isolated antibody or fragment thereof according to any one of claims 1-7 and 14-21, in combination with one or more of a pharmaceutically acceptable excipient, diluent or carrier.

24. A kit comprising an antibody or fragment thereof according to claim 1.

25. The kit of claim 24 further comprising instructions for using the antibody or fragment thereof to detect sclerostin, a labeled binding partner to the antibody or fragment thereof, a solid phase upon which the antibody or fragment thereof is immobilized, or a combination of any of the foregoing.

* * * * *

UNITED STATES PATENT AND TRADEMARK OFFICE
CERTIFICATE OF CORRECTION

PATENT NO. : 7,872,106 B2
APPLICATION NO. : 12/276889
DATED : January 18, 2011
INVENTOR(S) : Christopher J. Paszty et al.

Page 1 of 1

It is certified that error appears in the above-identified patent and that said Letters Patent is hereby corrected as shown below:

In the Specification:

At Column 161, line 55, "*ofimmunological*" should be -- *of immunological* --.

At Column 182, line 62, "the encompasses" should be -- that encompasses --.

At Column 185, line 61, "show" should be -- shows --.

At Column 186, line 53, "it's" should be -- its --.

At Column 188, line 35, "know" should be -- known --.

At Column 191, line 35, "1001" should be -- 100 µl --.

At Column 191, line 54, "was" should be -- were --.

At Column 196, line 27, "everyday" should be -- every day --.

In the Claims:

At Column 565, line 37, "a the" should be -- the --.

Signed and Sealed this
Nineteenth Day of November, 2013

Teresa Stanek Rea
*Deputy Director of the United States Patent and Trademark Office*

UNITED STATES PATENT AND TRADEMARK OFFICE
Certificate

Patent No. 7,872,106 B2  Patented: January 18, 2011

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Martyn K. Robinson, Woodburn Green (GB); Alistair J. Henry, Middlesex (GB); Alastair Lawson, Hampshire (GB); and Andy Popplewell, Berkshire (GB).

Signed and Sealed this First Day of July 2014.

DANIEL E. KOLKER
*Supervisory Patent Examiner*
Art Unit 1644
Technology Center 1600